United States Patent
Salituro et al.

(10) Patent No.: US 11,613,556 B2
(45) Date of Patent: *Mar. 28, 2023

(54) OXYSTEROLS AND METHODS OF USE THEREOF

(71) Applicant: Sage Therapeutics, Inc., Cambridge, MA (US)

(72) Inventors: Francesco G. Salituro, Marlborough, MA (US); Albert Jean Robichaud, Boston, MA (US); Gabriel Martinez Botella, Wayland, MA (US); Boyd L. Harrison, Princeton Junction, NJ (US); Andrew Griffin, L'ile Bizard (CA)

(73) Assignee: SAGE THERAPEUTICS, INC., Cambridge, MA (US)

( * ) Notice: Subject to any disclaimer, the term of this patent is extended or adjusted under 35 U.S.C. 154(b) by 57 days.

This patent is subject to a terminal disclaimer.

(21) Appl. No.: 17/386,364

(22) Filed: Jul. 27, 2021

(65) Prior Publication Data

US 2022/0024968 A1    Jan. 27, 2022

Related U.S. Application Data

(63) Continuation of application No. 16/343,238, filed as application No. PCT/US2017/057276 on Oct. 18, 2017, now Pat. No. 11,111,266.

(60) Provisional application No. 62/409,768, filed on Oct. 18, 2016, provisional application No. 62/409,756, filed on Oct. 18, 2016.

(51) Int. Cl.
    *C07J 43/00*    (2006.01)
    *C07J 9/00*     (2006.01)
    *C07J 17/00*    (2006.01)

(52) U.S. Cl.
    CPC ............ *C07J 43/003* (2013.01); *C07J 9/00* (2013.01); *C07J 9/005* (2013.01); *C07J 17/00* (2013.01)

(58) Field of Classification Search
    None
    See application file for complete search history.

(56) References Cited

U.S. PATENT DOCUMENTS

| | | |
|---|---|---|
| 2,259,698 A | 10/1941 | Johannessohn et al. |
| 2,594,323 A | 4/1952 | Levin et al. |
| 3,079,385 A | 2/1963 | Bertin et al. |
| 3,206,459 A | 9/1965 | Cross |
| 4,071,625 A | 1/1978 | Grunwell et al. |
| 5,232,917 A | 8/1993 | Bolger et al. |
| 5,376,645 A | 12/1994 | Stella et al. |
| 5,512,570 A | 4/1996 | Dorn et al. |
| 5,595,996 A | 1/1997 | Graham et al. |
| 5,888,996 A | 3/1999 | Farb |
| 5,925,630 A | 7/1999 | Upasani et al. |
| 6,407,086 B2 | 6/2002 | Faarup et al. |
| 6,645,953 B2 | 11/2003 | Gronvald et al. |
| 6,884,796 B2 | 4/2005 | Faarup et al. |
| 6,933,312 B2 | 8/2005 | Price et al. |
| 8,034,798 B2 | 10/2011 | Baulieu et al. |
| 8,247,436 B2 | 8/2012 | Baettig et al. |
| 8,604,011 B2 | 12/2013 | Mellon |
| 8,673,843 B2 | 3/2014 | Moskal et al. |
| 8,829,213 B2 | 9/2014 | Peng et al. |
| 10,201,550 B2 | 2/2019 | Salituro et al. |
| 10,227,375 B2 | 3/2019 | Botella et al. |
| 10,259,840 B2 | 4/2019 | Harrison et al. |
| 10,696,712 B2 | 6/2020 | Salituro et al. |
| 10,723,758 B2 | 7/2020 | Harrison et al. |
| 10,759,828 B2 | 9/2020 | Upasani et al. |
| 11,104,701 B2 | 8/2021 | Botella et al. |
| 11,111,266 B2 | 9/2021 | Salituro et al. |
| 11,149,054 B2 | 10/2021 | Salituro et al. |

(Continued)

FOREIGN PATENT DOCUMENTS

| | | |
|---|---|---|
| AU | 728843 | 1/2001 |
| CN | 1254716 | 5/2008 |

(Continued)

OTHER PUBLICATIONS

U.S. Appl. No. 14/343,603, filed Nov. 25, 2014, Ravindra B. Upasani et al., Abandoned.
U.S. Appl. No. 14/775,401, filed Sep. 11, 2015, Kiran Reddy et al., Abandoned.
U.S. Appl. No. 14/775,678, filed Sep. 12, 2015, Gabriel Martinez Botella et al., Abandoned.

(Continued)

*Primary Examiner* — Amy C Bonaparte
(74) *Attorney, Agent, or Firm* — Haley Guiliano LLP; Karen Mangasarian; Jacob E. Dander

(57) ABSTRACT

Compounds are provided according to Formula (A): and pharmaceutically acceptable salts thereof, and pharmaceutical compositions thereof; wherein $R^1$, $R^2$, $R^3$, $R^4$, $R^5$, $R^6$, and $R^G$ are as defined herein. Compounds of the present invention are contemplated useful for the prevention and treatment of a variety of conditions.

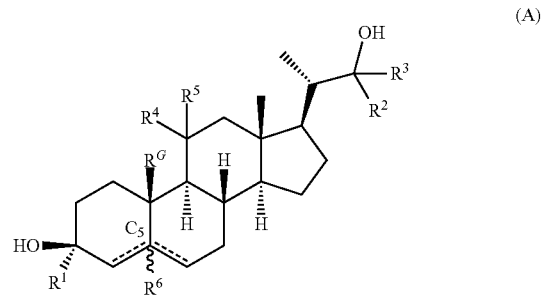

(A)

20 Claims, No Drawings

(56) References Cited

U.S. PATENT DOCUMENTS

| | | |
|---|---|---|
| 2004/0048838 A1 | 3/2004 | Gronvald et al. |
| 2005/0101573 A1 | 5/2005 | Faarup et al. |
| 2006/0199790 A1 | 9/2006 | Baulieu et al. |
| 2008/0193423 A1 | 8/2008 | Brunton et al. |
| 2008/0269183 A1 | 10/2008 | Mellon et al. |
| 2008/0319026 A1 | 12/2008 | Gant et al. |
| 2010/0034781 A1 | 2/2010 | Parhami et al. |
| 2010/0087411 A1 | 4/2010 | Barraclough et al. |
| 2011/0160223 A1 | 6/2011 | Dingledine et al. |
| 2011/0190249 A1 | 8/2011 | Rees et al. |
| 2012/0035156 A1 | 2/2012 | Alberati et al. |
| 2012/0040916 A1 | 2/2012 | Moon et al. |
| 2012/0041016 A1 | 2/2012 | Frincke |
| 2012/0115169 A1 | 5/2012 | Mullenix et al. |
| 2013/0210792 A1 | 8/2013 | Song et al. |
| 2014/0045943 A1 | 2/2014 | Khan et al. |
| 2014/0148412 A1 | 5/2014 | Hogenkamp |
| 2014/0235600 A1 | 8/2014 | Covey et al. |
| 2014/0335050 A1 | 11/2014 | Haggerty et al. |
| 2015/0158903 A1 | 6/2015 | Upasani |
| 2015/0291654 A1 | 10/2015 | Upasani et al. |
| 2015/0376225 A1 | 12/2015 | Dugar et al. |
| 2016/0022701 A1 | 1/2016 | Reddy et al. |
| 2016/0031930 A1 | 2/2016 | Botella et al. |
| 2017/0247405 A1 | 8/2017 | Harrison et al. |
| 2017/0304321 A1 | 10/2017 | Quirk et al. |
| 2017/0305960 A1 | 10/2017 | Botella et al. |
| 2018/0194797 A1 | 7/2018 | Salituro et al. |
| 2018/0200267 A1 | 7/2018 | Salituro et al. |
| 2018/0201643 A1 | 7/2018 | Salituro et al. |
| 2018/0237470 A1 | 8/2018 | Botella et al. |
| 2018/0362573 A1 | 12/2018 | Upasani et al. |
| 2018/0371009 A1 | 12/2018 | Pellicciari et al. |
| 2019/0125764 A1 | 5/2019 | Salituro et al. |
| 2019/0127414 A1 | 5/2019 | Botella et al. |
| 2019/0135854 A1 | 5/2019 | Harrison et al. |
| 2019/0160078 A1 | 5/2019 | Masuoka et al. |
| 2019/0233465 A1 | 8/2019 | Robichaud et al. |
| 2019/0248829 A1 | 8/2019 | Salituro et al. |
| 2019/0330259 A1 | 10/2019 | Robichaud et al. |
| 2019/0359646 A1 | 11/2019 | Botella et al. |
| 2020/0002371 A1 | 1/2020 | Salituro et al. |
| 2020/0024300 A1 | 1/2020 | Salituro et al. |
| 2021/0040138 A1 | 2/2021 | Harrison et al. |
| 2021/0101925 A1 | 4/2021 | Salituro et al. |
| 2021/0145848 A1 | 5/2021 | Salituro et al. |
| 2021/0147468 A1 | 5/2021 | Salituro et al. |
| 2021/0147470 A1 | 5/2021 | Upasani et al. |
| 2021/0171567 A1 | 6/2021 | Botella et al. |
| 2021/0380631 A1 | 12/2021 | Sallituro et al. |
| 2022/0081465 A1 | 3/2022 | Salituro et al. |

FOREIGN PATENT DOCUMENTS

| | | |
|---|---|---|
| FR | 2850023 | 7/2004 |
| JP | 50140435 | 11/1975 |
| JP | 53082766 | 7/1978 |
| JP | 54163565 | 12/1979 |
| JP | 57035597 | 2/1982 |
| JP | 61254599 | 11/1986 |
| JP | 62187485 | 8/1987 |
| JP | 08268917 | 10/1996 |
| JP | 09328498 | 12/1997 |
| JP | H11509844 A | 8/1999 |
| JP | 2005508368 | 3/2005 |
| RU | 2194712 | 12/2002 |
| RU | 2458065 C2 | 8/2012 |
| WO | WO1994027608 | 12/1994 |
| WO | WO1995002409 | 1/1995 |
| WO | WO1995013287 | 5/1995 |
| WO | WO1995021617 | 8/1995 |
| WO | WO1996012705 | 5/1996 |
| WO | WO1996040043 | 12/1996 |
| WO | WO1997000884 | 1/1997 |
| WO | WO1997003677 | 2/1997 |
| WO | WO1998007740 | 2/1998 |
| WO | WO1999058497 | 11/1999 |
| WO | WO2000063228 | 10/2000 |
| WO | WO2000068246 | 11/2000 |
| WO | WO2001049703 | 7/2001 |
| WO | WO2002011708 | 2/2002 |
| WO | WO2002053577 | 7/2002 |
| WO | WO2002079221 | 10/2002 |
| WO | WO2003039480 | 5/2003 |
| WO | WO2003049685 | 6/2003 |
| WO | WO2003082893 | 10/2003 |
| WO | WO2004055201 | 7/2004 |
| WO | WO2005079810 | 9/2005 |
| WO | WO2008041003 | 4/2008 |
| WO | WO2008063128 | 5/2008 |
| WO | WO2009001097 | 12/2008 |
| WO | WO2009059961 | 5/2009 |
| WO | WO2009073186 | 6/2009 |
| WO | WO2009090063 | 7/2009 |
| WO | WO2010075282 | 7/2010 |
| WO | WO2010088414 | 8/2010 |
| WO | WO2011014661 | 2/2011 |
| WO | WO2011028794 | 3/2011 |
| WO | WO2011067501 | 6/2011 |
| WO | WO2011092127 | 8/2011 |
| WO | WO2012064501 | 5/2012 |
| WO | WO2012142039 | 10/2012 |
| WO | WO2013019711 | 2/2013 |
| WO | WO2013036835 | 3/2013 |
| WO | WO2013056181 | 4/2013 |
| WO | WO2013163455 | 10/2013 |
| WO | WO2014025942 | 2/2014 |
| WO | WO2014115167 | 7/2014 |
| WO | WO2014120786 | 8/2014 |
| WO | WO2014160441 | 10/2014 |
| WO | WO2014160480 | 10/2014 |
| WO | WO2015195967 | 12/2015 |
| WO | WO2016007762 | 1/2016 |
| WO | WO2016057713 | 4/2016 |
| WO | WO2017007832 | 1/2017 |
| WO | WO2017007836 | 1/2017 |
| WO | WO2017007840 | 1/2017 |
| WO | WO2017037465 | 3/2017 |
| WO | WO2017173358 | 10/2017 |
| WO | WO2018064649 | 4/2018 |
| WO | WO2018075698 | 4/2018 |
| WO | WO2018075699 | 4/2018 |
| WO | WO2018170336 | 9/2018 |

OTHER PUBLICATIONS

U.S. Appl. No. 15/319,504, filed Dec. 16, 2016, Boyd L. Harrison et al., Issued.
U.S. Appl. No. 15/517,886, filed Apr. 7, 2017, Michael C. Quirk et al., Pending.
U.S. Appl. No. 15/588,305, filed May 5, 2017, Gabriel Martinez Botella et al., Abandoned.
U.S. Appl. No. 15/742,422, filed Jan. 5, 2018, Francesco G. Salituro et al., Issued.
U.S. Appl. No. 15/742,424, filed Jan. 5, 2018, Francesco G. Salituro et al., Issued.
U.S. Appl. No. 15/742,425, filed Jan. 5, 2018, Francesco G. Salituro et al., Issued.
U.S. Appl. No. 15/917,263, filed Mar. 9, 2018, Gabriel Martinez Botella et al., Issued.
U.S. Appl. No. 15/917,272, filed Mar. 9, 2018, Gabriel Martinez Botella et al., Abandoned.
U.S. Appl. No. 16/028,790, filed Jul. 6, 2018, Boyd L. Harrison et al., Issued.
U.S. Appl. No. 16/089,896, filed Sep. 28, 2018, Albert Jean Robichaud et al., Abandoned.
U.S. Appl. No. 16/099,122, filed Nov. 5, 2018, Gabriel Martinez Botella et al., Issued.
U.S. Appl. No. 16/114,791, filed Aug. 28, 2018, Ravindra B. Upasani et al., Issued.
U.S. Appl. No. 16/227,013, filed Dec. 20, 2018, Gabriel Martinez Botella et al., Issued.

(56) References Cited

OTHER PUBLICATIONS

U.S. Appl. No. 16/227,099, filed Dec. 20, 2018, Francesco G. Salituro et al., Issued.
U.S. Appl. No. 16/315,250, filed Jan. 4, 2019, Francesco G. Salituro et al., Issued.
U.S. Appl. No. 16/338,315, filed Mar. 29, 2019, Francesco G. Salituro et al., Issued.
U.S. Appl. No. 16/343,235, filed Apr. 18, 2019, Francesco G. Salituro et al., Issued.
U.S. Appl. No. 16/343,238, filed Apr. 18, 2019, Francesco G. Salituro et al., Issued.
U.S. Appl. No. 16/879,460, filed May 20, 2020, Francesco G. Salituro et al., Pending.
U.S. Appl. No. 16/902,730, filed Jun. 16, 2020, Boyd L. Harrison et al., Pending.
U.S. Appl. No. 16/930,047, filed Jul. 15, 2020, Gabriel Martinez Botella et al., Pending.
U.S. Appl. No. 16/938,348, filed Jul. 24, 2020, James J. Doherty, Pending.
U.S. Appl. No. 16/942,235, filed Jul. 29, 2020, Ravindra B. Upasani et al., Pending.
U.S. Appl. No. 16/942,245, filed Jul. 29, 2020, Francesco G. Salituro et al., Pending.
U.S. Appl. No. 16/943,649, filed Jul. 30, 2020, Francesco G. Salituro et al., Allowed.
U.S. Appl. No. 17/242,860, filed Apr. 28, 2021, Albert Jean Robichaud et al., Pending.
U.S. Appl. No. 17/381,829, filed Jul. 21, 2021, Gabriel Martinez Botella et al., Pending.
U.S. Appl. No. 17/395,155, filed Aug. 5, 2021, Francesco G. Salituro et al., Pending.
U.S. Appl. No. 17/396,034, filed Aug. 6, 2021, Francesco G. Salituro et al., Pending.
U.S. Appl. No. 17/476,153, filed Sep. 15, 2021, Francesco G. Salituro et al., Pending.
U.S. Appl. No. 16/930,047, filed Jul. 15, 2020, Gabriel Martinez Botella et al., Allowed.
U.S. Appl. No. 16/942,235, filed Jul. 29, 2020, Ravindra B. Upasani et al., Abandoned.
U.S. Appl. No. 16/943,649, filed Jul. 30, 2020, Francesco G. Salituro et al., Issued.
U.S. Appl. No. 17/707,303, filed Mar. 29, 2022, Ravindra B. Upasani et al., Pending.
Berge et al., "Pharmaceutical salts," Journal of Pharmaceutical Sciences, 66(1):1-19 (1977).
Bjorkhem et al., "Oxysterols in the circulation of patients with the Smith-Lemli-Opitz syndrome: abnormal levels of 24S- and 27-hydroxycholesterol," Journal of Lipid Research, 42(3):366-371 (2001).
Bukelis et al., "Smith-Lemli-Opitz syndrome and autism spectrum disorder," American Journal of Psychiatry, 164(11):1655-1661 (2007).
Cais et al., "Temperature dependence of NRI/NR2B NMDA receptor channels," Neuroscience, 151(2):428-438 (2008).
Cancer [online], [retrieved on Jul. 6, 2007], Retrieved from the internet, URL http://www.nlm.nih.gov/medlineplus/ cancer.html> (11 pages).
Chen et al., "The chemical biology of clinically tolerated NMDA receptor antagonists," Journal of Neurochemistry, 97(6):1611-1626 (2006).
Citraro et al., "Effects of some neurosteroids injected into some brain areas of WAG/Rij rats, an animal model of generalized absence epilepsy," Neuropharmacology, 50(8):1059-1071 (2006).
Collingridge et al., "The NMDA receptor as a target for cognitive enhancement," Neuropharmacology, 64:13-26 (2013).
Connick et al., "Program No. 613 1/B86," 2009 Neuroscience Meeting Planner, Chicago, IL: Society for Neuroscience (2009) (2 pages).
Cook et al., "24-hydroxycholesterol sulfation by human cytosolic sulfotransferases: formation of monosulfates and disulfates, molecular modeling, sulfatase sensitivity, and inhibition of liver X receptor activation," Drug Metabolism and Disposition, 37(10):2069-2078 (2009).
Corman et al., "Structure-activity relationships for side chain oxy sterol agonists of the hedgehog signaling pathway," ACS Medicinal Chemistry Letters, 3(10):828-833 (2012).
Costa et al., "A novel family of negative and positive allosteric modulators of NMDA receptors," Journal of Pharmacology and Experimental Therapeutics, 335(3):614-21 (2010).
Cross et al., "Steroids CCLXXIN[1]. Biologically-active labile ethers IV[2]. The synthesis of 22-oxa-25-azacholesterol and related compounds," Steroids, 5(5):585-598 (1965).
Dale et al., "Nuclear magnetic resonance enantiomer regents. Configurational correlations via nuclear magnetic resonance chemical shifts of diastereomeric mandelate, O-methylmandelate, and .alpha.-methoxy-.alpha.-trifluoromethylphenylacetate (MTPA) esters," Journal of the American Chemical Society, 95(2):512-519 (1973).
Dayal et al., "Stereospecific synthesis of 3 beta-hydroxylated bile alcohols," Journal of Lipid Research, 25(6):646-650 (1984).
Deng et al., "Fluoro analogs of bioactive oxy-steroids: Synthesis of an EBI2 agonist with enhanced metabolic stability," Bioorganic and Medicinal Chemistry Letters, 26:4888-4891 (2016).
Damasio, "Alzheimer's disease and related dementias," Cecil Textbook of Medicine, 20th edition, 2:1992-1996 (1996).
Extended European Search Report for European Application No. 14774060.9, dated Aug. 17, 2016 (11 pages).
European Search Partial Supplementary Report for European Application No. 14775126.7, dated Sep. 14, 2016 (7 pages).
Extended European Search Report for European Application No. 14775126.7, dated Dec. 15, 2016 (7 pages).
Extended European Search Report for Application No. 15809462.3, dated Nov. 29, 2017 (8 pages).
Extended European Search Report for European Application No. 15849514.3, dated May 23, 2018 (7 pages).
Extended European Search Report for Application No. 16821920.2, dated Jan. 31, 2019 (12 pages).
Extended European Search Report for Application No. 16821924.4, dated Jan. 31, 2019 (12 pages).
Extended European Search Report for Application No. 16821926.9, dated Jan. 31, 2019 (10 pages).
Elbarbry et al., "Cyclosporine-induced changes in drug metabolizing enzymes in hyperlipemic rabbit kidneys could explain its toxicity," Xenobiotica, 40(11):772-781 (2010).
FDA mulls drug to slow late-stage Alzheimer's [online] (cnn.com/health), [retrieved on Sep. 23, 2003], Retrieved from the Internet, URL; http://www.cnn.com/2003/HEALTH/conditions/09/24/alzheimers.drug.ap/indexhtml> (2 pages).
Ferriz et al., "Prodrug Design of Phenolic Drugs", Current Pharmaceutical Designs, vol. 16, pp. 2033-2052 (2010).
Festa et al., "Exploitation of cholane scaffold for the discovery of potent and selective famesoid X receptor (FXR) and G-protein coupled bile acid receptor 1 (GP-BAR$_1$) ligands," Journal of Medicinal Chemistry, 57(20):8477-8495 (2014).
Foster et al., "Effect of steroids on beta-adrenoceptor-mediated relaxation of pig bronchus," British Journal of Pharmacology, 78(2):441-445 (1983).
Fukuto et al., "Determination of the Mechanism of Demethlenation of (methylenedioxy phenyl compounds by cytochrome P450 using deuterium isotope effects," Journal of Medicinal Chemistry, 34(9):2871-2876 (1991).
Gee et al., "GABA-dependent modulation of the Cl-ionophore by steroids in rat brain," European Journal of Pharmacology, 136(3):419-423 (1987).
Golub et al., "Molecular classification of cancer: class discovery and class prediction by gene expression monitoring," Science, 286(5439):531-537 (1999).
Groden et al., "Determination of Fura-2 dissociation constants following adjustment of the apparent Ca-EGTA association constant for temperature and ionic strength," Cell Calcium, 12:(4)279-287 (1991).
Grynkiewicz et at., "A new generation of Ca2+ indicators with greatly improved fluorescence properties," Journal of Biological Chemistry, 260(6):3440-3345 (1985).

(56) References Cited

OTHER PUBLICATIONS

Gunatilaka et al., "Bioactive ergost-5-ene-3 beta, 7 alpha-diol derivatives from *Pseudobersama mossambicensis*," Journal of Natural Products, 55(11):1648-1654 (1992).
Guthrie et al., "Morphological and biochemical differences expressed in separate dissociated cell cultures of dorsal and ventral halves of the mouse spinal cord," Brain Research, 420(2):313-323 (1987).
Hoeve et al., "The design of resolving agents. Chiral cyclic phosphoric acids," Journal of Organic Chemistiy, 50(23):4508-4514 (1985).
Hoffmeister et al., "Zur chemie des ecdysons, III: Vergleichende spektrometrische untersuchungen an a.b-ungesättigten steroidketonen," Chemische Berichte, 98(7):2361-2375 (1965).
Hogg et al., "An automated system for intracellular and intranuclear injection," Journal of Neuroscience, Methods, 169(1):65-75 (2008).
Hollmann et al., "Zinc potentiates agonist-induced currents at certain splice variants of the NMDA receptor," Neuron, 10(5):943-954 (1993).
Horak et al., "Molecular mechanism of pregnenolone sulfate action at NR1/NR2B receptors," Journal of Neuroscience, 24(46):10318-10325 (2004).
Huttunen et al., "Prodrugs—from serendipity to rational design," Pharmacological Reviews, 63(3):750-771 (2011).
Iida et al., "An improved method for the capillary gas chromatographic derivatization of polyhydroxylated steroids having tert-hydroxyl groups," Analytical Sciences, 19(9):1317-1321 (2003).
Irwin et al., "Steroid potentiation and inhibition of N-methyl-D-aspartate receptor-mediated intracellular Ca++ responses: structure-activity studies," Journal of Pharmacology and Experimental Therapeutics, 271(2):677-682 (1994).
Jurman et al., "Visual identification of individual transfected cells for electrophysiology using antibody-coated beads," Biotechniques, 17(5):876-881 (1994), abstract only.
Karaki et al., "Structure-activity relationship studies of Niemann-Pick type C1-like 1 (NPC1L1) ligands identified by screening assay monitoring pharmacological chaperone effect," Bioorganic and Medicinal Chemistry, 21(17):5297-5309 (2013).
Khripach et al., "Synthesis of (24S)-hydroxy-and (24S)-24,25-epoxycholesterol analogues, potential agonists of nuclear LXR receptors," Russian Journal of Bioorganic Chemistry, 32(6):586-594 (2006).
Knoppert et al., "Position paper: Paediatric age categories to be used in differentiating between listing on a model essential medicines list for children," pp. 1-5 (2007).
Kurosawa et al., "Synthesis of 19-hydroxylated bile acids and identification of 3 alpha,7 alpha,12 alpha,19-tetrahydroxy-5 beta-cholan-24oic acid in human neonatal urine," Chemical and Pharmaceutical Bulletin, 43(9):1551-1557 (1995).
Lakhan et al.," NMDA receptor activity in neuropsychiatric disorders," Frontiers in Psychiatry, 4:1-7 (2013).
Lala et al., "Role of nitric oxide in tumor progression: Lessons from experimental tumors," Cancer and Metastasis Reviews, 17(1):91-106 (1998).
Layzer, "Section five-degenerative diseases of the nervous system," Cecil Textbook of Medicine, 20th edition, 2:2050-2057 (1996).
Leoni et al., "Changes in human plasma levels of the brain specific oxy sterol 24S-hydroxycholesterol during progression of multiple sclerosis," Neuroscience Letters, 331(3):163-166 (2002).
Leoni et al., "Oxysterols as biomarkers in neurodegenerative diseases," Chemistry and Physics of Lipids, 164(6):515-524 (2011).
Lettré et al., "Mehrwertige alkohole aus sterinen und sterinderivaten, VI Steroide mit strukturmerkmalen des ecdysons und der elatericine," Justus Liebigs Annalen der Chemie, 758:89-110 (1972) (English Abstract).
Li et al., "Synthesis of 7alpha-hydroxy derivatives of regulatory oxysterols," Steroids, 65(9):529-535 (2000).
Linsenbardt et al., "Different oxysterols have opposing actions at N-methyl-D-aspartate receptors," Neuropharmacology, 85:232-242 (2014).

Lutjohann et al., "Cholesterol homeostasis in human brain: evidence for an agedependent flux of 24S-hydroxycholesterol from the brain into the circulation," PNAS, 93(18):9799-804 (1996).
Luu et al., "Oxysterols: Old Tale, New Twists," Annual Review of Pharmacology and Toxicology, 56:447-467 (2016).
Madau et al., Program No. 613.2/B87. 2009 Neuroscience Meeting Planner. Chicago, IL: Society for Neuroscience (2009) (3 pages).
Mateos et al., "Activity-regulated cytoskeleton-associated protein in rodent brain is down regulated by high fat diet in vivo and by 27-hydroxycholesterol in vitro," Brain Pathology, 19(1):69-80 (2009).
Monyer et al., "Heteromeric NMDA receptors: molecular and functional distinction of subtypes," Science, 256(5060):1217-1221 (1992).
Mourino et al., "Studies on vitamin D (calciferol) and its analogs. 15. 24-nor-1a,25-dihydroxyvitamin D3 and 24-nor-25¬,hydroxy-5,6-trans-vitaminD3," Journal of Medicinal Chemistry, 21(10):1025-1029 (1978).
Nagano et al., "Chemistry and biochemistry of Chinese drugs. Part II. Hydroxylated sterols, cytotoxic towards cancerous cells: synthesis and testing," Journal of Chemical Research, 9:218 (1977).
Nagasaka et al., "Oxysterol changes along with cholesterol and vitamin D changes in adult phenylketonuric patients diagnosed by newborn mass-screening," Clinica Chimica Acta, 416:54-59 (2013).
Niemann-Pick diagnosis—treatment [online] retrieved from the internet on Jul. 17, 2021 (URL: https://www.mayoclinic.org/diseases-conditions/niemann-pick/diagnosis-treatment/drc-20355890).
Niemann-Pick overview [online] retrieved from the internet on Jul. 17, 2021 (URL: https://www.mayoclinic.org/diseases-conditions/niemann-pick/symptoms-causes/syc-20355887).
Olkkonen et al., "Oxysterols and their cellular effectors," Biomolecules, 2(1):76-103 (2012).
Papassotiropoulos et al., "Plasma 24S-hydroxycholesterol a peripheral indicator of neuronal degeneration and potential state marker for Alzheimer's disease," NeuroReport 11(9): 1959-1962 (2000).
Park-Chung et al., "Distinct sites for inverse modulation of N-methyl-D-aspartate receptors by sulfated steroids," Molecular Pharmacology, 52(6):1113-1123 (1997).
Paul et al., "The major brain cholesterol metabolite 24(S)-hydroxycholesterol is a potent allosteric modulator of N-methyl-D-aspartate receptors," The Journal of Neuroscience, 33(44):17290-17300 (2013).
PCT International Search Report and Written Opinion for corresponding International Application No. PCT/US2012/054261, dated Nov. 28, 2012 (10 pages).
PCT International Search Report and Written Opinion for corresponding International Application No. PCT/US2014/026633, dated Jul. 14, 2014 (6 pages).
PCT International Search Report and Written Opinion for corresponding International Application No. PCT/US2014/026784, dated Jul. 8, 2014 (13 pages).
PCT International Search Report and Written Opinion for corresponding International Application No. PCT/US2015/036510, dated Sep. 15, 2015 (7 pages).
PCT International Search Report and Written Opinion for corresponding International Application No. PCT/US2015/054551, dated Jan. 8, 2016 (10 pages).
PCT International Search Report and Written Opinion for corresponding International Application No. PCT/US2016/041160, dated Oct. 28, 2016 (7 pages).
PCT International Search Report and Written Opinion for corresponding International Application No. PCT/US2016/041168, dated Sep. 15, 2016 (6 pages).
PCT International Search Report and Written Opinion for corresponding International Application No. PCT/US2016/041175, dated Sep. 16, 2016 (6 pages).
PCT International Search Report and Written Opinion for corresponding International Application No. PCT/US2017/025535, dated Jul. 3, 2017 (7 pages).
PCT International Search Report and Written Opinion for corresponding International Application No. PCT/US2017/031374, dated Aug. 14, 2017 (8 pages).

(56) References Cited

OTHER PUBLICATIONS

PCT International Search Report and Written Opinion for corresponding International Application No. PCT/US2017/041199, dated Aug. 29, 2017 (12 pages).
PCT International Search Report and Written Opinion for corresponding International Application No. PCT/US2017/054657, dated Nov. 21, 2017 (18 pages).
PCT International Search Report and Written Opinion for corresponding International Application No. PCT/US2017/057276, dated Dec. 11, 2017 (13 pages).
PCT International Search Report and Written Opinion for corresponding International Application No. PCT/US2017/057277, dated Feb. 20, 2018 (19 pages).
PCT Invitation to Correct Fees and Partial International Search Report and Provisional Opinion for corresponding International Application No. PCT/US2017/057277, dated Dec. 20, 2017 (13 pages).
Petrovic et al., "Pregnenolone sulfate modulation of N-methyl-D-aspartate receptors is phosphorylation dependent," Neuroscience, 160:616-628 (2009).
Pritchett et al., "Transient expression shows ligand gating and allosteric potentiation of GABAA receptor subunits," Science, 242(4883):1306-1308 (1988).
Pubchem, CID 65094, 25-Hydroxycholesterol, Nov. 18, 2016 (17 pages).
Pubchem, CID 132021, Ergostan-3,24-diol, Mar. 5, 2018 (15 pages).
Pubchem, CID 54083335, Schembl4961477, Nov. 8, 2016 (13 pages).
Pubchem, CID 54160779, Schembl4961477, Nov. 8, 2016 (13 pages).
Pubchem, CID 58455549, Schembl12198161, Nov. 8, 2016 (13 pages).
Pubchem, CID 66966798, Cholane-3alpha,24,-diol, Nov. 8, 2016 (11 pages).
Pubchem, CID 70604305, Schembl11528874, Nov. 8, 2016 (13 pages).
Pubchem, CID 71508953, Mar. 5, 2018 (13 pages).
Reddy, "Pharmacology of endogenous neuroactive steroids," Critical Reviews in Neurobiology, 15(3-4):197-234 (2013).
Roh et al., "Neuroprotective effects of ginsenoside Rg3 against 24-OH-cholesterol-induced cytotoxicity in cortical neurons," Journal of Ginseng Research, 34(3):246-253 (2010).
Schmidt et al., "Inhibitory effect of oxygenated cholestan-3b-ol derivatives on the growth of *Mycobacterium tuberculosis*," Bioorganic & Medicinal Chemistry Letters, 23(22):6111-6113 (2013).
Segal, "Pat hippocampal Neurons in Culture: Responses to Electrical and Chemical Stimuli," Journal of Neurophysiology, 50(6):1249-1264 (1983).
Sepe et al., "Total synthesis and pharmacological characterization of solomonsterol A, a potent marine pregnane-X-receptor agonist endowed with anti-inflammatory activity," Journal of Medicinal Chemistry, 54:4590-4599 (2011).
Solomon et al., "Plasma levels of 24S-hydroxycholesterol reflect brain volumes in patients without objective cognitive impairment but not in those with Alzheimer's disease," Neuroscience Letters 462(1): 89-93 (2009).
Stamp et al., "Plasma levels and therapeutic effect of 25-hydroxycholecalciferol in epileptic patients taking anticonvulsant drugs," British Medical Journal, 4(5831):9-12 (1972).
Stastna et al., "Synthesis of C3, C5, and C7 pregnane derivatives and their effect on NMDA receptor responses in cultured rat hippocampal neurons," Steroids, 74(2):256-263 (2008).
Steinrauf et al., "Synthesis and evaluation of sulfur-containing steroids against methylmercuric chloride toxicity," Journal of Pharmaceutical Sciences, 67(12):1739-1743 (1978).
Svoboda et al., "Treatment of Smith-Lemli-Opitz syndrome and other sterol disorders," American Journal of Medical Genetics Part C: Seminars in Medical Genetics, 160C(4): 285-294 (2012).
Takahashi et al., "Stereochemistry of reduction of the C-24,25 double bond in the conversion of desmosterol into cholesterol," Tetrahedron Letters, 44(2):341-344 (2003).
Takano et al., "Simple synthesis of 3b,24-dihydroxychol-5-en-7-one by oxidative cleavage of the side chain of cholesterol," Chemistry Letters, 14(8):1265-1266 (1985).
Tierney et al., "Abnormalities of cholesterol metabolism in autism spectrum disorders," American Journal of Medical Genetics Part B: Neuropsychiatric Genetics, 141B(6):666-668 (2006).
Tomek et al., "NMDA receptor modulators in the treatment of drug addiction," Pharmaceuticals (Basel), 6(2):251-258 (2013).
Verdoorn et al., "Functional properties of recombinant rat GABAA receptors depend upon subunit composition," Neuron, 4(6):919-928 (1990).
Vyklicky et al., "Calcium-mediated modulation of N-methyl-D-aspartate (NMDA) responses in cultured rat hippocampal neurones," Journal of Physiology, 470:575-600 (1993).
Wieland et al., "Comparative behavioral characterization of the neuroactive steroids 3 alpha-OH,5 alpha-pregnan-20-one and 3 alpha-OH,5 beta-pregnan-20-one in rodents," Psychopharmacology 118(1):65-71 (1995).
Wilen et al., "Strategies in Optical Resolutions," Tetrahedron 33:2725-2736 (1977).
Wolozin et al., "The cellular biochemistry of cholesterol and statins: Insights into the pathophysiology and therapy of Alzheimer's disease," CNS Drug Review, 10(2):127-146 (2004).
Wong et al., "An efficient and convenient transformation of a-haloketones to a-hydroxyketones using cesium formate," Journal of Organometallic Chemistry, 694(21):3452-3455 (2004).
Xiangdong et al., "Highly stereoselective synthesis of 24R,25- and 24S, 25-dihydroxy steroid," Database Chemical Abstracts Service, Database accession No. 2001:174431 (2000) (4 pages).
Xilouri et al., "Neuroprotective effects of steroid analogues on P19-N neurons," Neurochemistry International, 50(4):660-670 (2007).
Yan et al., "Characterization of a synthetic steroid 24-keto-cholest-5-en-3b,19-diol as a neuroprotectant," CNS Neuroscience & Therapeutics, 21(6):486-495 (2015).
Yang et al., "New cytotoxic oxygenated sterols from marine bryozoan *Bugula neritina*," Natural Product Research, 25(16):1505-1511 (2011).
Zhou et al., "Properties of HERG channels stably expressed in HEK 293 cells studied at physiological temperature," Biophysical Journal, 74(1):230-241 (1998).
Zuliani et al., "Plasma 24S-hydroxycholesterol levels in elderly subjects with late onset Alzheimer's disease or vascular dementia: a case-control study," BMC Neurology, 11(121):1-8 (2011).

OXYSTEROLS AND METHODS OF USE THEREOF

CROSS-REFERENCE TO RELATED APPLICATIONS

This application is a continuation of U.S. patent application Ser. No. 16/343,238, filed Apr. 18, 2019, which is a U.S. National Phase Application under 35 U.S.C. § 371 of International Application PCT/US2017/057276, filed Oct. 18, 2017, which claims priority to and the benefit of U.S. Provisional Application No. 62/409,756, filed Oct. 18, 2016, and U.S. Provisional Application No. 62/409,768, filed Oct. 18, 2016. The disclosures of each of the foregoing applications are incorporated herein by reference in their entirety.

BACKGROUND OF THE INVENTION

NMDA receptors are heteromeric complexes comprised of NR1, NR2, and/or NR3 subunits and possess distinct recognition sites for exogenous and endogenous ligands. These recognition sites include binding sites for glycine, and glutamate agonists and modulators. NMDA receptors are expressed in the peripheral tissues and the CNS, where they are involved in excitatory synaptic transmission. Activating these receptors contributes to synaptic plasticity in some circumstances and excitotoxicity in others. These receptors are ligand-gated ion channels that admit $Ca^{2+}$ after binding of the glutamate and glycine, and are fundamental to excitatory neurotransmission and normal CNS function. Positive modulators may be useful as therapeutic agents with potential clinical uses as cognitive enhancers and in the treatment of psychiatric disorders in which glutamatergic transmission is reduced or defective (see, e.g., Horak et al., J. of Neuroscience. 2004, 24(46), 10318-10325). In contrast, negative modulators may be useful as therapeutic agents with potential clinical uses in the treatment of psychiatric disorders in which glutamatergic transmission is pathologically increased (e.g., treatment resistant depression).

Oxysterols are cholesterol analogs that are modulators of NMDA receptor function. There is a need for new oxysterols that modulate the NMDA receptor for the prevention and treatment of conditions associated with NMDA expression and function. Compounds, compositions, and methods described herein are directed toward this end.

SUMMARY OF THE INVENTION

Provided herein are substituted oxysterols useful for preventing and/or treating a broad range of disorders, including, but not limited to, NMDA-mediated disorders. Further provided are pharmaceutical compositions comprising the compounds of the present invention, and methods of their use and treatment.

In one aspect, provided herein are compounds according to Formula (A):

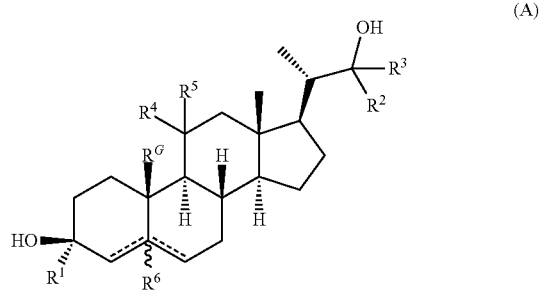

or a pharmaceutically acceptable salt thereof, wherein:

$R^1$ is hydrogen or alkyl (e.g., $C_1$-$C_6$ alkyl); each of $R^2$ and $R^3$ is independently hydrogen, alkyl (e.g., $C_1$-$C_6$ alkyl), alkenyl, alkynyl, carbocyclyl, heterocyclyl, aryl, or heteroaryl, or $R^2$ and $R^3$, together with the carbon atom to which they are attached form a 3-8 membered ring; each of $R^4$ and $R^5$ is independently hydrogen, halo, or —$OR^C$ wherein $R^C$ is hydrogen or $C_1$-$C_6$ alkyl (e.g., $C_1$-$C_3$ alkyl), or $R^4$ and $R^5$, together with the carbon atom to which they are attached form an oxo group; $R^6$ is absent or hydrogen; $R^G$ is hydrogen or alkyl; and ----- represents a single or double bond, wherein when one of ----- is a double bond, the other ----- is a single bond and $R^6$ is absent; and when both of ----- are single bonds, then $R^6$ is hydrogen.

In some embodiments, $R^1$ is alkyl (e.g., $C_1$-$C_6$ alkyl). In some embodiments, $R^1$ is $C_1$-$C_6$ alkyl (e.g., —$CH_3$, —$CH_2CH_3$, —$CH_2OCH_3$, or —$CF_3$). In some embodiments, $R^1$ is —$CH_3$, —$CF_3$, or —$CH_2CH_3$. In some embodiments, $R^1$ is —$CH_2OR^A$, wherein $R^A$ is $C_1$-$C_6$ alkyl (e.g., $C_1$-$C_3$ alkyl).

In some embodiments, $R^2$ is hydrogen or alkyl (e.g., $C_1$-$C_6$ alkyl).

In some embodiments, each of $R^2$ and $R^3$ is independently hydrogen or alkyl (e.g., $C_1$-$C_6$ alkyl). In some embodiments, each of $R^2$ and $R^3$ is independently hydrogen or $C_1$-$C_6$ haloalkyl (e.g., —$CF_3$). In some embodiments, each of $R^2$ and $R^3$ is independently hydrogen, —$CF_3$, or —$CH_3$.

In some embodiments, $R^4$ is —OH or halo (e.g., —F).

In some embodiments, $R^4$ and $R^5$, together with the carbon atom to which they are attached form an oxo group. In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, $R^2$ is aryl or heteroaryl and $R^3$ is hydrogen. In some embodiments, $R^2$ is carbocyclyl or heterocyclyl and $R^3$ is hydrogen. In some embodiments, $R^2$ and $R^3$ are hydrogen. In some embodiments, $R^2$ and $R^3$, together with the carbon atom to which they are attached form a 3-8 membered carbocyclic or heterocyclic ring.

In some embodiments, $R^6$ is hydrogen and ----- represents a single bond.

In some embodiments, $R^G$ is hydrogen or —$CH_3$.

In one aspect, provided herein are compounds according to Formula (I-63):

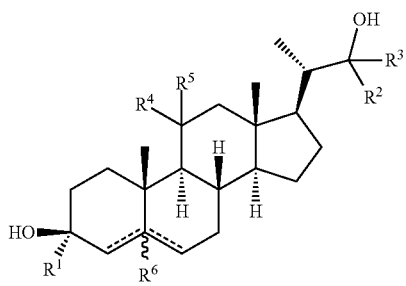

(I-63)

or a pharmaceutically acceptable salt thereof, wherein: $R^1$ is alkyl (e.g., $C_1$-$C_6$ alkyl); each of $R^2$ and $R^3$ is independently hydrogen, alkyl (e.g., $C_1$-$C_6$ alkyl), alkenyl, alkynyl, carbocyclyl, heterocyclyl, aryl, or heteroaryl, or $R^2$ and $R^3$, together with the carbon atom to which they are attached form a 3-8 membered ring; each of $R^4$ and $R^5$ is independently hydrogen, halo, or —$OR^C$, wherein $R^C$ is hydrogen or $C_1$-$C_6$ alkyl (e.g., $C_1$-$C_3$ alkyl), or $R^4$ and $R^5$, together with the carbon atom to which they are attached form an oxo group; $R^6$ is absent or hydrogen; and ===== represents a single or double bond, wherein when one of ===== is a double bond, the other ===== ===== is a single bond and $R^6$ is absent; and when both of ===== are single bonds, then $R^6$ is hydrogen.

In some embodiments, $R^1$ is alkyl (e.g., $C_1$-$C_6$ alkyl). In some embodiments, $R^1$ is $C_1$-$C_6$ alkyl (e.g., —$CH_3$, —$CH_2CH_3$, —$CH_2OCH_3$, or —$CF_3$). In some embodiments, $R^1$ is —$CH_3$, —$CF_3$, or —$CH_2CH_3$. In some embodiments, $R^1$ is —$CH_2OR^A$, wherein $R^A$ is $C_1$-$C_6$ alkyl (e.g., $C_1$-$C_3$ alkyl). In some embodiments, $R^1$ is unsubstituted alkyl. In some embodiments $R^1$ is —$CH_2OR^A$, wherein $R^A$ is $C_1$-$C_6$ alkyl (e.g., —$CH_3$).

In some embodiments, $R^2$ is alkyl (e.g., $C_1$-$C_6$ alkyl), carbocyclyl, heterocyclyl, aryl, or heteroaryl and $R^3$ is hydrogen, alkyl (e.g., $C_1$-$C_6$ alkyl), alkenyl, alkynyl, carbocyclyl, heterocyclyl, aryl, or heteroaryl or $R^2$ and $R^3$, together with the carbon atom to which they are attached form a 3-8 membered ring.

In some embodiments, $R^2$ is alkyl (e.g., $C_1$-$C_6$ alkyl), carbocyclyl, heterocyclyl, aryl, or heteroaryl and $R^3$ is hydrogen, alkyl (e.g., $C_1$-$C_6$ alkyl), carbocyclyl, heterocyclyl, aryl, or heteroaryl or $R^2$ and $R^3$, together with the carbon atom to which they are attached form a 3-8 membered ring.

In some embodiments, $R^2$ is hydrogen or alkyl (e.g., $C_1$-$C_6$ alkyl).

In some embodiments, each of $R^2$ and $R^3$ is independently hydrogen or alkyl (e.g., $C_1$-$C_6$ alkyl). In some embodiments, each of $R^2$ and $R^3$ is independently hydrogen or $C_1$-$C_6$ haloalkyl (e.g., —$CF_3$). In some embodiments, each of $R^2$ and $R^3$ is independently $C_5$ alkyl (e.g., substituted or unsubstituted isopentyl) or hydrogen. In some embodiments, each of $R^2$ and $R^3$ is independently isopentyl (e.g., substituted or unsubstituted isopentyl) or hydrogen. In some embodiments, each of $R^2$ and $R^3$ is independently hydrogen, —$CF_3$, or —$CH_3$.

In some embodiments, $R^4$ is —OH or halo (e.g., —F).

In some embodiments, $R^4$ and $R^5$, together with the carbon atom to which they are attached form an oxo group. In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, $R^2$ is aryl or heteroaryl and $R^3$ is hydrogen. In some embodiments, $R^2$ is carbocyclyl or heterocyclyl and $R^3$ is hydrogen. In some embodiments, $R^2$ and $R^3$ are hydrogen. In some embodiments, $R^2$ is isopentyl (e.g., substituted or unsubstituted isopentyl) and $R^3$ is hydrogen. In some embodiments, $R^2$ is —$CF_3$ or —$CH_3$ and $R^3$ is hydrogen or —$CH_3$. In some embodiments, $R^2$ and $R^3$, together with the carbon atom to which they are attached form a 3-8 membered carbocyclic or heterocyclic ring.

In some embodiments, $R^1$ is —$CH_3$ or —$CH_2CH_3$, $R^2$ is isopentyl (e.g., substituted or unsubstituted isopentyl), and $R^3$ is hydrogen. In some embodiments, $R^1$ is —$CH_3$ or —$CH_2CH_3$, $R^2$ is unsubstituted isopentyl, and $R^3$ is hydrogen.

In some embodiments, $R^2$ is unsubstituted $C_1$-$C_6$ alkyl or $C_1$-$C_6$ haloalkyl. In some embodiments, $R^2$ is unsubstituted $C_1$-$C_6$ alkyl. In some embodiments, $R^2$ is pyridyl. In some embodiments, each of $R^2$ is isopentyl and $R^3$ is hydrogen. In some embodiments, $R^2$ is —$CF_3$ and $R^3$ is hydrogen. In some embodiments, $R^2$ is unsubstituted alkyl (e.g., unsubstituted $C_1$-$C_6$ alkyl). In some embodiments, $R^2$ is carbocyclylalkyl. In some embodiments, $R^2$ is carbocyclylalkyl and $R^3$ is hydrogen. In some embodiments, $R^2$ is aralkyl (e.g., benzyl). In some embodiments, $R^2$ is heterocyclylalkyl. In some embodiments, wherein $R^2$ is unsubstituted $C_1$-$C_6$ alkyl, $C_1$-$C_6$ haloalkyl, carbocyclyl, carbocyclylalkyl, aralkyl, or heterocyclylalkyl.

In some embodiments, the compound of Formula (I-63) is selected from a compound of Formula (I-A63), (I-B63), or (I-C63):

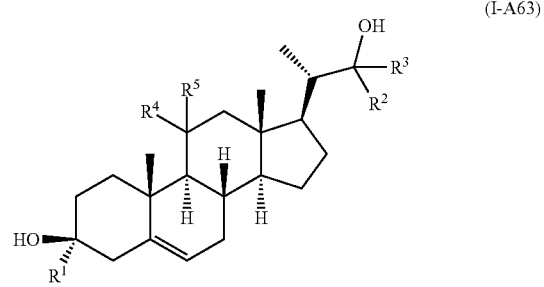

(I-A63)

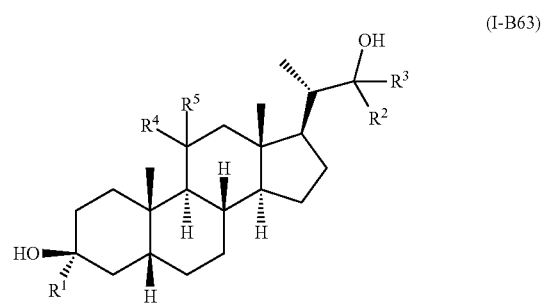

(I-B63)

-continued

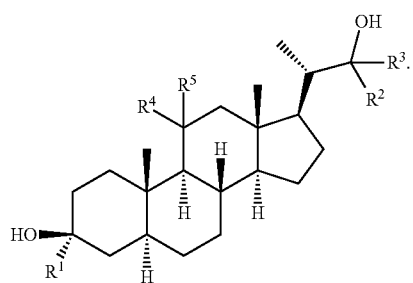
(I-C63)

In some embodiments, the compound of Formula (I-63) is selected from a compound of Formula (I-A63):

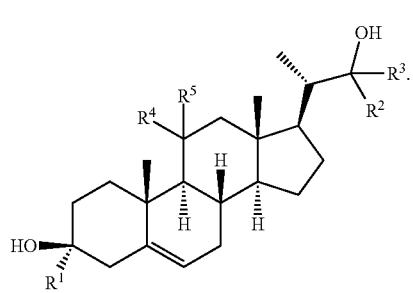
(I-A63)

In some embodiments, the compound of Formula (I-63) is selected from a compound of Formula (I-C63)

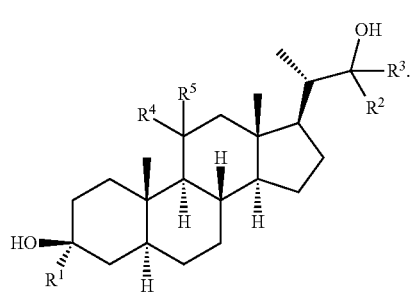
(I-C63)

In some embodiments, the compound of Formula (I-63) is selected from a compound of Formula (I-B63):

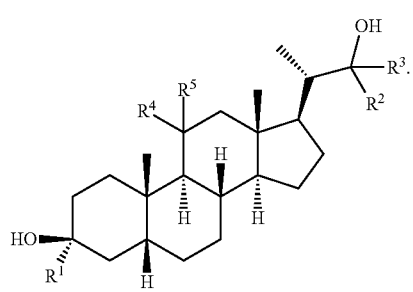
(I-B63)

In some embodiments, the compound of Formula (I63) is selected from a compound of Formula (I-D63)

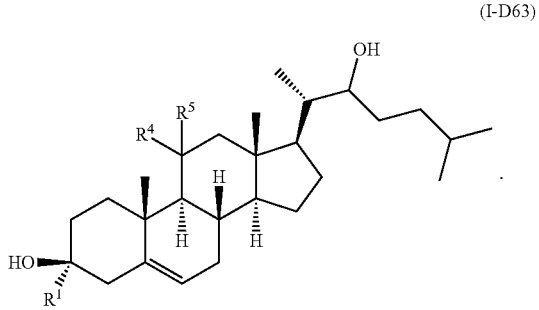
(I-D63)

In some embodiments, the compound of Formula (I-63) is selected from a compound of Formula (I-E63):

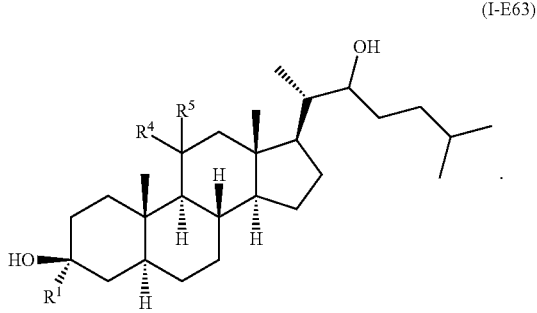
(I-E63)

In some embodiments, the compound of Formula (I-63) is selected from a compound of Formula (I-D-i63) or (I-D-ii63):

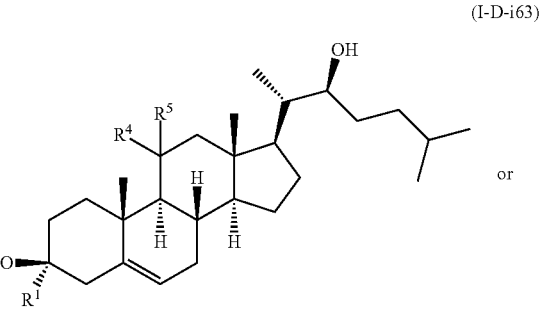
(I-D-i63)

or

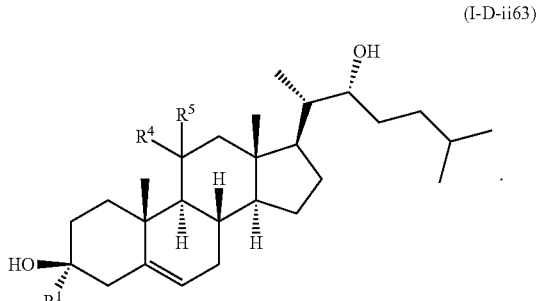
(I-D-ii63)

In some embodiments, the compound of Formula (I-63) is selected from a compound of Formula (I-E-i63) or (I-E-ii63):

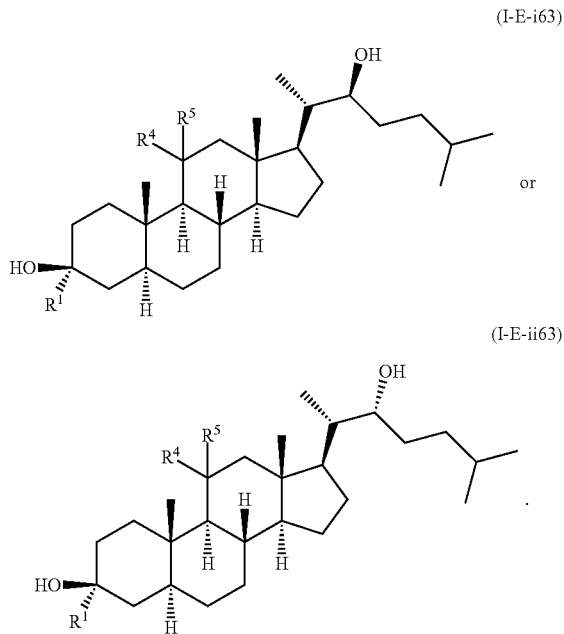

In
In one aspect, provided herein are compounds according to Formula (I-67):

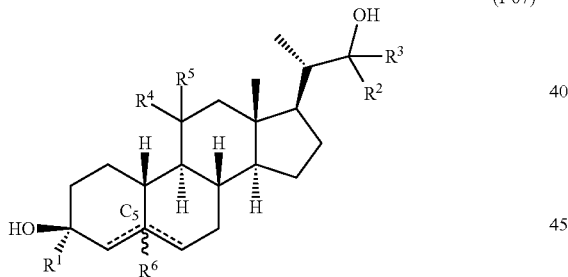

or a pharmaceutically acceptable salt thereof, wherein: $R^1$ is hydrogen or alkyl (e.g., $C_1$-$C_6$ alkyl); each of $R^2$ and $R^3$ is independently hydrogen, alkyl (e.g., $C_1$-$C_6$ alkyl), carbocyclyl, heterocyclyl, aryl, or heteroaryl, or $R^2$ and $R^3$, together with the carbon atom to which they are attached form a 3-8 membered ring; each of $R^4$ and $R^5$ is independently hydrogen, halo, or —$OR^C$, wherein $R^C$ is hydrogen or $C_1$-$C_6$ alkyl (e.g., $C_1$-$C_3$ alkyl), or $R^4$ and $R^5$, together with the carbon atom to which they are attached form an oxo group; $R^6$ is absent or hydrogen; and ═══ represents a single or double bond, wherein when one of ═══ is a double bond, the other ═══ is a single bond and $R^6$ is absent; and when both of ═══ are single bonds, then $R^6$ is hydrogen.

In some embodiments, $R^1$ is alkyl. In some embodiments, $R^1$ is unsubstituted alkyl. In some embodiments, $R^1$ is $C_1$-$C_6$ alkyl. In some embodiments, $R^1$ is —$CH_3$, —$CF_3$, or —$CH_2CH_3$. In some embodiments, R is —$CH_2OR^A$, wherein $R^A$ is $C_1$-$C_6$ alkyl (e.g., —$CH_3$).

In some embodiments, $R^2$ is alkyl (e.g., $C_1$-$C_6$ alkyl), carbocyclyl, heterocyclyl, aryl, or heteroaryl and $R^3$ is hydrogen, alkyl (e.g., $C_1$-$C_6$ alkyl), carbocyclyl, heterocyclyl, aryl, or heteroaryl or $R^2$ and $R^3$, together with the carbon atom to which they are attached form a 3-8 membered ring.

In some embodiments, $R^2$ is hydrogen or alkyl. In some embodiments, each of $R^2$ and $R^3$ is independently hydrogen or alkyl. In some embodiments, each of $R^2$ and $R^3$ is independently hydrogen or $C_1$-$C_6$ haloalkyl. In some embodiments, each of $R^2$ and $R^3$ is independently hydrogen, —$CF_3$, or —$CH_3$. In some embodiments, $R^4$ is —OH or halo. In some embodiments, $R^4$ and $R^5$, together with the carbon atom to which they are attached form an oxo group. In some embodiments, $R^4$ is hydrogen and $R^5$ is halo. In some embodiments, $R^4$ and $R^5$ are halo. In some embodiments, $R^4$ and $R^5$ are hydrogen. In some embodiments, $R^2$ is aryl or heteroaryl and $R^3$ is hydrogen. In some embodiments, $R^2$ is carbocyclyl or heterocyclyl and $R^3$ is hydrogen. In some embodiments, $R^2$ and $R^3$ are hydrogen. In some embodiments, $R^2$ and $R^3$, together with the carbon atom to which they are attached form a 3-8 membered carbocyclic or heterocyclic ring.

In some embodiments, the compound of Formula (I-67) is selected from a compound of Formula (I-A67), (I-B67), or (I-C67):

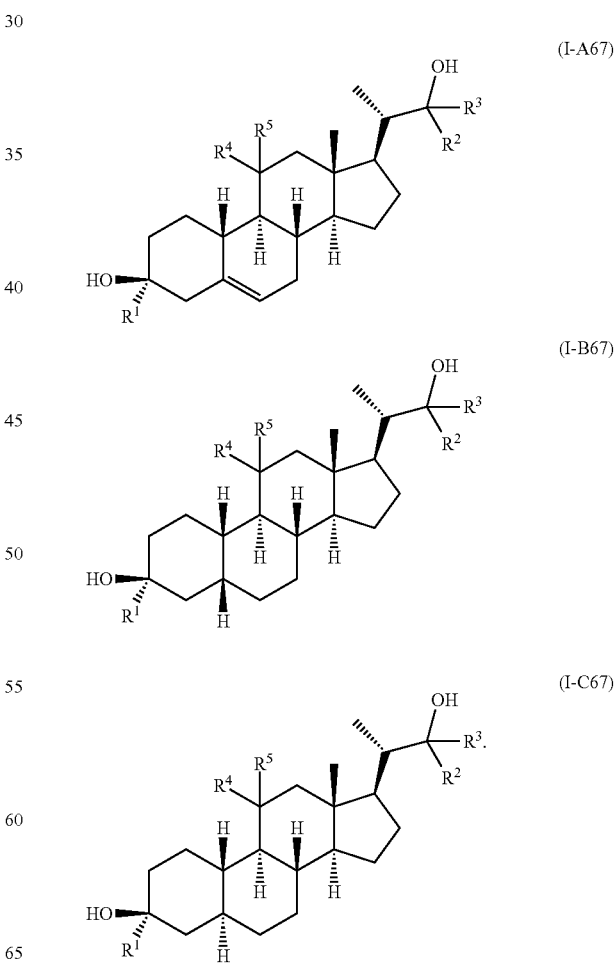

In some embodiments, the compound of Formula (I-67) is selected from a compound of Formula (I-A67):
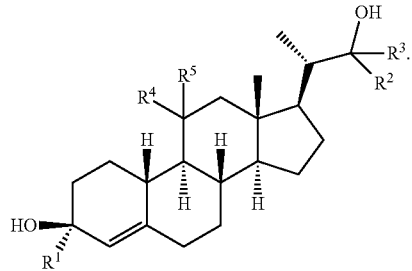
(I-A67)
In some embodiments, the compound of Formula (I-67) is selected from a compound of Formula (I-C67):
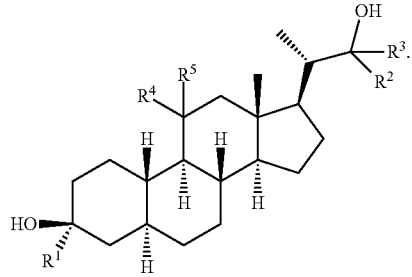
(I-C67)
In an aspect, provided herein are compounds of selected from the group consisting of:
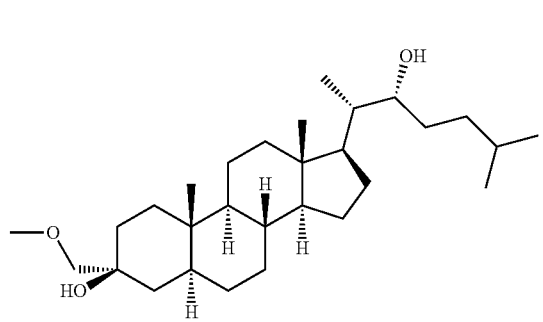
1
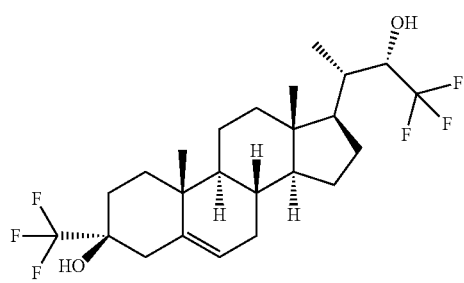
2
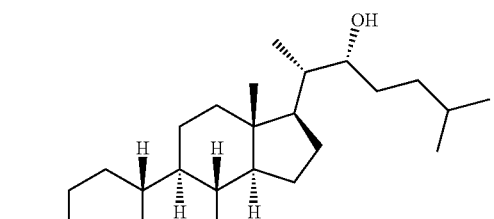
3
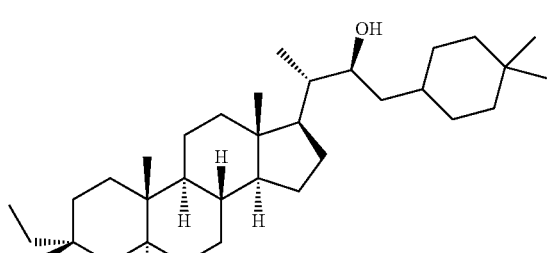
4
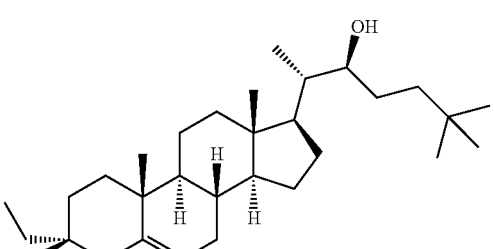
5
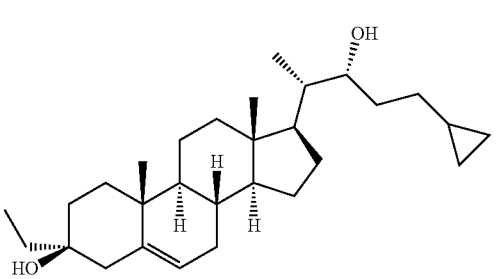
6
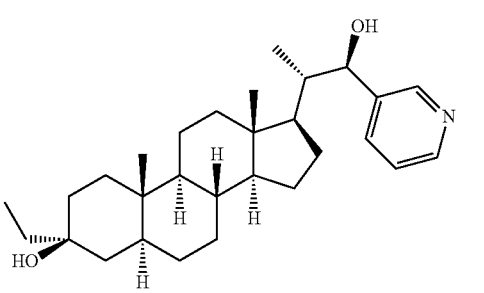
7

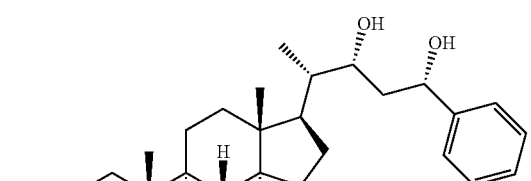
8
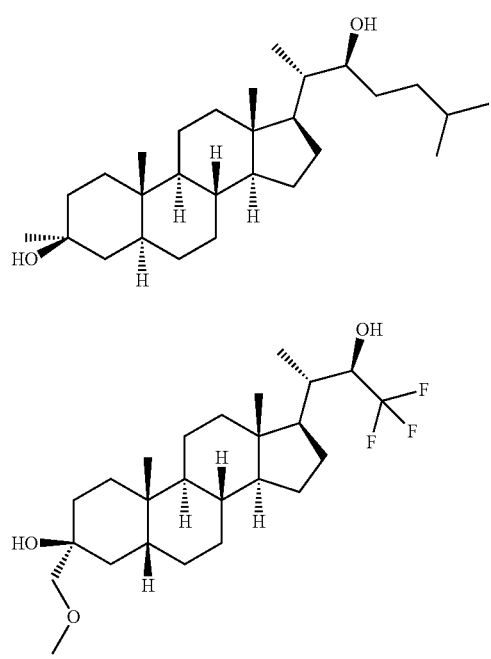
9
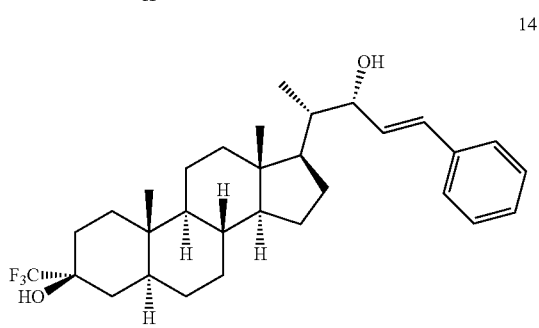
13
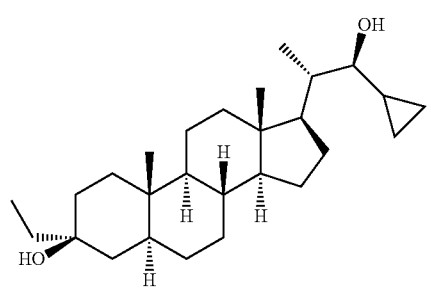
10
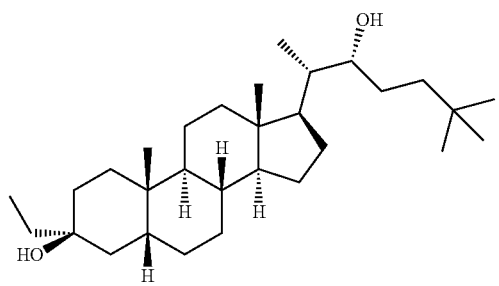
14
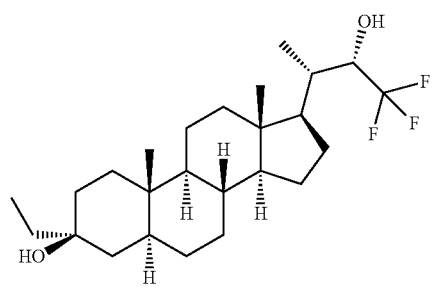
11
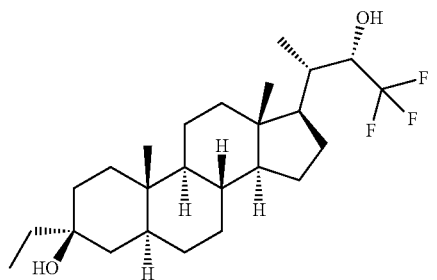
15
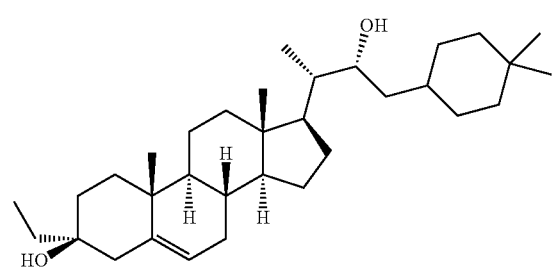
12
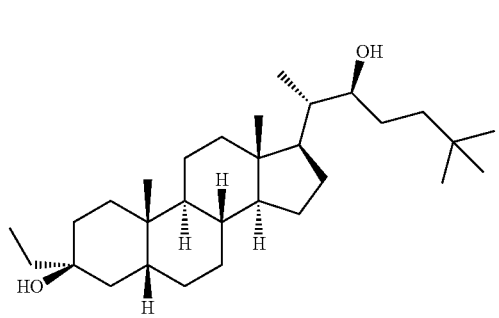
16
17

-continued
18
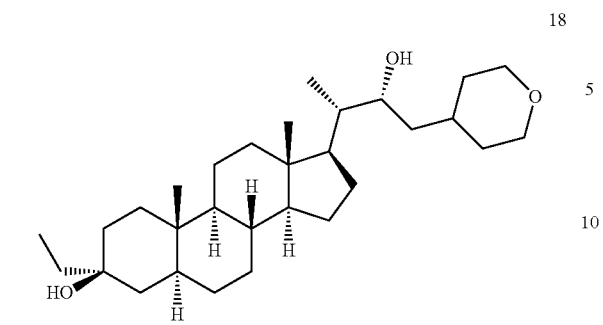
19
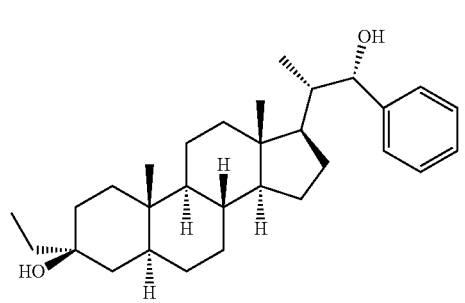
20
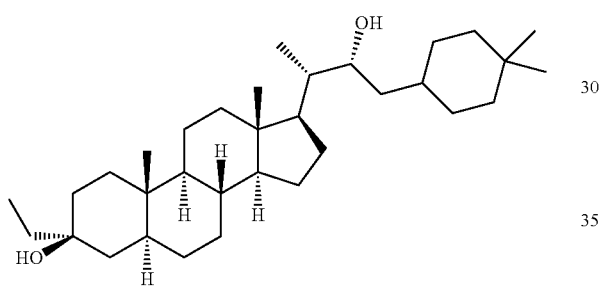
21
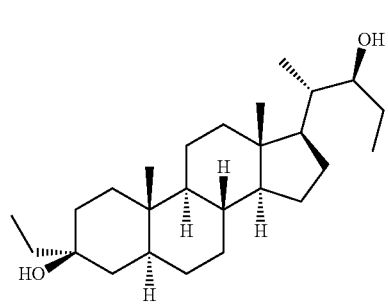
22
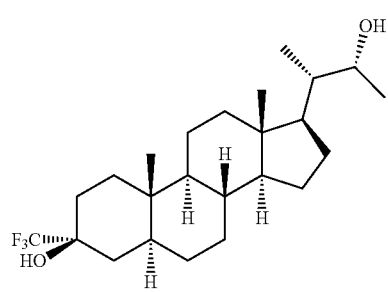
-continued
23
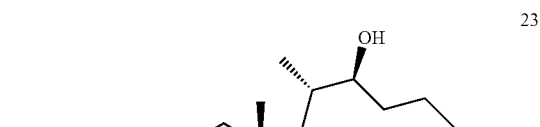
24
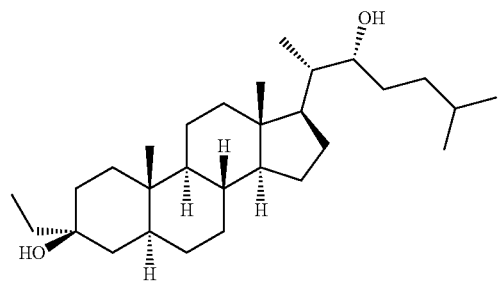
25
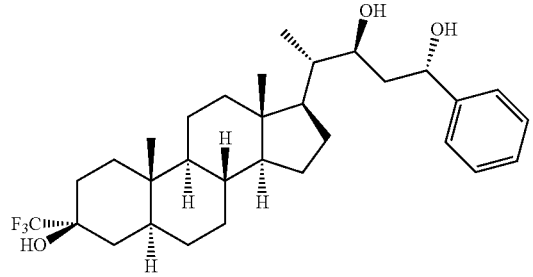
26
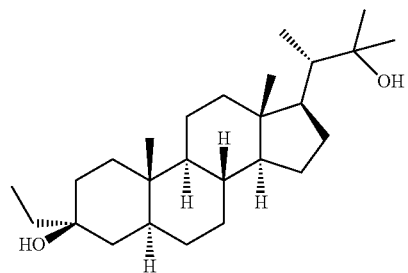
27
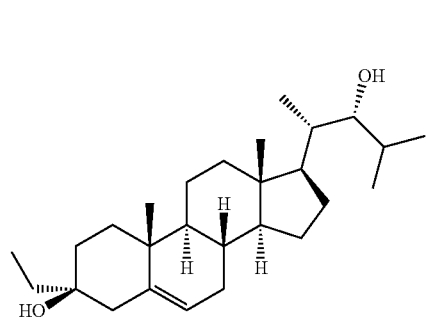

-continued
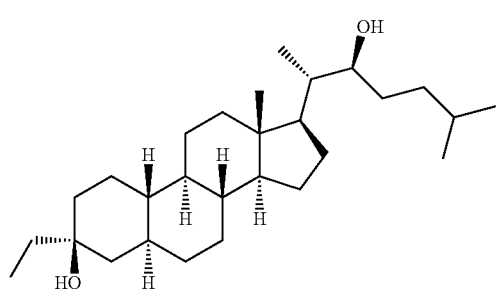
28
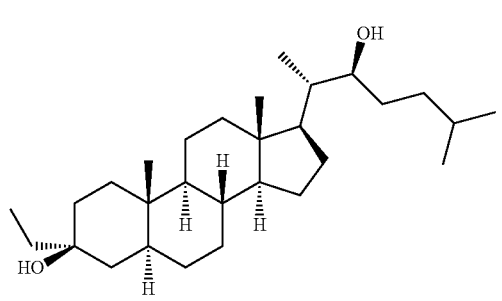
29
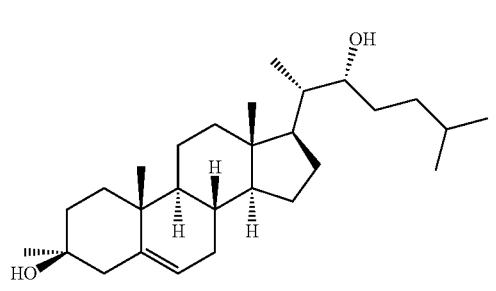
30
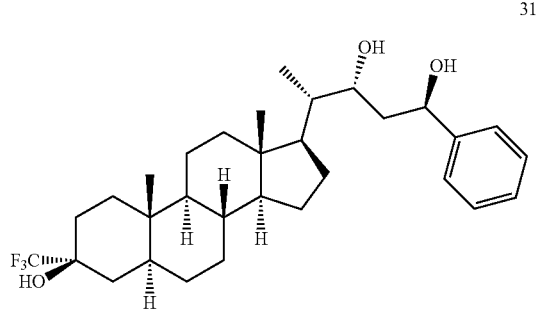
31
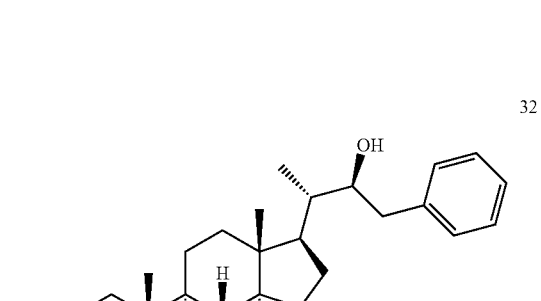
32
-continued
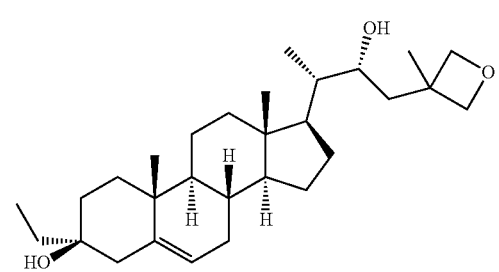
33
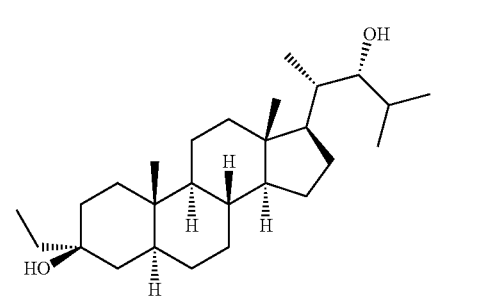
34
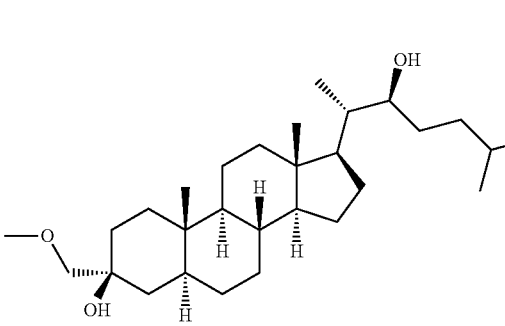
35
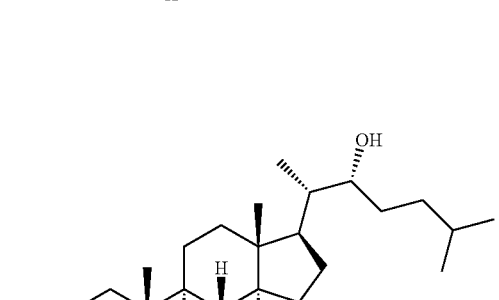
36
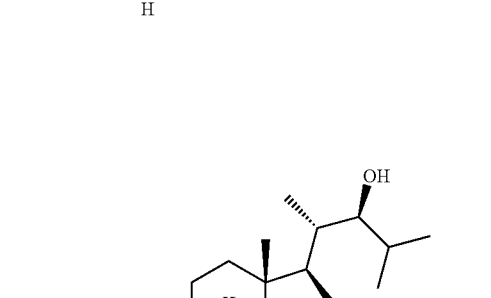
37

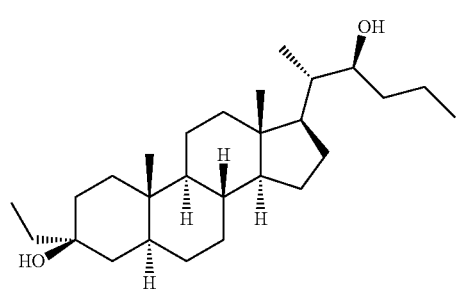
38
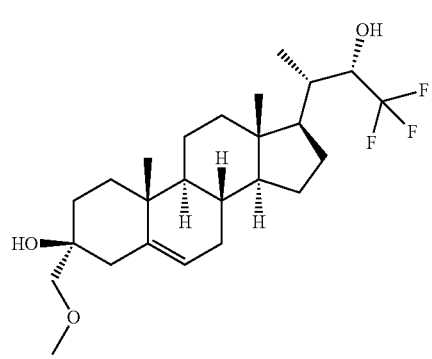
39
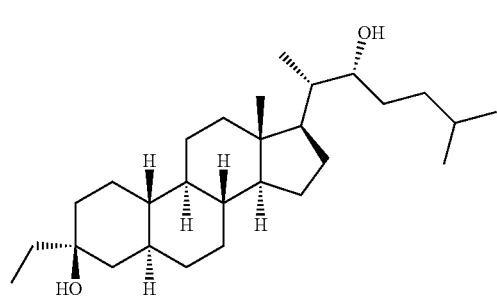
40
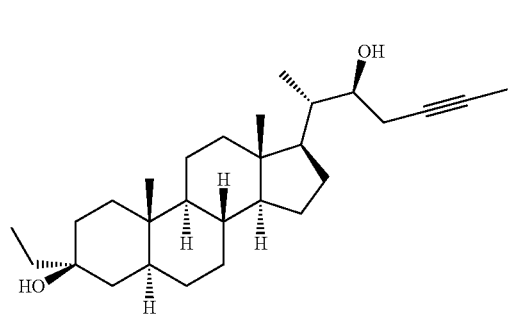
41
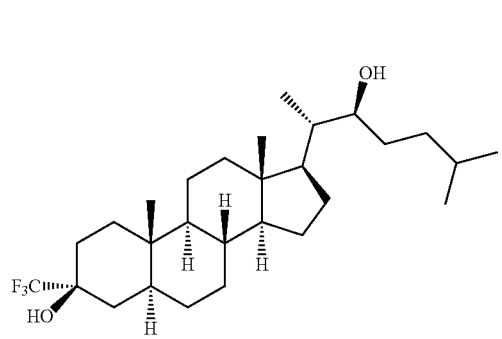
42
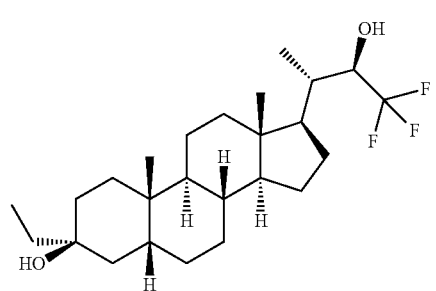
43
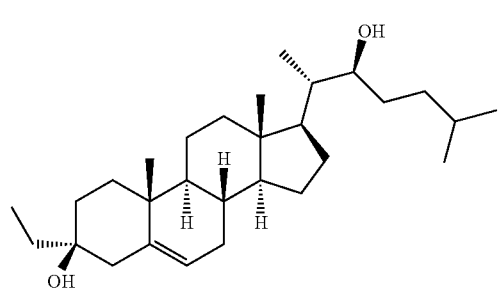
44
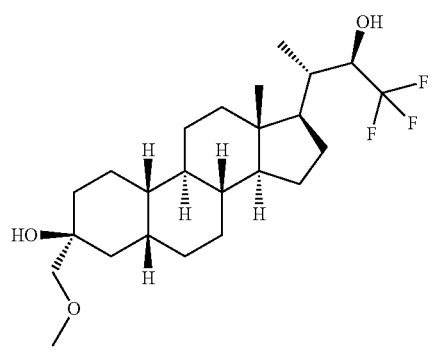
45
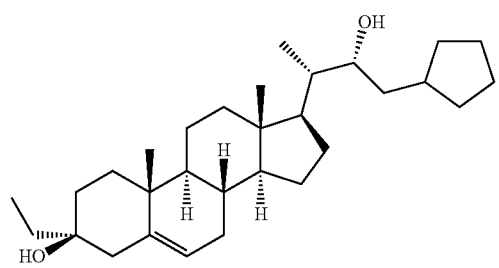
46
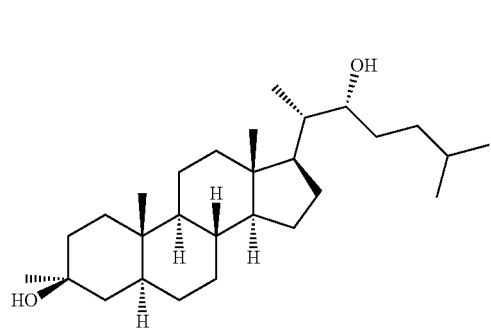
47

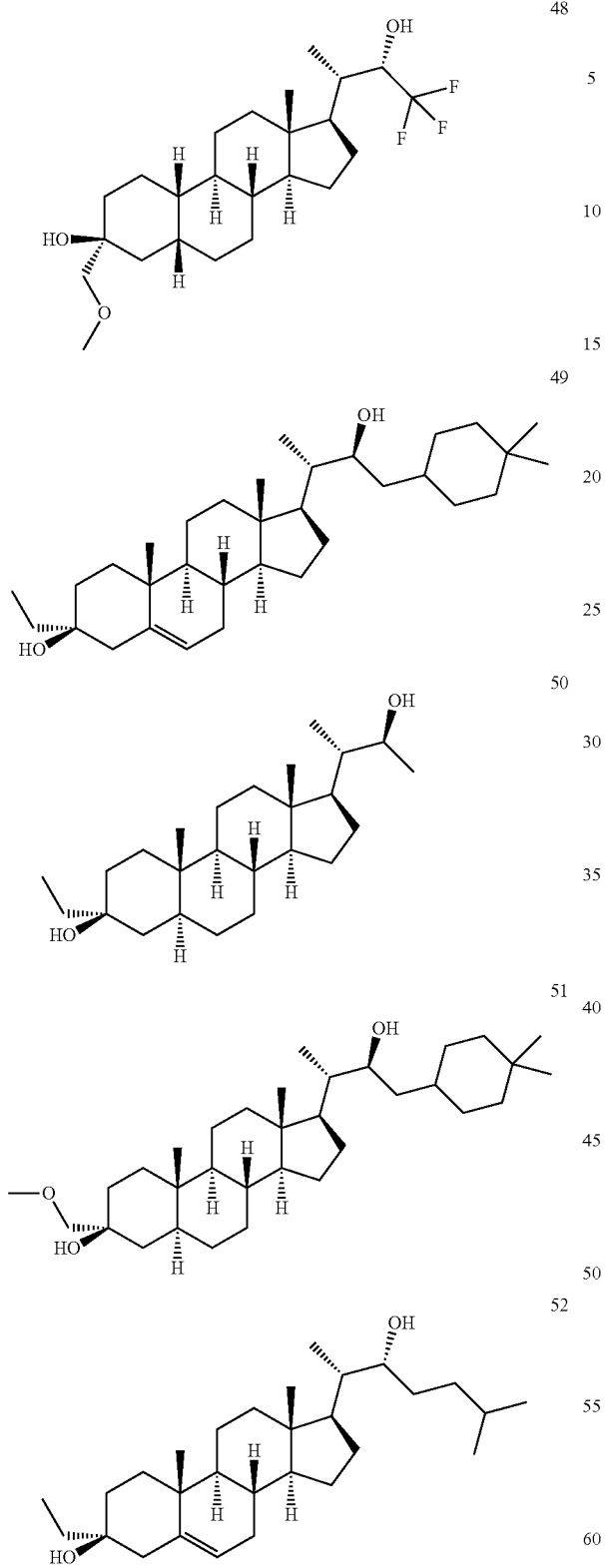
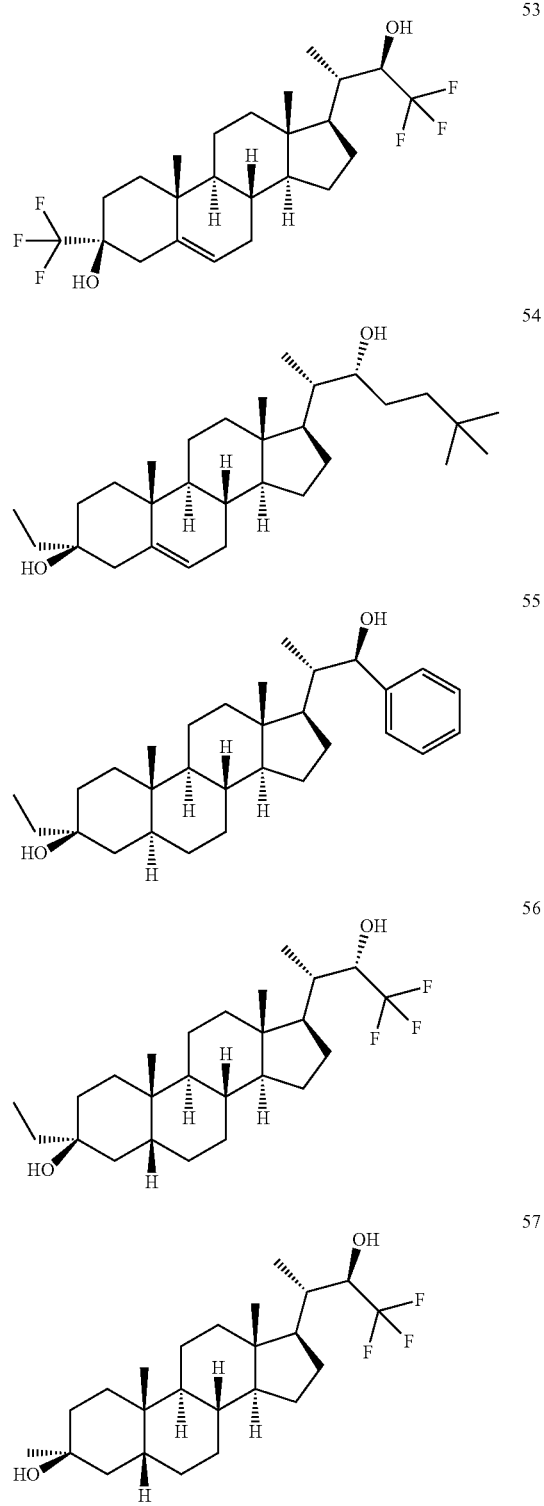

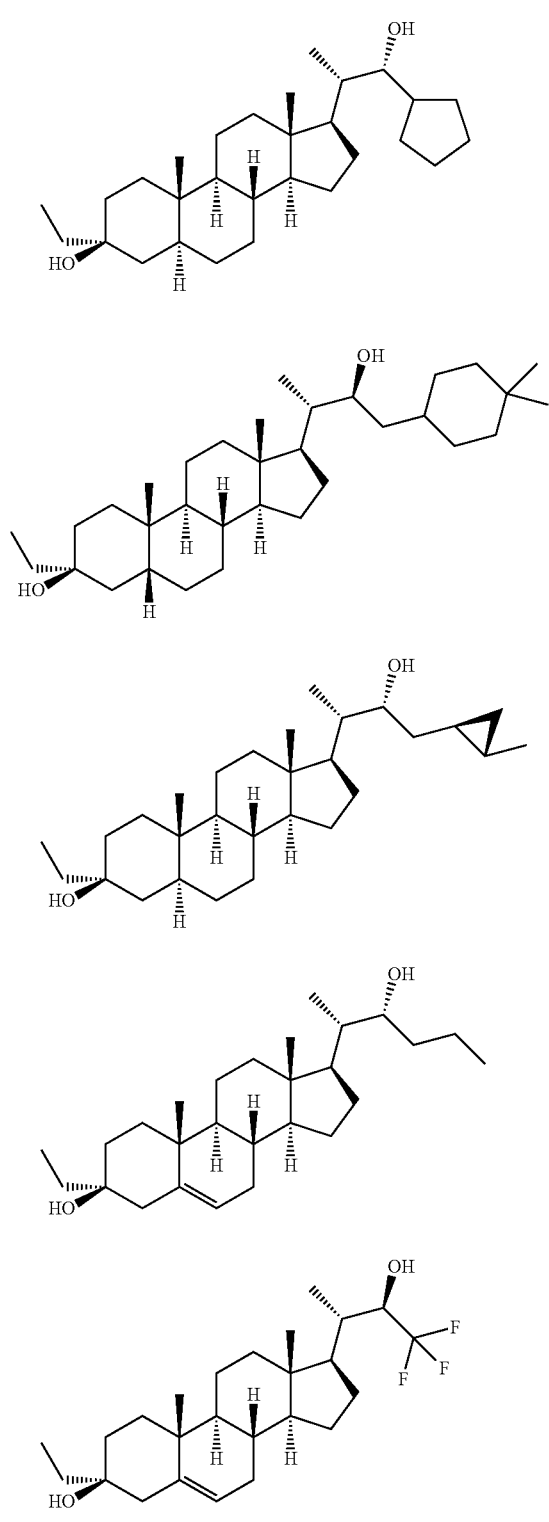
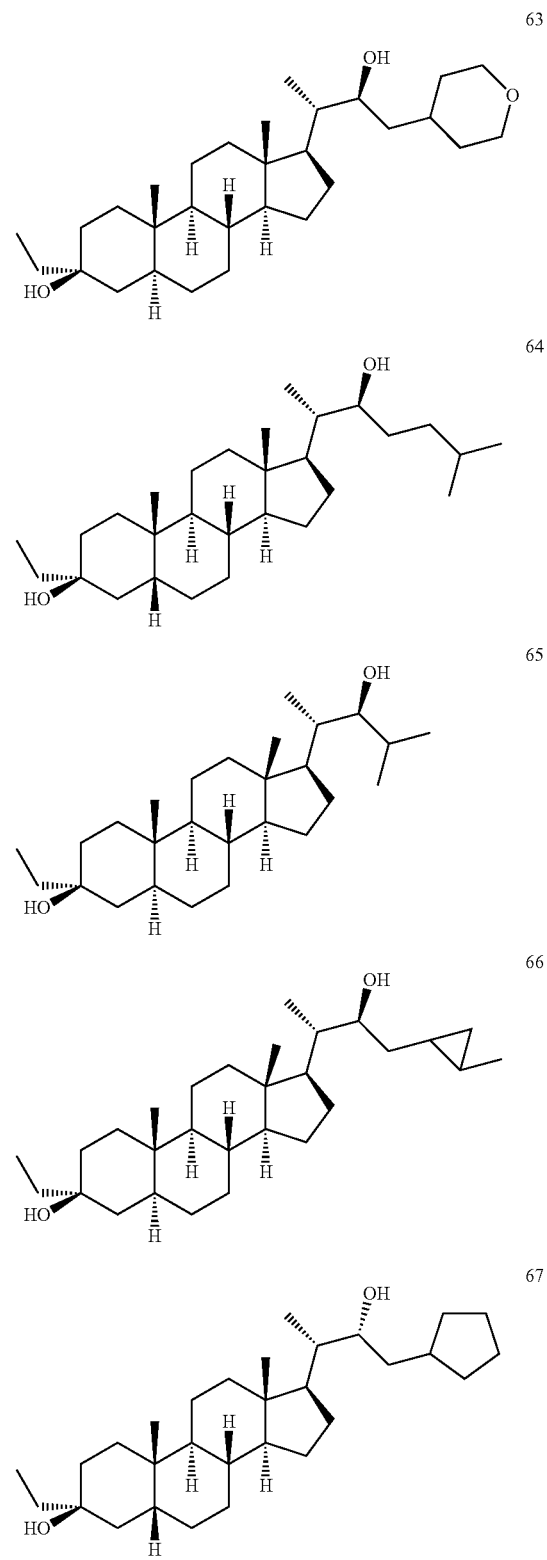

23
-continued
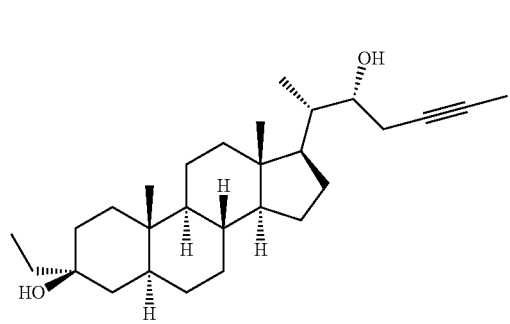
68
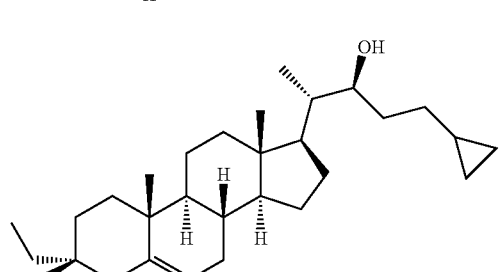
69
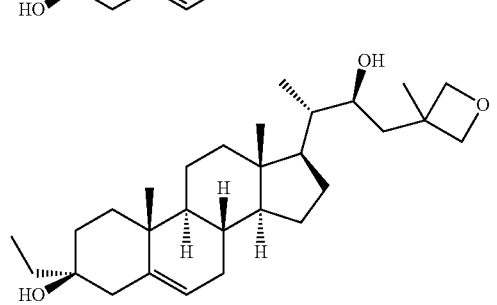
70
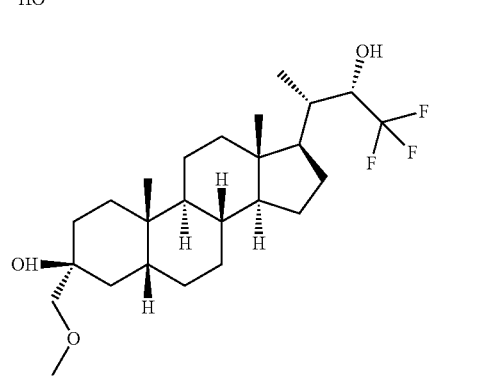
71
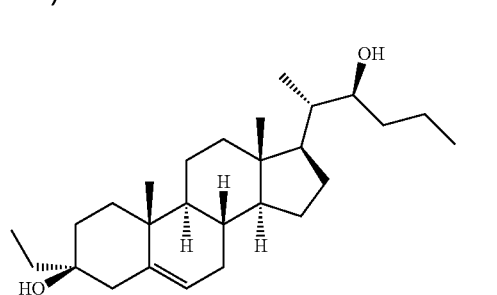
72
24
-continued
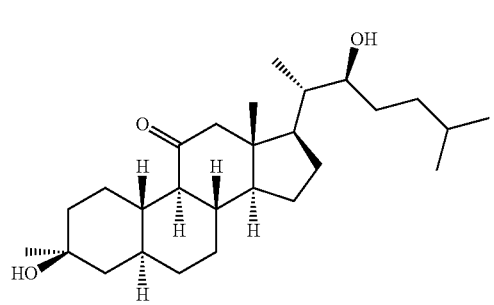
73
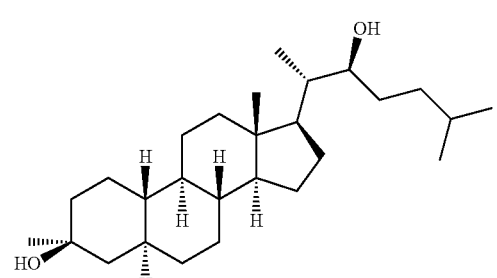
74
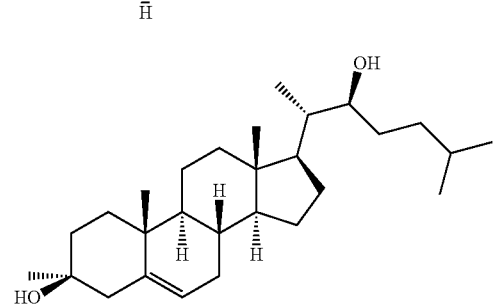
75
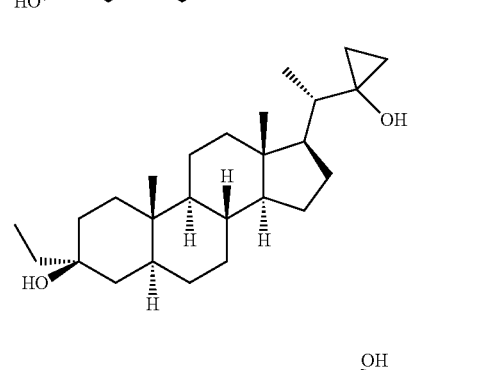
76
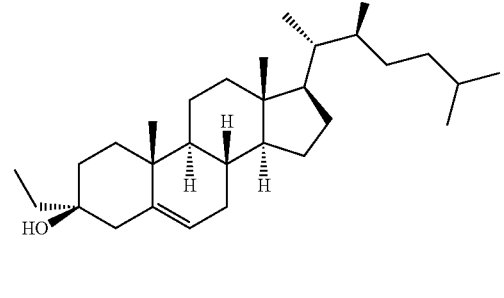
77

-continued
78
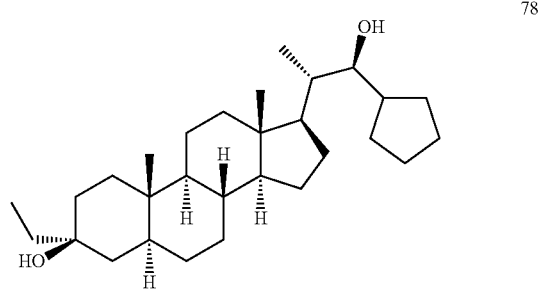
79
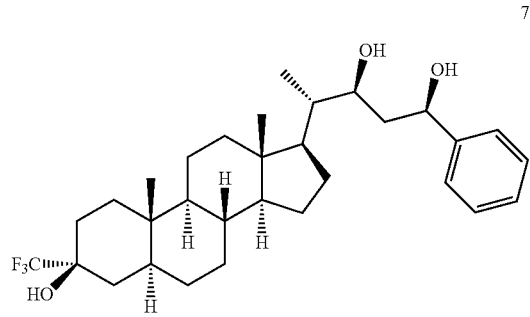
81
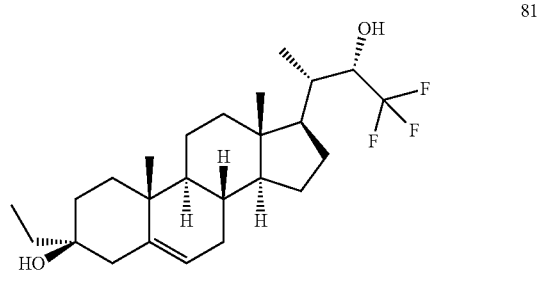
82
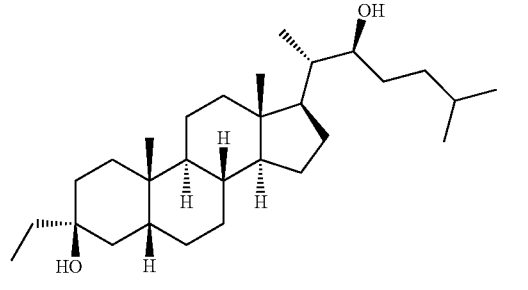
83
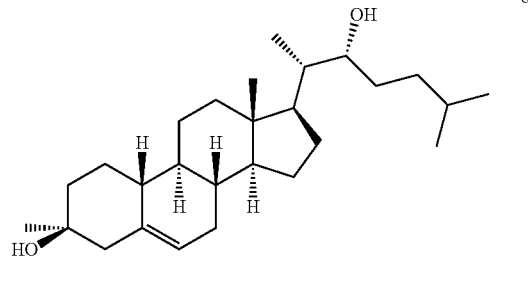
-continued
84
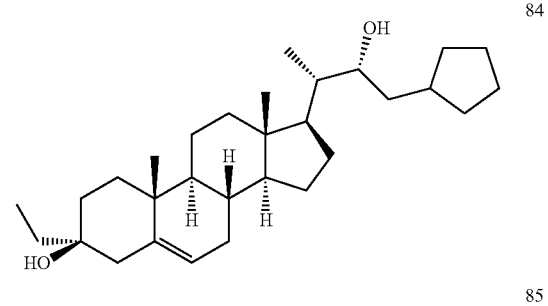
85
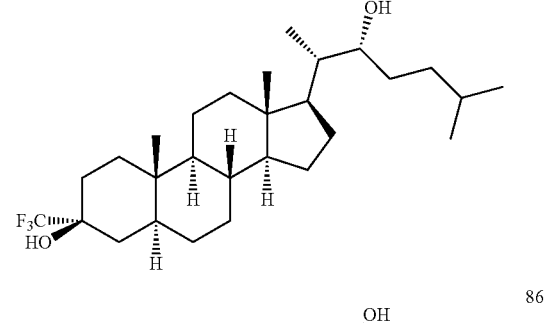
86
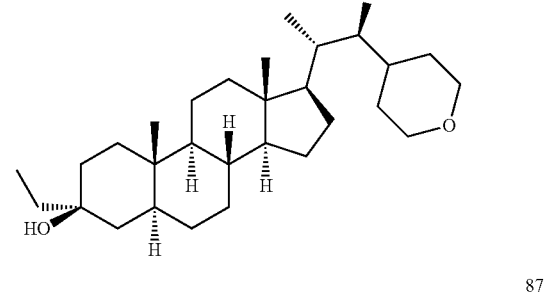
87
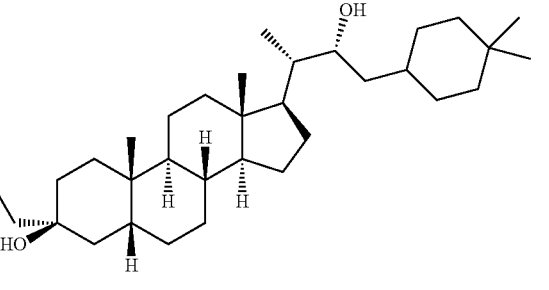
88
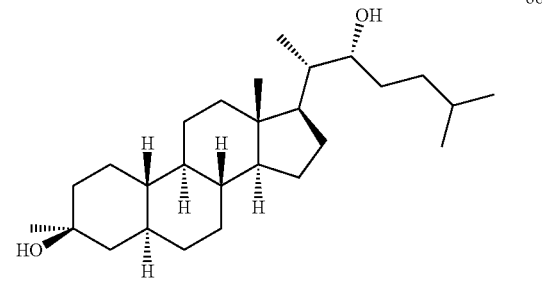

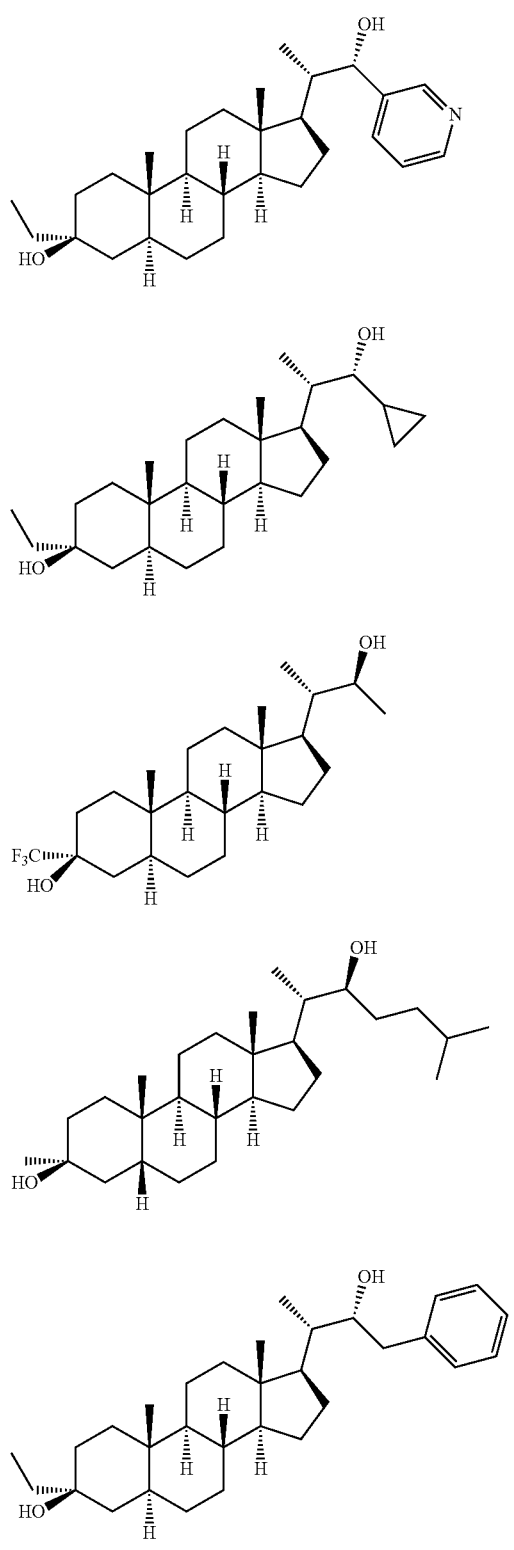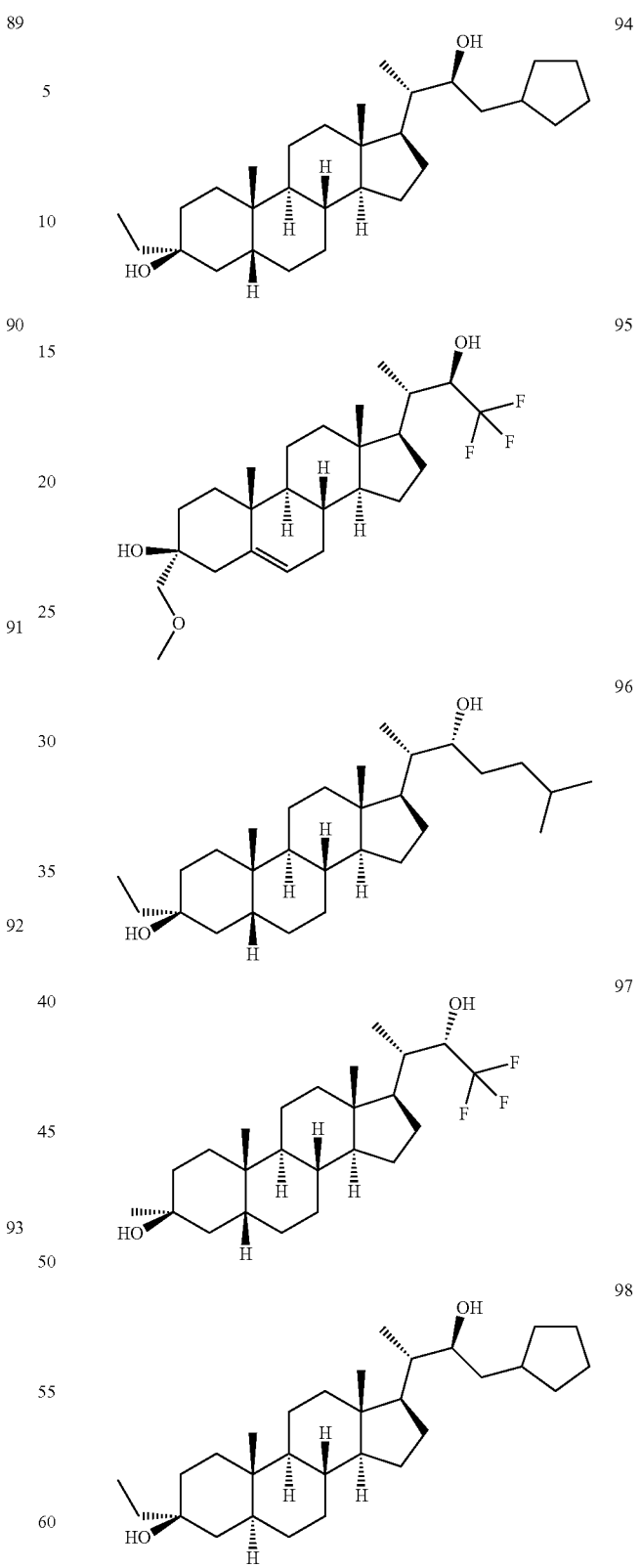

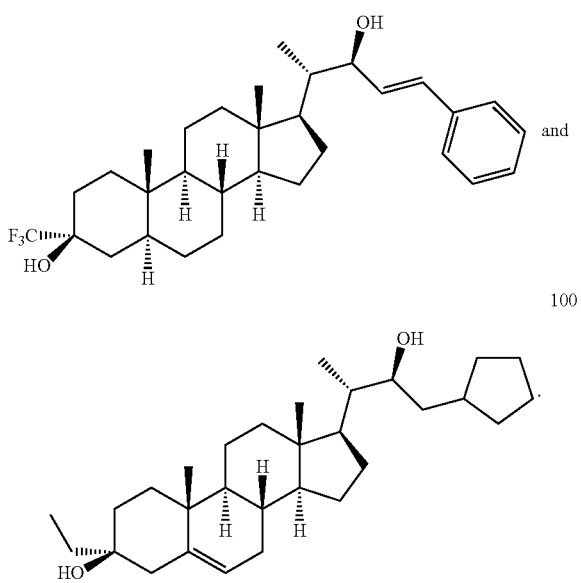

In an aspect, provided herein is a pharmaceutical composition comprising a compound described herein, or pharmaceutically acceptable salt thereof, and a pharmaceutically acceptable carrier.

In an aspect, provided herein is a method of inducing sedation or anesthesia comprising administering to a subject an effective amount of a compound described herein, or pharmaceutically acceptable salt thereof, or pharmaceutical composition thereof.

In an aspect, provided herein is a method for treating or preventing a disorder described herein, comprising administering to a subject in need thereof an effective amount of a compound described herein, or pharmaceutically acceptable salt thereof, or pharmaceutical composition thereof.

In some embodiments, the disorder is a metabolic disorder.

In some embodiments, the disorder is an autoimmune disorder.

In some embodiments, the disorder is rheumatoid arthritis, juvenile idiopathic arthritis, ankylosing spondylitis, psoriatic arthritis, Crohn's disease, ulcerative colitis, and plaque psoriasis.

In some embodiments, the disorder is a gastrointestinal (GI) disorder e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, or colitis.

In some embodiments, the disorder is inflammatory bowel disease.

In some embodiments, the disorder is cancer, diabetes, or a sterol synthesis disorder.

In an aspect, provided herein is a method for treating or preventing a CNS-related condition comprising administering to a subject in need thereof an effective amount of a compound described herein, or pharmaceutically acceptable salt thereof, or pharmaceutical composition thereof. In some embodiments, the CNS-related condition is an adjustment disorder, anxiety disorder (including obsessive-compulsive disorder, posttraumatic stress disorder, and social phobia), cognitive disorder (including Alzheimer's disease and other forms of dementia (e.g., frontotemporal dementia), dissociative disorder, eating disorder, mood disorder (including depression (e.g., postpartum depression), bipolar disorder, dysthymic disorder, suicidality), schizophrenia or other psychotic disorder (including schizoaffective disorder), sleep disorder (including insomnia), substance-related disorder, personality disorder (including obsessive-compulsive personality disorder), autism spectrum disorders (including those involving mutations to the Shank group of proteins (e.g., Shank3)), neurodevelopmental disorder (including Rett syndrome, Tuberous Sclerosis complex), multiple sclerosis, sterol synthesis disorders, pain (including acute and chronic pain; headaches, e.g., migraine headaches), encephalopathy secondary to a medical condition (including hepatic encephalopathy and anti-NMDA receptor encephalitis), acute liver failure, glycine encephalopathy, seizure disorder (including status epilepticus and monogenic forms of epilepsy such as Dravet's disease), stroke, traumatic brain injury, movement disorder (including Huntington's disease and Parkinson's disease), vision impairment, hearing loss, or tinnitus.

In some embodiments, the disorder is Huntington's disease. In some embodiments, the disorder is Parkinson's disease. In some embodiments, the disorder is an inflammatory disease (e.g., lupus).

In some embodiments, the disorder is a sterol synthesis disorder.

In some embodiments, the disorder is Smith-Lemli-Opitz Syndrome (SLOS). In some embodiments, the disorder is desmosterolosis. In some embodiments, the disorder is sitosterolemia. In some embodiments, the disorder is cerebrotendinous xanthomatosis (CTX). In some embodiments, the disorder is Mevalonate Kinase Deficiency (MKD). In some embodiments, the disorder is SC4MOL gene mutation (SMO Deficiency). In some embodiments, the disorder is Niemann-Pick disease. In some embodiments, the disorder is autism spectrum disorder (ASD). In some embodiments, the disorder is associated with phenylketonuria.

In an aspect, provided herein is a method of effecting negative allosteric modulation of an NMDA receptor in a subject, comprising administering to the subject a compound described herein, e.g., a compound of Formula (A), a compound of Formula (I-63), or a compound of Formula (I-67).

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

The "enantiomeric excess" ("e.e.") or "% enantiomeric excess" ("% e.e.") of a composition as used herein refers to an excess of one enantiomer relative to the other enantiomer present in the composition. For example, a composition can contain 90% of one enantiomer, e.g., the S enantiomer, and 10% of the other enantiomer, i.e., the R enantiomer.

$$e.e.=(90-10)/100=80\%.$$

Thus, a composition containing 90% of one enantiomer and 10% of the other enantiomer is said to have an enantiomeric excess of 80%.

The "diastereomeric excess" ("d.e.") or "% diastereomeric excess" ("% d.e.") of a composition as used herein refers to an excess of one diastereomer relative to one or more different diastereomers present in the composition. For example, a composition can contain 90% of one diastereomer, and 10% of one or more different diastereomers.

$$d.e.=(90-10)/100=80\%.$$

Thus, a composition containing 90% of one diastereomers and 10% of one or more different diastereomers is said to have a diastereomeric excess of 80%.

The absolute configuration of an asymmetric center can be determined using methods known to one skilled in the art. In some embodiments, the absolute configuration of an asymmetric center in a compound can be elucidated from the X-ray single-crystal structure of the compound. In some embodiments, the absolute configuration of an asymmetric center elucidated by the X-ray crystal structure of a compound can be used to infer the absolute configuration of a corresponding asymmetric center in another compound obtained from the same or similar synthetic methodologies. In some embodiments, the absolute configuration of an asymmetric center elucidated by the X-ray crystal structure of a compound can be used to infer the absolute configuration of a corresponding asymmetric center in another compound coupled with a spectroscopic technique, e.g., NMR spectroscopy, e.g., $^1$H NMR spectroscopy or $^{19}$F NMR spectroscopy.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Aliphatic" refers to an alkyl, alkenyl, alkynyl, or carbocyclyl group, as defined herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$) n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), isopentyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —CH$_3$). In certain embodiments, the alkyl group is substituted $C_{1-10}$ alkyl. Common alkyl abbreviations include Me (—CH$_3$), Et (—CH$_2$CH$_3$), iPr (—CH(CH$_3$)$_2$), nPr (—CH$_2$CH$_2$CH$_3$), n-Bu (—CH$_2$CH$_2$CH$_2$CH$_3$), or i-Bu (—CH$_2$CH(CH$_3$)$_2$).

"Alkylene" refers to an alkyl group wherein two hydrogens are removed to provide a divalent radical, and which may be substituted or unsubstituted. Unsubstituted alkylene groups include, but are not limited to, methylene (—CH$_2$—), ethylene (—CH$_2$CH$_2$—), propylene (—CH$_2$CH$_2$CH$_2$—), butylene (—CH$_2$CH$_2$CH$_2$CH$_2$—), pentylene (—CH$_2$CH$_2$CH$_2$CH$_2$CH$_2$—), hexylene (—CH$_2$CH$_2$CH$_2$CH$_2$CH$_2$CH$_2$—), and the like. Exemplary substituted alkylene groups, e.g., substituted with one or more alkyl (methyl) groups, include but are not limited to, substituted methylene (—CH(CH$_3$)—, —(C(CH$_3$)$_2$—), substituted ethylene (—CH(CH$_3$)CH$_2$—, —CH$_2$CH(CH$_3$)—, —C(CH$_3$)$_2$CH$_2$—, —CH$_2$C(CH$_3$)$_2$—), substituted propylene (—CH(CH$_3$)CH$_2$CH$_2$—, —CH$_2$CH(CH$_3$)CH$_2$—, —CH$_2$CH$_2$CH(CH$_3$)—, —C(CH$_3$)$_2$CH$_2$CH$_2$—, —CH$_2$C(CH$_3$)$_2$CH$_2$—, —CH$_2$CH$_2$C(CH$_3$)$_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and 1 or 2 heteroatoms ("hetero$C_{1-4}$ alkyl"). In some embodiments, a heteroalkyl group is a saturated group having 1 to 3 carbon atoms and 1 heteroatom ("hetero$C_{1-3}$ alkyl"). In some embodiments, a heteroalkyl group is a saturated group having 1 to 2 carbon atoms and 1 heteroatom ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

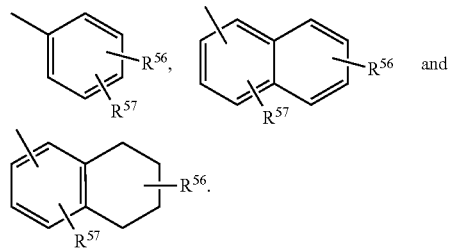

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^6$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$haloalkyl, $C_3$-$C_{10}$ cycloalkyl, 4-10 membered heterocyclyl, $C_6$-$C_{10}$ aryl, substituted $C_6$-$C_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system.

"Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cimmolinyl, quinoxalinyl, phthalazinyl, and quinazolinyl.

Examples of representative heteroaryls include the following:

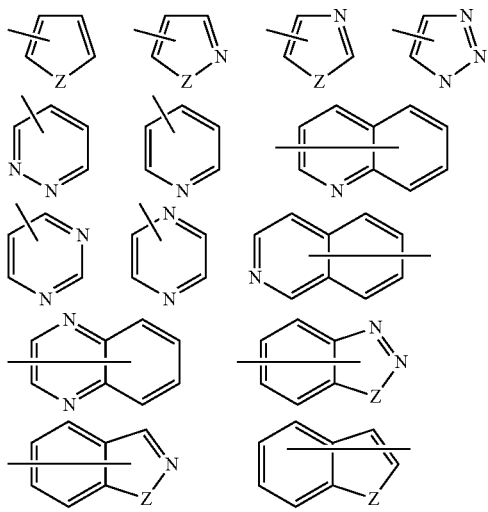

wherein each Z is selected from carbonyl, N, NR$^{65}$, O, and S; and R$^{65}$ is independently hydrogen, $C_1$-$C_8$ alkyl, $C_3$-$C_{10}$ cycloalkyl, 4-10 membered heterocyclyl, $C_6$-$C_{10}$ aryl, and 5-10 membered heteroaryl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)R$^{20}$, where R$^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein R$^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocyclyl), wherein t is an integer from 0 to 4. In certain embodiments, R$^2$ is C$_1$-C$_8$ alkyl, substituted with halo or hydroxy; or C$_3$-C$_{10}$ cycloalkyl, 4-10 membered heterocyclyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

"Alkoxy" refers to the group —OR$^{29}$ where R$^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, C$_6$-C$_{10}$ aryl, aryloxy, carboxyl, cyano, C$_3$-C$_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are —OCF$_3$, —OCH$_2$CF$_3$, —OCH$_2$Ph, —OCH$_2$-cyclopropyl, —OCH$_2$CH$_2$OH, and —OCH$_2$CH$_2$NMe$_2$.

"Amino" refers to the radical —NH$_2$.

"Oxo group" refers to —C(=O)—.

"Substituted amino" refers to an amino group of the formula —N(R$^{38}$)$_2$ wherein R$^{38}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each R$^{38}$ is independently selected from hydrogen, C$_1$-C$_8$ alkyl, C$_3$-C$_8$ alkenyl, C$_3$-C$_8$ alkynyl, C$_6$-C$_{10}$ aryl, 5-10 membered heteroaryl, 4-10 membered heterocyclyl, or C$_3$-C$_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —$(CH_2)_t(C_6$-$C_{10}$ aryl), —$(CH_2)_t$(5-10 membered heteroaryl), —$(CH_2)_t$($C_3$-$C_{10}$ cycloalkyl), or —$(CH_2)_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both $R^{38}$ groups are joined to form an alkylene group.

Exemplary "substituted amino" groups include, but are not limited to, —$NR^{39}$—$C_1$-$C_8$ alkyl, —$NR^{39}$—$(CH_2)_t(C_6$-$C_{10}$ aryl), —$NR^{39}$—$(CH_2)_t$(5-10 membered heteroaryl), —$NR^{39}$—$(CH_2)_t$($C_3$-$C_{10}$ cycloalkyl), and —$NR^{39}$—$(CH_2)_t$(4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro ($C_1$), bromo (Br), and iodo (I). In certain embodiments, the halo group is either fluoro or chloro.

"Haloalkyl" refers to an alkyl radical in which the alkyl group is substituted with one or more halogens. Typical haloalkyl groups include, but are not limited to, trifluoromethyl (—$CF_3$), difluoromethyl (—$CHF_2$), fluoromethyl (—$CH_2F$), chloromethyl (—$CH_2Cl$), dichloromethyl (—$CHCl_2$), tribromomethyl (—$CH_2Br$), and the like.

"Hydroxy" refers to the radical —OH.

"Nitro" refers to the radical —$NO_2$.

"Thioketo" refers to the group =S.

"Carbocyclylalkyl" refers to an alkyl radical in which the alkyl group is substituted with a cycloalkyl group. Typical carbocyclylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Aralkyl" is a subset of alkyl and aryl, as defined herein, and refers to an optionally substituted alkyl group substituted by an optionally substituted aryl group.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$ —$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)_2R^{aa}$, —$OP(=O)_2R^{aa}$, —$P(=O)(R^{aa})_2$, —$OP(=O)(R^{aa})_2$, —$OP(=O)(OR^{cc})_2$, —$P(=O)_2N(R^{bb})_2$, —$OP(=O)_2N(R^{bb})_2$, —$P(=O)(NR^{bb})_2$, —$OP(=O)(NR^{bb})_2$, —$NR^{bb}P(=O)(OR^{cc})_2$, —$NR^{bb}P(=O)(NR^{bb})_2$, —$P(R^{cc})_2$, —$P(R^{cc})_3$, —$OP(R^{cc})_2$, —$OP(R^{cc})_3$, —$B(R^{aa})_2$, —$B(OR^{cc})_2$, —BR—$(OR^{cc})$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{aa}$ groups;

or two geminal hydrogens on a carbon atom are replaced with the group =O, =S, =$NN(R^{bb})_2$, =$NNR^{bb}C(=O)R^{aa}$, =$NNR^{bb}C(=O)OR^{aa}$, =$NNR^{bb}S(=O)_2R^{aa}$, =$NR^{bb}$, or =$NOR^{cc}$;

each instance of $R^{aa}$ is, independently, selected from $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})$ $OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, $-CN$, $-NO_2$, $-N_3$, $-SO_2H$, $-SO_3H$, $-OH$, $-OR^{ee}$, $-ON(R^{ff})_2$, $-N(R^{ff})_2$, $-N(R^{ff})_3^+X^-$, $-N(OR^{ee})R^{ff}$, $-SH$, $-SR^{ee}$, $-SSR^{ee}$, $-C(=O)R^{ee}$, $-CO_2H$, $-CO_2R^{ee}$, $-OC(=O)R^{ee}$, $-OCO_2R^{ee}$, $-C(=O)N(R^{ff})_2$, $-OC(=O)N(R^{ff})_2$, $-NR^{ff}C(=O)R^{ee}$, $-NR^{ff}CO_2R^{ee}$, $-NR^{ff}C(=O)N(R^{ff})_2$, $-C(=NR)OR^{ee}$, $-OC(=NR^{ff})R^{ee}$, $-OC(=NR^{ff})OR^{ee}$, $-C(=NR^{ff})N(R^{ff})_2$, $-OC(=NR^{ff})N(R^{ff})_2$, $-NR^{ff}(=NR^{ff})N(R^{ff})_2$, $-NR^{ff}SO_2R^{ee}$, $-SO_2N(R^{ff})_2$, $-SO_2R^{ee}$, $-SO_2OR^{ee}$, $-OSO_2R^{ee}$, $-S(=O)R^{ee}$, $-Si(R^{ee})_3$, $-OSi(R^{ee})_3$, $-C(=S)N(R^{N})_2$, $-C(=O)SR^{ee}$, $-C(=S)SR^{ee}$, $-SC(=S)SR^{ee}$, $-P(=O)_2R^{ee}$, $-P(=O)(R^{ee})_2$, $-OP(=O)(R^{ee})_2$, $-OP(=O)(OR^{ee})_2$, $C_{1-6}$ alkyl, $C_{1-6}$ haloalkyl, $C_{2-4}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form $=O$ or $=S$;

each instance of $R^{ee}$ is, independently, selected from $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ haloalkyl, $C_{2-4}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^f$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, $-CN$, $-NO_2$, $-N_3$, $-SO_2H$, $-SO_3H$, $-OH$, $-OC_{1-6}$ alkyl, $-ON(C_{1-6}$ alkyl)$_2$, $-N(C_{1-6}$ alkyl)$_2$, $-N(C_{1-6}$ alkyl)$_3^+X^-$, $-NH(C_{1-6}$ alkyl)$_2^+X^-$, $-NH_2(C_{1-6}$ alkyl)$^+X^-$, $-NH_3^+X^-$, $-N(OC_{1-6}$ alkyl)$(C_{1-6}$ alkyl), $-N(OH)(C_{1-6}$ alkyl), $-NH(OH)$, $-SH$, $-SC_{1-6}$ alkyl, $-SS(C_{1-6}$ alkyl), $-C(=O)(C_{1-6}$ alkyl), $-CO_2H$, $-CO_2(C_{1-6}$ alkyl), $-OC(=O)(C_{1-6}$ alkyl), $-OCO_2(C_{1-6}$ alkyl), $-C(=O)NH_2$, $-C(=O)N(C_{1-6}$ alkyl)$_2$, $-OC(=O)NH(C_{1-6}$ alkyl), $-NHC(=O)(C_{1-6}$ alkyl), $-N(C_{1-6}$ alkyl)$C(=O)(C_{1-6}$ alkyl), $-NHCO_2(C_{1-6}$ alkyl), $-NHC(=O)N(C_{1-6}$ alkyl)$_2$, $-NHC(=O)NH(C_{1-6}$ alkyl), $-NHC(=O)NH_2$, $-C(=NH)O(C_{1-6}$ alkyl), $-OC(=NH)(C_{1-6}$ alkyl), $-OC(=NH)OC_{1-6}$ alkyl, $-C(=NH)N(C_{1-6}$ alkyl)$_2$, $-C(=NH)NH(C_{1-6}$ alkyl), $-C(=NH)NH_2$, $-OC(=NH)N(C_{1-6}$ alkyl)$_2$, $-OC(NH)NH(C_{1-6}$ alkyl), $-OC(NH)NH_2$, $-NHC(NH)N(C_{1-6}$ alkyl)$_2$, $-NHC(=NH)NH_2$, $-NHSO_2(C_{1-6}$ alkyl), $-SO_2N(C_{1-6}$ alkyl)$_2$, $-SO_2NH(C_{1-6}$ alkyl), $-SO_2NH_2$, $-SO_2C_{1-6}$ alkyl, $-SO_2OC_{1-6}$ alkyl, $-OSO_2C_{1-6}$ alkyl, $-SOC_{1-6}$ alkyl, $-Si(C_{1-6}$ alkyl)$_3$, $-OSi(C_{1-6}$ alkyl)$_3$-$C(=S)N(C_{1-6}$ alkyl)$_2$, $C(=S)NH(C_{1-6}$ alkyl), $C(=S)NH_2$, $-C(=O)S(C_{1-6}$ alkyl), $-C(=S)SC_{1-6}$ alkyl, $-SC(=S)SC_{1-6}$ alkyl, $-P(=O)_2(C_{1-6}$ alkyl), $-P(=O)(C_{1-6}$ alkyl)$_2$, $-OP(=O)(C_{1-6}$ alkyl)$_2$, $-OP(=O)(OC_{1-6}$ alkyl)$_2$, $C_{1-6}$ alkyl, $C_{1-6}$ haloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form $=O$ or $=S$; wherein $X^-$ is a counterion.

A "counterion" or "anionic counterion" is a negatively charged group associated with a cationic quaternary amino group in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, $SO_4^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quaternary nitrogen atoms. Exemplary nitrogen atom substitutents include, but are not limited to, hydrogen, $-OH$, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{bb})R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, $C_{1-10}$ alkyl, $C_{1-10}$ haloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides substituted oxysterols useful for preventing and/or treating a broad range of disorders, including, but not limited to, NMDA-mediated disorders. These compounds are expected to show improved in vivo potency, pharmacokinetic (PK) properties, oral bioavailability, formulatability, stability, and/or safety as compared to other oxysterols.

Compounds

In one aspect, provided herein are compounds according to Formula (A):

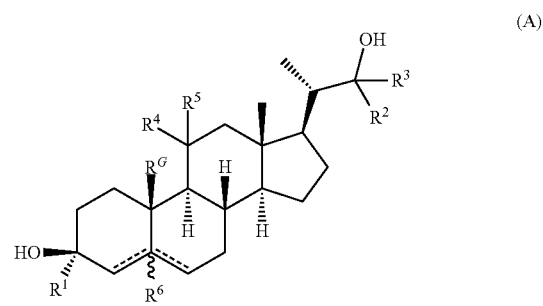

(A)

or a pharmaceutically acceptable salt thereof, wherein:

$R^1$ is hydrogen or alkyl (e.g., $C_1$-$C_6$ alkyl); each of $R^2$ and $R^3$ is independently hydrogen, alkyl (e.g., $C_1$-$C_6$ alkyl), alkenyl, alkynyl, carbocyclyl, heterocyclyl, aryl, or heteroaryl, or $R^2$ and $R^3$, together with the carbon atom to which they are attached form a 3-8 membered ring; each of $R^4$ and $R^5$ is independently hydrogen, halo, or —$OR^C$ wherein $R^C$ is hydrogen or $C_1$-$C_6$ alkyl (e.g., $C_1$-$C_3$ alkyl), or $R^4$ and $R^5$, together with the carbon atom to which they are attached form an oxo group; $R^6$ is absent or hydrogen; $R^G$ is hydrogen or alkyl; and ===== represents a single or double bond, wherein when one of ===== is a double bond, the other ===== is a single bond and $R^6$ is absent; and when both of ===== are single bonds, then $R^6$ is hydrogen.

In some embodiments, $R^1$ is alkyl (e.g., $C_1$-$C_6$ alkyl). In some embodiments, $R^1$ is $C_1$-$C_6$ alkyl (e.g., —$CH_3$, —$CH_2CH_3$, —$CH_2OCH_3$, or —$CF_3$). In some embodiments, $R^1$ is —$CH_3$, —$CF_3$, or —$CH_2CH_3$. In some embodiments, $R^1$ is —$CH_2OR^A$, wherein $R^A$ is $C_1$-$C_6$ alkyl (e.g., $C_1$-$C_3$ alkyl).

In some embodiments, $R^2$ is hydrogen or alkyl (e.g., $C_1$-$C_6$ alkyl).

In some embodiments, each of $R^2$ and $R^3$ is independently hydrogen or alkyl (e.g., $C_1$-$C_6$ alkyl). In some embodiments, each of $R^2$ and $R^3$ is independently hydrogen or $C_1$-$C_6$ haloalkyl (e.g., —$CF_3$). In some embodiments, each of $R^2$ and $R^3$ is independently hydrogen, —$CF_3$, or —$CH_3$.

In some embodiments, $R^4$ is —OH or halo (e.g., —F).

In some embodiments, $R^4$ and $R^5$, together with the carbon atom to which they are attached form an oxo group. In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, $R^2$ is aryl or heteroaryl and $R^3$ is hydrogen. In some embodiments, $R^2$ is carbocyclyl or heterocyclyl and $R^3$ is hydrogen. In some embodiments, $R^2$ and $R^3$ are hydrogen. In some embodiments, $R^2$ and $R^3$, together with the carbon atom to which they are attached form a 3-8 membered carbocyclic or heterocyclic ring.

In some embodiments, $R^6$ is hydrogen and ----- represents a single bond.

In some embodiments, $R^G$ is hydrogen or —$CH_3$.

In one aspect, provided herein are compounds according to Formula (I-63):

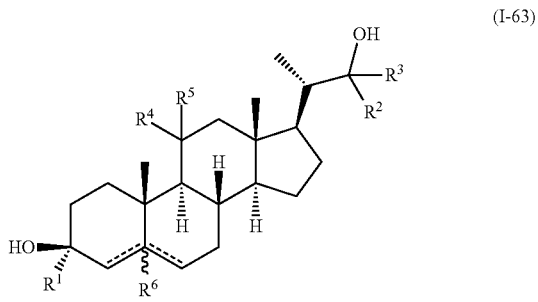

(I-63)

or a pharmaceutically acceptable salt thereof, wherein: $R^1$ is alkyl (e.g., $C_1$-$C_6$ alkyl); each of $R^2$ and $R^3$ is independently hydrogen, alkyl (e.g., $C_1$-$C_6$ alkyl), alkenyl (e.g., $C_2$-$C_6$ alkenyl), alkynyl (e.g., $C_2$-$C_6$ alkynyl), carbocyclyl, heterocyclyl, aryl, or heteroaryl, or $R^2$ and $R^3$, together with the carbon atom to which they are attached form a 3-8 membered ring; each of $R^4$ and $R^5$ is independently hydrogen, halo, or —$OR^C$, wherein $R^C$ is hydrogen or $C_1$-$C_6$ alkyl (e.g., $C_1$-$C_3$ alkyl), or $R^4$ and $R^5$, together with the carbon atom to which they are attached form an oxo group; $R^6$ is absent or hydrogen; and ----- represents a single or double bond, wherein when one of ----- is a double bond, the other ----- is a single bond and $R^6$ is absent; and when both of ----- are single bonds, then $R^6$ is hydrogen.

In some embodiments, $R^1$ is alkyl (e.g., $C_1$-$C_6$ alkyl). In some embodiments, $R^1$ is $C_1$-$C_6$ alkyl (e.g., —$CH_3$, —$CH_2CH_3$, —$CH_2OCH_3$, or —$CF_3$). In some embodiments, $R^1$ is —$CH_3$, —$CF_3$, or —$CH_2CH_3$. In some embodiments, $R^1$ is —$CH_2OR^A$, wherein $R^A$ is $C_1$-$C_6$ alkyl (e.g., $C_1$-$C_3$ alkyl). In some embodiments, $R^1$ is unsubstituted alkyl. In some embodiments $R^1$ is —$CH_2OR^A$, wherein $R^A$ is $C_1$-$C_6$ alkyl (e.g., —$CH_3$).

In some embodiments, $R^2$ is alkyl (e.g., $C_1$-$C_6$ alkyl), carbocyclyl, heterocyclyl, aryl, or heteroaryl and $R^3$ is hydrogen, alkyl (e.g., $C_1$-$C_6$ alkyl), alkenyl, alkynyl, carbocyclyl, heterocyclyl, aryl, or heteroaryl or $R^2$ and $R^3$, together with the carbon atom to which they are attached form a 3-8 membered ring.

In some embodiments, $R^2$ is alkyl (e.g., $C_1$-$C_6$ alkyl), carbocyclyl, heterocyclyl, aryl, or heteroaryl and $R^3$ is hydrogen, alkyl (e.g., $C_1$-$C_6$ alkyl), carbocyclyl, heterocyclyl, aryl, or heteroaryl or $R^2$ and $R^3$, together with the carbon atom to which they are attached form a 3-8 membered ring.

In some embodiments, $R^2$ is hydrogen or alkyl (e.g., $C_1$-$C_6$ alkyl).

In some embodiments, each of $R^2$ and $R^3$ is independently hydrogen or alkyl (e.g. $C_1$-$C_3$ alkyl). In some embodiments, each of $R^2$ and $R^3$ is independently hydrogen or $C_1$-$C_6$ haloalkyl (e.g., —$CF_3$). In some embodiments, each of $R^2$ and $R^3$ is independently $C_5$ alkyl (e.g., substituted or unsubstituted isopentyl) or hydrogen. In some embodiments, each of $R^2$ and $R^3$ is independently isopentyl (e.g., substituted or unsubstituted isopentyl) or hydrogen. In some embodiments, each of $R^2$ and $R^3$ is independently hydrogen, —$CF_3$, or —$CH_3$.

In some embodiments, $R^4$ is —OH or halo (e.g., —F).

In some embodiments, $R^4$ and $R^5$, together with the carbon atom to which they are attached form an oxo group. In some embodiments, $R^4$ is hydrogen and $R^5$ is halo (e.g., —F). In some embodiments, $R^4$ and $R^5$ are halo (e.g., —F). In some embodiments, $R^4$ and $R^5$ are hydrogen.

In some embodiments, $R^2$ is aryl or heteroaryl and $R^3$ is hydrogen. In some embodiments, $R^2$ is carbocyclyl or heterocyclyl and $R^3$ is hydrogen. In some embodiments, $R^2$ and $R^3$ are hydrogen. In some embodiments, $R^2$ is isopentyl (e.g., substituted or unsubstituted isopentyl) and $R^3$ is hydrogen. In some embodiments, $R^2$ is —$CF_3$ or —$CH_3$ and $R^3$ is hydrogen or —$CH_3$. In some embodiments, $R^2$ and $R^3$, together with the carbon atom to which they are attached form a 3-8 membered carbocyclic or heterocyclic ring.

In some embodiments, $R^1$ is —$CH_3$ or —$CH_2CH_3$, $R^2$ is isopentyl (e.g., substituted or unsubstituted isopentyl), and $R^3$ is hydrogen. In some embodiments, $R^1$ is —$CH_3$ or —$CH_2CH_3$, $R^2$ is unsubstituted isopentyl, and $R^3$ is hydrogen.

In some embodiments, $R^2$ is unsubstituted $C_1$-$C_6$ alkyl or $C_1$-$C_6$ haloalkyl. In some embodiments, $R^2$ is unsubstituted $C_1$-$C_6$ alkyl. In some embodiments, $R^2$ is pyridyl. In some embodiments, each of $R^2$ is isopentyl and $R^3$ is hydrogen. In some embodiments, $R^2$ is —$CF_3$ and $R^3$ is hydrogen. In some embodiments, $R^2$ is unsubstituted alkyl (e.g., unsubstituted $C_1$-$C_6$ alkyl). In some embodiments, $R^2$ is carbocyclylalkyl. In some embodiments, $R^2$ is carbocyclylalkyl and $R^3$ is hydrogen. In some embodiments, $R^2$ is aralkyl (e.g., benzyl). In some embodiments, $R^2$ is heterocyclylalkyl. In some embodiments, wherein $R^2$ is unsubstituted $C_1$-$C_6$ alkyl, $C_1$-$C_6$ haloalkyl, carbocyclyl, carbocyclylalkyl, aralkyl, or heterocyclylalkyl.

In some embodiments, the compound of Formula (I-63) is selected from a compound of Formula (I-A63), (I-B63), or (I-C63):

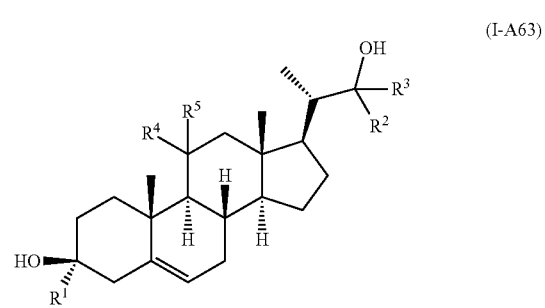

(I-A63)

-continued

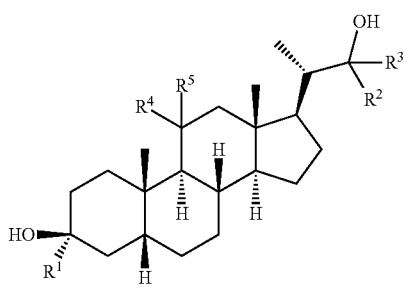
(I-B63)

In some embodiments, the compound of Formula (I-63) is selected from a compound of Formula (I-C63):

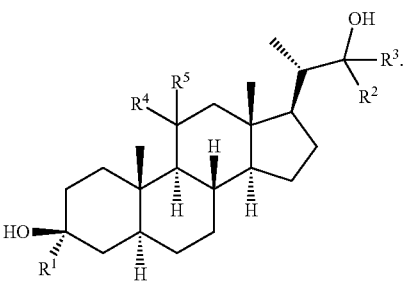
(I-C63)

In some embodiments, the compound of Formula (I-63) is selected from a compound of Formula I-D63):

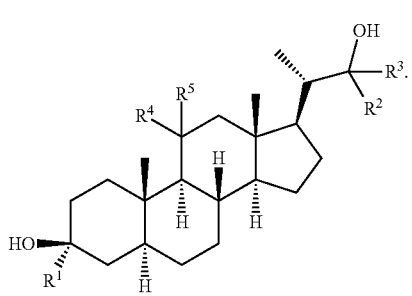
(I-C63)

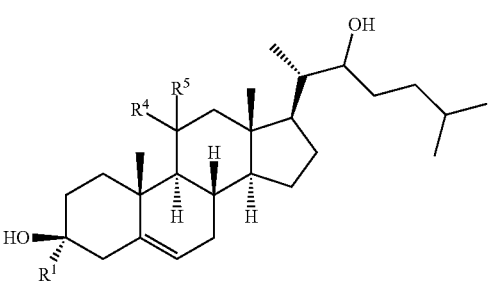
(I-D63)

In some embodiments, the compound of Formula (I-63) is selected from a compound of Formula (I-A63):

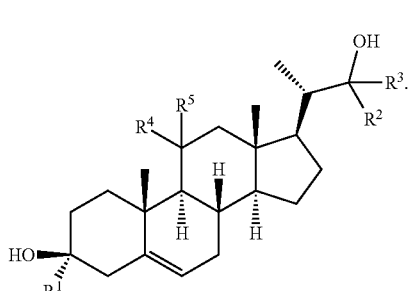
(I-A63)

In some embodiments, the compound of Formula (I-63) is selected from a compound of Formula (I-E63):

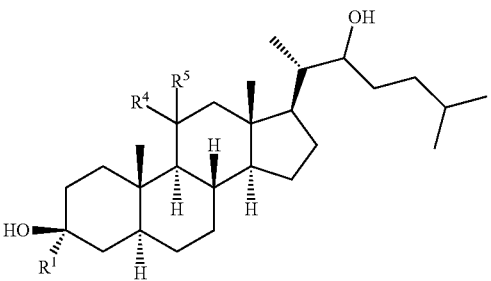
(I-E63)

In some embodiments, the compound of Formula (I-63) is selected from a compound of Formula (I-B63):

In some embodiments, the compound of Formula (I-63) is selected from a compound of Formula (I-D-i63) or (I-D-ii63):

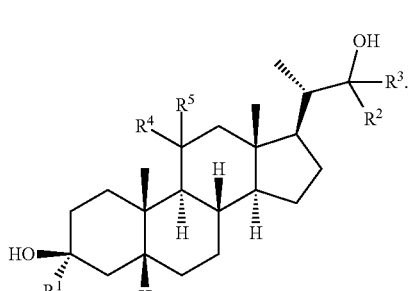
(I-B63)

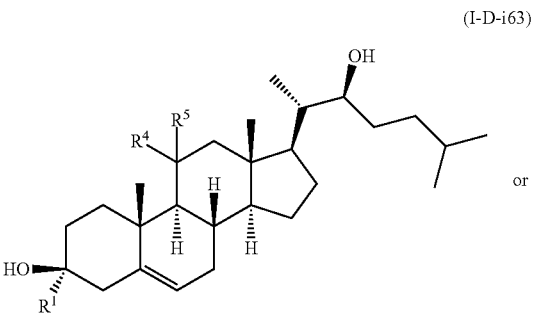
(I-D-i63)

or (I-D-ii63)

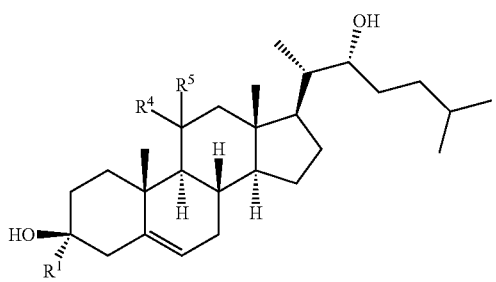

In some embodiments, the compound of Formula (I-63) is selected from a compound of Formula (I-E-i63) or (I-E-ii63):

(I-E-i63)

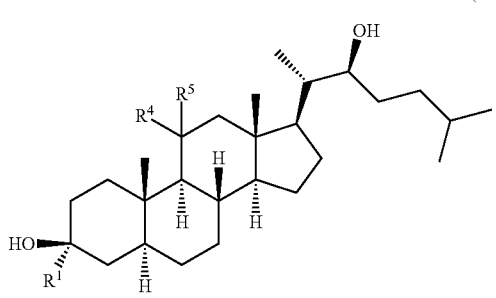

or (I-E-ii63)

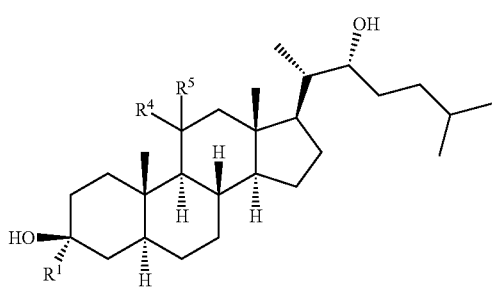

In one aspect, provided herein are compounds according to Formula (I-67):

(I-67)

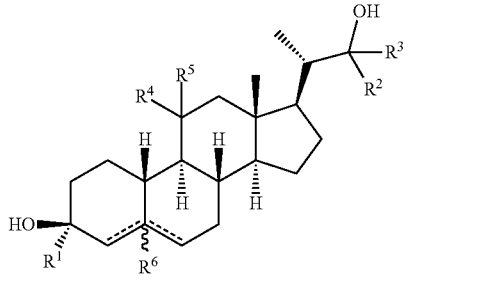

or a pharmaceutically acceptable salt thereof, wherein: $R^1$ is hydrogen or alkyl (e.g., $C_1$-$C_6$ alkyl); each of $R^2$ and $R^3$ is independently hydrogen, alkyl (e.g., $C_1$-$C_6$ alkyl), carbocyclyl, heterocyclyl, aryl, or heteroaryl, or $R^2$ and $R^3$, together with the carbon atom to which they are attached form a 3-8 membered ring; each of $R^4$ and $R^5$ is independently hydrogen, halo, or —$OR^C$, wherein $R^C$ is hydrogen or $C_1$-$C_6$ alkyl (e.g., $C_1$-$C_3$ alkyl), or $R^4$ and $R^5$, together with the carbon atom to which they are attached form an oxo group; $R^6$ is absent or hydrogen; and ===== represents a single or double bond, wherein when one of ===== is a double bond, the other ===== ===== is a single bond and $R^6$ is absent; and when both of ===== are single bonds, then $R^6$ is hydrogen.

In some embodiments, $R^1$ is alkyl. In some embodiments, $R^1$ is unsubstituted alkyl. In some embodiments, R is $C_1$-$C_6$ alkyl. In some embodiments, R is —$CH_3$, —$CF_3$, or —$CH_2CH_3$. In some embodiments, $R^1$ is —$CH_2OR^A$, wherein $R^A$ is $C_1$-$C_6$ alkyl (e.g., —$CH_3$).

In some embodiments, $R^2$ is alkyl (e.g., $C_1$-$C_6$ alkyl), carbocyclyl, heterocyclyl, aryl, or heteroaryl and $R^3$ is hydrogen, alkyl (e.g., $C_1$-$C_6$ alkyl), carbocyclyl, heterocyclyl, aryl, or heteroaryl or $R^2$ and $R^3$, together with the carbon atom to which they are attached form a 3-8 membered ring.

In some embodiments, $R^2$ is hydrogen or alkyl. In some embodiments, each of $R^2$ and $R^3$ is independently hydrogen or alkyl. In some embodiments, each of $R^2$ and $R^3$ is independently hydrogen or $C_1$-$C_6$ haloalkyl. In some embodiments, each of $R^2$ and $R^3$ is independently hydrogen, —$CF_3$, or —$CH_3$. In some embodiments, $R^4$ is —OH or halo. In some embodiments, $R^4$ and $R^5$, together with the carbon atom to which they are attached form an oxo group. In some embodiments, $R^4$ is hydrogen and $R^5$ is halo. In some embodiments, $R^4$ and $R^5$ are halo. In some embodiments, $R^4$ and $R^5$ are hydrogen. In some embodiments, $R^2$ is aryl or heteroaryl and $R^3$ is hydrogen. In some embodiments, $R^2$ is carbocyclyl or heterocyclyl and $R^3$ is hydrogen. In some embodiments, $R^2$ and $R^3$ are hydrogen. In some embodiments, $R^2$ and $R^3$, together with the carbon atom to which they are attached form a 3-8 membered carbocyclic or heterocyclic ring.

In some embodiments, the compound of Formula (I-67) is selected from a compound of Formula (I-A67), (I-B67), or (I-C67):

(I-A67)

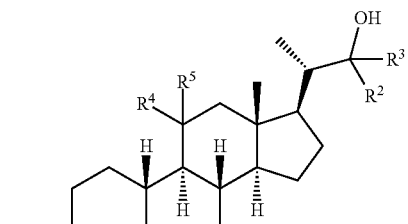

(I-B67)

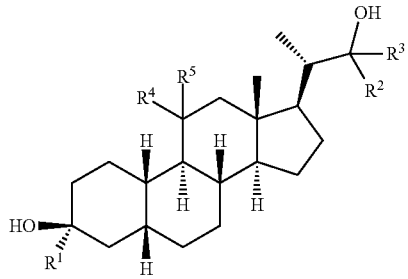

(I-C67)
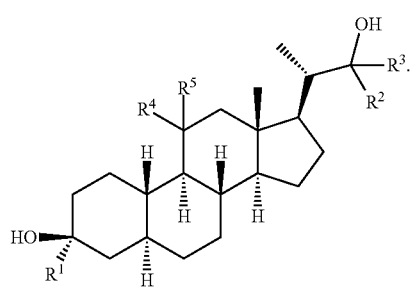
In some embodiments, the compound of Formula (I-67) is selected from a compound of Formula (I-A67):
(I-A67)
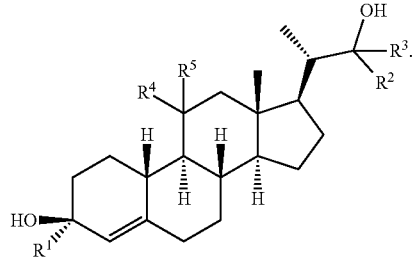
In some embodiments, the compound of Formula (I-67) is selected from a compound of Formula (I-C67):
(I-C67)
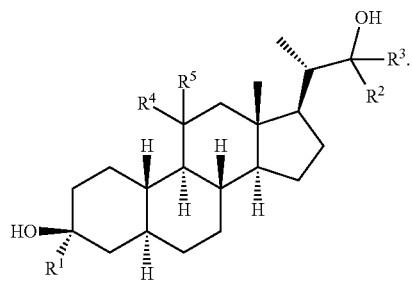
Exemplary compounds of the invention include:
1
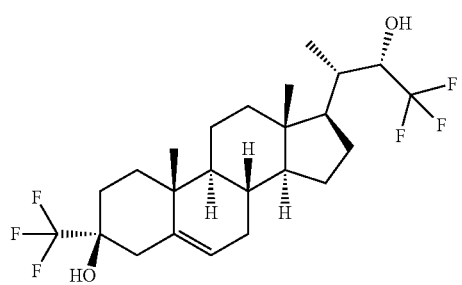
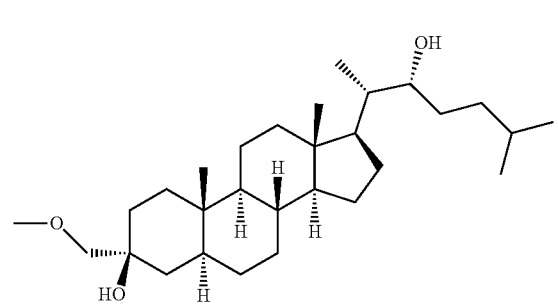
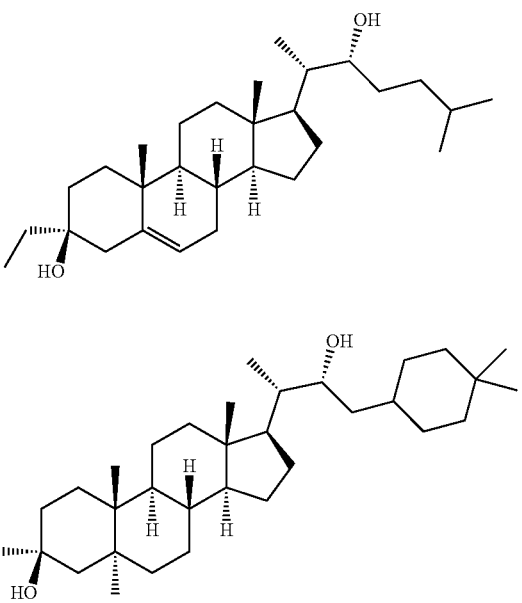
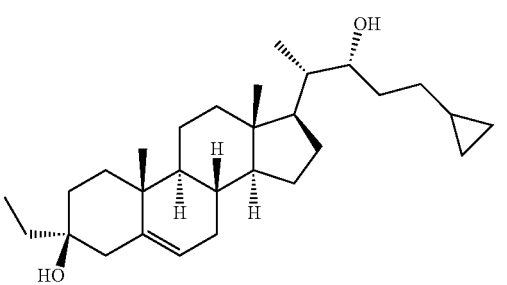

-continued

-continued
17
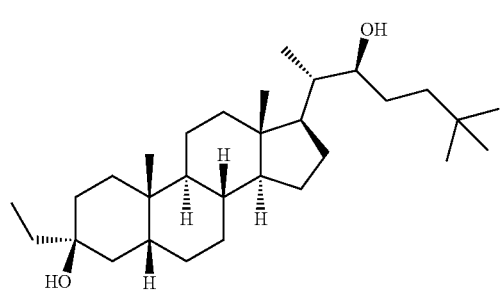
18
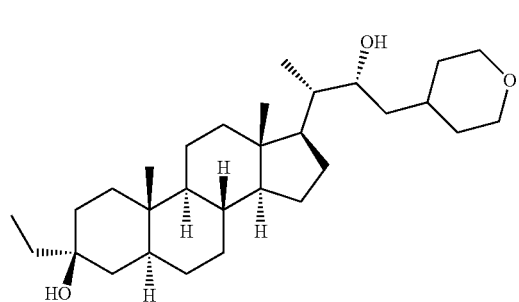
19
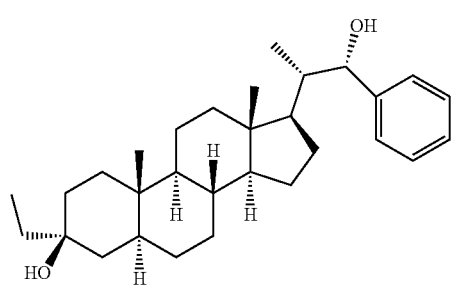
20
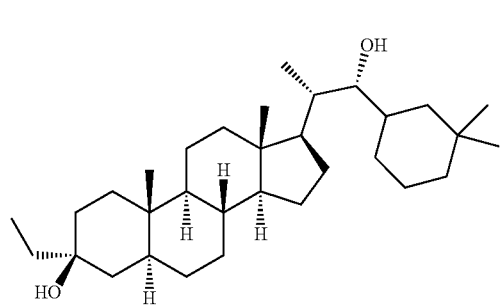
21
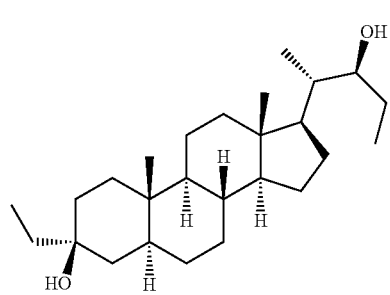
-continued
22
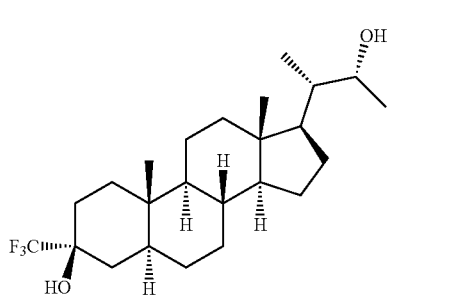
23
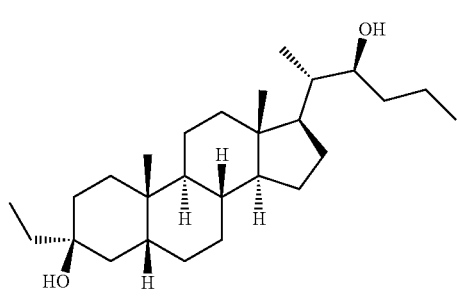
24
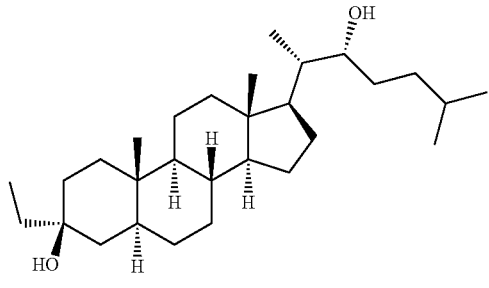
25
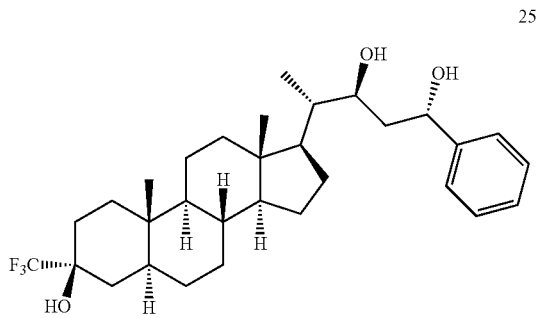
26
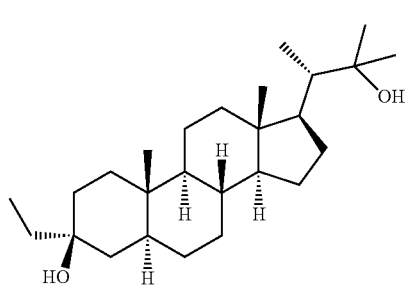

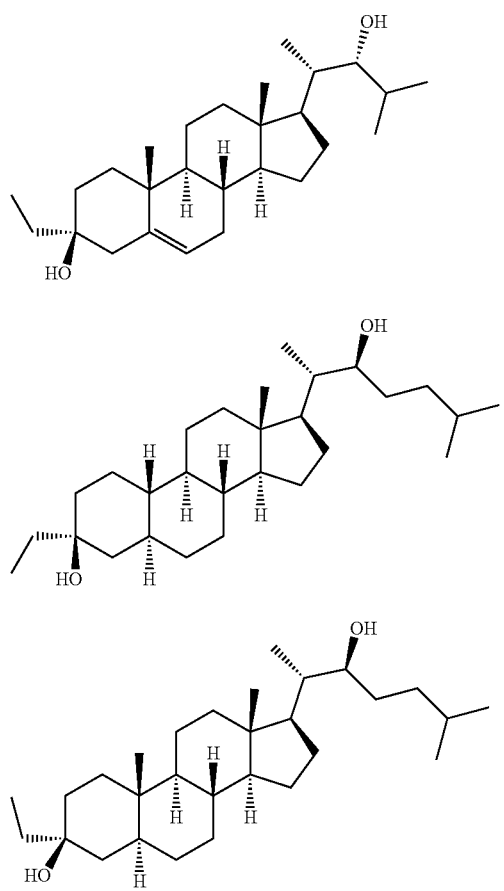
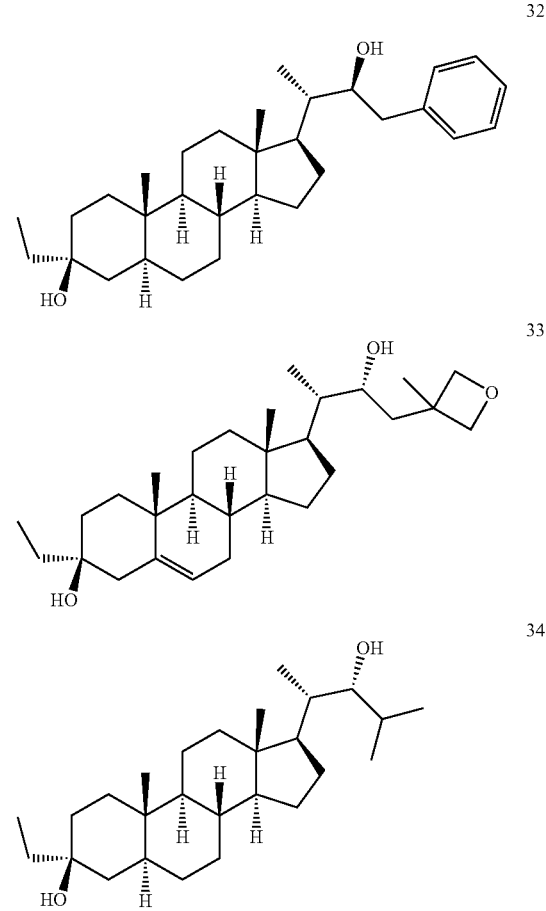
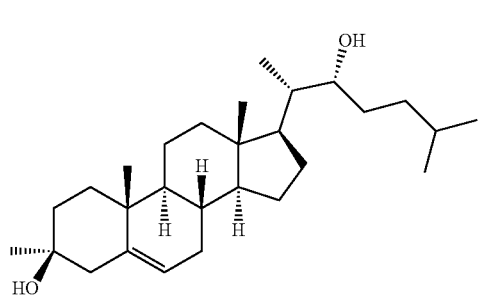
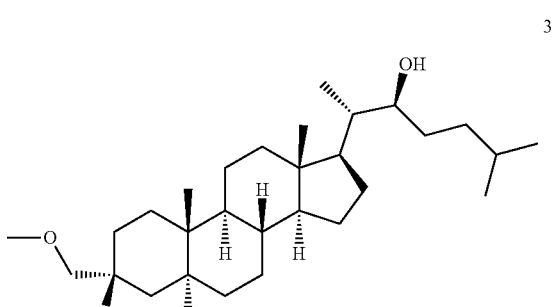
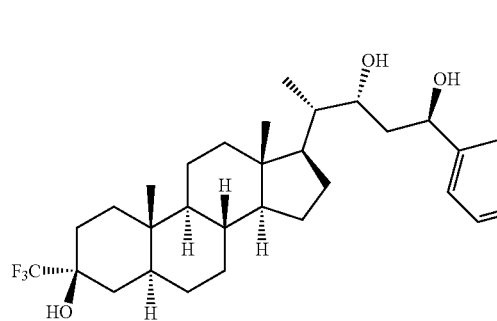
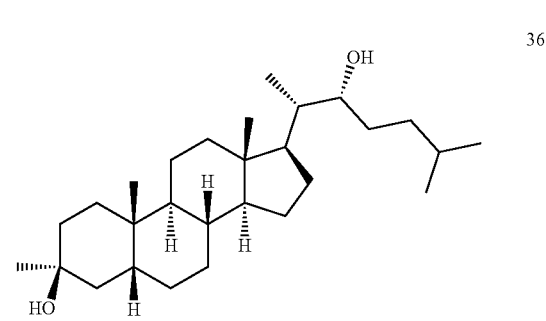

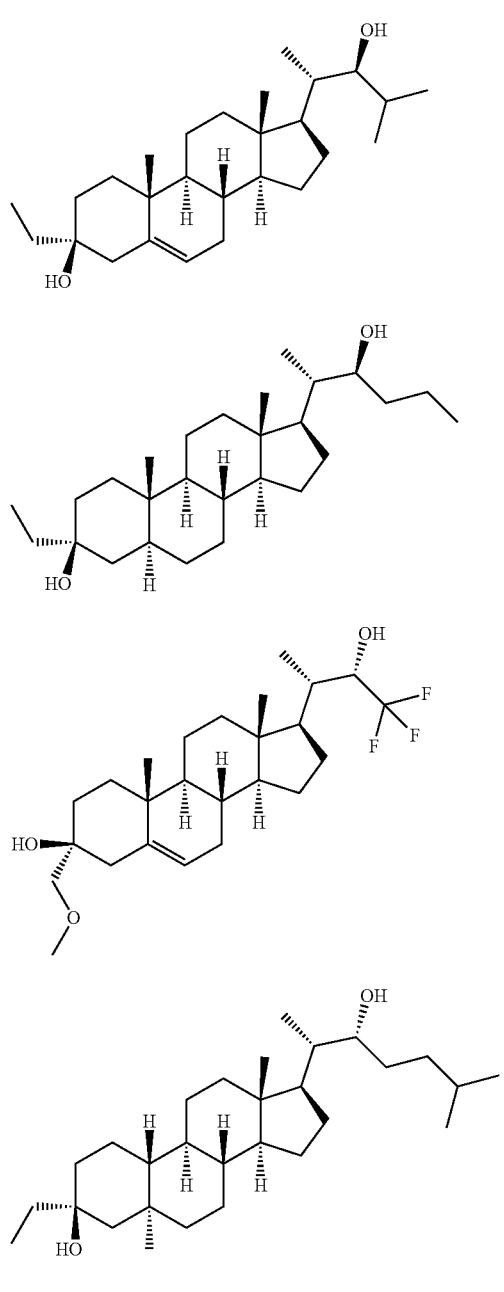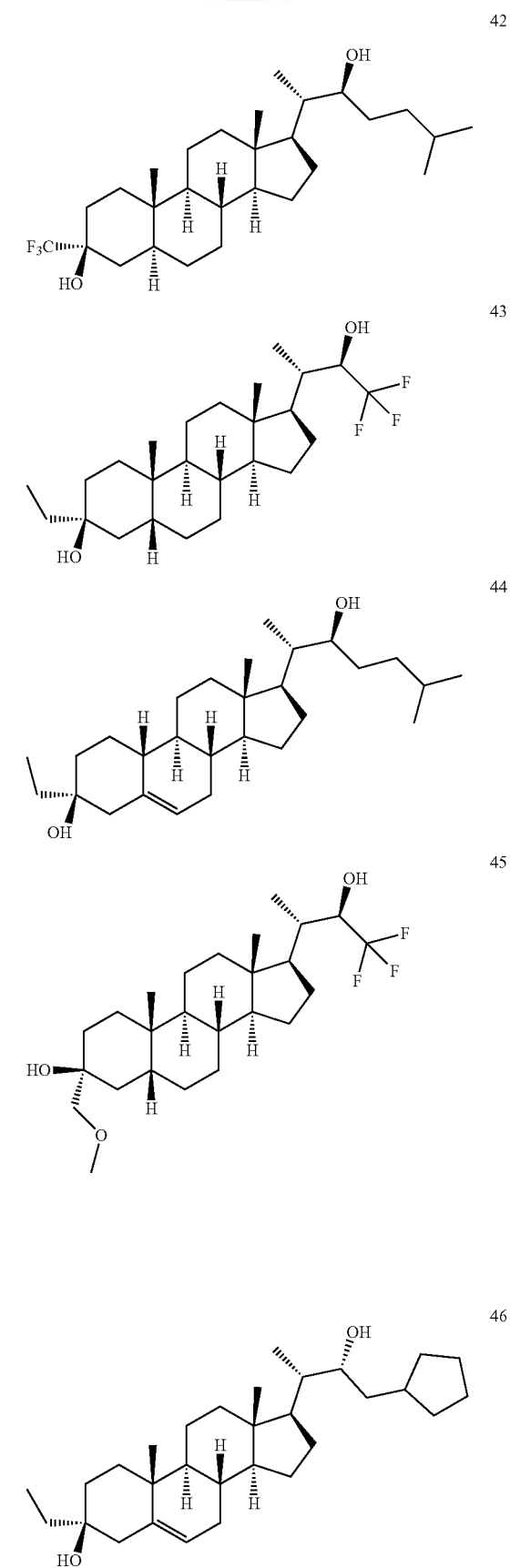

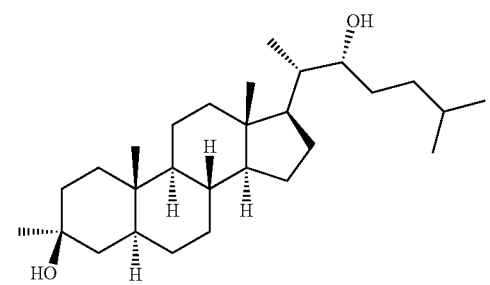
47
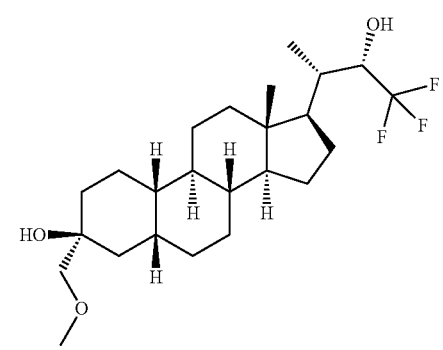
48
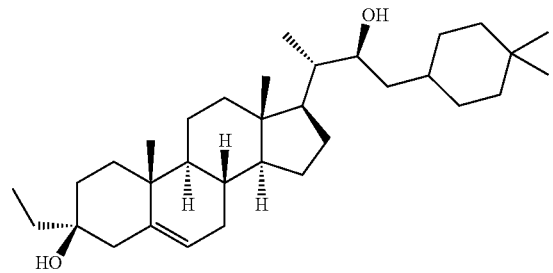
49
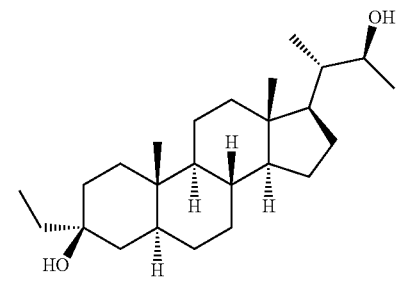
50
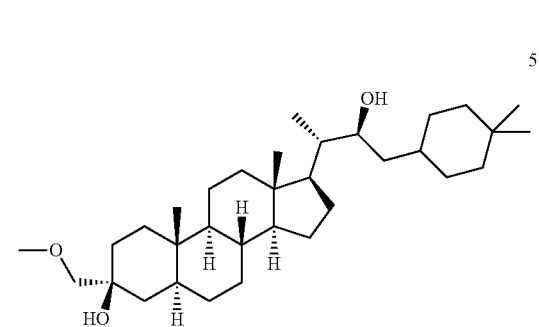
51
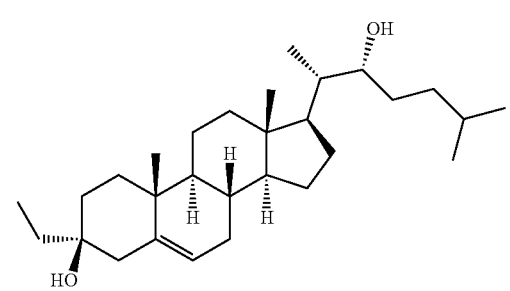
52
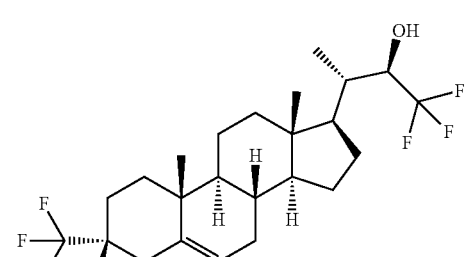
53
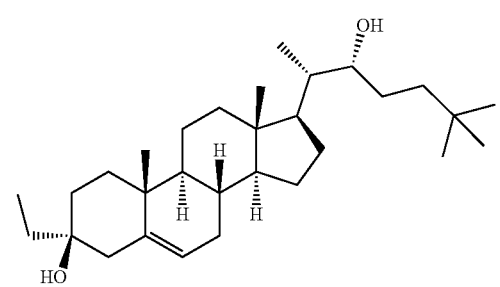
54
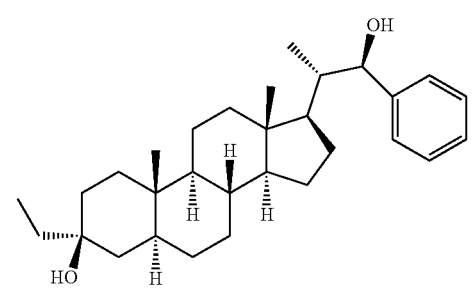
55
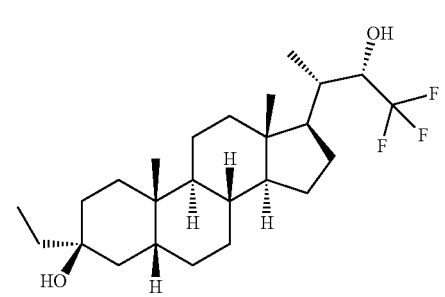
56

-continued
57
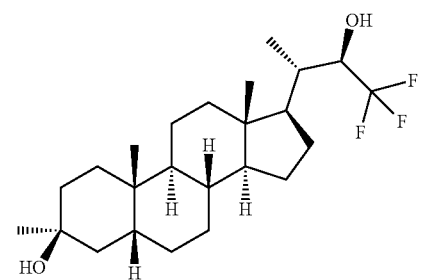
58
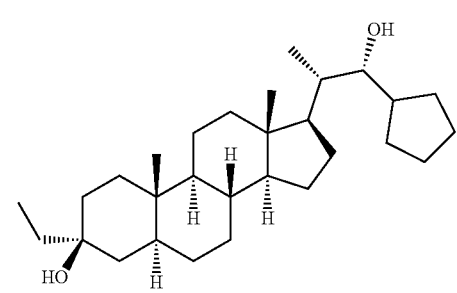
59
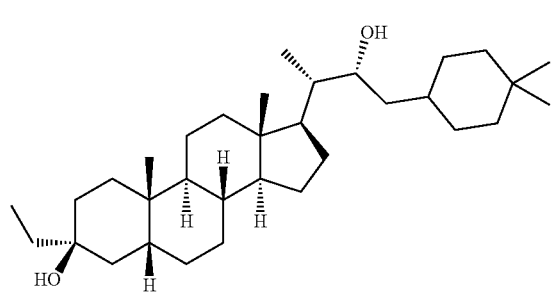
60
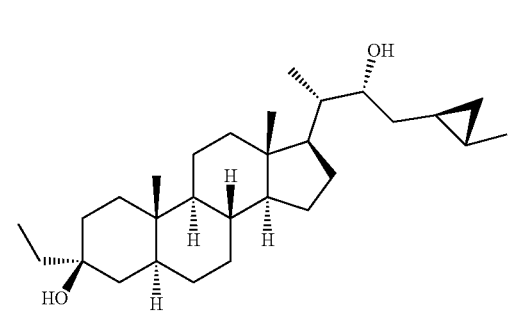
61
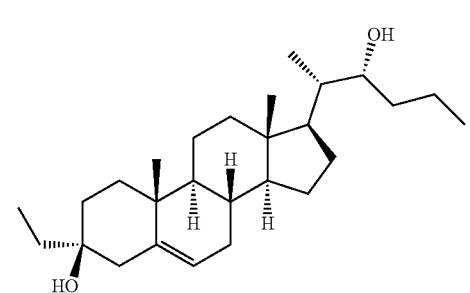
-continued
62
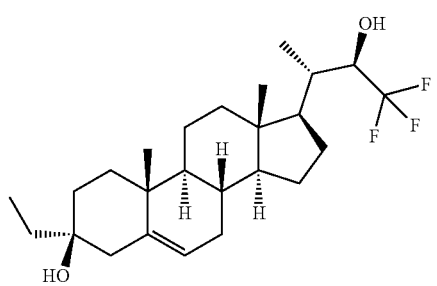
63
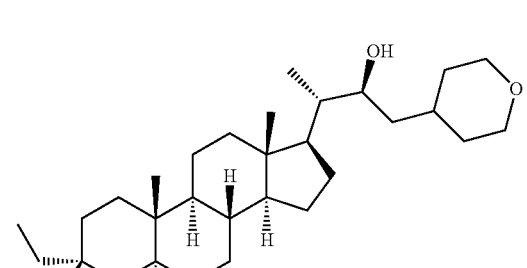
64
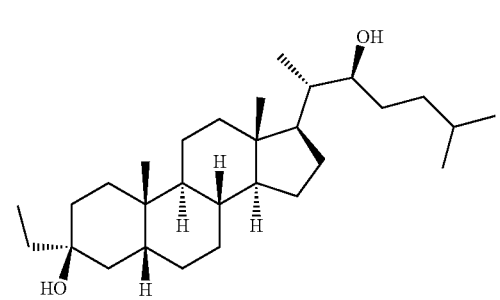
65
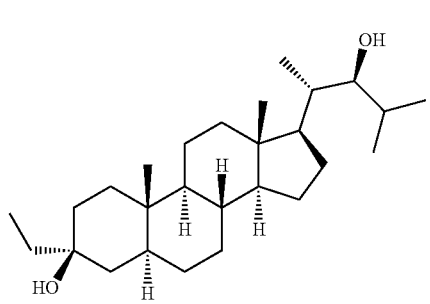
66
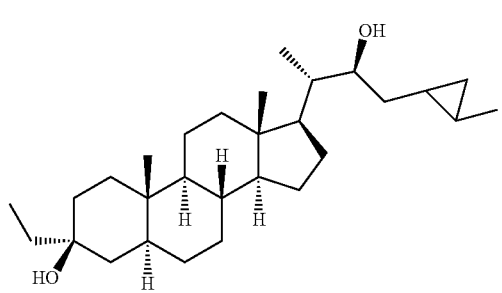

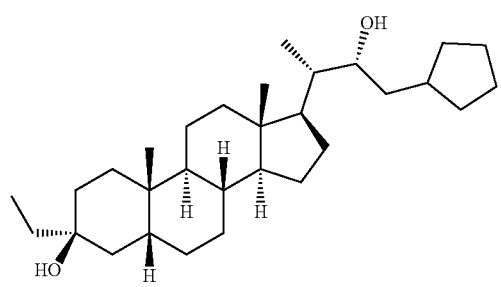
67
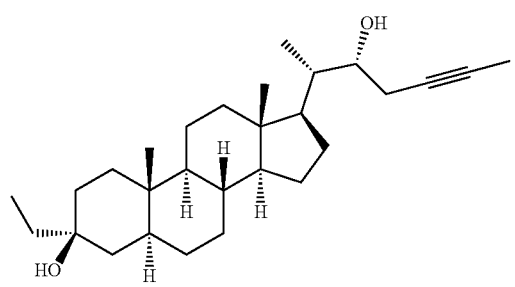
68
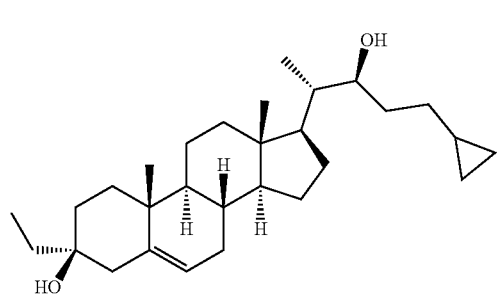
69
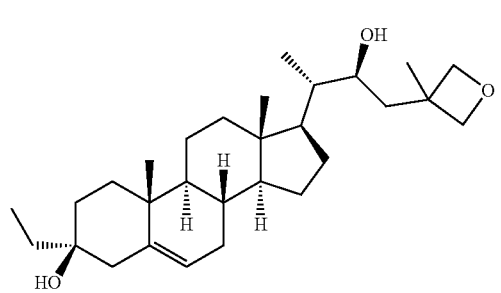
70
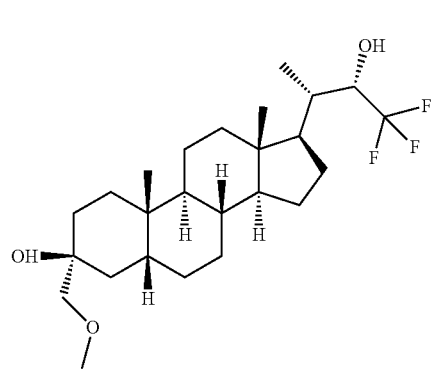
71
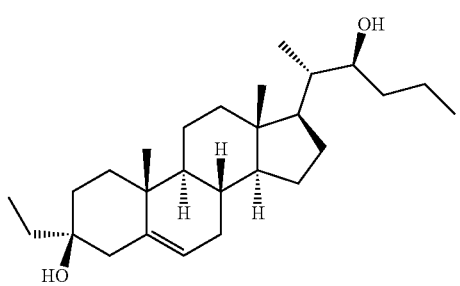
72
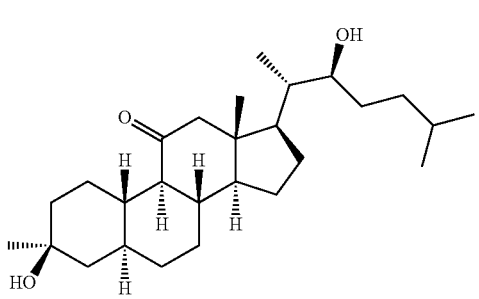
73
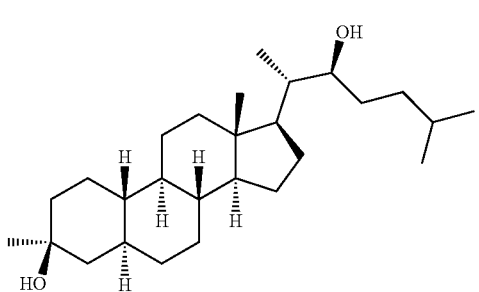
74
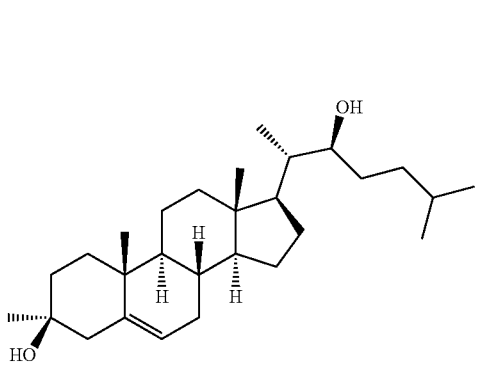
75
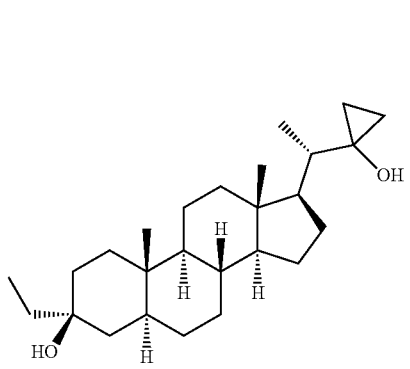
76

77
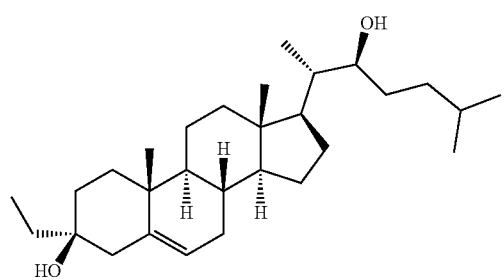
78
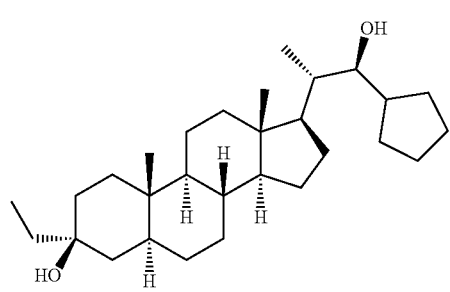
79
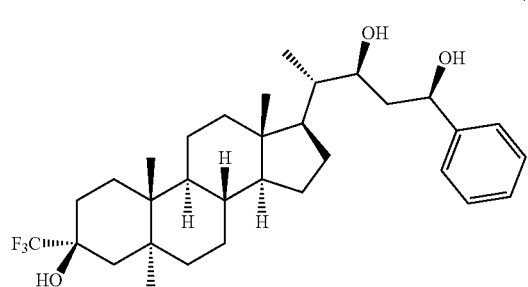
81
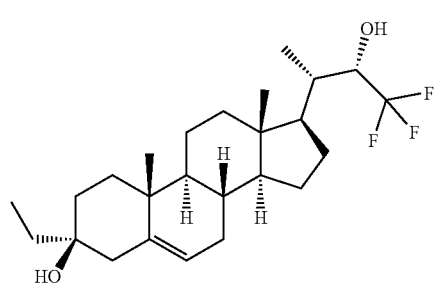
82
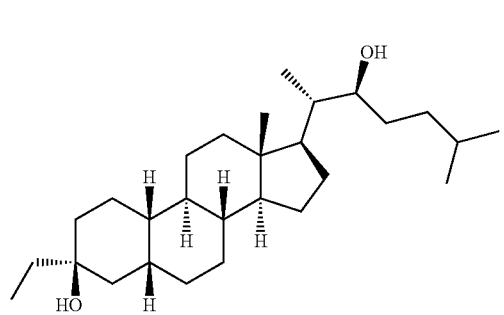
83
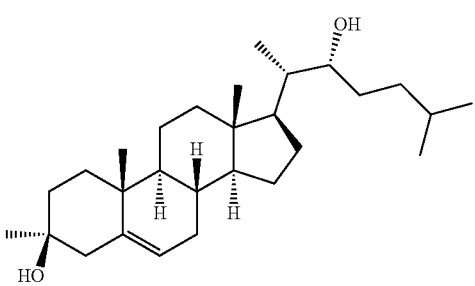
84
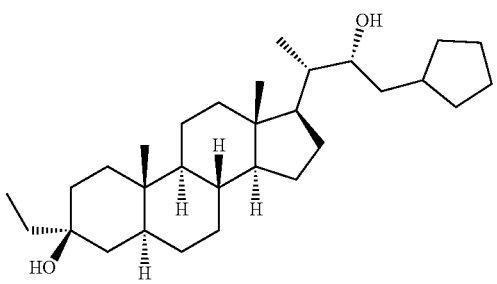
85
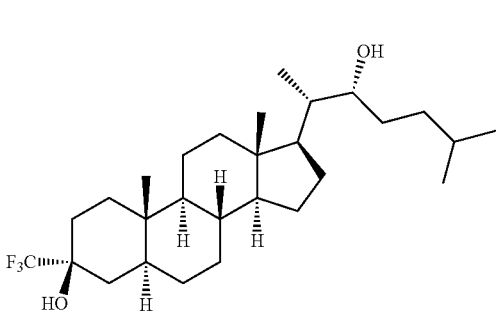
86
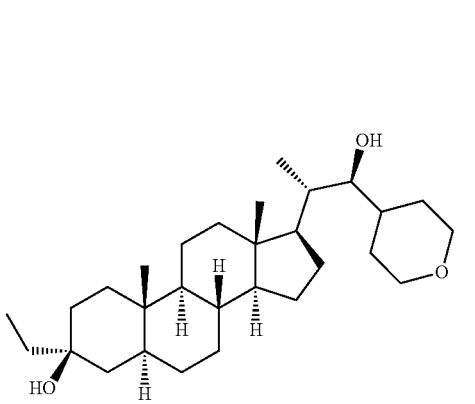
87
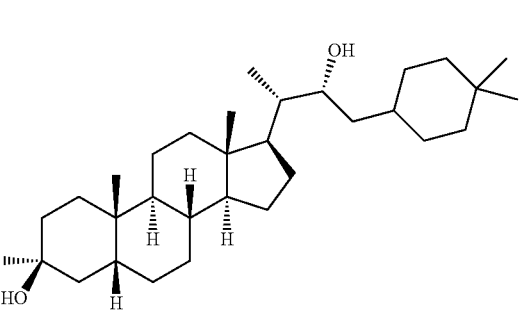

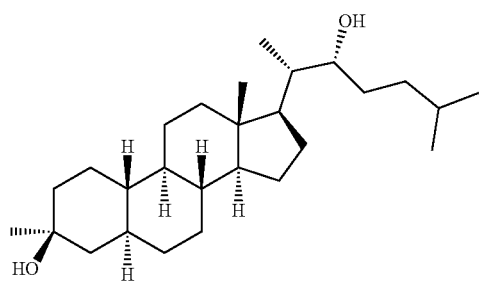 88
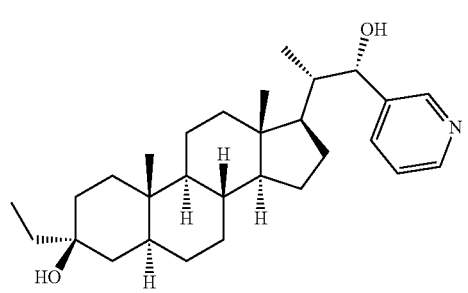 89
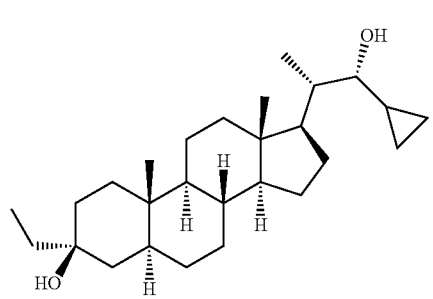 90
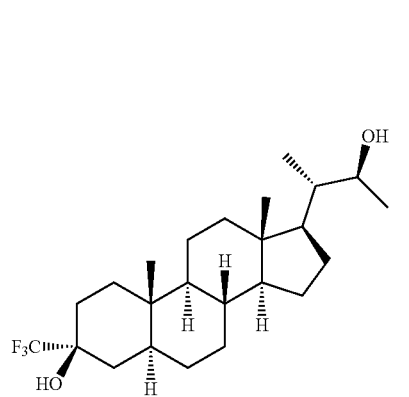 91
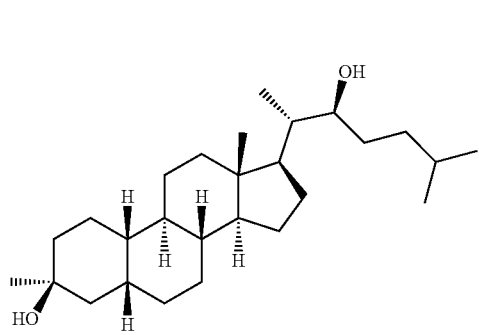 92
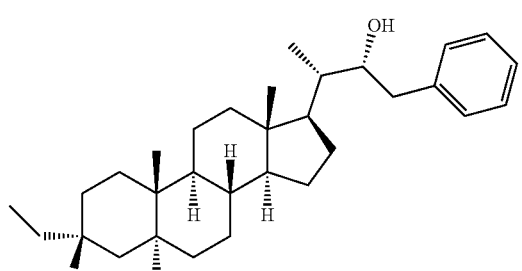 93
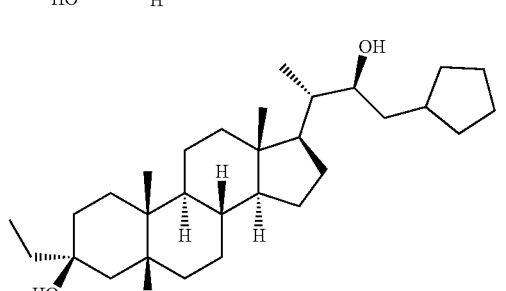 94
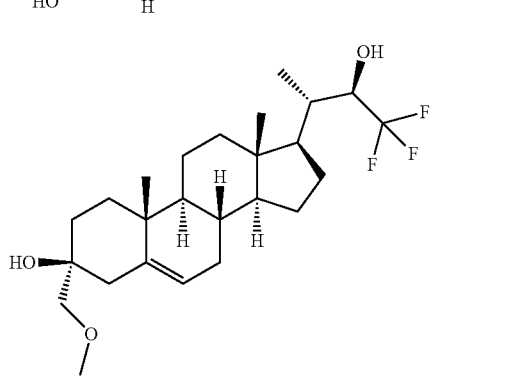 95
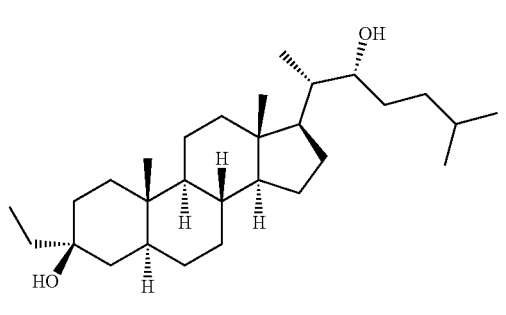 96
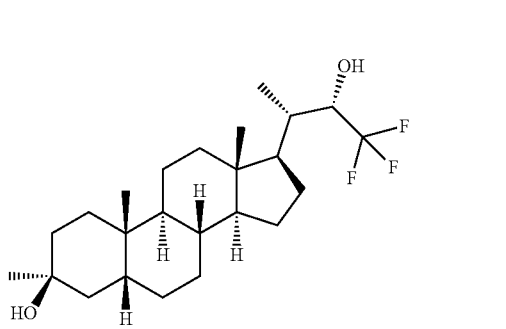 97

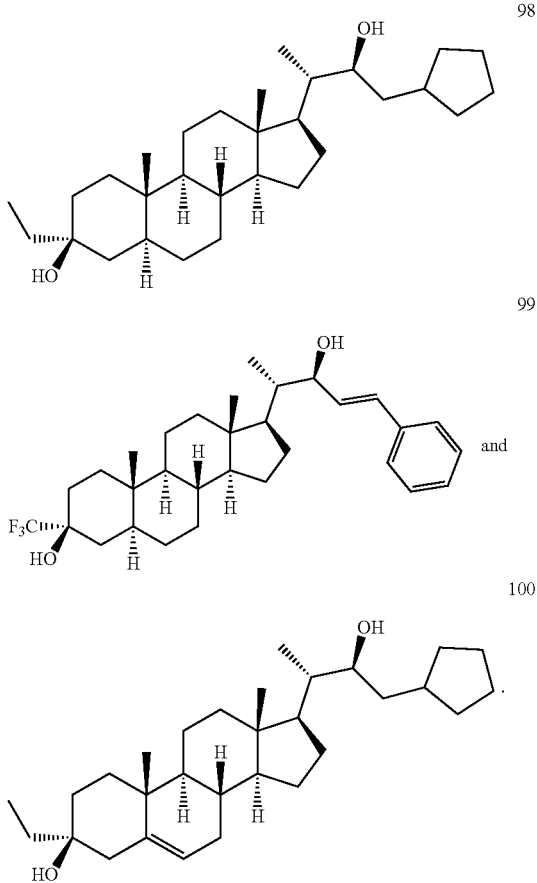

Alternative Embodiments

In an alternative embodiment, compounds described herein may also comprise one or more isotopic substitutions. For example, hydrogen may be $^2$H (D or deuterium) or $^3$H (T or tritium); carbon may be, for example, $^{13}$C or $^{14}$C; oxygen may be, for example, $^{18}$O; nitrogen may be, for example, $^{15}$N, and the like. In other embodiments, a particular isotope (e.g., $^3$H, $^{13}$C, $^{14}$C, $^{18}$O, or $^{15}$N) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Pharmaceutical Compositions

In another aspect, the invention provides a pharmaceutical composition comprising a pharmaceutically acceptable carrier and an effective amount of a compound described herein, or a pharmaceutically acceptable salt thereof.

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound described herein or pharmaceutical composition thereof for use as a pharmaceutical or a medicament.

Generally, the compounds provided herein are administered in a therapeutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient (s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's *Pharmaceutical Sciences,* 17th edition, 1985, Mack Publishing Company, Easton, Pa., which is incorporated herein by reference.

The above-described components for orally administrable, injectable, or topically administrable compositions are merely representative. Other materials as well as processing techniques and the like are set forth in Part 8 of *Remington's The Science and Practice of Pharmacy,* 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences.*

The present invention also relates to the pharmaceutically acceptable formulations of a compound described herein. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether R-cyclodextrin, e.g., for example, sulfobutyl ether β-cyclodextrin, also known as Captisol®. See, e.g., U.S. Pat. No. 5,376,645. In certain embodiments, the formulation comprises hexapropyl-β-cyclodextrin. In a more particular embodiment, the formulation comprises hexapropyl-β-cyclodextrin (10-50% in water).

The present invention also relates to the pharmaceutically acceptable acid addition salt of a compound of described herein. The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound described herein, or pharmaceutically acceptable salt thereof, may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound described herein, or pharmaceutically acceptable salt thereof, may be admixed as a dry powder with a starch diluent in an approximate 1:1 weight ratio. The mixture is filled into 250 mg capsules (125 mg of active compound per capsule).

Exemplary Formulation 3—Liquid: A compound described herein, or pharmaceutically acceptable salt thereof, (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets: A compound described herein, or pharmaceutically acceptable salt thereof, may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection: A compound described herein, or pharmaceutically acceptable salt thereof, may be dissolved or suspended in a buffered sterile saline injectable aqueous medium to a concentration of approximately 5 mg/mL.

Exemplary Formulation 6—Tablets: A compound described herein, or pharmaceutically acceptable salt thereof, may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: A compound described herein, or pharmaceutically acceptable salt thereof, may be may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound described herein, or pharmaceutically acceptable salt thereof, may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound described herein, or pharmaceutically acceptable salt thereof, may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets: A compound described herein, or pharmaceutically acceptable salt thereof, may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Treatment and Use

Compounds of the present invention, e.g., a compound of Formula (A), (I-63), or (I-67), and pharmaceutically acceptable salts thereof, as described herein, are generally designed to modulate NMDA function, and therefore to act as oxysterols for the treatment and prevention of, e.g., CNS-related conditions in a subject. In some embodiments, the compounds described herein, e.g., a compound of Formula (A), (I-63), or (I-67), and pharmaceutically acceptable salts thereof, as described herein, are generally designed to penetrate the blood brain barrier (e.g., designed to be transported across the blood brain barrier). Modulation, as used herein, refers to, for example, the inhibition or potentiation of NMDA receptor function. In certain embodiments, a compound described herein, e.g., a compound of Formula (A), (I-63), or (I-67), or pharmaceutically acceptable salt thereof, acts as a negative allosteric modulator (NAM) of NMDA receptor function, and inhibit NMDA receptor function. In certain embodiments, a compound described herein, e.g., a compound of Formula (A), (I-63), or (I-67), or pharmaceutically acceptable salt thereof, acts as a positive allosteric modulator (PAM) of NMDA receptor function, and potentiate NMDA receptor function. In certain embodiments, a compound described herein, e.g., a compound of Formula (A), (I-63), or (I-67), or pharmaceutically acceptable salt thereof, blocks or reduces the potentiation or inhibition of NMDA receptor function by a naturally-occurring substrate. Such compounds do not act as negative allosteric modulators (NAMs) or positive allosteric modulators (PAMs) of NMDA receptor function—these compounds can be referred to as neutral allosteric ligands (NALs) In some embodiments, the disorder is cancer. In some embodiments, the disorder is diabetes. In some embodiments, the disorder is a sterol synthesis disorder. In some embodiments, the disorder is a gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, or colitis. In some embodiments, the disorder is inflammatory bowel disease.

Exemplary conditions related to NMDA-modulation include, but are not limited to, gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis, and CNS conditions, e.g., as described herein.

Exemplary conditions (e.g., CNS conditions) related to NMDA-modulation include, but are not limited to, adjustment disorders, anxiety disorders (including obsessive-compulsive disorder, posttraumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, Smith-Lemli-Opitz syndrome, pain (including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketoneuria), post-partum psychosis, syndromes associated with high titers of anti-NMDA receptor antibodies (including anti-NMDA receptor encephalitis), neurodegenerative disorders, neuroinflammation, neuropsychiatric lupus, Niemann-Pick C disorder, and tinnitus.

In certain embodiments, compounds of the present invention, e.g., a compound described herein, e.g., a compound of Formula (A), (I-63), or (I-67), or pharmaceutically acceptable salt thereof, can be used to induce sedation or anesthesia.

In certain embodiments, a compound described herein, or pharmaceutically acceptable salt thereof, is useful in the treatment or prevention of adjustment disorders, anxiety disorders (including obsessive-compulsive disorder, posttraumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, Smith-Lemli-Opitz syndrome, pain (including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketoneuria), post-partum psychosis, syndromes associated with high titers of anti-NMDA receptor antibodies (including anti-NMDA receptor encephalitis), neurodegenerative disorders, neuroinflammation, neuropsychiatric lupus, Niemann-Pick C disorder, and tinnitus.

In certain embodiments, a compound described herein, or pharmaceutically acceptable salt thereof, is useful in the treatment or prevention of adjustment disorders, anxiety disorders (including obsessive-compulsive disorder, post-traumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), substance abuse-related disorders, dissociative disorders, eating disorders mood disorders (including depression (e.g., postpartum depression), bipolar disorder, dysthymic disorder, suicidality), schizophrenia or other psychotic disorders (including schizoaffective disorder), personality disorders (including obsessive-compulsive personality disorder), autism spectrum disorders (including those involving mutations to the Shank group of proteins (e.g., Shank3)), or post-partum psychosis.

In certain embodiments, a compound described herein, or pharmaceutically acceptable salt thereof, is useful in the treatment or prevention of neurodevelopmental disorders (including Rett syndrome), multiple sclerosis, sterol synthesis disorders, Smith-Lemli-Opitz syndrome, pain (including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketoneuria), syndromes associated with high titers of anti-NMDA receptor antibodies (including anti-NMDA receptor encephalitis), neurodegenerative disorders, neuroinflammation, neuropsychiatric lupus, Niemann-Pick C disorder, or tinnitus.

In certain embodiments, a compound described herein, or pharmaceutically acceptable salt thereof, is useful in the treatment or prevention of obsessive compulsive disorder, depression, neuropsychiatric lupus, or schizophrenia.

In certain embodiments, a compound described herein, or pharmaceutically acceptable salt thereof, is useful in the treatment or prevention of Huntington's disease, amyotrophic lateral sclerosis, multiple sclerosis, Alzheimer's disease, dementia, Parkinson's disease, ataxia, Fragile X syndrome, Tourette syndrome, levodopa-induced dyskinesia, Rett syndrome, autism spectrum disorder, or traumatic brain injury.

In certain embodiments, a compound described herein, or pharmaceutically acceptable salt thereof, is useful in the treatment or prevention of tinnitus, neuropathic pain, or migraine.

In certain embodiments, a compound described herein, or pharmaceutically acceptable salt thereof, is useful in the treatment or prevention of acute liver failure or glycine encephalopathy, In certain embodiments, a compound described herein, or pharmaceutically acceptable salt thereof, is useful in the treatment or prevention of seizures or genetic epilepsy.

In some embodiments, a compound of the invention, a compound described herein, e.g., a compound of Formula (A), a compound of Formula (I-63), or a compound of Formula (I-67) that acts as a PAM of NMDA receptor function can be useful in the treatment or prevention of conditions (e.g., CNS-related conditions) including schizophrenia or other psychotic disorders (including schizoaffective disorder), sleep disorders (including insomnia), autism spectrum disorders (including those involving mutations to the Shank group of proteins (e.g., Shank3)), multiple sclerosis, movement disorders (including Huntington's disease and Parkinson's disease), attention deficit disorder, attention deficit hyperactivity disorder, metabolic encephalopathies (including phenylketoneuria), post-partum psychosis, and syndromes associated with high titers or anti-NMDA receptor antibodies (including anti-NMDA receptor encephalitis).

In some embodiments, a compound of the invention, e.g., a compound of Formula (A), a compound of Formula (I-63), or a compound of Formula (I-67), that acts as a NAM of NMDA receptor function can be useful in the treatment or prevention of conditions (e.g., CNS-related conditions) including anxiety disorders (including obsessive-compulsive disorder, posttraumatic stress disorder, social phobia, generalized anxiety disorder), mood disorders (including depression (e.g., postpartum depression), bipolar disorder, dysthymic disorder, suicidality), personality disorders (including obsessive-compulsive personality disorder), neurodevelopmental disorders (including Rett syndrome), pain (including acute and chronic pain), seizure disorders (including status epilepticus and monogenic forms of epilepsy such as Dravet's disease, and Tuberous Sclerosis Complex (TSC)), stroke, traumatic brain injury, adjustment disorders, neuropsychiatric lupus, and tinnitus.

In some embodiments, a compound of the invention, e.g., a compound of Formula (A), a compound of Formula (I-63), or a compound of Formula (I-67), that acts as a PAM or a NAM of NMDA receptor function can be useful in the treatment or prevention of conditions (e.g., CNS-related conditions) including cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), sterol synthesis disorders, and eating disorders.

In another aspect, provided is a method of treating or preventing brain excitability in a subject susceptible to or afflicted with a condition associated with brain excitability, comprising administering to the subject an effective amount of a compound of the present invention, e.g., a compound of Formula (A), a compound of Formula (I-63), or a compound of Formula (I-67), or a pharmaceutically acceptable salt thereof.

In yet another aspect, the present invention provides a combination of a compound of the present invention, e.g., a compound of Formula (A), a compound of Formula (I-63), or a compound of Formula (I-67), or pharmaceutically acceptable salt thereof, and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

In another aspect, the present invention provides a method of effecting negative allosteric modulation of an NMDA receptor in a subject, comprising administering to the subject a compound described herein, e.g., a compound of Formula (A), a compound of Formula (I-63), or a compound of Formula (I-67).

Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and Parkinsonism (defined particularly by bradykinesia), dystonia, chorea and Huntington's disease, ataxia, levodopa-induced dyskinesia, tremor (e.g., essential tremor), myoclonus and startle, tics and Tourette syndrome, Restless legs syndrome, stiff person syndrome, and gait disorders.

Tremor is an involuntary, at times rhythmic, muscle contraction and relaxation that can involve oscillations or twitching of one or more body parts (e.g., hands, arms, eyes, face, head, vocal folds, trunk, legs). Tremor includes hereditary, degenerative, and idiopathic disorders such as Wilson's disease, Parkinson's disease, and essential tremor, respectively; metabolic diseases (e.g., thyroid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor. Other forms of tremor include cerebellar tremor or intention tremor, dystonic tremor, essential tremor, orthostatic tremor, parkinsonian tremor, physiological tremor, psychogenic tremor, or rubral tremor.

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occur in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face.

Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myoclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part.

Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Mood Disorders

Also provided herein are methods for treating a mood disorder, for example clinical depression, postnatal depression or postpartum depression, perinatal depression, atypical depression, melancholic depression, psychotic major depression, cationic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior.

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or sommolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self-harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

Anxiety Disorders

Provided herein are methods for treating anxiety disorders. Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Epilepsy

Epilepsy is a brain disorder characterized by repeated seizures over time. Types of epilepsy can include, but are not limited to generalized epilepsy, e.g., childhood absence epilepsy, juvenile myoclonic epilepsy, epilepsy with grandmal seizures on awakening, West syndrome, Lennox-Gastaut syndrome, partial epilepsy, e.g., temporal lobe epilepsy, frontal lobe epilepsy, benign focal epilepsy of childhood.

Epileptogenesis

Epileptogenesis is a gradual process by which a normal brain develops epilepsy (a chronic condition in which seizures occur). Epileptogenesis results from neuronal damage precipitated by the initial insult (e.g., status epilepticus).

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well-known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope. In the synthetic examples below, the descriptions of experimental procedures within a reaction sequence are listed in numerical order.

In some cases, the stereochemistry assigned herein (e.g., the assignment of "R" or "S" to the C22 position of the steroid) may be tentatively (e.g., randomly) assigned. For example, a C22 position may be drawn in the "R" configuration when the absolute configuration is "S." A C22 position may also be drawn in the "S" configuration when the absolute configuration is "R." Such random assignment applies to compounds 7, 13, 14, 18, 19, 22, 25, 27, 31, 37, 41, 50, 55, 60, 63, 66, 68, 73, 79, 86, 89, 91, and 99.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative pyrazoles that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB—H, CHIRALCEL® OD, CHIRALCEL® OD-H, CHIRALCEL® OF, CHIRALCEL® OG, CHIRALCEL® OJ and CHIRALCEL® OK.

Exemplary general method for preparative HPLC: Column: Waters RBridge prep 10 μm C18, 19*250 mm. Mobile phase: acetonitrile, water ($NH_4HCO_3$) (30 L water, 24 g $NH_4HCO_3$, 30 mL $NH_3 \cdot H_2O$). Flow rate: 25 mL/min Exemplary general method for analytical HPLC: Mobile phase: A: water (10 mM $NH_4HCO_3$), B: acetonitrile Gradient: 5%-95% B in 1.6 or 2 min Flow rate: 1.8 or 2 mL/min; Column: XBridge C18, 4.6*50 mm, 3.5 μm at 45° C.

NMDA Modulation

NMDA potentiation in mammalian cells which expressed NMDA receptors was assessed using the automatic patch-clamp system can be used determine the NAM activity of compounds as described below. An whole cell patch-clamp system can be used determine the PAM activity of compounds as described below.

Automated Patch-Clamp System (OPatch HTX):

In this study, HEK 293 cells stably transfected with glutamate-activated channels of the GRIN1/2A subtype will be used together with submaximal NMDA concentrations (300 μM NMDA, co-application with 8 μM Glycine) to investigate the negative allosteric modulation of the test compounds. Percent potentiation results obtained with this method are shown in Table 1.

Cell Culture

In general, cells will be passaged at a confluence of about 80% to ~90%. For electrophysiological measurements cells will be harvested at a confluence of about 80% to 90% from sterile culture flasks containing culture complete medium. Cells will be transferred as suspension in PBS to the QPatch 16X or QPatch HTX system to the centrifuge/washer directly.

Standard Laboratory Conditions: Cells will be incubated at 37° C. in a humidified atmosphere with 5% $CO_2$ (rel. humidity about 95%).

Culture media: The cells will be continuously maintained in and passaged in sterile culture flasks containing a 1:1 mixture of Dulbecco's modified eagle medium and nutrient mixture F-12 (D-MEM/F-12 1x, liquid, with L-Glutamine) supplemented with 10% fetal bovine serum, 1% Penicillin/Streptomycin solution, and 50 μM AP-5 blocker.

Antibiotics: The complete medium as indicated above is supplemented with 100 μg/mL hygromycin, 15 μg/mL blasticidin and 1 μg/mL puromycin.

Induction of Expression: 2.5 μg/mL tetracycline is added 24 h before start of experiments.

Dose Formulation

Dose levels are in terms of test compounds, as supplied. Vehicle will be added to achieve a stock concentration of 10 mM (storage at −10° C. to −30° C.). A further stock solutions of 1.0 mM will be prepared in DMSO. Details of stock solution usage (thawing, dose formulations) will be documented in the raw data. The time period of stock solution usage will be detailed in the report.

Test Compound Concentrations

Dose levels are in terms of test compounds, as supplied. Vehicle will be added to achieve a stock concentration of 10 mM (storage at −10° C. to −30° C.). A further stock solutions of 1.0 mM will be prepared in DMSO. Details of stock solution usage (thawing, dose formulations) will be documented in the raw data. The time period of stock solution usage will be detailed in the report.

One test concentration of 1.0 μM will be tested.

All test solutions will be prepared by diluting the stock solutions with either Mg-free bath solution only or Mg-free bath solution containing NMDA (300 μM) and glycine (8.0 μM) shortly prior to the electrophysiological experiments and kept at room temperature (19° C. to 30° C.) when in use. 0.1% DMSO will be used as vehicle.

Frequency of preparation: For each test concentration, fresh solutions of test compounds will be prepared every day.

Stability of dose formulation: All preparation times will be documented in the raw data. Any observations regarding instability of test compounds will be mentioned in the raw data.

Storage of dose formulation: On the day of experimentation dose formulations will be maintained at room temperature (19° C. to 30° C.) when in use.

Bath Solutions

For preparing the experiments and for formation of the giga-ohm-seal, the following standard bath solution will be used:

Sodium Chloride: 137 mM; Potassium Chloride: 4 mM; Calcium Chloride: 1.8 mM; Magnesium Chloride: 1 mM; HEPES: 10 mM; D-Glucose: 10 mM; Cremophor: 0.02%; pH (NaOH): 7.4

The 1x bath solution will be prepared by diluting 10x bath solution without Glucose and 100x Glucose solution with water at least every 7 days. Both stock solutions have been prepared prior to the experimental start of the present study and stored at 1° C. to 9° C. (10x bath solution) or −10° C. to −30° (100x Glucose solution). The batch number(s) of the bath solution(s) used in the experiments will be documented in the raw data. When in use, the 1x bath solution will be kept at room temperature (19° C. to 30° C.). When not in use, the 1x bath solution will be stored at 1° C. to 9° C.

After the giga-seal was formed the following Mg-free bath solution will be used:

Sodium Chloride: 137 mM; Potassium Chloride: 4 mM; Calcium Chloride; 2.8 mM; HEPES: 10 mM; D-Glucose: 10 mM; Cremophor: 0.02%; pH (NaOH): 7.4

This Mg-free bath solution will be prepared as a 1x solution and stored at 1° C. to 9° C. It will be prepared freshly at least every 10 days.

Intracellular Solution

The 1x intracellular solution will be thawed every day out of a frozen 1x intracellular solution, which has been prepared prior to the experimental start of the present study, aliquoted and stored at −10° C. to −30° C. When in use, the 1x intracellular solution will kept at room temperature (19° C. to 30° C.). Remaining 1x intracellular solution will be stored in the fridge (1° C. to 9° C.). The 1x intracellular solution will include the components outlined below:

Potassium Chloride: 130 mM; Magnesium Chloride: 1 mM; Mg-ATP: 5 mM; HEPES: 10 mM; EGTA: 5 mM; pH (KOH): 7.2

Cell Treatment

For this study, cells will continuously be perfused with NMDA/Glycine, Test Compound or Test Compound/NMDA/Glycin.

In every case, at least 30-second prewash steps with a test compound will be performed in between applications. For details see Table A below.

Each experiment type will be analyzed in at least n=3 isolated cells. The NMDA and Glycine stock solutions will be prepared prior to the experimental start of the present study, stored frozen (−10° C. to −30° C.) until the day of experimentation. Shortly prior to the electrophysiological experiments, frozen stock solutions will be thawed and diluted.

Control: The effect of vehicle (0.1% DMSO) and D-(−)-2-Amino-5-phosphonopentanoic acid (AP-5) (100 μM) will be measured at three cells every second week, in order to assure successful expression of NMDA receptors.

The 50 mM stock solution of AP-5 has been prepared prior to the experimental start of the present study, aliquoted and stored frozen (−10° C. to −30° C.) until the day of experimentation. Shortly prior to the electrophysiological experiments the frozen stock solution will be thawed and then diluted in Mg-free bath solution containing NMDA (300 μM) and glycine (8.0 μM), to give a final perfusion concentration of 100 μM.

Experimental Procedure

Cells are transferred as suspension in serum-free medium to the QPatch HTX system and kept in the cell storage tank/stirrer during experiments. All solutions applied to cells including the intracellular solution will be maintained at room temperature (19° C. to 30° C.).

During the sealing process standard bath solution described above will be used. All solutions applied to cells including the pipette solution will be maintained at room temperature (19° C. to 30° C.). After formation of a Gigaohm seal between the patch electrodes and transfected individual HEK293 cells only Mg-free bath solution will be perfused and the cell membrane will be ruptured to assure electrical access to the cell interior (whole-cell patch-configuration). Inward currents will be measured upon application of 300 μM NMDA (and 8.0 μM Glycine) to patch-clamped cells for 5 sec. During the entire experiment the cells will be voltage-clamped at a holding potential of −80 mV.

For the analysis of test compounds, NMDA receptors will be stimulated by 300 μM NMDA and 8.0 uM Glycine and test compound combinations described below. Thirty-second prewash steps with a test compound will be performed in between applications.

TABLE A

Application Protocol; use dependence of test compounds

| Appl. # | Duration (s) | Application |
|---|---|---|
| 1 | 4 | NMDA / Glycine |
| 2 | 30 | Bath |
| 3 | 4 | NMDA / Glycine 2 repetitions |
| 4 | 30 | 1 μM Test Compound |
| 5 | 4 | 1 μM Test Compound + NMDA / Glycine 6 repetitions |
| 6 | 30 | Bath |
| 7 | 4 | NMDA / Glycine 2 repetitions |

TABLE B

Application Protocol; control experiments

| Appl. # | Duration (s) | Application |
|---|---|---|
| 1 | 4 | NMDA / Glycine |
| 2 | 30 | Bath |
| 3 | 4 | NMDA / Glycine 2 repetitions |
| 4 | 30 | Bath |
| 5 | 4 | NMDA / Glycine 6 repetitions |
| 6 | 30 | Bath |
| 7 | 4 | NMDA / Glycine + 100 μM AP-5 2 repetitions |

Whole-Cell Patch Clamp of Mammalian Cells (Ionworks Barracuda (IWB)):

The whole-cell patch-clamp technique was used to investigate the effects of positive allosteric modulating activity of test compounds on GlunN1/GluN2A and GluN2B glutamate receptors expressed in mammalian cells. $EC_{50}$ and $E_{max}$ data are shown in Table 1.

HEK293 cells were transformed with adenovirus 5 DNA and transfected with cDNA encoding the human GRIN1/GRIN2A genes. Stable transfectants were selected using G418 and Zeocin-resistance genes incorporated into the expression plasmid and selection pressure maintained with G418 and Zeocin in the medium. Cells were cultured in Dulbecco's Modified Eagle Medium/Nutrient Mixture (D-MEM/F-12) supplemented with 10% fetal bovine serum, 100 μg/ml penicillin G sodium, 100 μg/ml streptomycin sulphate, 100 μg/ml Zeocin, 5 μg/ml blasticidin and 500 μg/ml G418.

Test article effects were evaluated in 8-point concentration-response format (4 replicate wells/concentration). All test and control solutions contained 0.3% DMSO and 0.01% Kolliphor® EL (C5135, Sigma). The test article formulations were loaded in a 384-well compound plate using an automated liquid handling system (SciClone ALH3000, Caliper LifeSciences). The measurements were performed using Ion Works Barracuda platform following this procedure:

Electrophysiological Procedures:
 a) Intracellular solution (mM): 50 mM CsCl, 90 mM CsF, 2 mM $MgCl_2$, 5 mM EGTA, 10 mM HEPES. Adjust to pH 7.2 with CsOH.
 b) Extracellular solution, HB-PS (composition in mM): NaCl, 137; KCl, 1.0; $CaCl_2$, 5; HEPES, 10; Glucose, 10; pH adjusted to 7.4 with NaOH (refrigerated until use).
 c) Holding potential: −70 mV, potential during agonist/PAM application: −40 mV.

Recording Procedure:
 a) Extracellular buffer will be loaded into the PPC plate wells (11 μL per well). Cell suspension will be pipetted into the wells (9 μL per well) of the PPC planar electrode.
 b) Whole-cell recording configuration will be established via patch perforation with membrane currents recorded by on-board patch clamp amplifiers.
 c) Two recordings (scans) will be performed. First, during pre-application of test article alone (duration of pre-application—5 min) and second, during test articles and agonist ($EC_{20}$ L-glutamate and 30 μM glycine) co-application to detect positive modulatory effects of the test article.

Test Article Administration: The first pre-application will consist of the addition of 20 μL of 2× concentrated test article solution and, second, of 20 μL of 1× concentrated test article and agonist at 10 μL/s (2 second total application time).

Potentiating Effect of Positive Allosteric Modulators (PAM) on the Channel

Potentiating effect of positive allosteric modulators (PAM) on the channel will be calculated as $$\% \text{ activation} = (I_{PAM}/I_{EC10-30}) \times 100\% - 100\%$$

where $I_{PAM}$ will be the L-glutamate $EC_{10-30}$—elicited current in presence of various concentrations of test articles and $I_{EC20}$ will be the mean current elicited with L-glutamate $EC_{20}$. PAM concentration-response data will be fitted to an equation of the form:

$$\% \text{ Activation} = \% \text{ L-glutamate } EC_{20} + \{(\% \text{ MAX} - \% \text{ L-glutamate } EC_{20})/[1+([Test]/EC_{50})^N]\},$$

where |Test| will be the concentration of PAM (test article), $EC_{50}$ will be the concentration of PAM producing half-maximal activation, N will be the Hill coefficient, % L-glutamate $EC_{20}$ will be the percentage of the current Elicited with L-glutamate $EC_{20}$, % MAX is the percentage of the current activated with the highest dose of PAM co-admitted with L-glutamate $EC_{20}$ and % Activation will be the percentage of the current elicited with L-glutamate $EC_{10-30}$ at each PAM concentration.

The maximal amplitude of the evoked currents are measured and defined as Peak Current Amplitude (PCA).

Abbreviations

PCC: pyridinium chlorochromate; t-BuOK: potassium tert-butoxide; 9-BBN: 9-borabicyclo[3.3.1]nonane; Pd(t-Bu$_3$P)$_2$: bis(tri-tert-butylphosphine)palladium(0); AcCl: acetyl chloride; i-PrMgCl: Isopropylmagnesium chloride; TBSCl: tert-Butyl(chloro)dimethylsilane; (i-PrO)$_4$Ti: titanium tetraisopropoxide; BHT: 2,6-di-t-butyl-4-methylphenoxide; Me: methyl; i-Pr: iso-propyl; t-Bu: tert-butyl; Ph: phenyl; Et: ethyl; Bz: benzoyl; BzCl: benzoyl chloride; CsF: cesium fluoride; DCC: dicyclohexylcarbodiimide; DCM: dichloromethane; DMAP: 4-dimethylaminopyridine; DMP: Dess-Martin periodinane; EtMgBr: ethylmagnesium bromide; EtOAc: ethyl acetate; TEA: triethylamine; AlaOH: alanine; Boc: t-butoxycarbonyl. Py: pyridine; TBAF: tetra-n-butylammonium fluoride; THF: tetrahydrofuran; TBS: t-butyldimethylsilyl; TMS: trimethylsilyl; TMSCF$_3$: (Trifluoromethyl)trimethylsilane; Ts: p-toluenesulfonyl; Bu: butyl; Ti(OiPr)$_4$: tetraisopropoxytitanium; LAH: Lithium Aluminium Hydride; LDA: lithium diisopropylamide; LiOH.H$_2$O: lithium hydroxide hydrates; MAD: methyl aluminum bis(2,6-di-t-butyl-4-methylphenoxide); MeCN: acetonitrile; NBS: N-bromosuccinimide; Na$_2$SO$_4$: sodium sulfate; Na$_2$S$_2$O$_3$: sodium thiosulfate; PE: petroleum ether; MeCN: acetonitrile; MeOH: methanol; Boc: t-butoxycarbonyl; MTBE: methyl tert-butyl ether; DIAD: diisopropyl azodicarboxylate; sat.: saturated; aq.: aqueous; hr/hrs: hour/hours; min/mins: minute/minutes.

Example 1: Synthesis of (3S,8S,9S,10R,13S,14S,17R)-10,13-dimethyl-17-((2S,3S)-4,4,4-trifluoro-3-hydroxybutan-2-yl)-3-(trifluoromethyl)-2,3,4,7,8,9,10,11,12,13,14,15,16,17-tetradecahydro-1H-cyclopenta[a]phenanthren-3-ol (1)

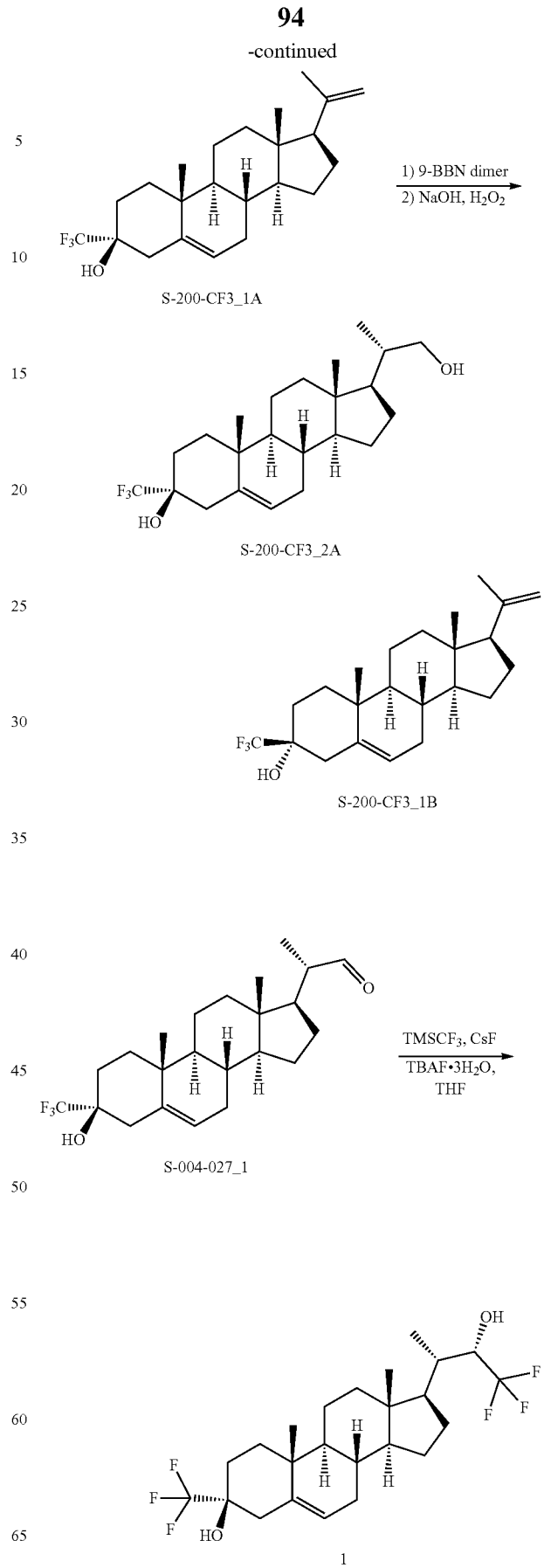

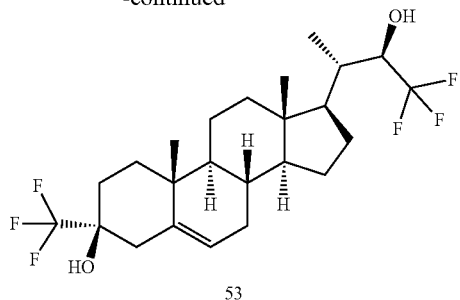

53

1. To a solution of TBAF (3.04 mL, 1 M in THF, 3.04 mmol, Aldrich) in THF (100 mL) was added TMSCF$_3$ (25.8 g, 182 mmol) followed by a solution of S-200-INT-2 (19 g, 60.8 mmol) in THF (100 mL) dropwise at 0° C. The mixture was stirred at 0° C. for 30 min. To the mixture was added TBAF (200 mL, 1 M in THF, 200 mmol, domestic) at 0° C. The mixture was stirred at 0° C. for another 30 mins. To the mixture was added NH$_4$Cl (100 mL, sat., aq.). The mixture was concentrated under vacuum. To the residue was added PE/EtOAc (400 mL, 1:1), the organic layer was separated, which was combined with other two batches (2×10 g of S200-INT-2). The combined organic layer was washed with water (300 mL), brine (300 mL), dried over Na$_2$SO$_4$, filtered and concentrated in vacuum to give an oil. The residue was dissolved in DCM (150 mL) and diluted with PE (750 mL). The solution was poured into a silica gel column (500 g, 100~200 mesh) and eluted with PE:DCM:EtOAc=5:1:0.05 to 5:1:0.1 to give S200-CF3_1B (12 g, 70% purity, 17% yield) as an oil and impure S200-CF3_1A. The impure was re-crystallized from MeCN (250 mL) to give S200-CF3_1A (6.5 g) as a solid. The filtrated form MeCN was purified by silica gel column (PE:DCM:EtOAc=50:1:1 to 20:1:1) to give a crude which was re-crystallized from MeCN (20 mL) to give S-200-CF3_1A (1 g, 16% total yield) as a solid.

Note: 200-CF3_1A and 200-CF3_1B were identified from $^3J_{H,CF}$, (FDCS). (*J. Org. Chem.* 2015, 80, 1754.

S-200-CF3_1A:

$^1$H NMR (400 MHz, CDCl$_3$) δ 5.43-5.33 (m, 1H), 4.85 (s, 1H), 4.71 (s, 1H); 2.49 (s, 2H); 2.11-1.97 (m, 4H), 1.95-1.32 (m, 14H), 1.30-0.98 (m, 7H), 0.59 (s, 3H).

S-200-CF3_1B:

$^1$H NMR (400 MHz, CDCl$_3$) δ 5.54-5.41 (m, 1H), 4.86 (s, 1H), 4.72 (s, 1H); 2.78-2.65 (m, 1H); 2.18-1.97 (m, 3H), 1.95-1.35 (m, 16H). 1.32-0.98 (m, 7H), 0.59 (s, 3H).

2. To a solution of S-200-CF3_1A (8 g, 20.9 mmol) in THF (80 mL) was added 9-BBN dimer (5.85 g, 24 mmol). The mixture was stirred at 40° C. for 1 h. The mixture was cooled to 0° C. To the mixture was added EtOH (12 mL), NaOH (41.8 mL, 5 M, aq.) and H$_2$O$_2$ (20.9 mL, 10 M, aq.) dropwise. The mixture was stirred at 50° C. for 1 h. To the mixture was added Na$_2$SO$_3$ (100 mL, 25%, aq.) after cooling. The mixture was extracted with EtOAc (300 mL). The organic layer was separated and purified by silica gel column (PE:EtOAc=10:1 to 5:1) to give S-200-CF3_2A (7.1 g, 85%) as a solid.

$^1$H NMR (400 MHz, CDCl$_3$) δ 5.42-5.32 (m, 1H), 3.64 (dd, J=3.2, 10.4 Hz, 1H), 3.37 (dd, J=6.8, 10.4 Hz, 1H), 2.49 (s, 2H), 2.32-1.92 (m, 4H), 1.92-1.70 (m, 4H), 1.70-1.29 (m, 8H), 1.29-0.91 (m, 11H), 0.71 (s, 3H).

3. DMP (6.31 g, 14.9 mmol) was added to a solution of S-200-CF3_5A (3 g, 7.49 mmol) in DCM (50 mL) at 25° C., after stirring at 25° C. for 30 min, the reaction mixture was quenched with saturated NaHCO$_3$ (100 mL) and DCM (100 mL) was added and stirred for 10 min. The DCM phase was separated and washed with saturated aqueous Na$_2$S$_2$O$_3$ (2×100 mL). The combined organic layer was washed with saturated brine (2×100 mL), dried over anhydrous Na$_2$SO$_4$, filtered and concentrated. The residue was purified by flash column (5~20% of EtOAc in PE) to give N-004-027_1 (1.5 g, 50%) as a solid.

$^1$H NMR (400 MHz, CDCl$_3$) δ 9.58-9.55 (m, 1H), 5.38-5.36 (m, 1H), 2.49 (s, 1H), 2.40-2.25 (m, 1H), 2.23-1.60 (m, 10H), 1.53-1.20 (m. 9H), 1.15-1.00 (m, 7H), 0.78-0.64 (m, 3H).

4. To a solution of N-004-027_1 (1.5 g, 3.76 mmol) in anhydrous THF (40 mL) was added CsF (1.42 g, 9.40 mmol) at 0° C. After stirring at 0° C. for 20 min, TMSCF$_3$ (1.33 g, 9.40 mmol) was added at 0° C. and stirred for 30 min. The color becomes light yellow. TBAF.3H$_2$O (4.74 g, 15.0 mmol) was added and stirred at 50° C. for 30 min. The reaction mixture was poured into ice-water (100 mL). The aqueous phase was extracted with EtOAc (2×100 mL). The combined organic phase was washed with saturated brine (2×100 mL), dried over anhydrous Na$_2$SO$_4$, filtered and concentrated to give a mixture of isomers (1.45 g, crude) as a yellow solid, which was purified by flash column (0~15% of EtOAc in PE) to give 53 (340 mg, 24%) as a white solid and 1 (200 mg, 14%) as a white solid.

1:

$^1$H NMR (400 MHz, CDCl$_3$) δ 5.38-5.36 (m, 1H), 4.10-4.00 (m, 1H), 2.49 (s, 2H), 2.19-2.12 (m, 1H), 2.06-1.61 (m, 10H), 1.53-1.29 (m, 6H), 1.27-0.98 (m, 10H), 0.71 (s, 3H).

LCMS Rt=1.121 min in 2 min chromatography, 30-90AB_2MIN_E, purity 100%,

MS 50-100_1_4 min·m, for C$_{24}$H$_{33}$F$_6$O [M+H—H$_2$O]$^+$ 451, found 451.

1:

$^1$H NMR (400 MHz, CDCl$_3$) δ 5.38-5.36 (m, 1H), 4.10-4.00 (m, 1H), 2.49 (s, 2H), 2.19-2.12 (m, 1H), 2.06-1.61 (m, 10H), 1.53-1.29 (m. 6H), 1.27-0.98 (m, 10H), 0.71 (s, 3H).

LCMS Rt=1.121 min in 2 min chromatography, 30-90AB_2MIN_E, purity 100%,

MS 50-100_1_4 min·m, for C$_{24}$H$_{33}$F$_6$O [M+H—H$_2$O]$^+$ 451, found 451.

Example 2: Synthesis of (3S,5S,8R,9S,10S,13S, 14S,17R)-17-((2S,3R)-3-hydroxy-6-methylheptan-2-yl)-3-(methoxymethyl)-10,13-dimethylhexadeca-hydro-1H-cyclopenta[a]phenanthren-3-ol (2)

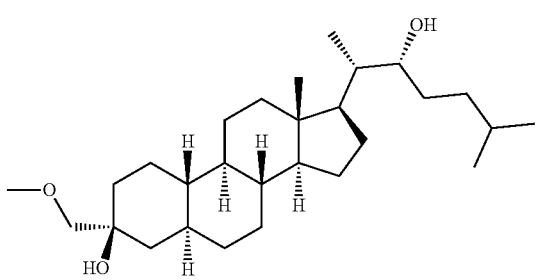

2

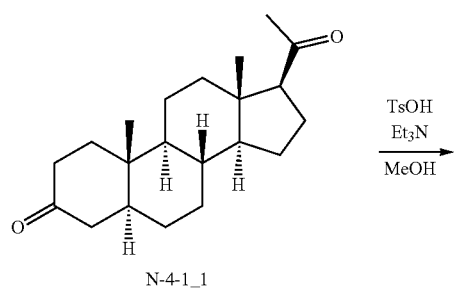
N-4-1_1
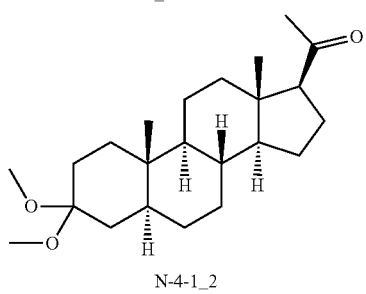
N-4-1_2
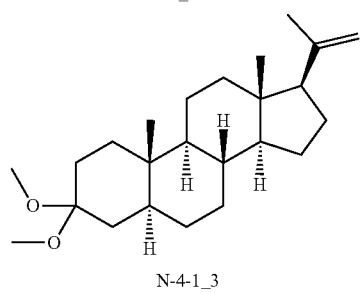
N-4-1_3
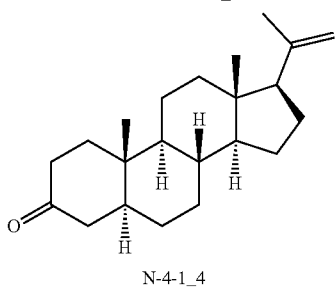
N-4-1_4
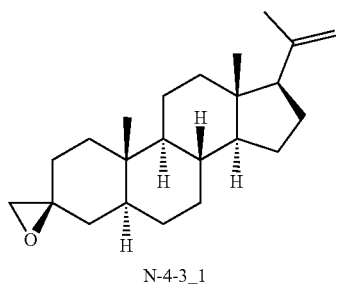
N-4-3_1
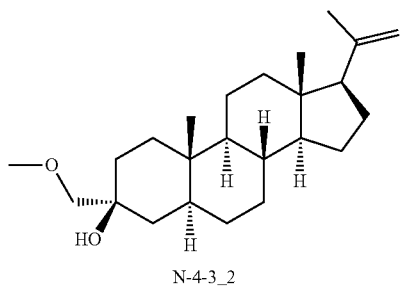
N-4-3_2
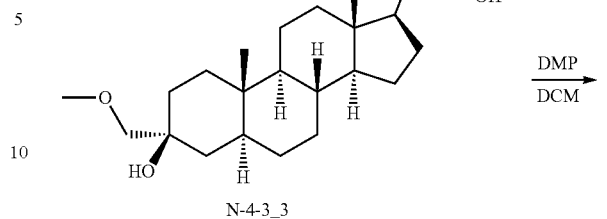
N-4-3_3
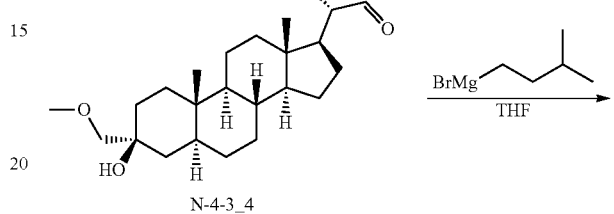
N-4-3_4
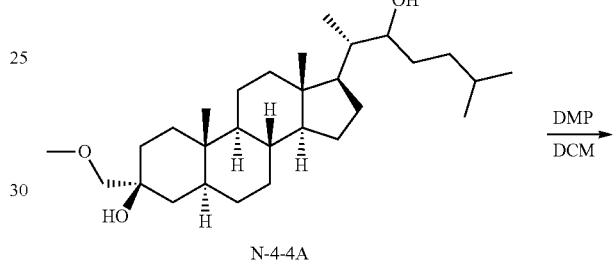
N-4-4A
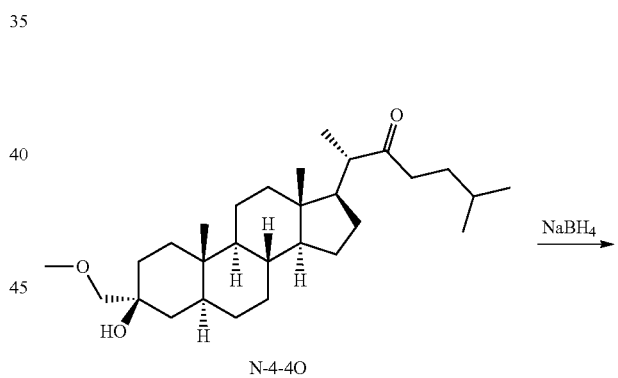
N-4-4O
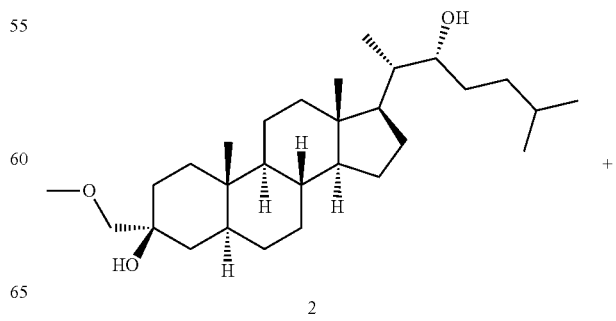
2

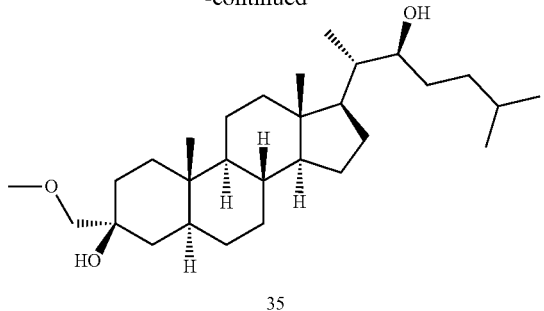

1. To a suspension of N-4-4_1 (50 g, 157 mmol) in anhydrous methanol (500 mL) at 20° C. was added anhydrous TsOH (2.84 g, 15.7 mmol) in one portion. The mixture was warmed up to 60° C. and stirred for 1 h. The reaction mixture was quenched with Et₃N (1.58 g, 15.7 mmol) and stirred for an additional 30 min. The precipitated solid was filtered out, washed with methanol (250 mL) and dried in air to give N-4-1_2 (51 g, 90%) as a solid.

$^1$H NMR (400 MHz, CDCl₃) δ 3.18 (s, 3H), 3.14 (s, 3H); 2.54-2.48 (m, 1H); 2.10-2.00 (m, 4H); 1.95-1.75 (m, 2H), 1.65-1.50 (m, 7H); 1.48-0.80 (m, 11H), 0.78-0.75 (m, 4H), 0.59 (s, 3H).

2. To a suspension of Ph₃PMeBr (75 g, 210 mmol) in anhydrous THF (500 mL) under N₂ at 20° C. was added t-BuOK (23.5 g, 210 mmol) in portions. The mixture became deep orange and stirred at 20° C. for 30 mins. Then N-4-1_2 (51 g, 140 mmol) was added. The mixture was warmed to 40° C. and stirred for 1 h. The reaction mixture was cooled and poured into aqueous NH₄Cl (ice)(400 mL) in portions. The resulting mixture was separated; the aqueous layer was extracted with THF (200 mL). The combined organic layer was used as a solution of N-4-1_3 directly without further purification.

3. To a solution of N-4-13 (50.4 g, 139 mmol) in THF (700 mL) was added aqueous HCl (1 M, 208 ml, 208 mmol) at 20° C. The mixture was stirred at 20° C. for 1 hr, and a solid precipitated. Water (200 mL) was added to the mixture, and the precipitated solid was filtered out, washed with water and dried to give N-4-1_4 (41 g, 94%) as a solid.

$^1$H NMR (400 MHz, CDCl₃) δ 4.85 (s, 1H), 4.70 (s, 1H); 2.38-2.25 (m, 3H); 2.10-1.98 (m, 3H), 1.88-1.49 (m, 10H), 1.40-1.08 (m, 11H), 0.97-0.72 (m, 2H), 0.58 (s, 3H).

4. To a solution of Me₃SI (101 g, 496 mmol) in anhydrous THF (400 mL) at 25° C. under N₂ was added t-BuOK (58.3 g, 520 mmol) in portions and stirred for 30 mins A solution of N-4-1_4 (39 g, 124 mmol) in anhydrous THF (300 mL) was added. The reaction mixture was warmed to 50° C. and stirred for 2 hrs. The reaction mixture was cooled to 25° C. and was treated with aq. NH₄Cl (500 mL). The aqueous phase was extracted with EtOAc (2×500 mL). The combined organic phase was washed with brine (2×300 mL), dried over anhydrous Na₂SO₄, filtered and concentrated under vacuum. The residue was purified by silica gel chromatography (PE/EtOAc=20/1 to 10/1) to afford N-4-3_1 (35 g, impure) as a solid.

$^1$H NMR (400 MHz, CDCl₃) δ 4.84 (s, 1H), 4.70 (s, 1H); 2.65-2.55 (m, 2H); 2.10-1.98 (m, 2H), 1.92-1.49 (m, 13H), 1.40-1.13 (m, 8H), 0.99-0.69 (m, 6H), 0.57 (s, 3H).

5. To a solution of N-4-3_1 (35 g, 647 mmol) in anhydrous MeOH (500 mL) was added MeONa (57.2 g, 1.06 mol) at 25° C. and the mixture was stirred 30 min under N₂. The reaction mixture was warmed to 70° C. and stirred at reflux for 3 hrs under N₂. The reaction mixture was cooled to 25° C. and treated with water (500 mL). The aqueous phase was extracted with DCM (2×300 mL). The combined organic phase was washed with saturated brine (2×300 mL), dried over anhydrous Na₂SO₄, filtered and concentrated in vacuum to obtain a solid. The residue was purified by silica gel chromatography (PE/EtOAc=10/1 to 6/1) to afford N-4-3_2 (25 g, impure) as a solid. The crude product was triturated from PE (250 mL) at 25° C. for 1 h. The suspension was filtered and the filter cake was dried under vacuum to obtain N-4-3_2 (15 g, 25%) as a solid.

$^1$H NMR (400 MHz, CDCl₃) δ 4.86 (s, 1H), 4.72 (s, 1H), 3.46-3.37 (m, 5H), 2.54 (s, 1H), 2.07-1.99 (m, 1H), 1.89-1.52 (m, 15H), 1.41-1.06 (m, 10H), 0.86 (s, 3H); 0.58 (s, 3H)

6. To a solution of N-4-3_2 (15 g, 41.6 mmol) in anhydrous THF (200 mL) was added 9-BBN dimer (27.7 g, 124 mmol) at 0° C. and stirred for 30 mins under N₂. The reaction mixture was warmed to 50° C. and stirred for 1 h. The reaction mixture was cooled to 0° C. and EtOH (50 mL) was added, then NaOH (41.6 mL, 5M, 208 mmol) at 0° C. was added very slowly. H₂O₂ (23.5 g, 208 mmol, 30% in water) was added slowly while keeping the inner temperature below 10° C. The mixture was warmed to 50° C. and stirred for another 1 h. The reaction mixture was cooled, poured into ice-water (500 mL) in portions and filtered. The filtrate was concentrated under vacuum to provide N-4-3_3 (14 g, crude) as an oil. The crude residue was used directly for the next step.

7. DMP (3.35 g, 7.92 mmol) was added to a mixture of N-4_3 (1 g, 2.64 mmol) in DCM (20 mL) at 25° C. The reaction mixture was warmed to 40° C. and stirred for 1 h. The reaction mixture was quenched with saturated aqueous NaHCO₃ at pH 7-8 and below 10° C. The suspension was filtered. The DCM phase in the filtrate was separated and washed with saturated NaHCO₃/Na₂S₂O₃ aqueous (1:1, 2×50 mL), brine (2×50 mL), dried over Na₂SO₄, filtrate and concentrated in vacuum to obtain a solid. The residue was purified by flash column (0-30% of EtOAc in PE) to give N-4-3_4 (0.6 g, 60%) as a solid.

$^1$H NMR (400 MHz, CDCl₃) δ 9.57 (s, 1H), 3.40-3.34 (m, 5H); 2.38-2.28 (m, 1H); 1.94-1.76 (m, 2H), 1.74-1.35 (m, 16H), 1.06-0.82 (m, 10H), 0.73-0.64 (m, 5H).

8. Isopentylmagnesium bromide (4.37 mL, 8.74 mmol 2 M in diethyl ether) was added to a solution of N-4-3_4 (0.6 g, 1.59 mmol) in anhydrous THF (10 mL) at 0° C. under N₂. The reaction mixture was warmed to 25° C. and stirred for 1 hour. To the reaction mixture was added saturated aqueous NH₄Cl (50 mL) solution. The aqueous phase was extracted with EtOAc (3×50 mL). The combined organic phase was washed with saturated brine (2×50 mL), dried over anhydrous Na₂SO₄, filtered and concentrated in to get N-4-4A (0.5 crude) as a solid.

$^1$H NMR (400 MHz, CDCl₃) δ 3.64-3.60 (m, 1H), 3.40-3.37 (m, 5H); 2.02-1.79 (m, 3H); 1.75-1.50 (m, 11H), 1.25-1.10 (m, 14H), 0.99-0.75 (m, 14H), 0.70-0.64 (m, 4H).

9. DMP (1.88 g, 4.44 mmol) was added to a solution of N-4-4A (0.5 g, crude) in DCM (20 mL) at 25° C. The reaction mixture was warmed to 40° C. and stirred for 1 hr. The reaction mixture was quenched with saturated NaHCO₃ aqueous at pH 7~8 and below 10° C. The suspension was filtered. The DCM phase was separated and washed with saturated NaHCO₃/Na₂S₂O₃ aqueous (1:1, 2×50 mL), brine (2×50 mL), dried over Na₂SO₄, filtered and concentrated under vacuum to get N-4-4O (0.4 g, crude) as a solid, which was used directly for the next step. NaBH₄ (0.340 g, 8.95 mmol) was slowly added to a solution of N-4-4O (0.4 g, 0.895 mmol) in MeOH (4 mL) was slowed added at 25° C.

and stirred for 2 hrs. The aqueous phase was extracted with DCM (2×20 mL). The combined organic phase was washed with saturated brine (2×20 mL), dried over anhydrous Na$_2$SO$_4$, filtered and concentrated under vacuum to obtain a solid. The residue was purified by silica gel chromatography (PE/EtOAc=8/1 to 5/1) to afford 35 (150 mg, impure) and 2 (130 mg, impure) as solids. 2 (130 mg, impure) was re-crystallized from MeCN (3 mL) at 82° C. reflux for 1 hr. The mixture was stirred and cooled to 25° C. The suspension was filtered and the filtrate concentrated under vacuum to provide 2 (50 mg, 12%) as a solid.

$^1$H NMR (400 MHz, CDCl$_3$) δ 3.63-3.61 (m, 1H), 3.41-3.38 (m, 5H); 2.51 (s, 1H); 1.97-1.81 (m, 2H), 1.71-1.31 (m, 15H), 1.26-1.03 (m, 10H), 0.97-0.78 (m, 14H), 0.71-0.59 (m, 4H). LCMS Rt=1.350 min in 2.0 min chromatography, 30-90 AB, purity 99%, MS ESI calcd. for C$_{29}$H$_{48}$O [M+H-2H$_2$O]$^+$413, found 413.

Example 3: Synthesis of (3S,8R,9S,10R,13S,14S, 17R)-3-ethyl-17-((2S,3R)-3-hydroxy-6-methylheptan-2-yl)-13-methyl-2,3,4,7,8,9,10,11,12,13,14,15,16,17-tetradecahydro-1H-cyclopenta[a]phenanthren-3-ol (3)

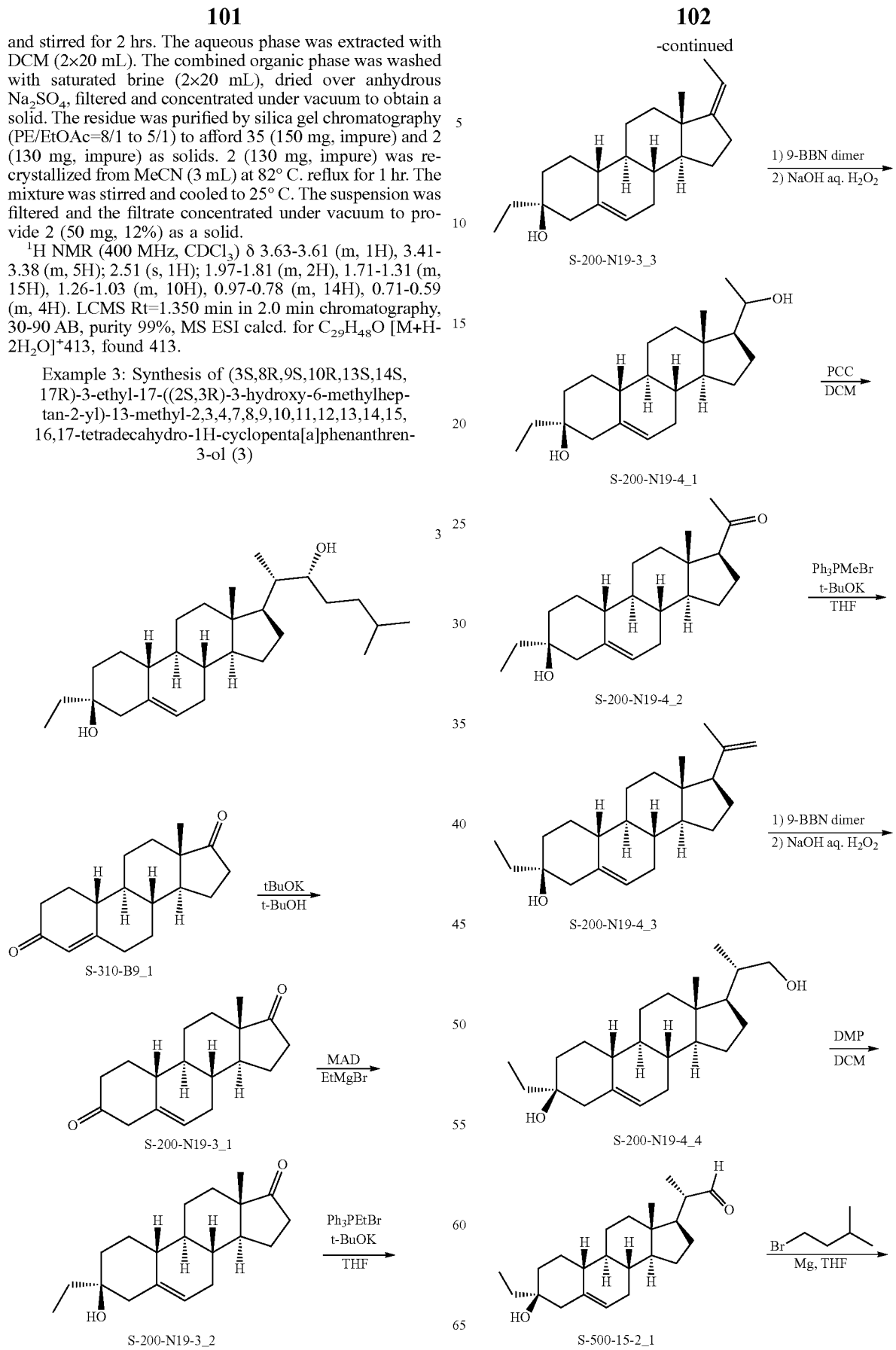

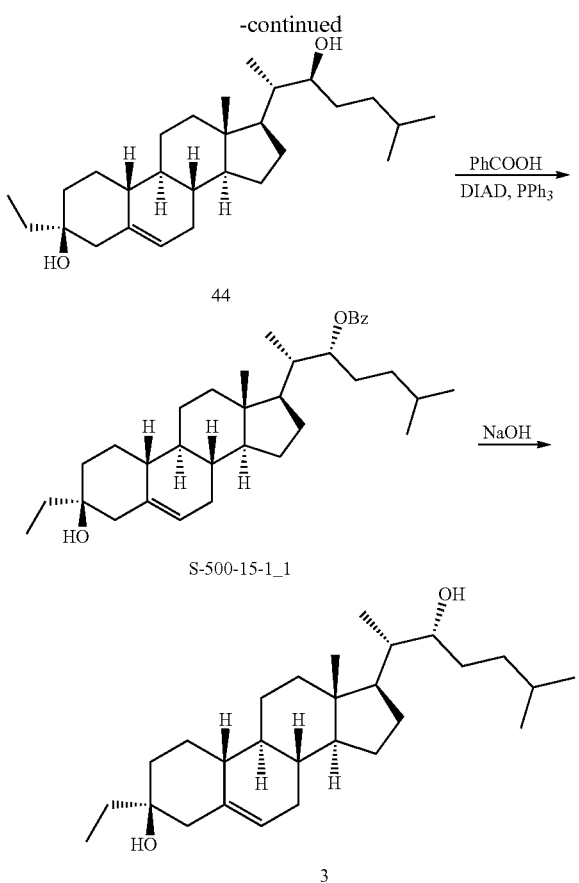

1. t-BuOH (350 mL) was charged into a three-neck round bottom flask under nitrogen at 35° C. and stirred under nitrogen gas for 10 mins. t-BuOK (90.5 g, 807 mmol) was added to the mixture and stirred under nitrogen gas for 15 mins. S-310-B9_1 (20 g, 73.4 mmol) was added to the above mixture and stirred under nitrogen gas at 35° C. for 1.5 hrs. The reaction mixture was poured into 10% aqueous acetic acid (500 mL) and stirred for 15 mins and below 35° C. Water (500 mL) was added and the mixture was stirred for 30 mins. The pH of the mixture was adjusted to 7~8 with sodium bicarbonate (500 ml) and stirred for 30 mins. The mixture was extracted with PE (2×500 mL). The organic layer was separated, washed with brine (500 mL), dried over anhydrous sodium sulfate, filtered and concentrated below 35° C. to give S-200-N19-3_1 (17 g, crude) as an oil. The crude residue was used directly for the next step.

2. To a solution of 2,6-di-tert-butyl-4-methylphenol (100 g, 453 mmol) in toluene (300 ml) was added, drop-wise, AlMe₃ (113 mL, 226 mmol, 2 M in toluene) at 0° C. The mixture was stirred at 25° C. for 1 hr to generate MAD. A solution of S-200-N19-3_1 (10 g, 36.7 mmol) in toluene (50 mL) was added dropwise to the MAD solution at −70° C. After stirring at −70° C. for 1 hour, MeMgBr (36.6 ml, 110 mmol, 3M in ethyl ether) was added drop wise at −70° C. The resulting solution was stirred at −70° C. for 1 hr. The reaction mixture was quenched by saturated citric acid (400 ml) at −70° C. After stirring at 25° C. for 10 min, the resulting mixture was filtered and washed with EtOAc (2×200 ml). The combined organic layer was separated, washed with brine (2×200 ml), dried over Na₂SO₄, filtered and concentrated under vacuum. The residue was purified by silica gel chromatography (PE/EtOAc=10/1 to 5/1) to yield S-200-N19-3_2 (7.6 g, impure) as a solid.

$^1$H NMR (400 MHz, CDCl$_3$) δ 5.45-5.40 (m, 1H), 2.51-2.38 (m, 1H), 2.49-2.21 (m, 1H), 2.14-1.88 (m, 5H), 1.86-1.77 (m, 2H), 1.73-1.38 (m, 8H), 1.34-1.22 (m, 4H), 0.95-0.81 (m, 8H).

3. To a suspension of PPh₃EtBr (37.1 g, 100 mmol) in THF (200 mL) under N₂ was added t-BuOK (11.2 g, 100 mmol) at 40° C. After stirring at 20° C. for 10 min, S-200-N19-3_2 (7.6 g, 25.1 mmol) was added. The reaction mixture was stirred at 40° C. for 1 hour. The reaction was quenched with aq.NH₄Cl (200 mL) at 0° C., extracted with EtOAc (3×200 mL). The combined organic phase was washed with brine (200 mL), dried over Na₂SO₄, filtered and concentrated. The residue was purified by Combi-flash (0%-30% of EtOAc in PE) to afford S-200-N19-3_3 (5 g, 63%) as a solid.

$^1$H NMR (400 MHz, CDCl$_3$) δ 5.45-5.35 (m, 1H), 5.20-5.00 (m, 1H), 2.41-2.30 (m, 1H), 2.29-2.12 (m, 3H), 2.09-1.76 (m, 6H), 1.69-1.38 (m, 15H), 1.35-0.94 (m, 7H).

4. To a solution of S-200-N19-3_3 (2 g, 6.35 mmol) in THF (20 mL) was added 9-BNN dimer (3.09 g, 12.7 mmol) at 0° C. under N₂. The solution was stirred at 60° C. for 1 hr. After cooling to 0° C., a solution of EtOH (20 ml) and NaOH (12.7 ml, 5M, 63.5 mmol) was added very slowly. After addition, H₂O₂ (2.15 mg, 6.35 mmol, 30% in water) was added slowly and the inner temperature was maintained below 10° C. The mixture was stirred at 60° C. under N₂ for 1 hr. The mixture was re-cooled to 30° C. Water (100 mL) was added to the solution and the aqueous layer extracted with EtOAc (100 mL). The organic layer was washed with brine (2×100 mL). The combined organic layer was dried over anhydrous Na₂SO₄, and was purified by silica gel chromatography (PE/EtOAc=2/1) to afford S-200-N19-4_1 (1.6 g, impure) as a solid.

$^1$H NMR (400 MHz, CDCl$_3$) δ 5.45-5.35 (m, 1H), 3.75-3.62 (m, 1H), 2.28-2.19 (m, 1H), 2.10-1.75 (m, 7H), 1.71-0.97 (m, 19H), 0.92-0.75 (m, 4H), 0.68 (s, 3H).

5. To a solution of S-200-N19-4_1 (1.6 g, 4.81 mmol) in DCM (20 mL) was added silica gel (2 g) and PCC (2.07 g, 9.62 mmol). The mixture was stirred at 25° C. for 3 hrs. To the mixture was added PE (50 mL). The mixture was filtered though a pad of silica gel and the solid was washed with PE/DCM (30 mL/30 mL). The mixture was filtered and the filtrate was concentrated under vacuum. The residue was purified by silica gel chromatography (PE/EtOAc=10/1 to 5/1) to afford S-200-N19-42 (1.2 g, impure) as a solid, which was re-crystallized from MeCN (10 mL) at reflux to provide S-200-N19-4_2 (1.0 g, 84.0%) as a solid.

$^1$H NMR (400 MHz, CDCl$_3$) δ 5.40-5.35 (m, 1H), 2.61-2.45 (m, 1H), 2.30-2.10 (m, 5H), 2.00-1.75 (m, 6H), 1.70-1.10 (m, 14H), 0.90-0.75 (m, 4H); 0.633 (s, 3H).

LCMS Rt=1.058 min in 2.0 min chromatography, 30-90 AB, purity 100% MS ESI calcd. for C$_{22}$H$_{34}$ [M+H—H$_2$O]$^+$ 313, found 313.

6. t-BuOK (3.51 g, 31.4 mmol) was added to a suspension of Ph₃PMeBr (11.1 g, 31.4 mmol) in THF (50 mL) under N₂ at 40° C. After stirring at 25° C. for 10 min, S-200-N19-4_2 (2.6 g, 7.86 mmol) was added. The reaction mixture was stirred at 40° C. for 1 h. The reaction was quenched with aqueous NH₄Cl (100 mL) at 0° C., which was extracted with EtOAc (2×100 mL). The combined organic phase was washed with brine (2×100 mL), dried over Na₂SO₄, filtered and concentrated. The residue was purified by Combi-flash (0%-30%, EtOAc in PE) to afford S-200-N19-43 (2.4 g, 93%) as a solid.

¹H NMR (400 MHz, CDCl₃) δ 5.45-5.35 (m, 1H), 4.86-4.83 (m, 1H), 8.70-4.65 (m, 1H), 2.27-2.20 (m, 1H), 2.10-1.90 (m, 4H), 1.89-1.50 (m, 11H), 1.49-1.30 (m, 3H), 1.28-1.00 (m, 6H), 0.80-0.60 (m, 5H), 0.59 (s, 3H).

7. 9-BBN dimer (9.27 g, 38.0 mmol) was added to a solution of S-200-N19-4_3 (5 g, 15.2 mmol) in THF (60 mL) at 0° C. under N₂. The solution was stirred at 60° C. for 1 h. After cooling to 0° C., a solution of EtOH (60 ml) and NaOH (30.4 ml, 5M, 152 mmol) was added very slowly. After addition, H₂O₂ (15.2 ml, 152 mmol, 30% in water) was added slowly and the inner temperature was maintained below 10° C. The mixture was stirred at 60° C. under N₂ for 1 hr. The mixture was re-cooled to 30° C. Water (100 mL) was added to the solution with EtOH (100 ml). A suspension was obtained, which was filtered and concentrated under vacuum to yield S-200-N19-4_4 (5 g, crude) as a solid.

¹H NMR (400 MHz, CDCl₃) δ 5.44-5.32 (m, 1H), 3.68-3.59 (m, 1H), 3.39-3.35 (m, 1H), 2.29-2.19 (m, 1H), 2.08-1.89 (m, 4H), 1.88-1.75 (m, 3H), 1.62-1.60 (m, 2H), 1.56-1.39 (m, 6H), 1.36-1.24 (m, 3H), 1.23-1.11 (m, 4H), 1.08-0.98 (m, 4H), 0.92-0.75 (m, 5H), 0.70 (s, 3H).

8. Dess-Martin periodinane (2.44 g, 5.76 mmol) was added to a solution of S-200-N19-4_4 (1 g, 2.88 mmol) in DCM (150 mL) at 25° C. The reaction was stirred at 25° C. for 1 hr. The reaction was stirred at 25° C. for 30 mins. The mixture was poured into saturated Na₂S₂O₃ (100 ml) at 0° C., which was extracted with DCM (3×100 ml). The combined organic layers were washed with saturated NaHCO₃ (100 mL×2), brine (100 mL), dried over Na₂SO₄, filtered and concentrated in vacuum to give crude product which was purified by a silica gel column (PE/EtOAc=10:1) to give S-500-15-2_1 (800 mg, 80%) as a solid.

¹H NMR (400 MHz, CDCl3) δ 9.58-9.57 (m, 1H), 5.40-5.38 (m, 1H), 2.37-2.35 (m, 1H), 2.25-2.23 (m, 1H), 2.08-1.76 (m, 7H), 1.65-1.63 (m, 2H), 1.53-1.37 (m, 5H), 1.31-1.21 (m, 4H), 1.19-1.00 (m, 6H), 0.90-0.80 (m, 5H), 0.73 (s, 3H).

9. A solution of 1-bromo-3-methylbutane (4 g, 26.4 mmol) in THF (27 mL) was added dropwise to a suspension of Mg (947 mg, 39.5 mmol) and I₂ (33.5 mg, 0.132 mmol) in THF (3 mL) at 60° C. The mixture was stirred at 60° C. for 1 hour. Freshly prepared isopentylmagnesium bromide (30 mL, 0.88 M in THF, 26.4 mmol) was added to a solution of S-500-15-2_1 (800 mg, 2.32 mmol) in THF (2 mL) under N₂ at 0° C. The mixture was stirred at 0° C. for 1 hour. To the mixture was added NH₄Cl (50 mL, sat. aq.). The mixture was extracted with EtOAc (2×50 mL). The combined organic phase was washed with brine (100 mL), dried over Na₂SO₄, filtered and concentrated in vacuum to give crude product which was purified by silica gel chromatography (PE/EtOAc=10/1 to 5/1) to give 44 (720 mg, 75%) as a solid.

¹H NMR (400 MHz, CDCl3) δ 5.40-5.38 (m, 1H), 3.63-3.61 (m, 1H), 2.23-2.21 (m, 1H), 2.10-1.74 (m, 7H), 1.69-1.58 (m, 2H), 1.54-1.34 (m, 8H), 1.33-1.00 (m, 11H), 0.95-0.75 (m, 14H), 0.70 (s, 3H).

LCMS Rt=1.289 min in 2 min chromatography, 30-90 AB, purity 100%, MS ESI calcd. For C₂₈H₄₅ [M+H-2H₂O]⁺ 381, found 381.

10a. To a solution of 44 (300 mg, 0.720 mmol) in THF (14 mL) was added benzoic acid (348 mg, 2.85 mmol) and triphenylphosphine (1.11 g, 4.27 mmol) at 25° C. under N2. After stirring at 25° C. for 20 mins, DIAD (780 mg, 3.86 mmol) was added at 0° C. under N₂. The mixture was stirred at 0° C. for 20 mins then warmed to 25° C. and stirred at 25° C. for 17 hrs. Water (100 mL) was added and the mixture was extracted with EtOAc (2×100 mL). The organic phase was washed with brine (100 mL), dried over Na₂SO₄, filtered, concentrated under vacuum to give crude product (1.5 g, crude) to be purified.

10b. To a solution of 44 (1.9 g, 4.55 mmol) in THF (70 mL) was added benzoic acid (2.19 g, 18.0 mmol) and triphenylphosphine (7.07 g, 27.0 mmol) at 25° C. under N₂. After stirring at 25° C. for 20 mins, DIAD (4.93 g, 24.4 mmol) was added at 0° C. under N₂. The mixture was stirred at 0° C. for 20 mins then warmed to 25° C. and stirred at 25° C. for 17 hrs. Water (250 mL) was added and the mixture extracted with EtOAc (2×250 mL). The organic phase was washed with brine (2×300 mL), dried over Na₂SO₄, filtered, concentrated in vacuum to give crude product. Combined with another batch from 300 mg of 44, to the crude product was purified by a silica gel column (PE/EtOAc=8/1) to give S-500-15-1_1 (1.2 g, impure) as an oil, which was used directly for the next step.

11. To a solution of S-500-15-1_1 (1.2 g, impure) in THF/MeOH (2 mL/2 ml) was added NaOH (400 mg) and H₂O (2 mL) at 25° C. The reaction was stirred at 50° C. for 16 h. After cooling, the reaction mixture was diluted with H₂O (20 mL) and extracted with EtOAc (2×30 mL). The combined organic layers were dried over Na₂SO₄, filtered and concentrated under vacuum. The crude product was purified by a silica gel column (PE/EtOAc=4/1) to give the product 3 (150 mg, impure), which was purified by triturated with MeCN (5 ml) at 25° C. to give 3 (30 mg, pure and 100 mg, impure) as a solid.

¹H NMR (400 MHz, CDCl3) δ 5.39-5.37 (m, 1H), 3.63-3.59 (m, 1H), 2.26-2.21 (m, 1H), 2.09-1.88 (m, 4H), 1.86-1.76 (m, 2H), 1.75-1.61 (m, 3H), 1.54-1.32 (m, 7H), 1.32-1.08 (m, 10H), 1.07-0.96 (m, 1H), 0.95-0.74 (m, 14H), 0.95-0.74 (m, 1H), 0.70 (s, 3H).

LCMS Rt=1.281 min in 2 min chromatography, 30-90 AB, purity 98%, MS ESI calcd. For C₂₈H₄₇O [M+H—H₂O]⁺399, found 399.

Example 4: Synthesis of (3S,5S,8R,9S,10S,13S, 14S,17R)-17-((2S,3S)-4-(4,4-dimethylcyclohexyl)-3-hydroxybutan-2-yl)-3-ethyl-10,13-dimethylhexadecahydro-1H-cyclopenta[a]phenanthren-3-ol (4)

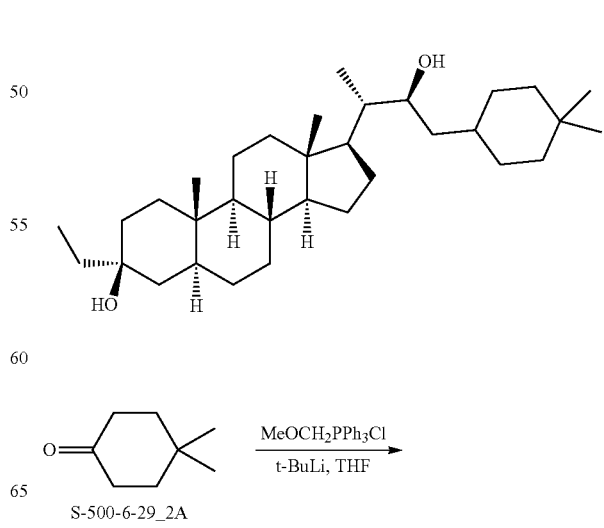

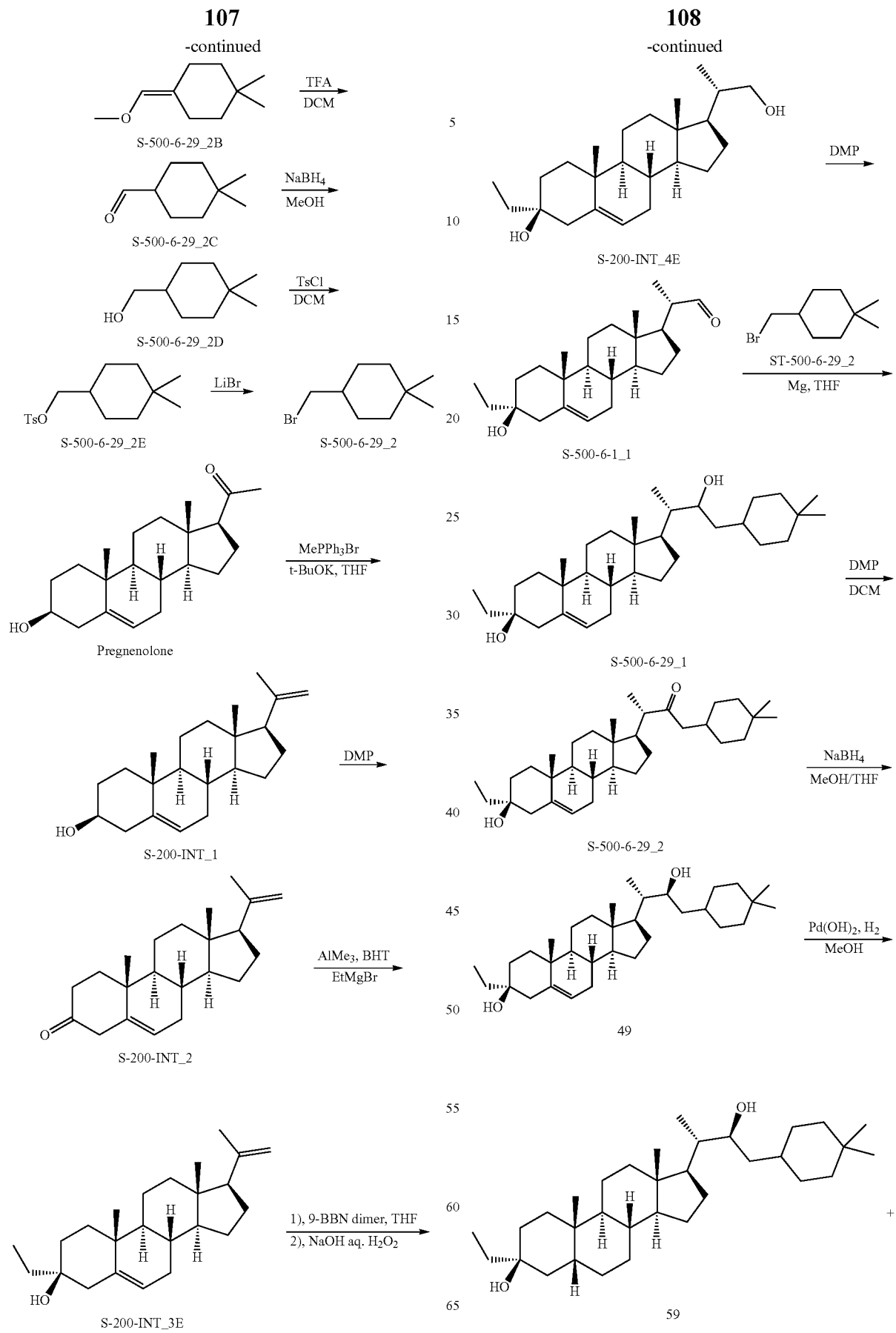

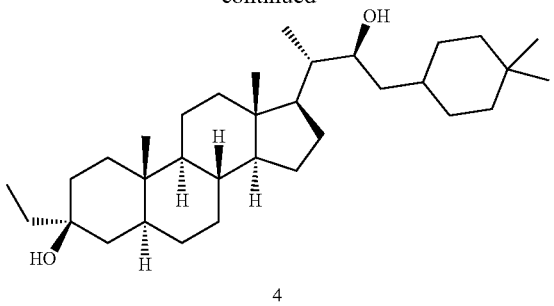

4

1. t-BuLi (90.7 mL, 118 mmol, 1.3 M in n-hexane, 3.0 eq) was added to a solution of chloro(methoxymethyl)triphenylphosphorane (40.4 g, 118 mmol, 3.0 eq) in THF (200 mL) at 0° C. After addition, the reaction mixture was stirred for 1 hour at 0° C. The mixture was added to a solution of S-500-6-29_2A (5 g, 39.6 mmol, 1.0 eq) in THF (50 mL) at 0° C. and the reaction mixture was stirred at 15° C. for 2 h. The mixture was treated with NH$_4$Cl (100 mL, 10%) and extracted with EtOAc (2×200 mL). The organic phase was separated and concentrated under vacuum to afford S-500-6-29_2B (18.0 g, crude).

$^1$H NMR (400 MHz, CDCl$_3$) δ 5.74 (s, 1H), 3.52 (s, 3H), 2.20-2.15 (m, 2H), 1.95-1.90 (m, 2H), 1.26-1.16 (m, 4H), 0.90 (s, 6H).

2. TFA (21.4 mL, 290 mmol) was added to a stirring solution of S-500-6-29_2B (5.6 g, impure) in DCM (25 mL) at 15° C. and stirred for 1.5 h at 15° C. The reaction mixture was quenched with saturated aqueous NaHCO$_3$ (10 mL) and extracted with EtOAc (2×20 mL). The combined organic layer was dried over anhydrous Na$_2$SO$_4$ and concentrated under reduced pressure to give S-500-6-29_2C (5.0 g, crude) as an oil, which was used for next step without purification.

$^1$H NMR (400 MHz, CDCl$_3$) δ 9.64 (s, 1H), 2.15-2.05 (m, 1H), 1.80-1.60 (m, 2H), 1.70-1.35 (m, 4H), 1.25-1.15 (m, 2H), 0.91 (s, 3H), 0.87 (s, 3H).

3. NaBH$_4$ (1.61 g, 42.7 mmol) was added to a solution of S-500-6-29_2C (5.0 g, 35.6 mmol) in MeOH (50 mL) at 15° C. under N$_2$. The mixture was stirred at 15° C. for 1 hr. The mixture was poured into water (50 mL) and stirred for 20 minutes. The aqueous phase was extracted with EtOAc (3×50 mL). The combined organic phase was washed with saturated brine (2×50 mL), dried over anhydrous Na$_2$SO$_4$, filtered and concentrated to give S-500-6-29_2D (5.6 g, crude) as an oil.

$^1$H NMR (400 MHz, CDCl$_3$) δ 3.47-3.42 (m, 2H), 1.60-1.50 (m, 2H), 1.42-1.30 (m, 4H), 1.25-1.0 (m, 4H), 0.91 (s, 3H), 0.87 (s, 3H).

4. TsCl (8.23 g, 43.2 mmol) was added to a solution of S-500-6-29_2D (5.6 g, 39.3 mmol) in pyridine (50 mL) at 15° C. under N$_2$. The mixture was stirred at 15° C. for 16 hrs. The mixture was poured into water (50 mL) and stirred for 20 minutes. The aqueous phase was extracted with DCM (3×40 mL). The combined organic phase was washed with saturated brine (2×200 mL), HCl (0.5M, 50 ml), dried over anhydrous Na$_2$SO$_4$, filtered and concentrated to give an oil, which was re-crystallized from hexane (50 mL) at 68° C. to give S-500-6-29_2E (4.2 g, 61%)} as a solid.

$^1$H NMR (400 MHz, CDCl$_3$) δ 7.80-7.76 (m, 2H), 7.35-7.25 (m, 2H), 3.86-3.80 (m, 2H), 2.45 (s, 3H), 1.60-1.45 (m, 3H), 1.40-1.30 (m, 2H), 1.20-1.05 (m, 4H), 0.88 (s, 3H), 0.82 (s, 3H).

5. LiBr (2.33 g, 26.9 mmol) was added to a solution of S-500-6-29_2E (2 g, 6.74 mmol) in acetone (50 mL). The mixture was stirred at 65° C. for 12 hrs. The mixture was quenched with water (50 mL) and extracted with MTBE (3×20 mL). The combined organic phase was washed with brine (50 mL), dried over Na$_2$SO$_4$, filtered and concentrated to give S-500-6-29_2 (1.3 g, crude) as a liquid. Combined with another batch from 2.2 g of S-500-6-29_2E, the combined crude product was filtered through a small silicone gel and washed with PE (100 mL) and concentrated to give S-500-6-29_2 (2.6 g, 90%) as an oil.

$^1$H NMR (400 MHz, CDCl$_3$) δ 3.34-3.28 (m, 2H), 1.72-1.64 (m, 2H), 1.60-1.48 (m, 1H), 1.42-1.35 (m, 2H), 1.28-1.18 (m, 4H), 0.91 (s, 3H), 0.87 (s, 3H).

6. To a solution of Ph$_3$PMeBr (167 g, 470 mmol) in THF (900 mL) was added t-BuOK (52.7 g, 470 mmol) at 25° C. The reaction mixture was heated to 60° C. and stirred for 1 hour. Pregnenolone (50 g, 157 mmol) was added. The reaction mixture was stirred at 60° C. for 1 hour. Sat. NH$_4$Cl (900 mL) was added. The mixture was extracted with EtOAc (2×1000 mL). The combined organic layer was washed with brine (2×2000 mL), dried over Na$_2$SO$_4$ and concentrated in vacuum to give a crude product as an oil, which was purified by column chromatography on silica gel (PE:EtOAc=20:1 to 5:1) to give S-200-INT_1 (45 g, 91.2%) as a solid.

$^1$H NMR (400 MHz, CDCl$_3$) δ 5.40-5.30 (m, 1H), 4.85 (s, 1H), 4.71 (s, 1H), 3.60-3.40 (m, 1H), 2.40-2.20 (m, 2H), 2.05-1.90 (m, 2H), 1.85-1.60 (m, 9H), 1.53-1.40 (m, 5H), 1.25-0.90 (m, 9H), 0.59 (s, 3H).

7. To a solution of S-200-INT_1 (45 g, 143 mmol) in DCM (1500 ml) was added DMP (108 g, 257 mmol) at 20° C. The reaction mixture was stirred at 20° C. for 2 hrs. Water (800 mL) was added and NaHCO$_3$ (200 g solid) was added. The mixture was filtered. The filtrate was washed with saturated Na$_2$S$_2$O$_3$ (2×2000 mL), dried over Na$_2$SO$_4$, filtered and concentrated under vacuum to give a solution of S-200-INT_2 in DCM (100 mL), which was used in the next step directly.

8. To a solution of BHT (191 g, 866 mmol) in toluene (500 mL) was added AlMe$_3$ (2 M in toluene, 216 mL, 433 mmol) at 10° C. and stirred for 1 hr. To the mixture was added a solution of S-200-INT_2 (Theoretical Mass: 44.6 g) in DCM (100 mL) at −78° C. The mixture was stirred at −78° C. for 1 hour. EtMgBr (141 mL, 426 mmol) was added at −78° C. The mixture was stirred at −78° C. for 20 mins. Saturated citric acid (1 L) was added. The organic phase was separated, washed with brine (600 mL), dried over Na$_2$SO$_4$ and concentrated in vacuum to give a crude product, which was purified by column chromatography on silica gel (PE:EtOAc=50:1 to 30:1) to give S-200-INT_3a (27 g, 55%) as a solid.

$^1$H NMR (400 MHz, CDCl$_3$) δ 5.35-5.25 (m, 1H), 4.85 (s, 1H), 4.71 (s, 1H), 2.40-2.30 (m, 1H), 2.10-1.60 (m, 14H), 1.50-0.75 (m, 17H), 0.58 (s, 3H).

9. 9-BBN dimer (17.6 g, 72.5 mmol) was added to a solution of S-200-INT_3E (5 g, 14.5 mmol) in THF (40 mL). The mixture was stirred at 60° C. under N2 for 3 hr, and a solid was formed. To the reaction mixture was added ethanol (8.33 mL, 145 mmol) and NaOH (28.9 mL, 5 M, 145 mmol). The mixture turned clear. H$_2$O$_2$ (14.4 mL, 10 M, 145 mmol) was added dropwise at 25° C. and the inner temperature was raised to reflux (75° C.). The mixture was cooled after addition and stirred for 1 hr, a solid was formed. To the mixture was added Na$_2$SO$_3$ (20 mL, 20% aq.) at 25° C. The mixture was extracted with EtOAc (2×100 mL). The combined organic phase was washed with brine (2×200 mL), dried over Na$_2$SO$_4$, concentrated under vacuum, and purified by silica gel column (PE/EtOAc=10/1 to 3/1) to provide S-200-INT_4E (3.5 g, 67%) as a solid.

¹H NMR (400 MHz, CDCl₃) δ 5.31-5.26 (m, 1H), 3.68-3.60 (m, 1H), 3.41-3.32 (m, 1H), 2.40-2.32 (m, 1H), 2.03-1.93 (m, 2H), 1.92-1.65 (m, 4H), 1.58-1.16 (m, 13H), 1.16-0.90 (m, 11H), 0.90-0.81 (m, 3H), 0.73-0.62 (s, 3H).

10. DMP (4.66 g, 11.0 mmol) was added to a solution of S-200-INT_4E (2 g, 5.54 mmol) in DCM (30 mL) at 25° C. The reaction mixture was stirred at 25° C. for 10 min. The reaction mixture was quenched with saturated aqueous NaHCO₃ (30 mL) at 25° C. The DCM layer was separated and the aqueous phase was extracted with DCM (30 mL). The combined organic phase was washed with saturated aqueous Na₂SO₃ (3×50 mL), brine (50 mL), dried over Na₂SO₄, filtered and concentrated under vacuum to give S-200-INT_5E (2.0 g, crude) as a solid.

¹H NMR (400 MHz, CDCl₃) δ 9.59-9.56 (m, 1H), 5.31-5.26 (m, 1H), 2.42-2.10 (m, 2H), 2.10-1.80 (m, 4H), 1.79-1.54 (m, 7H), 1.54-1.31 (m, 7H), 1.28-0.90 (m, 9H), 0.90-0.81 (m, 4H), 0.73 (s, 3H).

11. A solution of S-500-6-29_2 (2.56 g, 12.5 mmol) in THF (8 mL) was added dropwise to a suspension of Mg (600 mg, 25.0 mmol) and I₂ (63.4 mg, 0.25 mmol) in THF (3 mL) was added at 75° C. The mixture was stirred at 75° C. for 1 hour. After cooling, a solution of S-500-6-1_1 (1 g, 2.78 mmol) in THF (30 ml) was added slowly at 15° C. After addition, the mixture was stirred at 15° C. for 2 hrs, quenched with saturated NH₄Cl (40 mL) and saturated citric acid (20 mL) and extracted with EtOAc (3×20 mL). The combined organic phase was washed with brine (2×30 mL), dried over Na₂SO₄, filtered and concentrated and purified by combi-flash (0-15% of EtOAc in PE) to give a mixture of S-500-6-29_1 (800 mg, 60%) as a solid.

¹H NMR (400 MHz, CDCl₃) δ 5.33-5.19 (m, 1H), 3.88-3.71 (m, 1H), 2.42-2.29 (m, 1H), 2.07-1.86 (m, 4H), 1.78-1.59 (m, 4H), 1.54-1.31 (m, 13H), 1.29-1.13 (m, 8H), 1.12-0.99 (m, 8H), 0.94-0.79 (m, 13H), 0.68 (s, 3H).

12. DMP (1.39 g, 3.30 mmol) was added to a solution of S-500-6-29_1 (800 mg, 1.65 mmol) in DCM (30 mL). After that, the reaction mixture was stirred at 15° C. for 10 min. The reaction mixture was quenched with saturated NaHCO₃ aqueous (50 mL) until the pH of the aqueous layer was about 9. The mixture was filtered. The DCM layer was separated and the aqueous phase was extracted with DCM (20 mL). The combined organic phase was washed with saturated Na₂S₂O₃ aqueous (3×40 mL), sat.NaHCO₃ (40 mL), brine (40 mL), dried over Na₂SO₄, filtered and concentrated to give crude S-500-6-29_2 (800 mg, crude) as a solid.

¹H NMR (400 MHz, CDCl₃) δ 5.31-5.25 (m, 1H), 2.54-2.43 (m, 1H), 2.40-2.21 (m, 3H), 2.07-1.87 (m, 3H), 1.81-1.57 (m, 7H), 1.53-1.39 (m, 7H), 1.38-1.29 (m, 3H), 1.27-1.16 (m, 4H), 1.15-1.04 (m, 8H), 1.03 (s, 3H), 1.00-0.92 (m, 2H), 0.91-0.80 (m, 9H), 0.69 (s, 3H).

13. NaBH₄ (2.80 g, 82.5 mmol) was added five times, every five minutes, to a solution of S-500-6-29_2 (800 mg, 1.65 mmol) in MeOH (5 mL) and THF (5 mL). The mixture was stirred at 15° C. for 30 minutes. The mixture was quenched with saturated NH₄Cl (50 ml) and extracted with EtOAc (3×20 mL). The combined organic phase was dried over Na₂SO₄, filtered, concentrated and purified by combi-flash (0-15% of EtOAc in PE) to give 49 (290 mg, 36%) and 12 (120 mg, 45%) as a solid.

49:

¹H NMR (400 MHz, CDCl₃) δ 5.31-5.26 (m, 1H), 3.85-3.77 (m, 1H), 2.40-2.32 (m, 1H), 2.07-1.87 (m, 4H), 1.76-1.69 (m, 1H), 1.66-1.55 (m, 5H), 1.53-1.42 (m, 7H), 1.41-1.31 (m, 5H), 1.30-1.12 (m, 8H), 1.11-1.05 (m, 3H), 1.03 (s, 3H), 1.01-0.92 (m, 2H), 0.91-0.82 (m, 12H), 0.68 (s, 3H).

LCMS Rt=1.718 min in 2.0 min chromatography, 30-90AB_E, purity 98%, MS ESI calcd. for C₃₃H₅₃ [M+H-2H₂O]⁺ 449, found 449.

12:

¹H NMR (400 MHz, CDCl₃) δ 5.31-5.26 (m, 1H), 3.85-3.77 (m, 1H), 2.40-2.32 (m, 1H), 2.06-1.95 (m, 3H), 1.77-1.58 (m, 7H), 1.54-1.28 (m, 12H), 1.27-1.06 (m, 11H), 1.03 (s, 3H), 1.00-0.95 (m, 2H), 0.93-0.82 (m, 12H), 0.69 (s, 3H).

LCMS Rt=1.708 min in 2.0 min chromatography, 30-90AB_E, purity 100%, MS ESI calcd. for C₃₃H₅₃ [M+H-2H₂O]⁺ 449, found 449.

14. Pd(OH)₂ (200 mg, dry) was added to a solution of 49 (140 mg, 0.288 mmol) in MeOH (30 mL). The mixture was stirred at 50° C. under H₂ (50 Psi) for 48 hrs. The mixture was filtered, concentrated and purified by combi-flash (0-15% of EtOAc in PE) to give 59 (27 mg, 19%) and 4 (42 mg, 30%) as a solid.

4:

¹H NMR (400 MHz, CDCl₃) δ 3.84-3.76 (m, 1H), 1.98-1.85 (m, 2H), 1.69-1.54 (m, 9H), 1.53-1.46 (m, 3H), 1.45-1.28 (m, 9H), 1.27-1.20 (m, 4H), 1.19-1.13 (m, 5H), 1.12-1.02 (m, 4H), 1.01-0.92 (m, 2H), 0.91-0.85 (m, 12H), 0.82 (s, 3H), 0.70-0.61 (m, 4H).

LCMS Rt=1.799 min in 2.0 min chromatography, 30-90AB_E, purity 100%, MS ESI calcd. for C₃₃H₅₅ [M+H—H₂O]⁺ 451, found 451.

Example 5: Synthesis of (3S,8S,9S,10R,13S,14S, 17R)-3-ethyl-17-((2S,3S)-3-hydroxy-6,6-dimethyl-heptan-2-yl)-10,13-dimethyl-2,3,4,7,8,9,10,11,12,13, 14,15,16,17-tetradecahydro-1H-cyclopenta[a] phenanthren-3-ol (5)

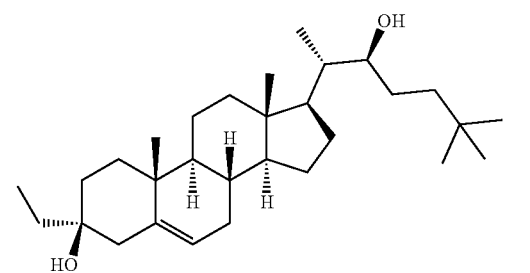

5

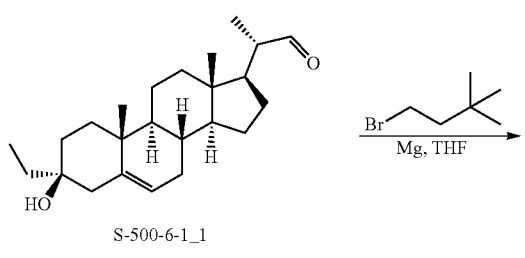

S-500-6-1_1

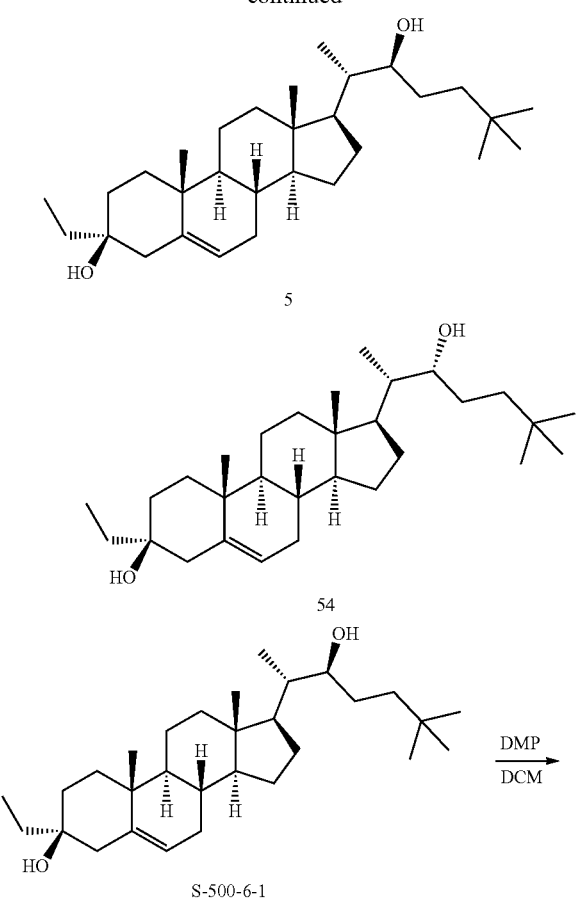

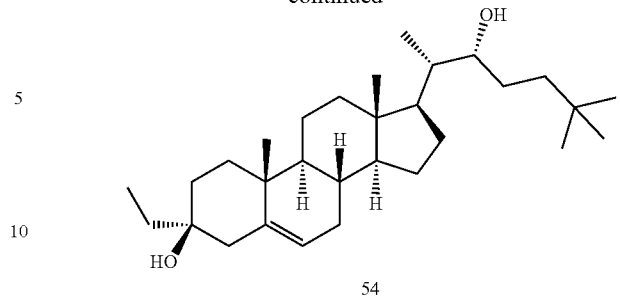

1. A solution of 1-bromo-3,3-dimethylbutane (3.68 g, 22.3 mmol) in THF (8 mL) was added dropwise to a suspension of Mg (1.08 g, 44.6 mmol) and $I_2$ (1 mg) in THF (2 mL) under $N_2$ at 50-55° C. The mixture was stirred at 55° C. for 1 hour. Then a solution of S-500-6-1_1 (0.8 g, 2.23 mmol) in THF (5 mL) was added to freshly prepared (3,3-dimethylbutyl)magnesium bromide (22.3 mmol in 10 mL of THF) at 0° C. The mixture was stirred at 15° C. for 2 hrs. To the mixture was added citric acid (20 mL, 10% aq.). The mixture was extracted with EtOAc (30 mL). The organic layer was separated and concentrated under vacuum to give a mixture which was separated by flash column (0~15% EtOAc in PE) to give 5 (580 mg, P1, 58%) and 54 (50 mg, 5%, impure).

5:
$^1$H NMR (400 MHz, $CDCl_3$) δ 5.33-5.24 (m, 1H), 3.65-3.54 (m, 1H), 2.41-2.31 (m, 1H), 2.11-1.84 (m, 4H), 1.76-1.38 (m, 15H), 1.38-1.00 (m, 12H), 0.93-0.80 (m, 15H), 0.70 (s, 3H).

54:
$^1$H NMR (400 MHz, $CDCl_3$) δ 5.33-5.24 (m, 1H), 3.62-3.52 (m, 1H), 2.41-2.31 (m, 1H), 2.11-1.90 (m, 3H), 1.75-1.00 (m, 28H), 1.00-0.75 (m, 18H), 0.70 (s, 3H).

2. DMP (1.1 g, 2.6 mmol) and water (1 drop) were added to a solution of 5 (580 mg, 1.3 mmol) in DCM (10 mL) at 20° C. The mixture was stirred at 20° C. for 2 h. Saturated $NaHCO_3$ solution (20 mL) and $Na_2S_2O_3$ (20 mL, sat.) were added to the mixture. The mixture was extracted with EtOAc (50 mL). The organic layer was washed with $NaHCO_3$/$Na_2S_2O_3$ (20+20 mL, sat.) twice, dried over $Na_2SO_4$, filtered, concentrated under vacuum to give S-500-6-1_3 (520 mg, 90%) as a solid.
$^1$H NMR (400 MHz, $CDCl_3$) δ 5.38-5.18 (m, 1H), 2.62-2.22 (m, 4H), 2.11-1.85 (m, 3H), 1.78-1.57 (m, 7H), 1.57-1.32 (m, 8H), 1.32-1.21 (m, 2H), 1.19-1.09 (m, 5H), 1.08-1.01 (m, 4H), 1.00-0.91 (m, 1H), 0.90-0.80 (m, 12H), 0.70 (s, 3H).

3. $NaBH_4$ (1.77 g, 46.8 mmol) was added in portions to a solution of S-500-6-1_3 (520 mg, 1.17 mmol) in THF (5 mL) and MeOH (10 mL) at 15° C. The mixture was stirred at 15° C. for 20 min. The mixture was quenched with $NH_4Cl$ (20 mL, sat. aq.) and extracted with EtOAc (50 mL). The organic layer was separated and concentrated in vacuum to give a mixture which was separated by flash column (0~15% EtOAc in PE) to give 5 (300 mg, impure) and 54 (170 mg, impure).

4. The impure 5 (300 mg, impure) was purified by flash column (0~12% EtOAc in PE) to give a solid. The solid was dissolved in MeCN (50 mL) at 60° C. and concentrated under vacuum to give 5 (270 mg, 52%) as a solid.

5:
$^1$H NMR (400 MHz, $CDCl_3$) δ 5.33-5.24 (m, 1H), 3.67-3.54 (m, 1H), 2.41-2.31 (m, 1H), 2.11-1.84 (m, 4H), 1.78-

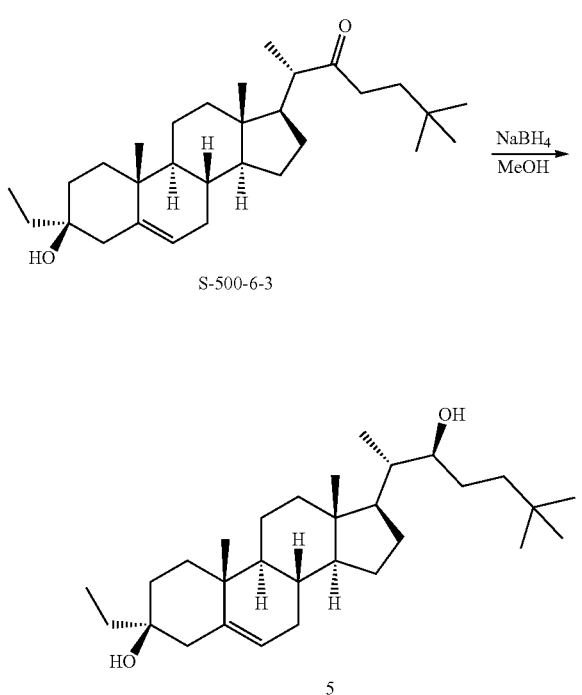

1.57 (m, 5H), 1.55-1.38 (m, 12H), 1.38-1.07 (m, 7H), 1.03 (s, 3H), 0.93-0.89 (m, 12H), 0.85 (t, J=7.6 Hz, 3H), 0.70 (s, 3H).

LCMS Rt=5.587 min in 7.0 min chromatography, 30-90_AB_E, purity 96.5%, MS ESI calcd. for $C_{30}H_{49}$ $[M+H-2H_2O]^+$ 409, found 409.

Example 6: Synthesis of (3S,8S,9S,10R,13S,14S, 17R)-17-((2S,3R)-5-cyclopropyl-3-hydroxypentan-2-yl)-3-ethyl-10,13-dimethyl-2,3,4,7,8,9,10,11,12, 13,14,15,16,17-tetradecahydro-1H-cyclopenta[a]phenanthren-3-ol (6)

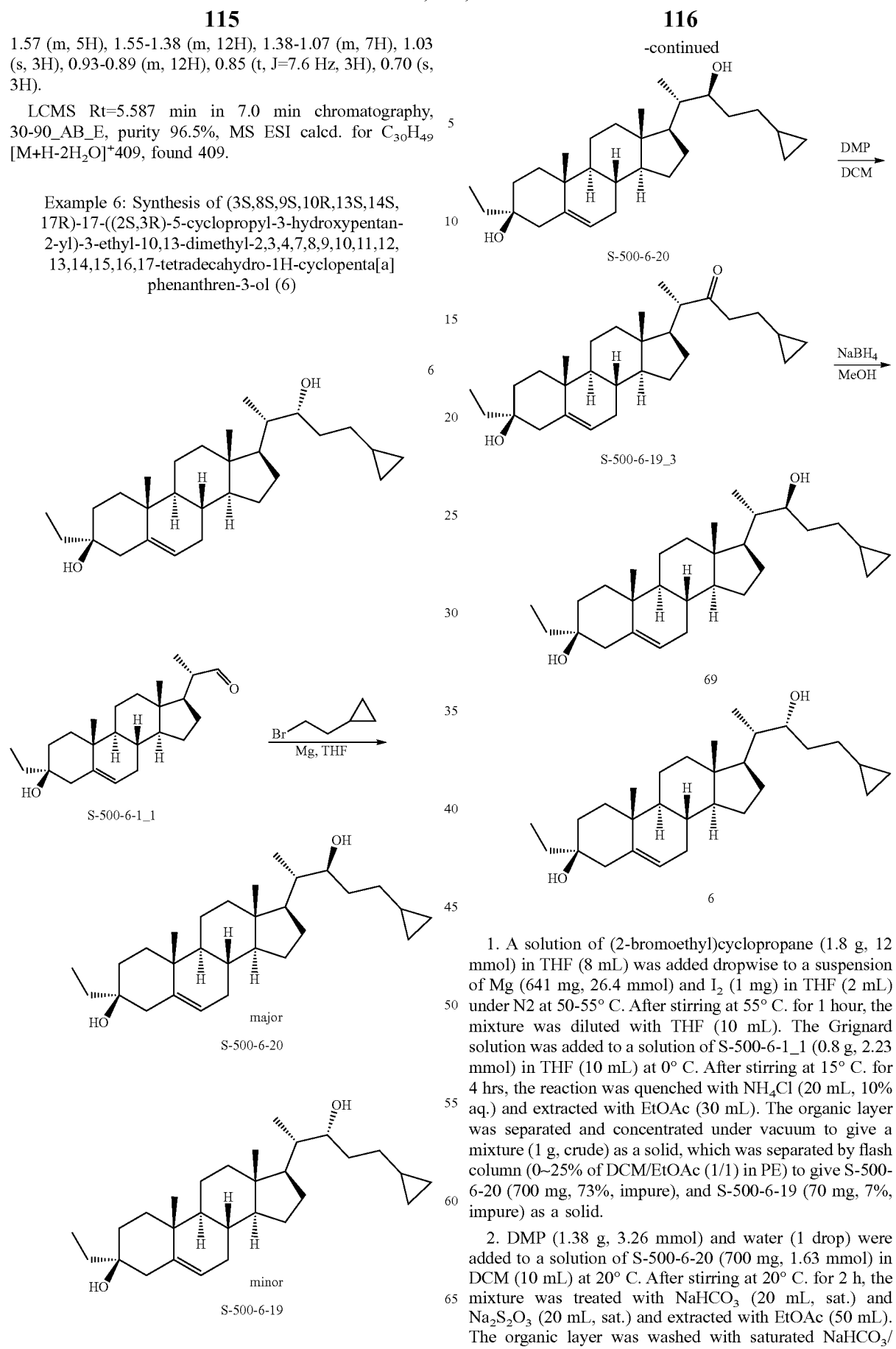

1. A solution of (2-bromoethyl)cyclopropane (1.8 g, 12 mmol) in THF (8 mL) was added dropwise to a suspension of Mg (641 mg, 26.4 mmol) and $I_2$ (1 mg) in THF (2 mL) under N2 at 50-55° C. After stirring at 55° C. for 1 hour, the mixture was diluted with THF (10 mL). The Grignard solution was added to a solution of S-500-6-1_1 (0.8 g, 2.23 mmol) in THF (10 mL) at 0° C. After stirring at 15° C. for 4 hrs, the reaction was quenched with $NH_4Cl$ (20 mL, 10% aq.) and extracted with EtOAc (30 mL). The organic layer was separated and concentrated under vacuum to give a mixture (1 g, crude) as a solid, which was separated by flash column (0~25% of DCM/EtOAc (1/1) in PE) to give S-500-6-20 (700 mg, 73%, impure), and S-500-6-19 (70 mg, 7%, impure) as a solid.

2. DMP (1.38 g, 3.26 mmol) and water (1 drop) were added to a solution of S-500-6-20 (700 mg, 1.63 mmol) in DCM (10 mL) at 20° C. After stirring at 20° C. for 2 h, the mixture was treated with $NaHCO_3$ (20 mL, sat.) and $Na_2S_2O_3$ (20 mL, sat.) and extracted with EtOAc (50 mL). The organic layer was washed with saturated $NaHCO_3$/

Na₂S₂O₃ (2×(20 mL/20 mL)), dried over Na₂SO₄, filtered, and concentrated under vacuum to give S-500-6-19_3 (700 mg, 100%) as a solid.

¹H NMR (400 MHz, CDCl₃) δ 5.35-5.20 (m, 1H), 2.72-2.26 (m, 4H), 2.17-1.87 (m, 3H), 1.82-1.35 (m, 13H), 1.35-1.20 (m, 2H), 1.20-0.91 (m, 12H), 0.85 (t, J=7.2 Hz, 3H), 0.80-0.62 (m, 4H), 0.53-0.33 (m, 2H), 0.12-0.00 (m, 2H).

3. NaBH₄ (2.46 g, 65.1 mmol) was added in portions to a solution of S-500-6-1_3 (700 mg, 1.63 mmol) in THF (5 mL) and MeOH (5 mL) at 15° C. After stirring at 15° C. for 20 mins, the mixture was quenched with NH₄Cl (20 mL, sat. aq.) and extracted with EtOAc (50 mL). The organic layer was separated and concentrated under vacuum to give 760 mg mixture as a solid, which was separated by flash column (0~35% of DCM/EtOAc (1/1) in PE) to give 69 (330 mg, 47%) and 6 (250 mg, 35%, impure) as a solid. The impure 6 (250 mg) was further separated by flash column (0~35% of DCM/EtOAc (1/1) in PE) to give 6 (170 mg, 23%) as a solid. 6:

¹H NMR (400 MHz, CDCl₃) δ 5.32-5.24 (m, 1H), 3.77-3.66 (m, 1H), 2.41-2.31 (m, 1H), 2.09-1.91 (m, 3H), 1.79-1.59 (m, 6H), 1.55-1.21 (m, 14H), 1.21-1.06 (m, 4H), 1.03 (s, 3H), 1.00-0.95 (m, 1H), 0.93 (d, J=6.8 Hz, 3H) 0.85 (t, J=7.6 Hz, 3H), 0.70 (s, 3H), 0.68-0.62 (m, 1H), 0.49-0.38 (m, 2H), 0.11-0.02 (m, 2H).

LCMS Rt=1.380 min in 2.0 min chromatography, 30-90_AB_E, purity 100%, MS ESI calcd. for C₂₉H₄₇O [M+H—H₂O]⁺411, found 411.

Example 7: Synthesis of (3S,5S,8R,9S,10S,13S,14S,17R)-3-ethyl-17-((1R,2S)-1-hydroxy-1-(pyridin-3-yl)propan-2-yl)-10,13-dimethylhexadecahydro-1H-cyclopenta[a]phenanthren-3-ol (7)

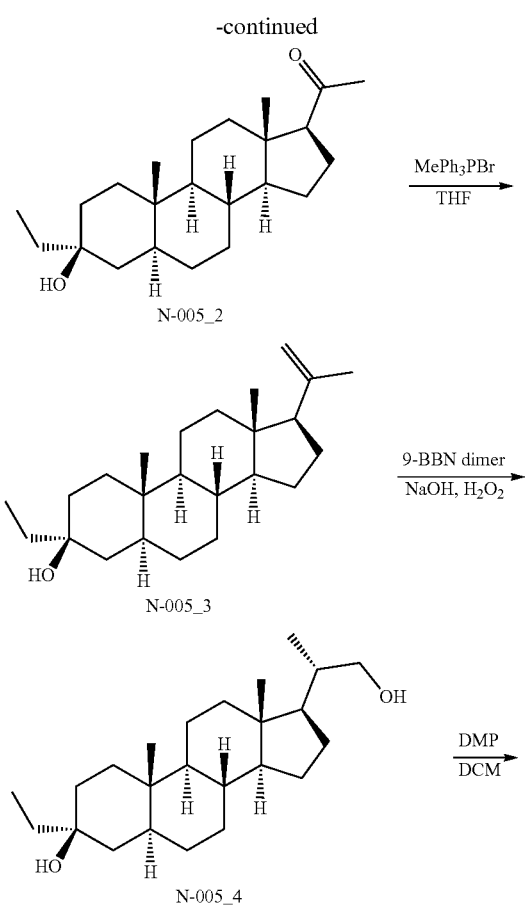

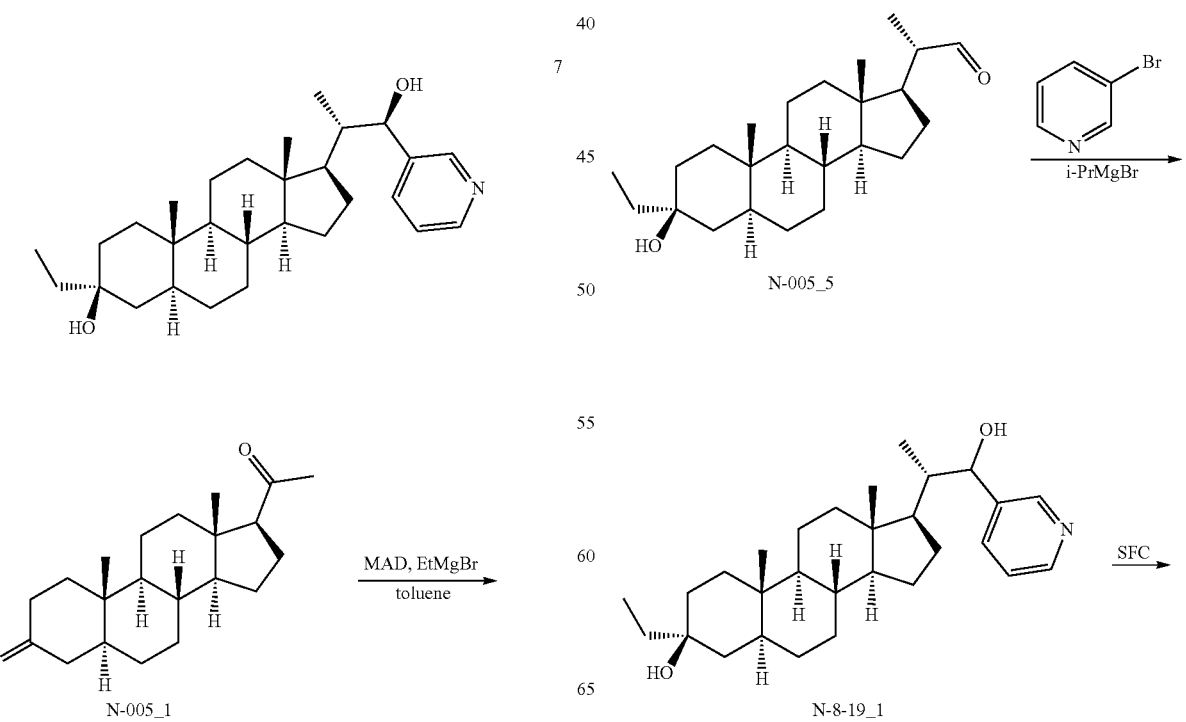

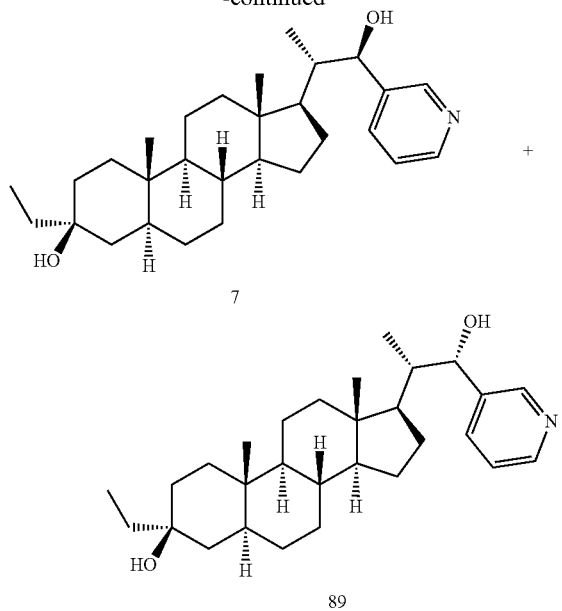

1. To a solution of BHT (416 g, 1.88 mol) in toluene (1500 mL) under $N_2$ at 0° C. was added trimethylaluminum (2 M in toluene, 469 mL, 939 mmol) dropwise. The mixture was stirred at 0° C. for 30 mins and used directly as a solution of MAD (0.47 M in toluene) without further purification. To a solution of MAD (0.47 M in toluene, 2.01 L, 945 mmol) under N2 at −70° C. was added a solution of N-005_1 (100 g, 315 mmol) in toluene (800 mL) dropwise. The mixture was stirred at −70° C. for 30 mins. To the above mixture was added EtMgBr (3 M in ethyl ether, 315 mL, 945 mmol) dropwise. The resulting mixture was stirred at −70° C. for 1 hr. The reaction mixture was poured to ice-cooled aqueous citric acid (1000 mL), extracted with EtOAc (2×600 mL). The combined organic layer was washed with brine (500 mL), dried over anhydrous sodium sulfate, filtered and concentrated. The residue was purified by silica gel chromatography (0-20% of EtOAc in PE) to give 85 g of N-005_2 as a solid (78% yield).

$^1$H NMR (400 MHz, $CDCl_3$) δ 2.55-2.46 (m, 1H), 2.19-2.12 (m, 1H), 2.11-2.09 (m, 3H), 2.08-1.96 (m, 1H), 1.71-1.48 (m, 10H), 1.47-1.31 (m, 5H), 1.30-1.09 (m, 7H), 1.06-0.94 (m, 2H), 0.92-0.87 (m, 3H), 0.86-0.79 (m, 3H), 0.75-0.64 (m, 1H), 0.60 (s, 3H).

2. To a suspension of $MePPh_3Br$ (174 g, 0.49 mol) in THF (1000 mL) was added t-BuOK (54.9 g, 0.49 mol) at 15° C. under $N_2$. After stirring at 50° C. for 30 mins, a solution of N-005_2 (85 g, 245 mmol) in THF (800 mL) was added in portions below 65° C. The mixture was stirred at 50° C. for 1 hr, quenched with $NH_4Cl$ (1000 mL), extracted with EtOAc (2×900 mL). The organic layer was separated, concentrated in vacuum to give a crude product which was triturated from MeOH/water (1.5 L, 1:1) at 50° C. The mixture was filtered after cooled and the filter cake was washed with MeOH/water (2×500 mL, 1:1), concentrated in vacuum to give N-005_3 (75 g, crude) as a solid.

$^1$H NMR (400 MHz, $CDCl_3$) δ 4.85-4.82 (m, 1H), 4.71-4.68 (m, 1H), 2.06-1.94 (m, 1H), 1.86-1.78 (m, 1H), 1.76-1.71 (m, 4H), 1.70-1.62 (m, 4H), 1.61-1.48 (m, 6H), 1.47-1.30 (m, 3H), 1.29-1.05 (m, 8H), 1.04-0.92 (m, 1H), 0.91-0.82 (m, 6H), 0.76-0.63 (m, 1H), 0.56 (s, 3H).

3. To a solution of N-0053 (75 g, 217 mmol) in THF (1800 mL) was added 9-BBN dimer (105 g, 434 mmol) under $N_2$. The mixture was stirred at 60° C. for 3 hrs. To the reaction mixture was added ethanol (124 mL, 2.17 mol) and NaOH aqueous (434 mL, 5 M, 2.17 mmol) in portions. Then $H_2O_2$ (217 mL, 10 M, 2.17 mol) was added dropwise at 0° C. The mixture was warmed to 65° C. and stirred for 1 hr and diluted with water (1.5 L). The reaction mixture was extracted with EtOAc (2×800 mL). The combined organic layer was added saturated aqueous $Na_2S_2O_3$ (600 mL) and stirred for 1 hour. The reaction was checked by potassium iodide-starch test paper to confirm excess $H_2O_2$ was destroyed. Then the organic phase was washed with saturated brine (2×500 mL), dried over anhydrous $Na_2SO_4$, filtered and concentrated in vacuum to give N-005_4 (78 g, crude) as a solid. The crude N-005_4 (78 g, impure) was triturated from MeOH/H2O=10/1 at 15° C. to give N-005_4 (70 g, impure) as a solid.

$^1$H NMR (400 MHz, $CDCl_3$) δ 3.68-3.60 (m, 1H), 3.41-3.32 (m, 1H), 1.99-1.92 (m, 1H). 1.88-1.75 (m, 1H), 1.69-1.45 (m, 10H), 1.44-1.29 (m, 4H), 1.28-1.15 (m, 6H), 1.14-0.91 (m, 8H), 0.90-0.79 (m, 7H), 0.67 (s, 3H).

4. To a solution of N-005_4 (70 g, 193 mmol) in DCM (800 mL) was added DMP (122 g, 289 mmol). After that, the reaction was stirred at 15° C. for 30 mins. The reaction mixture was added saturated aqueous $NaHCO_3$ (500 mL) solution and stirred at 15° C. for 20 mins. Saturated aqueous $Na_2S_2O_3$ (600 mL) was added and the mixture was stirred at 15° C. for another 1 hr. The reaction was checked by potassium iodide-starch test paper to confirm excess DMP was destroyed. The aqueous phase was extracted with DCM (2×400 mL). The combined organic layer was washed with aqueous saturated $NaHCO_3$ (400 mL) solution and brine (400 mL), dried over $Na_2SO_4$, filtered and concentrated in vacuum to give N-005_5 (70 g, impure) as a solid.

$^1$H NMR (400 MHz, $CDCl_3$) δ 9.58-9.55 (m, 1H), 2.39-2.30 (m, 1H), 1.95-1.78 (m, 2H), 1.69-1.42 (m, 10H), 1.41-1.30 (m, 4H), 1.29-1.14 (m, 5H), 1.13-0.95 (m, 6H), 0.94-0.86 (m, 4H), 0.85-0.81 (m, 3H), 0.69 (m, 4H).

5. i-PrMgCl (2.49 mL, 4.98 mmol, 2M in ether) was added to a solution of 3-bromopyridine (875 mg, 5.54 mmol) in THF (5 mL) dropwise. After stirring at 25° C. for 1 h, a solution of N-8-7_1 (200 mg, 0.554 mmol) in THF (5 mL) was added. After stirring at 25° C. for 16 hrs, the reaction mixture was quenched with $NH_4Cl$ (50 mL, 10% aq.) and extracted with EtOAc (2×20 mL). The combined organic phase was dried over $Na_2SO_4$, filtered, concentrated and purified by flash column (0-50% of EtOAc in DCM) to give N-8-19_1 (100 mg, 41%) as a solid.

6. N-8-19_1 (100 mg, 0.227 mmol) was separated by SFC (column: AD (250 mm*30 mm, 5 um), gradient: 50-50% B (A=0.05% $NH_3/H_2O$, B=MeOH), flow rate: 80 mL/min) to give 7 (Peak 1, 57 mg, 57%) and 89 (Peak 2, 8 mg, 8%) as a solid.

SFC Peak 1: Rt=1.798 min and Peak 2 Rt=1.985 min in 3 min chromatography, AD-H_3UM_4_5_40_4ML ("Chiralpak AD-350*4.6 mm I.D., 3 um Mobile phase: A: $CO_2$ B: iso-propanol (0.05% DEA) Gradient: from 5% to 40% of B in 1.4 min and hold 40% for 1.05 min, then 5% of B for 0.35 min Flow rate: 4 mL/min Column temp.: 40° C.").

7:

$^1$H NMR (400 MHz, $CDCl_3$) δ 8.56-8.52 (m, 1H), 8.49-8.45 (m, 1H), 7.68-7.62 (m, 1H), 7.29-7.24 (m, 1H), 5.01-4.95 (m, 1H), 2.11-2.01 (m, 1H), 1.96-1.89 (m, 1H), 1.83-1.76 (m, 1H), 1.73-1.63 (m, 4H), 1.59-1.47 (m, 6H), 1.43-

1.29 (m, 4H), 1.27-1.20 (m, 4H), 1.19-1.06 (m, 4H), 1.03-0.92 (m, 1H), 0.91-0.85 (m, 4H), 0.83 (s, 3H), 0.77-0.73 (m, 3H), 0.70-0.64 (m, 4H).

LCMS Rt=1.017 min in 2.0 min chromatography, 10-80AB_E, purity 100%, MS ESI calcd. for C$_{29}$H$_{46}$NO$_2$ [M+H]$^+$ 440, found 440.

SFC Rt=1.780 min in 3 min chromatography, AD-H_3UM_4_5_40_4ML, 100% de.

Example 8: Synthesis of (3S,5S,8R,9S,10S,13S,14S,17R)-17-((2S,3S)-3-hydroxy-6-methylheptan-2-yl)-3,10,13-trimethylhexadecahydro-1H-cyclopenta[a]phenanthren-3-ol (8)

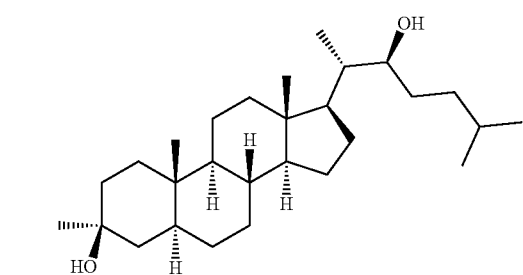

8

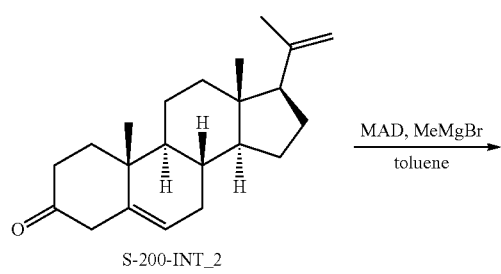

S-200-INT_2

MAD, MeMgBr
toluene

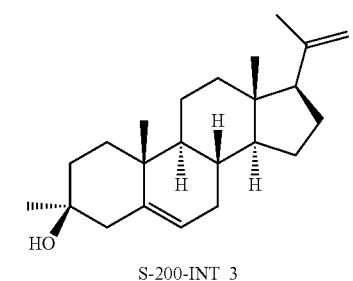

S-200-INT_3

1), 9-BBN dimer, THF
2), NaOH aq. H$_2$O$_2$

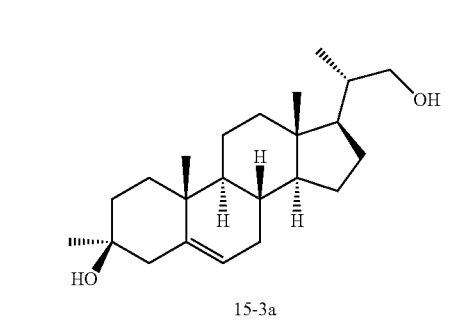

15-3a

DMP / DCM

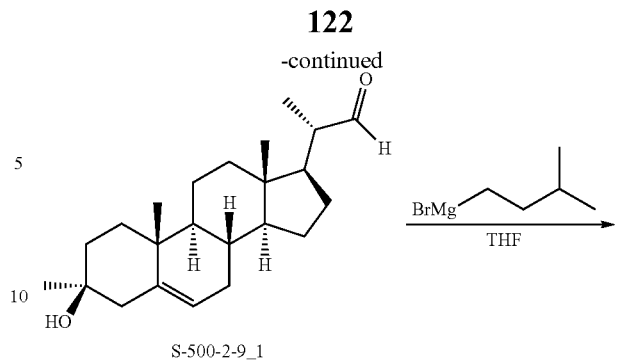

S-500-2-9_1

BrMg⟶ / THF

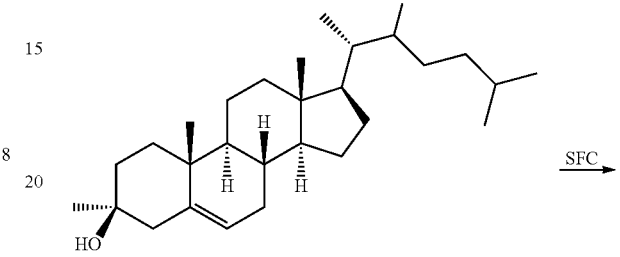

S-500-2-9-1A

SFC

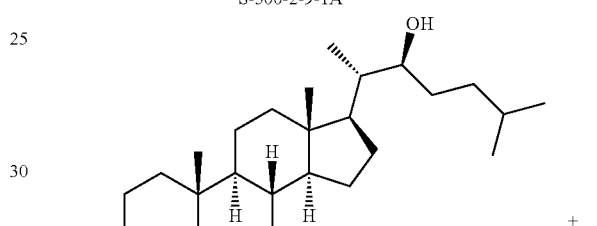

75

+

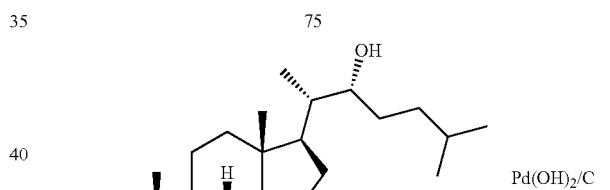

30

Pd(OH)$_2$/C

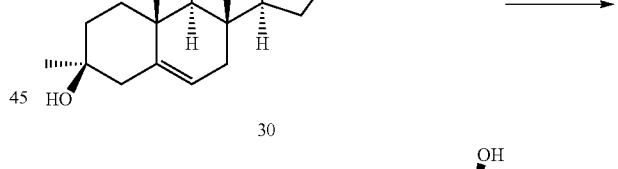

8

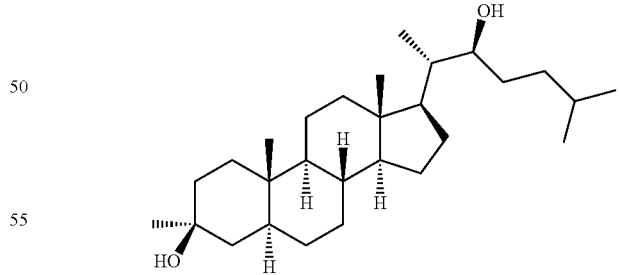

1. To a solution of BHT (1.97 kg, 8.94 mol) in toluene (1 L) was added AlMe$_3$ (2.14 L, 2.0 M in toluene, 4.28 mol) drop-wise blew 25° C. under N$_2$ atmosphere. The resulting mixture was stirred at 25° C. for 1 hour. S-200-INT_2 (794 g, 85% percent weight, 2.16 mol) in DCM (3 L) was added at −70° C. The mixture was stirred at −70° C. for 1 hour. MeMgBr (862 mL, 3.0 M in diethyl ether, 2.59 mol) was added at −70° C. The reaction mixture was stirred at −70° C. for 10 mins. The mixture was quenched by saturated critic acid (3 L), extracted with EtOAc (2×2 L). The combined organic phase was washed with brine (2 L), dried over Na$_2$SO$_4$, filtered and concentrated under vacuum to give a residue, which was triturated from MeCN (3 L) at 25° C. to give S-200-INT_3 (340 g, 43%) as a solid.

$^1$H NMR (400 MHz, CDCl$_3$) δ 5.34-5.26 (m, 1H), 4.85 (s, 1H), 4.71 (s, 1H), 2.50-2.35 (m, 1H), 2.07-1.94 (m, 3H), 1.91-1.84 (m, 1H), 1.83-.63 (m, 8H), 1.58-1.33 (m, 6H), 1.27-1.13 (m, 3H), 1.12 (s, 3H), 1.10-1.05 (m, 1H), 1.02 (s, 3H), 1.00-0.92 (m, 1H), 0.58 (s, 3H).

2. To a mixture of S-200-INT_3 (149 g, 453 mmol) and 9-BBN dimer (127 g, 520 mmol) was added THF (1 L) at 15° C. under N$_2$. The reaction mixture was stirred at 60° C. for 1 hour. The mixture was cooled to 15° C. EtOH (208 g, 4.53 mol) was added at 15° C. NaOH aqueous (906 mL, 5 M, 4.53 mol) was added drop-wise at 15° C. H$_2$O$_2$ (514 g, 30%, 4.53 mol) was added dropwise at 15° C. The obtained mixture was stirred at 60° C. for 1 hour. A solid was produced. The solid was washed with ethanol (200 mL) to give a solid, which was triturated with EtOH (2.3 L) at reflux and water (2.5 L) at 80° C. successively to give 15-3b (131 g, 84%) as a solid. The filtrate from ethanol was concentrated under vacuum to give 15-3b (30 g, crude) as a solid.

$^1$H NMR (400 MHz, CDCl$_3$) δ5.35-5.24 (m, 1H), 3.67-3.61 (m, 1H), 3.42-3.33 (m, 1H), 2.50-2.35 (m, 1H), 2.07-1.92 (m, 3H), 1.88-1.65 (m, 3H), 1.60-1.38 (m, 9H), 1.37-1.26 (m, 1H), 1.26-1.12 (m, 4H), 1.11 (s, 3H), 1.08 (s, 1H), 1.05 (d, J=6.8 Hz, 3H), 1.01 (s, 3H), 1.00-0.91 (m, 1H), 0.70 (s, 3H).

3. DMP (2.44 g, 5.76 mmol) was added to a solution of 15-3b (1 g, 2.88 mmol) in DCM (10 mL). After that, the reaction was stirred at 25° C. for 10 min. The reaction mixture was quenched by adding aqueous saturated NaHCO$_3$ solution (20 mL) and aqueous saturated Na$_2$S$_2$O$_3$ (20 mL) solution, extracted with DCM (2×50 mL). The combined organic layer was washed with aqueous saturated NaHCO$_3$ (3×50 mL) solution and brine (50 mL), dried over Na$_2$SO$_4$, filtered and concentrated under vacuum to give S-500-2-9_1 (1 g, crude) as a solid.

$^1$H NMR (400 MHz, CDCl$_3$) δ 9.57 (brs, 1H), 5.35-5.25 (m, 1H), 2.50-2.30 (m, 2H), 2.05-1.95 (m, 3H), 1.95-1.80 (m, 1H), 1.75-1.65 (m, 1H), 1.65-1.60 (m, 1H), 1.55-1.50 (m, 2H), 1.50-1.40 (m, 2H), 1.40-1.30 (m, 1H), 1.25-1.20 (m, 2H), 1.20-1.15 (m, 2H), 1.15-1.10 (m, 6H), 1.05-0.95 (m, 5H), 0.90-0.70 (m, 1H), 0.68 (s, 3H).

4. A mixture of magnesium (641 mg, 26.4 mmol) and I2 (33.5 mg, 0.132 mmol) was stirred at 60° C. and a solution of isopentylmagnesium bromide (2 g, 13.2 mmol) in THF (20 mL) was added dropwise under N$_2$. After that, the reaction mixture was stirred at 60° C. for 1 hr. The reaction mixture was used directly as isopentylmagnesium bromide solution without any purification. The Grignard solution was added to a solution of S-500-2-9_1 (1 g, 2.90 mmol) in THF (10 mL) at 0° C. under N$_2$. After that, the reaction mixture was stirred at 25° C. for 1 hr. The reaction mixture was added saturated aqueous NH$_4$Cl (50 mL) solution, extracted with EtOAc (2×50 mL), washed with brine (50 mL), dried over Na$_2$SO$_4$, filtered and concentrated in vacuum to give a crude product. The crude product was purified by silica gel column (EtOAc/PE=1/4) to give impure S-500-2-9-1A (560 mg) as a solid.

$^1$H NMR (400 MHz, CDCl$_3$) δ 5.28-5.25 (m, 1H), 3.90-3.80 (m, 0.25H), 3.68-3.58 (m, 0.75H), 2.48-2.36 (m, 1H), 2.05-1.95 (m, 3H), 1.95-1.80 (m, 1H), 1.80-1.75 (m, 1H), 1.75-1.52 (m, 6H) 1.52-1.42 (m, 6H), 1.42-1.32 (m, 3H), 1.32-1.22 (m, 3H), 1.22-1.12 (m, 3H), 1.12-1.02 (m, 2H), 1.01 (s, 3H), 1.00-0.92 (m, 1H), 0.92-0.85 (m, 9H), 0.85-0.77 (m, 1H), 0.69 (s, 3H).

5. S-500-2-9-1A (560 mg) was purified by SFC (Column: Chiralcel OD-3150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.) to give impure 30 (160 mg) as a solid and 75 (265 mg, 47%) as a solid.

$^1$H NMR (400 MHz, CDCl$_3$) δ 5.35-5.30 (m, 1H), 3.70-3.60 (m, 1H), 2.50-2.40 (m, 1H), 2.05-1.90 (m, 4H), 1.85-1.75 (m, 2H), 1.75-1.60 (m, 1H), 1.55-1.45 (m, 8H), 1.45-1.25 (m, 8H), 1.25-1.10 (m, 4H), 1.10-1.05 (m, 2H), 1.02 (s, 3H), 0.99-0.91 (m, 3H), 0.91-0.89 (m, 4H), 0.88 (s, 3H), 0.69 (s, 3H).

LCMS Rt=1.162 min in 1.5 min chromatography, 5-95 AB, purity 99%, MS ESI calcd. for C$_{28}$H$_{45}$[M+H-2H$_2$O]$^+$ 381, found 381.

6. Dry Pd(OH)$_2$/C (100 mg) was added to a solution of 75 (230 mg, 0.551 mmol) in THF (5 mL) and MeOH (5 mL). The reaction mixture was stirred at 50° C. for 24 h under H$_2$ and 50 Psi. After that, HNMR showed the reaction was completed. The reaction mixture was filtered with filter paper and concentrated in vaccum to give impure product. The impure product was re-crystallized with MeCN (3 mL) to give 8 (68 mg, 30%) as an off-white solid.

$^1$H NMR (400 MHz, CDCl$_3$) δ 3.65-3.55 (m, 1H), 2.00-1.80 (m, 2H), 1.76-1.60 (m, 3H), 1.55-1.48 (m, 3H), 1.48-1.38 (m, 4H), 1.38-1.26 (m, 7H), 1.26-1.23 (m, 4H), 1.23-1.06 (m, 5H), 1.06-1.02 (m, 3H), 1.02-095 (m, 1H), 0.95-0.85 (m, 10H), 0.81 (s, 3H), 0.70-0.60 (m, 4H).

LCMS Rt=1.171 min in 1.5 min chromatography, 5-95 AB, purity 100%.

MS MS ESI calcd. for C$_{28}$H$_{47}$[M+H-2H$_2$O]$^+$ 383, found 383.

Example 9: Synthesis of (3S,5R,8R,9S,10S,13S, 14S,17R)-3-(methoxymethyl)-10,13-dimethyl-17-((2S,3R)-4,4,4-trifluoro-3-hydroxybutan-2-yl)hexa-decahydro-1H-cyclopenta[a]phenanthren-3-ol (9)

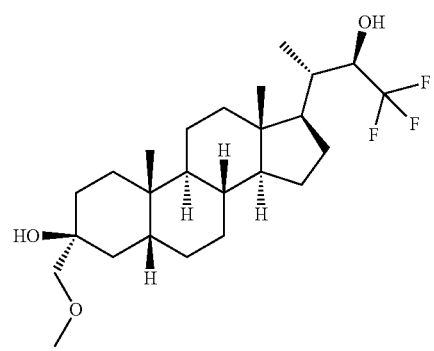

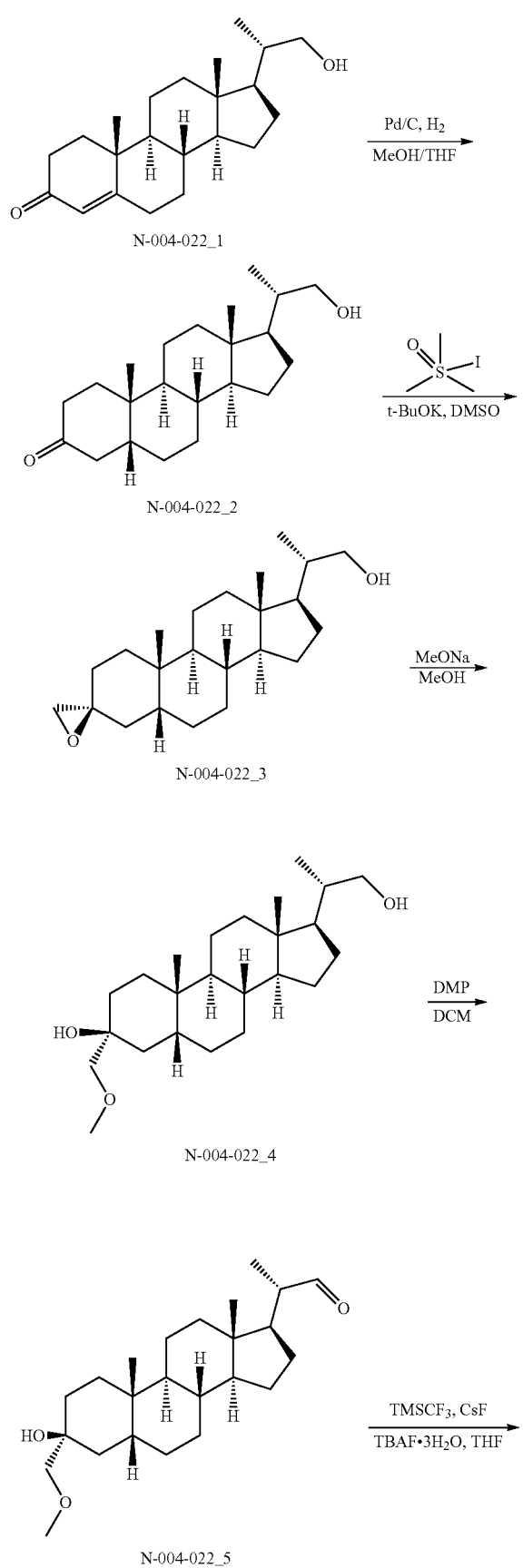

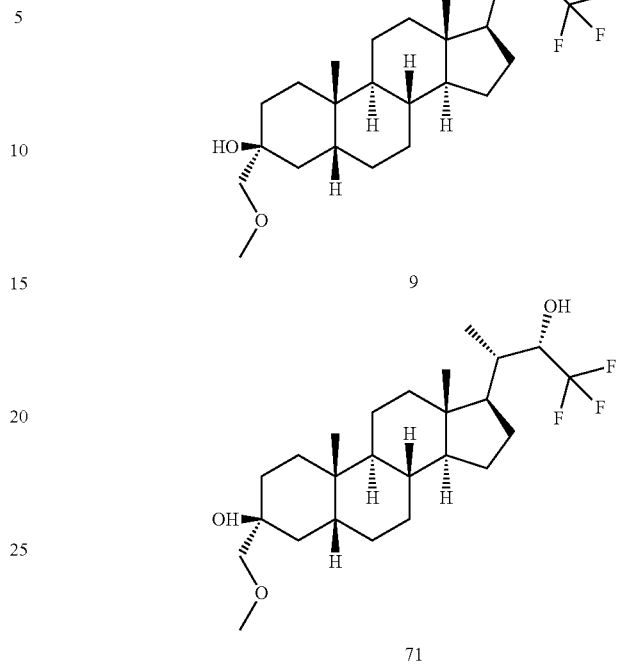

1. Pd/C (5 g, <1% water) was added to a solution of N-004-022_1 (50 g, 151 mmol) in MeOH (100 mL) and THF (100 mL). Then the solution was hydrogenated under 30 psi of hydrogen at 25° C. for 48 hrs. The mixture was filtered through a pad of celite and the filtrate was concentrated in vacuum to give N-004-022_2 (50 g, crude) as a solid.

$^1$H NMR (400 MHz, CDCl$_3$) δ 3.65-3.55 (m, 1H), 3.40-3.3 (m, 1H), 2.80-2.60 (m, 1H), 2.40-2.30 (m, 1H), 2.25-2.10 (m, 1H), 2.10-1.95 (m, 3H), 1.80-1.65 (m, 3H), 1.65-1.53 (m, 1H), 1.53-1.40 (m, 4H), 1.40-1.01 (m, 17H), 0.70 (s, 3H).

2. A stirred solution of trimethylsulfoxonium iodide (19.8 g, 90.2 mmol) and t-BuOK (10.1 g, 90.2 mmol) in DMSO (200 mL) was heated at 60° C. for 1 hr under N$_2$. N-004-022_2 (15 g, 45.1 mmol) was added to the reaction mixture and stirred at 60° C. for 10 mins. The reaction was treated with water (1000 mL), extracted with EtOAc (2×500 mL). The combined organic phase was washed with water (2×500 mL), brine (300 mL), dried over anhydrous Na$_2$SO$_4$, filtered, concentrated under vacuum to afford N-004-022_3 (15.5 g, crude) as a solid.

$^1$H NMR (400 MHz, CDCl$_3$) δ 4.18-4.08 (m, 1H), 3.67-3.60 (m, 1H), 3.40-3.30 (m, 1H), 2.70-2.50 (m, 3H), 2.40-2.30 (m, 1H), 2.01-1.50 (m, 14H), 1.40-0.65 (m, 14H), 0.68 (s, 3H).

3. MeONa (12.0 g, 223 mmol) was added to a solution of N-004-022_3 (15.5 g, 44.7 mmol) in MeOH (500 mL) at 25° C. under N$_2$. The mixture was stirred at 70° C. reflux for 16 hrs under N$_2$. The reaction was treated with water (500 mL). The aqueous phase was extracted with DCM (2×300 mL). The combined organic phase was washed with saturated brine (2×300 mL), dried over anhydrous Na$_2$SO$_4$, filtered and concentrate to give N-004-022_4 (15 g, crude) as a solid. The crude N-004-022_4 (15 g) was purified by silica gel chromatography (PE/EtOAc=10/1 to 5/1) to afford N-004-022_4 (7.4 g, 50%) as a solid.

$^1$H NMR (400 MHz, CDCl$_3$) δ 3.76-3.73 (m, 1H), 3.64-3.60 (m, 1H), 3.40-3.33 (m, 4H), 3.22-3.16 (m, 2H), 2.01-1.69 (m, 6H), 1.62-1.51 (m, 4H), 1.44-1.31 (m, 13H), 1.10-0.99 (m, 5H), 0.97 (s, 3H), 0.67 (s, 3H).

4. DMP (1.56 g, 3.69 mmol) was added to a solution of N-004-022_4 (1.4 g, 3.69 mmol) in DCM (15 mL). After that, the reaction mixture was stirred at 25° C. for 10 min. The reaction mixture was quenched with saturated NaHCO$_3$ aqueous (20 mL) until pH=9. The mixture was filtered. The DCM layer was separated and the aqueous phase was extracted with DCM (20 mL). The combined organic phase was washed with saturated Na$_2$S$_2$O$_3$ aqueous solution (3×10 mL), sat. NaHCO$_3$ solution (10 mL), brine (20 mL), dried over Na$_2$SO$_4$, filtered and concentrated. The residue was triturated with MeCN (10 mL) to give N-004-022_5 (700, impure) as a solid.

$^1$H NMR (400 MHz, CDCl$_3$) δ 9.56-9.58 (m, 1H), 3.39 (s, 3H), 3.24-3.18 (m, 2H), 2.40-2.31 (m, 1H), 2.01-1.50 (m, 11H), 1.47-1.01 (m, 16H), 0.97 (s, 3H), 0.70 (s, 3H).

5. To a solution of N-004-022_5 (200 mg, 0.531 mmol), CsF (40.2 mg, 0.265 mmol) in THF (5 mL) was added TMSCF$_3$ (187 mg, 1.32 mmol) under N$_2$ at 0° C. The mixture was stirred at 25° C. for 1 hrs. To the mixture was added TBAF.3H2O (836 mg, 2.65 mmol). After stirring at 25° C. for 2 hrs, the mixture was quenched 50% NH$_4$Cl (20 mL) and extracted with EtOAc (2×10 mL). The combined organic phase was washed with brine (20 mL), dried over anhydrous Na$_2$SO$_4$, filtered and concentrated in vacuum. The residue was purified by silica gel chromatography (100-200 mesh silica gel, PE/EA=10/1) to afford 9 (56 mg, 24%) and 71 (30 mg, impure) as a white solid.

9:

$^1$H NMR (400 MHz, CDCl$_3$) δ 4.05-3.95 (m, 1H), 3.39 (s, 3H), 3.24-3.18 (m, 2H), 2.00-1.83 (m, 5H), 1.77-1.68 (m, 2H), 1.64-1.47 (m, 8H), 1.43-1.35 (m, 5H), 1.31-1.08 (m, 6H), 1.06-1.00 (m, 3H), 0.97 (s, 3H), 0.70 (s, 3H).

LCMS Rt=1.156 min in 2 min chromatography, 30-90AB_2 min·1 cm, purity 100%, MS ESI calcd. for C$_{25}$H$_{41}$F$_3$O$_3$ [M+Na]$^+$ 469, found 469.

Example 10: Synthesis of (3S,5S,8R,9S,10S,13S, 14S,17R)-17-((1S,2S)-1-cyclopropyl-1-hydroxypropan-2-yl)-3-ethyl-10,13-dimethylhexadecahydro-1H-cyclopenta[a]phenanthren-3-ol (10)

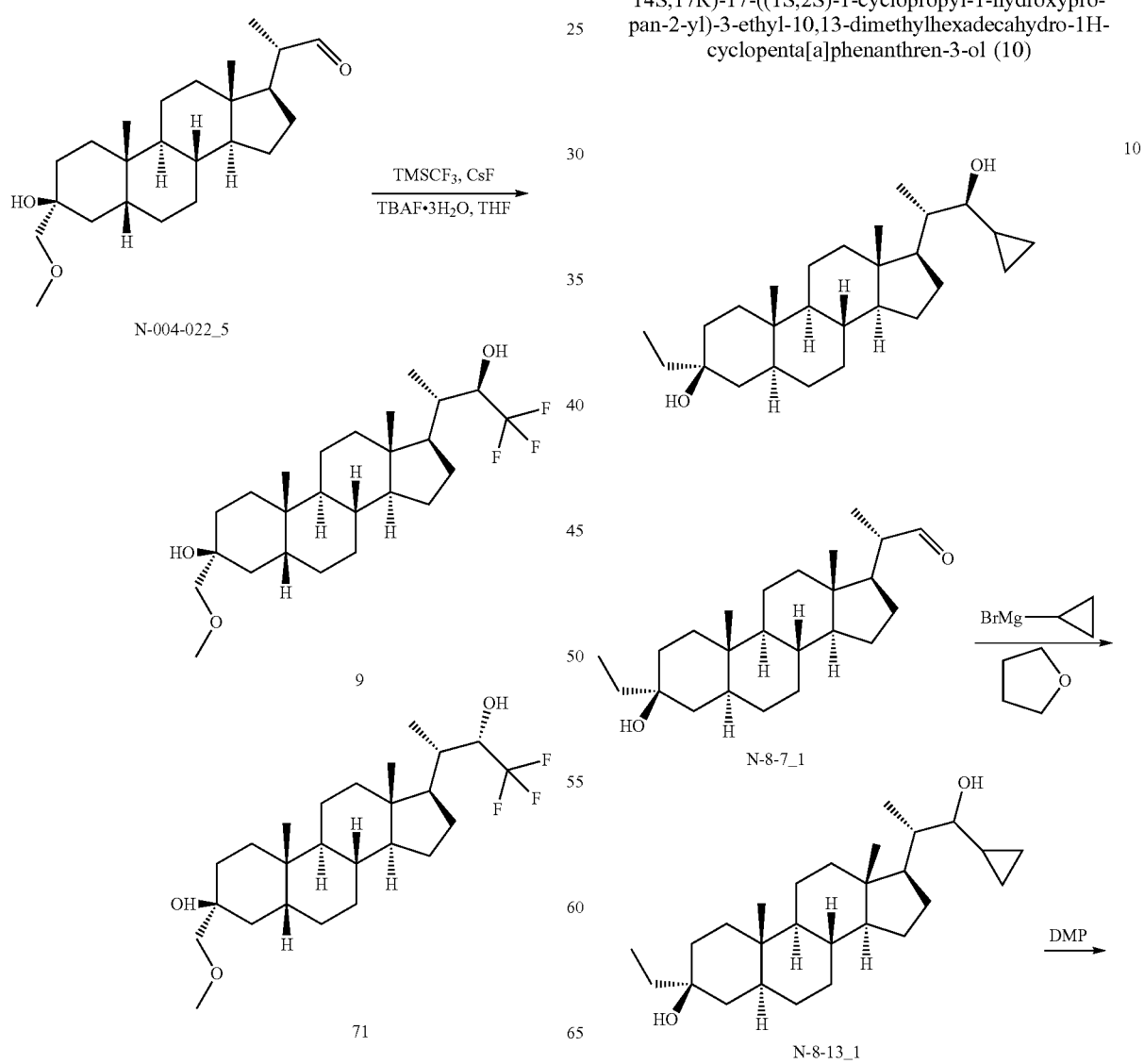

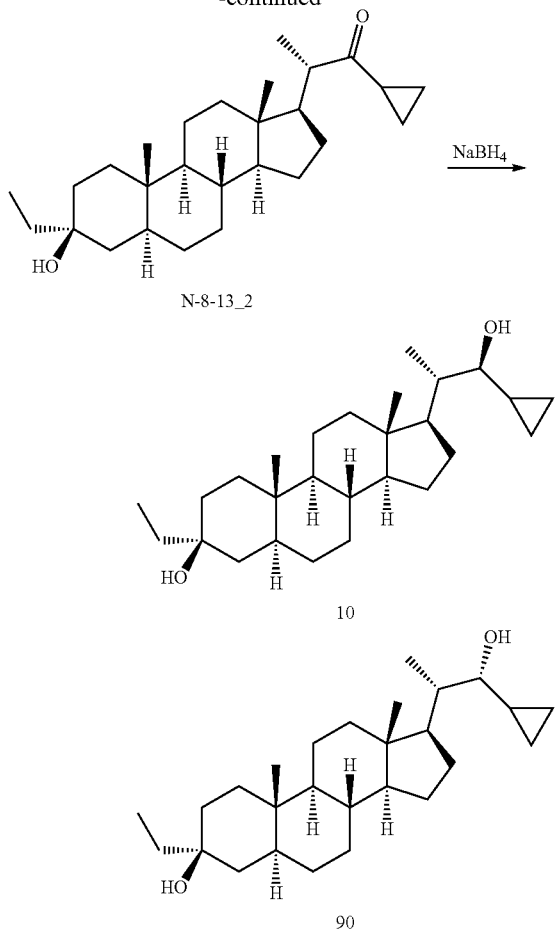

1. N-8-7_1 (500 mg, 1.38 mmol) in THF (5 mL) was added to a solution of cyclopropyl magnesium bromide (1 g, 13.7 mL, 0.5M in THF) in THF (5 ml) at 0° C. and stirred for 4 hrs at 25° C. The mixture was added NH$_4$Cl (20 mL, 10% aq.) and extracted with EtOAc (2×30 mL). The organic layer was separated and concentrated in vacuum to give a residue. The residue was purified by silica gel chromatography eluted with PE/EtOAc=1/1 to afford N-8-13_1 (140 mg, 25%) as a solid.

LCMS Rt=1.192 min in 2.0 min chromatography, 30-90AB_2MIN_E, purity 99%, MS ESI calcd. for C$_{27}$H$_{43}$ [M+H-2H$_2$O]$^+$367, found 367.

2. DMP (294 mg, 0.694 mmol) was added to a solution of N-8-13_1 (140 mg, 0.347 mmol) in DCM (5 mL). After that, the reaction mixture was stirred at 25° C. for 1 h. The reaction mixture was quenched with saturated NaHCO$_3$ aqueous (50 ml) until the pH of the aqueous layer became about 9. The mixture was filtered. The DCM layer was separated and the aqueous phase was extracted with DCM (100 mL). The combined organic phase was washed with saturated Na$_2$S$_2$O$_3$ aqueous solution (3×100 mL), sat. NaHCO$_3$ (100 mL), brine (40 mL), dried over Na$_2$SO$_4$, filtered and concentrated to give N-8-13_2 (140 mg, crude) as a solid.

$^1$H NMR (400 MHz, CDCl$_3$) δ 2.65-2.55 (m, 1H), 1.95-1.90 (m, 2H), 1.50-1.15 (m, 19H), 1.14-0.95 (m, 7H), 0.94-0.80 (m, 12H), 0.69 (s, 3H).

3. NaBH$_4$ (1.18 g, 17.4 mmol) was added five times, every five minutes, to a solution of N-8-13_2 (140 mg, 0.347 mmol) in MeOH (1 mL) and THF (1 mL). The mixture was stirred at 15° C. for 30 minutes. The mixture was quenched with sat. NH$_4$Cl (50 mL) and extracted with EtOAc (3×20 mL). The combined organic phase was dried over Na$_2$SO$_4$, filtered, concentrated and purified by combi-flash (25% of EtOAc in PE) to give 10 (26 mg, 19%) as a solid and 90 (12 mg, 9%) as a solid.

10:
$^1$H NMR (400 MHz, CDCl$_3$) δ 2.85-2.80 (m, 1H), 2.00-1.95 (m, 1H), 1.90-1.80 (m, 1H), 1.55-1.10 (m, 16H), 1.09-0.80 (m, 17H), 0.70-0.60 (m, 5H), 0.58-0.43 (m, 3H), 0.32-0.34 (m, 1H), 0.13-0.06 (m, 1H).

LCMS Rt=3.840 min in 7.0 min chromatography, 30-90AB_7MIN_E, purity 97%, MS ESI calcd. for C$_{27}$H$_{43}$ [M+H-2H$_2$O]$^+$367, found 367.

HPLC Rt=13.470 min in 30 min chromatography, 70-90AB_1_30MIN·M, purity 97%.

Example 11: Synthesis of (3S,5S,8R,9S,10S,13S, 14S,17R)-3-ethyl-10,13-dimethyl-17-((2S,3S)-4,4,4-trifluoro-3-hydroxybutan-2-yl)hexadecahydro-1H-cyclopenta[a]phenanthren-3-ol (11)

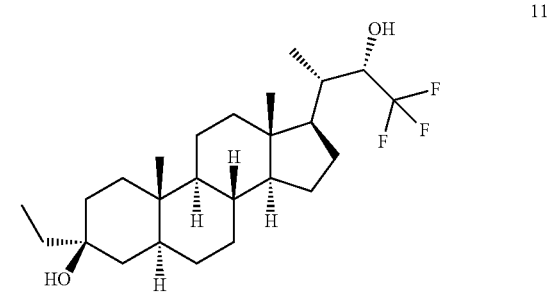

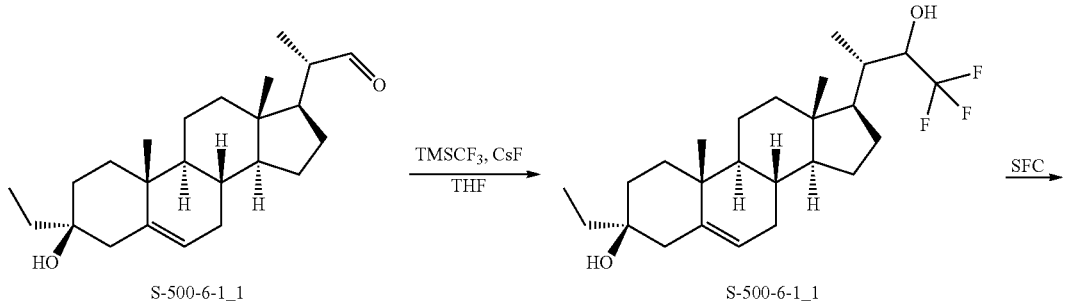

-continued

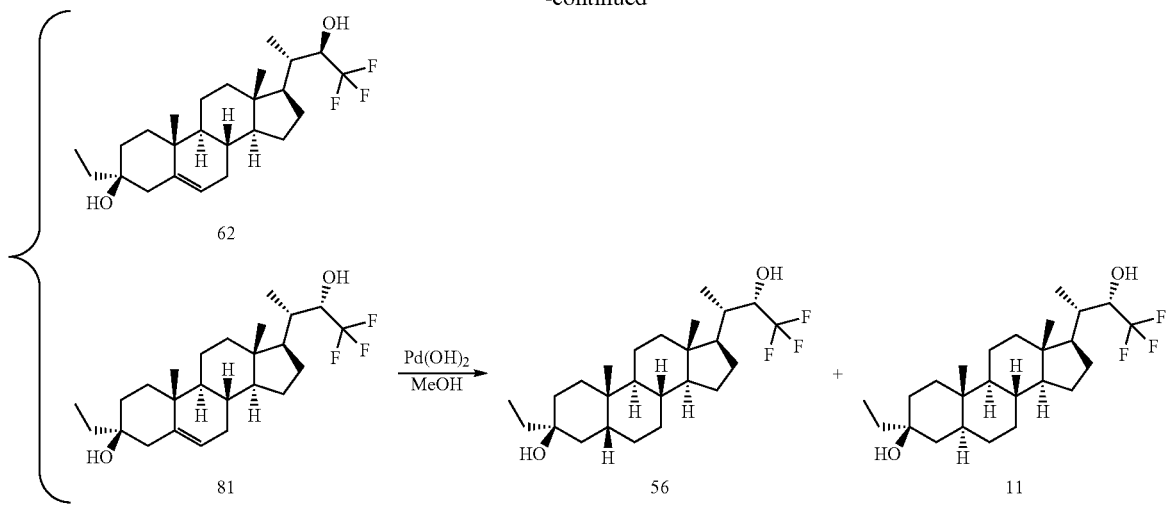

1. TMSCF₃ (493 mg, 3.47 mmol) was added to a solution of S-500-6-1_1 (500 mg, 1.39 mmol) and CsF (105 mg, 695 umol) in THF (5 mL) at 0° C. The mixture was stirred at 25° C. for 1 hr and treated with TBAF.3H₂O (1.09 g, 3.47 mmol). The mixture was stirred at 25° C. for 2 hrs, quenched with water (100 mL) and extracted with EtOAc (2×50 mL). The combined organic phase was washed with brine (100 mL), dried over anhydrous Na₂SO₄, filtered and concentrated in vacuum. The residue was purified by silica gel chromatography (100-200 mesh silica gel, PE/EA=10/1) to afford S-500-6-12 (400 mg, 67%) as a solid.

¹H NMR (400 MHz, CDCl3) δ 5.33-5.24 (m, 1H), 4.06-4.00 (m, 1H), 2.38-2.35 (m, 1H), 2.08-1.82 (m, 6H), 1.77-1.69 (m, 1H), 1.62-1.20 (m, 13H), 1.16-1.00 (m, 8H), 0.99-0.92 (m, 1H), 0.87-0.83 (m, 4H), 0.74-0.64 (m, 3H).

2. S-500-6-1_2 (350 mg) was purified by SFC (Column: AD (250 mm*30 mm, 5 um), Condition: 0.1% NH₃.H₂O ETOH, Gradient: from 35% to 35%, Flow Rate (ml/min): 60 mL/min, 25° C.) to afford 81 (Peak 1, 130 mg, 37%) and 62 (Peak 2, 180 mg, 52%) as a solid.

81:
¹H NMR (400 MHz, CDCl3) δ 5.34-5.24 (m, 1H), 4.09-4.00 (m, 1H), 2.43-2.33 (m, 1H), 2.14 (d, J=4 Hz, 1H), 2.07-1.80 (m, 5H), 1.77-1.55 (m, 5H), 1.53-1.30 (m, 7H), 1.28-1.00 (m, 11H), 1.00-0.91 (m, 1H), 0.85 (t, J=8 Hz, 3H), 0.70 (s, 3H).

LCMS Rt=1.220 min in 2.0 min chromatography, 30-90 AB, purity 100%, MS ESI calcd. For C₂₅H₃₈F₃O [M+H—H₂O]⁺411, found 411.

SFC Peak 1: Rt=4.561 min in 10 min chromatography, AD_3_EtOH_DEA_5_40_25ML ("Column: Chiralpak AD-3150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C."), 100% de.

3. Pd(OH)₂ (0.2 g, <1% water) was added to a solution of 81 (110 mg, 0.256 mmol) in MeOH (2 mL) and THF (1 mL). The solution was hydrogenated under 50 psi of hydrogen at 50° C. for 48 hrs. Then the mixture was filtered through a pad of celite and the filtrate was concentrated under vacuum. The residue was purified by flash column (PE/EtOAc=10/1 to 5/1) to give 56 (38 mg, 35%) and 11 (42 mg, 38%) as a solid.

11:
¹H NMR (400 MHz, CDCl3) δ 4.09-3.99 (m, 1H), 2.11 (d, J=6.0 Hz, 1H), 1.99-1.80 (m, 3H), 1.70-1.55 (m, 6H), 1.53-1.30 (m, 8H), 1.27-0.96 (m, 11H), 0.95-0.81 (m, 7H), 0.70-0.61 (m, 4H).

LCMS Rt=1.247 min in 2.0 min chromatography, 30-90 AB, purity 100%, MS ESI calcd. For C₂₅H₄₀F₃O [M+H—H₂O]⁺ 413, found 413.

Example 12: Synthesis of (3S,8S,9S,10R,13S,14S, 17R)-17-((2S,3R)-4-(4,4-dimethylcyclohexyl)-3-hydroxybutan-2-yl)-3-ethyl-10,13-dimethyl-2,3,4,7, 8,9,10,11,12,13,14,15,16,17-tetradecahydro-1H-cyclopenta[a]phenanthren-3-ol (12)

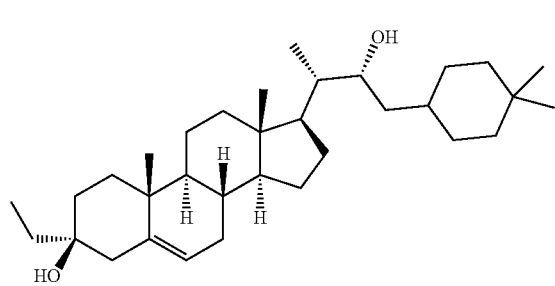

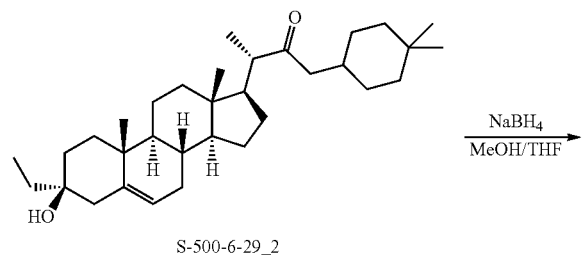

S-500-6-29_2

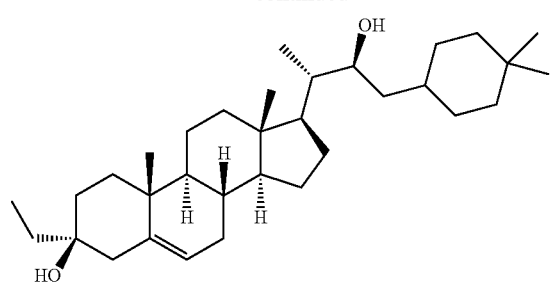

49

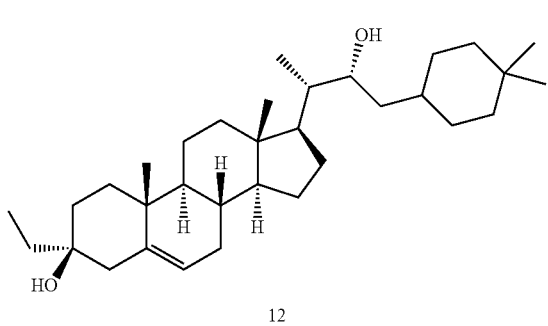

12

1. NaBH₄ (2.80 g, 82.5 mmol) was added five times, every five minutes, to a solution of S-500-6-29_2 (800 mg, 1.65 mmol) in MeOH (5 mL) and THF (5 mL). The mixture was stirred at 15° C. for 30 minutes. The mixture was quenched with sat. NH₄Cl (50 mL) and extracted with EtOAc (3×20 mL). The combined organic phase was dried over Na₂SO₄, filtered, concentrated and purified by combi-flash (0-15% of EtOAc in PE) to give S-500-6-30 (290 mg, 36%) and 12 (120 mg, 45%) as a solid.

12:

¹H NMR (400 MHz, CDCl₃) δ 5.31-5.26 (m, 1H), 3.85-3.77 (m, 1H), 2.40-2.32 (m, 1H), 2.06-1.95 (m, 3H), 1.77-1.58 (m, 7H), 1.54-1.28 (m, 12H), 1.27-1.06 (m, 11H), 1.03 (s, 3H), 1.00-0.95 (m, 2H), 0.93-0.82 (m, 12H), 0.69 (s, 3H).

LCMS Rt=1.708 min in 2.0 min chromatography, 30-90AB_E, purity 100%, MS ESI calcd. for C₃₃H₅₃ [M+H-2H₂O]⁺ 449, found 449.

Example 13: Synthesis of (1S,3R,4S)-4-((3S,5S,8R, 9S,10S,13S,14S,17R)-3-hydroxy-10,13-dimethyl-3-(trifluoromethyl)hexadecahydro-1H-cyclopenta[a]phenanthren-17-yl)-1-phenylpentane-1,3-diol (13)

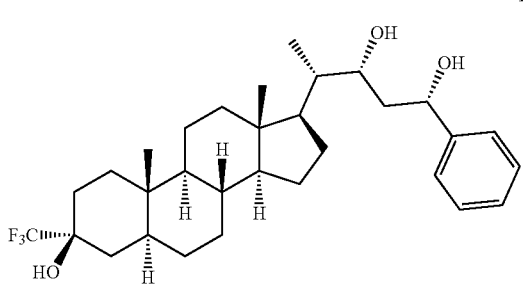

13

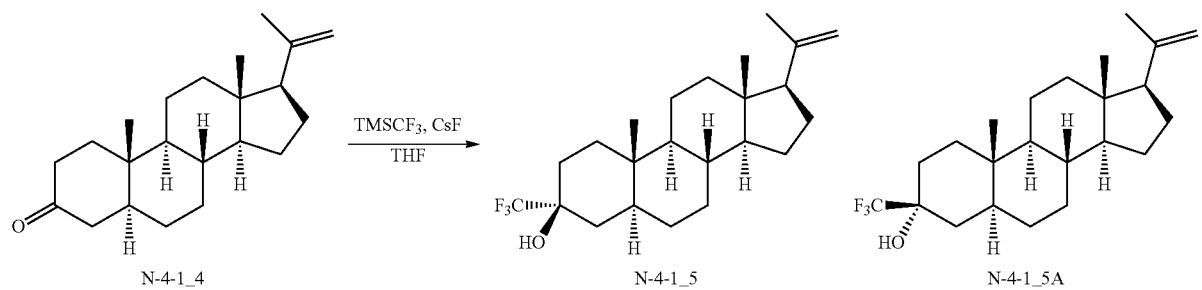

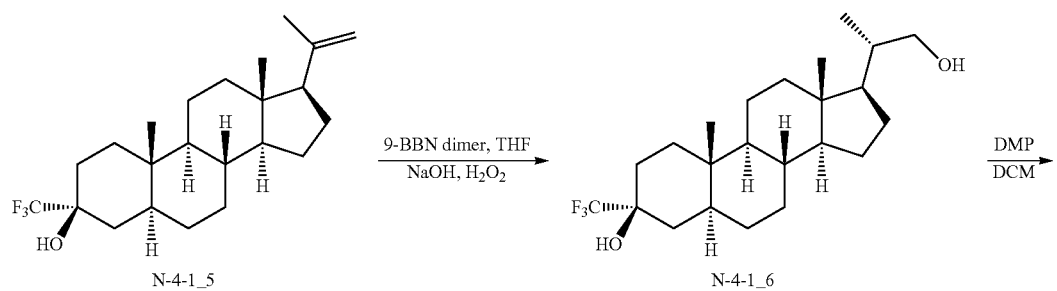

-continued
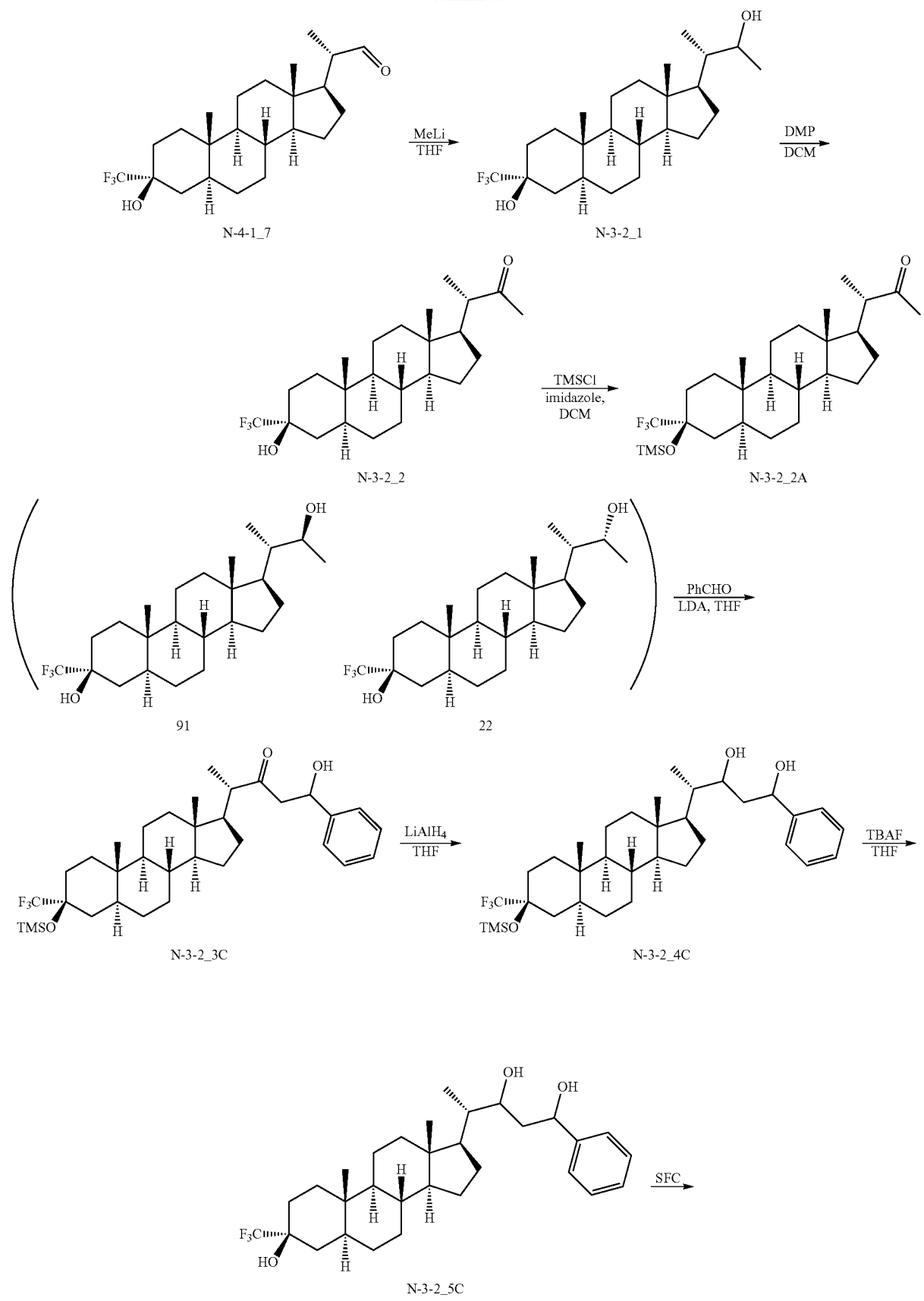

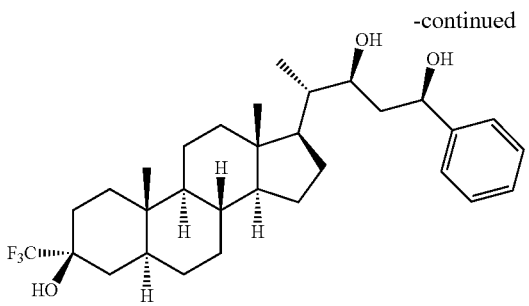

79

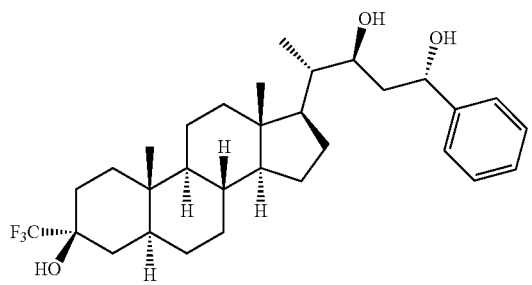

25

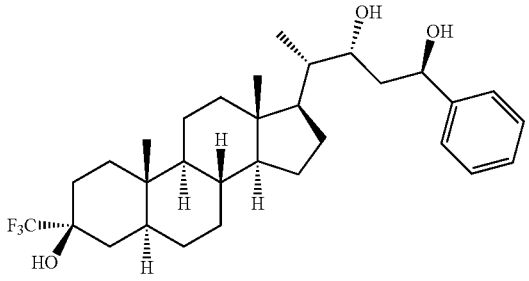

31

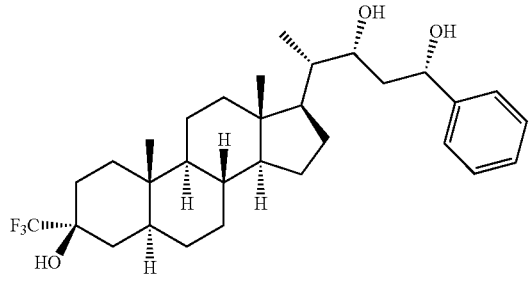

13

1. To a solution of N-4-1_4 (27 g, 85.8 mmol) in THF (200 mL) was added CsF (25.9 g, 171 mmol) and TMSCF$_3$ (24.3 g, 171 mmol). The mixture was stirred at 10° C. for 1 hr. To the mixture was added water (10 ml) and TBAF.3H$_2$O (30 g). The mixture was stirred at 30° C. for another 2 hrs. The mixture was concentrated under vacuum. The residue was dissolved in EtOAc (500 mL), washed with water (2×500 mL), dried over Na$_2$SO$_4$, filtered, concentrated under vacuum and purified by flash column (DCM/EtOAc (1:1) in PE, 0~10%) to give N-4-1_5 (27 g, 82%) and N-4-1_5A (3.5 g, 11%) as a solid.

N-4-1_5:

$^1$H NMR (400 MHz, CDCl$_3$) δ 4.84 (s, 1H), 4.70 (s, 1H), 2.12-1.94 (m, 3H), 1.89-1.78 (m, 2H), 1.75 (s, 3H), 1.72-1.60 (m, 5H), 1.58-1.48 (m, 2H), 1.45-1.09 (m, 10H), 1.01-0.89 (m, 1H), 0.85 (s, 3H), 0.78-0.68 (m, 1H), 0.56 (s, 3H).

$^1$H NMR (400 MHz, CDCl$_3$) δ 4.84 (s, 1H), 4.70 (s, 1H), 2.09-1.99 (m, 1H), 1.89-1.78 (m, 2H), 1.75 (s, 3H), 1.72-1.52 (m, 9H), 1.45-1.06 (m, 10H), 1.00-1.81 (m, 2H), 0.79 (s, 3H), 0.56 (s, 3H).

2. To a solution of N-4-1_5 (23 g, 59.8 mmol) in THF (250 mL) was added 9-BBN dimer (29 g, 119 mmol) was stirred at 40° C. under N$_2$ for 16 hrs. To the reaction mixture was added ethanol (34.3 mL, 598 mmol) and NaOH (119 mL, 5 M, 598 mmol). The mixture turned clear. H$_2$O$_2$ (59.8 mL, 10 M, 598 mmol) was added dropwise at 25° C. and the inner temperature was raised to reflux (70° C.). The mixture was cooled to 30° C. after the addition. To the mixture was added Na$_2$SO$_3$ (100 mL, 20% aq.). The organic layer was separated and poured into water (800 mL). A solid was formed. The mixture was filtered and the solid was washed with water, dried in vacuum and triturated with MeCN (250 ml) to give a solid. The solid was triturated form MeOH/water (250 mL/12.5 mL) at 60° C. and filtered after cooled to 15° C. The solid was dried in vacuum to give N-4-1_6 (16.4 g, 68%) as a solid.

$^1$H NMR (400 MHz, CDCl$_3$) δ 3.69-3.60 (m, 1H), 3.39-3.29 (m, 1H), 2.09-2.01 (m, 1H), 1.99-1.92 (m, 1H), 1.87-1.75 (m, 2H), 1.72-1.43 (m, 7H), 1.42-1.07 (m, 11H), 1.03 (d, J=6.8 Hz, 3H), 1.01-0.86 (m, 3H), 0.85 (s, 3H), 0.73-0.69 (m, 1H), 0.67 (s, 3H).

3. To a suspension of N-4-1_6 (5 g, 12.4 mmol) in DCM (200 mL) was added water (223 mg, 12.4 mmol) and DMP (10.5 g, 24.8 mmol). The mixture was stirred at 15° C. for 15 mins. The mixture was washed with NaHCO$_3$/Na$_2$S$_2$O$_3$ (200 mL/200 mL, sat.) twice, dried over Na$_2$SO$_4$, filtered and concentrated in vacuum to give N-4-1_7 (4.5 g, 90%) as a solid.

$^1$H NMR (400 MHz, CDCl$_3$) δ 9.60-9.51 (m, 11H), 2.40-2.30 (m, 11H), 2.12-1.78 (m, 5H), 1.75-1.59 (m, 4H), 1.57-1.15 (m, 11H), 1.14-0.84 (m, 8H), 0.78-0.63 (m, 5H).

4. MeLi (7.75 mL, 1.6 M, 12.4 mmol) was added to a solution of N-4-1_7 (1 g, 2.49 mmol) in THF (10 mL) at 0° C. The mixture was stirred at 15° C. for 1 h. To the mixture was added NH$_4$Cl (10%, 20 mL). The mixture was extracted with EtOAc (2×30 mL). The combined organic layer was dried over Na$_2$SO$_4$, filtered and concentrated in vacuum to give a mixture (1 g) as agum. The mixture N-3-2_1 (1 g) was purified by flash column (0~15% EtOAc in PE) to give 91 (450 mg) and 22 (460 mg) and 130 mg of a mixture. The 91 (450 mg) was re-crystallized form MeCN (10 mL) to give 91 (50 mg) as a solid, 22 (460 mg) was re-crystallized twice form MeCN (10 mL) to give 22 (50 mg) as a solid.

91:

$^1$H NMR (400 MHz, CDCl$_3$) δ 3.98-3.88 (m, 1H), 2.11-2.02 (m, 1H), 2.00 (s, 1H), 1.98-1.88 (m, 2H), 1.85-1.79 (m, 1H), 1.73-1.58 (m, 4H), 1.52-1.20 (m, 11H), 1.19-1.11 (m, 4H), 1.10-1.00 (m, 3H), 0.97-0.89 (m, 4H), 0.85 (s, 3H), 0.75-0.68 (m, 1H), 0.66 (s, 3H).

LCMS Rt=1.155 min in 2.0 min chromatography, 30-90_AB_E, purity 100%, MS ESI calcd. for C$_{24}$H$_{38}$F$_3$O [M+H—H$_2$O]$^+$ 399, found 399.

HPLC Rt=5.23 min in 10.0 min chromatography, 30-90_AB_E, purity 98.88%, d.e. 100%. 22:

$^1$H NMR (400 MHz, CDCl$_3$) δ 3.97-3.82 (m, 1H), 2.10-1.92 (m, 3H), 1.85-1.78 (m, 1H), 1.77-1.60 (m, 5H), 1.59-1.06 (m, 13H), 1.05-0.81 (m, 12H), 0.74-0.62 (m, 4H).

LCMS Rt=1.136 min in 2.0 min chromatography, 30-90_AB_E, purity 100%, MS ESI calcd. for $C_{24}H_{38}F_3O$ [M+H—H$_2$O]$^+$399, found 399.

HPLC Rt=5.05 min in 10.0 min chromatography, 30-90_AB_E, purity 100%, d.e. 100%.

5. To a solution of N-3-2_1 (0.88 g, 2.11 mmol) in DCM (20 mL) was added water (2 drops) and DMP (1.78 g, 4.22 mmol). The mixture was stirred at 25° C. for 30 min. The mixture was washed with NaHCO$_3$/Na$_2$S$_2$O$_3$ (30 mL/30 mL, sat.) twice, dried over Na$_2$SO$_4$, filtered and concentrated in vacuum to give N-3-2_2 (0.85 g, 97%) as a solid.

$^1$H NMR (400 MHz, CDCl$_3$) δ 2.53-2.42 (m, 1H), 2.13-2.00 (m, 4H), 1.97-1.78 (m, 2H), 1.75-1.45 (m, 9H), 1.43-1.13 (m, 9H), 1.11 (d, J=8.4 Hz, 3H), 1.07-1.00 (m, 1H), 0.98-0.88 (m, 1H), 0.85 (s, 3H), 0.78-0.68 (m, 1H), 0.67 (s, 3H).

6. To a solution of N-3-2_2 (0.85 g, 2.05 mmol) in DCM (5 mL) was added imidazole (279 mg, 4.10 mmol) and TMSCl (333 mg, 3.07 mmol) at 0° C. The mixture was stirred at 0° C. for 0.5 h. The mixture was added quenched by NaHCO$_3$ (20 mL, sat) and extracted with PE (15 mL). The organic layer was separated, dried over Na$_2$SO$_4$, filtered and concentrated in vacuum to give N-3-2_2A (0.98 g, 98%) as a solid.

$^1$H NMR (400 MHz, CDCl$_3$) δ 2.53-2.42 (m, 1H), 2.13-2.03 (m, 4H), 1.97-1.78 (m, 2H), 1.75-1.31 (m, 11H), 1.31-1.00 (m, 10H), 1.00-0.88 (m, 1H), 0.83 (s, 3H), 0.75-0.61 (m, 4H), 0.15 (s, 9H).

7. BuLi (0.384 mL, 2.5 M, 0.615 mmol) was added to i-Pr$_2$NH (62.2 mg, 0.615 mmol) in THF (0.5 mL) at −70° C. and stirred at 0° C. for 10 min. N-3-2_2A (0.2 g, 0.41 mmol) in THF (1 mL) was added at −70° C. and stirred at −70° C. for 30 min. A solution of benzaldehyde (91.3 mg, 0.861 mmol) in THF (0.5 mL) was added at −70° C. and stirred at −70° C. for 15 min. NH$_4$Cl (1 mL, sat., aq.) was added to the mixture and extracted with EtOAc (10 mL). The organic layer was separated, dried over Na$_2$SO$_4$, filtered and concentrated in vacuum to give N-3-2_3C (250 mg, crude) as an oil.

$^1$H NMR (400 MHz, CDCl$_3$) δ 7.46-7.30 (m, 5H), 5.70-5.55 (m, 1H), 3.60-3.25 (m, 1H), 2.90-2.70 (m, 2H), 2.55-2.41 (m, 1H), 2.16-2.00 (m, 2H), 1.96-1.75 (m, 3H), 1.50-1.15 (m, 9H), 1.13-1.05 (m, 4H), 1.05-0.88 (m, 4H), 0.87-0.80 (m, 5H), 0.73-0.62 (m, 5H). 0.15 (s, 9H).

8. LiAlH$_4$ (159 mg, 4.20 mmol) was added to a solution of N-3-2_3C (250 mg, 0.421 mmol) in THF (10 mL) at 0° C. The mixture was stirred at 0° C. for 5 min. Water (0.16 mL), NaOH (0.16 mL, 15% aq.), and water (0.48 mL) were added to the mixture in the order written here. The mixture was filtered and the solid was washed with THF (30 mL). The combined filtrate was concentrated in vacuum to give N-3-2_4C (250 mg, 100%) as a solid.

$^1$H NMR (400 MHz, CDCl$_3$) δ 7.42-7.28 (m, 5H), 5.70-5.30 (m, 1H), 4.15-3.65 (m, 1H), 2.18-1.55 (m, 9H), 1.53-1.00 (m, 15H), 1.00-0.75 (m, 9H), 0.75-0.50 (m, 4H), 0.15 (s, 9H).

9. TBAF (219 mg, 0.84 mmol) was added to a solution of N-3-2_4C (250 mg, 0.42 mmol) in THF (2 mL). The mixture was stirred at 25° C. for 3 h. The mixture was concentrated in vacuum. The residue was dissolved in EtOAc (10 mL) and washed with water (3×10 mL), purified by flash column (10-25% EtOAc in PE) to give N-3-2_5C (150 mg, 68%) as a solid.

10. The mixture N-3-2_5C (150 mg) was separated by SFC (Instrument: MG-II; Column: IC (250 mm*30 mm, 10 um); Condition: 0.1% NH$_3$H$_2$O MeOH; Begin B: 30%; End B: 30%; FlowRate (mL/min): 60; Injections: 300) to give impure 79 (35 mg, impure), mixture of 31 and 25 (55 mg) and 13 (28 mg, impure).

The impure 79 (35 mg) was purified by flash column (10-30% EtOAc in PE), the eluent was concentrated in vacuum. The residue was dissolved in MeCN/water (20 mL, 4:1) and concentrated in vacuum to give 79 (12 mg) as a solid.

25 and 13 (55 mg) was separated by SFC (Instrument: MG-II; Column:

AD (250 mm*30 mm, 5 um); Condition: 0.1% NH$_3$H$_2$O MeOH; Begin B: 35%; End B: 35%;

FlowRate (mL/min): 60; Injections: 70). Each of the eluent was respectively concentrated in vacuum, dissolved in MeCN/water (20 ml, 4:1) and concentrated in vacuum to give 25 (28 mg) and 13 (7 mg) both as a solid.

The impure 31 (28 mg) was purified by SFC (Instrument: SFC 17; Column:

AS (250 mm*30 mm, 5 um); Condition: 0.1% NH$_3$H$_2$O EtOH; Begin B: 30%; End B: 30%;

FlowRate (mL/min): 50; Injections: 60) to give a solid. The residue was dissolved in MeCN/water (20 mL, 4:1) and concentrated in vacuum to give 31 (9 mg) as a solid.

SFC of four isomer: Peak 1: Rt=1.501 min, Peak 2: Rt=1.730 min and Peak 3: Rt=1.943 min in 10 min chromatography, IC-3_MeOH(DEA)_40_2.5ML ("Column: ChiralPak IC-3 150×4.6 mm I.D., 3 um; Gradient: 40% of Methanol (0.05% DEA) in CO$_2$; Flow rate: 2.5 mL/min; Column temperature: 40° C.".

SFC of 25 and 13: Peak 1: Rt=4.411 min and Peak 2: Rt=4.920 min in 8 min chromatography, AD_MEOH (DEA)_5_40_2,8ML_8MIN ("Column: Chiralpak AD-3 100×4.6 mm I.D., 3 um; Mobile phase: A: CO$_2$ B: Methanol (0.05% DEA); Gradient: from 5% to 40% of B in 4.5 min and hold 40% for 2.5 min, then 5% of B for 1 min; Flow rate: 2.8 mL/min; Column temperature: 40° C.".

79:
$^1$H NMR (400 MHz, CDCl$_3$) δ 7.43-7.28 (m, 5H), 5.05-4.94 (m, 1H), 4.04-3.91 (m, 1H), 2.51 (brs, 1H), 2.07-1.78 (m, 6H), 1.70-1.61 (m, 4H), 1.51-1.41 (m, 3H), 1.39-1.12 (m, 11H), 1.05-0.98 (m, 2H), 0.91-0.81 (m, 7H), 0.71-0.60 (m, 4H).

LCMS Rt=1.298 min in 2 min chromatography, 10-80AB_2MIN_E, purity 96.7%, MS ESI calcd. for $C_{31}H_{45}F_3O_3Na$ [M+Na]$^+$ 545, found 545.

SFC Rt=1.483 min in 10 min chromatography, IC-3_MeOH(DEA)_40_2.5ML, 100% de.

25:
$^1$H NMR (400 MHz, CDCl$_3$) δ 7.42-7.28 (m, 5H), 4.97-4.81 (m, 1H), 4.12-3.92 (m, 1H), 3.23 (brs, 1H), 2.69 (brs, 1H), 2.10-1.88 (m, 3H), 1.82-1.62 (m, 7H), 1.48-1.18 (m, 10H), 1.10-0.88 (m, 8H), 0.87-0.78 (m, 4H), 0.70-0.58 (m, 4H).

LCMS Rt=1.319 min in 2 min chromatography, 10-80AB_2MIN_E, purity 97.0%, MS ESI calcd. for $C_{31}H_{45}F_3O_3Na$ [M+Na]$^+$545, found 545.

SFC Rt=1.718 min in 5 min chromatography, IC-3_MeOH(DEA)_40_2.5ML, 98.26% de.

SFC Rt=4.367 min in 8 min chromatography, AD_MEOH (DEA)_5_40_2,8ML_8MIN, 100% de.

31:
$^1$H NMR (400 MHz, CDCl$_3$) δ 7.45-7.28 (m, 5H), 5.02-4.81 (m, 1H), 4.18-3.98 (m, 1H), 3.35 (brs, 1H), 2.47 (brs, 1H), 2.15-1.72 (m, 8H), 1.53-1.31 (m, 8H), 1.30-1.03 (m, 8H), 0.99-0.89 (m, 4H), 0.89-0.78 (m, 4H), 0.75-0.60 (m, 4H).

LCMS Rt=1.327 min in 2 min chromatography, 10-80AB_2MIN_E, purity 100%, MS ESI calcd. for $C_{31}H_{45}F_3O_3Na$ $[M+Na]^+$545, found 545.

SFC Rt=1.929 min in 10 min chromatography, IC-3_MeOH(DEA)_40_2.5ML, 98.4% de.

13:

$^1$H NMR (400 MHz, CDCl$_3$) δ 7.40-7.28 (m, 5H), 5.12-5.07 (m, 1H), 3.95-3.88 (m, 1H), 2.76 (brs, 1H), 2.08-1.78 (m, 6H), 1.75-1.60 (m, 5H), 1.51-1.38 (m, 4H), 1.36-1.09 (m, 9H), 1.00-0.89 (m, 6H), 0.83 (s, 3H), 0.71-0.64 (m, 1H), 0.63 (s, 3H).

LCMS Rt=1.309 min in 2 min chromatography, 10-80AB_2MIN_E, purity 100%, MS ESI calcd. for $C_{31}H_{45}F_3O_3Na$ $[M+Na]^+$545, found 545.

SFC Rt=1.683 min in 5 min chromatography, IC-3_MeOH(DEA)_40_2.5ML, 98.94% de.

SFC Rt=4.785 min in 8 min chromatography, AD_MEOH (DEA)_5_40_2,8ML_8MIN, 94.03% de.

Example 14: Synthesis of (3S,5S,8R,9S,10S,13S,14S,17R)-17-((2S,3R,E)-3-hydroxy-5-phenylpent-4-en-2-yl)-10,13-dimethyl-3-(trifluoromethyl)hexadecahydro-1H-cyclopenta[a]phenanthren-3-ol (14)

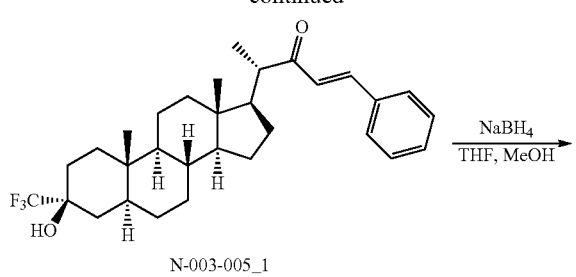

1. BuLi (0.384 mL, 2.5 M, 0.615 mmol) was added to i-Pr$_2$NH (62.2 mg, 0.615 mmol) in THF (0.5 mL) at −70° C. and stirred at 0° C. for 10 min. N-3-2_2A (0.2 g, 0.41 mmol) in THF (1 mL) was added at −70° C. and stirred at −70° C. for 1 h. A solution of benzaldehyde (91.3 mg, 0.861 mmol) in THF (0.5 ml) was added at −70° C. and stirred at 20° C. for 4 h. NH$_4$Cl (1 mL, sat., aq.) was added to the mixture and extracted with EtOAc (10 mL). The organic layer was separated, dried over Na$_2$SO$_4$, filtered and concentrated in vacuum, purified by flash column (0~10% EtOAc in PE) to give N-3-2_3D (150 mg, 64%) as a solid.

$^1$H NMR (400 MHz, CDCl$_3$) δ 7.64-7.55 (m, 3H), 7.43-7.39 (m, 3H), 6.79 (d, J=16.0 Hz, 1H), 2.86-2.73 (m, 1H), 2.15-2.08 (m, 1H), 2.00-1.90 (m, 1H), 1.88-1.80 (m, 1H), 1.72-1.59 (m, 5H), 1.53-1.22 (m, 9H), 1.21-1.03 (m, 7H), 0.99-0.88 (m, 1H), 0.84 (s, 3H), 0.75-0.61 (m, 4H), 0.15 (s, 9H).

2. TBAF (135 mg, 0.52 mmol) was added to a solution of N-3-2_3D (150 mg, 0.26 mmol) in THF (1 mL). The mixture was stirred at 20° C. for 20 h. To the mixture was added EtOAc (5 mL). The mixture was washed with water (2×5 mL), brine (5 mL), concentrated in vacuum to give N-003-005_1 (140 mg, crude) as a solid.

$^1$H NMR (400 MHz, CDCl$_3$) δ 7.64-7.53 (m, 3H), 7.43-7.35 (m, 3H), 6.79 (d, J=16.0 Hz, 1H), 2.88-2.73 (m, 1H), 2.13-1.90 (m, 3H), 1.88-1.78 (m, 1H), 1.77-1.90 (m, 5H), 1.60-1.22 (m, 8H), 1.21-0.88 (m, 9H), 0.86 (s, 3H), 0.75-0.61 (m, 4H).

3. NaBH$_4$ (419 mg, 11.1 mmol) was added in portions to a solution of N-003-005_1 (140 mg, 0.278 mmol) in THF (2 mL) and MeOH (1 mL) at 20° C. The mixture was stirred at 20° C. for 10 min. The reaction was quenched with water (20 mL) and NH$_4$Cl (20 mL, sat.). The mixture was extracted with EtOAc (50 mL). The organic layer was concentrated in vacuum and purified by prep-TLC (PE/EtOAc=4/1) to give N-003-005 (50 mg, impure) and N-003-006 (50 mg) both as a solid.

14 (50 mg) was dissolved in MeCN (20 mL) and concentrated in vacuum to give 14 (29 mg) as a solid.

14:

$^1$H NMR (400 MHz, CDCl$_3$) δ 7.44-7.38 (m, 2H), 7.37-7.29 (m, 2H), 7.25-7.18 (m, 1H), 6.59 (d, J=16.0 Hz, 1H), 6.24 (dd, J=7.2, 16.0 Hz, 1H), 4.40-4.30 (m, 1H), 2.08-1.92 (m, 3H), 1.89-1.77 (m, 3H), 1.68-1.60 (m, 3H), 1.50-1.08 (m, 13H), 1.03-0.82 (m, 9H), 0.72-0.62 (m, 4H).

LCMS Rt=1.236 min in 2 min chromatography, 30-90AB_2MIN_E, purity 99.0%, MS ESI calcd. for C$_{31}$H$_{42}$F$_3$O [M+H—H$_2$O]$^+$487, found 487.

HPLC Rt=5.89 min in 8 min chromatography, 30-90_AB_1.2 ml, 98.1% d.e. (220 nm)

Example 15: Synthesis (3S,5R,8R,9S,10S,13S,14S,17R)-3-ethyl-17-((2S,3R)-3-hydroxy-6,6-dimethyl-heptan-2-yl)-10,13-dimethylhexadecahydro-1H-cyclopenta[a]phenanthren-3-ol (15)

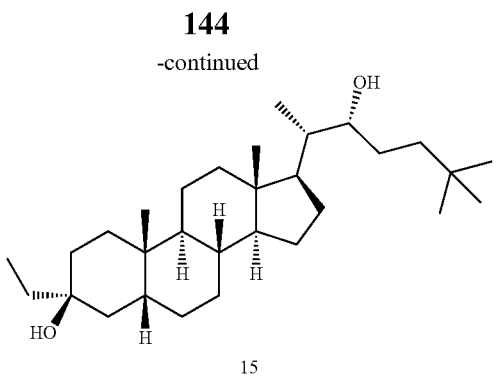

1. Pd(OH)$_2$/C (100 mg) was added to a solution of 44 (100 mg) in MeOH/THF (2 mL/2 mL) was added. The mixture was stirred at 50° C. under H$_2$ (50 psi) for 20 h. The mixture was filtered. The filtered was concentrated to give 100 mg of a solid. NMR showed 9% 54 was remained. The impure sample was hydrogenated at the same condition for another 3 times. The mixture was filtered. The filtrate was concentrated and separated by flash column (0~15% EtOAc in PE) to give 5 (7 mg) as a solid.

$^1$H NMR (400 MHz, CDCl$_3$) δ 3.66-3.48 (m, 1H), 2.00-1.55 (m, 9H), 1.50-1.22 (m, 15H), 1.19-1.03 (m, 8H), 0.96 (s, 3H), 0.91-0.81 (m, 15H), 0.67 (s, 3H).

LCMS Rt=1.492 min in 2.0 min chromatography, 30-90_AB_E, purity 100%, MS ESI calcd. for C$_{30}$H$_{51}$ [M+H-2H$_2$O]$^+$ 411, found 411.

Example 16: Synthesis of (3S,5S,8R,9S,10S,13S,14S,17R)-3-ethyl-10,13-dimethyl-17-((2S,3R)-4,4,4-trifluoro-3-hydroxybutan-2-yl)hexadecahydro-1H-cyclopenta[a]phenanthren-3-ol (16)

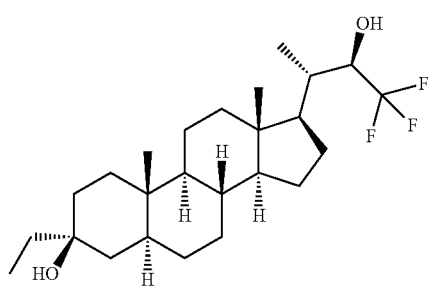

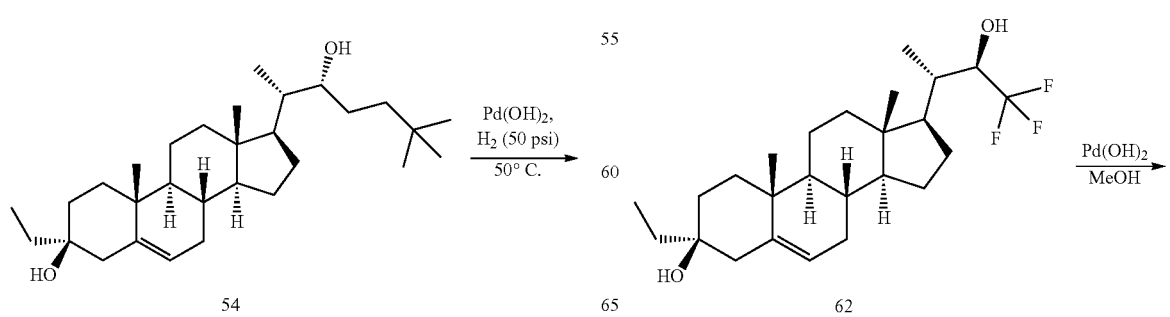

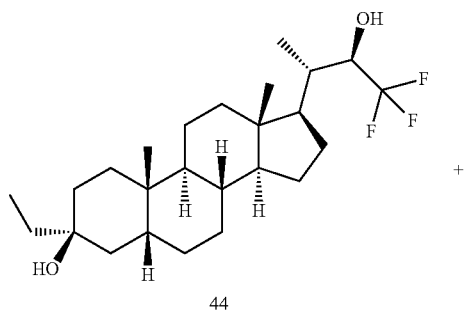

44

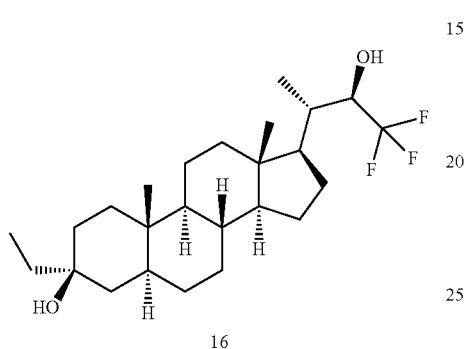

16

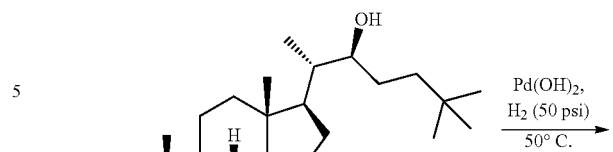

5

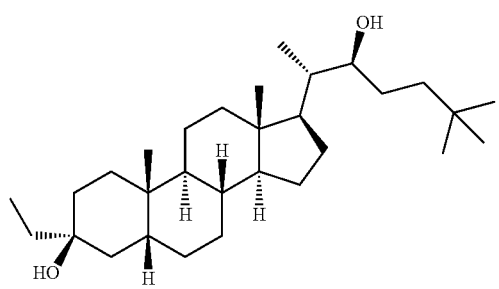

17

1. Pd(OH)₂ (0.2 g, <1% water) was added to a solution of 62 (160 mg, 0.373 mmol) in MeOH (2 mL) and THF (1 mL). The solution was hydrogenated under 50 psi of hydrogen at 50° C. for 16 hrs. Then the mixture was filtered through a pad of celite and the filtrate was concentrated in vacuum. The residue was purified by flash column (PE/EtOAc=10/1 to 5/1) to give 44 (27 mg, 17%) and 16 (117 mg, 73%) as solids.

16:

$^1$H NMR (400 MHz, CDCl3) δ 4.04-3.96 (m, 1H), 1.98-1.83 (m, 4H), 1.69-1.59 (m, 3H), 1.56-1.20 (m, 13H), 1.17-0.95 (m, 8H), 0.91-0.83 (m, 8H), 0.70-0.62 (m, 4H).

LCMS Rt=1.240 min in 2.0 min chromatography, 30-90 AB, purity 100%, MS ESI calcd. For $C_{25}H_{40}F_3O$ [M+H—H₂O]⁺ 413, found 413.

Example 17: Synthesis of (3S,5R,8R,9S,10S,13S,14S,17R)-3-ethyl-17-((2S,3S)-3-hydroxy-6,6-dimethylheptan-2-yl)-10,13-dimethylhexadecahydro-1H-cyclopenta[a]phenanthren-3-ol (17)

1. Pd(OH)₂/C (100 mg) was added to a solution of 5 (250 mg) in MeOH/THF (2 mL/2 mL). The mixture was stirred at 50° C. under H₂ (50 psi) for 20 hrs. The mixture was filtered. The filtered was concentrated to give 250 mg of a solid. NMR showed 70% of 5 remained. The impure sample was hydrogenated at the same condition for another 3 times. The mixture was filtered. The filtrate was concentrated and separated by flash column (0~15% EtOAc in PE) to give 17 (3 mg) as a solid.

$^1$H NMR (400 MHz, CDCl₃) δ 3.63-3.50 (m, 1H), 1.98-1.55 (m, 8H), 1.49-1.37 (m, 8H), 1.35-1.21 (m, 8H), 1.19-1.01 (m, 8H), 0.97 (s, 3H), 0.91-0.82 (m, 15H), 0.66 (s, 3H).

LCMS Rt=1.529 min in 2.0 min chromatography, 30-90_AB_E, purity 95.6%, MS ESI calcd. for $C_{30}H_{51}$ [M+H-2H₂O]⁺ 411, found 411.

Example 18: Synthesis of (3S,5S,8R,9S,10S,13S,14S,17R)-3-ethyl-17-((2S,3R)-3-hydroxy-4-(tetrahydro-2H-pyran-4-yl)butan-2-yl)-10,13-dimethylhexadecahydro-1H-cyclopenta[a]phenanthren-3-ol (18)

17

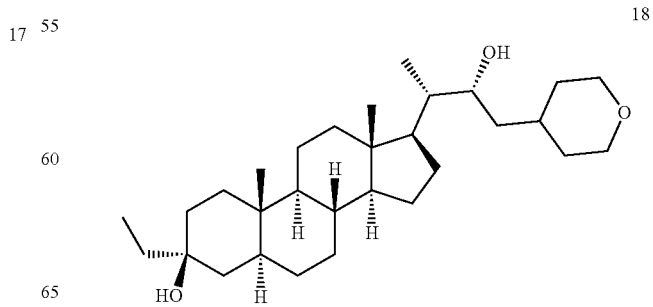

18

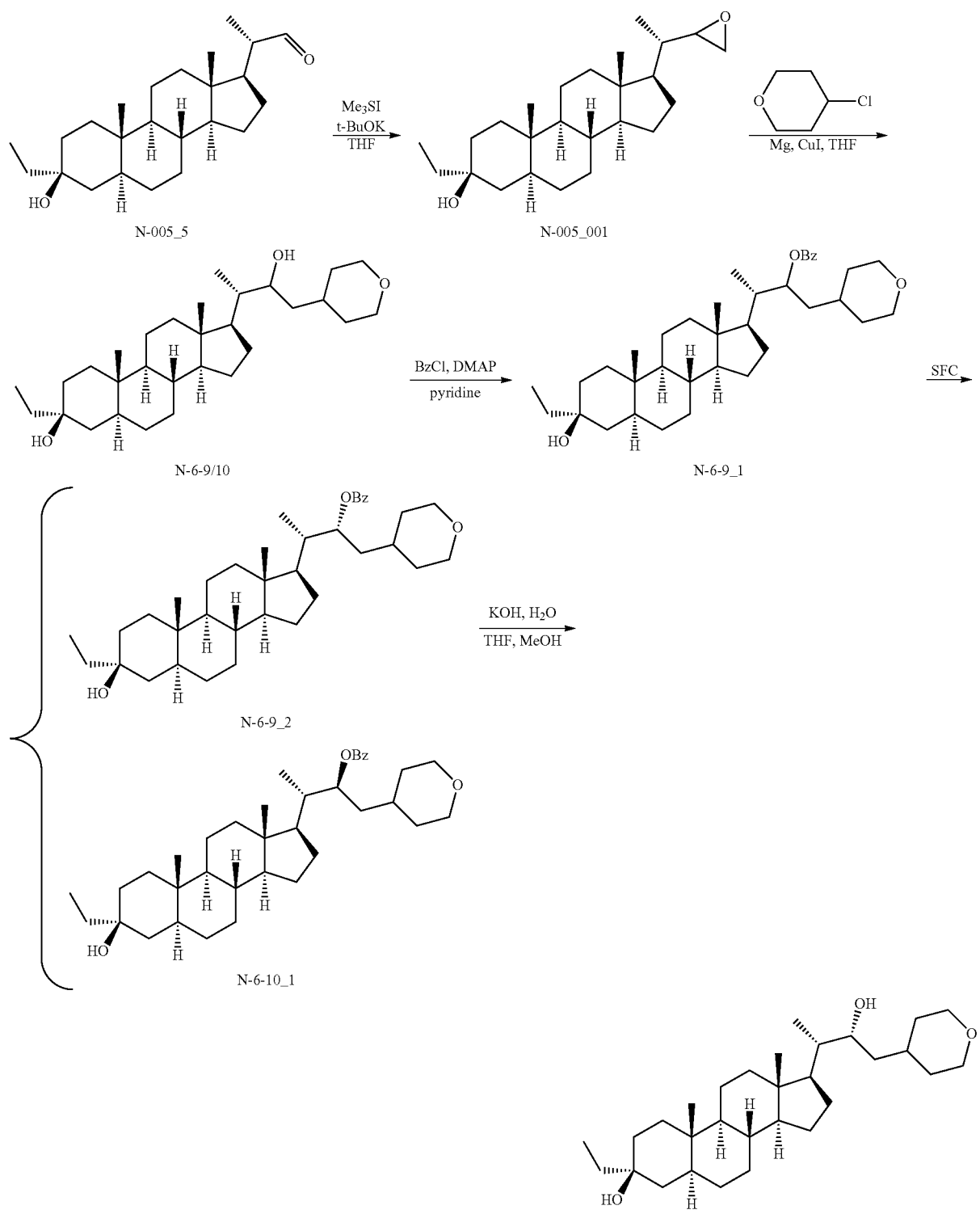

1. To suspension of Me₃SI (8.44 g, 41.4 mmol) in anhydrous THF (50 mL) at 20° C. under nitrogen was added t-BuOK (4.64 g, 41.4 mmol). The mixture was stirred at 20° C. for 1 hr, and N-005_5 (5 g, 13.8 mmol) was added. The resulting mixture was warmed to 45° C. and stirred for 4 hrs. The reaction mixture was cooled to room temperature, quenched with water (50 mL) and extracted with EtOAc (2×50 mL). The combined organic layer was dried over anhydrous sodium sulfate, filtered and concentrated. The residue was purified by column chromatography on silica gel (0~10% EtOAc in PE) to give N-005_001 (2.7 g, 52%) as a solid.

LCMS Rt=1.324 min in 2.0 min chromatography, 30-90AB_E, purity 92%, MS ESI calcd. for $C_{25}H_{41}O$ [M+H—$H_2O$]*+ 357, found 357.

2. A solution of 4-chlorotetrahydro-2H-pyran (1 g, 8.29 mmol) in anhydrous THF (8 mL) was added dropwise to a mixture of Mg (401 mg, 16.5 mmol) and $I_2$ (105 mg, 0.414 mmol) in anhydrous THF 2 mL) under $N_2$ at 60° C. The mixture was stirred at 60° C. for 10 min. The temperature rose to 66° C. The reaction mixture was stirred for additional 30 min, cooled to room temperature which was used directly as a solution of (tetrahydro-2H-pyran-4-yl)magnesium chloride (0.83 M in THF).

3. A solution of (tetrahydro-2H-pyran-4-yl)-magnesium chloride (0.83 M in THF, 6.38 mL, 5.30 mmol) was added dropwise to a suspension of N-005_001 (400 mg, 1.06 mmol) and CuI (20.1 mg, 0.106 mmol) in anhydrous THF (10 mL) under nitrogen at 20° C. The mixture was stirred at 20° C. for 18 hrs. The reaction mixture was quenched with water (10 mL) and saturated $NH_4Cl$ (10 mL), extracted with EtOAc (2×15 mL). The combined organic layer was washed with brine (15 mL), dried over anhydrous sodium sulfate, filtered and concentrated to give N-6-9/10 (760 mg, crude) as a solid.

$^1$H NMR (400 MHz, CDCl$_3$) δ 4.01-3.92 (m, 3H), 3.83-3.62 (m, 1H), 3.42-3.32 (m, 3H), 1.97-1.87 (m, 1H), 1.68-1.58 (m, 7H), 1.57-1.45 (m, 6H), 1.43-1.29 (m, 8H), 1.24-0.95 (m, 10H), 0.91-0.79 (m, 9H), 0.73-0.56 (m, 4H).

LCMS Rt=1.332 min in 2.0 min chromatography, 10-80AB, purity 93%, MS ESI calcd. for $C_{30}H_{52}NaO_3$ [M+Na]$^+$483, found 483.

4. BzCl (691 mg, 4.92 mmol) and DMAP (20 mg, 0.164 mmol) were added to a solution of N-6-9/10 (760 mg, 1.64 mmol) in pyridine (10 mL). The mixture was stirred at 20° C. for 2 hrs. The reaction mixture was quenched with water (15 mL), extracted with EtOAc (2×20 mL). The combined organic layer was washed with 10% aqueous HCl (2×20 mL), saturated NaHCO$_3$ (40 mL) and brine (20 mL), dried over anhydrous sodium sulfate, filtered and concentrated. The residue was purified by column chromatography on silica gel (0~10% of EtOAc in PE) to give N-6-9_1 (400 mg, 43%) as a solid.

$^1$H NMR (400 MHz, CDCl$_3$) δ 8.08-8.01 (m, 1H), 8.08-8.01 (m, 1H), 7.61-7.42 (m, 3H), 5.42-5.29 (m, 1H), 3.99-3.85 (m, 2H), 3.41-3.24 (m, 2H), 2.06-1.65 (m, 5H), 1.65-1.57 (m, 5H), 1.54-1.42 (m, 6H), 1.42-1.14 (m, 11H), 1.14-0.90 (m, 8H), 0.89-0.77 (m, 7H), 0.69-0.51 (m, 4H). N-6-9_1 (400 mg, 0.708 mmol) was separated and purified by SFC (column: C2 250 mm*30 mm, 10 um, gradient: 45-45% B (A=0.1% NH$_3$/H$_2$O, B=MeOH), flow rate: 60 mL/min) to give N-6-9_2 (peak 1, Rt=3.926 min, 80 mg, 20%) as a solid and N-6-10_1 (peak 2, Rt=4.893 min, 180 mg, 45%) as a solid.

N-6-9_2:
$^1$H NMR (400 MHz, CDCl$_3$) δ 8.06-8.00 (m, 2H), 7.60-7.53 (m, 1H), 7.49-7.42 (m, 2H), 5.35-5.28 (m, 1H), 3.98-3.91 (m, 2H), 3.41-3.31 (m, 2H), 1.88-1.67 (m, 5H), 1.66-1.57 (m, 4H), 1.54-1.36 (m, 10H), 1.35-1.16 (m, 8H), 1.08-0.88 (m, 8H), 0.88-0.82 (m, 4H), 0.80 (s, 3H), 0.64 (s, 3H), 0.61-0.54 (m, 1H).

LCMS Rt=1.540 min in 2.0 min chromatography, 30-90AB, purity 96%, MS ESI calcd. for $C_{30}H_{49}O$ [M-BzOH—H$_2$O+H]$^+$ 425, found 425.

SFC Rt=3.789 min in 8 min chromatography, Column: Lux Cellulose-2 150×4.6 mm I.D., 3 m; Mobile phase: 40% of Methanol (0.05% DEA) in CO$_2$; Flow rate: 2.5 mL/min; Column temperature: 40° C., 97% de.

N-6-10_1:
$^1$H NMR (400 MHz, CDCl$_3$) δ 8.06-8.01 (m, 2H), 7.61-7.53 (m, 1H), 7.49-7.42 (m, 2H), 5.41-5.33 (m, 1H), 3.98-3.86 (m, 2H), 3.40-3.27 (m, 2H), 2.05-1.91 (m, 2H), 1.84-1.72 (m, 2H), 1.66-1.59 (m, 3H), 1.55-1.38 (m, 9H), 1.37-1.16 (m, 11H), 1.13-1.00 (m, 6H), 1.00-0.90 (m, 2H), 0.89-0.79 (m, 7H), 0.67 (s, 3H), 0.63-0.54 (m, 1H).

LCMS Rt=1.507 min in 2.0 min chromatography, 30-90AB, purity 97%, MS ESI calcd. for $C_{30}H_{49}O$ [M-BzOH—H$_2$O+H]$^+$425, found 425.

SFC Rt=4.699 min in 8 min chromatography, Column: Lux Cellulose-2 150×4.6 mm I.D., 3 μm; Mobile phase: 40% of Methanol (0.05% DEA) in CO$_2$; Flow rate: 2.5 mL/min; Column temperature: 40° C., 97% de.

5. Water (1 mL) and KOH (78.5 mg, 1.40 mmol) were added to a solution of N-6-9_2 (80 mg, 0.141 mmol) in THF (2 mL) and methanol (1 mL). The mixture was stirred at 50° C. for 18 hrs. The reaction mixture was cooled, diluted with water (5 mL), acidified with 10% HCl (0.2 mL) and extracted with EtOAc (3×5 mL). The combined organic layer was dried over anhydrous sodium sulfate, filtered and concentrated. The residue was purified by column chromatography on silica gel (10-30% of EtOAc in PE) to give 18 (13 mg, 20%) as a solid.

$^1$H NMR (400 MHz, CDCl$_3$) δ 4.05-3.89 (m, 3H), 3.45-3.34 (m, 2H), 1.94-1.87 (m, 1H), 1.86-1.76 (m, 1H), 1.72-1.59 (m, 6H), 1.54-1.45 (m, 4H), 1.44-1.28 (m, 9H), 1.28-1.15 (m, 7H), 1.13-0.92 (m, 5H), 0.91-0.85 (m, 4H), 0.84-0.79 (m, 6H), 0.70-0.62 (m, 4H).

LCMS Rt=1.213 min in 2.0 min chromatography, 30-90AB, purity 100%.

MS MS ESI calcd. for $C_{30}H_{49}O$ [M-2H$_2$O+H]$^+$ 425, found 425.

Example 19: Synthesis of (3S,5S,8R,9S,10S,13S, 14S,17R)-3-ethyl-17-((1S,2S)-1-hydroxy-1-phenyl-propan-2-yl)-10,13-dimethylhexadecahydro-1H-cyclopenta[a]phenanthren-3-ol (19) OH

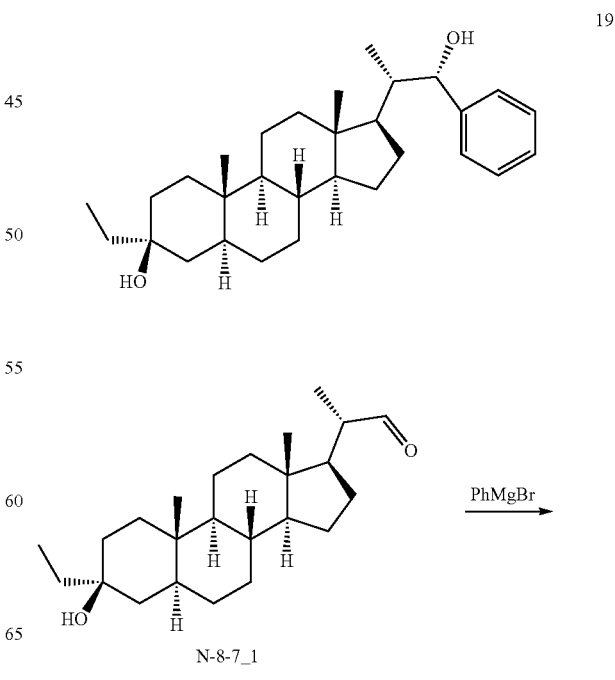

-continued

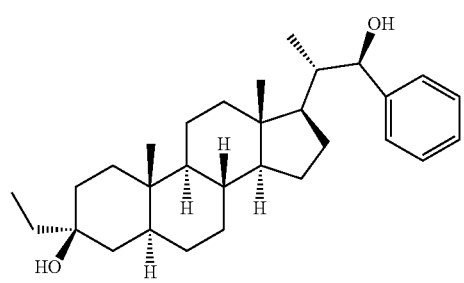

55

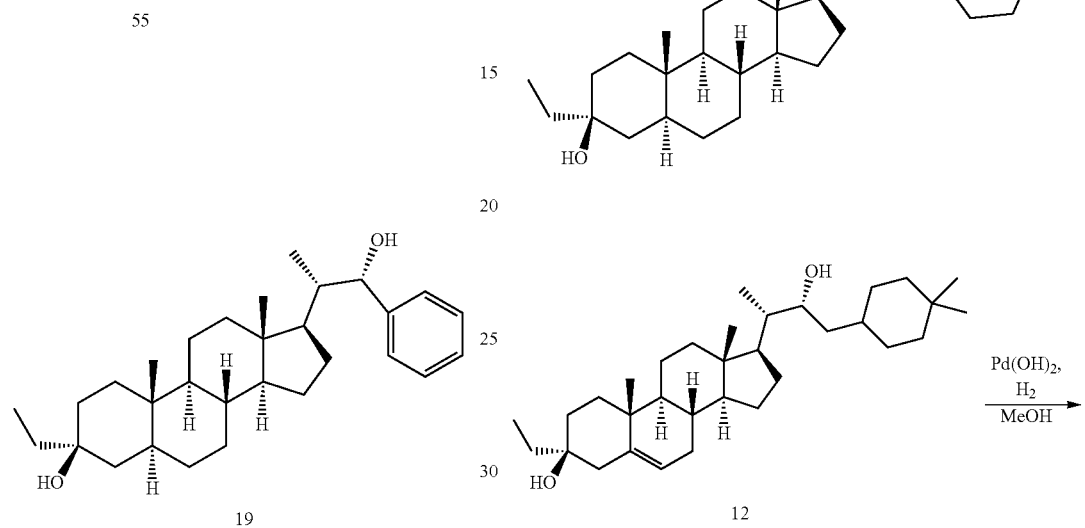

Example 20: Synthesis of (3S,5S,8R,9S,10S,13S,14S,17R)-17-((2S,3R)-4-(4,4-dimethylcyclohexyl)-3-hydroxybutan-2-yl)-3-ethyl-10,13-dimethylhexadecahydro-1H-cyclopenta[a]phenanthren-3-ol (20)

1. A solution N-8-7_1 (300 mg, 0.832 mmol) in THF (5 mL) was added to a solution of PhMgBr (1.38 mL, 3 M in ether, 4.15 mmol) in THF (10 mL) at 0° C., then the reaction mixture was stirred at 0° C. for 3 hours. Next, the reaction mixture was stirred at 25° C. for 5 hrs. The reaction mixture was quenched by water (10 mL) at 0° C. The solution was filtered and the filter cake was washed with EtOAc (10 mL). The aqueous phase was extracted with EtOAc (3×15 mL). The combined organic phase was washed with saturated brine (2×10 mL), dried over anhydrous $Na_2SO_4$, filtered and concentrated. The residue was purified by silica gel chromatography (PE/EtOAc=20/1 to 1/1) to afford crude product (200 mg) as a solid. The crude product was purified by SFC (column: AD (250 mm*30 mm, 5 um)), gradient: 25-25% B (A=0.1% NH3/H2O, B=EtOH), flow rate: 60 mL/min) to give 55 (Peak2, 55 mg, 15%) and 19 (Peak1, 21 mg, 6%) as a solid.

19:

$^1$H NMR (400 MHz, $CDCl_3$) δ 7.40-7.20 (m, 5H), 4.85-4.80 (m, 1H), 2.10-1.60 (m, 5H), 1.55-1.05 (m, 17H), 0.95-0.75 (m, 14H), 0.71 (s, 3H), 0.60-0.50 (m, 1H).

LCMS Rt=1.208 min in 2.0 min chromatography, 30-90AB_2 min., purity 100%, MS ESI calcd. For $C_{30}H_{43}$ $[M-2H_2O+H]^+$ 403, found 403.

SFC Rt=1.047 min in 3 min chromatography, OJ_3_EtOH_DEA_5_40_25ML, 100% de.

1. Pd(OH)$_2$ (150 mg, dry) was added to a solution of 12 (100 mg, 0.206 mmol) in MeOH (20 mL). The mixture was stirred at 50° C. under H$_2$ (50 Psi) for 48 hrs. The mixture was filtered, concentrated and purified by combi-flash (0-15% of EtOAc in PE) to give 87 (12 mg, 12%) and 20 (11 mg, 11%) as a solid.

20:

$^1$H NMR (400 MHz, $CDCl_3$) δ 3.83-3.75 (m, 1H), 1.99-1.92 (m, 1H), 1.71-1.57 (m, 8H), 1.52-1.43 (m, 3H), 1.41-1.29 (m, 8H), 1.27-1.13 (m, 11H), 1.12-1.04 (m, 4H), 1.03-0.94 (m, 3H), 0.91-0.86 (m, 12H), 0.82 (s, 3H), 0.68-0.59 (m, 4H).

LCMS Rt=1.748 min in 2.0 min chromatography, 30-90AB_E, purity 100%, MS ESI calcd. for $C_{33}H_{55}$ [M+H—$H_2O$]$^+$ 451, found 451.

Example 21: Synthesis of (3S,5S,8R,9S,10S,13S, 14S,17R)-3-ethyl-17-((2S,3S)-3-hydroxypentan-2-yl)-10,13-dimethylhexadecahydro-1H-cyclopenta[a]phenanthren-3-ol (21)

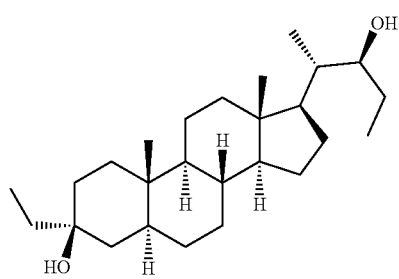

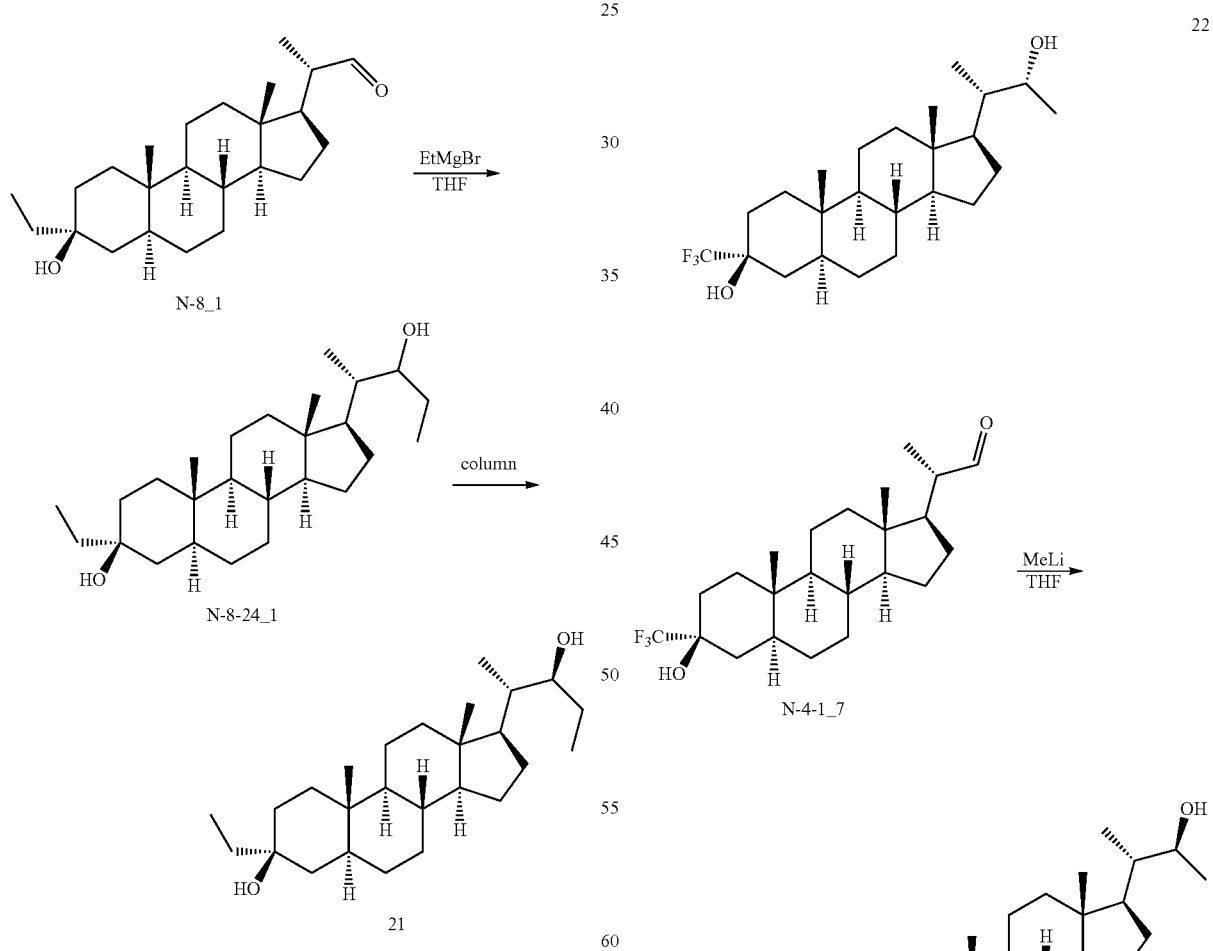

1. EtMgBr (0.553 mL, 3 M in ether, 1.66 mmol) was added dropwise to a solution of N-8_1 (250 mg, 0.8320 mmol) in THF (3 mL) at 25° C. under N2. The mixture was stirred at 25° C. for 1 hr, quenched with sat. $NH_4Cl$ (10 mL) and extracted with EtOAc (3×15 mL). The organic layers were washed with brine (20 mL), dried over $Na_2SO_4$, filtered, concentrated under vacuum to give a crude product N-8-24_1, which was purified by flash column (0~15% of EtOAc in PE) to give 21 (130 mg, impure) as a solid. The impure N-8-24 (130 mg, 0.3327 mmol) was re-crystallized from MeCN (3 mL) at 85° C. to give pure 21 (111 mg, 86%) as a solid.

$^1$H NMR (400 MHz, CDCl$_3$) δ 3.62-3.50 (m, 1H), 2.02-1.81 (m, 2H), 1.72-1.59 (m, 3H), 1.56-1.46 (m, 4H), 1.45-1.17 (m, 12H), 1.16-1.00 (m, 5H), 0.99-0.85 (m, 11H), 0.84-0.78 (m, 4H), 0.66 (s, 4H).

HPLC Rt=5.73 min in 10 min chromatography, 30-90_AB_1.2 mL_E, purity 100%.

MS MS ESI calcd. for $C_{26}H_{43}$ [M+H-2$H_2O$]$^+$ 355, found 355.

Example 22: Synthesis of (3S,5S,8R,9S,10S,13S, 14S,17R)-17-((2S,3R)-3-hydroxybutan-2-yl)-10,13-dimethyl-3-(trifluoromethyl)hexadecahydro-1H-cyclopenta[a]phenanthren-3-ol (22)

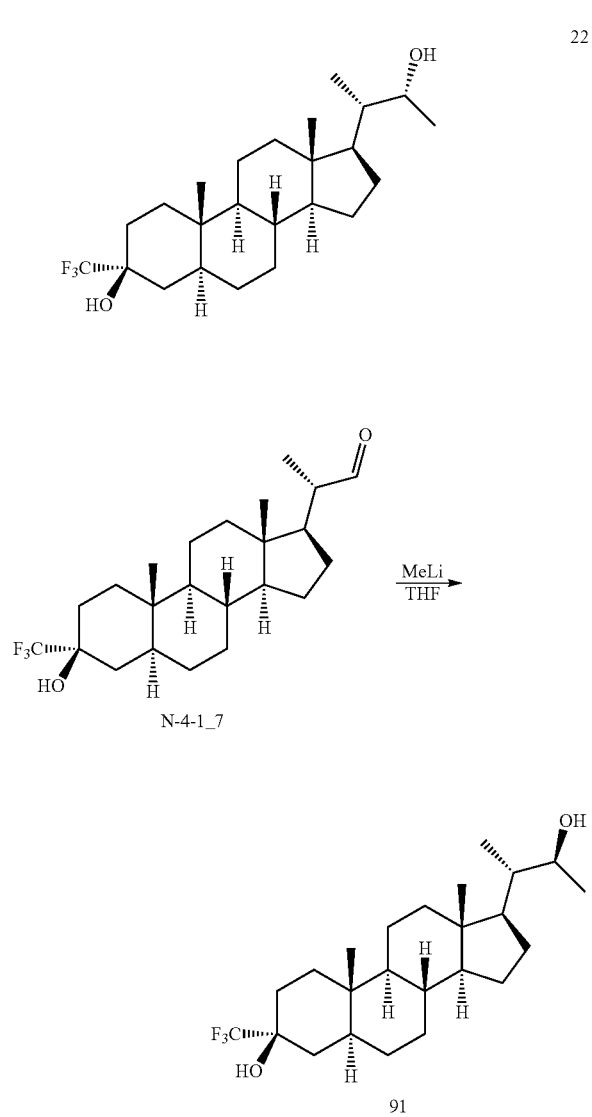

-continued

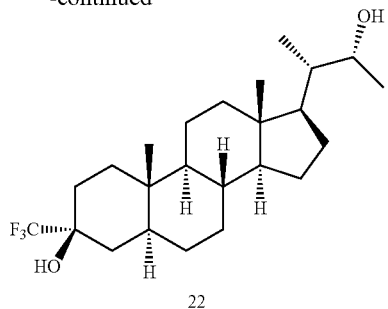

22

1. MeLi (7.75 mL, 1.6 M, 12.4 mmol) was added to a solution of N-4-1_7 (1 g, 2.49 mmol) in THF (10 mL) at 0° C. The mixture was stirred at 15° C. for 1 hr. To the mixture was added NH₄Cl (10%, 20 mL). The mixture was extracted with EtOAc (2×30 mL). The combined organic layer was dried over Na₂SO₄, filtered and concentrated in vacuum to give a mixture (1 g) as a gum. The mixture (1 g) was purified by flash column (0~15% EtOAc in PE) to give 91 (450 mg) and 22 (460 mg) and 130 mg of a mixture. 91 (450 mg) was re-crystallized from MeCN (10 mL) to give 91 (50 mg) as a solid. 22 (460 mg) was re-crystallized twice form MeCN (10 mL) to give 22 (50 mg) as a solid.

22:
$^1$H NMR (400 MHz, CDCl₃) δ 3.97-3.82 (m, 1H), 2.10-1.92 (m, 3H), 1.85-1.78 (m, 1H), 1.77-1.60 (m, 5H), 1.59-1.06 (m, 13H), 1.05-0.81 (m, 12H), 0.74-0.62 (m, 4H).

LCMS Rt=1.136 min in 2.0 min chromatography, 30-90_AB_E, purity 100%, MS ESI calcd. for $C_{24}H_{38}F_3O$ [M+H—H₂O]⁺ 399, found 399.

HPLC Rt=5.05 min in 10.0 min chromatography, 30-90_AB_E, purity 100%, d.e. 100%.

Example 23: Synthesis of (3S,5R,8R,9S,10S,13S,14S,17R)-3-ethyl-17-((2S,3S)-3-hydroxyhexan-2-yl)-10,13-dimethylhexadecahydro-1H-cyclopenta[a]phenanthren-3-ol (23)

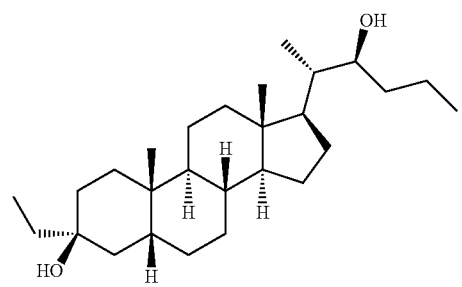

23

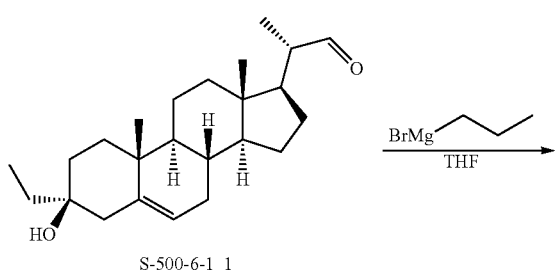

-continued

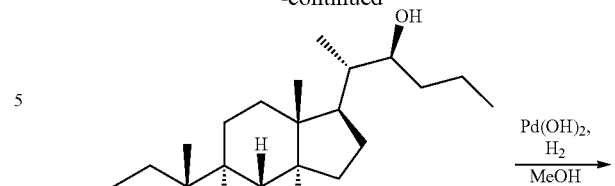

72

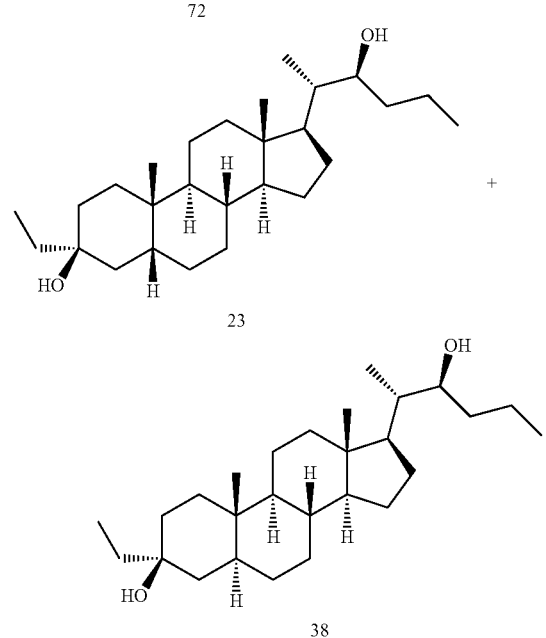

1. Propylmagnesium bromide (3.34 mL, 6.69 mmol, 2M in THF) was slowly added to a solution of S-500-6-1_1 (800 mg, 2.23 mmol) in THF (30 mL) at 0° C. After addition, the mixture was stirred at 15° C. for 1 hr. The mixture was quenched with sat.NH₄Cl (40 mL) and extracted with EtOAc (3×20 mL). The combined organic phase was washed with brine (2×30 mL), dried over Na₂SO₄, filtered and concentrated and purified by combi-flash (0-15% of EtOAc in PE) to give 1572 (500 mg, 56%) as a solid.

$^1$H NMR (400 MHz, CDCl₃) δ 5.31-5.26 (m, 1H), 3.72-3.64 (m, 1H), 2.41-2.31 (m, 1H), 2.07-1.85 (m, 4H), 1.77-1.69 (m, 1H), 1.62-1.54 (m, 3H), 1.52-1.38 (m, 9H), 1.37-1.16 (m, 6H), 1.15-1.01 (m, 7H), 0.99-0.88 (m, 7H), 0.87-0.82 (m, 3H), 0.68 (s, 3H).

LCMS Rt=4.979 min in 7.0 min chromatography, 30-90AB_E, purity 98.8%, MS ESI calcd. for $C_{27}H_{43}$ [M+H-2H₂O]⁺367, found 367.

2. Pd(OH)₂ (300 mg, dry) was added to a solution of 72 (150 mg, 0.372 mmol) in MeOH (20 mL). The mixture was stirred at 50° C. under H₂ (50 Psi) for 48 hrs. The mixture was filtered, concentrated and purified by combi-flash (0-15% of EtOAc in PE) to give 23 (9 mg, 6%) and 38 (43 mg, 29%) as solids.

23:
$^1$H NMR (400 MHz, CDCl₃) δ 3.71-3.62 (m, 1H), 2.01-1.83 (m, 3H), 1.82-1.72 (m, 1H), 1.69-1.57 (m, 3H), 1.51-1.37 (m, 9H), 1.36-1.22 (m, 9H), 1.20-1.00 (m, 8H), 0.97 (s, 3H), 0.94-0.87 (m, 8H), 0.66 (s, 3H).

LCMS Rt=1.440 min in 2.0 min chromatography, 30-90AB_E, purity 98.8%, MS ESI calcd. for $C_{27}H_{45}$ [M+H-2H$_2$O]$^+$369, found 369.

Example 24: Synthesis of (3S,5S,8R,9S,10S,13S,14S,17R)-3-ethyl-17-((2S,3R)-3-hydroxy-6-methyl-heptan-2-yl)-10,13-dimethylhexadecahydro-1H-cyclopenta[a]phenanthren-3-ol (24)

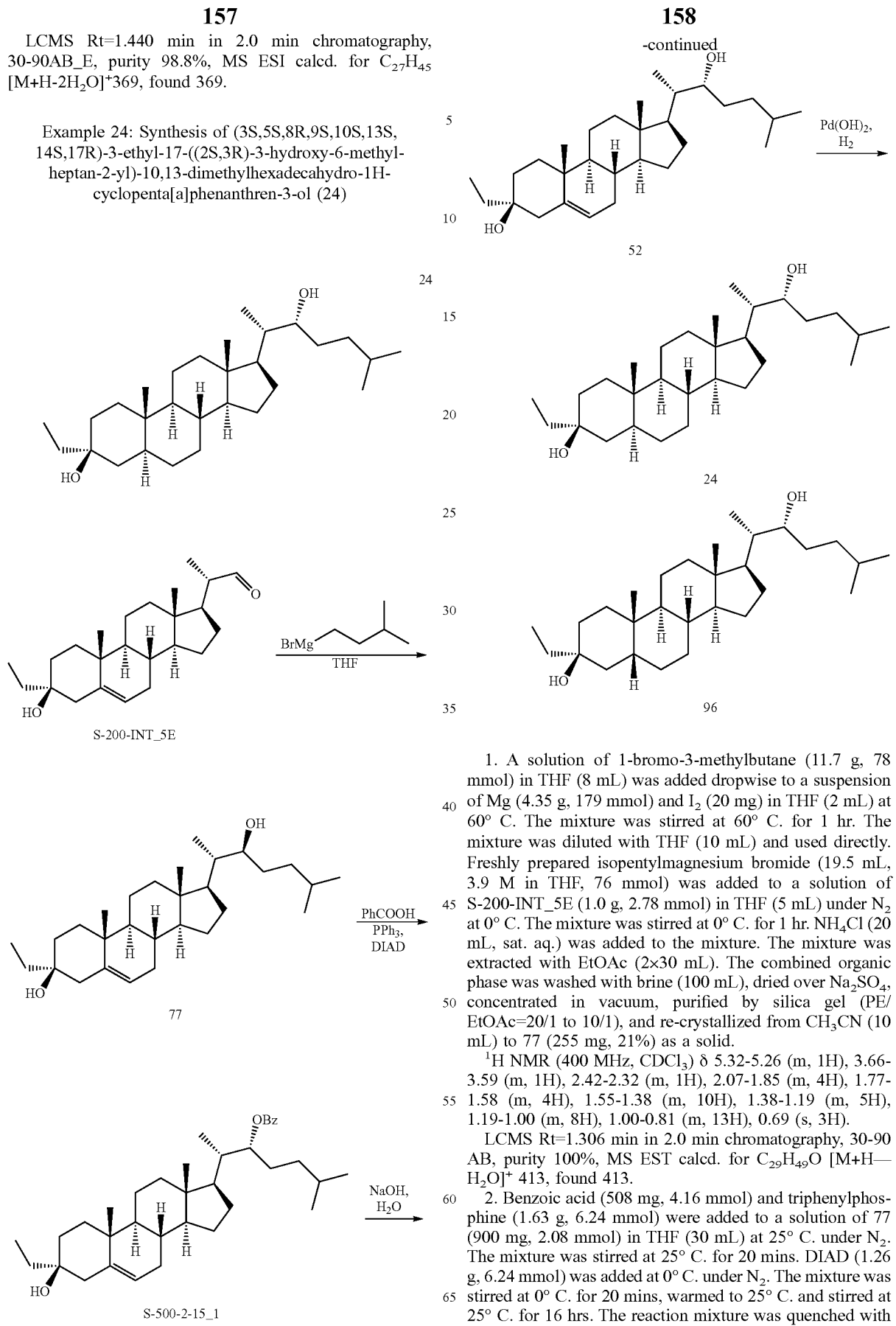

1. A solution of 1-bromo-3-methylbutane (11.7 g, 78 mmol) in THF (8 mL) was added dropwise to a suspension of Mg (4.35 g, 179 mmol) and I$_2$ (20 mg) in THF (2 mL) at 60° C. The mixture was stirred at 60° C. for 1 hr. The mixture was diluted with THF (10 mL) and used directly. Freshly prepared isopentylmagnesium bromide (19.5 mL, 3.9 M in THF, 76 mmol) was added to a solution of S-200-INT_5E (1.0 g, 2.78 mmol) in THF (5 mL) under N$_2$ at 0° C. The mixture was stirred at 0° C. for 1 hr. NH$_4$Cl (20 mL, sat. aq.) was added to the mixture. The mixture was extracted with EtOAc (2×30 mL). The combined organic phase was washed with brine (100 mL), dried over Na$_2$SO$_4$, concentrated in vacuum, purified by silica gel (PE/EtOAc=20/1 to 10/1), and re-crystallized from CH$_3$CN (10 mL) to 77 (255 mg, 21%) as a solid.

$^1$H NMR (400 MHz, CDCl$_3$) δ 5.32-5.26 (m, 1H), 3.66-3.59 (m, 1H), 2.42-2.32 (m, 1H), 2.07-1.85 (m, 4H), 1.77-1.58 (m, 4H), 1.55-1.38 (m, 10H), 1.38-1.19 (m, 5H), 1.19-1.00 (m, 8H), 1.00-0.81 (m, 13H), 0.69 (s, 3H).

LCMS Rt=1.306 min in 2.0 min chromatography, 30-90 AB, purity 100%, MS EST calcd. for $C_{29}H_{49}O$ [M+H—H$_2$O]$^+$ 413, found 413.

2. Benzoic acid (508 mg, 4.16 mmol) and triphenylphosphine (1.63 g, 6.24 mmol) were added to a solution of 77 (900 mg, 2.08 mmol) in THF (30 mL) at 25° C. under N$_2$. The mixture was stirred at 25° C. for 20 mins. DIAD (1.26 g, 6.24 mmol) was added at 0° C. under N$_2$. The mixture was stirred at 0° C. for 20 mins, warmed to 25° C. and stirred at 25° C. for 16 hrs. The reaction mixture was quenched with water (60 ml) and extracted with MTBE (3×30 mL). The combined organic phase was washed with brine (60 mL), dried over Na$_2$SO$_4$, filtered, concentrated under vacuum to give a crude product, which was purified by flash column (0-10% EtOAc in PE) to give impure product S-500-2-15_1 (900 mg) as an oil, which was used directly for the next step.

3. NaOH solution (974 mg in 6 mL H$_2$O, 16.8 mmol) was added to a solution of 5-500-2-15_1 (900 mg, 1.68 mmol) in THF (10 mL) and MeOH (5 mL). The mixture was heated at 50° C. for 16 hrs. The reaction mixture was quenched with sat. NH$_4$Cl (60 mL) and extracted with EtOAc (3×20 mL). The combined organic phase was washed with brine (60 mL), dried over Na$_2$SO$_4$, filtered concentrated, and purified by combi-flash (0-15% of EtOAc in PE) to give 210 mg of a solid, which was purified by SFC (column: AD (250 mm*30 mm, 5 um), gradient: 35-35% B (A=0.1% NH$_3$/H$_2$O, B=MeOH), flow rate: 80 mL/min) to give 52 (150 mg, 68%) as a solid.

$^1$H NMR (400 MHz, CDCl$_3$) δ 5.30-5.26 (m, 1H), 3.64-3.58 (m, 1H), 2.40-2.30 (m, 1H), 2.02-1.92 (m, 3H), 1.80-1.58 (m, 7H), 1.56-1.31 (m, 9H), 1.30-1.05 (m, 8H), 1.03 (s, 3H), 1.02-0.96 (m, 2H), 0.95-0.86 (m, 9H), 0.85-0.80 (m, 3H), 0.69 (s, 3H).

LCMS $t_R$=1.335 min in 2 min chromatography, 30-90AB_ELSD, purity 100.0%, MS ESI calcd. for C$_{29}$H$_{47}$ [M+H-2H$_2$O]$^+$ 395, found 395.

4. Pd(OH)$_2$ (200 mg) was added to a solution of 52 (50 mg, 0.116 mmol) in MeOH (10 mL). The mixture was stirred at 50° C. under H$_2$ (50 Psi). The mixture was filtered, concentrated and purified by combi-flash (0-10% of EtOAc in PE) to give 24 (15 mg, 30%) as a solid and 96 (1.2 mg, 3%) as a solid.

24:

$^1$H NMR (400 MHz, CDCl$_3$) δ 3.66-3.52 (m, 1H), 2.02-1.91 (m, 1H), 1.74-1.57 (m, 7H), 1.52-1.44 (m, 2H), 1.43-1.29 (m, 7H), 1.28-1.04 (m, 11H), 1.03-0.94 (m, 3H), 0.94-0.85 (m, 13H), 0.82 (s, 3H), 0.71-0.60 (m, 4H).

LCMS $t_R$=1.342 min in 2 min chromatography, 30-90AB_ELSD, purity 100.0%, MS ESI calcd. for C$_{29}$H$_{49}$ [M+H-2H$_2$O]$^+$ 397, found 397.

Example 25: Synthesis of (1S,3S,4S)-4-((3S,5S,8R,9S,10S,13S,14S,17R)-3-hydroxy-10,13-dimethyl-3-(trifluoromethyl)hexadecahydro-1H-cyclopenta[a]phenanthren-17-yl)-1-phenylpentane-1,3-diol (25)

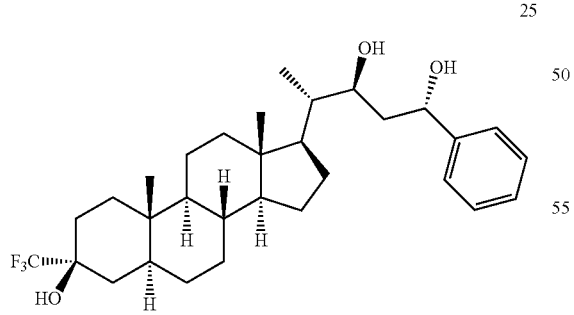

The preparation of 25 can be found in Example 13.

25:

$^1$H NMR (400 MHz, CDCl$_3$) δ 7.42-7.28 (m, 5H), 4.97-4.81 (m, 1H), 4.12-3.92 (m, 1H), 3.23 (brs, 1H), 2.69 (brs, 1H), 2.10-1.88 (m, 3H), 1.82-1.62 (m, 7H), 1.48-1.18 (m, 10H), 1.10-0.88 (m, 8H), 0.87-0.78 (m, 4H), 0.70-0.58 (m, 4H).

LCMS Rt=1.319 min in 2 min chromatography, 10-80AB_2MIN_E, purity 97.0%, MS ESI calcd. for C$_{31}$H$_{45}$F$_3$O$_3$Na [M+Na]$^+$ 545, found 545.

SFC Rt=1.718 min in 5 min chromatography, IC-3_MeOH(DEA)_40_2.5ML, 98.26% de.

SFC Rt=4.367 min in 8 min chromatography, AD_MEOH(DEA)_5_40_2,8ML_8MIN, 100% de.

Example 26: Synthesis of (3S,5S,8R,9S,10S,13S,14S,17R)-3-ethyl-17-((S)-3-hydroxy-3-methylbutan-2-yl)-10,13-dimethylhexadecahydro-1H-cyclopenta[a]phenanthren-3-ol (26)

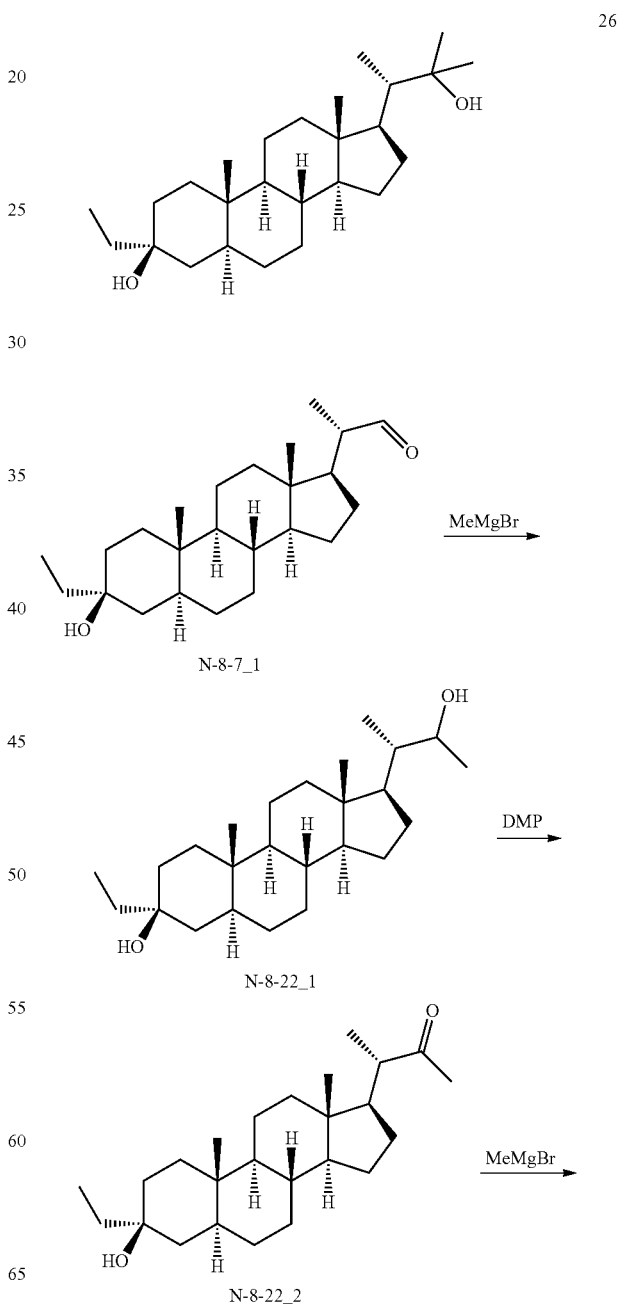

-continued

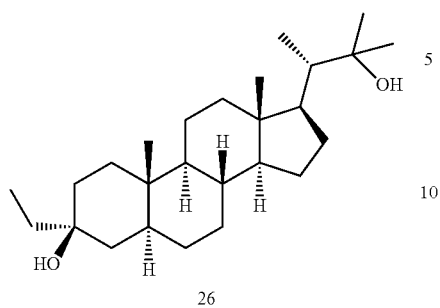

26

1. MeMgBr (0.83 mL, 2.49 mmol, 3M in ether) was added dropwise to a solution of N-8-7_1 (300 mg, 0.832 mmol) in THF (20 mL) at 0° C. under $N_2$. After stirring at 20° C. for 30 minutes, the reaction mixture was quenched with sat. $NH_4Cl$ (50 mL) and extracted with EtOAc (2×10 mL). The combined layer was washed with brine (10 mL), dried over $Na_2SO_4$, filtered and concentrated to give a residue, which was purified by flash column (0-10% EtOAc in PE) to give N-8-22_1 (100 mg, 31%) as a solid.

$^1$H NMR (400 MHz, $CDCl_3$) δ 3.99-3.88 (m, 1H), 1.98-1.84 (m, 2H), 1.69-1.57 (m, 6H), 1.52-1.45 (m, 2H), 1.44-1.28 (m, 3H), 1.26-1.17 (m, 5H), 1.16-1.11 (m, 5H), 1.10-0.95 (m, 5H), 0.93-0.86 (m, 7H), 0.84-0.80 (m, 4H), 0.69-0.62 (m, 4H).

2. DMP (224 mg, 0.53 mmol) was added to a solution of N-8-22_1 (100 mg, 0.265 mmol) in DCM (10 mL). After stirring at 20° C. for 10 min, the reaction mixture was quenched with saturated $NaHCO_3$ solution (30 mL) until pH of the aqueous layer was about 9. The mixture was filtered. The DCM layer was separated and the aqueous phase was extracted with DCM (20 mL). The combined organic phase was washed with saturated $Na_2S_2O_3$ (3×40 mL), sat. $NaHCO_3$ (40 mL), brine (40 mL), dried over $Na_2SO_4$, filtered, concentrated and purified by combi-flash (0-20% of EtOAc in DCM) to give N-8-22_2 (80 mg, 80%) as a solid.

$^1$H NMR (400 MHz, $CDCl_3$) δ 2.54-2.42 (m, 1H), 2.09 (s, 3H), 1.94-1.87 (m, 1H), 1.71-1.59 (m, 4H), 1.54-1.45 (m, 3H), 1.44-1.30 (m, 4H), 1.29-1.16 (m, 6H), 1.15-1.07 (m, 5H), 1.06-0.92 (m, 4H), 0.91-0.79 (m, 7H), 0.74-0.61 (m, 4H).

3. MeMgBr (0.353 mL, 1.06 mmol, 3M in ether) was added to a solution of N-8-22_2 (80 mg, 0.213 mmol) in THF (5 mL) under $N_2$. After stirring at 20° C. for 30 minutes, the reaction mixture was quenched with saturated aqueous $NH_4Cl_1$ (30 mL) solution and extracted with EtOAc (20 mL×3). The combined organic layer was washed with brine (50 mL), dried over $Na_2SO_4$, filtered and concentrated under vacuum to give a crude product, which was purified by silica gel column (0-10% of EtOAc in PE) to afford 26 (7 mg, 8%) as a solid.

$^1$H NMR (400 MHz, $CDCl_3$) δ 2.08-2.01 (m, 1H), 1.97-1.86 (m, 1H), 1.69-1.57 (m, 6H), 1.53-1.45 (m, 3H), 1.40-1.27 (m, 5H), 1.26-1.17 (m, 8H), 1.14 (s, 3H), 1.13-1.01 (m, 3H), 0.99-0.92 (m, 5H), 0.91-0.85 (m, 4H), 0.82 (s, 3H), 0.70 (s, 3H), 0.67-0.60 (m, 1H).

LCMS Rt=1.240 min in 2.0 min chromatography, 30-90AB_E, purity 100%, MS ESI calcd. for $C_{26}H_{43}$ [M+H-2$H_2$O]$^+$ 355, found 355.

Example 27: Synthesis of (3S,8S,9S,10R,13S,14S,17R)-3-ethyl-17-((2S,3R)-3-hydroxy-4-methylpentan-2-yl)-10,13-dimethyl-2,3,4,7,8,9,10,11,12,13,14,15,16,17-tetradecahydro-1H-cyclopenta[a]phenanthren-3-ol (27)

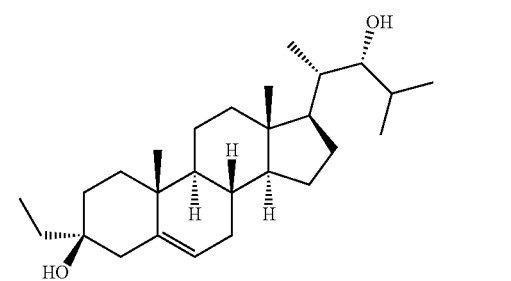

27

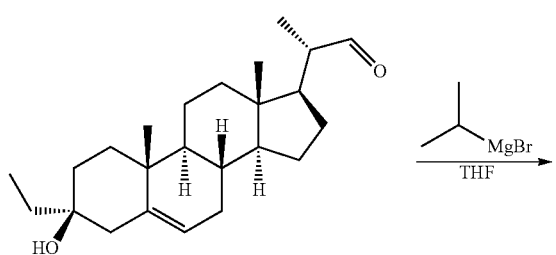

N-014-012_4

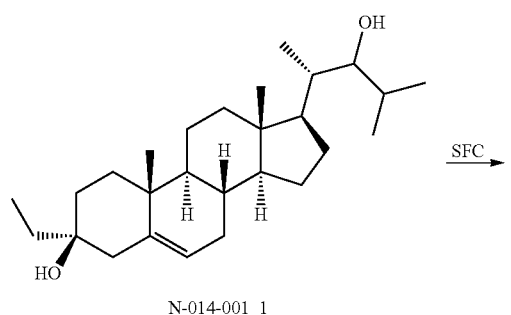

N-014-001_1

SFC

163

-continued

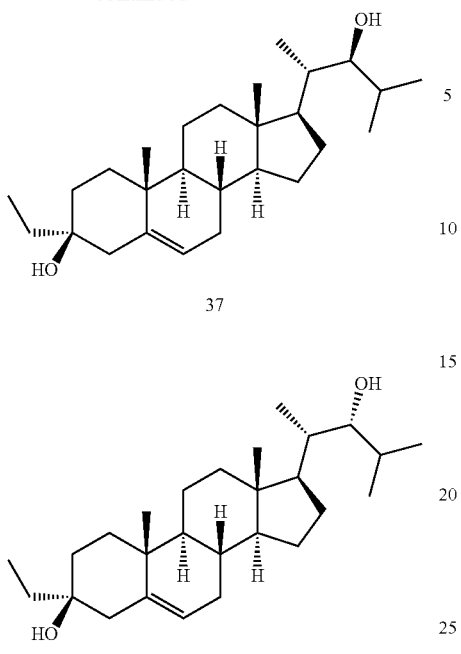

37

27

1. To a solution of N-014-012_4 (300 mg, 0.8366 mmol) in THF (20 mL) was added a solution of isopropylmagnesium chloride (1.25 mL, 2.50 mmol, 2 M) drop-wise at 0° C. over a period of 30 mins under $N_2$, during which the temperature was maintained below 0° C. The reaction mixture was stirred at 20° C. for another 2 hours to give a suspension. The reaction mixture was added saturated aq. $NH_4Cl$ (15 mL) and stirred for 20 min, then the mixture was extracted with EtOAc (3×10 mL). The combined organic phase was washed with brine (2×10 mL), dried over anhydrous $Na_2SO_4$, filtered and concentrated to obtain N-014-001_1 (360 mg, crude) as a solid, $^1H$ NMR showed the desired product, and was used directly for the next step.

2. X1 (150 mg, 0.37 mmol) was purified by SFC (Column: Chiralpak AS-H 250*305u; Condition: 0.1% $NH_3H_2O$ EtOH; Begin B: 20%; End B: 20%; FlowRate (ml/min): 65) to obtain 37 (Peak 2, 46 mg, 31%) and 27 (Peak 1, 27 mg, 18%) as a solid.

37:

27:

$^1$H NMR (400 MHz, CDCl$_3$) δ 5.32-5.26 (m, 1H), 3.42-3.34 (m, 1H), 2.43-2.34 (m, 1H), 2.06-1.91 (m, 3H), 1.90-1.75 (m, 2H), 1.74-1.66 (m, 2H), 1.63-1.58 (m, 3H), 1.54-1.26 (m, 11H), 1.22-1.04 (m, 3H), 1.03-0.99 (m, 3H), 0.97-0.93 (m, 7H), 0.92-0.87 (m, 3H), 0.86-0.77 (m, 3H), 0.70 (s, 3H).

LCMS Rt=1.228 min in 2 min chromatography, 30-90AB_2MIN_E, purity 100%, MS ESI calcd. for $C_{27}H_{45}O$ [M+H—H$_2$O]$^+$385, found 385.

SFC Rt=2.440 min in 10 min chromatography, OJ_3_EtOH_DEA_5_40_25ML ("Column: Chiralcel OJ-3150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C."), 97.38% de.

164

Example 28: Synthesis of (3S,5S,8R,9R,10S,13S,14S,17R)-3-ethyl-17-((2S,3S)-3-hydroxy-6-methylheptan-2-yl)-13-methylhexadecahydro-1H-cyclopenta[a]phenanthren-3-ol (28)

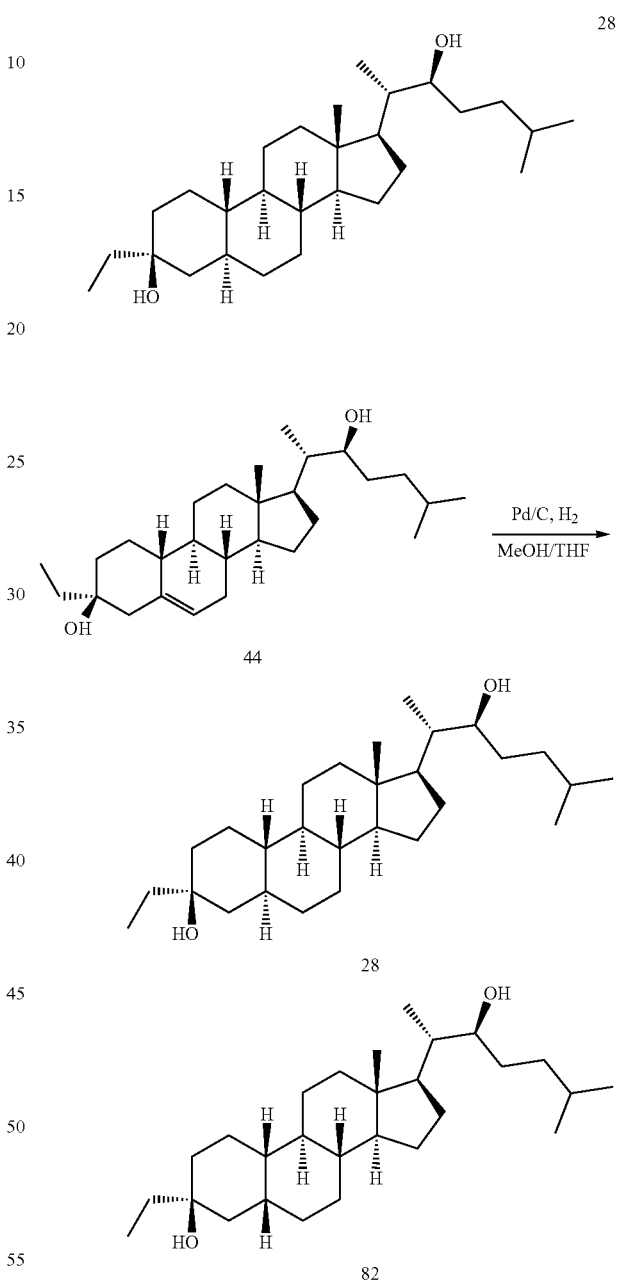

1. Pd/C (dry, 200 mg) was added to a solution of 44 (200 mg, 0.480 mmol) in MeOH/THF (10 mL/10 mL) under Ar. The suspension was degassed under vacuum and purged with H$_2$ three times. The mixture was stirred under H$_2$ (50 psi) at 50° C. for 48 hrs to give a black suspension. The reaction mixture was filtered through a pad of Celite and washed with THF (100 mL). The filtrate was concentrated to give 28 (30 mg, 15%) as a solid and 82 (30 mg, 15%) as a solid.

28:

¹H NMR (400 MHz, CDCl3) δ 3.63-3.61 (m, 1H), 1.98-1.76 (m, 4H), 1.72-1.55 (m, 7H), 1.55-1.47 (m, 4H), 1.46-1.23 (m, 6H), 1.22-0.97 (m, 11H), 0.92-0.78 (m, 12H), 0.76-0.54 (m, 5H).

LCMS Rt=1.298 min in 2 min chromatography, 30-90 AB, purity 100%, MS ESI calcd. For $C_{28}H_{47}$ [M+H-2H$_2$O]$^+$ 383, found 383.

Example 29: Synthesis of (3S,5S,8R,9S,10S,13S,14S,17R)-3-ethyl-17-((2S,3S)-3-hydroxy-6-methylheptan-2-yl)-10,13-dimethylhexadecahydro-1H-cyclopenta[a]phenanthren-3-ol (29)

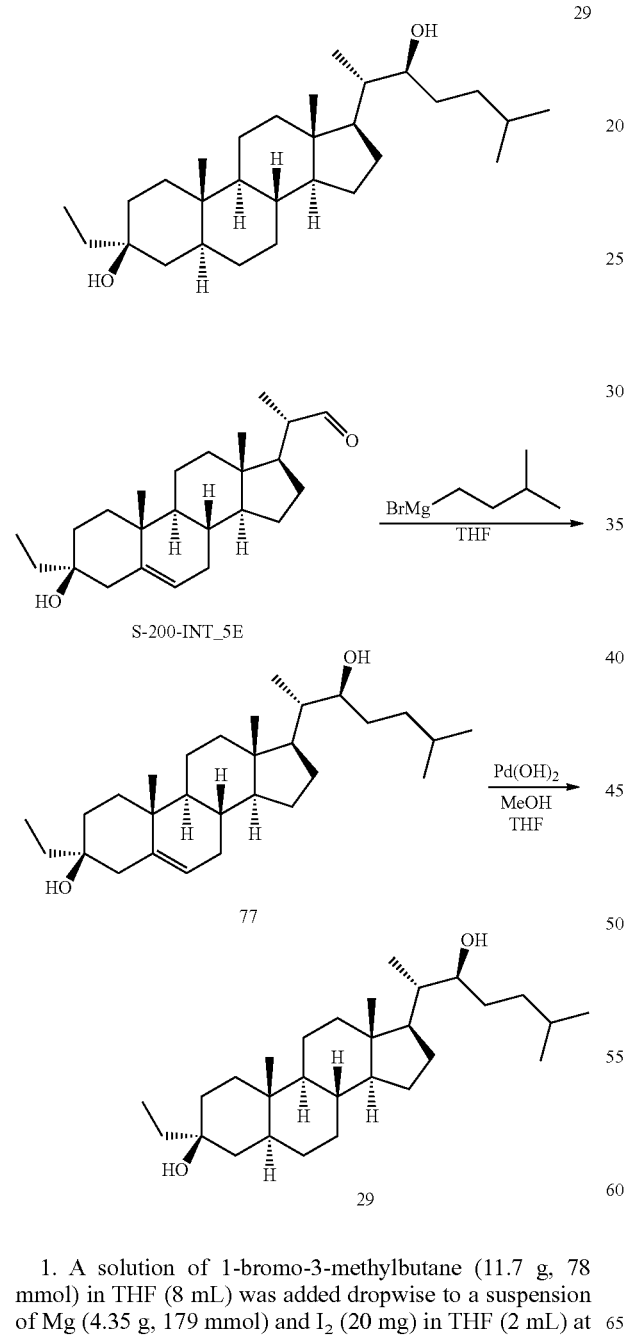

1. A solution of 1-bromo-3-methylbutane (11.7 g, 78 mmol) in THF (8 mL) was added dropwise to a suspension of Mg (4.35 g, 179 mmol) and I$_2$ (20 mg) in THF (2 mL) at 60° C. The mixture was stirred at 60° C. for 1 hr. The mixture was diluted with THF (10 mL) and used directly.

Freshly prepared isopentylmagnesium bromide (19.5 mL, 3.9 M in THF, 76 mmol) was added to a solution of S-200-INT_5E (1.0 g, 2.78 mmol) in THF (5 mL) under N$_2$ at 0° C. The mixture was stirred at 0° C. for 1 hr. NH$_4$Cl (20 mL, sat. aq.) was added to the mixture. The mixture was extracted with EtOAc (2×30 mL). The combined organic phase was washed with brine (100 mL), dried over Na$_2$SO$_4$, concentrated under vacuum, purified by silica gel (PE/EtOAc=20/1 to 10/1), and re-crystallized from CH$_3$CN (10 ml) to give 77 (255 mg, 21%) as a solid.

¹H NMR (400 MHz, CDCl$_3$) δ 5.32-5.26 (m, 1H), 3.66-3.59 (m, 1H), 2.42-2.32 (m, 1H), 2.07-1.85 (m, 4H), 1.77-1.58 (m, 4H), 1.55-1.38 (m, 10H), 1.38-1.19 (m, 5H), 1.19-1.00 (m, 8H), 1.00-0.81 (m, 13H), 0.69 (s, 3H).

LCMS Rt=1.306 min in 2.0 min chromatography, 30-90 AB, purity 100%, MS ESI calcd. for $C_{29}H_{49}O$ [M+H—H$_2$O]$^+$ 413, found 413.

2. Pd(OH)$_2$ (dry, 20%, 50.0 mg) was added to a solution of 77 (100 mg, 232 umol) in THF (10 mL) and MeOH (10 mL) under Ar. The suspension was degassed under vacuum and purged with H$_2$ three times. The mixture was stirred under H$_2$ (50 psi) at 50° C. for 16 hrs. The reaction mixture was filtered through a pad of Celite and washed with THF (3×10 mL). The filtrate was concentrated. The residue was purified by silica gel chromatography (PE/EtOAc=20/1) to afford 29 (7.00 mg, 7%) as a solid.

¹H NMR (400 MHz, CDCl$_3$) δ 3.68-3.60 (m, 1H), 1.96-1.88 (m, 2H), 1.68-1.60 (m, 3H), 1.53-1.47 (m, 7H), 1.39-1.23 (m, 13H), 1.16-0.95 (m, 7H), 0.90-0.86 (m, 12H), 0.83 (s, 3H), 0.66-0.63 (m, 4H).

LCMS Rt=1.603 min in 2.0 min chromatography, 30-90 AB_ELSD, purity 97%, MS ESI calcd. for $C_{29}H_{49}$ [M+H—H$_2$O]$^+$ 397, found 397.

Example 30: Synthesis of (3S,8S,9S,10R,13S,14S,17R)-17-((2S,3R)-3-hydroxy-6-methylheptan-2-yl)-3,10,13-trimethyl-2,3,4,7,8,9,10,11,12,13,14,15,16,17-tetradecahydro-1H-cyclopenta[a]phenanthren-3-ol (30)

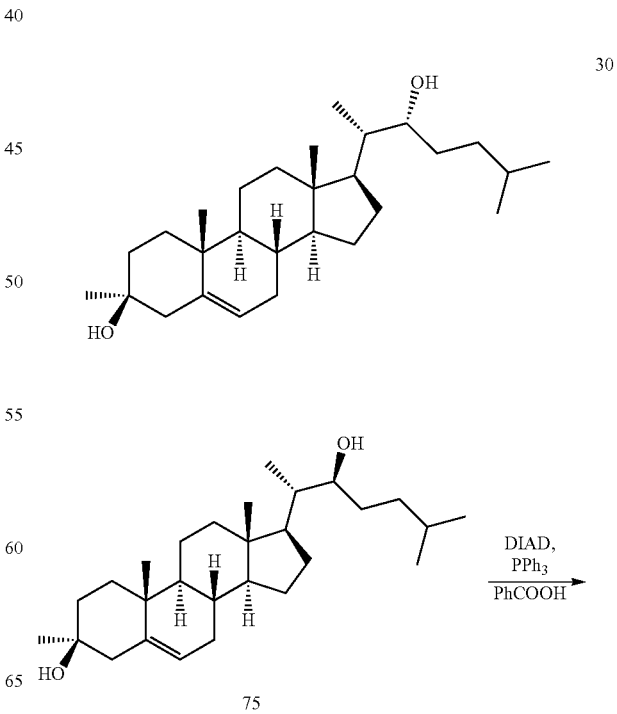

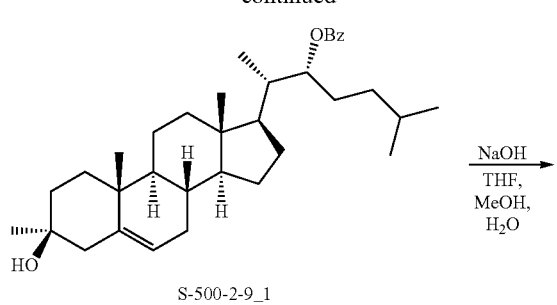

S-500-2-9_1

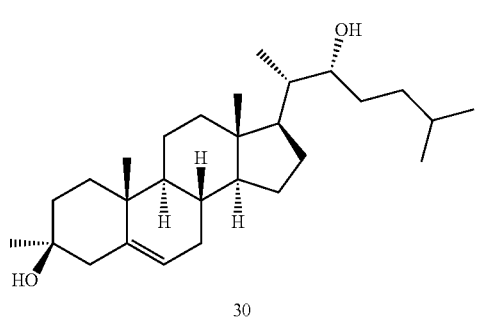

30

1. Benzoic acid (2.03 g, 16.7 mmol) and triphenylphosphine (6.57 g, 25.1 mmol) were added to a solution of S-500-2-10 (3.5 g, 8.39 mmol) in THF (30 mL) at 25° C. under N₂. The mixture was stirred at 25° C. for 20 mins. DIAD (5.07 g, 25.1 mmol) was added at 0° C. under N₂. The mixture was stirred at 0° C. for 20 mins then warmed to 25° C. and stirred for 1 h. The reaction mixture was quenched with water (100 mL) and extracted with MTBE (3×30 mL). The combined organic phase was washed with brine (60 mL), dried over Na₂SO₄, filtered, concentrated in vacuum to give a crude, which was purified by flash column (0-10% EtOAc in PE) to give 300 mg crude product S-500-2-9_1 as an oil, which was used directly for the next step.

2._NaOH (1.14 g in 3 mL H₂O, 28.7 mmol) was added to a solution of S-500-2-9_1 (300 mg, 0.576 mmol) in THF (5 mL) and MeOH (3 mL). The mixture was stirred at 50° C. for 16 hrs. The mixture was quenched with sat. NH₄Cl (20 mL) and extracted with EtOAc (3×10 mL). The combined organic phase was washed with brine (30 mL), dried over Na₂SO₄, filtered, concentrated and purified by combi-flash (0-10% of EtOAc in PE) to give 30 (12 mg, 5%) as a solid.

$^1$H NMR (400 MHz, CDCl₃) δ 5.32-5.28 (m, 1H), 3.63-3.59 (m, 1H), 2.44-2.40 (m, 1H), 2.05-1.90 (m, 3H), 1.80-1.62 (m, 4H), 1.61-1.58 (m, 3H), 1.56-1.30 (m, 9H), 1.28-1.03 (m, 10H), 1.01 (s, 3H), 0.99-0.85 (m, 10H), 0.69 (s, 3H).

LCMS $t_R$=1.260 min in 2 min chromatography, 30-90AB_ELSD, purity 100.0%, MS ESI calcd. for $C_{28}H_{45}$ [M+H-2H₂O]⁺381, found 381.

Example 31: Synthesis of (1R,3R,4S)-4-((3S,5S,8R,9S,10S,13S,14S,17R)-3-hydroxy-10,13-dimethyl-3-(trifluoromethyl)hexadecahydro-1H-cyclopenta[a]phenanthren-17-yl)-1-phenylpentane-1,3-diol (31)

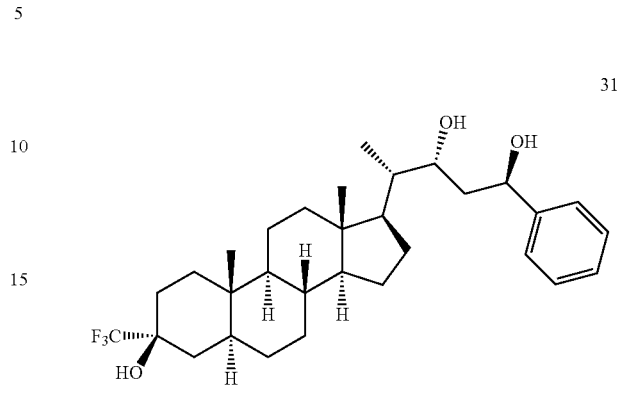

31

The synthesis of 31 can be found in Example 13.

31:
$^1$H NMR (400 MHz, CDCl₃) δ 7.45-7.28 (m, 5H), 5.02-4.81 (m, 1H), 4.18-3.98 (m, 1H), 3.35 (brs, 1H), 2.47 (brs, 1H), 2.15-1.72 (m, 8H), 1.53-1.31 (m, 8H), 1.30-1.03 (m, 8H), 0.99-0.89 (m, 104H), 0.89-0.78 (m, 4H), 0.75-0.60 (m, 4H).

LCMS Rt=1.327 min in 2 min chromatography, 10-80AB_2MIN_E, purity 100%, MS ESI calcd. for C₃₁H₄₅F₃O₃Na [M+Na]⁺545, found 545.

SFC Rt=1.929 min in 10 min chromatography, IC-3_MeOH(DEA)_40_2.5ML, 98.4% de.

Example 32: Synthesis of (3S,5S,8R,9S,10S,13S,14S,17R)-3-ethyl-17-((2S,3S)-3-hydroxy-4-phenylbutan-2-yl)-10,13-dimethylhexadecahydro-1H-cyclopenta[a]phenanthren-3-ol (32)

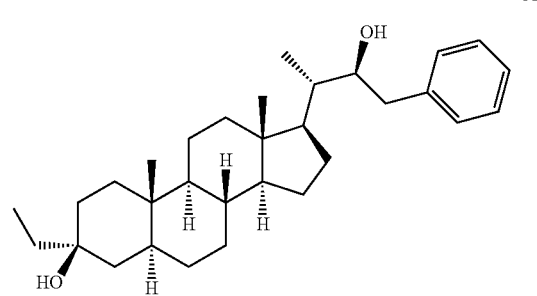

32

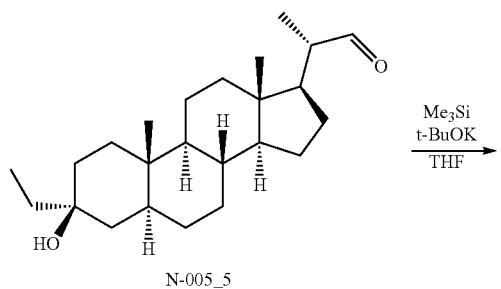

N-005_5

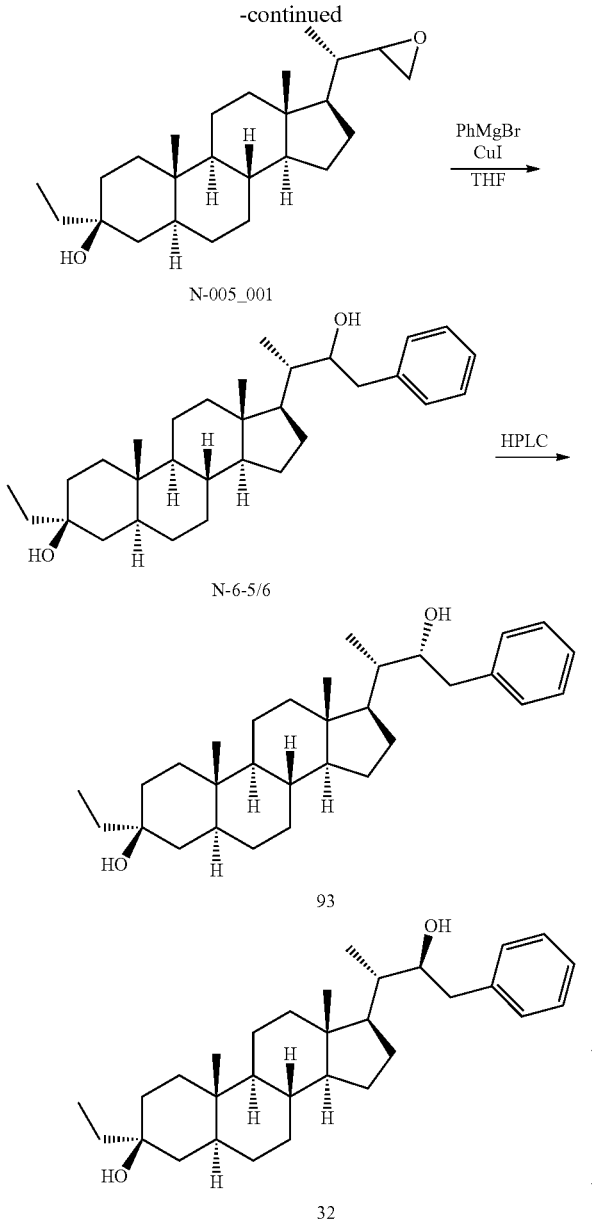

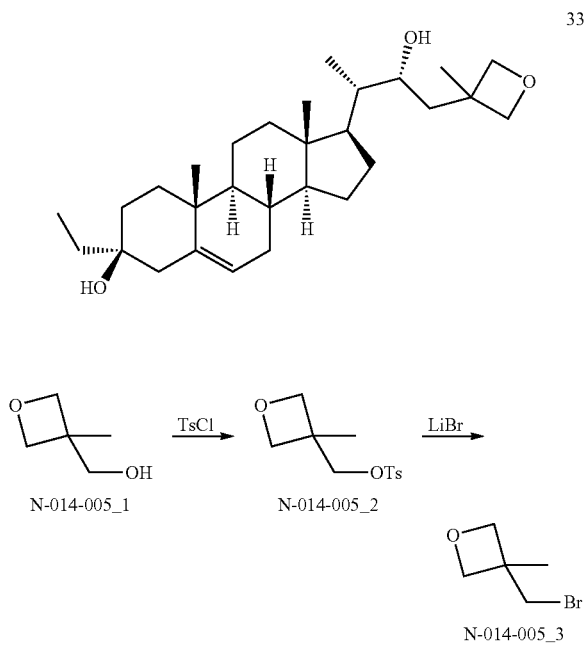

quenched with aqueous NH₄Cl (20 mL), extracted with EtOAc (2×10 mL). The combined organic layer was dried over anhydrous sodium sulfate, filtered and concentrated. The residue was purified by column chromatography on silica gel (0~5% of EtOAc in PE) to give NA-6-5/6 (190 mg, 79%) as a solid.

$^1$H NMR (400 MHz, CDCl$_3$) δ 7.35-7.27 (m, 2H), 7.25-7.18 (m, 3H), 3.95-3.81 (m, 1H), 2.87-2.39 (m, 2H), 2.04-1.92 (m, 1H), 1.89-1.80 (m, 1H), 1.71-1.58 (m, 4H), 1.56-1.43 (m, 6H), 1.41-1.27 (m, 5H), 1.26-1.18 (m, 4H), 1.18-1.08 (m, 2H), 1.06-0.96 (m, 5H), 0.92-0.79 (m, 8H), 0.73-0.55 (m, 4H).

3. N-6-5/6 (190 mg, 0.420 mmol) was separated by prep. HPLC (Column: YMC-Actus Triart C18 100*30 mm*5 um; condition: water (0.05% HCl)-ACN; Gradient: 90-100% B; Flow rate: 25 mL/min) to give 93 (56 mg, 30%) as a solid and 32 (12 mg, 6%) as a solid.

32:

$^1$H NMR (400 MHz, CDCl$_3$) δ 7.36-7.29 (m, 2H), 7.25-7.19 (m, 3H), 3.89-3.83 (m, 1H), 2.79-2.72 (m, 1H), 2.49-2.40 (m, 1H), 2.05-1.98 (m, 1H), 1.92-1.79 (m, 2H), 1.72-1.51 (m, 9H), 1.44-1.31 (m, 5H), 1.30-1.09 (m, 7H), 1.08-0.96 (m, 5H), 0.92-0.81 (m, 7H), 0.74-0.63 (m, 4H).

LCMS Rt=1.343 min in 2.0 min chromatography, 30-90AB, purity 100%, MS ESI calcd. for C$_{31}$H$_{47}$O [M+H—H$_2$O]$^+$ 435, found 435.

Example 33: Synthesis of (3S,8S,9S,10R,13S,14S,17R)-3-ethyl-17-((2S,3R)-3-hydroxy-4-(3-methyloxetan-3-yl)butan-2-yl)-10,13-dimethyl-2,3,4,7,8,9,10,11,12,13,14,15,16,17-tetradecahydro-1H-cyclopenta[a]phenanthren-3-ol (33)

1. t-BuOK (4.64 g, 41.4 mmol) was added to a suspension of Me₃SI (8.44 g, 41.4 mmol) in anhydrous THF (50 mL) at 20° C. under nitrogen. The mixture was stirred at 20° C. for 1 hr, and N-005_5 (5 g, 13.8 mmol) was added. The resulting mixture was warmed to 45° C. and stirred for 4 hrs. The reaction mixture was cooled to room temperature, quenched with water (50 mL), extracted with EtOAc (2×50 mL). The combined organic layer was dried over anhydrous sodium sulfate, filtered and concentrated. The residue was purified by column chromatography on silica gel (0~10% EtOAc in PE) to give N-005_001 (2.7 g, 52%) as a solid.

LCMS Rt=1.324 min in 2.0 min chromatography, 30-90AB_E, purity 92%, MS ESI calcd. for C$_{25}$H$_{41}$O [M+H—H$_2$O]$^+$357, found 357.

2. CuI (10.1 mg, 0.0534 mmol) and PhMgBr (1 M in THF, 2.66 mL, 2.66 mmol) were added to a solution of N-005_001 (200 mg, 0.534 mmol) in anhydrous THF (20 mL) was at 0° C. under nitrogen. The mixture was warmed to 15° C. gradually and stirred for 16 hrs. The reaction mixture was 1. To a solution of N-014-005_1 (10 g, 97.9 mmol) in DCM (100 mL) was added 1-methyl-1H-imidazole (16.0 g, 195 mmol) and TEA (19.7 g, 195 mmol) at 25° C. TsCl (37.1 g, 195 mmol) was added into the solution. The reaction mixture was stirred at 25° C. for 2 hours. The mixture was washed with water (2×100 mL), brine (100 mL), dried over Na₂SO₄, filtered and concentrated under vacuum to give N-014-005_2 (25 g, crude) as a light yellow solid, which was purified by column chromatography on silica gel (0~15% of EtOAc in PE) to give N-014-005_2 (23.6 g, 95%) as a white solid.

¹H NMR (400 MHz, CDCl₃) δ 7.80-7.68 (m, 2H), 7.41-7.26 (m, 2H), 3.40-3.29 (m, 4H), 4.12-4.00 (s, 2H), 2.44 (s, 3H), 1.28 (s, 3H).

2. To a solution of N-014-005_2 (10 g, 39.0 mmol) in acetone (100 mL) was added LiBr (13.5 g, 156 mmol). The mixture was stirred at 65° C. for 1 hrs. The mixture was quenched with water (200 mL) at 0° C. and extracted with hexane (3×200 mL). The combined organic phase was washed with brine (50 mL), dried over Na₂SO₄, filtered and concentrated to give N-014-005_3 (2.54 g, crude) as yellow liquid.

¹H NMR (400 MHz, CDCl₃) δ 4.50-4.30 (m, 4H), 3.64 (s, 2H), 1.58 (s, 1H), 1.43 (s, 3H).

layer was separated and concentrated in vacuum. The residue was purified by flash column (0~30% of EtOAc in PE) to give a mixture (190 mg, 15%) as a white solid, which was purified by SFC (Column: AD (250 mm*30 mm, 5 um), Condition: 0.1% NH3H2O ETOH, Gradient: from 50% to 50%, FlowRate (ml/min): 60 mL/min, 25° C.) to afford 33 (Peak 1, 110 mg, 9%) and 70 (Peak 2, 30 mg, impure) as a white solid. The impure 70 (30 mg, impure) was purified by column chromatography on silica gel (15% of EtOAc in PE) to give 70 (10 mg, 5%) as a white solid.

33:

¹H NMR (400 MHz, CDCl₃) δ 5.30-5.26 (m, 1H), 4.59-4.70 (m, 1H), 4.50-4.48 (m, 1H), 4.36-4.33 (m, 1H), 3.83 (s, 1H), 2.40-2.33 (m, 1H), 2.10-1.50 (m, 17H), 1.49-1.35 (m, 9H), 1.30-0.80 (m, 13H), 0.68 (s, 3H).

LCMS Rt=1.069 min in 3 min chromatography, 30-90AB_2MIN_E.M, purity 100%, MS ESI calcd. for $C_{29}H_{49}O_3[M+H]^+$ 445, found 445.

Example 34: Synthesis of (3S,5S,8R,9S,10S,13S,14S,17R)-3-ethyl-17-((2S,3R)-3-hydroxy-4-methyl-pentan-2-yl)-10,13-dimethylhexadecahydro-1H-cyclopenta[a]phenanthren-3-ol (34)

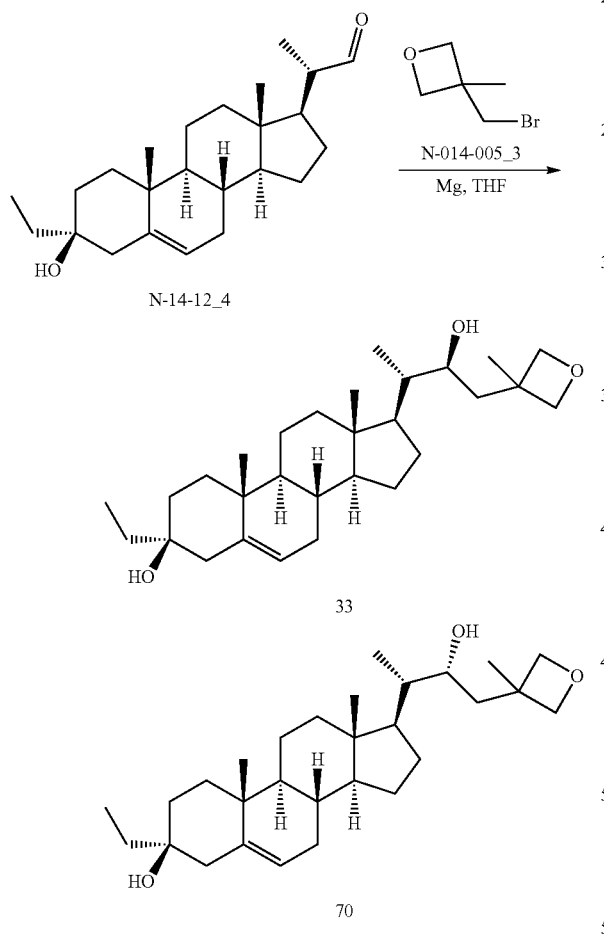

3. To a suspension of Mg (807 mg, 33.2 mmol) and I₂ (1 mg) in THF (2 mL) was added solution of N-014-005_3 (2.5 g, 15.1 mmol) in THF (8 mL) drop wise under N₂ at 50-55° C. The mixture was stirred at 55° C. for 1 h. The mixture was diluted with THF (10 mL) and used in the next step directly without monitored. To a solution of N-14-12_4 (1.01 g, 2.83 mmol) in THF (10 mL) was added fresh prepared 3-[(bromomagnesio) methyl]-3-methyloxetane (15 mmol in 20 mL of THF) at 0° C. The mixture was stirred at 15° C. for 4 h. To the mixture was added NH₄Cl (20 mL, 10% aq.). The mixture was extracted with EtOAc (30 mL). The organic

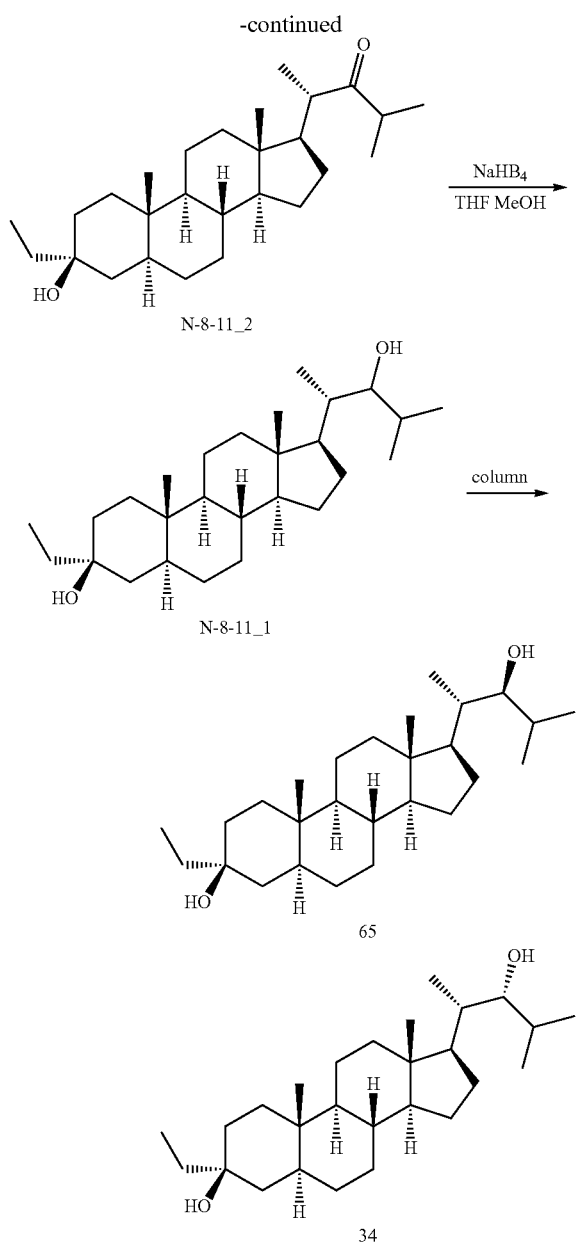

quenched with saturated NaHCO₃ aqueous (50 mL) until pH of the aqueous layer became about 9. The mixture was filtered. The DCM layer was separated and the aqueous phase was extracted with DCM (100 mL). The combined organic phase was washed with saturated $Na_2S_2O_3$ aqueous (3×100 mL), sat. NaHCO₃ (100 mL), brine (40 mL), dried over $Na_2SO_4$, filtered and concentrated to give crude N-8-11_2 (140 mg, 64%) as a solid.

LCMS Rt=1.300 min in 2.0 min chromatography, 30-90AB_2MIN_E, purity 100%, MS ESI calcd. for $C_{27}H_{45}O$ [M+H—$H_2O$]⁺ 385, found 385.

3. NaBH₄ (1.17 g, 17.3 mmol) was added five times, every five minutes, to a solution of N-8-11_2 (140 mg, 0.347 mmol) in MeOH (2 mL) and THF (2 mL). The mixture was stirred at 15° C. for 30 minutes. The mixture was quenched with sat.NH₄Cl (50 mL) and extracted with EtOAc (3×20 mL). The combined organic phase was dried over $Na_2SO_4$, filtered, concentrated and purified by combi-flash (25% of EtOAc in PE) to give N-8-11_1 (140 mg, impure). N-8-11_1 was purified by combi-flash (25% of EtOAc in PE) to give 34 (50 mg, impure) as a solid and 65 (10 mg, impure) as a solid.

4. N-8-11_1 (50 mg, 0.123 mmol, impure) was purified by combi-flash (25% of EtOAc in PE) to give 34 (30 mg, impure) as a solid.

N-8-11_1 (30 mg, 0.0741 mmol, impure) was purified by combi-flash (25% of EtOAc in PE) to give 34 (9 mg, 30%) as a solid.

34:
¹H NMR (400 MHz, CDCl₃) δ 3.18-3.07 (m, 1H), 1.98-1.81 (m, 2H), 1.71-1.58 (m, 6H), 1.53-1.31 (m, 7H), 1.30-0.98 (m, 14H), 0.97-0.78 (m, 14H), 0.70-0.60 (m, 4H).

LCMS Rt=4.387 min in 7.0 min chromatography, 30-90AB_7MIN_E, purity 97.6%, MS ESI calcd for $C_{27}H_{45}$ [M+H-2H₂O]⁺ 369, found 369.

Example 35: Synthesis of (3S,5S,8R,9S,10S,13S, 14S,17R)-17-((2S,3S)-3-hydroxy-6-methylheptan-2-yl)-3-(methoxymethyl)-10,13-dimethylhexadeca-hydro-1H-cyclopenta[a]phenanthren-3-ol (35)

1. N-8-7_1 (500 mg, 1.38 mmol) in THF (5 mL) was added to a solution of isopropylmagnesium chloride (708 mg, 3.44 mL, 2M in THF) in THF (5 mL) at 0° C. The mixture was stirred at 25° C. for 4 hrs. To the mixture was added NH₄Cl (20 mL, 10% aq.). The mixture was extracted with EtOAc (2×30 mL). The organic layer was separated and concentrated in vacuum to give a residue. The residue was purified by silica gel chromatography eluted with PE/EtOAc=3/1 to afford N-8-11_1 (170 mg, 30%) as a solid. The impure product (120 mg) was further purified by silica gel chromatography eluted with PE/EtOAc=3/1 to afford N-8-11_1 (50 mg, 42%) as a solid.

¹H NMR (400 MHz, CDCl₃) δ 3.20-3.10 (m, 1H), 2.00-1.80 (m, 2H), 1.70-1.60 (m, 2H), 1.55-1.40 (m, 4H), 1.39-0.95 (m, 19H), 0.90-0.80 (m, 15H), 0.70-0.60 (m, 5H).

2. DMP (457 mg, 1.08 mmol) was added to a solution of N-8-11_1 (220 mg, 0.543 mmol) in DCM (5 mL). After stirring at 25° C. for 10 min, the reaction mixture was

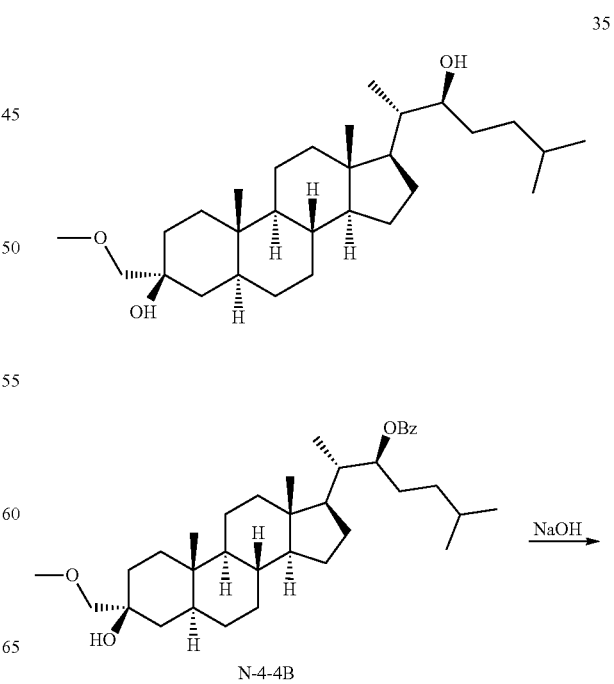

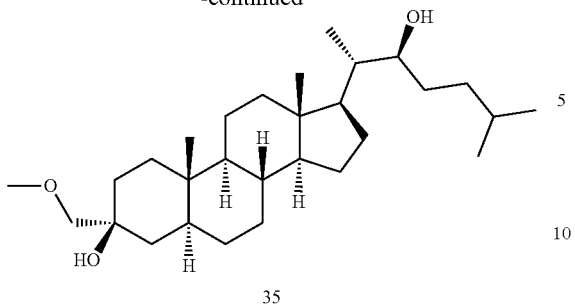

35

1. NaOH (71.9 mg, 180 mmol) was added to a solution of N-4-4B (20 mg, 0.0361 mmol) in THF/MeOH (2 mL) at 25° C. The reaction mixture warmed to 50° C. and stirred for 1 h. The reaction mixture was cooled and water (20 mg) was added. The aqueous phase was extracted with EtOAc (3×10 mL). The combined organic phase was washed with saturated brine (2×20 mL), dried over anhydrous $Na_2SO_4$.filtered and concentrated. The residue was purified by flash column (0~30% of EtOAc in PE) to provide 35 (8 mg, 50%) as a white solid.

$^1$H NMR (400 MHz, $CDCl_3$) δ 3.63-3.61 (m, 1H), 3.41-3.38 (m, 5H); 2.51 (s, 1H); 1.97-1.81 (m, 1H), 1.71-1.54 (m, 8H), 1.51-1.48 (m, 4H), 1.25-1.10 (m, 15H), 0.99-0.80 (m, 9H), 0.78-0.75 (m, 4H), 0.71-0.59 (m, 4H).

LCMS Rt=1.301 min in 2.0 min chromatography, 30-90 AB, purity 96%, MS ESI calcd. for $C_{29}H_{48}O$ $[M+H-2H_2O]^+$ 413, found 413.

Example 36: Synthesis of (3S,5R,8R,9S,10S,13S, 14S,17R)-17-((2S,3R)-3-hydroxy-6-methylheptan-2-yl)-3,10,13-trimethylhexadecahydro-1H-cyclopenta[a]phenanthren-3-ol (36)

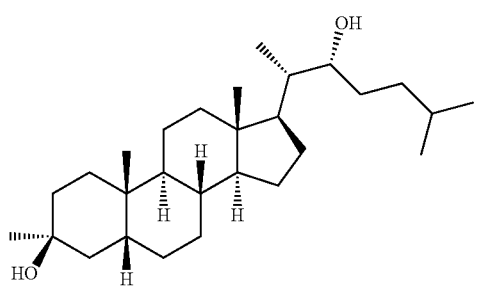

36

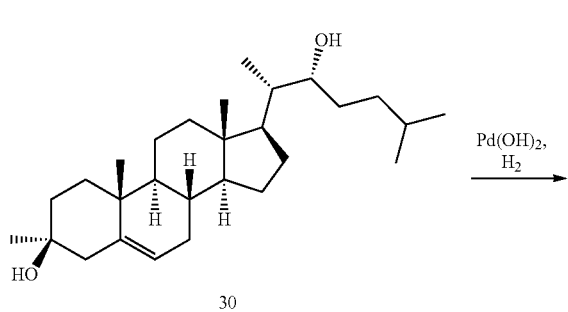

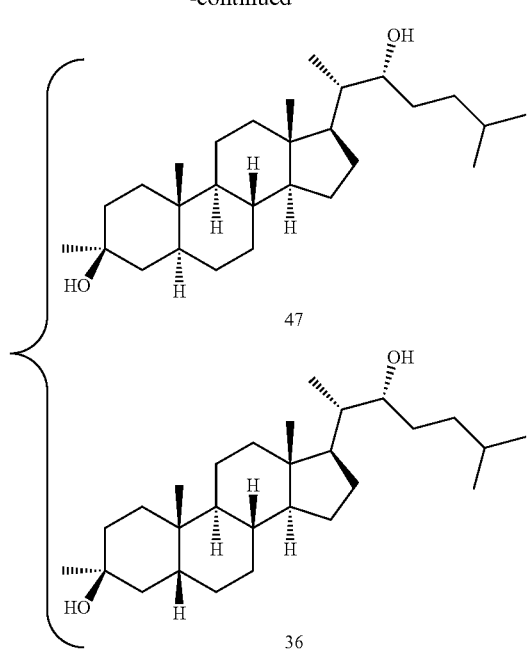

1. $Pd(OH)_2$ (200 mg) was added to a solution of 30 (100 mg, 0.239 mmol) in MeOH (10 mL). The mixture was stirred at 50° C. under $H_2$ (50 Psi). The mixture was filtered, concentrated and purified by combi-flash (0-10% of EtOAc in PE) to give 47 (21 mg, 21%) and 36 (1 mg, 1%) as a solid.

37:

$^1$H NMR (400 MHz, $CDCl_3$) δ 3.66-3.55 (m, 1H), 2.05-1.77 (m, 3H), 1.72-1.63 (m, 3H), 1.55-1.48 (m, 3H), 1.47-1.31 (m, 9H), 1.29-1.12 (m, 13H), 1.11-1.00 (m, 3H), 0.96 (s, 3H), 0.93-0.87 (m, 9H), 0.67 (s, 3H).

LCMS $t_R$=1.296 min in 2 min chromatography, 30-90AB_ELSD, purity 100.0%, MS ESI calcd. for $C_{28}H_{47}$ $[M+H-2H_2O]^+$ 383, found 383.

Example 37: Synthesis of (3S,8S,9S,10R,13S,14S, 17R)-3-ethyl-17-((2S,3S)-3-hydroxy-4-methylpentan-2-yl)-10,13-dimethyl-2,3,4,7,8,9,10,11,12,13,14, 15,16,17-tetradecahydro-1H-cyclopenta[a]phenanthren-3-ol (37)

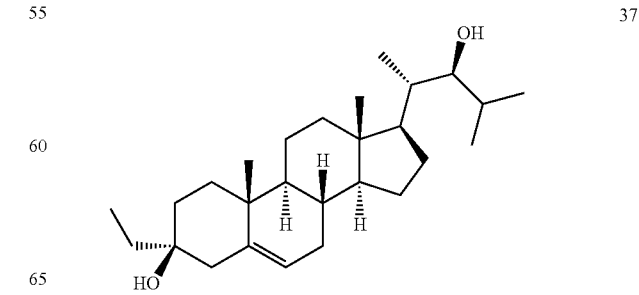

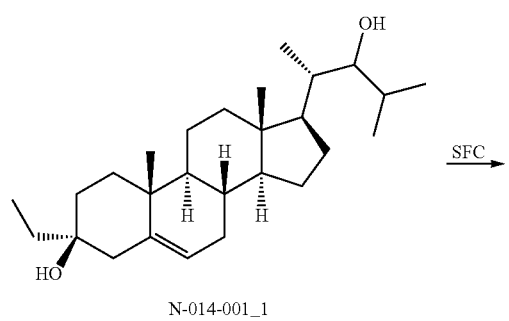

N-014-001_1

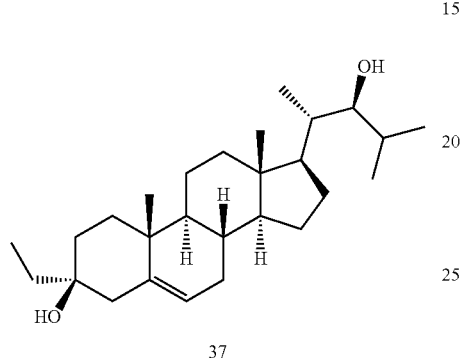

37

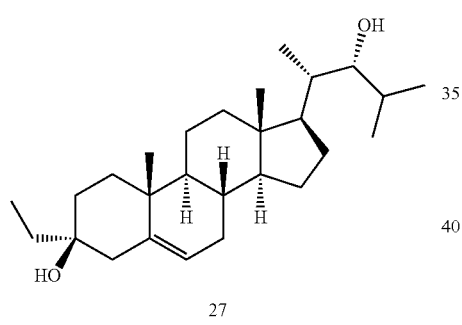

27

1. N-014-001_1 (150 mg, 0.37 mmol) was purified by SFC (Column: Chiralpak AS-H 250*30 5u; Condition: 0.1% NH₃H₂O EtOH; Begin B: 20%; End B: 20%; FlowRate (ml/min): 65) to obtain 37 (Peak 2, 46 mg, 31%) and 27 (Peak 1, 27 mg, 18%) as a solid. 014-001A:

¹H NMR (400 MHz, CDCl₃) δ 5.35-5.28 (m, 1H), 3.18-3.09 (m, 1H), 2.39-2.35 (m, 1H), 2.06-1.81 (m, 4H), 1.73-1.57 (m, 6H), 1.54-1.41 (m, 8H), 1.40-1.26 (m, 3H), 1.24-1.11 (m, 3H), 1.10-0.97 (m, 6H), 0.96-0.92 (m, 1H), 0.90-0.85 (m, 5H), 0.84-0.76 (m, 4H), 0.69 (s, 3H).

LCMS Rt=1.207 min in 2 min chromatography, 30-90AB_2MIN_E, purity 100%, MS ESI calcd. for C₂₇H₄₅O [M+H—H₂O]⁺ 385, found 385.

SFC Rt=2.635 min in 10 min chromatography, OJ_3_EtOH_DEA_5_40_25ML ("Column: Chiralcel OJ-3150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 152.5 mL/min Column temp.: 35° C."), 98.66% de.

Example 38: Synthesis of (3S,5S,8R,9S,10S,13S,14S,17R)-3-ethyl-17-((2S,3S)-3-hydroxyhexan-2-yl)-10,13-dimethylhexadecahydro-1H-cyclopenta[a]phenanthren-3-ol (38)

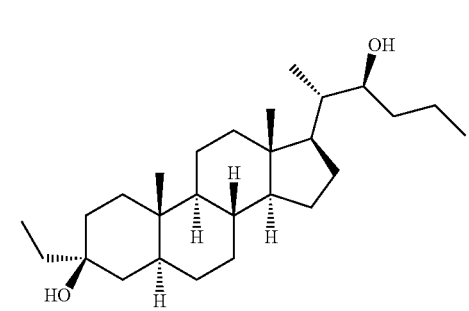

38

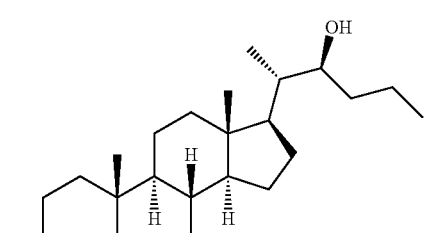

S-500-6-1_1

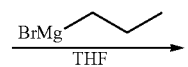

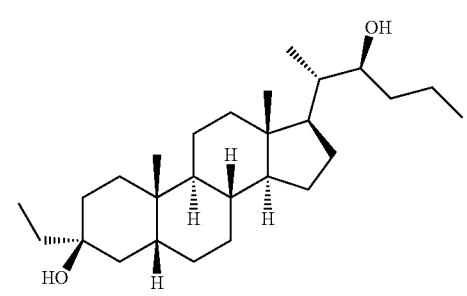

72

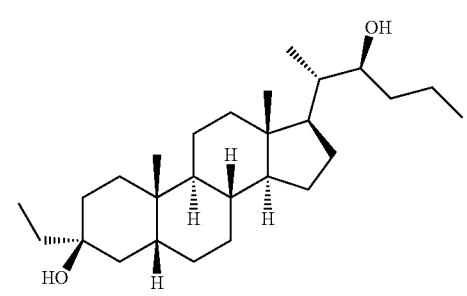

23

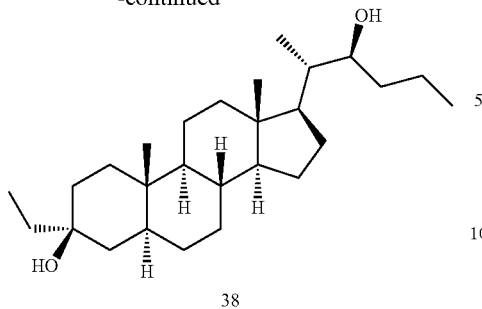

38

1. Propylmagnesium bromide (3.34 mL, 6.69 mmol, 2M in THF) was slowly added to a solution of S-500-6-1_1 (800 mg, 2.23 mmol) in THF (30 mL) at 0° C. After addition, the mixture was stirred at 15° C. for 1 hr. The mixture was quenched with sat. NH$_4$Cl (40 mL) and extracted with EtOAc (3×20 mL). The combined organic phase was washed with brine (2×30 mL), dried over Na$_2$SO$_4$, filtered and concentrated and purified by combi-flash (0-15% of EtOAc in PE) to give 72 (500 mg, 56%) as a solid.

$^1$H NMR (400 MHz, CDCl$_3$) δ 5.31-5.26 (m, 1H), 3.72-3.64 (m, 1H), 2.41-2.31 (m, 1H), 2.07-1.85 (m, 4H), 1.77-1.69 (m, 1H), 1.62-1.54 (m, 3H), 1.52-1.38 (m, 9H), 1.37-1.16 (m, 6H), 1.15-1.01 (m, 7H), 0.99-0.88 (m, 7H), 0.87-0.82 (m, 3H), 0.68 (s, 3H).

LCMS Rt=4.979 min in 7.0 min chromatography, 30-90AB_E, purity 98.8%, MS ESI calcd. for C$_{27}$H$_{43}$ [M+H-2H$_2$O]$^+$ 367, found 367.

2. Pd(OH)$_2$ (300 mg, dry) was added to a solution of 72 (150 mg, 0.372 mmol) in MeOH (20 mL). The mixture was stirred at 50° C. under H$_2$ (50 Psi) for 48 hrs. The mixture was filtered, concentrated and purified by combi-flash (0-15% of EtOAc in PE) to give 23 (9 mg, 6%) and 38 (43 mg, 29%) as a solid.

38:

$^1$H NMR (400 MHz, CDCl$_3$) δ 3.71-3.62 (m, 1H), 1.99-1.82 (m, 2H), 1.70-1.56 (m, 6H), 1.54-1.45 (m, 3H), 1.44-1.38 (m, 3H), 1.37-1.17 (m, 10H), 1.16-1.01 (m, 5H), 1.00-0.85 (m, 11H), 0.82 (s, 3H), 0.70-0.60 (m, 4H).

LCMS Rt=1.397 min in 2.0 min chromatography, 30-90AB_E, purity 100%, MS ESI calcd. for C$_{27}$H$_{45}$ [M+H-2H$_2$O]$^+$ 369, found 369.

Example 39: Synthesis of (3S,8S,9S,10R,13S,14S,17R)-3-(methoxymethyl)-10,13-dimethyl-17-((2S,3S)-4,4,4-trifluoro-3-hydroxybutan-2-yl)-2,3,4,7,8,9,10,11,12,13,14,15,16,17-tetradecahydro-1H-cyclopenta[a]phenanthren-3-ol (39)

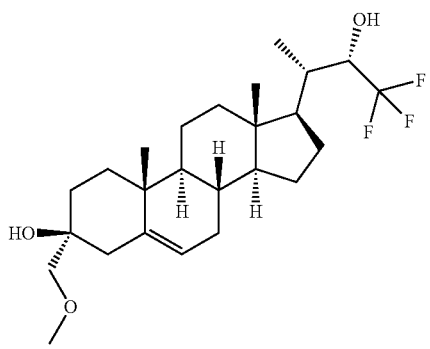

39

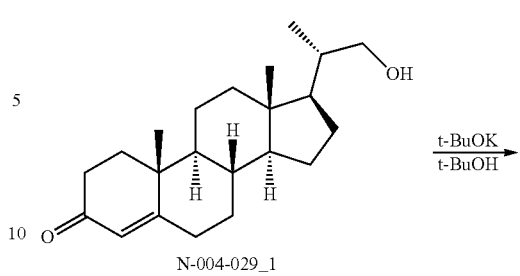

N-004-029_1

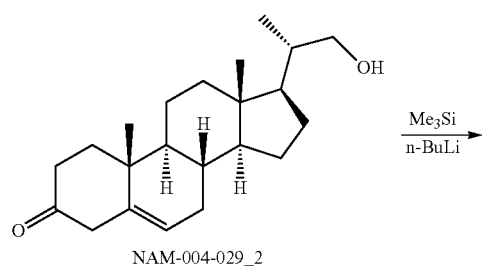

NAM-004-029_2

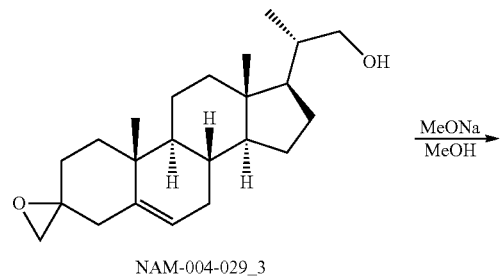

NAM-004-029_3

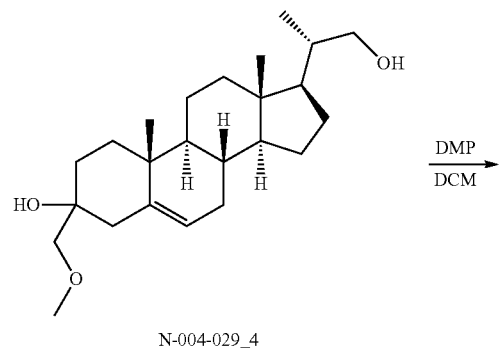

N-004-029_4

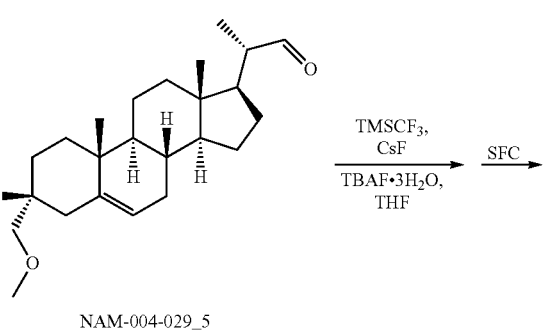

NAM-004-029_5

-continued

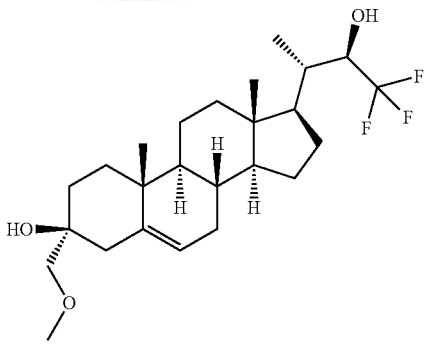

95

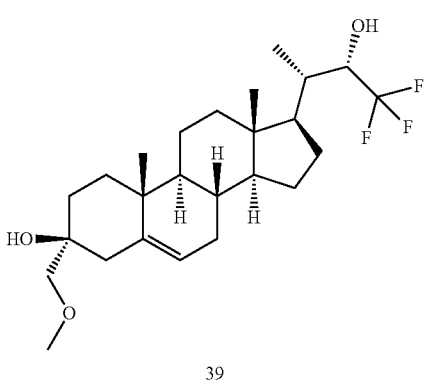

39

1. t-BuOH (600 mL) was charged into a three-neck round bottom flask under N₂ at 35° C., followed by adding t-BuOK (101 g, 905 mmol). After stirring at 35° C. for 30 mins, N-004-029_1 (50 g, 151 mmol) was added to the above mixture and stirred at 35° C. for 1 hr. The reaction mixture was poured into 5% aqueous acetic acid (2 L), during which the temperature was maintained below 10° C. Ice-water (1 L) was added. The pH of the mixture was adjusted to about 7-8 with NaHCO₃ and filtered. The filter cake was dissolved in DCM (1.5 L). The combined organic phase was washed with water (2×500 ml), brine (2×500 ml), dried over Na₂SO₄, filtered and concentrated in vacuum at below 35° C. to give N-004-029_2 (45 g, crude) as a solid.

$^1$H NMR (400 MHz, CDCl₃) δ 5.35-5.32 (m, 1H), 3.71-3.58 (m, 1H), 3.38-3.25 (m, 2H), 2.90-2.78 (m, 1H), 2.55-2.20 (m, 2H), 2.13-1.92 (m, 3H), 1.90-1.59 (m, 5H), 1.46-1.14 (m, 10H), 1.12-0.96 (m, 6H), 0.72 (s, 3H).

2. n-BuLi (108 mL, 272 mmol, 2.5 M in h-hexane) was added dropwise to a mixture of Me₃SI (73.8 g. 362 mmol) in anhydrous THF (300 mL) at 0° C. under N₂. After stirring at 0° C. for 30 mins, a solution of N-004-029_2 (30 g, 90.7 mmol) in anhydrous THF (600 mL) was added at −40° C. The mixture was stirred −40° C. for 2 hours and at 25° C. for 16 hours. The reaction mixture was poured into ice-water (1 L). The aqueous phase was extracted with EtOAc (2×500 mL). The combined organic phase was washed with brine (2×500 mL), dried over anhydrous Na₂SO₄, filtered and concentrated, the residue was purified by flash column (0~20% of EtOAc in PE) to give N-004-029_3 (1.8 g, 6%) as a solid.

$^1$H NMR (400 MHz, CDCl₃) δ 5.33-5.25 (m, 1H), 3.66-3.61 (m, 1H), 3.39-3.31 (m, 1H), 2.93-2.86 (m, 1H), 2.59-2.53 (m, 1H), 2.20-1.93 (m, 4H), 1.89-1.14 (m, 15H), 1.12-0.90 (m, 9H), 0.71 (s, 3H).

3. MeONa (5.61 g, 104 mmol) was added to a solution of N-004-029_3 (1.8 g, 5.22 mmol) in MeOH (20 mL) at 25° C. under N2. After stirring at 50° C. for 12 hrs, water (100 mL) was added into the mixture and stirred for 10 mins. The aqueous phase was extracted with EtOAc (2×80 mL). The combined organic phase was washed with saturated brine (2×50 mL), dried over anhydrous Na₂SO₄, filtered and concentrated. The residue was purified by flash column (0~30% of EtOAc in PE) to give N-004-029_4 (1.5 g, 76%) as a solid.

$^1$H NMR (400 MHz, CDCl₃) δ 5.31-5.28 (m, 1H), 3.70-3.54 (m, 1H), 3.40-3.35 (m, 6H), 3.28-3.16 (m, 2H), 2.40-2.35 (m, 1H), 2.09-1.90 (m, 5H), 1.87-1.57 (m, 11H), 1.34-1.06 (m, 10H), 0.70 (s, 3H).

4. DMP (2.53 g, 5.97 mmol) was added to a solution of N-004-029_4 (1.5 g, 3.98 mmol) in DCM (30 mL) at 25° C. and after stirring at 25° C. for 30 min. The reaction mixture was quenched with saturated NaHCO₃ (50 mL) at 25° C. DCM (50 mL) was added into the mixture and stirred for 10 min. The DCM phase was separated and washed with saturated Na₂S₂O₃ aqueous (2×50 mL), brine (2×50 mL), dried over Na₂SO₄, filtered and concentrated. The residue was purified by flash column (5-25% of EtOAc in PE) to give N-004-029_5 (0.6 g, 40%) as a solid.

$^1$H NMR (400 MHz, CDCl₃) δ 9.59-9.57 (m, 1H), 5.32-5.29 (m, 1H), 3.37 (s, 3H), 3.30-3.15 (m, 2H), 2.44-2.31 (m, 2H), 2.13-1.40 (m, 16H), 1.27-1.02 (m, 10H), 0.73 (s, 3H).

5. CsF (607 mg, 4.00 mmol) was added to a solution of N-004-029_5 (0.6 g, 1.60 mmol) in anhydrous THF (20 mL) at 0° C. After stirring for 20 min, TMSCF₃ (568 mg, 4.00 mmol) was added at 0° C. and the mixture was stirred for 1 hr. TBAF.3H₂O (2.02 g, 6.40 mmol) was added into the mixture, which was stirred at 50° C. for 1 hr. The reaction mixture was poured into ice-water (50 mL). The aqueous phase was extracted with EtOAc (2×80 mL). The combined organic phase was washed with saturated brine (2×80 mL), dried over anhydrous Na₂SO₄, filtered and concentrated. The residue was purified by flash column (0~30% of EtOAc in PE) to give N-004-029A (450 mg, 63%) as a solid.

$^1$H NMR (400 MHz, CDCl₃) δ 5.33-5.29 (m, 1H), 4.11-3.99 (m, 1H), 3.37 (s, 3H), 3.30-3.19 (m, 2H), 2.54 (s, 1H), 2.43-2.36 (m, 1H), 2.26-1.82 (m, 7H), 1.78-1.61 (m, 5H), 1.34-0.80 (m, 15H), 0.75-0.67 (m, 3H).

6. The N-004-029A (0.45 g, 1.01 mmol) was purified by SFC (Column: AD (250 mm*30 mm, 5 um), Condition: 0.1% NH₃H₂O ETOH, Begin B: 30%, End B: 30%) to afford 39 (PK1: 120 mg, 26.7%) as a white solid and 95 (PK2: 200 mg, 44.5%) as a white solid.

The structure of 39 was confirmed by NOE.

39:

$^1$H NMR (400 MHz, CDCl₃) δ 5.32-5.29 (m, 1H), 4.06-3.99 (m, 1H), 3.37 (s, 3H), 3.30-3.19 (m, 2H), 2.54 (s, 1H), 2.43-2.36 (m, 1H), 2.25-2.19 (m, 1H), 2.15-2.07 (m, 1H), 2.04-1.60 (m, 9H), 1.55-1.34 (m, 5H), 1.25-0.88 (m, 11H), 0.70 (s, 3H).

LCMS Rt=1.078 min in 2 min chromatography, 30-90AB_2MIN_E, purity 100%, MS ESI calcd. for C₂₄H₃₄F₃O [M-CH₅O₂]⁺ 395, found 395.

Example 40: Synthesis of (3S,5S,8R,9R,10S,13S,14S,17R)-3-ethyl-17-((2S,3R)-3-hydroxy-6-methyl-heptan-2-yl)-13-methylhexadecahydro-1H-cyclopenta[a]phenanthren-3-ol (40)

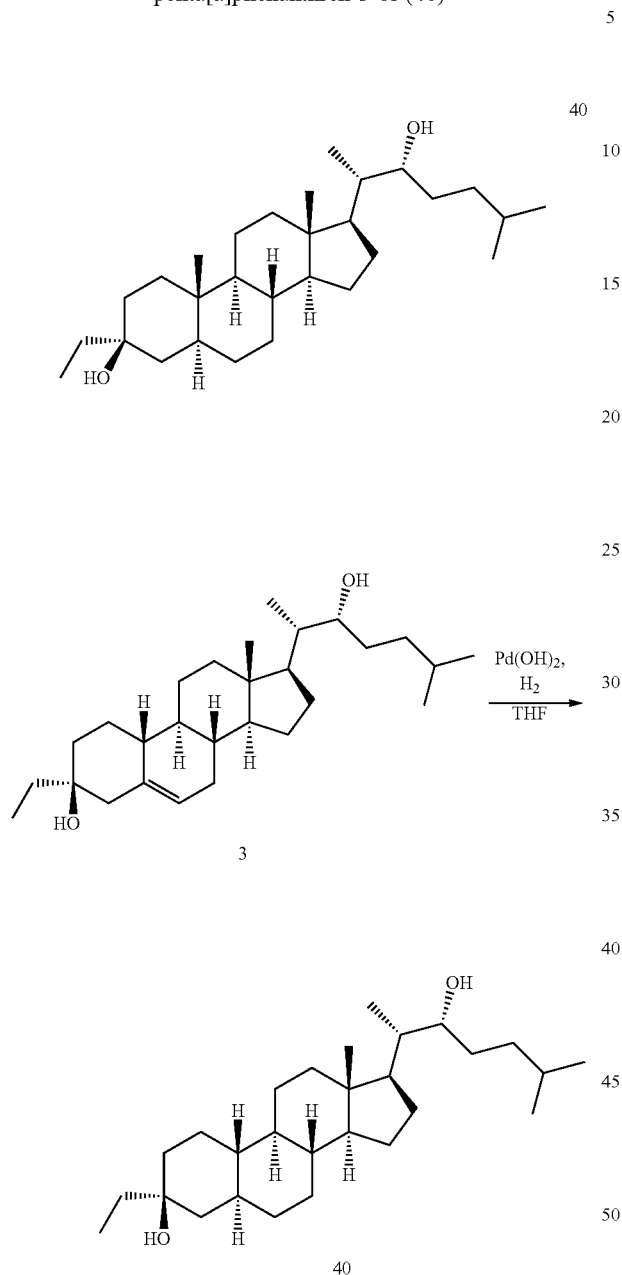

1. Pd(OH)₂ (100 mg, dry) was added to a solution of 3 (30 mg, 0.072 mmol) in MeOH/THF (5 mL/5 mL) at 25° C. under Ar. The reaction was stirred at 50° C. under H₂ (50 Psi) for 48 h. The mixture was filtered and the filtrate was concentrated in vacuum to give crude product, which was purified by a silica gel column (PE/EtOAc=10/1-5/1) to give 41 (10 mg, 33%) as a solid.

¹H NMR (400 MHz, CDCl3) δ 3.62-3.59 (m, 1H), 1.99-1.91 (m, 1H), 1.88-1.76 (m, 2H), 1.74-1.61 (m, 6H), 1.46-1.29 (m, 6H), 1.26-1.09 (m, 9H), 1.08-0.99 (m, 6H), 0.95-0.78 (m, 14H), 0.74-0.58 (m, 5H).

LCMS Rt=1.491 min in 2 min chromatography, 30-90 AB, purity 99%, MS ESI calcd. For $C_{28}H_{47}$ $[M+H-2H_2O]^+$ 383, found 383.

Example 41: Synthesis of (3S,5S,8R,9S,10S,13S,14S,17R)-3-ethyl-17-((2S,3S)-3-hydroxyhept-5-yn-2-yl)-10,13-dimethylhexadecahydro-1H-cyclopenta[a]phenanthren-3-ol (41)

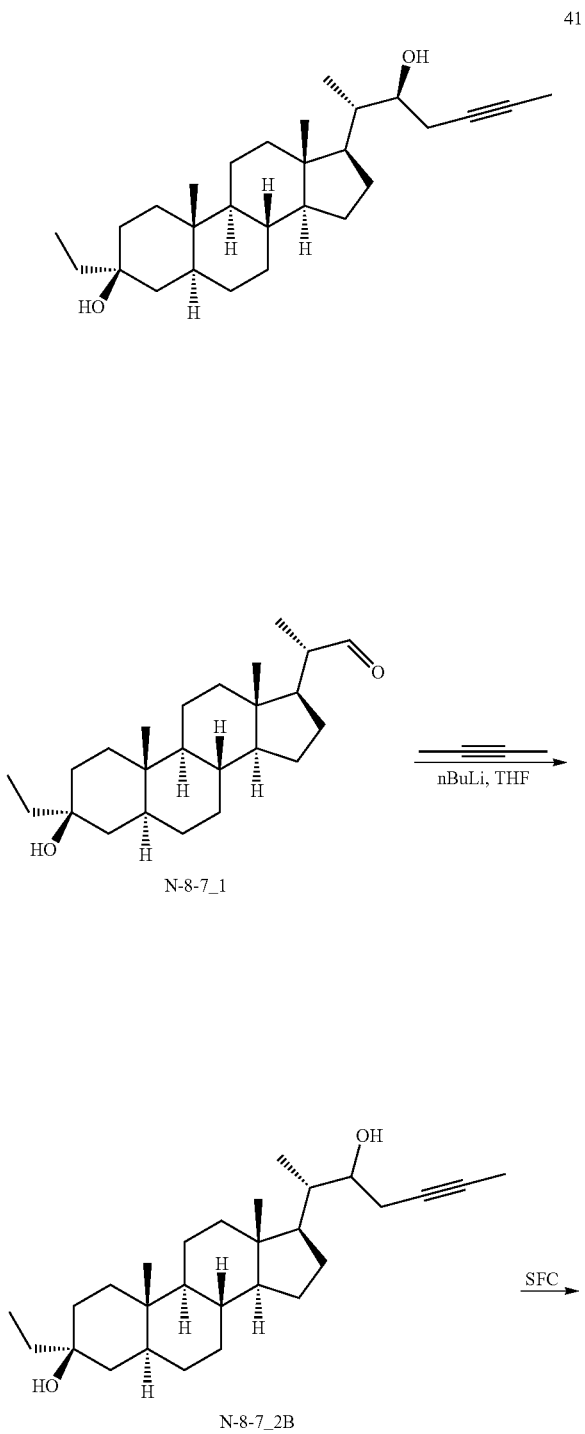

-continued

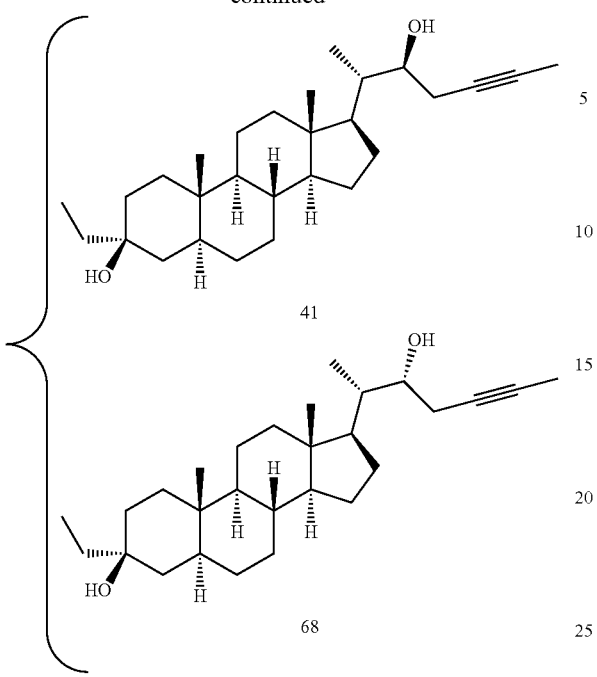

1. n-BuLi (13.8 mL, 34.5 mmol, 2.5 M in hexane) was added dropwise to a solution of but-2-yne (1.86 g, 34.5 mmol) in THF (100 mL) at −20° C. The solution was stirred for 2.5 hrs −20° C. and then it was cooled to −78° C., N-8-71 (5.0 g, 13.8 mmol) in THF (100 mL) was added. The solution was stirred for 30 mins at this temperature, then at −20° C. for 1 hr, and followed by 20° C. for 18 hrs. The resulting gel was quenched by pouring into sat. NH₄Cl (100 mL), followed by extraction with EtOAc (2×150 mL). The combined organic layers were washed with water (40 mL) and brine (40 mL), dried over Na₂SO₄, filtered and purified by flash column eluting with 0~20% of EtOAc in PE to give N-8-7_2B (1 g, crude) as an oil and N-8-7_2B (1.7 g, crude) as an oil.

$^1$H NMR (400 MHz, CDCl$_3$) δ 3.90-3.75 (m, 1H), 2.45-2.35 (m, 1H), 2.25-2.05 (m, 3H), 1.95-1.85 (m, 2H), 1.85-1.40 (m, 8H), 1.40-1.20 (m, 9H), 1.20-0.75 (m, 18H), 0.65 (s, 4H).

SFC Peak 1: Rt=3.008 min in 10 min chromatography, AD_3_EtOH_DEA_5_40_25ML ("Column: Chiralpak AD-3150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.).

2. The crude N-8-72B (250 mg, 0.868 mmol) was further purified by SFC (column: AD (250 mm*30 mm, 10 um)), gradient: 35-35% B (A=0.1% NH₃/H₂O, B=EtOH), flow rate: 60 mL/min) to give 41 (peak 2, 81 mg, 33%) as a solid and 68 (peak 1, 78 mg, 31%) as a solid.

41:
$^1$H NMR (400 MHz, CDCl$_3$) δ 3.82-3.70 (m, 1H), 2.79-2.08 (m, 2H), 2.00-1.90 (m, 1H), 1.80 (s, 4H), 1.78-1.69 (m, 1H), 1.69-1.42 (m, 10H), 1.40-1.31 (m, 4H), 1.31-1.18 (m, 4H), 1.18-0.92 (m, 6H), 0.92-0.85 (m, 7H), 0.82 (s, 3H), 0.66 (s, 3H).

LCMS Rt=1.206 min in 2 min chromatography, 30-90AB_2MIN_E, purity 100%, MS ESI calcd. for C$_{28}$H$_{45}$O [M+H—H$_2$O]$^+$ 397 found 397.

SFC Rt=5.823 min in 10 min chromatography, AD_3_EtOH_DEA_5_40_25ML, 100% de.

Example 42: Synthesis of (3S,5S,8R,9S,10S,13S, 14S,17R)-17-((2S,3S)-3-hydroxy-6-methylheptan-2-yl)-10,13-dimethyl-3-(trifluoromethyl)hexadecahydro-1H-cyclopenta[a]phenanthren-3-ol (42)

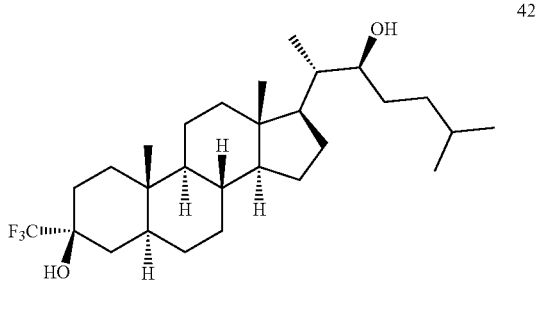

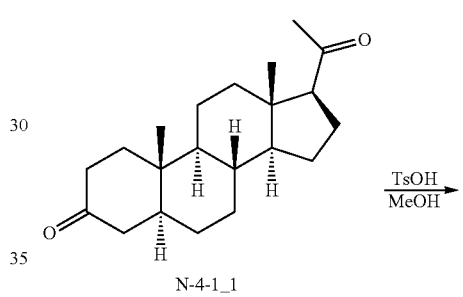

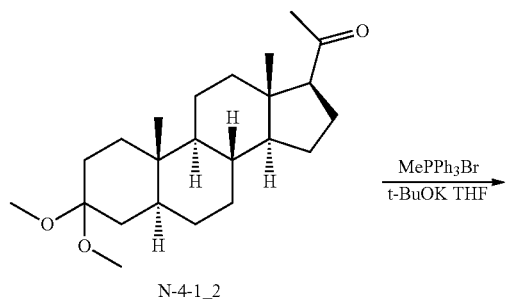

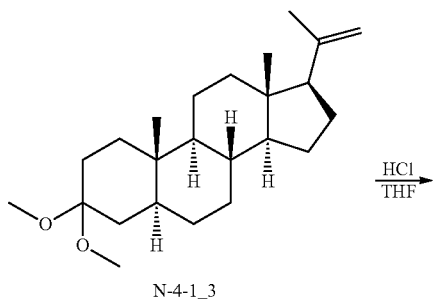

-continued

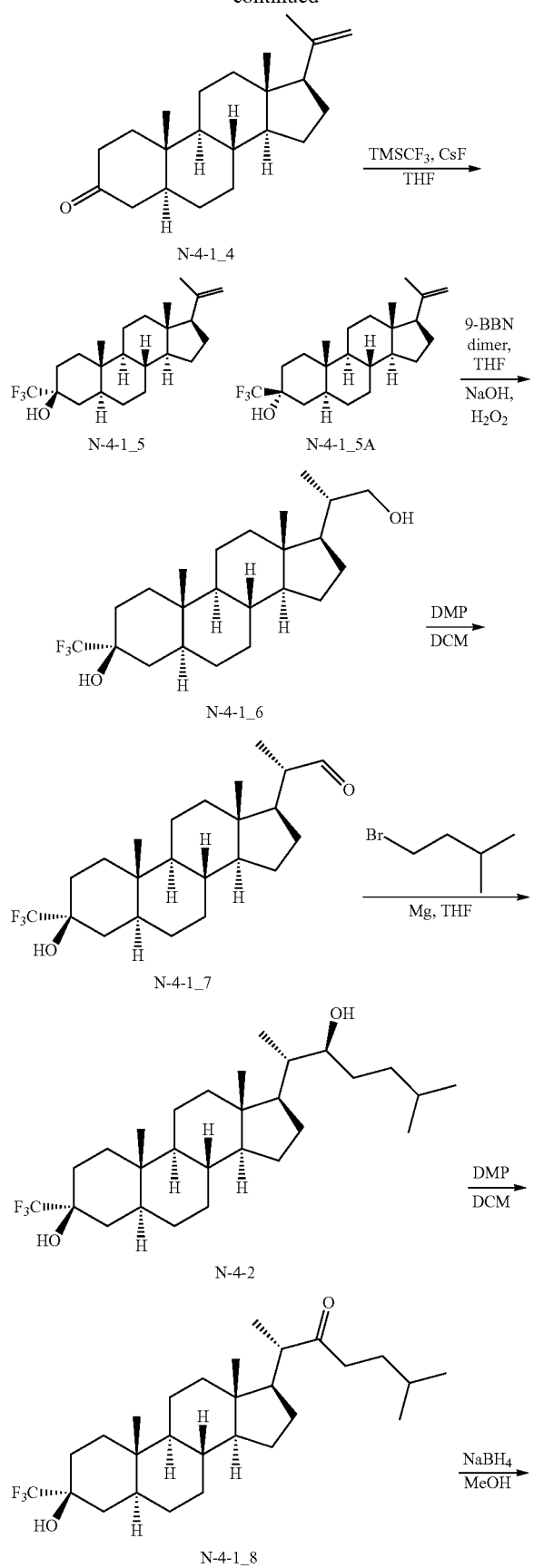

-continued

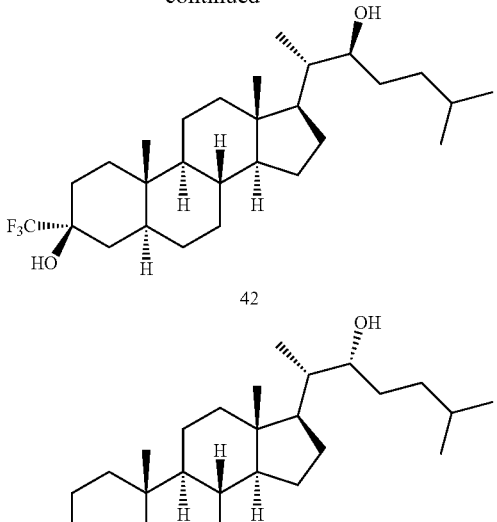

1. 4-methylbenzenesulfonic acid (2.70 g, 15.7 mmol) was added to a solution of N-4-1_1 (50 g, 157 mmol) in MeOH (500 mL) at 25° C. The mixture was stirred at 65° C. for 1 hr. The reaction mixture was cooled to 25° C. and TEA (2.16 mL, 15.7 mmol) was added. The mixture was stirred for 0.5 h. The precipitate was collected by filtration and washed with methanol (2×100 ml) to give N-4-1_2 (50 g, crude) as a solid.

$^1$H NMR (400 MHz, CDCl$_3$) δ 3.25-3.05 (m, 6H), 2.60-2.40 (m, 1H), 2.20-2.05 (m, 4H), 2.00-1.95 (m, 1H), 1.90-1.80 (m, 1H), 1.75-1.50 (m, 6H), 1.49-1.05 (m, 12H), 1.04-0.95 (m, 1H), 0.78 (s, 3H), 0.59 (s, 3H).

2. t-BuOK (23.0 g, 205 mmol) was added to a solution of bromo(methyl)triphenylphosphorane (73.2 g, 205 mmol) in THF (500 mL) at 25° C. The mixture was heated to 45° C. and stirred for 1 hr. N-4-1_2 (50 g, 137 mmol) was added. The mixture was stirred at 45° C. for 2 hrs. The mixture was quenched with NH$_4$Cl (200 ml) and extracted with THF (3×100 mL). The organic layer was washed brine (200 mL), dried over Na$_2$SO$_4$ and filtered to give a mixture (50 g, 500 mL), which was used in next step without further purification.

3. Aqueous HCl (207 mL, 1 M in water) was added to a solution of N-4-1_3 (50 g, 138 mmol) in THF (500 mL). The mixture was stirred at 25° C. for 0.5 h. The mixture was filtered and the filter cake was dissolved in DCM (200 mL) and washed with brine (100 mL), dried over anhydrous Na$_2$SO$_4$, filtered and concentrated in vacuum to afford N-4-1_4 (39 g, 90%) as a solid.

$^1$H NMR (400 MHz, CDCl$_3$) δ 4.84 (s, 1H), 4.70 (s, 1H), 2.45-2.20 (m, 3H), 2.15-2.00 (m, 3H), 1.90-1.65 (m, 8H), 1.60-1.50 (m, 2H), 1.45-1.05 (m, 8H), 1.00 (s, 3H) 0.90-0.85 (m, 1H), 0.80-0.75 (m, 1H), 0.58 (s, 3H).

4. CsF (25.9 g, 171 mmol) and TMSCF$_3$ (24.3 g, 171 mmol) were added to a solution of N-4-1_4 (27 g, 85.8 mmol) in THF (200 mL). The mixture was stirred at 10° C. for 1 hr. Water (10 mL) and TBAF.3H$_2$O (30 g) were added to the mixture. The mixture was stirred at 30° C. for another 2 hrs. The mixture was concentrated in vacuum. The residue was dissolved in EtOAc (500 mL), washed with water (2×500 mL), dried over Na$_2$SO$_4$, filtered, concentrated in vacuum and purified by flash column (DCM/EtOAc (1:1) in PE, 0~10%) to give N-4-1_5 (27 g, 82%) and N-4-15A (3.5 g, 11%) as a solid.

N-4-1_5:

$^1$H NMR (400 MHz, CDCl$_3$) δ 4.84 (s, 1H), 4.70 (s, 1H), 2.12-1.94 (m, 3H), 1.89-1.78 (m, 2H), 1.75 (s, 3H), 1.72-1.60 (m, 5H), 1.58-1.48 (m, 2H), 1.45-1.09 (m, 10H), 1.01-0.89 (m, 1H), 0.85 (s, 3H), 0.78-0.68 (m, 1H), 0.56 (s, 3H).

$^1$H NMR (400 MHz, CDCl$_3$) δ 4.84 (s, 1H), 4.70 (s, 1H), 2.09-1.99 (m, 1H), 1.89-1.78 (m, 2H), 1.75 (s, 3H), 1.72-1.52 (m, 9H), 1.45-1.06 (m, 10H), 1.00-1.81 (m, 2H), 0.79 (s, 3H), 0.56 (s, 3H).

5. 9-BBN dimer (29 g, 119 mmol) was added to a solution of N-4-1_5 (23 g, 59.8 mmol) in THF (250 mL) and the mixture was stirred at 40° C. under N$_2$ for 16 hrs. Ethanol (34.3 mL, 598 mmol) and NaOH (119 mL, 5 M, 598 mmol) were added to the reaction mixture. The mixture became clear. H$_2$O$_2$ (59.8 mL, 10 M, 598 mmol) was added dropwise at 25° C. and the inner temperature was raised to reflux (70° C.). The mixture was cooled to 30° C. after the addition. To the mixture was added Na$_2$SO$_3$ (100 mL, 20% aq.). The organic layer was separated and poured into water (800 mL). A solid formed. The mixture was filtered and the solid was washed with water, dried under vacuum and triturated with MeCN (250 mL) to give a solid. The solid was triturated from MeOH/water (250 mL/12.5 mL) at 60° C. and filtered after cooled to 15° C. The solid was dried under vacuum to give N-4-1_6 (16.4 g, 68%) as a solid.

$^1$H NMR (400 MHz, CDCl$_3$) δ 3.69-3.60 (m, 1H), 3.39-3.29 (m, 1H), 2.09-2.01 (m, 1H), 1.99-1.92 (m, 11H), 1.87-1.75 (m, 2H), 1.72-1.43 (m, 7H), 1.42-1.07 (m, 11H), 1.03 (d, J=6.8 Hz, 3H), 1.01-0.86 (m, 3H), 0.85 (s, 3H), 0.73-0.69 (m, 1H), 0.67 (s, 3H).

6. Water (223 mg, 12.4 mmol) and DMP (10.5 g, 24.8 mmol) were added to a suspension of N-4-1_6 (5 g. 12.4 mmol) in DCM (200 mL). The mixture was stirred at 15° C. for 15 mins. The mixture was washed with NaHCO$_3$/Na$_2$S$_2$O$_3$ (200 mL/200 mL, sat.) twice, dried over Na$_2$SO$_4$, filtered and concentrated in vacuum to give N-4-1_7 (4.5 g, 90%) as a solid.

$^1$H NMR (400 MHz, CDCl$_3$) δ 9.60-9.51 (m, 1H), 2.40-2.30 (m, 1H), 2.12-1.78 (m, 5H), 1.75-1.59 (m, 4H), 1.57-1.15 (m, 11H), 1.14-0.84 (m, 8H), 0.78-0.63 (m, 5H).

7. A solution of 1-bromo-3-methylbutane (2.79 g, 18.5 mmol) in THF (8 mL) was added dropwise to a suspension of Mg (899 mg, 37 mmol) and I$_2$ (1 mg) in THF (2 mL) under N$_2$ at 50-55° C. The mixture was stirred at 55° C. for 1 hr to give the isopentylmagnesium bromide solution. The freshly prepared isopentylmagnesium bromide (18.5 mmol in 10 mL of THF) was added to a solution of N-4-1_7 (0.5 g, 1.24 mmol) in THF (5 ml) at 0° C. The mixture was stirred at 15° C. for 2 hrs. To the mixture was added NH$_4$Cl (20 mL, 10% aq.). The mixture was extracted with EtOAc (2×30 mL). The combined organic layer was dried over Na$_2$SO$_4$, filtered and concentrated in vacuum to give N-4-2 (0.6 g, crude) as a solid.

8. Water (1 drop) and DMP (1.06 g, 2.52 mmol) were added to a solution of N-4-2 (0.6 g, 1.26 mmol) in DCM (20 mL) at 15° C. The mixture was stirred at 15° C. for 1 h. The mixture was washed with NaHCO$_3$/Na$_2$S$_2$O$_3$ (20 mL/20 mL, sat.) twice, dried over Na$_2$SO$_4$, filtered and concentrated in vacuum to give N-4-1_8 (0.6 g, crude) as a solid.

$^1$H NMR (400 MHz, CDCl$_3$) δ 2.59-2.30 (m, 3H), 2.11-1.78 (m, 4H), 1.75-1.36 (m, 13H), 1.35-0.98 (m, 11H), 0.91-0.82 (m, 10H), 0.78-0.70 (m, 1H), 0.67 (s, 3H).

9. NaBH$_4$ (0.96 g, 25.4 mmol) was added in portions to a solution of N-4-1_8 (0.6 g, 1.27 mmol) in THF (10 mL) and MeOH (5 mL) at 15° C. The mixture was stirred at 15° C. for 30 mins. To the mixture was added NH$_4$Cl (50 mL, 10%). The mixture was extracted with EtOAc (2×50 mL). The combined organic layer was dried over Na$_2$SO$_4$, filtered and concentrated under vacuum and purified by flash column (0~15% EtOAc in PE) to give impure 42 and 85. N42 was triturated from MeCN (10 ml) at 15° C. and dried in vacuum to give 42 (153 mg, 25%) as a solid. 85 was purified by flash column (0~15% EtOAc in PE) to give an oil, which was treated with MeCN (5 mL) and water (5 mL), and concentrated under vacuum to give 85 (70 mg, 12%) as a solid.

42:

$^1$H NMR (400 MHz, CDCl$_3$) δ 3.66-3.55 (m, 1H), 2.01-1.78 (m, 6H), 1.71-1.59 (m, 4H). 1.51-1.15 (m, 16H), 1.09-1.02 (m, 3H), 0.92-0.81 (m, 13H), 0.72-0.61 (m, 4H).

LCMS Rt=1.378 min in 2.0 min chromatography, 30-90_AB_E, purity 100%, MS ESI calcd. for C$_{2-8}$H$_{46}$F$_3$O [M+H—H$_2$O]$^+$ 455, found 455.

HPLC Rt=5.38 min in 10.0 min chromatography, 50-100_AB_E, purity 99.58%.

Example 43: Synthesis of (3S,5R,8R,9S,10S,13S, 14S,17R)-3-ethyl-10,13-dimethyl-17-((2S,3R)-4,4,4-trifluoro-3-hydroxybutan-2-yl)hexadecahydro-1H-cyclopenta[a]phenanthren-3-ol (43)

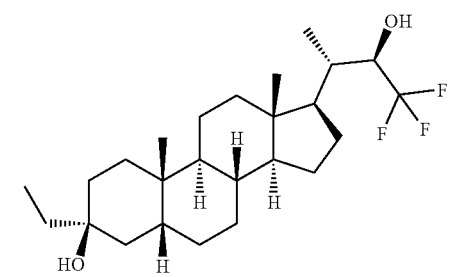

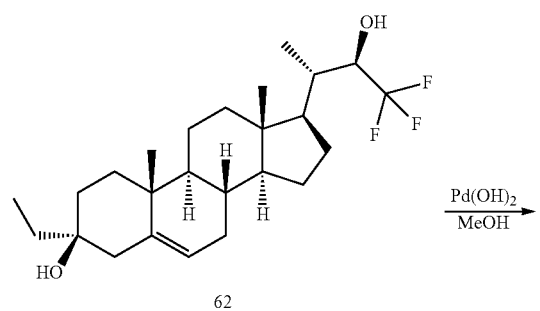

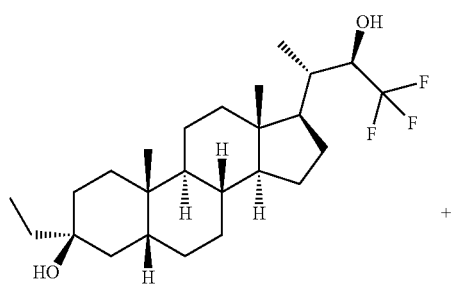

43

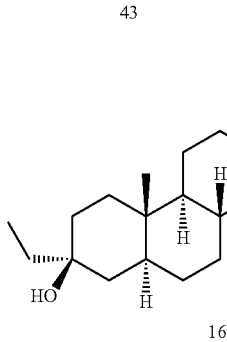

16

1. To a solution of 62 (160 mg, 0.373 mmol) in MeOH (2 mL) and THF (1 mL) was added Pd(OH)₂ (0.2 g, <1% water). The solution was hydrogenated under 50 psi of hydrogen at 50° C. for 16 hrs. Then the mixture was filtered through a pad of celite and the filtrate was concentrated in vacuum. The residue was purified by flash column (PE/EtOAc=10/1 to 5/1) to give 43 (27 mg, 17%) and 16 (117 mg, 73%) as a white solid.

43:

$^1$H NMR (400 MHz, CDCl3) δ. 4.05-3.99 (m, 1H), 1.99-1.81 (m, 5H), 1.79-1.72 (m, 1H), 1.70-1.56 (m, 3H), 1.53-1.35 (m, 7H), 1.35-1.07 (m, 12H), 1.04-1.02 (m, 3H), 0.97 (s, 3H), 0.92 (t, J=8 Hz, 3H), 0.70 (s, 3H).

LCMS Rt=1.271 min in 2.0 min chromatography, 30-90 AB, purity 100%, MS ESI calcd. For $C_{25}H_{40}F_3O$ [M+H—H₂O]⁺ 413, found 413.

Example 44: Synthesis of (3S,8R,9S,10R,13S,14S, 17R)-3-ethyl-17-((2S,3S)-3-hydroxy-6-methylheptan-2-yl)-13-methyl-2,3,4,7,8,9,10,11,12,13,14,15, 16,17-tetradecahydro-1H-cyclopenta[a]phenanthren-3-ol (44)

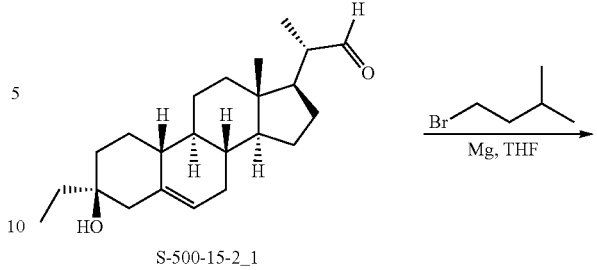

S-500-15-2_1

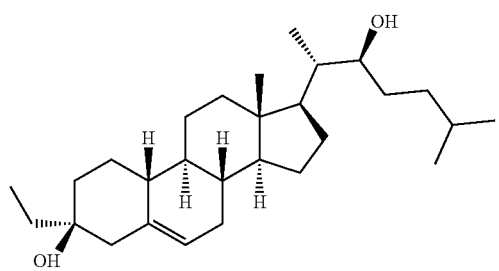

44

1. A solution of 1-bromo-3-methylbutane (4 g, 26.4 mmol) in THF (27 ML) was added dropwise to a suspension of Mg (947 mg, 39.5 mmol) and 12 (33.5 mg, 0.132 mmol) in THF (3 mL) at 60° C. The mixture was stirred at 60° C. for 1 hr. Freshly prepared isopentylmagnesium bromide (30 mL, 0.88 M in THF, 26.4 mmol) was added to a solution of S-500-15-2_1 (800 mg, 2.32 mmol) in THF (2 mL) under N2 at 0° C. The mixture was stirred at 0° C. for 1 h. To the mixture was added NH₄Cl (50 mL, sat. aq.), the mixture was extracted with EtOAc (2×50 mL). The combined organic phase was washed with brine (100 mL), dried over Na₂SO₄, filtered and concentrated in vacuum to give crude product which was purified by silica gel (PE/EtOAc=10/1 to 5/1) to give 44 (720 mg, 75%) as a white solid. 1H NMR (400 MHz, CDCl3) δ 5.40-5.38 (m, 1H), 3.63-3.61 (m, 1H), 2.23-2.21 (m, 1H). 2.10-1.74 (m, 7H), 1.69-1.58 (m, 2H), 1.54-1.34 (m, 8H), 1.33-1.00 (m, 11H), 0.95-0.75 (m, 14H), 0.70 (s, 3H).

LCMS Rt=1.289 min in 2 min chromatography, 30-90 AB, purity 100%, MS ESI calcd. For $C_{28}H_{45}$ [M+H-2H2O]⁺ 381, found 381.

Example 45: Synthesis of (3S,5R,8R,9R,10S,13S, 14S,17R)-3-(methoxymethyl)-13-methyl-17-((2S, 3R)-4,4,4-trifluoro-3-hydroxybutan-2-yl)hexadecahydro-1H-cyclopenta[a]phenanthren-3-ol (45)

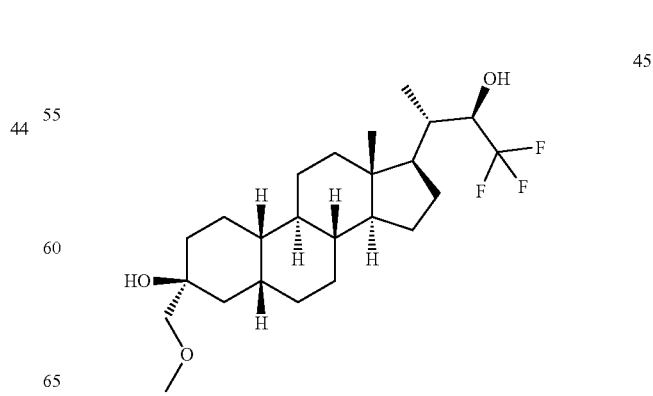

45

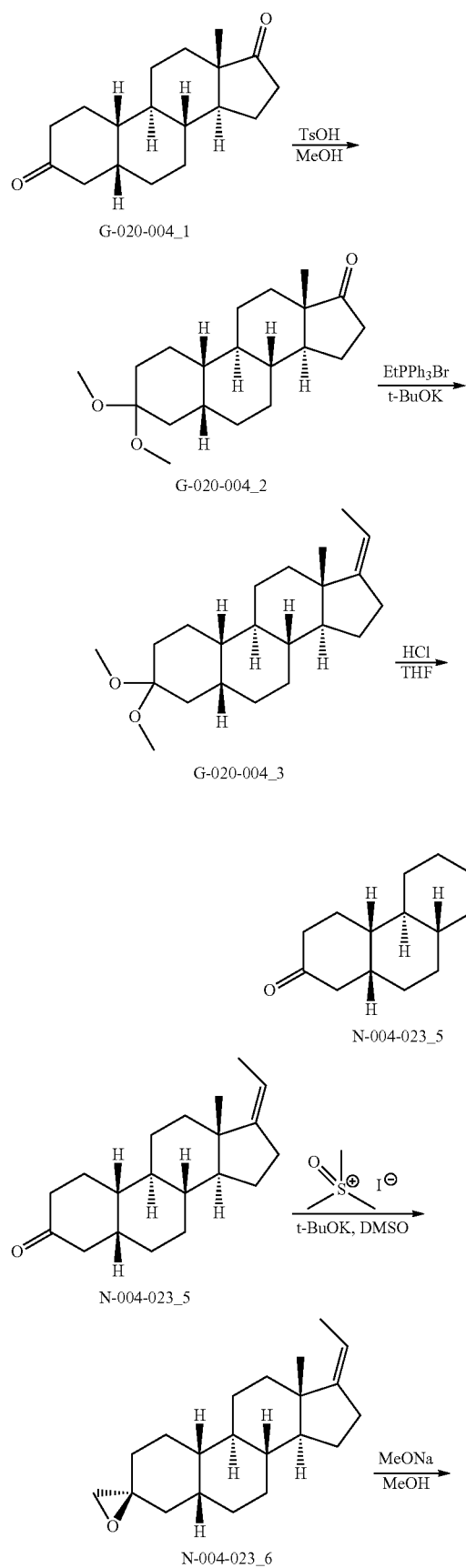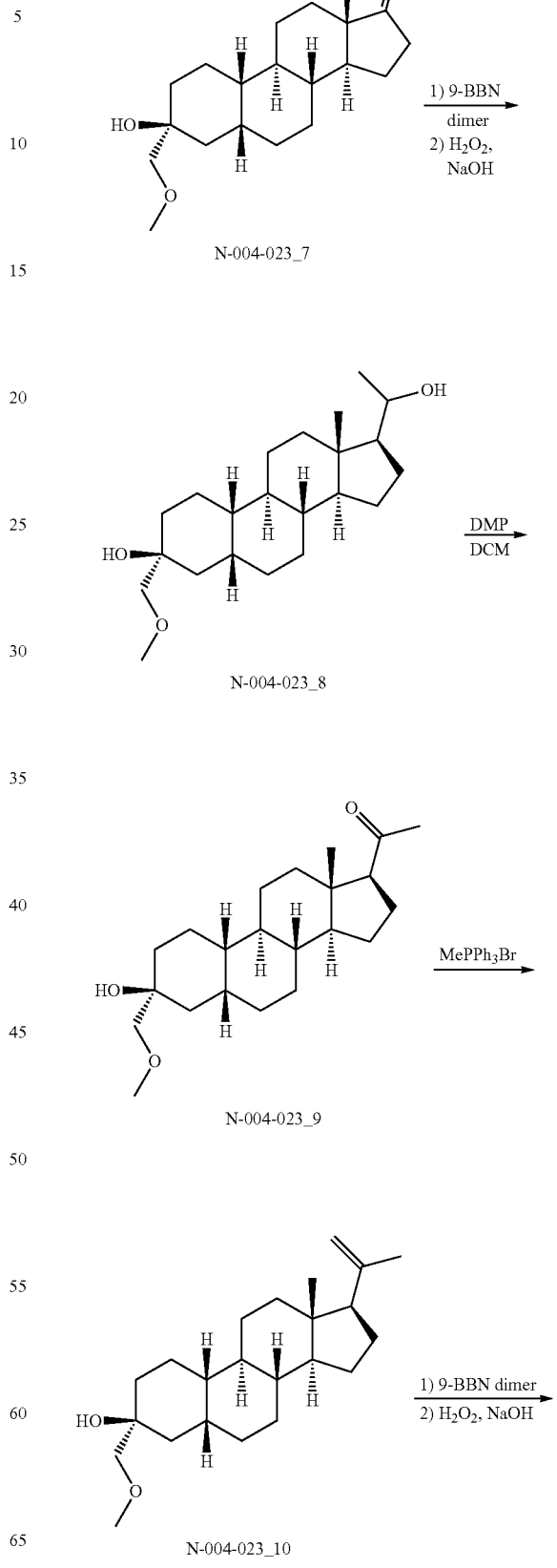

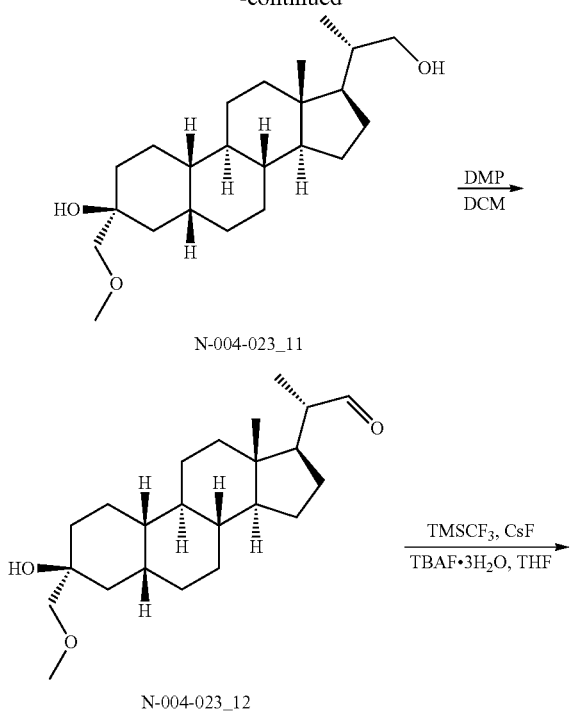

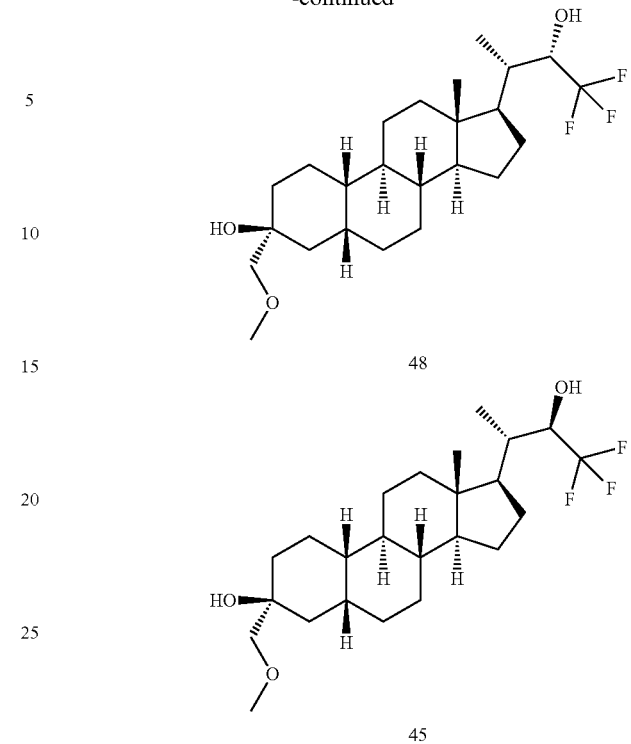

1. To a solution of G-020-004_1 (100 g, 364 mmol) in anhydrous methanol (1 L) was added TsOH (6.26 g, 36.4 mmol). The mixture was stirred at 60° C. for 18 hrs. The reaction mixture was concentrated to remove most of the solvent, neutralized with $Et_3N$ (3.7 g), diluted with EtOAc (600 mL), washed with water (500 ml) and brine (500 mL). The organic layer was concentrated to give G-020-004_2 (133 g, crude) as an oil.

$^1$H NMR (400 MHz, $CDCl_3$) δ 3.20 (s, 3H), 3.14 (s, 3H), 2.63-2.39 (m, 2H), 2.14-2.03 (m, 2H), 1.97-1.89 (m, 2H), 1.86-1.77 (m, 3H), 1.64-1.60 (m, 2H), 1.56-1.49 (m, 3H), 1.47-1.42 (m, 2H), 1.40-1.32 (m, 2H), 1.29-1.23 (m, 3H), 1.16-1.06 (m, 2H), 0.87 (s, 3H).

2. To a suspension of $Ph_3PEtBr$ (308 g, 830 mmol) in anhydrous THF (700 mL) under nitrogen at 20° C. was added t-BuOK (93.1 g, 830 mmol). After stirring at 20° C. for 1 hr, a solution of G-020-004_2 (133 g, 415 mmol) in anhydrous THF (300 mL) was added to the mixture. The resulting mixture was warmed to 50° C. and stirred for 4 hrs. The reaction mixture was cooled, quenched with water (400 mL) and sat. $NH_4Cl$ (300 mL), stirred for 30 min. The organic layer was separated, and the water phase was extracted with THF (300 mL). The combined organic layer was used directly in next step.

3. To a solution of G-020-004_3 (137 g, 412 mmol, theoretical) in THF (1.3 L) was added aqueous HCl (1 M, 618 mL, 618 mmol). After stirring at 20° C. for 1 hr, the reaction mixture was quenched with saturated $NaHCO_3$ (800 mL) and extracted with EtOAc (2×500 mL). The combined organic layer was dried over anhydrous sodium sulfate, filtered and concentrated to give a solid (300 g). The solid was triturated from petroleum ether (800 mL) for 18 hrs. The solid was filtered off, and the filter cake was washed with petroleum ether (400 mL). The filtrate was concentrated to give a residue (117 g). The residue was purified by column chromatography on silica gel (0~10% of EtOAc in PE) to give N-004-023_5 (70 g) as a solid.

¹H NMR (400 MHz, CDCl₃) δ 5.17-5.09 (m, 1H), 2.65-2.55 (m, 1H), 2.43-2.34 (m, 1H), 2.33-2.15 (m, 6H), 2.11-2.05 (m, 1H), 1.83-1.70 (m, 2H), 1.68-1.64 (m, 4H), 1.63-1.59 (m, 2H), 1.58-1.46 (m, 3H), 1.42-1.25 (m, 3H), 1.25-1.14 (m, 3H), 0.91 (s, 3H).

4. A stirred solution of trimethylsulfoxonium iodide (30.5 g, 139 mmol) and t-BuOK (15.5 g, 139 mmol) in DMSO (200 mL) was heated at 60° C. for 1.0 h under N₂; N-004-023_5 (20 g, 69.8 mmol) was added to the reaction mixture and stirred at 60° C. for 10 mins. The reaction was treated with water (1000 mL). The aqueous phase was extracted with EtOAc (2×500 mL). The combined organic phase was washed with water (2×500 mL), brine (300 mL), dried over anhydrous Na₂SO₄, filtered and concentrated under vacuum to afford N-004-023_6 (20.5 g, crude) as a solid.

¹H NMR (400 MHz, CDCl₃) δ 5.13-5.10 (m, 1H), 2.62-2.60 (m, 2H), 2.25-2.20 (m, 5H), 2.00-1.48 (m, 12H), 1.46-1.00 (m, 8H), 0.98-0.89 (m, 4H).

5. MeONa (18.4 g, 341 mmol) was added to a solution of N-004-023_6 (20.5 g, 68.2 mmol) in MeOH (500 mL) at 25° C. under N₂, The mixture was stirred at 70° C. reflux for 16 h under N2, The reaction was treated with water (500 mL). The aqueous phase was extracted with DCM (2×300 mL). The combined organic phase was washed with saturated brine (2×300 mL), dried over anhydrous Na₂SO₄, filtered and concentrate was purified by silica gel chromatography (PE/EtOAc=10/1 to 6/1) to afford N-004-023_7 (20 g, 88%) as a solid.

¹H NMR (400 MHz, CDCl₃) δ 5.12-5.06 (m, 1H), 3.38 (s, 3H), 3.19 (s, 2H), 2.25-2.22 (m, 1H), 2.20-2.09 (m, 3H), 1.66-1.63 (m, 3H), 1.60-1.24 (m, 14H), 1.22-1.00 (m, 6H), 0.87 (s, 3H).

6. 9-BBN dimer (29.2 g, 120 mmol) was added to a solution of N-004-023_7 (20 g, 60.1 mmol) in THF (100 mL) at 0° C. under N₂. The solution was stirred at 65° C. for 2 hrs. After cooling to 0° C., EtOH (34.9 mL, 601 mmol) was added. Then a solution of NaOH (120 mL, 5M, 601 mmol) was added very slowly. After addition, H₂O₂ (68.0 g, 601 mmol, 30% in water) was added slowly and the inner temperature was maintained below 10° C. The mixture was stirred at 75° C. under N₂ for 1 hr. The mixture was re-cooled to 25° C. The mixture was added to H₂O (2 L). The mixture was stirred 30 mins. The precipitate was collected by filtration and washed with H₂O (2×500 mL) to give N-004-023_8 (17.8 g, 85%) as a solid.

¹H NMR (400 MHz, CDCl₃) δ 3.70-3.55 (m, 1H), 3.38 (s, 3H), 3.19 (m, 2H), 2.11-1.86 (m, 4H), 1.80-1.25 (m, 13H), 1.23-0.88 (m, 12H), 0.68 (s, 3H).

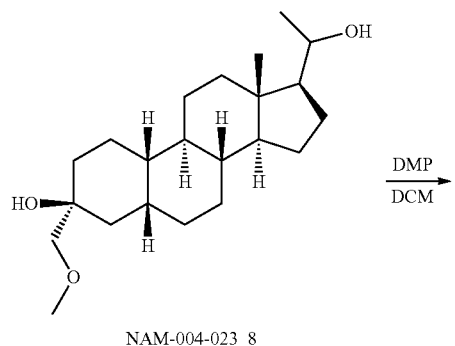

NAM-004-023_8

DMP / DCM

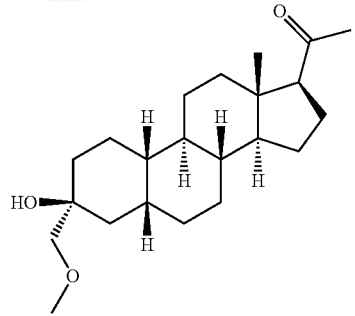

NAM-004-023_9

7. Silica gel (24 g) and PCC (24.5 g, 114 mmol) were added to a suspension of N-004-0238 (20 g, 57.0 mmol) in DCM (500 mL) at 25° C. The mixture was stirred at 25° C. for 2 hrs. The mixture was filtered and the filtered cake was washed with DCM (2×100 mL). The combined filtrate was concentrated under vacuum. The residue was purified by flash column (0~30% of EtOAc in PE) to give NA-004-023_9 (19 g, 95%) as a solid.

¹H NMR (400 MHz, CDCl₃) δ 3.39 (s, 3H), 3.20 (s, 2H), 2.60-2.52 (m, 1H), 2.20-2.10 (m, 5H), 1.99-1.80 (m, 3H), 1.75-1.40 (m, 12H), 1.30-1.04 (m, 7H), 0.61 (s, 3H).

8. t-BuOK (12.2 g, 54.5 mmol) was added to a suspension of MePPh₃Br (38.9 g, 109 mmol) in THF (300 mL) at 25° C. After addition, the reaction mixture was heated to 45° C. and stirred for 1 hr. Then N-004-023_9 (19 g, 35.9 mmol) was added and the reaction mixture was stirred at 45° C. for 16 hrs. The mixture was treated with NH₄Cl (100 mL, sat. aq.). The organic layer was separated. The aqueous phase was extracted with EtOAc (2×300 mL). The combined organic phase was washed with saturated brine (2×200 mL), dried over anhydrous Na₂SO₄, filtered and concentrated. The residue was triturated from MeOH/H₂O (100 mL/100 mL) at 25° C. to give N-004-023_10 (17 g, 90%) as a solid.

¹H NMR (400 MHz, CDCl₃) δ 4.84 (s, 1H), 4.68 (s, 1H), 3.39 (s, 3H), 3.19 (s, 2H), 2.10-2.04 (m, 1H), 2.03-1.90 (m. 3H), 1.75-1.56 (m, 12H), 1.49-1.25 (m, 4H), 1.22-0.89 (m, 8H), 0.57 (s, 3H).

9. 9-BBN dimer (29.5 g, 122 mmol) was added to a solution of N-004-023_10 (17 g, 49.0 mmol) in anhydrous THF (300 mL) and stirred at 0° C. for 30 min under N₂. The reaction mixture was warned to 25° C. (room temperature) and stirred for 2 hrs. The reaction mixture was cooled. The mixture was quenched by EtOH (100 mL) at 0° C. NaOH (98.0 mL, 490 mol, 5M in water) was added very slowly. After addition, H₂O₂ (44.5 mL, 490 mmol, 11M) was added slowly until the inner temperature no longer rises and during which the temperature was maintained below 30° C. The mixture was stirred at 50° C. for another 1 hr. then the mixture was cooled, treated with water (2 L) and stirred for 30 min. The suspension was filtration in vacuum to give N-004-023_11 (17 g, crude) as a solid. The N-004-023_11 (17 g, 46.6 mmol) was triturated from MeOH/H₂O (100/100 mL) at 25° C. and stirred for 1 hr. The suspension was filtered under vacuum to obtain N-004-023_11 (14 g, impure) as a solid.

¹H NMR (400 MHz, CDCl₃) δ 3.79-3.66 (m, 1H), 3.50-3.37 (m, 4H), 3.28 (s, 2H), 2.43 (s, 1H), 2.26-1.98 (m, 3H), 2.18-2.12 (m, 1H), 1.95-1.60 (m, 11H), 1.34-1.04 (m, 14H), 0.76 (s, 3H).

10. DMP (9.24 g, 21.8 mmol) was added to a solution of N-004-023_11 (4 g, 10.9 mmol) in DCM (80 ml) at 25° C.

One drop of water was added to the mixture and was stirred for 30 mins. The reaction mixture was quenched with saturated NaHCO$_3$, aqueous pH=7-8 at below 10° C. The DCM phase in the filtrate was separated and washed with saturated NaHCO$_3$/Na$_2$S$_2$O$_3$ aqueous (1:1, 2×50 mL). The organic phase was washed with saturated brine (2×50 mL), dried over anhydrous Na$_2$SO$_4$, filtered and concentrated in vacuum to give N-004-023_12 (1.8 g, 46%) as an oil.

$^1$H NMR (400 MHz, CDCl$_3$) δ 9.57-9.55 (m, 1H), 3.38 (s, 3H), 3.20 (s, 2H), 2.39-2.26 (m, 1H), 2.17-2.06 (m, 1H), 2.05-1.75 (m, 4H), 1.74-1.53 (m, 8H), 1.85-1.00 (m, 15H), 0.74 (s, 3H).

11. CsF (1.86 g, 12.3 mmol) was added to a solution of N-004-023_12 (1.8 g, 4.96 m mol) in anhydrous THF (20 mL) at 0° C. After stirring at 0° C. for 20 min, TMSCF$_3$ (1.74 g, 12.3 mmol) was added at 0° C. and stirred for 1 hr, then TBAF.3H$_2$O (6.25 g, 19.8 mmol) was added. The mixture reaction was warmed to 50° C. and stirred for another 1 hr. The reaction mixture was poured into ice-water (50 mL) and stirred for 10 min. The aqueous phase was extracted with EtOAc (2×80 mL). The combined organic phase was washed with saturated brine (2×80 mL), dried over anhydrous Na$_2$SO$_4$, filtered and concentrated. The residue was purified by flash column (0~20% of EtOAc in PE) to give N-004-023_13 (1.2 g, 56%) as an oil.

$^1$H NMR (400 MHz, CDCl$_3$) δ 4.03-3.98 (m, 1H), 3.39 (s. 3H), 3.20 (s. 2H), 2.17-1.80 (m, 7H), 1.73-1.41 (m, 10H), 1.28-0.95 (m, 13H), 0.71 (s, 3H).

12. DMP (2.34 g, 5.54 mmol) was added to a solution of N-004-023_13 (1.2 g, 2.77 mmol) in DCM (30 ml) at 25° C. After stirring at 25° C. for 30 mins, the reaction mixture was quenched with saturated NaHCO$_3$ (30 mL), aqueous pH=7-8 at below 10° C. Then DCM (30 mL) was added and the mixture was stirred for 10 min. The suspension was filtered. The DCM phase in the filtrate was separated and washed with saturated NaHCO$_3$/Na$_2$S$_2$O$_3$ aqueous (1:1, 2×50 mL). The organic phase was washed with saturated brine (2×50 mL). dried over anhydrous Na$_2$SO$_4$, filtered and concentrated in vacuum to give N-004-023_13A (1.2 g, crude) as an oil.

$^1$H NMR (400 MHz, CDCl$_3$) δ 3.39 (s, 3H), 3.20 (s, 2H), 3.05-2.95 (m, 1H), 1.91-1.51 (m, 10H), 1.46-1.20 (m, 10H), 1.17-0.96 (m, 8H), 0.72 (s, 3H).

13. NaBH$_4$ (210 mg, 5.56 mmol) was added to a solution of N-004-023_13A (1.2 g, 2.78 mmol) in MeOH (5 mL) at 0° C. and stirred for 30 min. After treating with MeOH/H$_2$O (20/20 mL), the mixture was stirred for 10 min. The aqueous phase was extracted whit EtOAc (2×50 mL). The combine organic phase was washed with saturated brine (2×50 mL), drive over anhydrous Na$_2$SO$_4$, filtered and concentrated. The residue was purified by flash column (0~20% of EtOAc in PE) to give 48 (57 mg, 5%) as a solid and 45 (200 mg, impure) as a solid. The 45 (200 mg, 0.462 mmol) was purified by flash column (0~30% of EtOAc in PE) to give 45 (120 mg, 10%) as a solid.

45:

$^1$H NMR (400 MHz, CDCl$_3$) δ 4.01-3.98 (m, 1H), 3.38 (s, 3H), 3.19 (s, 2H), 2.15-2.10 (m, 1H), 2.05-1.80 (m, 5H), 1.72-1.55 (m, 5H), 1.54-1.34 (m, 6H), 1.31-1.20 (m, 4H), 1.16-0.95 (m, 9H), 0.71 (s, 3H).

LCMS Rt=1.129 min in 2 min chromatography, 30-90AB_2MIN_E, purity 100%, MS ESI calcd. for C$_{24}$H$_{38}$F$_3$ [M−HO$_3$]$^+$ 383, found 383.

Example 46: Synthesis of (3S,8S,9S,10R,13S,14S,17R)-17-((2S,3R)-4-cyclopentyl-3-hydroxybutan-2-yl)-3-ethyl-10,13-dimethyl-2,3,4,7,8,9,10,11,12,13,14,15,16,17-tetradecahydro-1H-cyclopenta[a]phenanthren-3-ol (46)

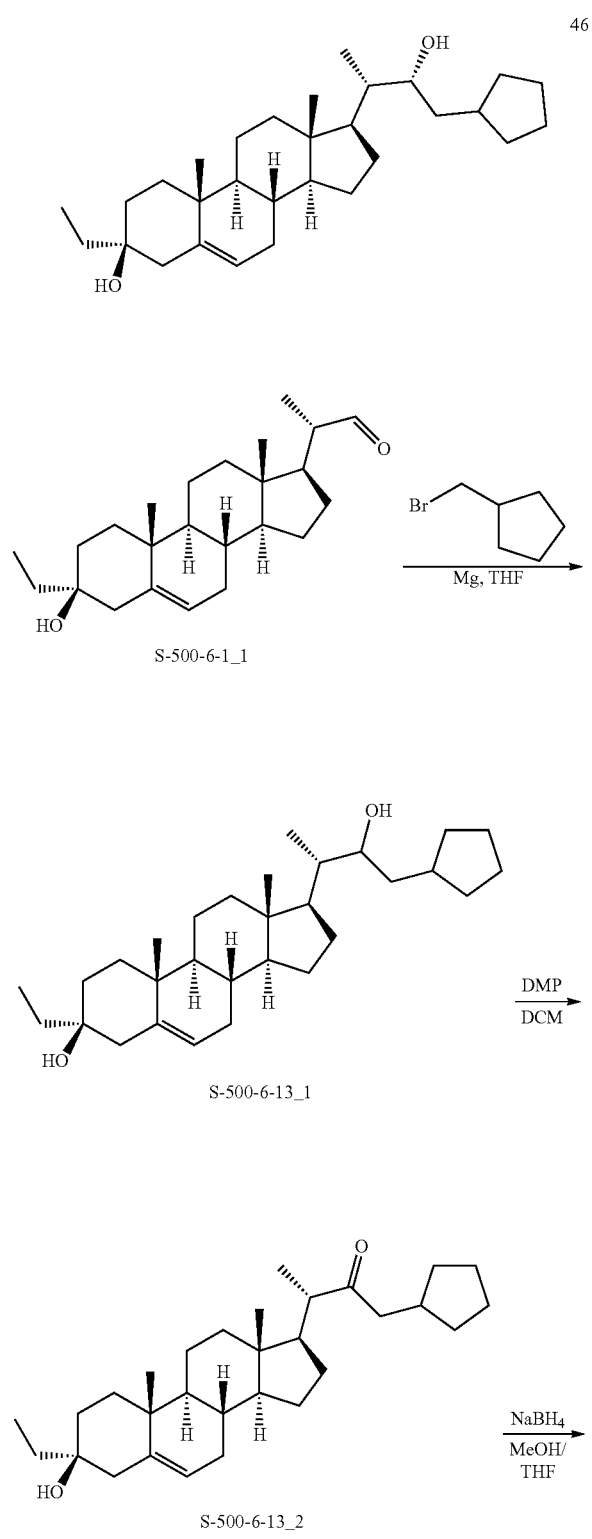

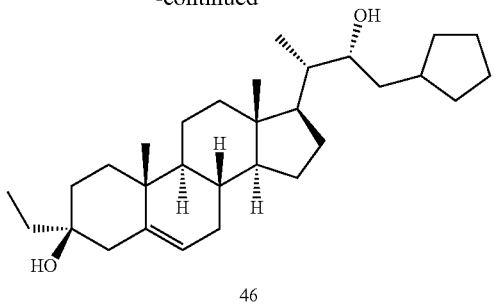

46

1. A solution of (bromomethyl)cyclopentane (2.25 g, 13.8 mmol) in THF (8 mL) was added dropwise to a suspension of Mg (662 mg, 27.6 mmol) and $I_2$ (70 mg, 0.276 mmol) in THF (3 mL) at 75° C. The mixture was stirred at 75° C. for 1 hr. After cooling, a solution of S-500-6-1_1 (1 g, 2.78 mmol) in THF (30 mL) was added slowly at 15° C. After addition, the mixture was stirred at 15° C. for 2 hrs, quenched with sat.NH$_4$Cl (40 mL) and sat. citric acid (20 mL) and extracted with EtOAc (3×20 mL). The combined organic phase was washed with brine (2×30 mL), dried over Na$_2$SO$_4$, filtered and concentrated and purified by combi-flash (0-15% of EtOAc in PE) to give a mixture of S-500-6-13_1 and an isomer at the 22 position (900 mg, 73%) as a solid.

$^1$H NMR (400 MHz, CDCl$_3$) δ 5.32-5.23 (m, 1H), 3.77-3.67 (m, 1H), 2.40-2.30 (m, 1H), 2.07-1.89 (m, 4H), 1.88-1.69 (m, 4H), 1.67-1.59 (m, 4H), 1.55-1.26 (m, 15H), 1.16-1.05 (m, 5H), 1.05-1.00 (m, 4H), 0.99-0.81 (m, 8H), 0.68 (s, 3H).

2. DMP (1.72 g, 4.06 mmol) was added to a solution of S-500-6-13_1 (900 mg, 2.03 mmol) in DCM (30 mL). After that, the reaction mixture was stirred at 15° C. for 10 min. The reaction mixture was quenched with saturated NaHCO$_3$ aqueous (50 mL) until pH of the aqueous layer became about 9. The mixture was filtered. The DCM layer was separated and the aqueous phase was extracted with DCM (20 mL). The combined organic phase was washed with saturated aqueous Na$_2$S$_2$O$_3$ (3×40 mL) and sat. NaHCO$_3$ (40 mL), brine (40 mL), dried over Na$_2$SO$_4$, filtered and concentrated to give crude S-500-6-13_2 (900 mg, crude) as a solid.

$^1$H NMR (400 MHz, CDCl$_3$) δ 5.30-5.25 (m, 1H), 2.54-2.42 (m, 2H), 2.41-2.33 (m, 1H), 2.30-2. (m, 1H). 2.06-1.90 (m, 3H), 1.87-1.78 (m, 2H), 1.73-1.66 (m, 2H), 1.65-1.35 (m, 15H), 1.33-1.21 (m, 2H), 1.17-0.92 (m, 13H), 0.88-0.82 (m, 3H), 0.69 (s, 3H).

3. NaBH$_4$ (3.46 g, 102 mmol) was added five times, every five minutes, to a solution of S-500-6-13_2 (900 mg, 2.04 mmol) in MeOH (5 mL) and THF (5 mL). The mixture was stirred at 15° C. for 30 minutes, quenched with sat. NH$_4$Cl (50 mL) and extracted with EtOAc (3×20 mL). The combined organic phase was dried over Na$_2$SO$_4$, filtered, concentrated and purified by combi-flash (0-15% of EtOAc in PE) to give impure 46 (120 mg) as a solid, which was separated by SFC ((column: AD (250 mm*30 mm, 5 um), gradient: 45-45% B (A=0.05% NH$_3$/H$_2$O, B=MeOH), flow rate: 60 mL/min) to give pure 46 (100 mg, 84%) as a solid.

$^1$H NMR (400 MHz, CDCl$_3$) δ 5.31-5.26 (m, 1H), 3.76-3.67 (m, 1H), 2.40-2.33 (m, 1H), 2.08-1.91 (m, 4H), 1.90-1.78 (m, 2H), 1.77-1.55 (m, 10H), 1.54-1.31 (m, 9H), 1.26-1.22 (m, 2H), 1.22-1.05 (m, 6H), 1.03 (s, 3H), 1.01-0.89 (m, 5H), 0.89-0.82 (m, 3H), 0.69 (s, 3H).

LCMS Rt=1.474 min in 2.0 min chromatography, 30-90AB_E, purity 99%, MS ESI calcd. for $C_{30}H_{49}O$ [M+H—H$_2$O]$^+$ 425, found 425.

Example 47: Synthesis of (3S,5S,8R,9S,10S,13S, 14S,17R)-17-((2S,3R)-3-hydroxy-6-methylheptan-2-yl)-3,10,13-trimethylhexadecahydro-1H-cyclopenta[a]phenanthren-3-ol (47)

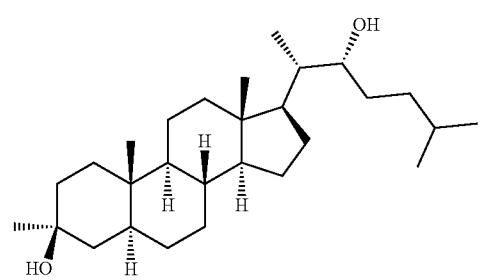

47

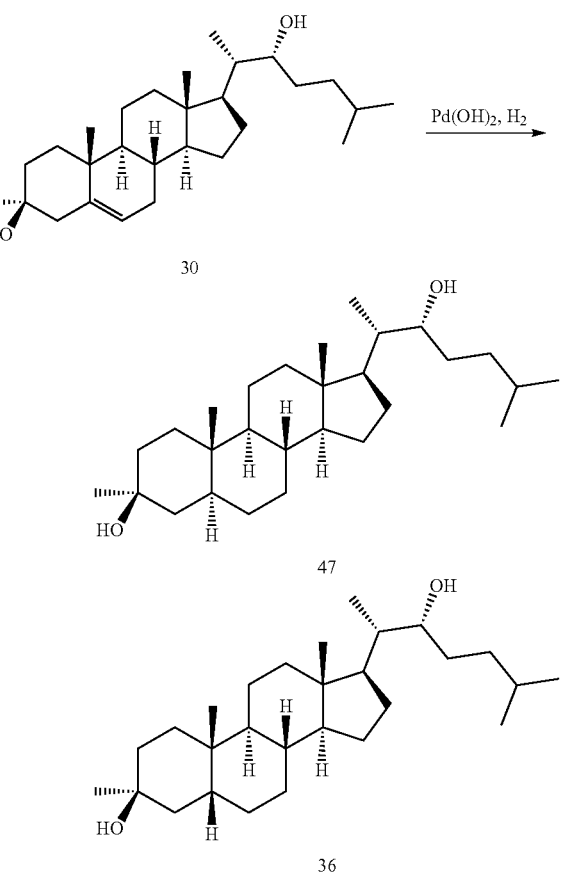

1. Pd(OH)$_2$ (200 mg) was added to a solution of 30 (100 mg, 0.239 mmol) in MeOH (10 mL). The mixture was stirred at 50° C. under H$_2$ (50 Psi). The mixture was filtered, concentrated and purified by combi-flash (0-10% of EtOAc in PE) to give 47 (21 mg, 21%) and 36 (1 mg, 1%) as a white solid.

47:

¹H NMR (400 MHz, CDCl₃) δ 3.68-3.54 (m, 1H), 2.02-1.90 (m, 1H), 1.76-1.57 (m, 6H), 1.54-1.27 (m, 10H), 1.26-1.21 (m, 7H), 1.20-1.08 (m, 5H), 1.07-0.95 (m, 3H), 0.94-0.83 (m, 10H), 0.81 (s, 3H), 0.72-0.60 (m, 4H).

LCMS t$_R$=1.290 min in 2 min chromatography, 30-90AB_ELSD, purity 100.0%, MS ESI calcd. for C$_{28}$H$_{47}$ [M+H-2H$_2$O]$^+$ 383, found 383.

Example 48: Synthesis of (3S,5R,8R,9R,10S,13S,14S,17R)-3-(methoxymethyl)-13-methyl-17-((2S,3S)-4,4,4-trifluoro-3-hydroxybutan-2-yl)hexadecahydro-1H-cyclopenta[a]phenanthren-3-ol (48)

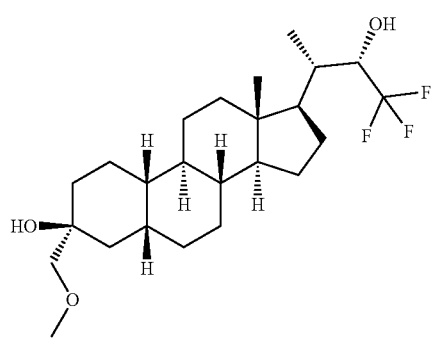

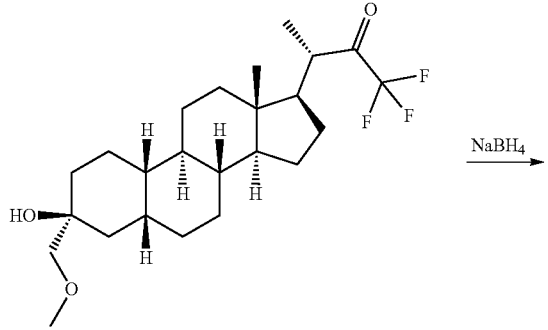

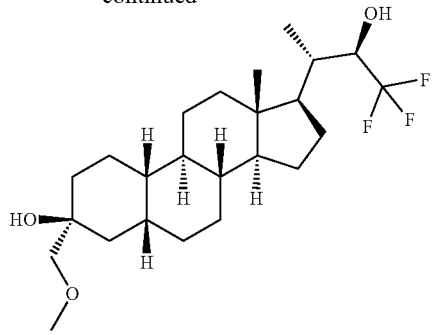

NaBH₄ (210 mg, 5.56 mmol) was added to a solution of N-004-023_13 (1.2 g, 2.78 mmol) in 1. MeOH (5 mL) at 0° C. and stirred for 30 min. After treating with MeOH/H₂O (20/20 mL), the mixture was stirred for 10 min. The aqueous phase was extracted whit EtOAc (2×50 mL). The combine organic phase was washed with saturated brine (2×50 mL), drive over anhydrous Na₂SO₄, filtered and concentrated. The residue was purified by flash column (0~20% of EtOAc in PE) to give 48 (57 mg, 5%) as a solid and 45 (200 mg, impure) as a solid. The 45 (200 mg, 0.462 mmol) was purified by flash column (0~30% of EtOAc in PE) to give 45 (120 mg, 10%) as a solid.

48:

¹H NMR (400 MHz, CDCl₃) δ 4.07-4.01 (m, 1H), 3.39 (s, 3H), 3.19 (s, 2H), 2.30-2.22 (m, 1H), 2.14-2.05 (m, 1H), 2.00-1.80 (m, 4H), 1.72-1.57 (m, 6H), 1.49-1.20 (m, 9H), 1.18-0.95 (m, 9H), 0.68 (s, 3H).

LCMS Rt=1.085 min in 2 min chromatography, 30-90AB_2MIN_E, purity 100%, MS ESI calcd. for C$_{24}$H$_{38}$F$_3$[M−HO$_3$]$^+$383, found 383.

Example 49: Synthesis of (3S,8S,9S,10R,13S,14S,17R)-17-((2S,3S)-4-(4,4-dimethylcyclohexyl)-3-hydroxybutan-2-yl)-3-ethyl-10,13-dimethyl-2,3,4,7,8,9,10,11,12,13,14,15,16,17-tetradecahydro-1H-cyclopenta[a]phenanthren-3-ol (49)

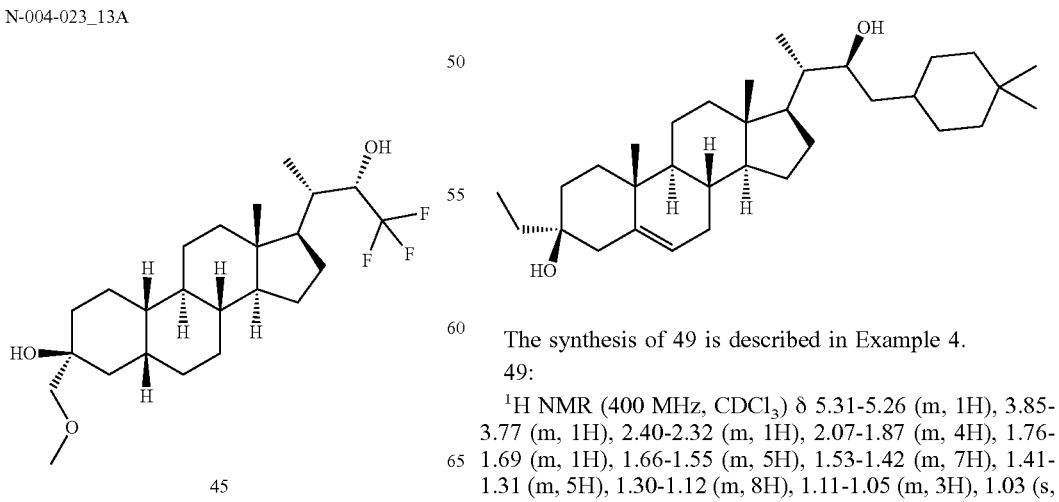

The synthesis of 49 is described in Example 4.

49:

¹H NMR (400 MHz, CDCl₃) δ 5.31-5.26 (m, 1H), 3.85-3.77 (m, 1H), 2.40-2.32 (m, 1H), 2.07-1.87 (m, 4H), 1.76-1.69 (m, 1H), 1.66-1.55 (m, 5H), 1.53-1.42 (m, 7H), 1.41-1.31 (m, 5H), 1.30-1.12 (m, 8H), 1.11-1.05 (m, 3H), 1.03 (s, 3H), 1.01-0.92 (m, 2H), 0.91-0.82 (m, 12H), 0.68 (s, 3H).

LCMS Rt=1.718 min in 2.0 min chromatography, 30-90AB_E, purity 98%, MS ESI calcd. for $C_{33}H_{53}$ [M+H-2H$_2$O]$^+$ 449, found 449.

Example 50: Synthesis of (3S,5S,8R,9S,10S,13S, 14S,17R)-3-ethyl-17-((2S,3S)-3-hydroxybutan-2-yl)-10,13-dimethylhexadecahydro-1H-cyclopenta[a]phenanthren-3-ol (50)

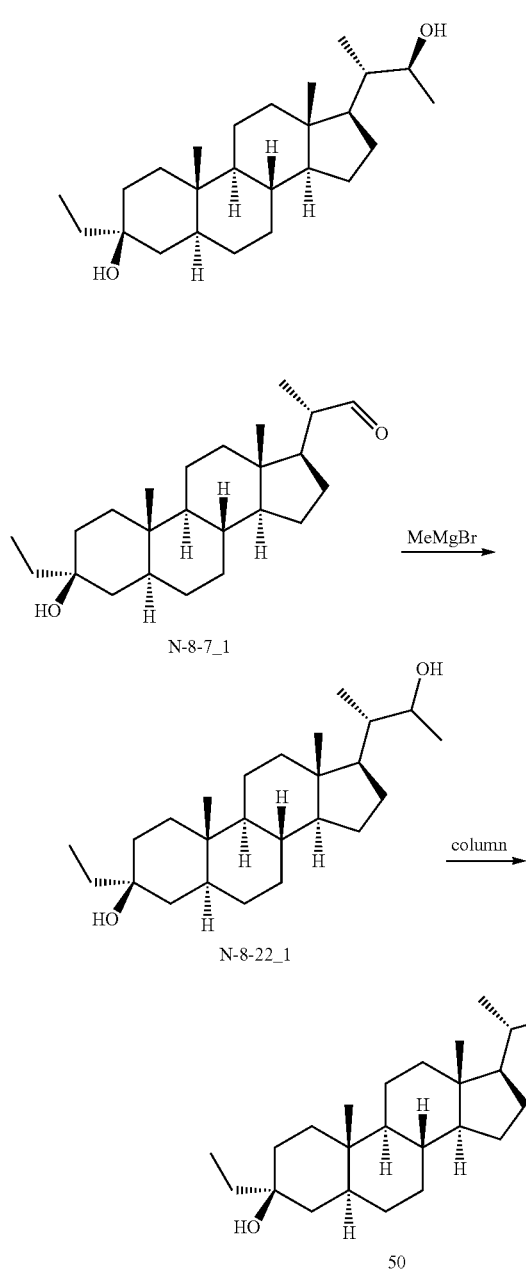

1. MeMgBr (0.83 mL, 2.49 mmol, 3M in ether) was added dropwise to a solution of N-8-7_1 (300 mg, 0.832 mmol) in THF (20 mL) at 0° C. under N$_2$. After stirring at 20° C. for 30 minutes, the reaction was quenched with sat. NH$_4$Cl (50 mL) and extracted with EtOAc (2×10 mL). The combined phase was washed with brine (10 mL), dried over Na$_2$SO$_4$, filtered, concentrated and purified by flash column (step 2) (0-10% EtOAc in PE) to give 50 (40 mg, 29%) as a solid.

$^1$H NMR (400 MHz, CDCl$_3$) δ 3.98-3.89 (m, 1H), 1.99-1.84 (m, 2H), 1.69-1.56 (m, 6H), 1.54-1.45 (m, 2H), 1.43-1.29 (m, 6H), 1.28-1.17 (m, 4H), 1.17-1.12 (m, 4H), 1.12-0.94 (m, 5H), 0.92-0.84 (m, 7H), 0.82 (s, 3H), 0.68-0.61 (m, 4H).

LCMS Rt=3.428 min in 7.0 min chromatography, 30-90AB_E, purity 100%, MS ESI calcd. for $C_{25}H_{41}$ [M+H-2H$_2$O]$^+$ 341, found 341.

Example 51: Synthesis of 3S,5S,8R,9S,10S,13S, 14S,17R)-17-((2S,3S)-4-(4,4-dimethylcyclohexyl)-3-hydroxybutan-2-yl)-3-(methoxymethyl)-10,13-dimethylhexadecahydro-1H-cyclopenta[a]phenanthren-3-ol (51)

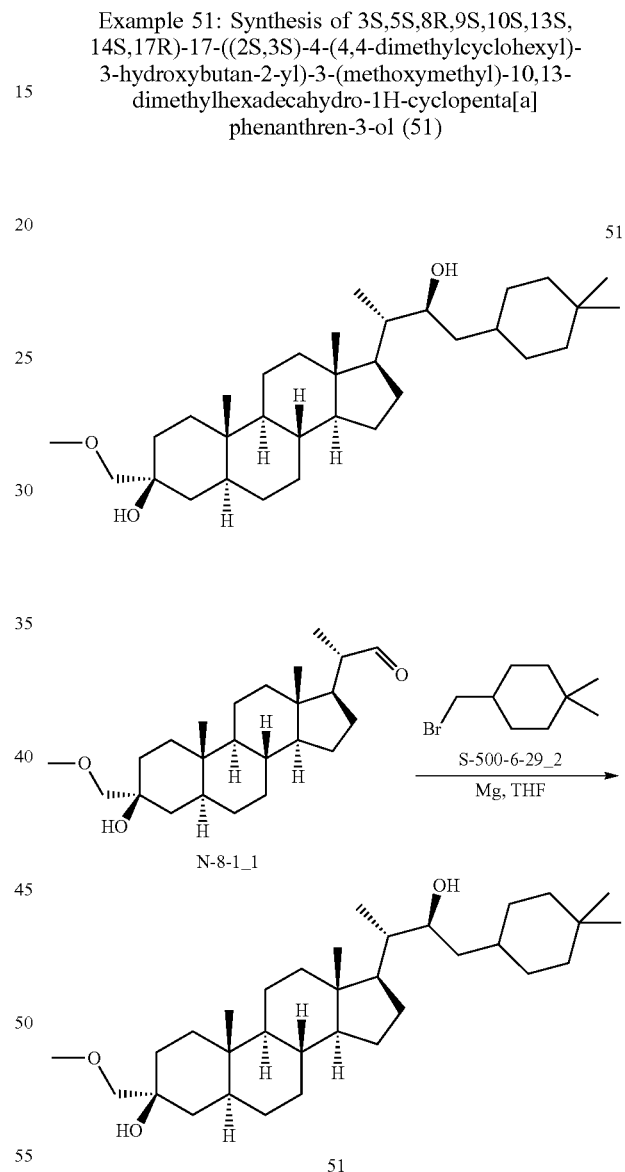

1. S-500-6-29_2 (999 mg, 1.22 M in THF, 4.87 mmol) was added dropwise to a solution of N-8-1_1 (210 mg, 05576 mmol) in THF (2 mL) at 25° C. under N2. After stirring at 25° C. for 16 hrs, the reaction mixture was quenched with saturated NH$_4$Cl (10 mL) and extracted with ethyl acetate (3×10 mL). The combined organic layer was washed with brine (30 mL), dried over Na$_2$SO$_4$, filtered and concentrated in vacuum to give a crude product, which was purified by flash column (0~15% of EtOAc in PE) for 2 times to give impure product (30 mg). The impure product was further purified by ELSD prep-HPLC (column: Phenomenex Synergi C18 150*30 mm*4 um), gradient: 90-95% B (A=water (0.05% HCl), B=MeCN), flow rate: 25 mL/min) to give pure 51 (4 mg, 1.4% yield) as a solid.

$^1$H NMR (400 MHz, CDCl$_3$) δ 3.84-3.76 (m, 1H), 3.45-3.32 (m, 5H), 2.62-2.39 (m, 1H), 1.99-1.85 (m, 2H), 1.73-1.62 (m, 4H), 1.53-1.40 (m, 7H), 1.39-1.31 (m, 5H), 1.30-1.21 (m, 7H), 1.20-1.13 (m, 4H), 1.12-1.10 (m, 5H), 0.99-0.93 (m, 1H), 0.89-0.86 (m, 6H), 0.85 (s, 3H), 0.83 (s, 3H), 0.68-0.61 (m, 4H).

LCMS Rt=5.669 min in 7.0 min chromatography, 30-90AB_E, purity 100%, MS ESI calcd. for C$_{33}$H$_{55}$O [M+H-2H$_2$O]$^+$ 467, found 467.

Example 52: Synthesis of (3S,8S,9S,10R,13S,14S, 17R)-3-ethyl-17-((2S,3R)-3-hydroxy-6-methylheptan-2-yl)-10,13-dimethyl-2,3,4,7,8,9,10,11,12,13,14, 15,16,17-tetradecahydro-1H-cyclopenta[a]phenanthren-3-ol (52)

mL), dried over Na$_2$SO$_4$, filtered, concentrated, and purified by combi-flash (0-15% of EtOAc in PE) to give 210 mg of a solid, which was purified by SFC (column: AD (250 mm*30 mm, 5 um), gradient: 35-35% B (A=0.1% NH$_3$/H$_2$O, B=MeOH), flow rate: 80 mL/min) to give 52 (150 mg, 68%) as a solid.

$^1$H NMR (400 MHz, CDCl$_3$) δ 5.30-5.26 (m, 1H), 3.64-3.58 (m, 1H), 2.40-2.30 (m, 1H), 2.02-1.92 (m, 3H), 1.80-1.58 (m, 7H), 1.56-1.31 (m, 9H), 1.30-1.05 (m, 8H), 1.03 (s, 3H), 1.02-0.96 (m, 2H), 0.95-0.86 (m, 9H), 0.85-0.80 (m, 3H), 0.69 (s, 3H).

LCMS t$_R$=1.335 min in 2 min chromatography, 30-90AB_ELSD, purity 100.0%, MS ESI calcd. for C$_{29}$H$_{47}$ [M+H-2H$_2$O]$^+$ 395, found 395.

Example 53: Synthesis of (3S,8S,9S,10R,13S,14S, 17R)-10,13-dimethyl-17-((2S,3R)-4,4,4-trifluoro-3-hydroxybutan-2-yl)-3-(trifluoromethyl)-2,3,4,7,8,9, 10,11,12,13,14,15,16,17-tetradecahydro-1H-cyclopenta[a]phenanthren-3-ol (53)

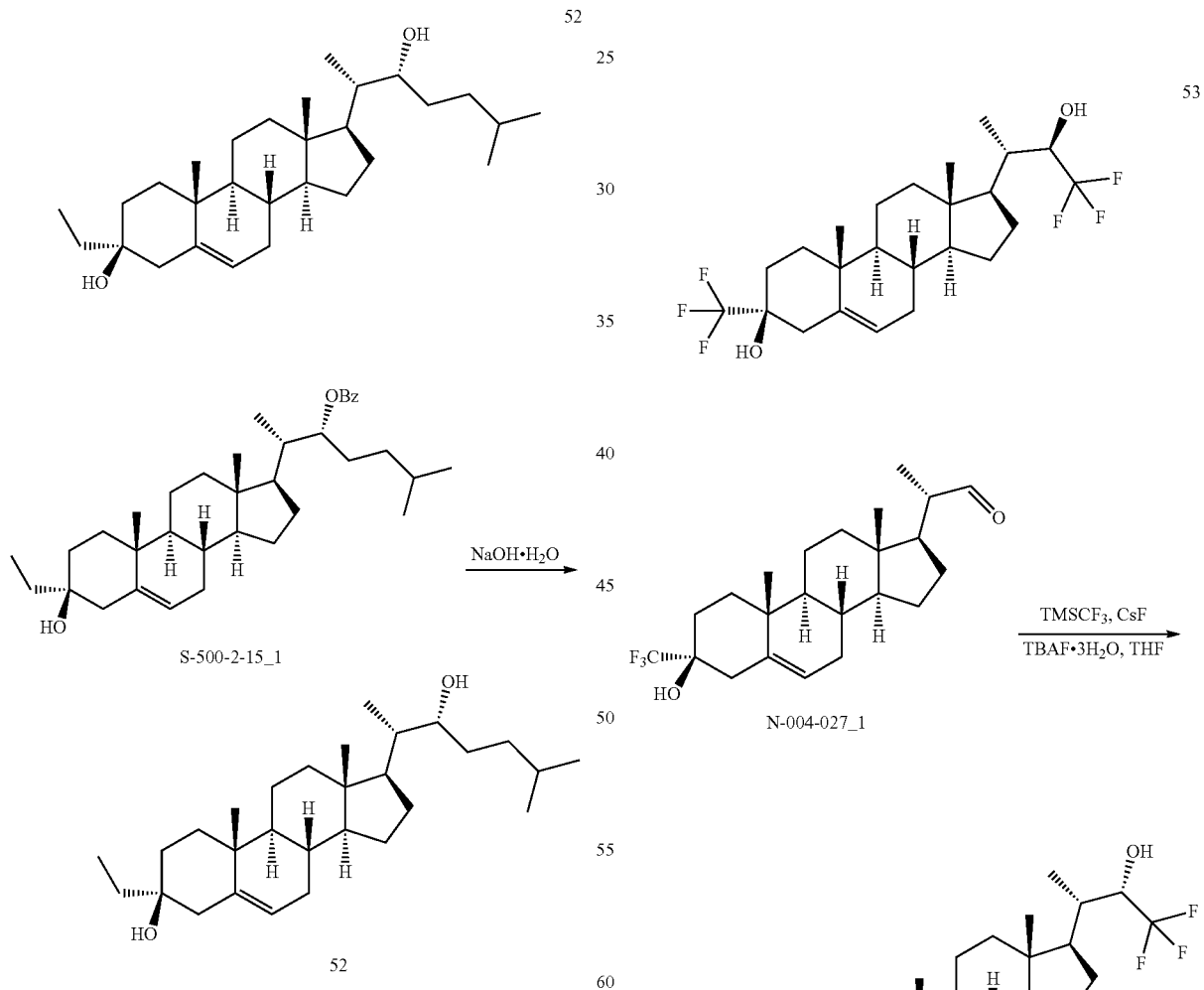

1. NaOH solution (974 mg in 6 mL H$_2$O, 16.8 mmol) was added to a solution of S-500-2-15_1 (900 mg, 1.68 mmol) in THF (10 mL) and MeOH (5 mL). The mixture was heated at 50° C. for 16 hrs. The reaction mixture was quenched with sat. NH$_4$Cl (60 ml) and extracted with EtOAc (3×20 mL). The combined organic phase was washed with brine (60

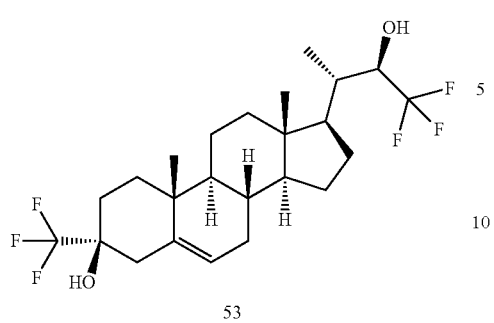

53

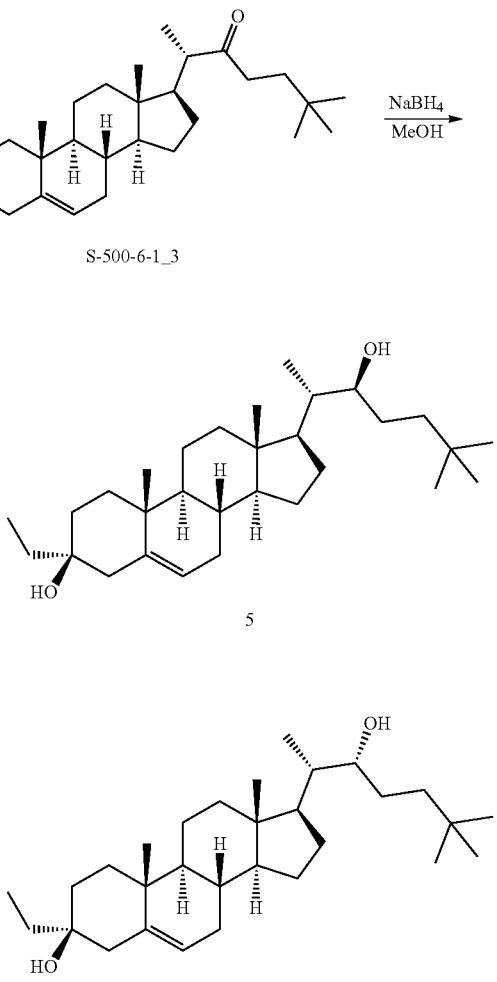

1. To a solution of N-004-027_1 (1.5 g, 3.76 mmol) in anhydrous THF (40 mL) was added CsF (1.42 g, 9.40 mmol) at 0° C. After stirring at 0° C. for 20 min, TMSCF$_3$ (1.33 g, 9.40 mmol) was added at 0° C. and stirred for 30 min. The color becomes light yellow. TBAF.3H$_2$O (4.74 g, 15.0 mmol) was added and stirred at 50° C. for 30 min. The reaction mixture was poured into ice-water (100 mL). The aqueous phase was extracted with EtOAc (2×100 mL). The combined organic phase was washed with saturated brine (2×100 mL), dried over anhydrous Na$_2$SO$_4$, filtered and concentrated to give a mixture of isomers (1.45 g, crude) as a yellow solid, which was purified by flash column (0~15% of EtOAc in PE) to give 53 (340 mg, 24%) as a white solid and 1 (200 mg, 14%) as a white solid.

53:

$^1$H NMR (400 MHz, CDCl$_3$) δ 5.38-5.36 (m, 1H), 4.06-3.94 (m, 1H), 2.49 (s, 2H), 2.09-1.58 (m, 13H), 1.48-0.85 (m, 14H), 0.73 (s, 3H).

LCMS Rt=1.134 min in 2 min chromatography, 30-90AB_2MIN_E, purity 99%,

MS 50-100_1_4 min·m, for C$_{24}$H$_{33}$F$_6$O [M+H—H$_2$O]$^+$ 451, found 451.

Example 54: Synthesis of (3S,8S,9S,10R,13S,14S, 17R)-3-ethyl-17-((2S,3R)-3-hydroxy-6,6-dimethyl-heptan-2-yl)-10,13-dimethyl-2,3,4,7,8,9,10,11,12,13, 14,15,16,17-tetradecahydro-1H-cyclopenta[a] phenanthren-3-ol (54)

1. NaBH$_4$ (1.77 g, 46.8 mmol) was added in portions to a solution of S-500-6-13 (520 mg, 1.17 mmol) in THF (5 mL) and MeOH (10 mL) at 15° C. The mixture was stirred at 15° C. for 20 min. The mixture was quenched with NH$_4$Cl (20 mL, sat. aq.) and extracted with EtOAc (50 mL). The organic layer was separated and concentrated under vacuum to give a mixture which was separated by flash column (0~15% EtOAc in PE) to give S-500-6-1 (300 mg, impure) and 54 (170 mg, impure).

The impure 54 (220 mg, impure) was purified by flash column (0~15% EtOAc in PE) to give a solid. The solid was dissolved in MeCN (50 mL) at 60° C. and concentrated under vacuum to give 54 (120 mg, 23%) as a solid.

54:

$^1$H NMR (400 MHz, CDCl$_3$) δ 5.33-5.24 (m, 1H), 3.62-3.52 (m, 1H), 2.42-2.31 (m, 1H), 2.11-1.90 (m, 3H), 1.72-1.35 (m, 15H), 1.29-1.08 (m, 8H), 1.03 (s, 3H), 1.01-0.96 (m, 2H), 0.93 (d, J=6.8 Hz, 3H), 0.90 (s, 9H), 0.85 (t, J=7.6 Hz, 3H), 0.70 (s, 3H).

LCMS Rt=5.463 min in 7.0 min chromatography, 30-90_AB_E, purity 100%, MS ESI calcd. for C$_{30}$H$_{49}$ [M+H-2H$_2$O+]$^+$ 409, found 409.

Example 55: Synthesis of (3S,5S,8R,9S,10S,13S, 14S,17R)-3-ethyl-17-((1R,2S)-1-hydroxy-1-phenyl-propan-2-yl)-10,13-dimethylhexadecahydro-1H-cyclopenta[a]phenanthren-3-ol (55)

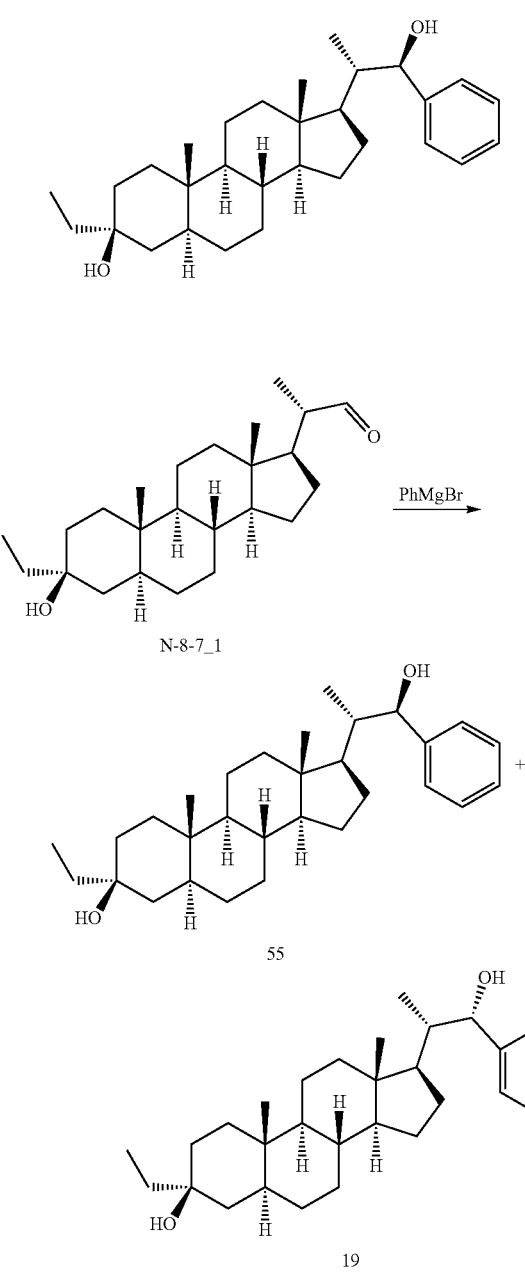

1. A solution N-8-7_1 (300 mg, 0.832 mmol) in THF (5 mL) was added to a solution of PhMgBr (1.38 mL, 3 M in ether, 4.15 mmol) in THF (10 mL) at 0° C., then the reaction mixture was stirred at 0° C. for 3 hours. Next, the reaction mixture was stirred at 25° C. for 5 hours. The reaction mixture was quenched by water (10 mL) at 0° C. The solution was filtered and the filter cake was washed with EtOAc (10 mL). The aqueous phase was extracted with EtOAc (3×15 mL). The combined organic phase was washed with saturated brine (2×10 mL), dried over anhydrous $Na_2SO_4$, filtered and concentrated. The residue was purified by silica gel chromatography (PE/EtOAc=20/1 to 1/1) to afford 59 and 19 (200 mg, crude) as a solid. The crude product was purified by SFC (column: AD (250 mm*30 mm, 5 um)), gradient: 25-25% B (A=0.1% $NH_3$/H2O, B=EtOH), flow rate: 60 mL/min) to give 55 (Peak2, 55 mg, 15%) and 19 (Peak1, 21 mg, 6%) as solids.

55:

$^1$H NMR (400 MHz, $CDCl_3$) δ 7.38-7.28 (m, 4H), 7.25-7.20 (m, 1H), 64.95-4.90 (m, 1H), 2.13-2.01 (m, 1H), 1.98-1.88 (m, 1H), 1.77-1.59 (m, 6H), 1.57-1.43 (m, 6H), 1.43-0.93 (m, 13H), 0.91-0.85 (m, 3H), 0.83 (s, 3H), 0.76-0.72 (m, 3H), 0.68 (s, 4H).

LCMS Rt=1.239 min in 2.0 min chromatography, 30-90AB_2 min., purity 100%, MS ESI calcd. For $C_{30}H_{43}$ $[M-2H_2O+H]^+$ 403, found 403.

SFC Rt=1.192 min in 3 min chromatography, OJ_3_EtOH_DEA_5_40_25ML, 99% de.

Example 56: Synthesis of (3S,5R,8R,9S,10S,13S, 14S,17R)-3-ethyl-10,13-dimethyl-17-((2S,3S)-4,4,4-trifluoro-3-hydroxybutan-2-yl)hexadecahydro-1H-cyclopenta[a]phenanthren-3-ol (56)

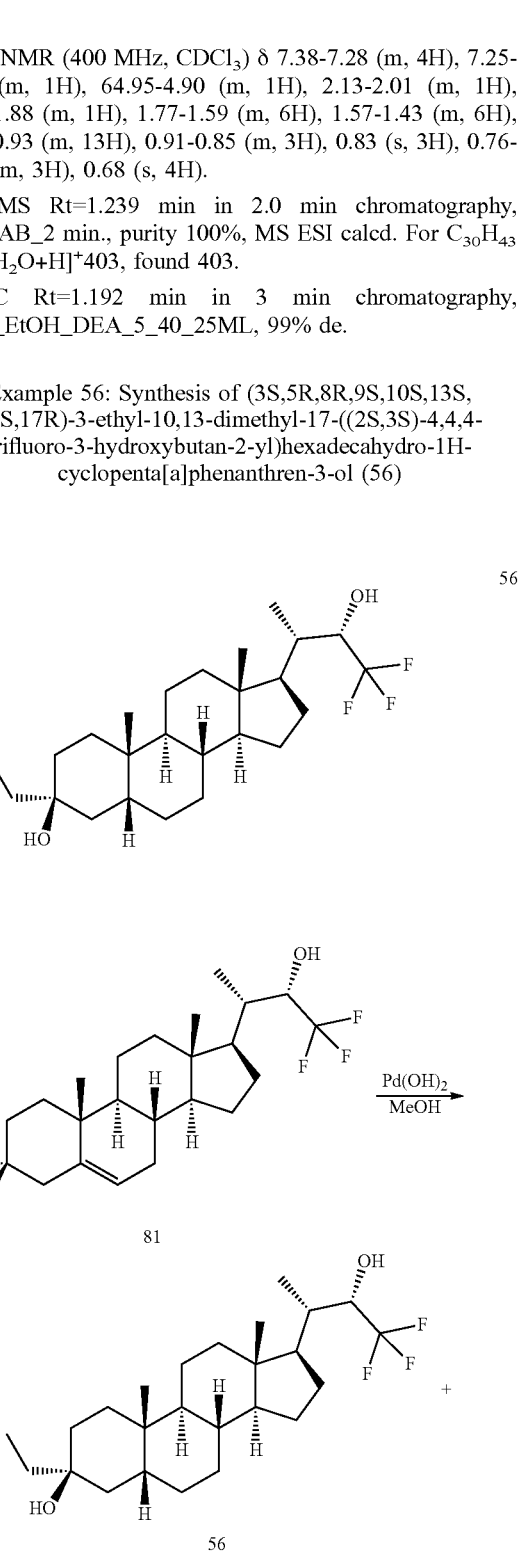

213

-continued

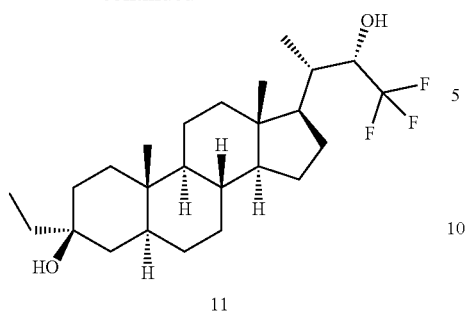

1. To a solution of 81 (1 g, 3.26 mmol) in MeOH (30 mL) and THF (10 ml) was added Pd(OH)₂ (1 g, <1% water). Then the mixture was hydrogenated under 50 psi at 50° C. for 48 hrs. The mixture was filtered through a pad of celite without monitor and the filtrate was concentrated in vacuum. The residue was purified by flash column (PE/EtOAc=10/1 to 5/1) to give 56 (331 mg, 33%) as a white solid.

$^1$H NMR (400 MHz, CDCl3) δ 4.09-3.99 (m, 1H), 2.18-2.13 (m, 1H), 1.99-1.78 (m, 4H), 1.75-1.59 (m, 3H), 1.50-1.3 (m, 7H), 1.34-1.22 (m, 6H), 1.21-1.00 (m, 10H), 0.96 (s, 3H), 0.94-0.89 (m, 3H), 0.67 (s, 3H).

LCMS Rt=1.184 min in 2.0 min chromatography, 30-90AB_E, purity 100%, MS ESI calcd. for $C_{25}H_{40}F_3O$ $[M+H—H_2O]^+$ 413, found 413.

Example 57: Synthesis of (3S,5R,8R,9S,10S,13S,14S,17R)-3,10,13-trimethyl-17-((2S,3R)-4,4,4-trifluoro-3-hydroxybutan-2-yl)hexadecahydro-1H-cyclopenta[a]phenanthren-3-ol (57)

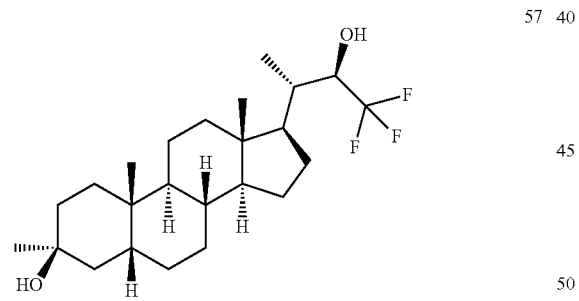

57

214

-continued

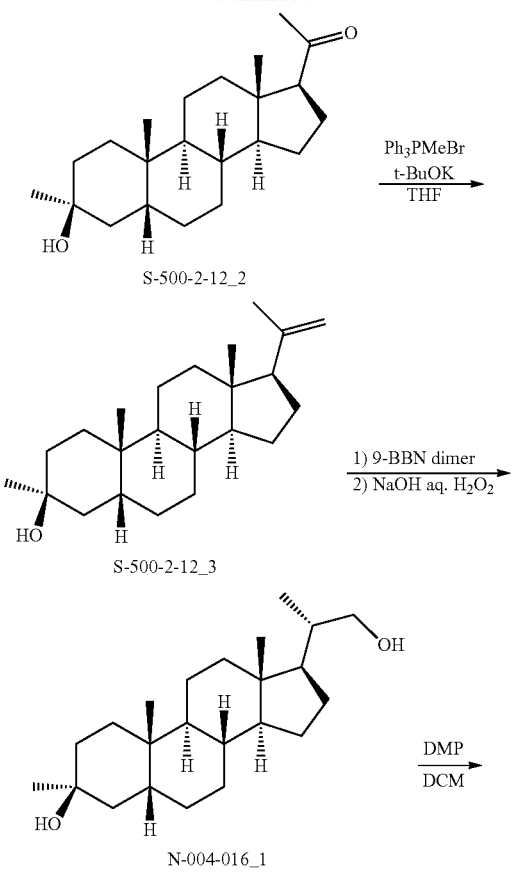

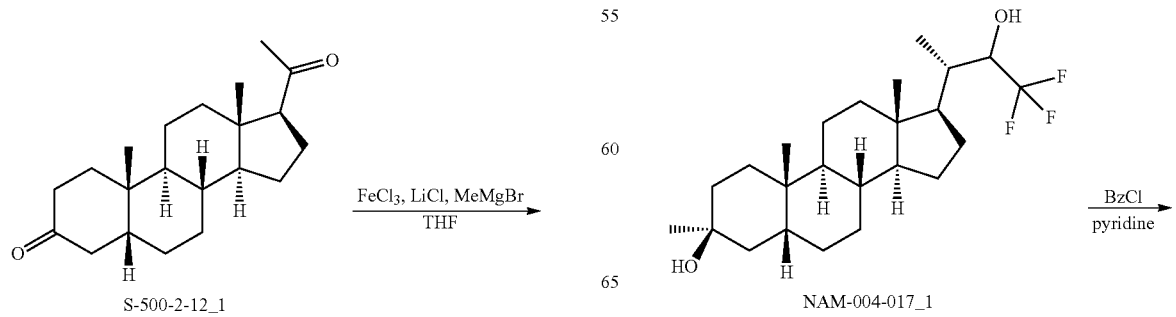

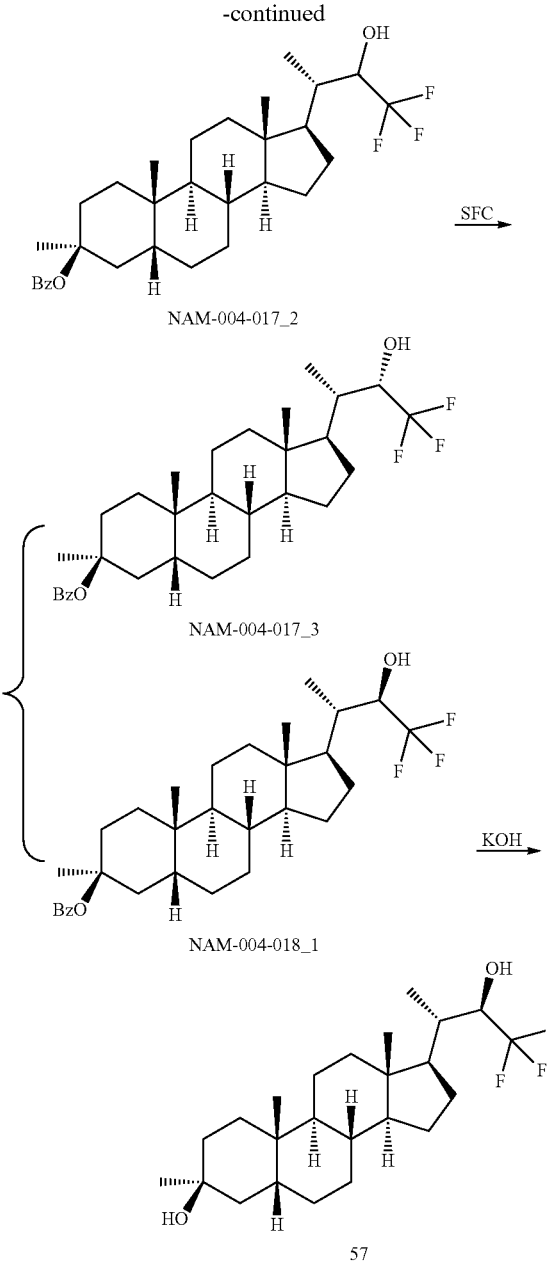

1. A suspension of LiCl (13.9 g, 329 mmol, anhydrous) in THF (500 mL, anhydrous) was stirred at 10° C. for 30 mins under N2. FeCl$_3$ (27.8 g, 172 mmol, anhydrous) was added at 10° C. The mixture was cooled to −30° C. To the mixture was added MeMgBr (209 mL, 3M in diethyl ether) dropped at −30° C. After stirring at −30° C. for 10 mins, S-500-2-12_1 (50 g, 157 mmol) was added at −30° C. The mixture was stirred at −15° C. for 2 hours and quenched with citric acid (500 mL, 10% aq.). The mixture was extracted with EtOAc (3×800 mL). The combined organic phase was washed with saturated brine (300 mL), dried over anhydrous Na$_2$SO$_4$, filtered and concentrated under vacuum to give crude product, which was purified by a silica gel column (PE/DCM/EtOAc=1/1/1) to give S-500-2-12_2 (50 g, 86%) as a solid.

$^1$H NMR (400 MHz, CDCl$_3$) δ 2.57-2.48 (m, 1H), 2.23-2.13 (m, 1H), 2.06-1.78 (m, 3H), 1.64-1.25 (m, 14H), 1.24-1.01 (m, 10H), 0.96 (s, 3H), 0.74 (s, 1H), 0.60 (s, 3H).

2. To a suspension of PPh$_3$MeBr (79.7 g, 244 mmol) in THF (400 mL) was added t-BuOK (25.1 g, 224 mmol) at 20° C. After stirring at 40° C. for 30 min, a solution of S-500-2-12_2 (50 g, 150 mmol) in THF (100 mL) was added at 40° C. and the reaction mixture was stirred at 40° C. for 1 hr. The reaction mixture was poured into 50 g of ice and stirred for 15 minutes. The organic layer was separated and the water phase was extracted with EtOAc (3×50 mL). The combined organic phase concentrated in vacuum to give an oil. The crude product was triturated in MeOH/H$_2$O (200 mL/200 mL) and filtered to give S-500-2-12_3 (55 g, 88%) as a solid.

$^1$H NMR (400 MHz, CDCl$_3$) δ 4.84 (s, 1H), 4.69 (s, 1H), 2.06-1.79 (m, 4H), 1.75 (s, 3H), 1.73-1.58 (m, 4H), 1.56-1.25 (m, 9H). 1.22 (s, 3H), 1.21-1.02 (m, 6H), 1.01-0.94 (s, 3H), 0.93-0.74 (m, 1H), 0.55 (s, 3H).

3. The solution of S-500-2-12_3 (55 g, 166 mmol) in THF (500 mL) was added 9-BBN dimer (60.7 g, 249 mmol) was stirred at 25° C. under N$_2$ for 1 hr, a solid was formed. To the reaction mixture was added ethanol (95.3 mL, 1.66 mol) and NaOH (166 mL, 5 M, 830 mmol). The mixture turned clear. H$_2$O$_2$ (132 mL, 10 M, 1.32 mol) was added dropwise at 25° C. and the inner temperature was raised to reflux (75° C.). The mixture was cooled after addition and stirred for 16 hrs, a solid was formed. To the mixture was added Na$_2$S$_2$O$_3$ (500 mL, 20% aq.) and water (1 L) at 25° C. The mixture was stirred for 1 hr. After the stirrer was turned off, a clear lower layer and a upper suspension layer were formed. The clear lower layer was discarded. To the upper suspension layer was added water (2 L). The mixture was stirred for 15 mins. The mixture was filtered to give S-500-2-12_4 (50 g, impure) as a solid. S-500-2-12_4 (50 g, 143 mmol, impure) was triturated in EtOH/H$_2$O (90 mL/10 mL) at 100° C. for 2 hours, then cooled to 15° C. and filtered to give S-500-2-12_4 (38 g, impure) as a solid. S-500-2-12_4 (38 g, 109 mmol, impure) was triturated in EtOH/H$_2$O (45 mL/5 mL) at 100° C. for 2 hours, then cooled to 15° C. and filtered to give S-500-2-12_4 (28 g, 43%) as a solid.

$^1$H NMR (400 MHz, CDCl$_3$) δ 3.67-3.59 (m, 1H), 3.39-3.32 (m, 1H), 2.01-1.75 (m, 4H), 1.69-1.58 (m, 3H), 1.54-1.24 (m, 10H), 1.23-1.14 (m, 9H), 1.09-1.02 (m, 5H), 0.96 (s, 3H), 0.74 (m, 1H), 0.67 (s, 3H).

4. To a solution of N-004-016_1 (10.0 g, 28.6 mmol) in DCM (100 mL) was added DMP (24.2 g, 57.2 mmol). Then H$_2$O (0.2 mL) was added to the mixture. After that, the reaction was stirred at 25° C. for 1 hour. To the reaction mixture was added saturated aqueous NaHCO$_3$ (100 mL) solution. The mixture was filtered and the filter cake was washed with DCM (2×100 mL). The mixture was liquid was separated, and the water phase was extracted with DCM (2×100 mL). The combined organic layer was washed with saturated aqueous NaHCO$_3$/Na$_2$S$_2$O$_3$ (100 mL/100 mL) and brine (100 mL), dried over Na$_2$SO$_4$, filtered and concentrated in vacuum to give a white solid. The residue was purified by silica gel chromatography (PE/EtOAc=0 to 20%) to afford N-004-016_2 (3.5 g, 35%) as a white solid.

$^1$H NMR (400 MHz, CDCl3) δ 9.58-9.54 (m, 1H), 2.39-2.32 (m, 1H), 1.96-1.77 (m, 4H), 1.69-1.31 (m, 14H), 1.23-1.16 (m, 6H), 1.14-1.02 (m, 5H), 0.96 (s, 3H), 0.76-0.59 (m, 4H).

5. To a solution of N-004-016_2 (1.5 g, 4.32 mmol), CsF (328 mg, 2.16 mmol) in THF (10 mL) was added TMSCF$_3$ (1.53 g, 10.8 mmol) at 0° C. The mixture was stirred at 25° C. for 1 hrs. To the mixture was added TBAF.$_3$H$_2$O (3.4 g, 10.8 mmol). The mixture was stirred at 25° C. for 2 hrs. The mixture was quenched with water (20 mL) and extracted with EtOAc (2×30 mL). The combined organic phase was washed with brine (50 mL), dried over anhydrous Na$_2$SO$_4$, filtered and concentrated in vacuum. The residue was purified by flash column (0~15% of EtOAc in PE) to afford N-004-017_1 (700 mg, 39%) as a white solid.

¹H NMR (400 MHz, CDCl3) δ 4.07-3.96 (m, 1H), 2.21-2.09 (m, 1H), 1.99-1.77 (m, 5H), 1.72-1.29 (m, 15H), 1.24-1.20 (m, 4H), 1.13-1.01 (m, 5H), 0.96 (s, 3H), 0.89-0.84 (m, 1H), 0.76-0.64 (m, 3H), 0.60 (s, 1H).

6. To a solution of N-004-0171 (700 mg, 1.68 mmol) in pyridine (5 mL) was added benzoyl chloride (354 mg, 2.52 mmol) and DMAP (102 mg, 0.84 mmol) at 25° C. The mixture was heated to 60° C. and stirred for 10 hours. The reaction mixture was diluted with EtOAc (10 mL), then quenched with water (10 mL). The aqueous was extracted with EtOAc (2×20 mL). The combined organic layer was washed with brine (20 mL), dried over Na₂SO₄, filtered and concentrated in vacuum to give a white solid. The residue was purified by flash column (0~15% of EtOAc in PE) to give N-004-017_2 (600 mg, 68%) as a white solid.

LCMS Rt=1.464 min in 2 min chromatography, 30-90AB_2MIN_E.M, purity 92%.

SFC condition: Peak 1: Rt=2.434 min and Peak 2: Rt=2.541 min in 8 min chromatography, OD_MEOH(DEA)_5_40_2,8ML_8MIN·M (Column: Chiralcel OD-3100×4.6 mm I.D., 3 um Mobile phase: A: CO2 B:methanol (0.05% DEA) Gradient: from 5% to 40% of B in 4.5 min and hold 40% for 2.5 min, then 5% of B for 1 min Flow rate: 2.8 mL/min Column temperature: 40° C.).

7. N-004-017_2 (600 mg, 1.15 mmol) was purified by SFC (column: Chiralcel OD (250 mm*30 mm, 5 um), gradient: 20-20% B (A=0.1% NH₃/H₂O, B=MeOH), flow rate: 60 mL/min) to give N-004-017_3 (Peak 2, 190 mg, impure, 31%), N-004-018_1 (Peak 1, 180 mg, 30%) as a white solid. The impure N-004-0173 (190 mg, 0.36 mmol) was purified by SFC (column: OD (250 mm*30 mm, 5 um), gradient: 20-20% B (A=0.1% NH₃/H₂O, B=MeOH), flow rate: 60 mL/min) to give N-004-017_3 (100 mg, 53%) as a white solid.

N-004-018_1:
¹H NMR (400 MHz, CDCl3) δ 8.12-8.06 (m, 2H), 7.65-7.59 (m, 1H), 7.53-7.46 (m, 2H), 5.68-5.58 (m, 1H), 2.15-2.03 (m, 2H), 1.97-1.69 (m, 3H), 1.67-1.57 (m, 3H), 1.44-1.24 (m, 9H), 1.23-1.13 (m, 11H), 1.12-1.97 (m, 3H), 0.94 (s, 3H), 0.72 (s, 3H).

LCMS Rt=1.525 min in 2 min chromatography, 30-90AB_2 min_220&254.1 cm, purity 100%.

SFC_D1 Rt=2.450 min in 8 min chromatography, OD_MEOH(DEA)_5_40_2,8ML_8MIN·M, 100% de.

N-004-017_3:
¹H NMR (400 MHz, CDCl3) δ 8.14-8.06 (m, 2H), 7.64-7.57 (m, 1H), 7.52-7.44 (m, 2H), 5.63-5.52 (m, 1H), 2.11 (s, 1H), 2.06-1.77 (m, 6H), 1.72-1.62 (m, 3H), 1.44-1.32 (m, 8H), 1.28-1.18 (m, 12H), 0.99-0.93 (m, 4H), 0.65 (s, 3H).

LCMS Rt=1.529 min in 2 min chromatography, 30-90AB_2 min_220&254.1 cm, purity 100%.

SFC Rt=2.544 min in 8 min chromatography, OD_MEOH (DEA)_5_40_2,8ML_8MIN·M, 98% de.

8. To a solution of N-004-018_1 (180 mg, 0.34 mmol) in THF (3 mL) and MeOH (1.5 mL) and water (1.5 mL) was added KOH (96.5 mg, 1.72 mmol). The mixture was stirred at 60° C. for 16 hrs. The mixture was poured into water (20 mL) and extracted with EtOAc (2×40 mL). The combined organic layer was washed with brine (30 mL), dried over Na₂SO₄, filtered and concentrated. The residue was purified by flash column (0~15% of EtOAc in PE) to give 57 (114 mg, 79%) as a white solid.

¹H NMR (400 MHz, CDCl3) δ 4.00 (brs, 1H), 2.03-1.77 (m, 8H), 1.69-1.61 (m, 2H), 1.54-1.49 (m, 1H), 1.47-1.24 (m, 10H), 1.22 (s, 3H), 1.21-1.10 (m, 4H), 1.08-1.01 (m, 4H), 0.96 (s, 3H), 0.69 (s, 3H).

LCMS Rt=1.169 min in 2 min chromatography, 30-90AB_2MIN_E.M, purity 95%, MS ESI calcd. for C₂₄H₃₈F₃O [M+H—H₂O]⁺399, found 399.

HPLC Rt=5.44 min in 10 min Ultimate C₁₈₃*₅₀ mm 3 um, 30-90_AB_1.2ML_E.MET, purity 100%.

Example 58: Synthesis of (3S,5S,8R,9S,10S,13S,14S,17R)-17-((1R,2S)-1-cyclopentyl-1-hydroxypropan-2-yl)-3-ethyl-10,13-dimethylhexadecahydro-1H-cyclopenta[a]phenanthren-3-ol (58)

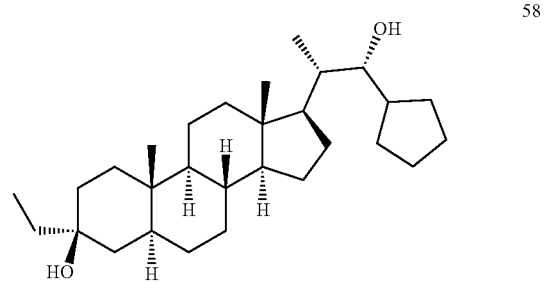

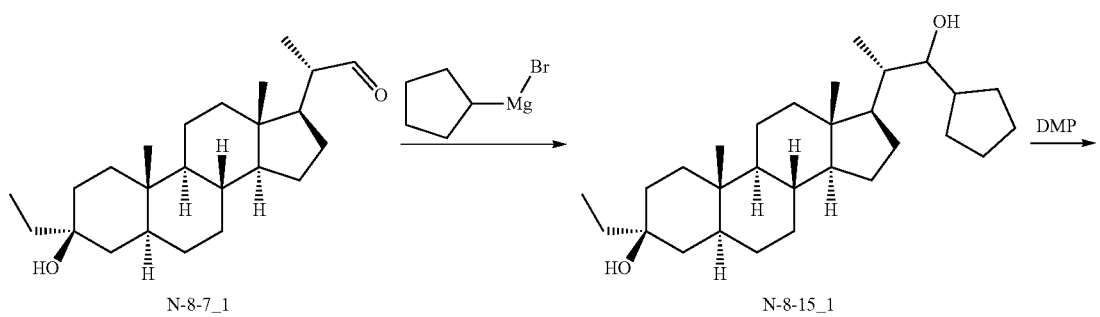

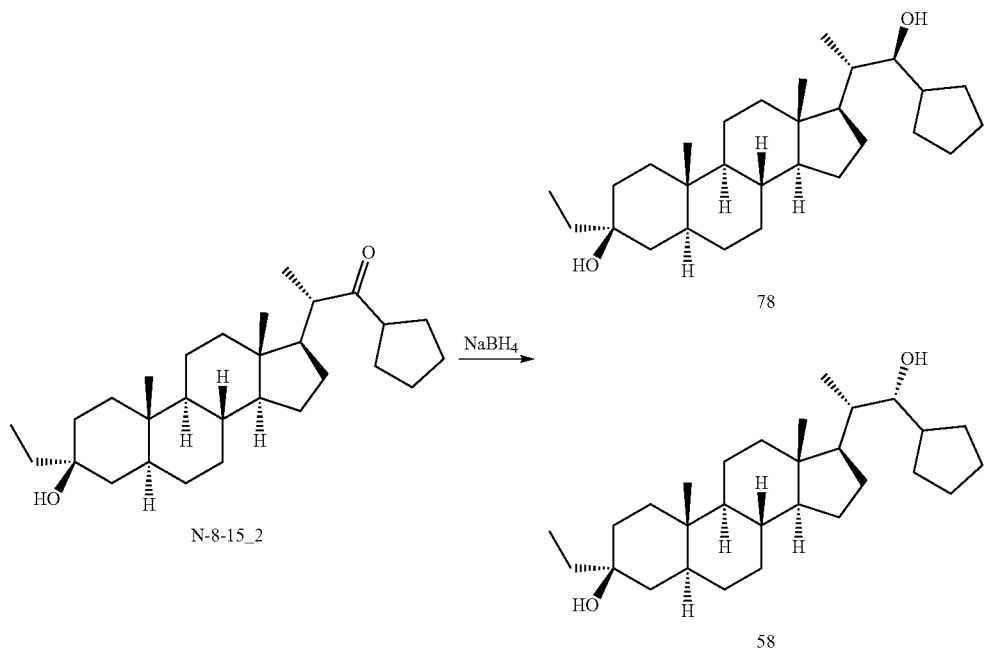

1. N-8-7_1 (500 mg, 1.38 mmol) in THF (5 mL) was added to cyclopentyl magnesium bromide (1.38 mL, 3 M in THF) at 0° C. under $N_2$. After stirring at 15° C. for 18 hrs, the reaction mixture was quenched with sat. $NH_4Cl$ (10 mL), and extracted with EtOAc (2×10 mL). The combined organic layer was washed with brine (10 mL), dried over $Na_2SO_4$, filtered and concentrated. The residue was purified by flash column (0-10% of EtOAc in PE) to give N-8-15_1 (170 mg, 29%) as a solid.

$^1$H NMR (400 MHz, $CDCl_3$) δ 3.39-3.22 (m, 1H), 2.00-1.81 (m, 4H), 1.70-1.41 (m, 12H), 1.41-1.13 (m, 13H), 1.13-0.95 (m, 6H), 0.95-0.79 (m, 11H), 0.65 (s, 3H).

2. DMP (0.881 g, 2.08 mmol) was added to a solution of N-8-15_1 (300 mg, 0.696 mmol) in DCM (20 mL). After stirring at 15° C. for 10 min, the reaction mixture was quenched with sat.$NaHCO_3$ (10 mL). The mixture was extracted with DCM (3×20 mL). The combined organic phase was washed with saturated $Na_2S_2O_3$ (3×20 mL) and brine (20 mL), dried over $Na_2SO_4$, filtered, concentrated and purified by combi-flash (0-20% of EtOAc in PE) to give N-8-15_2 (240 mg) as a solid.

$^1$H NMR (400 MHz, $CDCl_3$) δ 2.98-2.89 (m, 1H), 2.62-2.55 (m, 1H), 1.98-1.87 (m, 1H), 1.81-1.72 (m, 4H), 1.71-1.49 (m, 10H), 1.41-1.29 (m, 4H), 1.29-1.19 (m, 6H), 1.14-0.98 (m, 9H), 0.94-0.87 (m, 4H), 0.82 (s, 3H), 0.67 (m, 5H).

3. $NaBH_4$ (550 mg, 14.5 mmol) was added to a mixture of N-8-15_2 (240 mg, 0.559 mmol) in MeOH (3 mL) and THF (2 mL). The mixture was stirred at 15° C. for 0.5 h. Another batch of $NaBH_4$ (550 mg, 14.5 mmol) was added. The reaction mixture was stirred for another 1 h. To the reaction mixture was added water (5 mL). The resulting mixture was extracted with EtOAc (2×10 mL). The combined organic layer was washed with brine (10 mL), dried over $Na_2SO_4$, filtered and concentrated. The residue was purified by flash column (0~5% EtOAc in PE) to give and 58 (7 mg, 5%) as a solid and 78 (50 mg, impure) was further purified by flash column (0~5% of EtOAc in PE) to give 78 (17 mg, 12%) as a solid.

58:

$^1$H NMR (400 MHz, $CDCl_3$) δ 3.64-3.59 (m, 1H), 2.09-1.90 (m, 2H), 1.89-1.70 (m, 4H), 1.70-1.45 (m, 11H), 1.45-1.32 (m, 5H), 1.32-1.19 (m, 9H), 1.19-1.08 (m, 3H), 1.08-0.98 (m, 5H), 0.98-0.89 (m, 4H), 0.84 (s, 3H), 0.68 (s, 3H).

LCMS Rt=4.832 min in 7 min chromatography, 30-90AB_7MIN_E, purity 100%, MS ESI calcd. for $C_{29}H_{47}$ $[M+H-2H_2O]^+$ 395, found 395.

HPLC Rt=6.338 min in 10 min chromatography, 50-100AB_10MIN·M, purity 98%.

Example 59: Synthesis of (3S,5R,8R,9S,10S,13S, 14S,17R)-17-((2S,3S)-4-(4,4-dimethylcyclohexyl)-3-hydroxybutan-2-yl)-3-ethyl-10,13-dimethylhexadecahydro-1H-cyclopenta[a]phenanthren-3-ol (59)

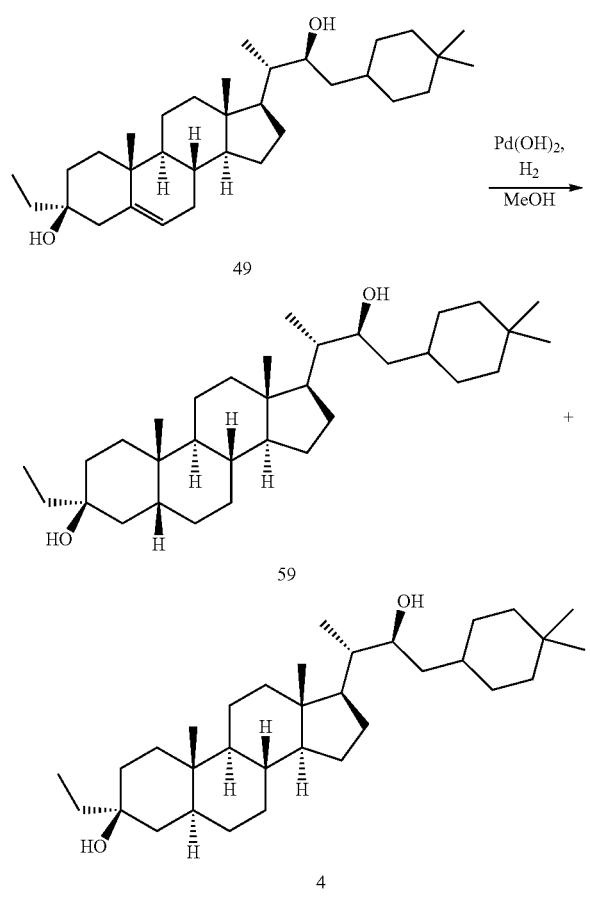

1. Pd(OH)$_2$ (200 mg, dry) was added to a solution of S-500-6-30 (140 mg, 0.288 mmol) in MeOH (30 mL). The mixture was stirred at 50° C. under H$_2$ (50 Psi) for 48 hrs. The mixture was filtered, concentrated and purified by combi-flash (0~15% of EtOAc in PE) to give S-500-6-25 (27 mg, 19%) and S-500-6-26 (42 mg, 30%) as a solid.

S-500-6-25:

$^1$H NMR (400 MHz, CDCl$_3$) δ 3.84-3.77 (m, 1H), 1.99-1.84 (m, 2H), 1.81-1.72 (m, 1H), 1.68-1.56 (m, 4H), 1.53-1.43 (m, 5H), 1.42-1.32 (m, 9H), 1.31-1.23 (m, 5H), 1.22-.12 (m, 7H), 1.12-1.00 (m, 5H), 0.99-0.95 (m, 4H), 0.94-0.85 (m, 12H), 0.66 (s, 3H).

LCMS Rt=1.797 min in 2.0 min chromatography, 30-90AB_E, purity 100%, MS ESI calcd. for C$_{33}$H$_{55}$ [M+H-2H$_2$O+]$^+$ 451, found 451.

Example 60: Synthesis of (3S,5S,8R,9S,10S,13S,14S,17R)-3-ethyl-17-((2S,3R)-3-hydroxy-4-((1R,2S)-2-methylcyclopropyl)butan-2-yl)-10,13-dimethylhexadecahydro-1H-cyclopenta[a]phenanthren-3-ol (60)

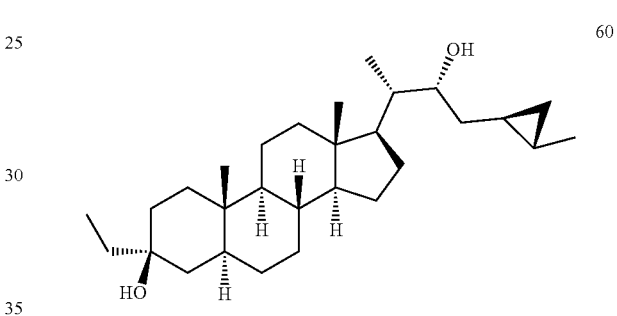

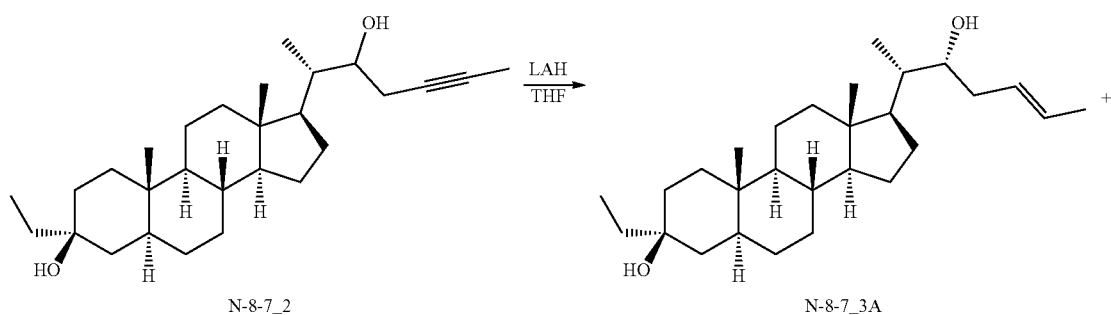

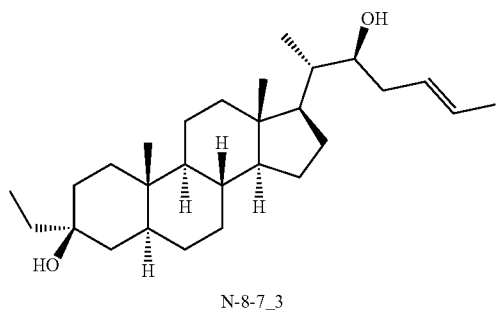

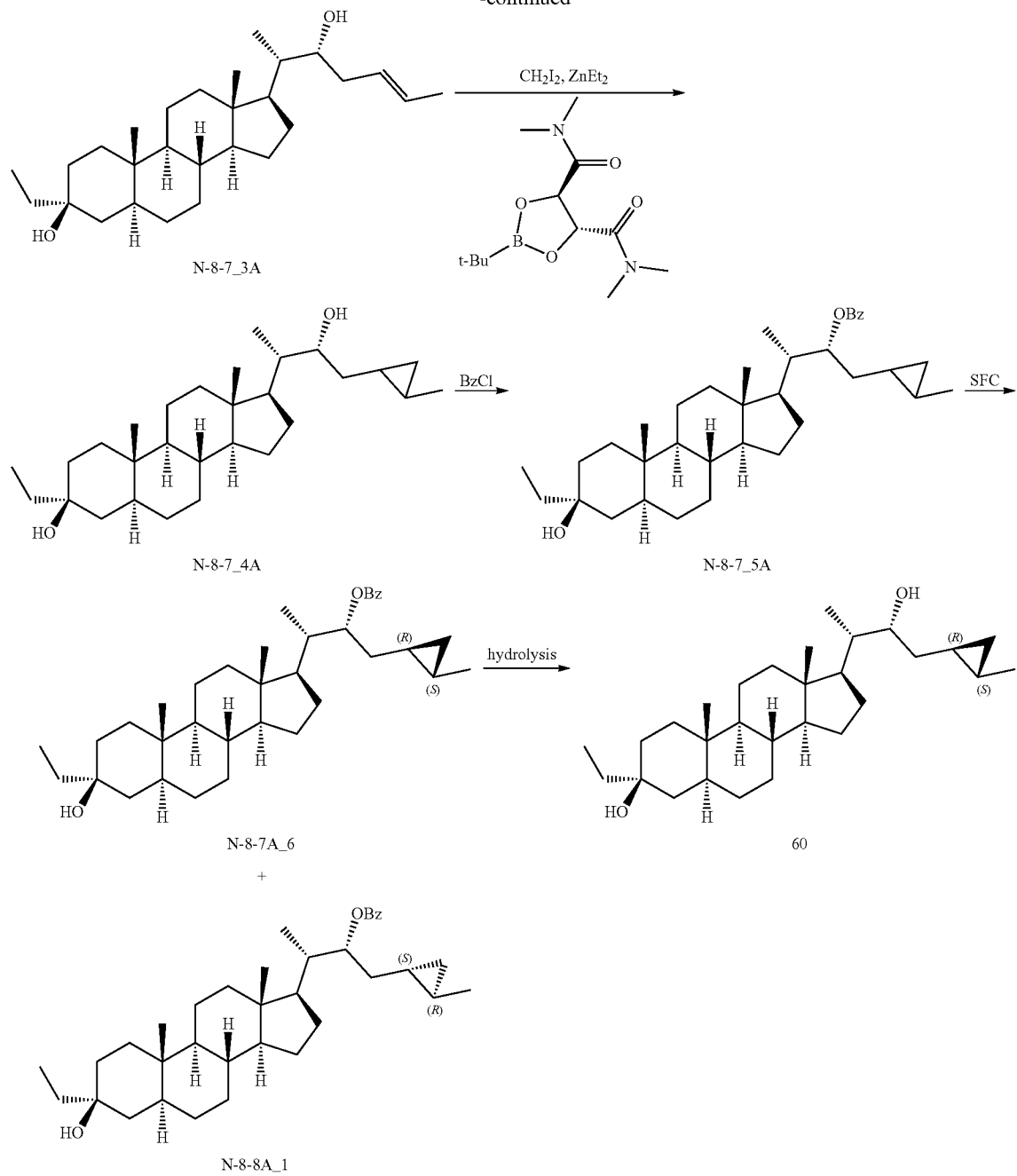

1. To a solution of N-8-7_2 (1 g, 2.41 mmol) in THF (50 mL) was added LiAlH₄ (914 mg, 24.1 mmol) at 0° C. The grey suspension was heated at 66° C. for 18 hrs. The reaction mixture was cooled to 0° C., quenched by ice-water (914 mg), then 15% w/w aqueous NaOH (914 mg), and water (2.74 g). The mixture was filtered and the filtrate cake was washed with DCM (3×50 mL). The filtrate was concentrated to give a residue, which was purified by flash chromatography twice (ethyl acetate 10% in PE) to give N-8-7_3 (192 mg, 19%) and N-8-7_3A (397 mg, 39%) as an oil.

N-8-7_3:

$^1$H NMR (400 MHz, CDCl3) δ 5.59-5.36 (m, 2H), 3.69-3.61 (m, 1H), 2.25-2.12 (m, 1H), 2.08-1.81 (m, 3H), 1.68 (d, J=10.0 Hz, 3H), 1.64-1.54 (m, 9H), 1.53-1.15 (m, 11H), 1.14-0.92 (m, 5H), 0.92-0.85 (m, 5H), 0.83 (s, 4H), 0.69-0.60 (m, 4H).

N-8-7_3A:

$^1$H NMR (400 MHz, CDCl$_3$) δ 5.62-5.37 (m, 2H), 3.62 (br d, J=10.0 Hz, 1H), 2.20-2.06 (m, 1H), 1.99-1.61 (m, 6H), 1.61-1.44 (m, 11H), 1.43-1.18 (m, 5H), 1.16-0.94 (m, 6H), 0.94-0.85 (m, 5H), 0.82 (s, 5H), 0.70-0.58 (m, 6H).

2. To a solution of diethylzinc (1 M in toluene, 4.31 mL, 4.31 mmol) in DCM (15 ml) at 0° C. was added CH$_2$I$_2$ (2.31 g, 8.63 mmol) over a period of 15 min at 0° C. The milky suspension was stirred for 10 min at 0° C. and a preformed solution of Charette ligand ((4R,5R)-2-(tert-butyl)-N4,N4,N5,N5-tetramethyl-1,3,2-dioxaborolane-4,5-dicarboxamide) (233 mg, 0.8638 mmol) and N-8-7_3A (300 mg, 0.7199 mmol) in DCM (20 ml) was rapidly added via syringe, whereupon the reaction mixture turned clear. The solution was allowed to reach 25° C. and stirred for 16 h at this temperature. The reaction was then quenched by addition of saturated aqueous NH$_4$Cl (150 ml), the phases were separated and the aqueous phase was extracted with DCM (3×100 ml). The combined organic phase was washed with saturated aqueous NaHCO$_3$ (150 mL), saturated aqueous Na$_2$S$_2$O$_3$ (150 mL), brine (100 mL), dried over Na$_2$SO$_4$, filtered and concentrated under reduced pressure and the residue was purified by flash column chromatography (11% of ethyl acetate in PE) to afford N-8-7_4A (140 mg, 45%) as a solid.

$^1$H NMR (400 MHz, CDCl$_3$) δ 3.81-3.72 (m, 1H), 1.97-1.90 (m, 1H), 1.76-1.58 (m, 4H), 1.53-1.44 (m, 4H), 1.43-1.15 (m, 10H), 1.13-0.91 (m, 8H), 0.90-0.78 (m, 12H), 0.66 (s, 3H), 0.54-0.34 (m, 4H), 0.32-0.22 (m, 2H), 0.19-0.12 (m, 1H).

3. To a solution of N-8-74A (140 mg, 0.325 mmol) in pyridine (5 mL) was added benzoyl chloride (91.3 mg, 0.65 mmol) followed by DMAP (15.8 mg, 0.13 mmol) at 25° C. The reaction mixture was stirred at 60° C. for 16 hours. The reaction mixture was diluted with DCM (80 mL). The DCM phase was washed with water (100 mL), 1.0 M HCl aqueous (2×100 mL), 10% NaHCO$_3$ aqueous (2×100 mL), brine (100 mL), dried over Na$_2$SO$_4$, filtered and concentrated under vacuum to give an oil, which was purified by flash column (1% of ethyl acetate in PE) to give N-8-7_5A (180 mg, impure) as an oil, which was further purified by flash column (PE) to give N-8-7_5A (110 mg, 61%) as a solid.

LCMS Rt=1.439 min in 2 min chromatography, 5-95AB_220&254, purity 93%, MS ESI calcd. for C$_{36}$H$_{53}$O$_2$[M–H$_2$O+H]$^+$ 517.8, found 517.8.

SFC Peak 1: Rt=4.079 min and Peak 2: Rt=4.345 min in 10 min chromatography, AD_3_EtOH_DEA_5_40_25ML ("Chiralpak AD-3150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.").

4. N-8-7A_5 (110 mg, 0.206 mmol) was purified by SFC (column: AD (250 mm*30 mm, 5 um)), gradient: 30-30% B (A=0.1% NH$_3$/H$_2$O, B=EtOH), flow rate: 60 mL/min) to give impure N-8-7A_6 (Peak 1, 54 mg, 50%) as a solid, and impure N-8-8A_1 (Peak 2, 23 mg, impure) as a solid.

SFC Rt=4.088 min in 10 min chromatography, AD_3_EtOH_DEA_5_40_25ML, 100% de.

5. To a solution of N-8-7A_6 (54 mg, 0.101 mmol) in THF/MeOH (1.5 mL/1.5 mL), was added KOH (45.2 mg, 0.807 mmol) in water (0.5 mL). The reaction mixture was stirred at 50° C. for 16 hours. To the mixture was added HCl (0.2 M, 50 mL). The suspension was extracted with DCM (2×60 mL). The combined organic phase was washed with 3% aqueous NaHCO$_3$ (80 mL), brine (80 mL), dried over Na$_2$SO$_4$, filtered and concentrated under vacuum to give a solid, which was purified by flash-chromatography (15% of ethyl acetate in PE) to give 60 (21 mg, 48%) as a solid.

$^1$H NMR (400 MHz, CDCl$_3$) δ 3.80-3.75 (m, 1H), 1.97-1.91 (m, 1H), 1.76-1.58 (m, 7H), 1.54-1.27 (m, 7H), 1.26-1.06 (m, 7H), 1.04 (d, J=6.0 Hz, 4H), 0.95 (s, 3H), 0.90-0.84 (m, 8H), 0.82 (s, 4H), 0.66 (s, 3H), 0.64-0.59 (m, 1H), 0.52-0.37 (m, 2H), 0.32-0.22 (m, 2H).

LCMS Rt=1.327 min in 2 min chromatography, 30-90AB_2MIN_E, purity 100%, MS ESI calcd. for C$_{29}$H$_{49}$O [M–H$_2$O+H]$^+$413.4, found 413.4.

Example 61: Synthesis of (3S,8S,9S,10R,13S,14S,17R)-3-ethyl-10,13-dimethyl-17-((2S,3S)-4,4,4-trifluoro-3-hydroxybutan-2-yl)-2,3,4,7,8,9,10,11,12,13,14,15,16,17-tetradecahydro-1H-cyclopenta[a]phenanthren-3-ol (61)

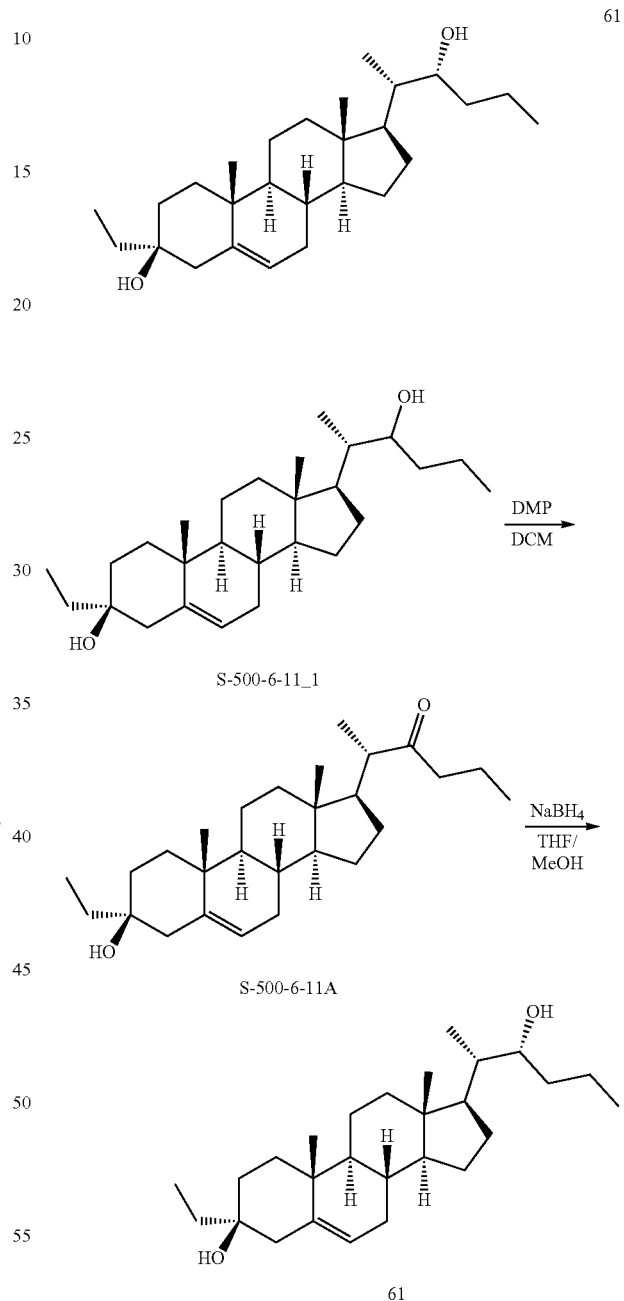

1. DMP (1.22 g, 2.88 mmol) was added to a solution of S-500-6-11_1 (580 mg, 1.44 mmol) in DCM (30 mL). After that, the reaction mixture was stirred at 15° C. for 10 min. The reaction mixture was quenched with Saturated NaHCO$_3$ aqueous (50 mL) until pH of the aqueous layer became about 9. The mixture was filtered. The DCM layer was separated and the aqueous phase was extracted with DCM (20 mL). The combined organic phase was washed with saturated Na₂S₂O₃ aqueous (3×40 mL), sat.NaHCO₃ (40 mL), brine (40 mL), dried over Na₂SO₄, filtered and concentrated to give crude S-500-6-11_1A (550 mg, Crude) as a white solid.

¹H NMR (400 MHz, CDCl₃) δ 5.34-5.25 (m, 1H), 2.58-2.29 (m, 4H), 2.08-1.90 (m, 3H), 1.78-1.56 (m, 9H), 1.54-1.35 (m, 6H), 1.31-1.21 (m, 2H), 1.19-1.08 (m, 5H), 1.06-0.99 (m, 5H), 0.93-0.82 (m, 6H), 0.69 (s, 3H).

2. NaBH₄ (1.39 g, 41.1 mmol) was added in five two-minute intervals to a solution of S-500-6-11A (550 mg, 1.37 mmol) in THE (4 mL) and MeOH (2 mL). The mixture was stirred at 15° C. for 30 minutes. The mixture was quenched with sat.NH₄Cl (20 mL) and extracted with EtOAc (3×6 mL). The combined organic phase was dried over Na₂SO₄, filtered, concentrated and purified by combi-flash (0-15% of EtOAc in PE) to give impure 61 (120 mg) as a white solid, which was further purified by combi-flash (0-15% of EtOAc in PE) again to give pure 61 (150 mg, 75%) as a white solid.

¹H NMR (400 MHz, CDCl₃) δ 5.31-5.25 (m, 1H), 3.73-3.59 (m, 1H), 2.44-2.29 (m, 1H), 2.08-1.92 (m, 3H), 1.76-1.57 (m, 6H), 1.54-1.26 (m, 10H), 1.25-1.18 (m, 3H), 1.17-1.06 (m, 4H), 1.03 (s, 3H), 1.00-0.88 (m, 8H), 0.87-0.82 (m, 3H), 0.69 (s, 3H).

LCMS Rt=1.345 min in 2.0 min chromatography, 30-90AB_E, purity 100%, MS ESI calcd. for C₂₇H₄₅O [M+H—H₂O]⁺ 385, found 385.

Example 62: Synthesis of (3S,8S,9S,10R,13S,14S, 17R)-3-ethyl-10,13-dimethyl-17-((2S,3R)-4,4,4-trifluoro-3-hydroxybutan-2-yl)-2,3,4,7,8,9,10,11,12, 13,14,15,16,17-tetradecahydro-1H-cyclopenta[a] phenanthren-3-ol (62)

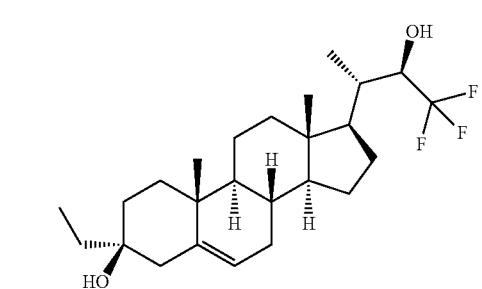

62

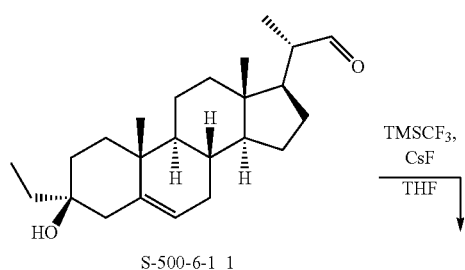

S-500-6-1_1

TMSCF₃, CsF
THF

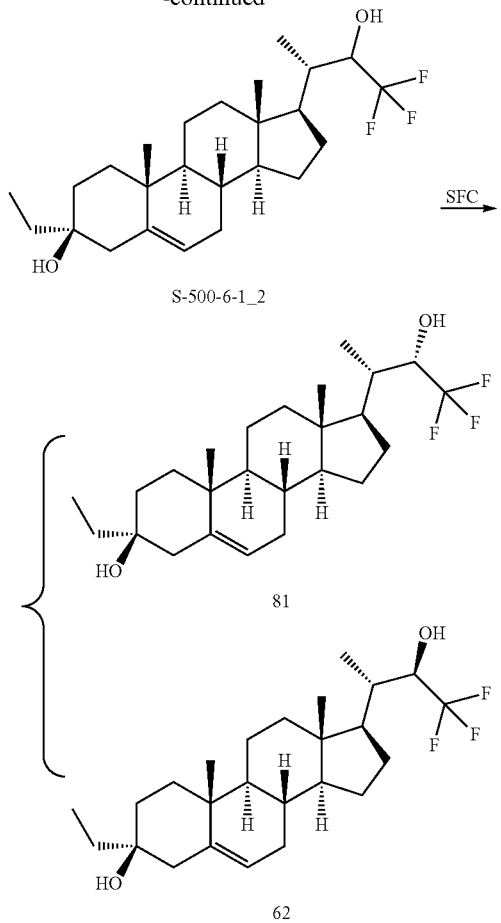

S-500-6-1_2

81

62

1. To a solution of S-500-6-1_1 (500 mg, 1.39 mmol) and CsF (105 mg, 695 umol) in THF (5 mL) was added TMSCF₃ (493 mg, 3.47 mmol) at 0° C. The mixture was stirred at 25° C. for 1 hr and treated with TBAF.3H₂O (1.09 g, 3.47 mmol). The mixture was stirred at 25° C. for 2 hrs, quenched with water (100 mL) and extracted with EtOAc (2×50 mL). The combined organic phase was washed with brine (100 mL), dried over anhydrous Na₂SO₄, filtered and concentrated in vacuum. The residue was purified by silica gel chromatography (100-200 mesh silica gel, PE/EA=10/1) to afford S-500-6-1_2 (400 mg, 67%) as a white solid.

¹H NMR (400 MHz, CDCl3) δ 5.33-5.24 (m, 1H), 4.06-4.00 (m, 1H), 2.38-2.35 (m, 1H), 2.08-1.82 (m, 6H), 1.77-1.69 (m, 1H), 1.62-1.20 (m, 13H), 1.16-1.00 (m, 8H), 0.99-0.92 (m, 1H), 0.87-0.83 (m, 4H), 0.74-0.64 (m, 3H).

2. 3.5 g of S-500-6-1_2 was separated by SFC (column: AD (250 mm*30 nm, 5 um), gradient: 40-40% B (A=0.05% NH₃/H₂O, B=MeOH), flow rate: 200 mL/min) to give pure 81 (1 g, 28%, Peak 1) and 62 (1871 mg, 53%, Peak 2) as a white solid. 62:

¹H NMR (400 MHz, CDCl3) δ 5.30-5.28 (m, 1H), 4.03-3.99 (m, 1H), 2.38-2.34 (m, 1H), 2.10-1.83 (m, 6H), 1.78-1.55 (m, 5H), 1.52-1.32 (m, 6H), 1.31-1.01 (m, 12H), 0.98-0.92 (s, 1H), 0.85 (t, J=8 Hz, 3H), 0.73 (s, 3H).

LCMS Rt=1.219 min in 2.0 min chromatography, 30-90 AB, purity 100%, MS ESI calcd. For C₂₅H₃₈F₃O [M+H—H₂O]⁺411, found 411.

SFC Peak 2: Rt=5.262 min in 10 min chromatography, AD_3_EtOH_DEA_5_40_25ML, 99% de.

Example 63: Synthesis of (3S,5S,8R,9S,10S,13S, 14S,17R)-3-ethyl-17-((2S,3S)-3-hydroxy-4-(tetrahydro-2H-pyran-4-yl)butan-2-yl)-10,13-dimethyl-hexadecahydro-1H-cyclopenta[a]phenanthren-3-ol (63)

LCMS Rt=1.167 min in 2.0 min chromatography, 30-90AB, purity 100%.

MS ESI calcd. for $C_{30}H_{49}O$ $[M-2H_2O+H]^+$ 425, found 425.

Example 64: Synthesis of (3S,5R,8R,9S,10S,13S, 14S,17R)-3-ethyl-17-((2S,3S)-3-hydroxy-6-methyl-heptan-2-yl)-10,13-dimethylhexadecahydro-1H-cyclopenta[a]phenanthren-3-ol (64)

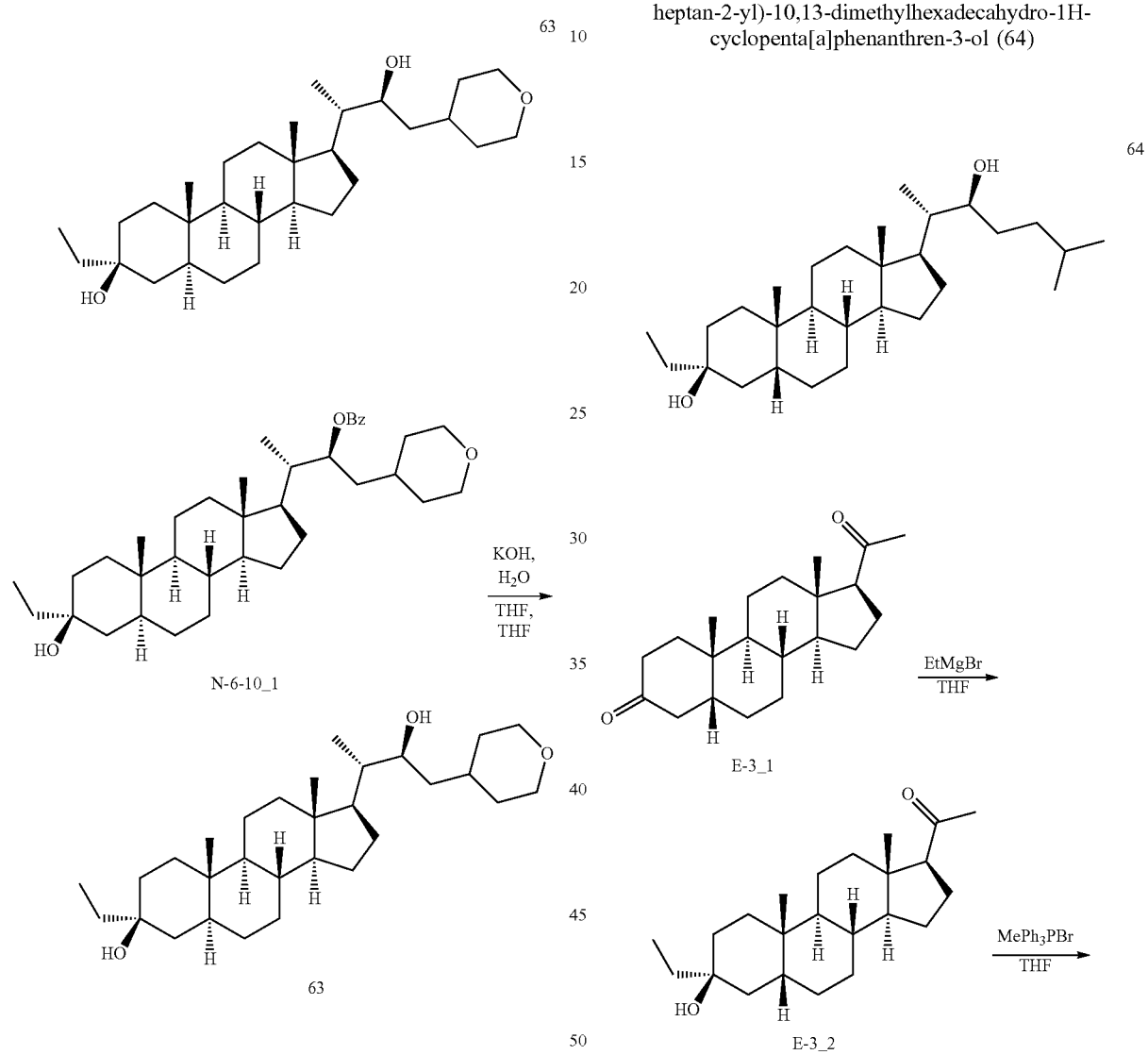

1. Water (1 mL) and KOH (177 mg, 3.17 mmol) were added to a solution of N-6-10_1 (180 mg, 0.318 mmol) in THF (2 mL) and methanol (1 mL). The mixture was stirred at 50° C. for 18 hrs. The reaction mixture was cooled, diluted with water (5 mL), acidified with 10% HCl (0.2 mL) and extracted with EtOAc (3×5 mL). The combined organic layer was dried over anhydrous sodium sulfate, filtered and concentrated. The residue was purified by column chromatography on silica gel (10~30% of EtOAc in PE) to give 63 (108 mg, 74%) as a solid.

$^1$H NMR (400 MHz, CDCl$_3$) δ 3.98-3.90 (m, 2H), 3.85-3.77 (m, 1H), 3.44-3.33 (m, 2H), 1.99-1.82 (m, 2H), 1.69-1.58 (m, 6H), 1.57-1.45 (m, 6H), 1.43-1.29 (m, 7H), 1.28-1.14 (m, 7H), 1.13-0.95 (m, 5H), 0.93-0.84 (m, 7H), 0.83 (s, 3H), 0.69-0.61 (m, 4H).

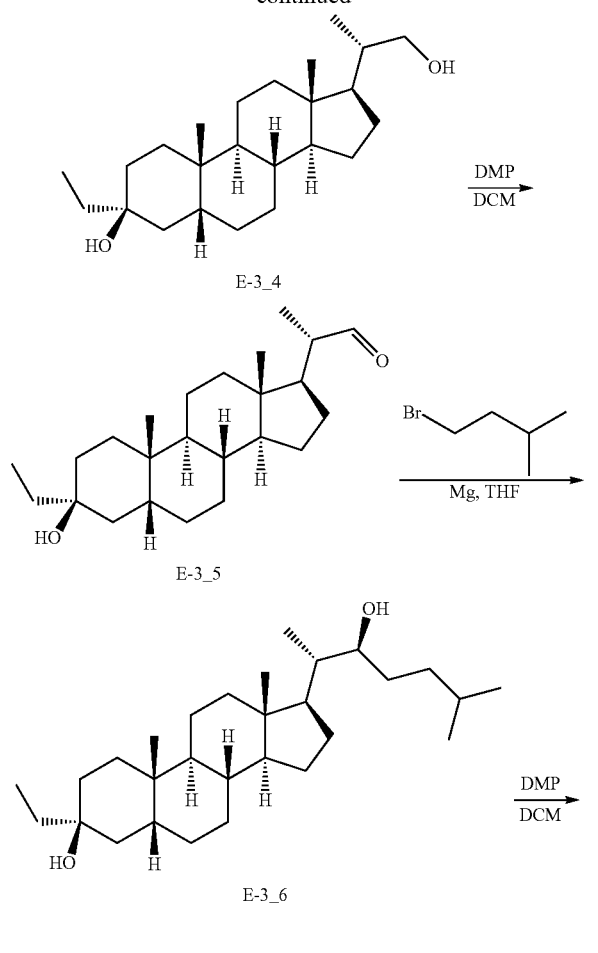

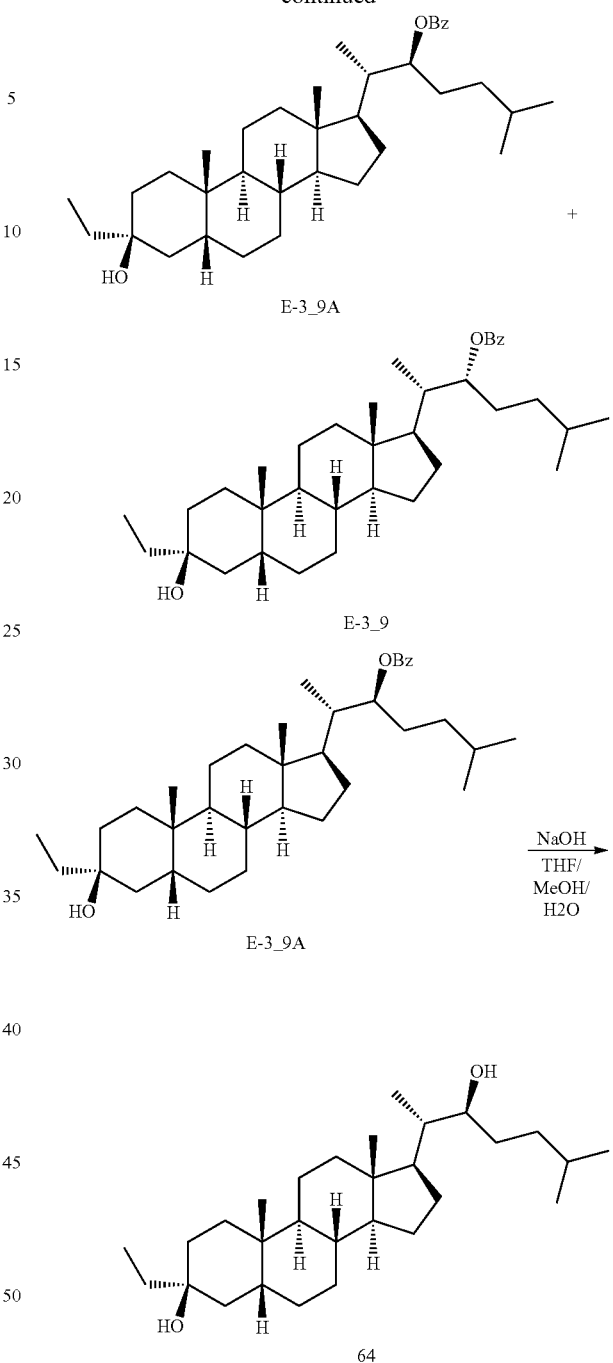

1. EtMgBr (42 mL, 126 mmol, 3 M in ether) was added slowly to a solution of E-3_1 (20.0 g, 63.1 mmol) in THF (300 mL) under $N_2$ at −70° C. After addition, the mixture was stirred at −70° C. for 2 hrs. The mixture was quenched with sat. $NH_4Cl$ (500 mL) and extracted with EtOAc (3×500 mL). The combined organic phase was washed with brine (500 mL), dried over $Na_2SO_4$, filtered, concentrated and purified by combi-flash (0~15% of EtOAc in PE) to give E-3_2 (6.50 g, 30%) as a solid.

$^1$H NMR (400 MHz, $CDCl_3$) δ 2.57-2.49 (m, 1H), 2.23-1.80 (m, 6H), 1.78-1.52 (m, 4H), 1.50-1.02 (m, 17H), 0.97 (s, 3H), 0.95-0.80 (m, 4H), 0.60 (s, 3H).

2. t-BuOK (4.19 g, 37.4 mmol) was added to a suspension of MePPh$_3$Br (13.3 g, 37.4 mmol) in THF (200 mL) at 15° C. under N$_2$. The mixture was stirred at 50° C. for 30 mins. To the mixture was added E-3_2 (6.50 g, 18.7 mmol) in portions below 50° C. The mixture was stirred at 50° C. for 1 hr. To the mixture was added NH$_4$Cl (400 mL). The organic layer was separated and concentrated under vacuum to give a crude product, which was triturated from MeOH/water (200 mL, 1:1) at 50° C. The mixture was filtered after cooled and the solid was washed with MeOH/water (2×30 mL, 1:1) and concentrated in vacuum to give E-3_3 (5.8 g, impure) as a solid.

$^1$H NMR (400 MHz, CDCl$_3$) δ 4.84 (s, 1H), 4.70 (s, 1H), 2.06-1.97 (m, 1H), 1.94-1.55 (m, 12H), 1.53-1.05 (m, 16H), 0.97 (s, 3H), 0.95-0.85 (m, 3H), 0.55 (s, 3H).

3. 9-BBN dimer (8.19 g, 33.6 mmol) was added to a mixture of E-33 (5.80 g, 16.8 mmol) in THF (100 ml) at 15° C. under N$_2$. The reaction mixture was stirred at 60° C. for 1 hour. The mixture was cooled to 15° C. Ethanol (7.72 g, 168 mmol) was added at 15° C. NaOH aqueous (33.6 mL, 5 M, 168 mmol) was added dropwise at 15° C. H$_2$O$_2$ (16.8 mL, 10.0 M, 168 mmol) was added dropwise at 15° C. The obtained mixture was stirred at 60° C. for 1 hour. The aqueous phase was extracted with EtOAc (3×100 mL). The combined organic phase was washed with brine (2×100 mL), dried over Na$_2$SO$_4$, filtered and concentrated. The residue was triturated from CH$_3$OH/H$_2$O=1/1 (150 mL) at 65° C. to give E-3_4 (2.80 g, 46%) as a solid.

$^1$H NMR (400 MHz, CDCl$_3$) δ 3.66-3.61 (m, 1H), 3.38-3.32 (m, 1H), 2.03-1.56 (m, 4H). 1.56-1.51 (m, 5H), 1.51-1.10 (m, 16H), 1.10-1.02 (m, 6H), 0.97 (s, 3H), 0.96-0.88 (m, 3H), 0.67 (s, 3H).

4. DMP (5.80 g, 13.7 mmol) was added to a solution of E-34 (2.50 g, 6.89 mmol) in DCM (50 mL). After that, the reaction was stirred at 20° C. for 30 min. The reaction mixture was added saturated aqueous NaHCO$_3$ (50 mL) solution, aqueous saturated Na$_2$S$_2$O$_3$ (30 mL) solution, extracted with DCM (2×20 mL). The combined organic layer was washed with aqueous saturated NaHCO$_3$ (3×10 mL) solution and brine (20 mL), dried over Na$_2$SO$_4$, filtered and concentrated under vacuum to give E-3_5 (2.45 g, crude) as a solid.

$^1$H NMR (400 MHz, CDCl$_3$) δ 9.60-9.55 (m, 1H), 2.26 (s, 1H), 1.98-1.70 (m, 6H), 1.70-1.51 (m, 6H), 1.51-1.00 (m, 12H), 1.00-0.89 (m, 10H), 1.75-0.65 (m, 4H).

5. Isobutylmagnesium bromide (33.9 mL, 2 M in THF, 67.9 mmol) was added to a solution of E-35 (2.45 g, 6.79 mmol) in THF (10 mL) under N$_2$ at 0° C. The mixture was stirred at 20° C. for 16 hrs. To the mixture was added NH$_4$Cl (20 mL, sat. aq.), the mixture was extracted with EtOAc (2×30 mL). The combined organic phase was washed with brine (20 mL), dried over Na$_2$SO$_4$, concentrated under vacuum, and purified by flash column (0~20% of EtOAc in PE) to give E-3_6 (1.6 g, 55%) as a solid.

$^1$H NMR (400 MHz, CDCl$_3$) δ 3.65-3.55 (m, 1H), 2.01-1.85 (m, 3H), 1.85-1.49 (m, 3H), 1.49-1.36 (m, 12H), 1.36-1.22 (m, 10H), 1.22-1.02 (m, 9H), 1.02-0.98 (m, 4H), 0.98-0.80 (m, 7H), 0.66 (s, 3H).

6. DMP (3.12 g, 7.38 mmol) was added to a solution of E-36 (1.6 g, 3.69 mmol) in DCM (30 mL). After that, the reaction was stirred at 20° C. for 30 min. The reaction mixture was added saturated aqueous NaHCO$_3$ (20 mL) solution, aqueous saturated Na$_2$S$_2$O$_3$ (20 mL) solution, followed by extraction with DCM (2×20 mL). The combined organic layer was washed with aqueous saturated NaHCO$_3$ (3×10 mL) solution and brine (20 mL), dried over Na$_2$SO$_4$, filtered and concentrated under vacuum to give E-3_7 (1.5 g, crude) as a solid.

$^1$H NMR (400 MHz, CDCl$_3$) δ 2.55-2.80 (m, 3H), 2.80-2.23 (m, 1H), 1.98-1.81 (m, 2H), 1.81-1.1.69 (m, 1H), 1.69-1.25 (m, 16H), 1.25-1.01 (m, 10H), 1.01-0.81 (m, 14H), 0.67 (s, 3H).

7. NaBH$_4$ (255 mg, 6.72 mmol) was added in one portion to a solution of E-3_7 (1.45 g, 3.36 mmol) in MeOH (20 mL) at 0° C. After addition, the mixture was stirred at 20° C. for 1 hr and quenched with NH$_4$Cl (20 mL, sat. aq.). The mixture was extracted with DCM (2×20 mL). The combined organic phase was washed with brine (2×10 mL), dried over Na$_2$SO$_4$, filtered, concentrated and purified by flash column (0~20% of EtOAc in PE) to give E-3_8 (1.2 g, 83%) as a solid.

$^1$H NMR (400 MHz, CDCl$_3$) δ 3.80-3.70 (m, 1H), 3.70-3.55 (m, 1H), 2.05-1.82 (m, 3H), 1.82-1.55 (m, 4H), 1.55-1.35 (m, 5H), 1.35-1.00 (m, 18H), 1.00-0.79 (m, 17H), 0.66 (s, 3H).

8. Benzoyl chloride (1.85 g, 13.2 mmol) was added to a solution of E-3_8 (1.15 g, 2.65 mmol) in pyridine (20 mL). The reaction mixture was stirred at 20° C. for 4 hours. The reaction mixture was poured into water (20 mL). The mixture was extracted with EtOAc (2×20 mL). The combined organic phase was washed with saturated brine (2×10 mL), dried over anhydrous Na$_2$SO$_4$, filtered concentrated and purified by flash column (0~10% of EtOAc in PE) to give the mixture product (1.45 g, impure) as a solid. The mixture product (1.45 g, impure) was purified by SFC (column: AD (250 mm*50 mm, 10 um), gradient: 30-30% B (A=0.1% NH3/H2O, B=EtOH), flow rate: 200 mL/min) to give E-3_9 (peak 2, 470 mg, 33%, DE %=100%) as a solid and E-3_9A (peak 1, 600 mg, 42%, DE %=99.1%) as a solid.

E-3_9A:

$^1$H NMR (400 MHz, CDCl$_3$) δ 8.10-7.99 (m, 2H), 7.60-7.50 (m, 1H), 7.50-7.38 (m, 2H), 5.15-5.05 (m, 1H), 2.05-1.70 (m, 6H), 1.70-1.35 (m, 5H), 1.35-1.05 (m, 19H), 1.05-0.82 (m, 17H), 0.65 (s, 3H).

SFC Rt=3.344 min in 10 min chromatography, AD_3_EtOH_DEA_5_40_25ML, 100% de. E-3_9:

$^1$H NMR (400 MHz, CDCl$_3$) δ 8.10-7.99 (m, 2H), 7.60-7.50 (m, 1H), 7.50-7.38 (m, 2H), 5.25-5.15 (m, 1H), 2.05-1.80 (m, 3H), 1.80-1.45 (m, 15H), 1.45-1.09 (m, 13H), 1.09-0.85 (m, 16H), 0.68 (s, 3H).

SFC Rt=3.851 min in 10 min chromatography, AD_3_EtOH_DEA_5_40_25ML, 99.1% de.

9. NaOH (531 mg, 13.3 mmol) and H$_2$O (0.5 mL) were added to a solution of E-3_9A (600 mg, 1.11 mmol) in THF (2 mL) and MeOH (2 mL) at 25° C. The solution was stirred at 50° C. for 48 hrs. Water (10 mL) was added. The mixture was extracted with EtOAc (2×10 mL). The combined organic layers were dried over Na$_2$SO$_4$, filtered and concentrated in vacuum to give crude product which was triturated with MeCN (10 mL) to give desired product 69 (473 mg, 99%) as a solid.

$^1$H NMR (400 MHz, CDCl$_3$) δ 3.68-3.55 (m, 1H), 2.01-1.85 (m, 3H), 1.85-1.70 (m, 1H), 1.70-1.45 (m, 8H), 1.45-1.22 (m, 13H), 1.22-1.05 (m, 8H), 1.05-1.86 (m, 15H), 0.66 (s, 3H). LCMS t$_R$=1.403 min in 2 min chromatography, 30-90AB_ELSD, purity 100.0%, MS ESI calcd. for C$_{29}$H$_{49}$ [M+H-2H$_2$O]$^+$397, found 397.

Example 65: Synthesis of (3S,5S,8R,9S,10S,13S,14S,17R)-3-ethyl-17-((2S,3S)-3-hydroxy-4-methylpentan-2-yl)-10,13-dimethylhexadecahydro-1H-cyclopenta[a]phenanthren-3-ol (65)

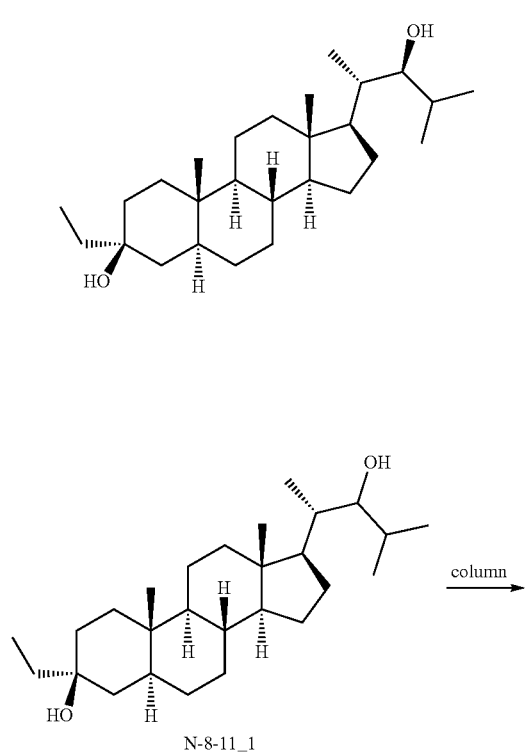

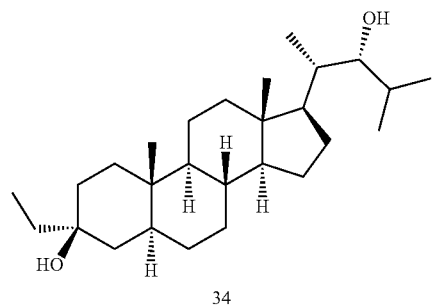

N-8-11_1 (30 mg, 0.0741 mmol, impure) was purified by combi-flash (25% of EtOAc in PE) to give 65 (9 mg, 30%) as a solid.

65:

$^1$H NMR (400 MHz, CDCl$_3$) δ 3.18-3.07 (m, 1H), 1.98-1.81 (m, 2H), 1.71-1.58 (m, 6H), 1.53-1.31 (m, 7H), 1.30-0.98 (m, 14H), 0.97-0.78 (m, 14H), 0.70-0.60 (m, 4H).

LCMS Rt=4.387 min in 7.0 min chromatography, 30-90AB_7MIN_E, purity 97.6%, MS ESI calcd for C$_{27}$H$_{45}$ [M+H-2H$_2$O]$^+$ 369, found 369.

Example 66: Synthesis of (3S,5S,8R,9S,10S,13S,14S,17R)-3-ethyl-17-((2S,3S)-3-hydroxy-4-(2-methylcyclopropyl)butan-2-yl)-10,13-dimethylhexadecahydro-1H-cyclopenta[a]phenanthren-3-ol (66)

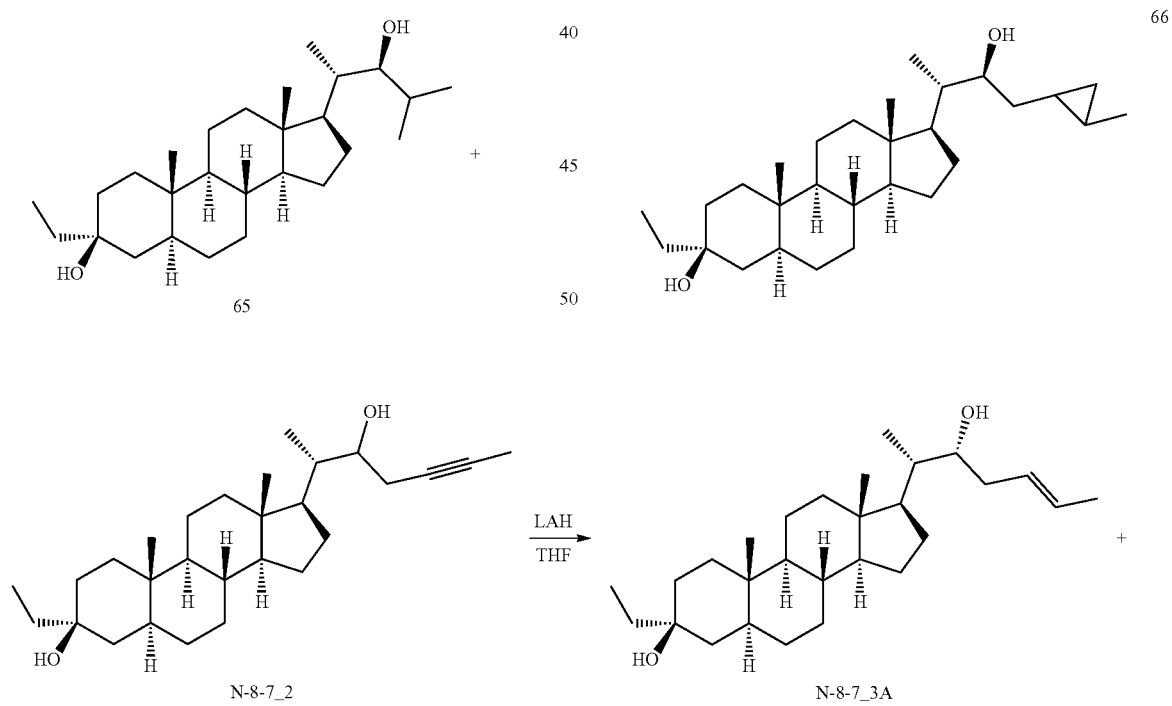

-continued

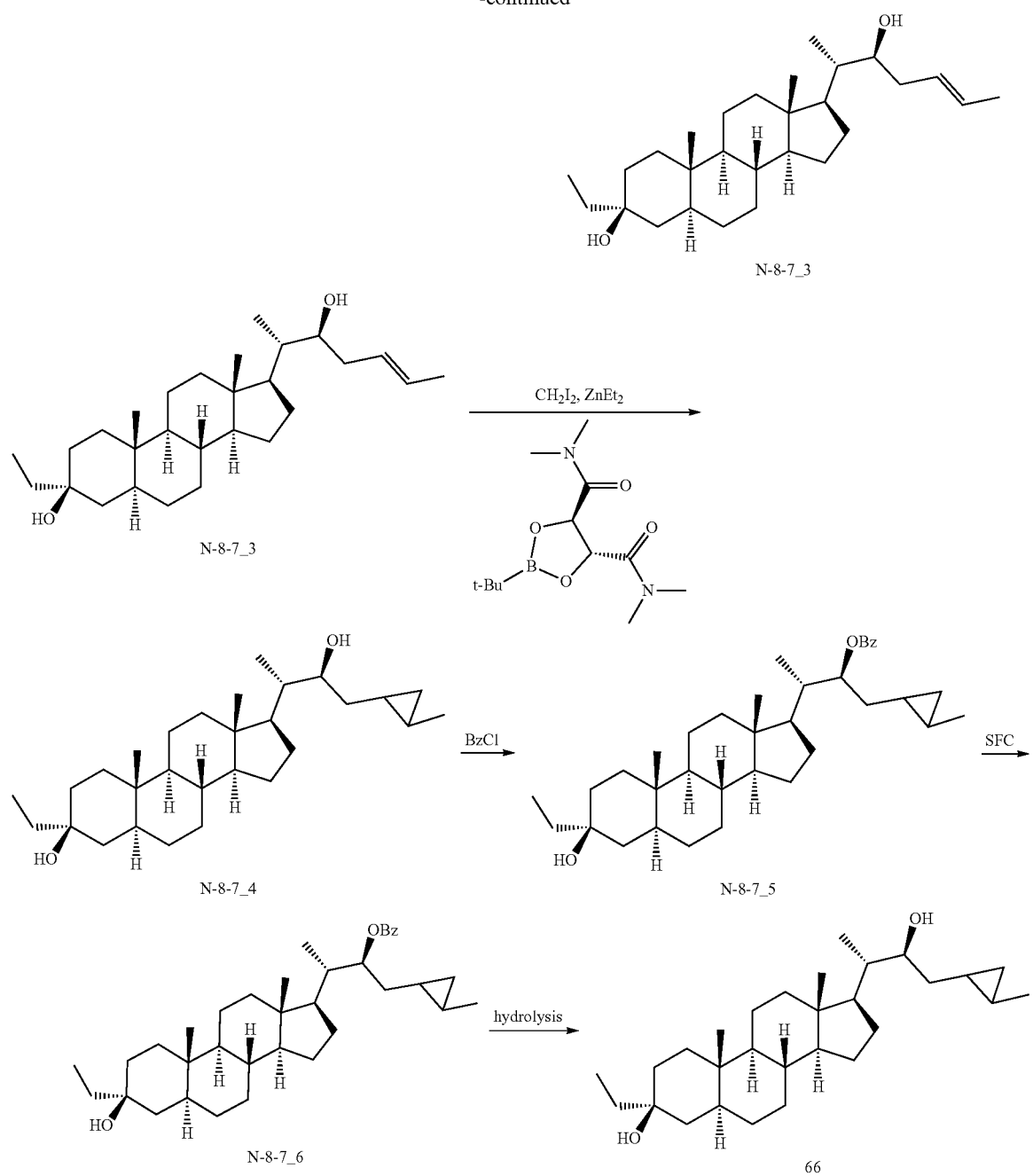

1. To a solution of N-8-7_2 (1 g, 2.41 mmol) in THF (50 mL) was added LiAlH₄ (914 mg, 24.1 mmol) at 0° C. The grey suspension was heated at 66° C. for 18 hrs. The reaction mixture was cooled to 0° C., quenched by ice-water (914 mg), then 15% w/w NaOH aqueous (914 mg), water (2.74 g). The mixture was filtered and the filtrate cake was washed with DCM (3×50 mL). The filtrate was concentrated to give a residue, which was purified by flash chromatography twice (ethyl acetate 10% in PE) to give N-8-7_3 (192 mg, 19%) and N-8-7_3A (397 mg, 39%) as an oil.

N-8-7_3:

1H NMR (400 MHz, CDCl3) δ 5.59-5.36 (m, 2H), 3.69-3.61 (m, 1H), 2.25-2.12 (m, 1H), 2.08-1.81 (m, 3H), 1.68 (d, J=10.0 Hz, 3H), 1.64-1.54 (m, 9H), 1.53-1.15 (m, 11H), 1.14-0.92 (m, 5H), 0.92-0.85 (m, 5H), 0.83 (s, 4H), 0.69-0.60 (m, 4H).

N-8-7_3A:

$^1$H NMR (400 MHz, CDCl$_3$) δ 5.62-5.37 (m, 2H), 3.62 (br d, J=10.0 Hz, 1H), 2.20-2.06 (m, 1H), 1.99-1.61 (m, 6H), 1.61-1.44 (m, 11H), 1.43-1.18 (m, 5H), 1.16-0.94 (m, 6H), 0.94-0.85 (m, 5H), 0.82 (s, 5H), 0.70-0.58 (m, 6H).

2. To a solution of diethylzinc (1 M in toluene, 2.59 mL, 2.59 mmol) in DCM (10 nil) was added CH₂I₂ (1.38 g, 5.18 mmol) over a period of 15 min at 0° C. The milky suspension was stirred for 10 min at 0 C and a preformed solution of Charette ligand ((4R,5R)-2-(tert-butyl)-N4,N4,N5,N5-tetramethyl-1,3,2-dioxaborolane-4,5-dicarboxamide) (139 mg, 0.5182 mmol) and N-8-7_3 (180 mg, 0.4319 mmol) in DCM (15 ml) was rapidly added via syringe, whereupon the reaction mixture turned clear. The solution was allowed to be warmed up to 25° C. and stirred for 16 h at 25° C. The reaction was then quenched by addition of saturated aqueous NH$_4$Cl (150 ml). The phases were separated and the aqueous phase was extracted with DCM (3×60 ml). The combined organic phase was washed with saturated NaHCO$_3$ aqueous (150 mL), saturated aqueous Na$_2$S$_2$O$_3$ (150 mL), and brine (100 mL), dried over Na$_2$SO$_4$, filtered and concentrated under reduced pressure and the residue was purified by flash column chromatography (11% of ethyl acetate in PE) to afford N-8-7_4 (60 mg, 32%) as a solid.

$^1$H NMR (400 MHz, CDCl$_3$) δ 3.77 (br s, 1H), 1.99-1.87 (m, 2H), 1.70-1.56 (m, 6H), 1.54-1.34 (m, 6H), 1.31-1.16 (m, 5H), 1.15-1.05 (m, 1H), 1.15-0.97 (m, 7H), 0.99-0.94 (m, 1H), 0.92-0.77 (m, 10H), 0.69-0.58 (m, 6H), 0.52-0.13 (m, 5H).

3. To a solution of N-8-7_4A (60 mg, 0.1393 mmol) in pyridine (3 mL) was added benzoyl chloride (39.1 mg, 0.2786 mmol) followed by DMAP (6.79 mg, 0.05572 mmol) at 25° C. The reaction mixture was stirred at 60° C. for 16 hours. The reaction mixture was diluted with DCM (80 mL). The DCM phase was washed with water (100 mL), 1.0 M HCl aqueous (2×100 mL), 10% NaHCO$_3$ aqueous (2×100 mL), brine (100 mL), dried over Na$_2$SO$_4$, filtered and concentrated under vacuum to give an oil, which was purified by flash column (1% of ethyl acetate in PE) to give N-8-7_5 (24 mg, 32%) as an oil.

LCMS Rt=1.431 min in 2 min chromatography, 5-95AB_220&254, purity 90%, MS ESI calcd. for C$_{36}$H$_{53}$O$_2$[M−H$_2$O+H]$^+$517.3, found 517.3.

SFC Peak 1: Rt=5.703 min in 10 min chromatography, AD_3_EtOH_DEA_5_40_25ML ("Chiralpak AD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.").

4. N-8-7_5 (24 mg, 0.04487 mmol) was purified by SFC (column: AD (250 mm*30 mm, 5 um)), gradient: 40-40% B (A=0.1% NH$_3$/H$_2$O, B=EtOH), flow rate: 50 m/min) to give impure N-8-7_6 (RT: 5.732, 19 mg, impure) as a solid. No isomer was obtained.

LCMS Rt=1.435 min in 2 min chromatography, 5-95AB_220&254, purity 98%, MS ESI calcd. for C$_{36}$H$_{53}$O$_2$[M−H$_2$O+H]$^+$ 517.3, found 517.3.

SFC Rt=5.732 min in 10 min chromatography, AD_3_EtOH_DEA_5_40_25ML, 97.76% de.

5. To a solution of N-8-7_6 (19 mg, 0.0355 mmol) in THF/MeOH (0.5 mL/0.5 mL), was added KOH (19.8 mg, 0.03552 mmol) in water (0.2 mL). The reaction mixture was stirred at 55° C. for 16 hours. To the mixture was added HCl (0.2 M, 50 mL). The suspension was extracted with DCM (2×60 mL). The combined organic phase was washed with 3% NaHCO$_3$ aqueous (80 mL) and brine (80 mL), dried over Na$_2$SO$_4$, filtered and concentrated under vacuum to give a solid, which was purified by flash-chromatography (ethyl acetate in PE, 15%) to give 66 (2 mg, 13%) as a solid.

$^1$H NMR (400 MHz, CDCl$_3$) δ 3.77 (br s, 1H), 1.98-1.87 (m, 2H), 1.70-1.57 (m, 7H), 1.54-1.28 (m, 11H), 1.26-0.94 (m, 12H), 0.91-0.84 (m, 7H), 0.83 (s, 3H), 0.72-0.60 (m, 4H), 0.51-0.15 (m, 3H).

LCMS Rt=1.315 min in 2 min chromatography, 30-90AB_2MIN_E, purity 100%, MS ESI calcd. for C$_{29}$H$_{49}$O [M−H$_2$O+H]$^+$395.3, found 395.3.

Example 67: Synthesis of (3S,5R,8R,9S,10S,13S,14S,17R)-17-((2S,3R)-4-cyclopentyl-3-hydroxybutan-2-yl)-3-ethyl-10,13-dimethylhexadecahydro-1H-cyclopenta[a]phenanthren-3-ol (67)

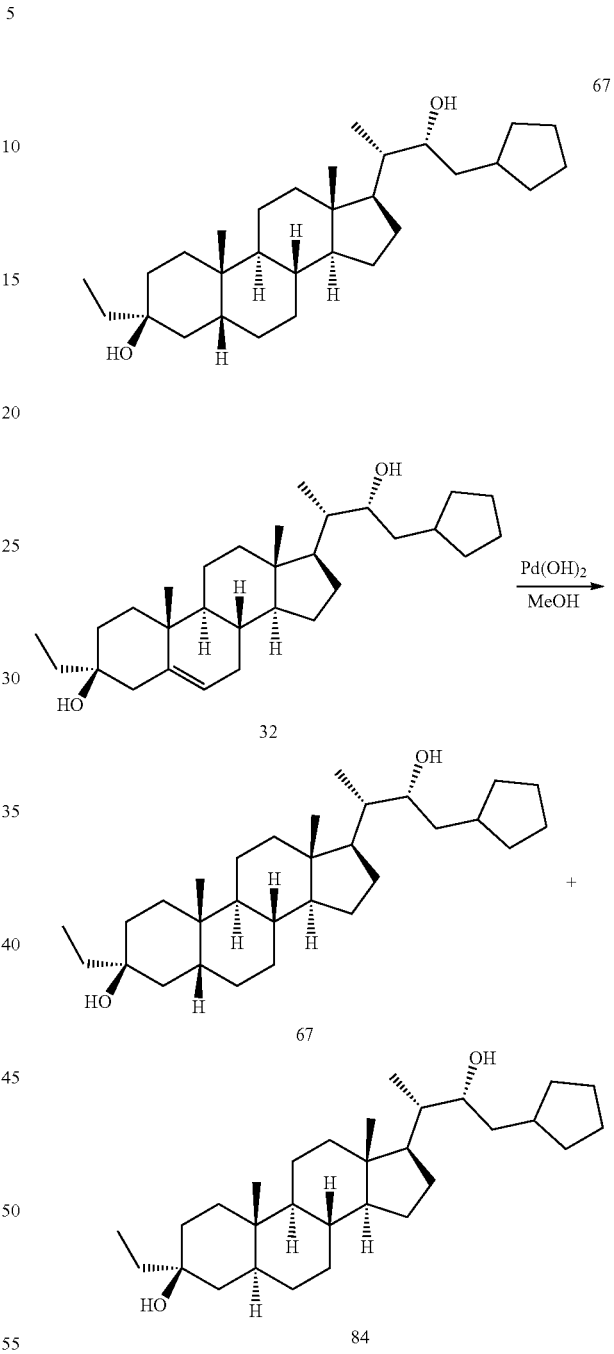

1. Pd(OH)$_2$ (160 mg, dry) was added to a solution of 32 (80 mg, 0.18 mmol) in MeOH (20 mL). The mixture was stirred at 50° C. under H$_2$ (50 Psi) for 48 hrs. The mixture was filtered, concentrated and purified by combi-flash (0~15% of EtOAc in PE) to give 67 (10 mg, 12%) and 84 (30 mg, 37%) as a solid.

67:

$^1$H NMR (400 MHz, CDCl$_3$) δ 3.76-3.66 (m, 1H), 2.01-1.78 (m, 5H), 1.76-1.58 (m, 7H), 1.52-1.31 (m, 13H), 1.28-1.10 (m, 10H), 1.09-0.99 (m, 4H), 0.96 (s, 3H), 0.93-0.86 (m, 6H), 0.67 (s, 3H).

LCMS Rt=1.508 min in 2.0 min chromatography, 30-90AB_E, purity 100%, MS ESI calcd. for C30H49 [M+H-2H2O]+ 409, found 409.

Example 68: Synthesis of (3S,5S,8R,9S,10S,13S,14S,17R)-3-ethyl-17-((2S,3R)-3-hydroxyhept-5-yn-2-yl)-10,13-dimethylhexadecahydro-1H-cyclopenta[a]phenanthren-3-ol (68)

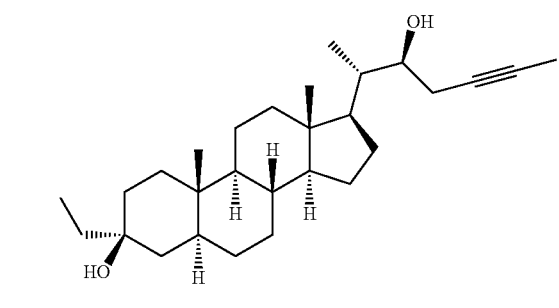
68

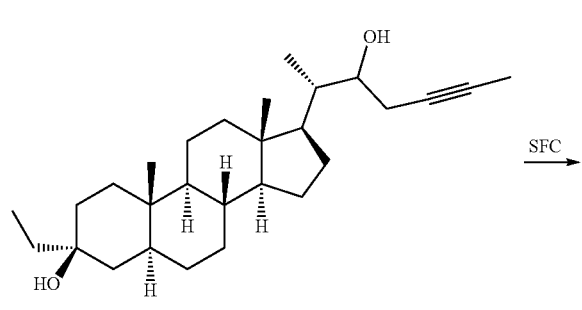
N-8-7_2B

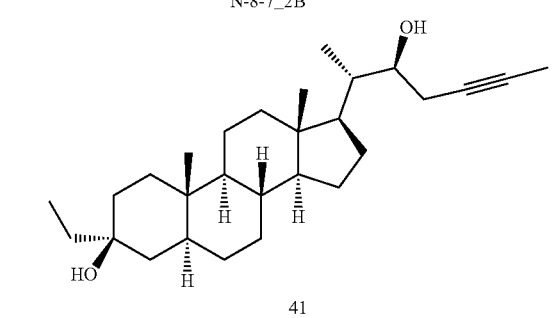
41

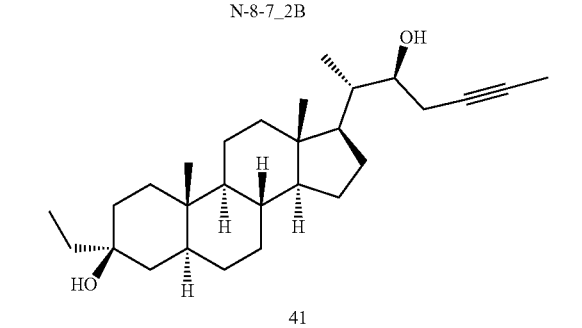

68

1. The crude N-8-7_2B (250 mg, 0.868 mmol) was further purified by SFC (column: AD (250 mm*30 mm, 10 um)), gradient: 35-35% B (A=0.1% NH3/H2O, B=EtOH), flow rate: 60 mL/min) to give 41 (peak 2, 81 mg, 33%) as a solid and 68 (peak 1, 78 mg, 31%) as a solid.

68:
$^{1}$H NMR (400 MHz, CDCl3) δ 3.87-3.78 (m, 1H), 2.21-2.12 (m, 1H), 1.99-1.86 (m, 2H), 1.80 (s, 3H), 1.73-1.51 (m, 8H), 1.51-1.42 (m, 4H), 1.42-1.20 (m, 8H), 1.20-0.95 (m, 7H), 0.95-0.79 (m, 8H), 0.95 (s, 4H).

LCMS Rt=1.188 min in 2 min chromatography, 30-90AB_2MIN_E, purity 100%, MS ESI calcd. for C28H45O [M+H—H2O]+ 397 found 397.

SFC Rt=6.465 min in 10 min chromatography, AD_3_EtOH_DEA_5_40_25ML, 100% de.

Example 69: Synthesis of (3S,8S,9S,10R,13S,14S,17R)-17-((2S,3S)-5-cyclopropyl-3-hydroxypentan-2-yl)-3-ethyl-10,13-dimethyl-2,3,4,7,8,9,10,11,12,13,14,15,16,17-tetradecahydro-1H-cyclopenta[a]phenanthren-3-ol (69)

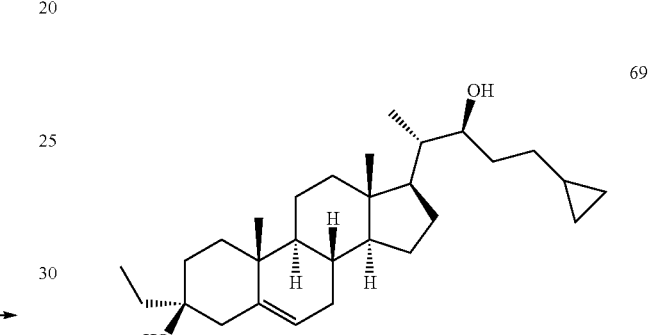
69

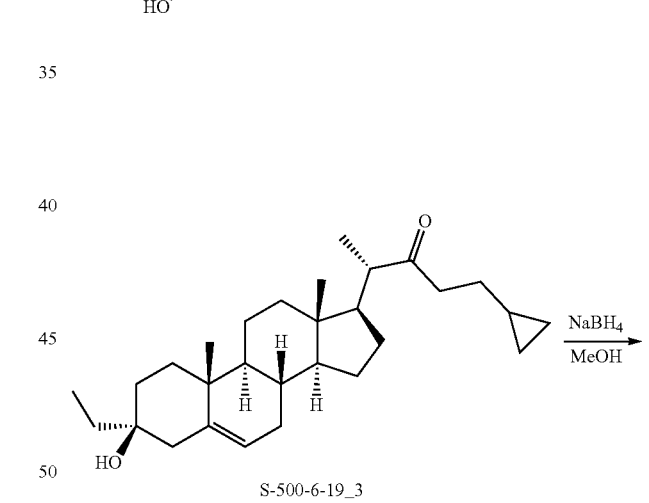
S-500-6-19_3

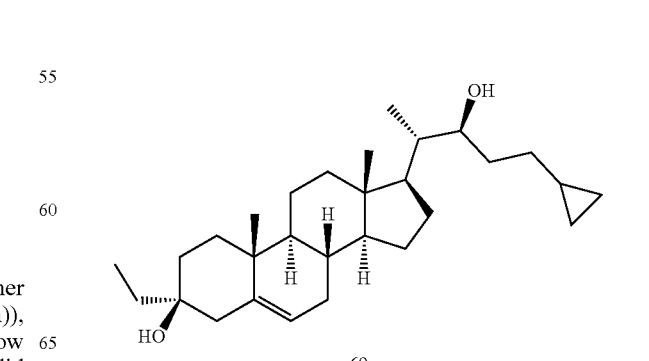
69

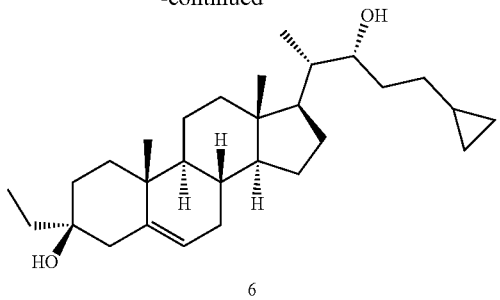

6

1. NaBH$_4$ (2.46 g, 65.1 mmol) was added in portions to a solution of S-500-6-19_3 (700 mg, 1.63 mmol) in THF (5 mL) and MeOH (5 mL) at 15° C. After stirring at 15° C. for 20 mins, the mixture was quenched with NH$_4$Cl (20 mL, sat. aq.) and extracted with EtOAc (50 mL). The organic layer was separated and concentrated in vacuum to give 760 mg mixture as a solid, which was separated by flash column (0~35% of DCM/EtOAc (1/1) in PE) to give 69 (330 mg, 47%) and 6 (250 mg, 35%, impure) as a solid. The impure 6 (250 mg) was further separated by flash column (0~35% of DCM/EtOAc (1/1) in PE) to give 6 (170 mg, 23%) as a solid.

69:

$^1$H NMR (400 MHz, CDCl$_3$) δ 5.33-5.23 (m, 1H), 3.75-3.63 (m, 1H), 2.41-2.31 (m, 1H), 2.09-1.85 (m, 4H), 1.78-1.59 (m, 5H), 1.53-1.38 (m, 9H), 1.38-1.05 (m, 9H), 1.03 (s, 3H), 1.00-0.91 (m, 1H), 0.91 (d, J=6.4 Hz, 3H) 0.85 (t, J=7.6 Hz, 3H), 0.69 (s, 3H), 0.68-0.60 (m, 1H), 0.45-0.36 (m, 2H), 0.09-0.08 (m, 2H).

LCMS Rt=1.387 min in 2.0 min chromatography, 30-90_AB_E, purity 98.1%, MS ESI calcd. for C$_{29}$H$_{47}$O [M+H—H$_2$O]$^+$411, found 411.

S-500-6-19:

$^1$H NMR (400 MHz, CDCl$_3$) δ 5.32-5.24 (m, 1H), 3.77-3.66 (m, 1H), 2.41-2.31 (m, 1H), 2.09-1.91 (m, 3H), 1.79-1.59 (m, 6H), 1.55-1.21 (m, 14H), 1.21-1.06 (m, 4H), 1.03 (s, 3H), 1.00-0.95 (m, 1H), 0.93 (d, J=6.8 Hz, 3H) 0.85 (t, J=7.6 Hz, 3H), 0.70 (s, 3H), 0.68-0.62 (m, 1H), 0.49-0.38 (m, 2H), 0.11-0.02 (m, 2H).

LCMS Rt=1.380 min in 2.0 min chromatography, 30-90_AB_E, purity 100%, MS ESI calcd. for C$_{29}$H$_{47}$O [M+H—H$_2$O]$^+$411, found 411.

Example 70: Synthesis of (3S,8S,9S,10R,13S,14S, 17R)-3-ethyl-17-((2S,3S)-3-hydroxy-4-(3-methyl-oxetan-3-yl)butan-2-yl)-10,13-dimethyl-2,3,4,7,8,9, 10,11,12,13,14,15,16,17-tetradecahydro-1H-cyclopenta[a]phenanthren-3-ol (70)

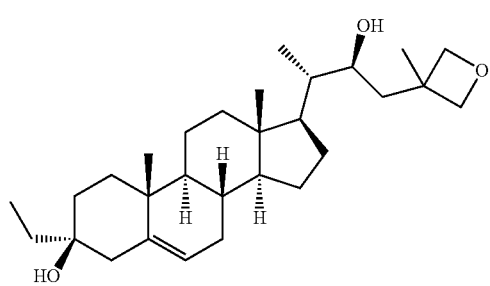

70

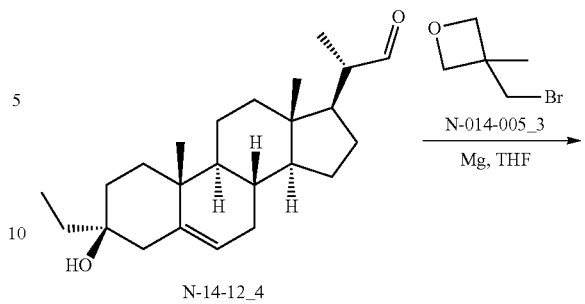

1. To a suspension of Mg (807 mg, 33.2 mmol) and I$_2$ (1 mg) in THF (2 mL) was added solution of N-014-005_3 (2.5 g, 15.1 mmol) in THF (8 mL) drop wise under N$_2$ at 50-55° C. The mixture was stirred at 55° C. for 1 h. The mixture was diluted with THF (10 mL) and used in the next step directly without monitored. To a solution of N-14-12_4 (1.01 g, 2.83 mmol) in THF (10 mL) was added fresh prepared 3-[(bromomagnesio) methyl]-3-methyloxetane (15 mmol in 20 mL of THF) at 0° C. The mixture was stirred at 15° C. for 4 h. To the mixture was added NH$_4$Cl (20 mL, 10% aq.). The mixture was extracted with EtOAc (30 mL). The organic layer was separated and concentrated in vacuum. The residue was purified by flash column (0-30% of EtOAc in PE) to give a mixture (190 mg, 15%) as a white solid, which was purified by SFC (Column: AD (250 nm*30 mm, 5 um), Condition: 0.1% NH3H2O ETOH, Gradient: from 50% to 50%, FlowRate (ml/min): 60 mL/min, 25° C.) to afford 33 (Peak 1, 110 mg, 9%) and 70 (Peak 2, 30 mg, impure) as a white solid. The impure 70 (30 mg, impure) was purified by column chromatography on silica gel (15% of EtOAc in PE) to give 70 (10 mg, 5%) as a white solid.

33:

$^1$H NMR (400 MHz, CDCl$_3$) δ 5.30-5.26 (m, i1H), 4.59-4.70 (m, i1H), 4.50-4.48 (m, 1H), 4.36-4.33 (m, 1H), 3.83 (s, 1H), 2.40-2.33 (m, 1H), 2.10-1.50 (m, 17H), 1.49-1.35 (m, 9H), 1.30-0.80 (m, 13H), 0.68 (s, 3H).

LCMS Rt=1.069 min in 3 min chromatography, 30-90AB_2MIN_E.M, purity 100%, MS ESI calcd. for C$_{29}$H$_{49}$O$_3$[M+H]$^+$ 445, found 445.

70:

¹H NMR (400 MHz, CDCl₃) δ 5.30-5.26 (m, 1H), 4.10-4.02 (m, 1H), 3.81-3.70 (m, 1H), 3.50-3.41 (m, 2H), 3.34-3.30 (m, 1H), 2.35-2.31 (m, 1H), 2.10-1.50 (m, 18H), 1.49-1.05 (m, 13H), 1.05-0.90 (m, 4H), 0.90-0.80 (m, 3H), 0.67 (s, 3H).

LCMS Rt=1.115 min in 3 min chromatography, 30-90AB_2MIN_E.M, purity 100%, MS ESI calcd. for $C_{29}H_{49}O_3[M+H]^+$ 445, found 445.

Example 71: Synthesis of (3S,5R,8R,9S,10S,13S,14S,17R)-3-(methoxymethyl)-10,13-dimethyl-17-((2S,3S)-4,4,4-trifluoro-3-hydroxybutan-2-yl)hexadecahydro-1H-cyclopenta[a]phenanthren-3-ol (71)

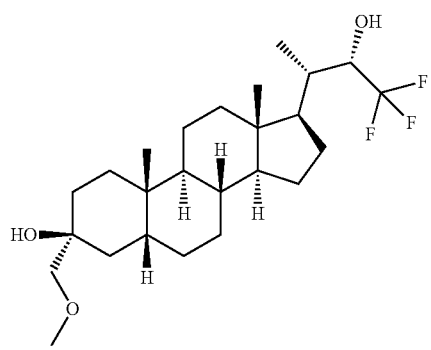

71

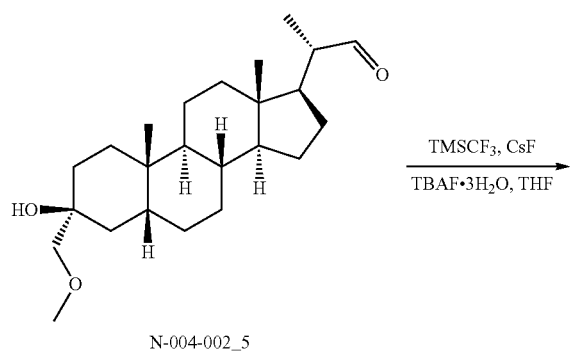

N-004-002_5 → TMSCF₃, CsF / TBAF·3H₂O, THF

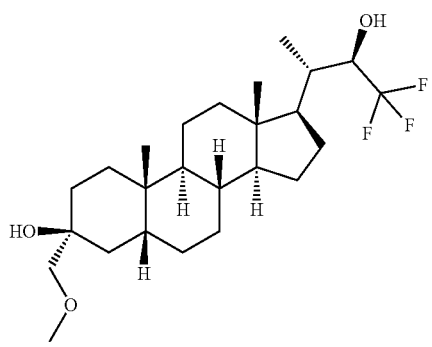

9

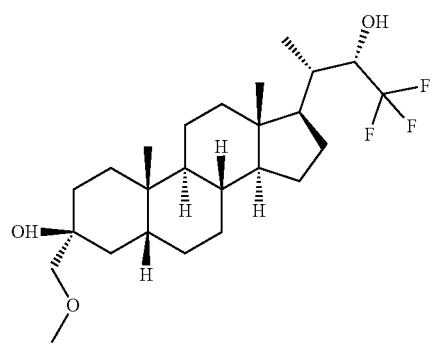

71

1. To a solution of N-004-022_5 (200 mg, 0.531 mmol), CsF (40.2 mg, 0.265 mmol) in THF (5 mL) was added TMSCF₃ (187 mg, 1.32 mmol) under N₂ at 0° C. The mixture was stirred at 25° C. for 1 hrs. To the mixture was added TBAF.3H2O (836 mg, 2.65 mmol). After stirring at 25° C. for 2 hrs, the mixture was quenched 50% NH₄Cl (20 ml) and extracted with EtOAc (2×10 mL). The combined organic phase was washed with brine (20 mL), dried over anhydrous Na₂SO₄, filtered and concentrated in vacuum. The residue was purified by silica gel chromatography (100-200 mesh silica gel, PE/EA=10/1) to afford 9 (56 mg, 24%) and 71 (30 mg, impure) as a white solid.

71 (30 mg, 0.067 mmol) was re-crystallized from n-hexane (2 mL) at 25° C. to give 71 (24 mg, 10%) as a white solid.

71:

¹H NMR (400 MHz, CDCl₃) δ 4.08-4.00 (m, 1H), 3.39 (s, 3H), 3.24-3.18 (m, 2H), 2.22-2.15 (m, 1H), 2.02-1.77 (m, 5H), 1.75-1.68 (m, 2H), 1.64-1.52 (m, 5H), 1.47-1.31 (m, 6H), 1.28-1.01 (m, 10H), 0.97 (s, 3H), 0.67 (s, 3H).

LCMS Rt=1.105 min in 2 min chromatography, 30-90AB_POS_E.M, purity 100%, MS ESI calcd. for $C_{25}H_{41}F_3O_3$ $[M+Na]^+$ 469, found 469.

Example 72: Synthesis of (3S,8S,9S,10R,13S,14S,17R)-3-ethyl-17-((2S,3S)-3-hydroxyhexan-2-yl)-10,13-dimethyl-2,3,4,7,8,9,10,11,12,13,14,15,16,17-tetradecahydro-1H-cyclopenta[a]phenanthren-3-ol (72)

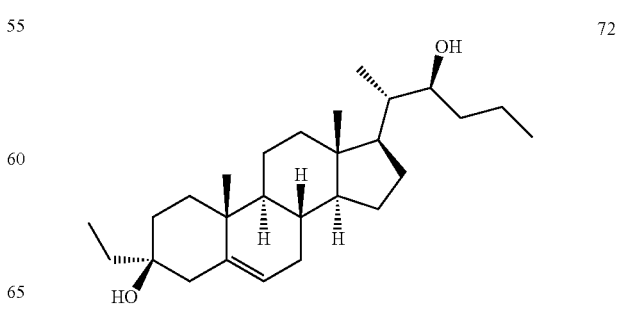

72

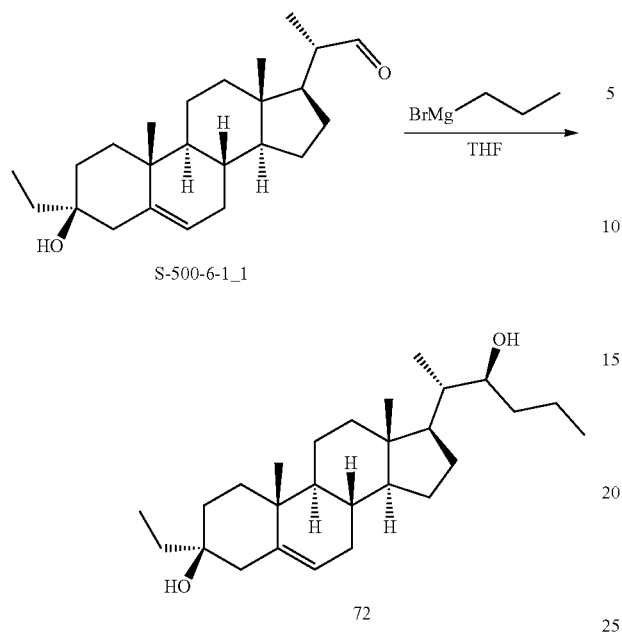

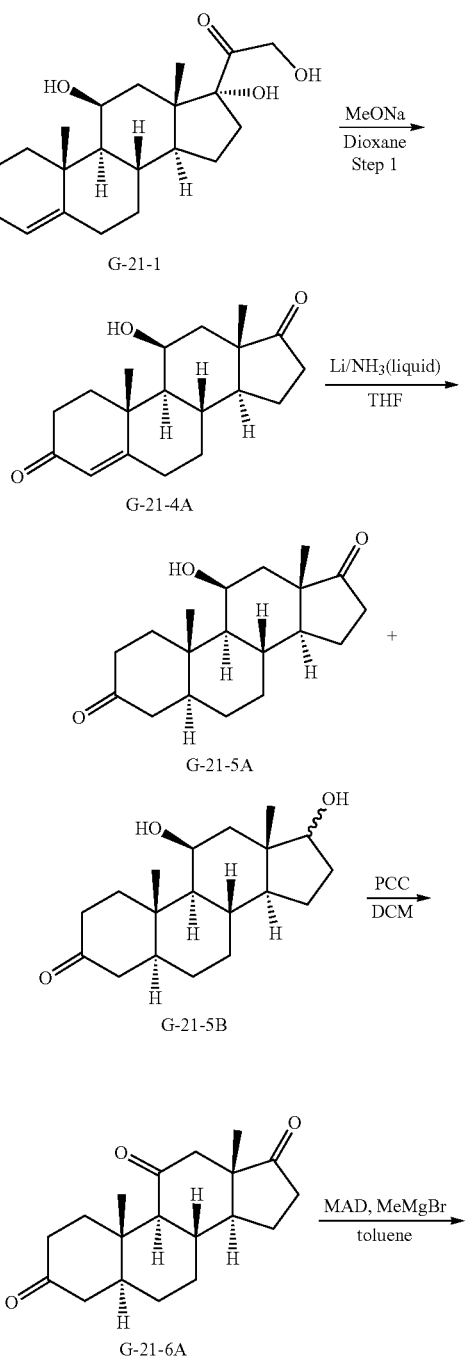

1. Propylmagnesium bromide (3.34 mL, 6.69 mmol, 2M in THF) was slowly added to a solution of S-500-6-1_1 (800 mg, 2.23 mmol) in THF (30 mL) at 0° C. After addition, the mixture was stirred at 15° C. for 1 hr. The mixture was quenched with sat.NH$_4$Cl (40 ml) and extracted with EtOAc (3×20 mL). The combined organic phase was washed with brine (2×30 mL), dried over Na$_2$SO$_4$, filtered and concentrated and purified by combi-flash (0~15% of EtOAc in PE) to give 72 (500 mg, 56%) as a solid.

$^1$H NMR (400 MHz, CDCl$_3$) δ 5.31-5.26 (m, 1H), 3.72-3.64 (m, 1H), 2.41-2.31 (m, 1H), 2.07-1.85 (m, 4H), 1.77-1.69 (m, 1H), 1.62-1.54 (m, 3H), 1.52-1.38 (m, 9H), 1.37-1.16 (m, 6H), 1.15-1.01 (m, 7H), 0.99-0.88 (m, 7H), 0.87-0.82 (m, 3H), 0.68 (s, 3H).

LCMS Rt=4.979 min in 7.0 min chromatography, 30-90AB_E, purity 98.8%, MS ESI calcd. for C$_{27}$H$_{43}$ [M+H-2H$_2$O]$^+$ 367, found 367.

Example 73: Synthesis of (3S,5S,8R,9R,10S,13S, 14S,17R)-17-((2S,3S)-3-hydroxy-6-methylheptan-2-yl)-3,13-dimethylhexadecahydro-1H-cyclopenta[a]phenanthren-3-ol (73)

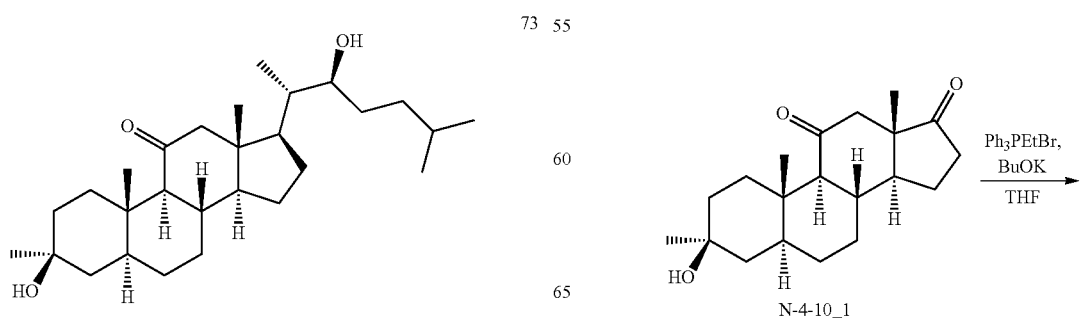

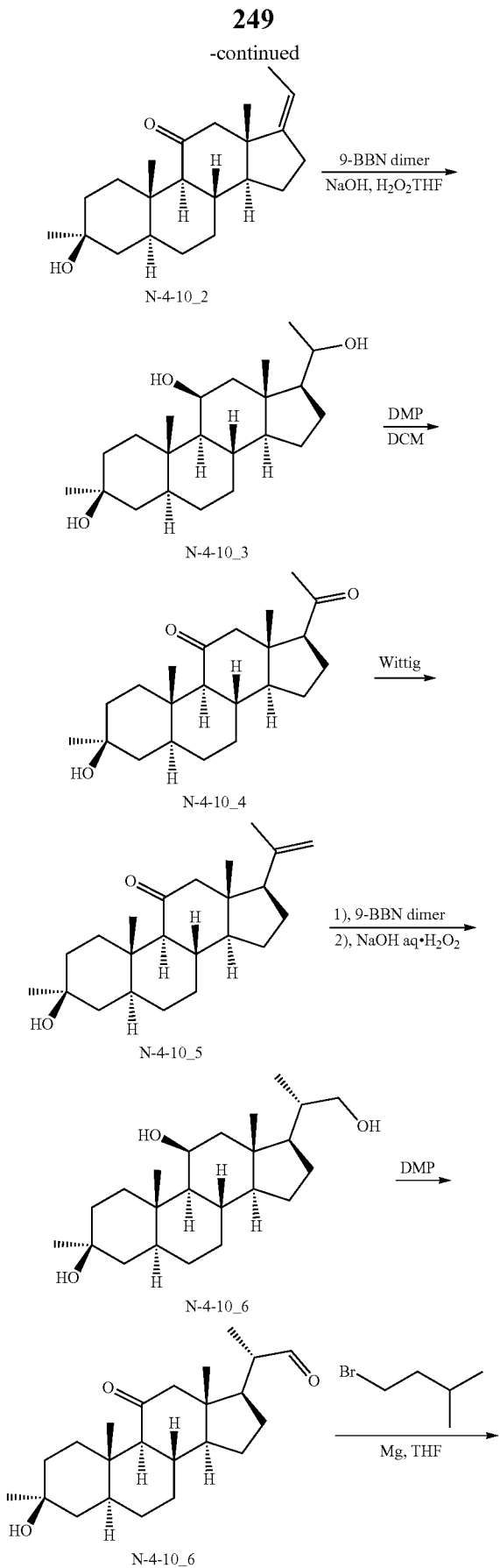

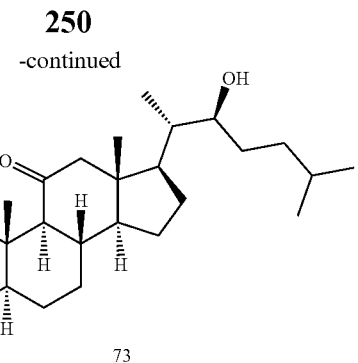

73

1. To solution of G-21-1 (40 g, 110 mmol) in dry dioxane (1 L) under N2 was added sodium methoxide (29.7 g, 550 mmol). The mixture was stirred at 110° C. for 16 hours. TLC showed the starting material was consumed almostly. Solvent was removed to ⅓ volume and mixture was acidified with 2 M HCl to pH=5-6, extracted with DCM (500 mL*3), washed with aqueous sodium bicarbonate (500 mL) and brine (500 mL), dried over sodium sulfate and concentrated. The residue was purified by column chromatography on silica gel (PE:EA:MeOH=3:1:0.1) to give G-21-4A (11 g, 33.1%) as white solid.

2. To a solution of Li (2.54 g, 363 mmol) was added to liquid ammonium (1000 mL, prepared in 13-601 over 1.5 hours) at −70° C. in portions. The mixture was stirred at −70° C. for 30 mins until all of Li was dissolved. A solution of G-21-4A (11 g, 36.3 mmol) and tert-BuOH (5.38 g, 72.6 mmol) in 400 ml of anhydrous tetrahydrofuran was added dropwise and stirred for 90 mins until the reaction mixture turned light yellow. TLC (PE:EA=1:1, PMA) showed most of STM was consumed. Ammonium chloride (15 g) was added and excess ammonia was left to evaporate. The residue was extracted with 0.5N HCl (500 mL.) and dichloromethane (500 mL×2). The combined organic layers were washed with saturated $NaHCO_3$ solution, dried over $Na_2SO_4$, filtered and concentrated to give a mixture of G-21-5A and G-21-5B (10 g, impure) which was directly used in the next step without further purification.

3. A solution of G-21-5A and G-21-5B (10 g, 27.9 mmol) in 100 mL of anhydrous dichloromethane was added PCC (16.6 g, 65.6 mmol) and silicon gel (16.6 g). After stirring at 25° C. for 2 h, TLC (PE:EA=1:1, PMA) showed the STM was consumed. The resulting solution was concentrated and purified by chromatography on silicon gel (petroleum ether/ethyl acetate=5:1 to 2:1) to afford G-21-6A (4.6 g, 46.4%) as a white solid.

4. To a solution of BHT (34.8 g, 158 mmol) in toluene (120 mL) under nitrogen at 0° C. was added trimethylaluminum (2 M in toluene, 39.5 mL, 79.1 mmol) dropwise. After stirring at 20° C. for 30 minutes, a solution of G-21-6A (8 g, 26.4 mmol) in toluene (80 mL) was added dropwise under nitrogen at −70° C. After stirring at −70° C. for 30 min, MeMgBr (3 M in diethyl ether, 26.3 mL, 79.1 mmol, 3M in ether) was added dropwise. The resulting mixture was stirred at −70° C. for 1 hr, poured to ice-cooled aqueous citric acid (300 mL) slowly and extracted with EtOAc (3×100 mL). The combined organic layer was washed with brine (300 mL), dried over anhydrous sodium sulfate, filtered, concentrated and purified by combi-flash (0-40% of EtOAc in PE) to give N-4-10_1 (6.5 g, 77%) as a white solid.

$^1$H NMR (400 MHz, $CDCl_3$) δ 2.60-2.49 (m, 1H), 2.47-2.37 (m, 2H), 2.34-2.19 (m, 3H), 2.14-2.03 (m, 1H), 2.00-1.82 (m, 3H), 1.73-1.58 (m, 3H), 1.56-1.46 (m, 2H), 1.36-

1.26 (m, 3H), 1.24 (s, 3H), 1.21-1.07 (m, 2H), 1.04 (s, 3H), 1.00-0.84 (m, 1H), 0.82 (s, 3H).

5. To a suspension of bromo(ethyl)triphenylphosphorane (22.6 g, 61.1 mmol) in anhydrous THF (200 mL) under $N_2$ at 20° C. was added potassium 2-methylpropan-2-olate (6.84 g, 61.1 mmol). After stirring at 40° C. for 30 minutes, a solution of N-4-10_1 (6.5 g, 20.4 mmol) in anhydrous THF (50 mL) was added slowly. The resultant mixture was stirred at 40° C. for 10 minutes, then quenched with aqueous $NH_4Cl$ (400 mL) and extracted with EtOAc (2×150 mL). The combined organic phase was dried over sodium sulfate, filtered, concentrated and purified by column chromatography on silica gel (0-25% of EtOAc in PE) to give N-4-10_2 (5.5 g, 82%) as a white solid.

$^1$H NMR (400 MHz, CDCl$_3$) δ 5.22-5.13 (m, 1H), 2.91-2.81 (m, 1H), 2.62-2.51 (m, 1H), 2.50-2.39 (m, 2H), 2.38-2.24 (m, 1H), 1.91-1.81 (m, 1H), 1.80-1.70 (m, 4H), 1.55-1.41 (m, 4H), 1.36-1.25 (m, 5H), 1.23 (s, 3H), 1.21-1.04 (m, 3H), 1.01 (s, 3H), 0.98-0.84 (m, 2H), 0.81 (s, 3H).

6. To a mixture of N-4-10_2 (5.5 g, 16.6 mmol) in THF (100 mL) was added 9-BBN dimer (8.10 g, 33.2 mmol) at 15° C. under $N_2$. After stirring at 50° C. for 1 hour, the mixture was cooled to 15° C. NaOH aqueous (33.2 mL, 5 M, 166 mmol) was added dropwise below 15° C., followed by a dropwise addition of $H_2O_2$ (18.8 g, 30%, 166 mmol) below 15° C. The mixture was extracted with EtOAc (3×100 mL). The combined organic phase was washed with sat.Na$_2$S$_2$O$_3$ (5×100 mL), dried over Na$_2$SO$_4$, filtered and concentrated to give 7 g crude, which was used in next step directly.

7. To a solution of N-4-10_3 (7 g, 19.9 mmol) in DCM (300 ml) was added DMP (25.2 g, 59.6 mmol). After stirring at 20° C. for 10 min, the reaction mixture was quenched with saturated NaHCO$_3$ solution (500 mL) until pH of the aqueous layer became about 9. The mixture was filtered. The DCM layer was separated and the aqueous phase was extracted with DCM (200 mL). The combined organic phase was washed with saturated Na$_2$S$_2$O$_3$ aqueous (3×400 mL), sat.NaHCO$_3$ (400 mL), brine (400 mL), dried over Na$_2$SO$_4$, filtered, concentrated and purified by combi-flash (0-20% of EtOAc in DCM) to give N-4-10_4 (4 g, 58%) as a white solid.

$^1$H NMR (400 MHz, CDCl$_3$) δ 2.77-2.67 (m, 1H), 2.65-2.38 (m, 3H), 2.32-2.17 (m, 1H), 2.09 (s, 3H), 1.88-1.63 (m, 7H), 1.59-1.49 (m, 3H), 1.35-1.21 (m, 7H), 1.19-1.09 (m, 2H), 1.01 (s, 3H), 0.96-0.84 (m, 1H), 0.57 (s, 3H).

8. To a suspension of MePh$_3$PBr (8.18 g, 23.0 mmol) in THF (100 mL) was added t-BuOK (2.57 g, 23.0 mmol). After stirring at 40° C. for 10 minutes, the mixture was slowly added dropwise to a solution of N-4-10_4 (4 g, 11.5 mmol) in THF (50 mL) at 20° C. After addition, the mixture was quenched with NH$_4$Cl (200 mL) and extracted with EtOAc (3×80 mL). The combined organic phase was dried over Na$_2$SO$_4$, filtered, concentrated and purified by combi-flash (0-25% of EtOAc in PE) to give N-4-10_5 (3.2 g, 80%) as a white solid.

$^1$H NMR (400 MHz, CDCl$_3$) δ 4.88 (s, 1H), 4.70 (s, 1H), 2.48-2.37 (m, 2H), 2.31-2.22 (m, 2H), 1.89-1.77 (m, 4H), 1.75-1.61 (m, 7H), 1.54-1.45 (m, 2H), 1.34-1.29 (m, 2H), 1.28-1.24 (m, 3H), 1.23 (s, 3H), 1.17-1.05 (m, 2H), 1.01 (s, 3H), 0.93-0.83 (m, 1H), 0.51 (s, 3H).

9. To a mixture of N-4-10_5 (3.2 g, 9.28 mmol) in THF (100 mL) was added 9-BBN dimer (4.51 g, 18.5 mmol) at 15° C. under N2. After stirring at 50° C. for 1 hour, the mixture was cooled to 15° C. NaOH aqueous (18.5 mL, 5 M, 92.8 mmol) was added dropwise below 15° C., followed by a dropwise addition of H$_2$O$_2$ (10.5 g, 30%, 92.8 mmol) below 15° C. The mixture was extracted with EtOAc (3×100 mL). The combined organic phase was washed with sat.Na$_2$S$_2$O$_3$ (5×100 mL), dried over Na$_2$SO$_4$, filtered and concentrated to give 5 g crude, which was used in next step directly.

10. To a solution of N-4-10_5A (5 g, 13.7 mmol) in DCM (300 mL) was added DMP (11.6 g, 27.4 mmol). After stirring at 20° C. for 10 min, the reaction mixture was quenched with saturated NaHCO$_3$ solution (300 mL) until pH of the aqueous layer became about 9. The mixture was filtered. The DCM layer was separated and the aqueous phase was extracted with DCM (100 mL). The combined organic phase was washed with saturated Na$_2$S$_2$O$_3$ aqueous (3×300 mL), sat.NaHCO$_3$ (300 mL), brine (300 mL), dried over Na$_2$SO$_4$, filtered, concentrated and purified by combi-flash (0-10% of Acetone in DCM) to give N-4-10_7 (1 g, 20%) as a white solid.

$^1$H NMR (400 MHz, CDCl$_3$) δ 9.58-9.55 (m, 1H), 2.52-2.27 (m, 4H), 2.08-1.96 (m, 1H), 1.84-1.62 (m, 8H), 1.51-1.39 (m, 3H), 1.32-1.21 (m, 7H), 1.17-1.06 (m, 5H). 1.01 (s, 3H), 0.94-0.83 (m, 1H), 0.66 (s, 3H).

11. To a solution of N-4-10_6 (400 mg, 0.832 mmol) in THF (20 mL) was added dropwise isopentylmagnesium bromide (1.65 mL, 3.30 mmol, 2M in ether) under N$_2$ at 0° C. After stirring at 0° C. for 10 minutes, the mixture was quenched with sat.NH$_4$Cl (60 mL) and extracted with EtOAc (2×30 mL). The combined organic phase was washed with brine (60 mL), dried over Na$_2$SO$_4$, filtered, concentrated and purified by combi-flash (0-10% of Acetone in DCM) to give 73 (200 mg, 42%) as a white solid.

$^1$H NMR (400 MHz, CDCl$_3$) δ 3.65-3.56 (m, 1H), 2.55-2.49 (m, 1H), 2.46-2.38 (m, 1H), 2.32-2.25 (m, 1H), 2.10-1.98 (m, 1H), 1.83-1.62 (m, 7H), 1.57-1.44 (m, 4H), 1.42-1.25 (m, 7H), 1.24-1.20 (m, 4H), 1.19-1.04 (m, 5H), 1.01 (s, 3H), 0.94-0.82 (m, 10H), 0.0.63 (s, 3H).

LCMS Rt=3.381 min in 7.0 min chromatography, 30-90AB_E, purity 100%, MS ESI calcd. for C$_{28}$H$_{47}$O$_2$[M+H—H$_2$O]$^+$ 415, found 415.

Example 74: Synthesis of (3S,5S,8R,9R,10S,13S,14S,17R)-17-((2S,3S)-3-hydroxy-6-methylheptan-2-yl)-3,13-dimethylhexadecahydro-1H-cyclopenta[a]phenanthren-3-ol (74)

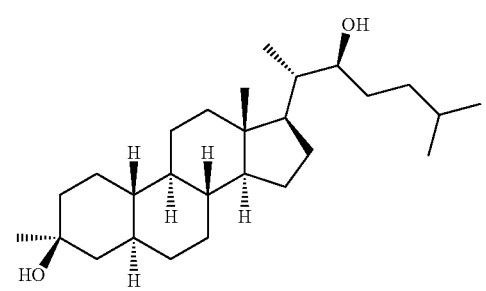

253 254
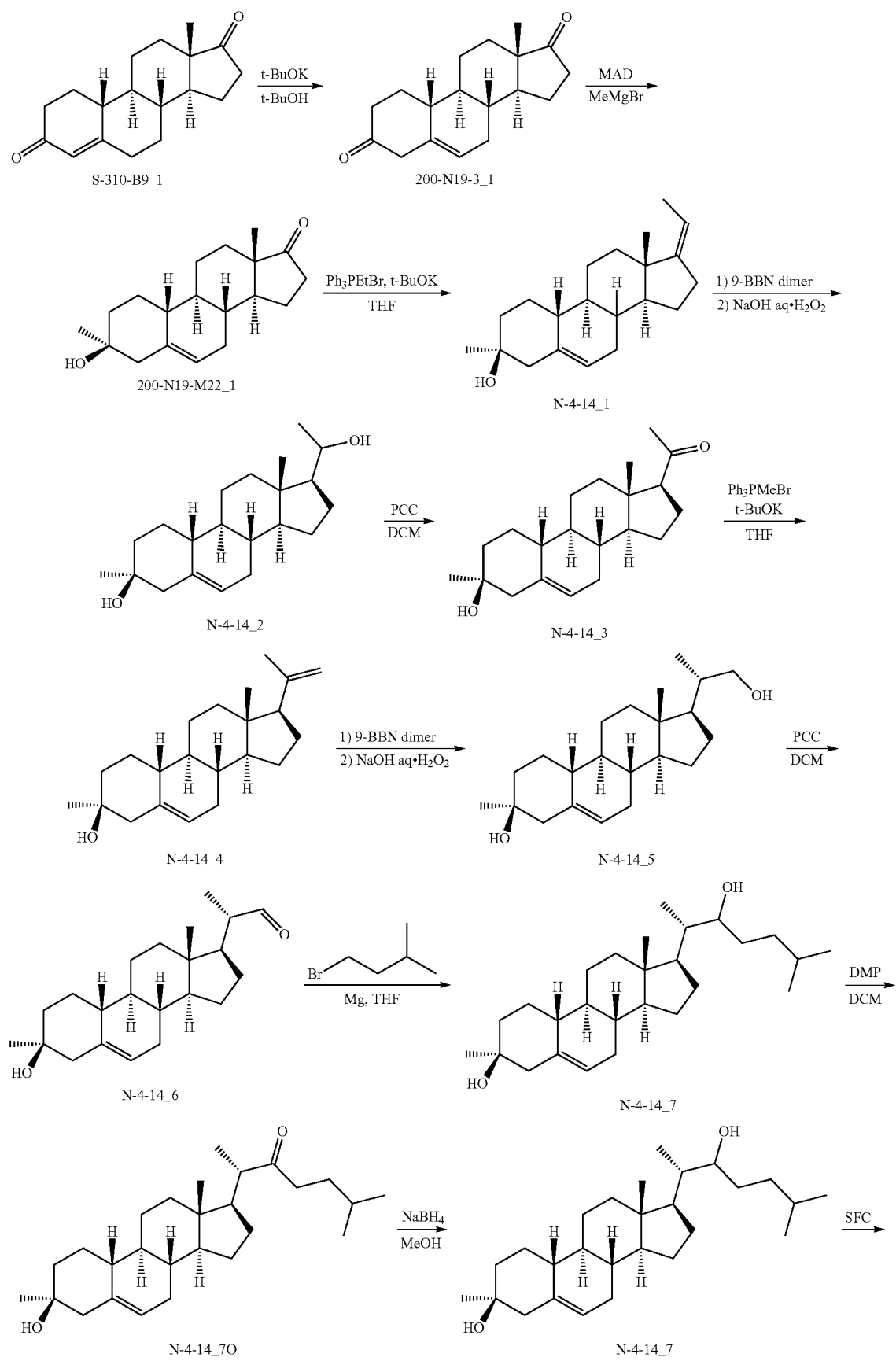

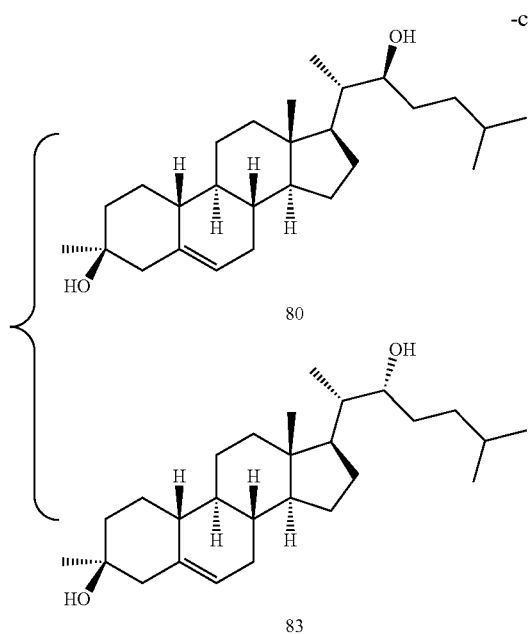
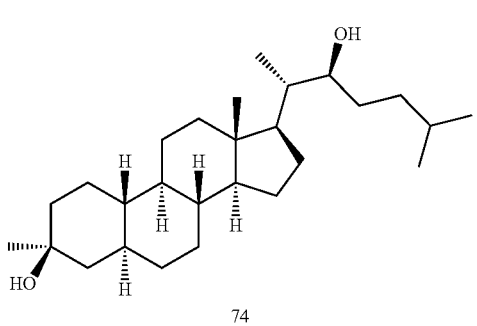

1. t-BuOH (1.7 L) was charged into a three-neck round bottom flask under N₂ at 35° C. and stirred for 10 mins. t-BuOK (292 g, 2.61 mol) was added to the mixture and stirred until the reaction became clear. After that, S-310-B9_1 (65 g, 238 mmol) was added to the above mixture and stirred for 1.5 h at 35° C. under N₂. The reaction mixture was poured into 10% aqueous acetic acid (2 L) and stirred for 30 mins, during which the temperature was maintained below 10° C. Then the mixture was treated with water (1.5 L) and the pH was adjusted to 7-8 with NaHCO₃ and the mixture was stirred for 30 mins. The aqueous phase was extracted with MTBE (3 L). The organic layer was separated, washed with brine (3×1 L), dried over anhydrous Na₂SO₄, filtered and concentrated below 35° C. to give S-200-N19-3_1 (65 g, crude) as an oil. The crude residue was used directly for the next step.

2. To a solution of 2,6-di-tert-butyl-4-methylphenol (340 g, 1.54 mol) in toluene (700 mL) was added drop-wise AlMe₃ (385 mL, 770 mmol, 2 M in toluene) at 0° C. The mixture was stirred at 25° C. for 1 hr and used directly as MAD solution. A solution of 200-N19-3_1 (60 g, 220 mmol) in anhydrous toluene (200 mL) and anhydrous DCM (200 mL) was added to MAD solution at −70° C. over a period of 30 mins under N₂. The reaction mixture stirring at −70° C. for 1 h. Then MeMgBr (220 mL, 660 mmol, 3M in ethyl ether) was added drop wise at −70° C. and stirred for 1 h. The reaction was poured into saturated aqueous citric acid (2 L) at 0° C. and stirring for 30 min, extracted with EtOAc (2×1 L). The combined organic phase was washed with saturated brine (2×1 L), dried over anhydrous Na₂SO₄, filtered and concentrated. The residue was purified by silica gel chromatography (PE/EtOAc=10/1 to 5/1) to afford 200-N19-M22_1 (33 g, 52%) as a solid.

¹H NMR (400 MHz, CDCl₃) δ 5.46-5.42 (m, 1H), 2.25-2.40 (m, 1H), 2.21-1.60 (m, 13H), 1.35-1.21 (m, 4H), 1.13 (s, 3H), 0.98-0.83 (m, 6H).

3. t-BuOK (31.0 g, 277 mmol) was added in one portion to a suspension of Ph₃PEtBr (102 g, 277 mmol) in Anhydrous THF (500 mL) at 25° C. under N2. After stirring at 25° C. for 30 min, 200-N19-M22_1 (20 g, 69.3 mmol) was added and stirred for 2 h at 25° C. The reaction was quenched with aq.NH₄Cl (800 mL) at 0° C., extracted with EtOAc (2×500 mL). The combined organic phase was washed with brine (2×500 mL), dried over Na₂SO₄, filtered and concentrated. The residue was purified by silica gel chromatography (PE/EtOAc=10/1 to 5/1) to afford N-4-14_1 (15 g, 72%) as a solid.

¹H NMR (400 MHz, CDCl₃) δ 5.43-5.40 (m, 1H), 5.16-5.10 (m, 1H), 2.41-2.33 (m, 1H), 2.28-1.86 (m, 8H), 1.78-1.71 (m, 1H), 1.69-1.50 (m, 11H), 1.41-1.10 (m, 6H), 0.94-0.81 (s, 3H).

4. 9-BNN dimer (66.9 g, 299 mmol) was added to a solution of N-4-14_1 (30 g, 99.8 mmol) in anhydrous THF (500 mL) and stirred for 30 mins at 0° C. under N₂. The reaction mixture was warmed to 50° C. and stirred for 1 hr. After cooling to 0° C. EtOH (100 mL) was added. NaOH.aq (99.8 mL, 5M, 499 mmol) was added very slowly. H₂O₂ (53.0 g, 499 mmol, 30% in water) was added slowly and the inner temperature was maintained below 30° C. The mixture was warmed to 50° C. and stirred for 1 hr. The reaction mixture was cooled and ice-water (1 L) was added and stirred 30 min. filtered and concentrated in vacuum to get N-4-11_2 (30 g, crude) as a solid. The crude residue was used directly for the next step.

5. Silica gel (150 g) and PCC (81.0 g, 376 mmol) were added to a solution of N-4-14_2 (30 g, crude) in DCM (500 mL). The reaction mixture was warmed to 40° C. and stirred for 1 hr. The reaction mixture was cooled, treated with PE (500 mL), filtered though a pad of silica gel and the solid was washed with PE/DCM (500/500 mL). The mother liquor was filtered and concentrated under vacuum to get crude product. The residue was purified by silica gel chromatography (PE/EtOAc=8/1 to 5/1) to afford N-4-14_3 (20 g, impure) as a solid.

¹H NMR (400 MHz, CDCl3) δ 5.43-5.40 (m, 1H), 2.57-2.50 (m, 1H), 2.21-2.08 (m, 6H), 1.77-1.43 (m, 10H), 1.37-1.12 (m, 9H), 1.00-0.82 (m, 2H), 0.64 (s, 3H).

6. t-BuOK (14.1 g, 126 mmol) was added in one portion to a suspension of Ph₃PMeBr (44.8 g, 126 mmol) in anhydrous THF (300 mL) at 0° C. under N₂. The reaction mixture was stirred at 25° C. for 30 min. N-4-14_3 (20 g, 63.1 mmol) was added. The reaction mixture was warmed to 40° C. and stirred for 1 hr. The reaction was poured into ice-water (500 mL) at 0° C. The aqueous phase was extracted with EtOAc (2×400 mL). The combined organic phase was washed with brine (2×300 mL), dried over anhydrous $Na_2SO_4$, filtered and concentrated. The residue was purified by a silica gel column (PE/EtOAc=8/1-5/1) to give N-4-14_4 (19 g, impure) as a solid.

$^1$H NMR (400 MHz, $CDCl_3$) δ 5.43-5.40 (m, 1H), 4.85 (s, 1H), 4.71 (s, 1H), 2.23-2.13 (m, 2H), 1.87-1.64 (m, 11H), 1.42-1.40 (m, 2H), 1.29-1.08 (m, 8H), 0.97-0.80 (m, 3H), 0.59 (s, 3H).

7. 9-BNN dimer (40.5 g, 181 mmol) was added in one portion to a solution of N-4-14_4 (19 g, 60.4 mmol) in anhydrous THF (300 mL) at 0° C. under $N_2$. The mixture was warmed to 50° C. and stirred for 1 h. The reaction mixture was cooled and EtOH (100 mL) was added. NaOH aq. (60.3 mL, 5M, 302 mmol) was added very slowly. $H_2O_2$ (34.0 g, 302 mmol, 30% in water) was added slowly and the inner temperature was maintained below 10° C. The mixture was warmed to 50° C. and stirred for 1 hr. After cooling, ice-water (1 L) was added and stirred for 30 min. The precipitated solid was filtered out. The filter cake dried in air to give N-4-11_5 (17 g, crude) as a solid, which was used directly for the next step.

8. To a solution of N-4-14_5 (17 g, crude) in DCM (300 mL) was added silica gel (60 g) and PCC (43.9 g, 204 mmol) in one portion at 25° C. The reaction mixture was warmed to 40° C. and stirred for 1 hr. The reaction mixture was cooled and PE (200 mL) was added. The mixture was filtered though a pad of silica gel and the solid was washed with PE/DCM (200/200 mL). filtered and concentrated in vacuum to yield a solid. The residue was purified by silica gel chromatography (PE/EtOAc=8/1 to 5/1) to afford N-4-14_6 (5.5 g, impure) as a solid. The residue was re-crystallized from MeCN (50 mL) at 82° C. to get N-4-14_6 (5 g, 91%) as a solid.

$^1$H NMR (400 MHz, $CDCl_3$) δ 9.60-9.56 (m, 1H), 5.42-5.40 (m, 1H), 2.58-2.51 (m, 1H), 2.40-1.85 (m, 9H), 1.44-1.04 (m, 16H), 1.00-0.80 (m, 3H), 0.75-0.71 (m, 3H).

9. To a suspension of Mg (3.96 g, 165 mmol) and $I_2$ (1 mg) in anhydrous THF (20 mL) was added solution of 1 (12.5 g, 82.7 mmol) in anhydrous THF (63 mL) drop-wise under $N_2$ at 25° C. and inner temperature was raised to 65° C. and stirred for 2 hrs. The mixture was used in the next step directly. Isopentylmagnesium bromide (83.0 mL, 1 M in THF) was added in one portion to a solution of N-4-14_6 (5 g, 15.1 mmol) in anhydrous THF (50 mL) was added at 0° C. under $N_2$. The reaction mixture was warmed to 15° C. and stirred for 1 hr. To the reaction mixture was added saturated aqueous $NH_4Cl$ (100 mL) solution. The aqueous phase was extracted with EtOAc (3×100 mL). The combined organic phase was washed with saturated brine (2×200 mL), dried over anhydrous $Na_2SO_4$, filtered and concentrated in vacuum to give a crude product. The crude product was purified by silica gel column (0~20% of EtOAc in PE) to give N-4-14_7 (2.5 g, impure) as a solid.

$^1$H NMR (400 MHz, $CDCl_3$) δ 5.40-5.37 (m, 1H), 3.67-3.61 (m, 1H), 2.19-1.71 (m, 9H), 1.64-1.28 (m, 13H), 1.18-1.03 (m, 7H), 0.95-0.78 (m, 12H), 0.69 (s, 3H).

10. To a solution of DMP (10.5 g, 24.8 mmol) was added N-4-14_7 (2.5 g, 6.20 mmol) in DCM (40 mL) at 25° C. The reaction mixture was warmed to 40° C. and stirred for 1 h. The reaction mixture was quenched with saturated $NaHCO_3$ aqueous pH 7~8 at below 10° C. The Suspension was filtered. The DCM phase in filtrate was separated and washed with saturated $NaHCO_3/Na_2S_2O_3$ aqueous (1:1, 2×30 mL), the combined organic phase was washed with saturated brine (2×30 mL), dried over $Na_2SO_4$, filtrate and concentrated in vacuum to get a solid. The residue was purified by flash column (0~30% of EtOAc in PE) to give N-4-14_7O (1.5 g, 60%) as a solid.

$^1$H NMR (400 MHz, $CDCl_3$) δ 5.41-5.39 (m, 1H), 2.56-2.31 (m, 3H), 2.19-1.83 (m, 5H), 1.84-1.42 (m, 12H), 1.30-0.97 (m, 12H), 0.96-0.77 (m, 8H), 0.74-0.70 (m, 3H).

11. To a solution of N-4-14_70 (1.5 g, 3.74) in MeOH (10 mL) was slowed added $NaBH_4$ (1.42 g, 37.4 mmol) at 25° C. and stirred for 2 hrs. Ice-water (100 mL) was added and the mixture was stirred for 30 mins. The aqueous phase was extracted with DCM (2×20 mL). The combined organic phase was washed with saturated brine (2×20 mL), dried over anhydrous $Na_2SO_4$, filtered and concentrated in vacuum to obtain a solid. The residue was purified by silica gel chromatography (PE/EtOAc=8/1 to 5/1) to afford N-4-14_7 (1 g, 67%) as a solid.

$^1$H NMR (400 MHz, $CDCl_3$) δ 5.41-5.39 (m, 1H), 3.65-3.63 (m, 1H), 2.20-2.16 (m, 1H), 2.11-1.88 (m, 5H), 1.86-1.54 (m, 10H), 1.33-0.99 (m, 14H), 0.95-0.79 (m, 11H), 0.70 (s, 3H).

SFC Peak 1: Rt=4.644 min and Peak 2 Rt=5.240 min in 10 min chromatography, AD_3_EtOH_DEA_5_40_25ML ("Column: Chiralpak AD-3150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.").

12. The N-4-14_7 (1 g, 2.48 mmol) was purified by SFC (Column: AD (250 mm*30 mm, 5 um), Condition: 0.1% $NH_3H_2O$ ETOH, Begin: B: 40%, End B: 40%) to afford 80 (Peak 2, 300 mg, impure) and 83 (Peak 1, 250 mg, impure) as a solid. The 80 (300 mg, impure) was re-crystallized from MeCN (4 mL) at 82° C. reflux for 1 hr. The stirred mixture was cooled to 25° C. The suspension was filtered under vacuum to get 80 (150 mg, 15%) as a solid. The 83 (250 mg, impure) was re-crystallized from MeCN (3 mL) at 82° C. reflux for 1 hr. The stirred mixture was cooled to 25° C. The suspension was filtered under vacuum to provide 83 (150 mg, 15%) as a solid. 83:

$^1$H NMR (400 MHz, $CDCl_3$) δ 5.41-5.39 (m, 1H), 3.62-3.60 (m, 1H), 2.22-1.89 (m, 6H), 1.64-1.49 (m, 9H), 1.46-1.11 (m, 16H), 0.98-0.86 (m, 10H), 0.70 (s, 3H).

LCMS Rt=1.268 min in 2.0 min chromatography, 30-90 AB, purity 100%, MS ESI calcd. for $C_{27}H_{42}$ $[M+H-2H_2O]^+$ 367, found 367.

SFC Rt=4.609 min in 10 min chromatography, AD_3_EtOH_DEA_5_40_25ML, 100% de. 80:

$^1$H NMR (400 MHz, $CDCl_3$) δ 5.41-5.39 (m, 1H), 3.63-3.62 (m, 1H), 2.22-1.67 (m, 10H), 1.64-1.36 (m, 12H), 1.16-1.03 (m, 8H), 0.98-0.80 (m, 1H), 0.70 (s, 3H).

LCMS Rt=1.276 min in 2.0 min chromatography, 30-90 AB, purity 99%, MS ESI calcd. for $C_{27}H_{42}$ $[M+H-2H_2O]^+$ 367, found 367.

SFC Rt=5.236 min in 10 min chromatography, AD_3_EtOH_DEA_5_40_25ML, 100% de.

13. Dry $Pd(OH)_2$ (200 mg) was added to a solution of 80 (150 mg, 0.372 mmol) in THF (3 mL) and MeOH (3 mL) under Ar. The suspension was degassed under vacuum and purged with $H_2$ three times. The mixture was stirred under $H_2$ (50 psi) at 50° C. for 12 h to give a black suspension. The reaction mixture was filtered through a pad of Celite and washed with DCM (3×50 mL). The filtrate was concentrated under vacuum to provide an oil. The residue was purified by silica gel chromatography (PE/EtOAc=8/1 to 5/1) to afford 74 (20 mg, 13%) as a solid.

$^1$H NMR (400 MHz, CDCl$_3$) δ 3.63-3.61 (m, 1H), 1.96-1.85 (m, 2H), 1.78-1.50 (m, 8H), 1.45-1.19 (s, 12H), 1.17-1.00 (m, 11H), 0.98-0.83 (m, 11H), 0.72-0.59 (m, 3H).

LCMS Rt=1.333 min in 2.0 min chromatography, 30-90 AB, purity 99%, MS ESI calcd. for C$_{27}$H$_{44}$ [M+H-2H$_2$O]$^+$ 369, found 369.

Example 75: Synthesis of (3S,8S,9S,10R,13S,14S, 17R)-17-((2S,3S)-3-hydroxy-6-methylheptan-2-yl)-3,10,13-trimethyl-2,3,4,7,8,9,10,11,12,13,14,15,16,17-tetradecahydro-1H-cyclopenta[a]phenanthren-3-ol (75)

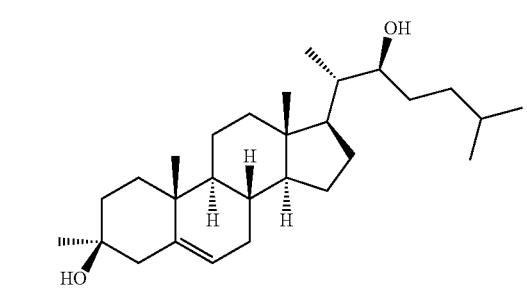
75

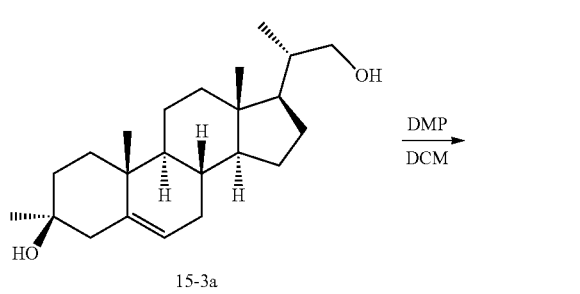
15-3a

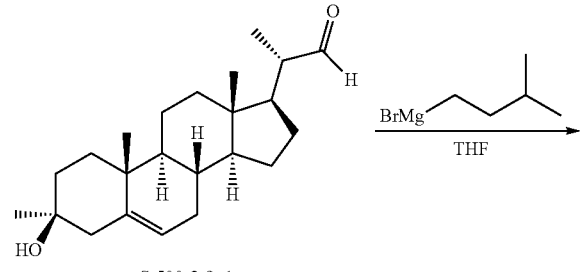
S-500-2-9_1

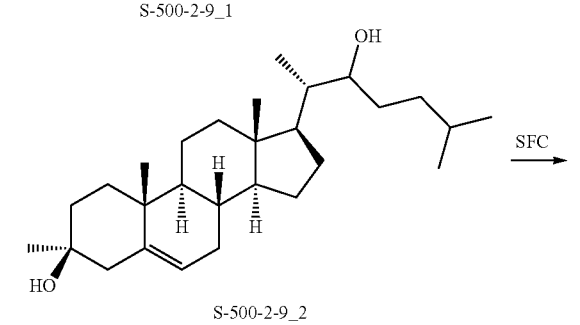
S-500-2-9_2

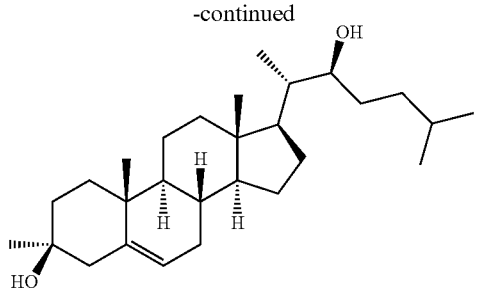
75

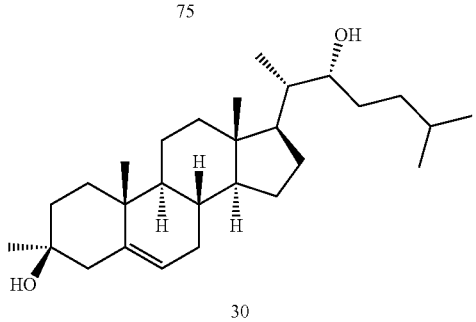
30

1. DMP (2.44 g, 5.76 mmol) was added to a solution of 153a (1 g, 2.88 mmol) in DCM (10 mL). After that, the reaction was stirred at 25° C. for 10 min. The reaction mixture was quenched by adding aqueous saturated NaHCO$_3$ (20 mL) solution and aqueous saturated Na$_2$S$_2$O$_3$ (20 mL) solution, extracted with DCM (2×50 mL). The combined organic layer was washed with aqueous saturated NaHCO$_3$ (3×50 mL) solution and brine (50 mL), dried over Na$_2$SO$_4$, filtered and concentrated in vacuum to give S-500-2-9_1 (1 g, crude) as a solid.

$^1$H NMR (400 MHz, CDCl$_3$) δ 9.57 (br. s, 1H), 5.35-5.25 (m, 1H), 2.50-2.30 (m, 2H), 2.05-1.95 (m, 3H), 1.95-1.80 (m, 1H), 1.75-1.65 (m, 1H), 1.65-1.60 (m, 3H), 1.55-1.50 (m, 2H), 1.50-1.40 (m, 2H), 1.40-1.30 (m, 1H), 1.25-1.20 (m, 2H), 1.20-1.15 (m, 2H), 1.15-1.10 (m, 6H), 1.05-0.95 (m, 5H), 0.90-0.70 (m, 1H), 0.68 (s, 3H).

2. A mixture of magnesium (641 mg, 26.4 mmol) and I2 (33.5 mg, 0.132 mmol) was stirred at 60° C. and a solution of isopentylmagnesium bromide (2 g, 13.2 mmol) in THF (20 mL) was added dropwise under N2. After that, the reaction mixture was stirred at 60° C. for 1 h. The reaction mixture was used directly as isopentylmagnesium bromide solution without any purification. The Grignard solution was added to a solution of S-500-2-9_1 (1 g, 2.90 mmol) in THF (10 mL) at 0° C. under N$_2$. After that, the reaction mixture was stirred at 25° C. for 1 h. The reaction mixture was added saturated aqueous NH$_4$Cl (50 ml) solution, extracted with EtOAc (2×50 mL), washed with brine (50 mL), dried over Na$_2$SO$_4$, filtered and concentrated in vacuum to give a crude product. The crude product was purified by silica gel column (EtOAc/PE=¼) to give impure S-500-2-9_2 (560 mg) as a solid.

$^1$H NMR (400 MHz, CDCl$_3$) δ 5.28-5.25 (m, 1H), 3.90-3.80 (m, 0.25H), 3.68-3.58 (m, 0.75H), 2.48-2.36 (m, 1H), 2.05-1.95 (m, 3H), 1.95-1.80 (m, 1H), 1.80-1.75 (m, 1H), 1.75-1.52 (m, 6H) 1.52-1.42 (m, 6H), 1.42-1.32 (m, 3H), 1.32-1.22 (m, 3H), 1.22-1.12 (m, 3H), 1.12-1.02 (m, 2H), 1.01 (s, 3H), 1.00-0.92 (m, 1H), 0.92-0.85 (m, 9H), 0.85-0.77 (m, 1H), 0.69 (s, 3H).

3. S-500-2-9_2 (560 mg) was purified by SFC (Column: Chiralcel OD-3 150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.) to give impure 30 (160 mg) as a solid and 75 (265 mg, 47%) as a solid. 75:

$^1$H NMR (400 MHz, CDCl$_3$) δ 5.35-5.30 (m, 1H), 3.70-3.60 (m, 1H), 2.50-2.40 (m, 1H), 2.05-1.90 (m, 4H), 1.85-1.75 (m, 2H), 1.75-1.60 (m, 1H), 1.55-1.45 (m, 8H), 1.45-1.25 (m, 8H), 1.25-1.10 (m, 4H), 1.10-1.05 (m, 2H), 1.02 (s, 3H), 0.99-0.91 (m, 3H), 0.91-0.89 (m, 4H), 0.88 (s, 3H), 0.69 (s, 3H).

LCMS Rt=1.162 min in 1.5 min chromatography, 5-95 AB, purity 99%, MS ESI calcd. for C$_{28}$H$_{45}$[M+H-2H$_2$O]$^+$ 381, found 381.

Example 76: Synthesis of (3S,5S,8R,9S,10S,13S,14S,17R)-3-ethyl-17-((S)-1-(1-hydroxycyclopropyl)ethyl)-10,13-dimethylhexadecahydro-1H-cyclopenta[a]phenanthren-3-ol (76)

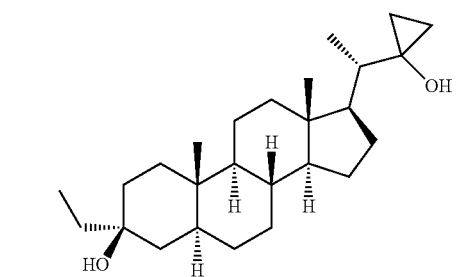

76

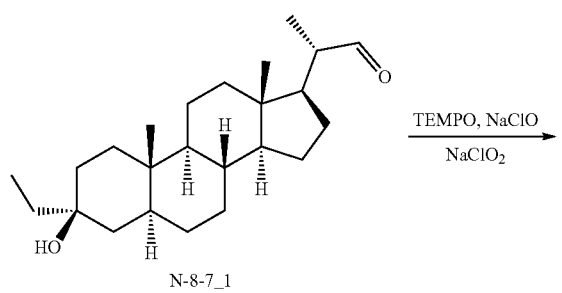

N-8-7_1

TEMPO, NaClO
NaClO$_2$

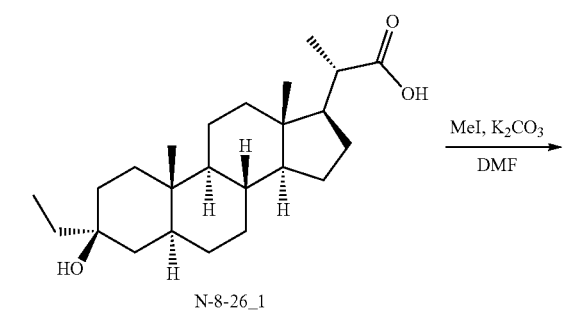

N-8-26_1

MeI, K$_2$CO$_3$
DMF

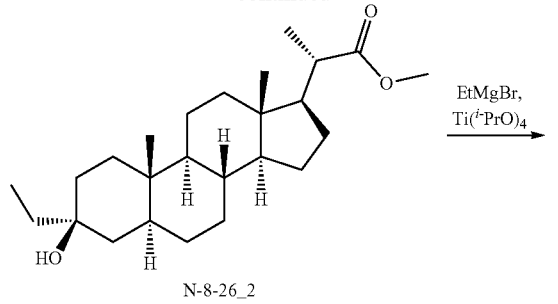

N-8-26_2

EtMgBr,
Ti($^i$PrO)$_4$

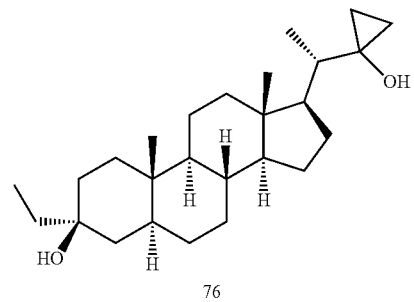

76

1. NaClO$_2$ (374 mg, 4.14 mmol), TEMPO (645 mg, 4.14 mmol) and NaClO (10 mL, 10% in water) were added to a solution of N-8-7_1 (500 mg, 1.38 mmol) in MeCN (30 mL). After the mixture was stirred at 50° C. for 48 hrs, a solid appeared. The solid was collected by filtration and trituration with DCM (5 mL) to give N-8-261 (180 mg, 34%) as a solid.

$^1$H NMR (400 MHz, MeOD) δ 2.30-2.20 (m, 1H), 1.98-1.91 (m, 1H), 1.86-1.72 (m, 1H), 1.71-1.63 (m, 1H), 1.62-1.49 (m, 8H), 1.43-1.31 (m, 4H), 1.30-1.20 (m, 4H), 1.19-1.07 (m, 8H), 1.06-0.86 (m, 8H), 0.75-0.65 (m, 4H).

2. K$_2$CO$_3$ (328 mg, 2.38 mmol) and MeI (686 mg, 4.77 mmol) were added to a solution of N-8-26_1 (180 mg, 0.477 mmol) in DMF (5 mL). After stirring at 20° C. for 16 hrs, the mixture was quenched with 50% NH$_4$Cl (20 ml) and extracted with EtOAc (3×10 mL). The combined organic phase was washed with LiCl (3% in water, 30 mL), dried over Na$_2$SO$_4$, filtered, concentrated and purified by combi-flash (0-10% of EtOAc in PE) to give N-8-26_2 (160 mg, 86%) as a solid.

$^1$H NMR (400 MHz, CDCl$_3$) δ 3.63 (s, 3H), 2.45-2.36 (m, 1H), 1.92-1.85 (m, 1H), 1.74-1.58 (m, 6H), 1.56-1.46 (m, 4H), 1.42-1.19 (m, 9H), 1.18-1.15 (m, 3H), 1.13-0.93 (m, 4H), 0.91-0.84 (m, 4H), 0.82 (s, 3H), 0.70-0.61 (m, 4H).

3. Ti(i-PrO)$_4$ (57.9 mg, 0.204 mmol) and EtMgBr (0.204 mL, 3 M in Et$_2$O, 0.612 mmol) were added to a solution of N-8-26_2 (80 mg, 0.204 mmol) in THF (2 mL) at 20° C. After stirring at 20° C. for 30 minutes, the reaction mixture was quenched with saturated NH$_4$Cl (30 mL) solution and extracted with EtOAc (3×20 mL). The combined organic layer was washed with brine (50 mL), dried over Na$_2$SO$_4$, filtered and concentrated in vacuum to give a crude product, which was purified by silica gel column (0-10% of EtOAc in PE) to afford 76 (16 mg, 20%) as a solid.

$^1$H NMR (400 MHz, CDCl$_3$) δ 1.98-1.86 (m, 2H), 1.69-1.58 (m, 6H), 1.54-1.44 (m, 3H), 1.44-1.29 (m, 4H), 1.28-1.18 (m, 4H), 1.18-1.10 (m, 5H), 1.09-0.93 (m, 4H), 0.91-0.81 (m, 7H), 0.71-0.57 (m, 6H), 0.31-0.24 (m, 1H).

LCMS Rt=1.184 min in 2.0 min chromatography, 30-90AB_E, purity 100%, MS ESI calcd. for C$_{26}$H$_{41}$ [M+H]$^+$ 353, found 353.

Example 77: Synthesis of (3S,8S,9S,10R,13S,14S, 17R)-3-ethyl-17-((2S,3S)-3-hydroxy-6-methylheptan-2-yl)-10,13-dimethyl-2,3,4,7,8,9,10,11,12,13,14, 15,16,17-tetradecahydro-1H-cyclopenta[a]phenanthren-3-ol (77)

Example 78: Synthesis of (3S,5S,8R,9S,10S,13S, 14S,17R)-17-((1S,2S)-1-cyclopentyl-1-hydroxypropan-2-yl)-3-ethyl-10,13-dimethylhexadecahydro-1H-cyclopenta[a]phenanthren-3-ol (78)

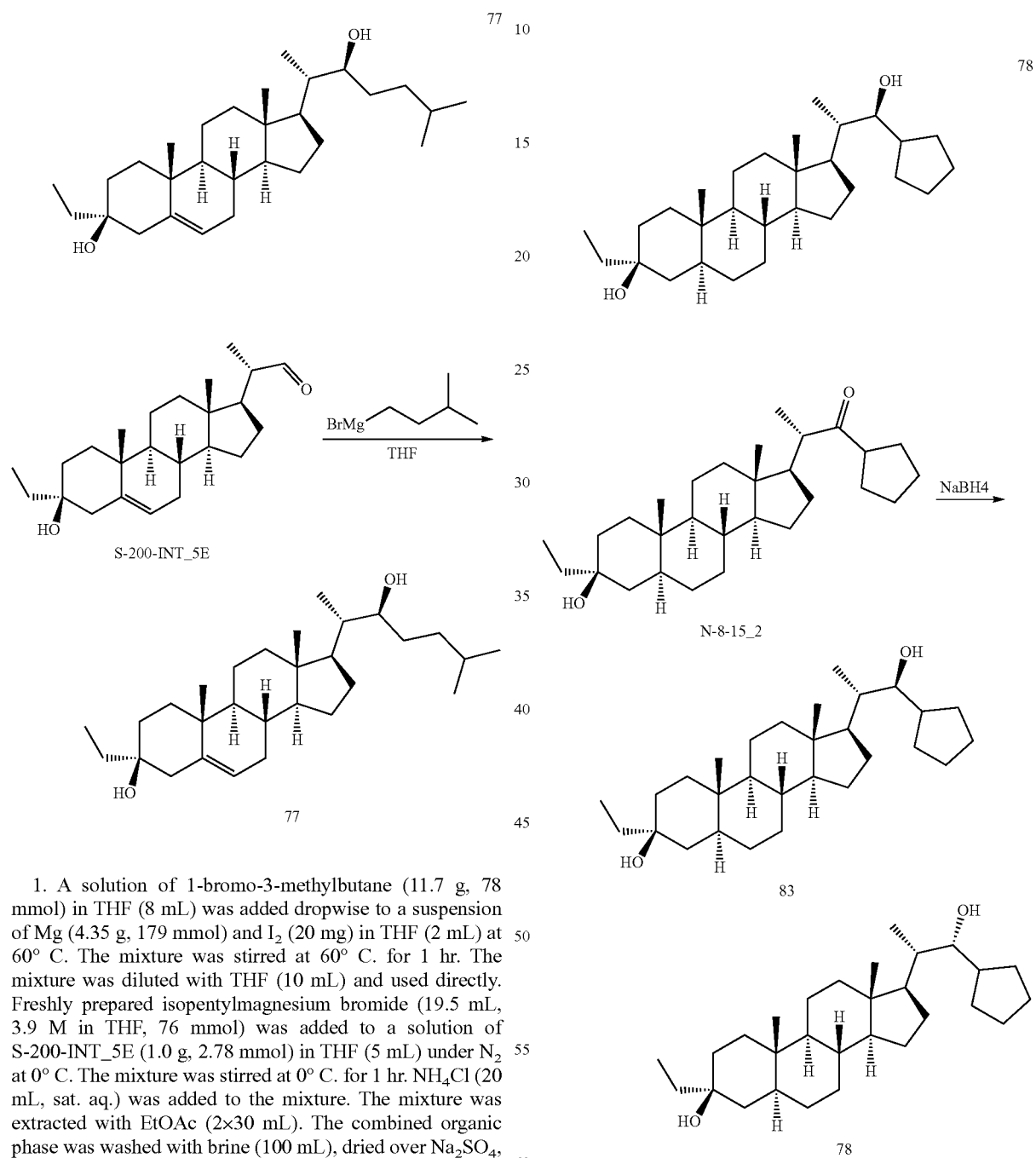

1. A solution of 1-bromo-3-methylbutane (11.7 g, 78 mmol) in THF (8 mL) was added dropwise to a suspension of Mg (4.35 g, 179 mmol) and $I_2$ (20 mg) in THF (2 mL) at 60° C. The mixture was stirred at 60° C. for 1 hr. The mixture was diluted with THF (10 mL) and used directly. Freshly prepared isopentylmagnesium bromide (19.5 mL, 3.9 M in THF, 76 mmol) was added to a solution of S-200-INT_5E (1.0 g, 2.78 mmol) in THF (5 mL) under $N_2$ at 0° C. The mixture was stirred at 0° C. for 1 hr. $NH_4Cl$ (20 mL, sat. aq.) was added to the mixture. The mixture was extracted with EtOAc (2×30 mL). The combined organic phase was washed with brine (100 mL), dried over $Na_2SO_4$, concentrated under vacuum, purified by silica gel (PE/EtOAc=20/1 to 10/1), and re-crystallized from $CH_3CN$ (10 mL) to give 77 (255 mg, 21%) as a solid.

$^1$H NMR (400 MHz, $CDCl_3$) δ 5.32-5.26 (m, 1H), 3.66-3.59 (m, 1H), 2.42-2.32 (m, 1H), 2.07-1.85 (m, 4H), 1.77-1.58 (m, 4H), 1.55-1.38 (m, 10H), 1.38-1.19 (m, 5H), 1.19-1.00 (m, 8H), 1.00-0.81 (m, 13H), 0.69 (s, 3H).

LCMS Rt=1.306 min in 2.0 min chromatography, 30-90 AB, purity 100%, MS ESI calcd. for $C_{29}H_{49}O$ [M+H—$H_2O$]$^+$413, found 413.

1. $NaBH_4$ (550 mg, 14.5 mmol) was added to a mixture of N-8-15_2 (240 mg, 0.559 mmol) in MeOH (3 mL) and THF (2 mL). The mixture was stirred at 15° C. for 0.5 h. Another batch of $NaBH_4$ (550 mg, 14.5 mmol) was added. The reaction mixture was stirred for another 1 hr. To the reaction mixture was added water (5 ml). The resulting mixture was extracted with EtOAc (2×10 mL). The combined organic layer was washed with brine (10 mL), dried over Na₂SO₄, filtered and concentrated. The residue was purified by flash column (0~5% EtOAc in PE) to give and 58 (7 mg, 5%) as a solid and 78 (50 mg, impure) was further purified by flash column (0~5% of EtOAc in PE) to give 78 (17 mg, 12%) as a solid.

78:

$^1$H NMR (400 MHz, CDCl₃) δ 3.38-3.47 (m, 1H), 2.01-1.82 (m, 4H), 1.71-1.53 (m, 11H), 1.53-1.48 (m, 4H), 1.48-1.30 (m, 5H), 1.30-1.11 (m, 7H), 1.11-0.98 (m, 5H), 0.98-0.85 (m, 7H), 0.85-0.80 (m, 3H), 0.65 (s, 3H).

LCMS Rt=1.358 min in 2 min chromatography, 30-90AB_7MIN_E, purity 100%, MS ESI calcd. for C₂₉H₄₇ [M+H-2H₂O]⁺ 395, found 395.

HPLC Rt=6.093 min in 10 min chromatography, 50-100AB_10 MIN·M, purity 98%.

Example 79: Synthesis of (1R,3S,4S)-4-((3S,5S,8R, 9S,10S,13S,14S,17R)-3-hydroxy-10,13-dimethyl-3-(trifluoromethyl)hexadecahydro-1H-cyclopenta[a]phenanthren-17-yl)-1-phenylpentane-1,3-diol (79)

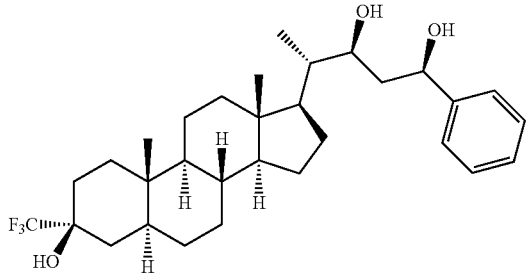

The synthesis of 79 is described in Example 13.

79:

$^1$H NMR (400 MHz, CDCl₃) δ 7.43-7.28 (m, 5H), 5.05-4.94 (m, 1H), 4.04-3.91 (m, 1H), 2.51 (brs, 1H), 2.07-1.78 (m, 6H), 1.70-1.61 (m, 4H), 1.51-1.41 (m, 3H), 1.39-1.12 (m, 11H), 1.05-0.98 (m, 2H), 0.91-0.81 (m, 7H), 0.71-0.60 (m, 4H).

LCMS Rt=1.298 min in 2 min chromatography, 10-80AB_2MIN_E, purity 96.7%, MS ESI calcd. for C₃₁H₄₅F₃O₃Na [M+Na]⁺545, found 545.

SFC Rt=1.483 min in 10 min chromatography, IC-3_MeOH(DEA)_40_2.5ML, 100% de. 13:

$^1$H NMR (400 MHz, CDCl₃) δ 7.40-7.28 (m, 5H), 5.12-5.07 (m, 1H), 3.95-3.88 (m, 1H), 2.76 (brs, 1H), 2.08-1.78 (m, 6H), 1.75-1.60 (m, 5H), 1.51-1.38 (m, 4H), 1.36-1.09 (m, 9H), 1.00-0.89 (m, 6H), 0.83 (s, 3H), 0.71-0.64 (m, 1H), 0.63 (s, 3H).

LCMS Rt=1.309 min in 2 min chromatography, 10-80AB_2MIN_E, purity 100%, MS ESI calcd. for C₃₁H₄₅F₃O₃Na [M+Na]⁺545, found 545.

SFC Rt=1.683 min in 5 min chromatography, IC-3_MeOH(DEA)_40_2.5ML, 98.94% de.

SFC Rt=4.785 min in 8 min chromatography, AD_MEOH (DEA)_5_40_2,8ML_8MIN, 94.03% de.

Example 80: Synthesis of (3S,8R,9S,10R,13S,14S, 17R)-17-((2S,3S)-3-hydroxy-6-methylheptan-2-yl)-3,13-dimethyl-2,3,4,7,8,9,10,11,12,13,14,15,16,17-tetradecahydro-1H-cyclopenta[a]phenanthren-3-ol (80)

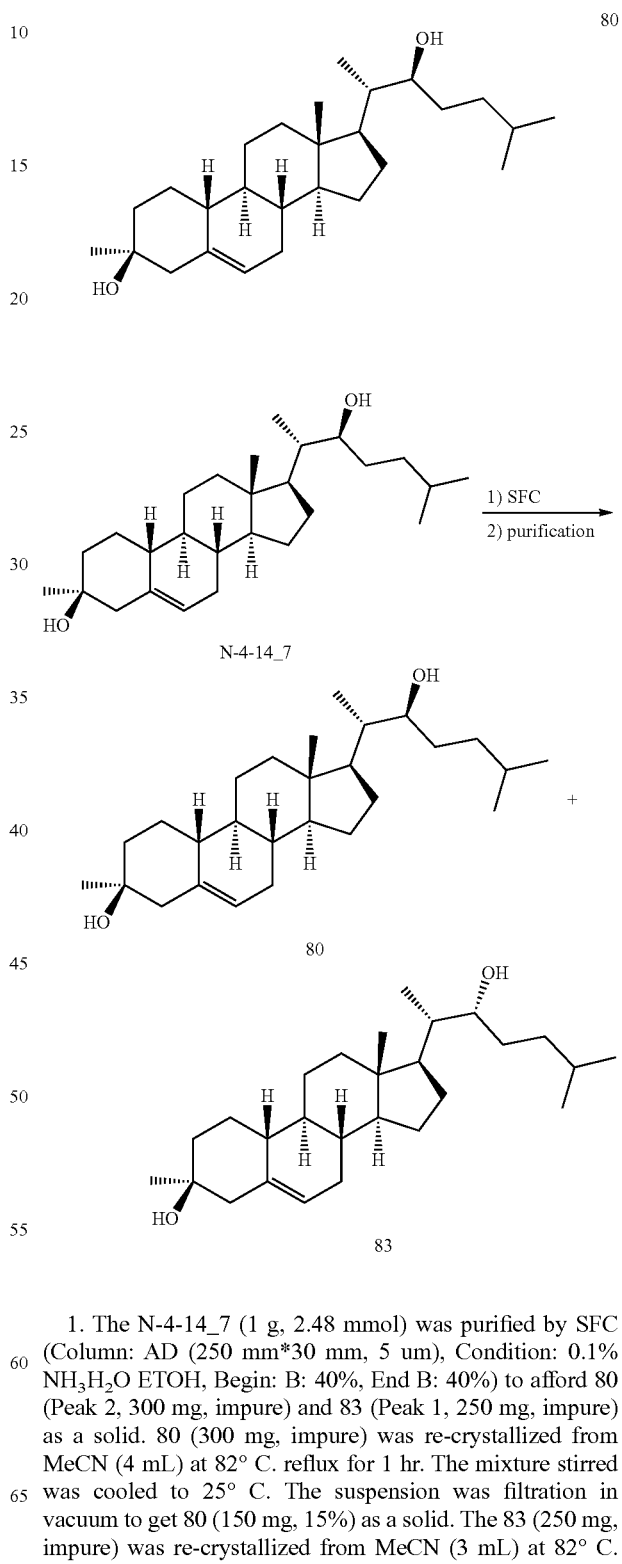

1. The N-4-14_7 (1 g, 2.48 mmol) was purified by SFC (Column: AD (250 mm*30 mm, 5 um), Condition: 0.1% NH₃H₂O ETOH, Begin: B: 40%, End B: 40%) to afford 80 (Peak 2, 300 mg, impure) and 83 (Peak 1, 250 mg, impure) as a solid. 80 (300 mg, impure) was re-crystallized from MeCN (4 mL) at 82° C. reflux for 1 hr. The mixture stirred was cooled to 25° C. The suspension was filtration in vacuum to get 80 (150 mg, 15%) as a solid. The 83 (250 mg, impure) was re-crystallized from MeCN (3 mL) at 82° C.

reflux for 1 hr. The mixture stirred was cool to 25° C. The suspension was filtration in vacuum to get 83 (150 mg, 15%) as a solid.

80:

$^1$H NMR (400 MHz, CDCl$_3$) δ 5.41-5.39 (m, 1H), 3.63-3.62 (m, 1H), 2.22-1.67 (m, 10H), 1.64-1.36 (m, 12H), 1.16-1.03 (m, 8H), 0.98-0.80 (m, 11H), 0.70 (s, 3H).

LCMS Rt=1.276 min in 2.0 min chromatography, 30-90 AB, purity 99%, MS ESI calcd. for $C_{27}H_{42}$ [M+H-2H$_2$O]$^+$ 367, found 367.

SFC Rt=5.236 min in 10 min chromatography, AD_3_EtOH_DEA_5_40_25ML, 100% de.

Example 81: Synthesis of (3S,8S,9S,10R,13S,14S,17R)-3-ethyl-10,13-dimethyl-17-((2S,3S)-4,4,4-trifluoro-3-hydroxybutan-2-yl)-2,3,4,7,8,9,10,11,12,13,14,15,16,17-tetradecahydro-1H-cyclopenta[a]phenanthren-3-ol (81)

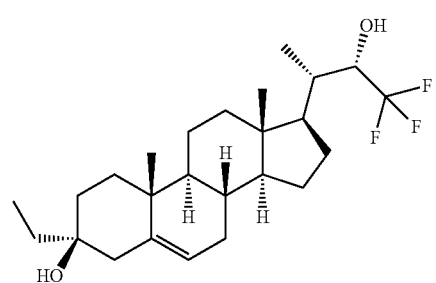

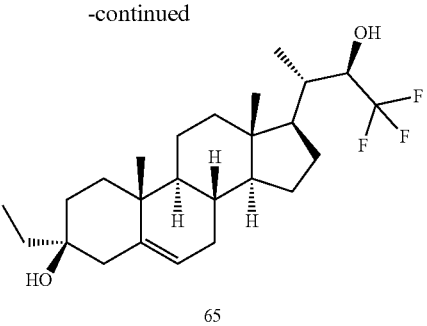

1. S-500-6-1_2 (350 mg) was purified by SFC (Column: AD (250 mm*30 mm, 5 um), Condition: 0.1% NH$_3$.H$_2$O EtOH, Gradient: from 35% to 35%, Flow Rate (ml/min): 60 mL/min, 25° C.) to afford 81 (Peak 1, 130 mg, 37%) and 65 (Peak 2, 180 mg, 52%) as a white solid.

81:

$^1$H NMR (400 MHz, CDCl3) δ 5.34-5.24 (m, 1H), 4.09-4.00 (m, 1H), 2.43-2.33 (m, 1H), 2.14 (d, J=4 Hz, 1H), 2.07-1.80 (m, 5H), 1.77-1.55 (m, 5H), 1.53-1.30 (m, 7H), 1.28-1.00 (m, 11H), 1.00-0.91 (m, 1H), 0.85 (t, J=8 Hz, 3H), 0.70 (s, 3H).

LCMS Rt=1.220 min in 2.0 min chromatography, 30-90 AB, purity 100%, MS ESI calcd. For $C_{25}H_{38}F_3O$ [M+H—H$_2$O]$^+$ 411, found 411.

SFC__E1 Peak 1: Rt=4.561 min in 10 min chromatography, AD_3_EtOH_DEA_5_40_25ML ("Column: Chiralpak AD-3150×4.6 mm I.D., 3 um Mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C."), 100% de.

Example 82: Synthesis of (3S,5R,8R,9R,10S,13S,14S,17R)-3-ethyl-17-((2S,3S)-3-hydroxy-6-methylheptan-2-yl)-13-methylhexadecahydro-1H-cyclopenta[a]phenanthren-3-ol (82)

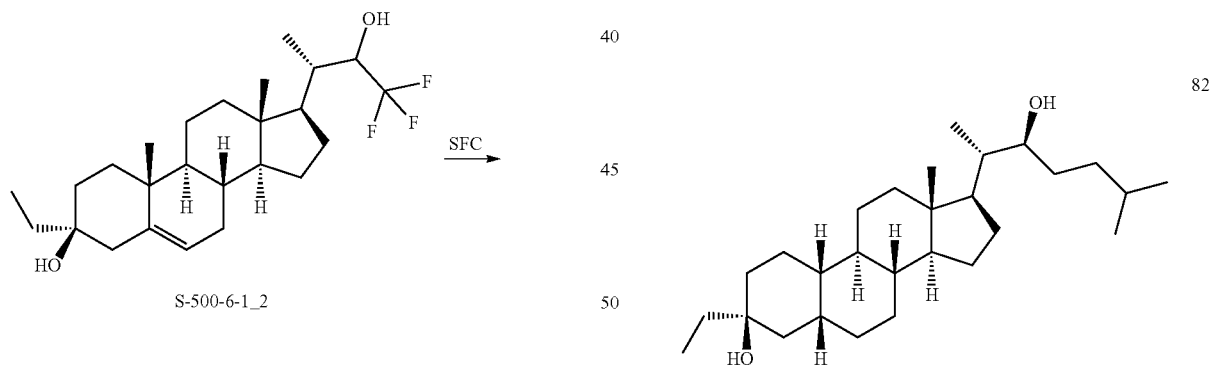

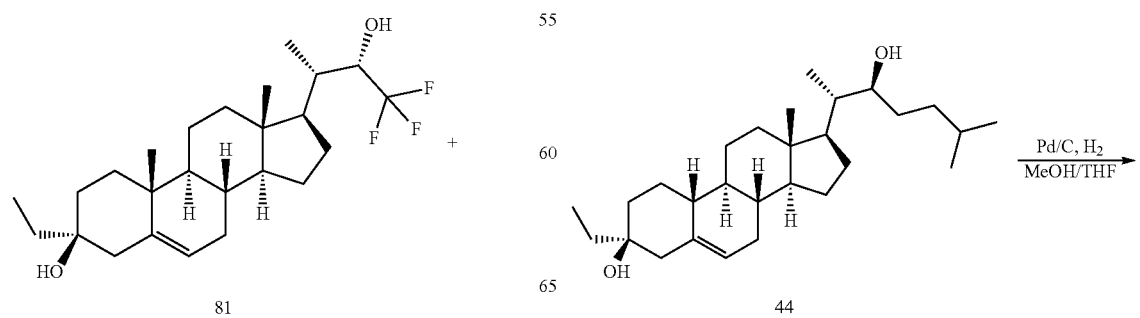

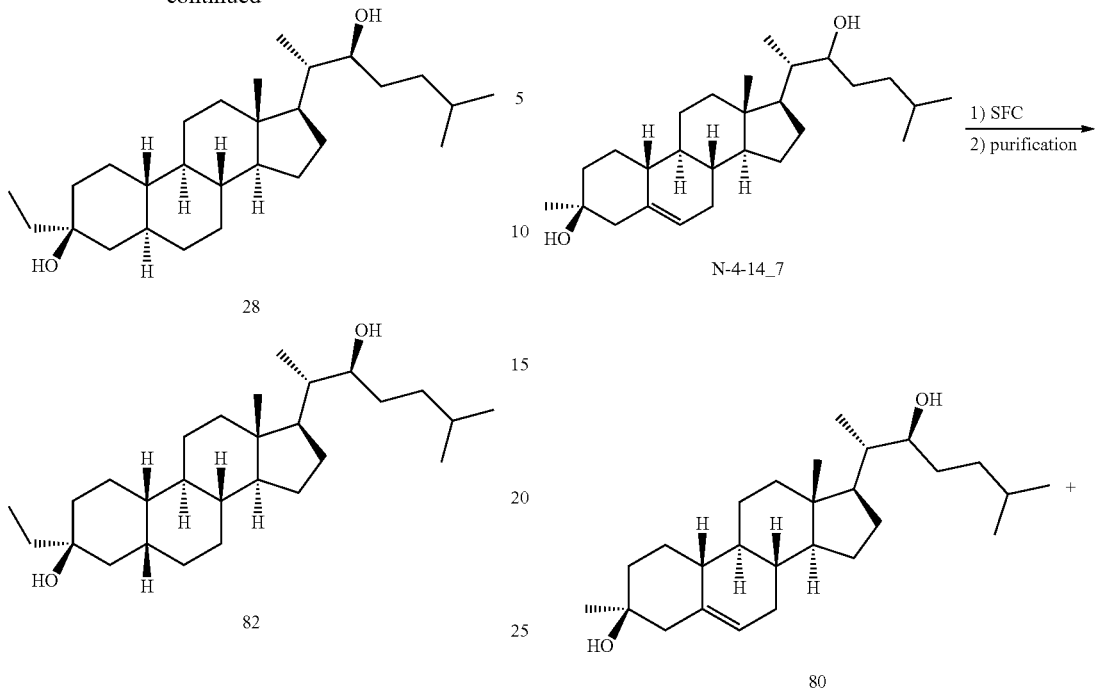

28

82

1. Pd/C (dry, 200 mg) was added to a solution of 44 (200 mg, 0.480 mmol) in MeOH/THF (10 mL/10 mL) under Ar. The suspension was degassed under vacuum and purged with $H_2$ three times. The mixture was stirred under $H_2$ (50 psi) at 50° C. for 48 hrs to give a black suspension. The reaction mixture was filtered through a pad of Celite and washed with THF (100 mL). The filtrate was concentrated to give 28 (30 mg, 15%) as a solid and 82 (30 mg, 15%) as a solid.

82:

$^1$H NMR (400 MHz, CDCl3) δ 3.63-3.61 (m, 1H), 2.13-2.00 (m, 1H), 1.99-1.81 (m, 2H), 1.72-1.57 (m, 6H), 1.54-1.34 (m, 11H), 1.33-1.16 (m, 7H), 1.15-0.96 (m, 5H), 0.92-0.85 (m, 13H), 0.81-0.69 (m, 1H), 0.67 (s, 3H).

LCMS Rt=1.348 min in 2 min chromatography, 30-90 AB, purity 100%, MS ESI calcd. For $C_{2-8}H_{47}$ $[M+H-2H_2O]^+$ 383, found 383.

Example 83: Synthesis of (3S,8R,9S,10R,13S,14S,17R)-17-((2S,3R)-3-hydroxy-6-methylheptan-2-yl)-3,13-dimethyl-2,3,4,7,8,9,10,11,12,13,14,15,16,17-tetradecahydro-1H-cyclopenta[a]phenanthren-3-ol (83)

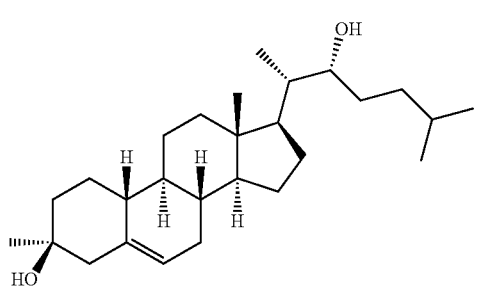

83

1. The N-4-14_7 (1 g, 2.48 mmol) was purified by SFC (Column: AD (250 mm*30 mm, 5 um), Condition: 0.1% $NH_3H_2O$ ETOH, Begin: B: 40%, End B: 40%) to afford 80 (Peak 2, 300 mg, impure) and 83 (Peak 1, 250 mg, impure) as a solid. The 80 (300 mg, impure) was re-crystallized from MeCN (4 mL) at 82° C. reflux for 1 hr. The mixture stirred was cooled to 25° C. The suspension was filtered under vacuum to yield 80 (150 mg, 15%) as a solid. The 83 (250 mg, impure) was re-crystallized from MeCN (3 mL) at 82° C. reflux for 1 h. The mixture stirred was cool to 25° C. The suspension was filtered under vacuum to yield 83 (150 mg, 15%) as a solid. 83:

$^1$H NMR (400 MHz, CDCl$_3$) δ 5.41-5.39 (m, 1H), 3.62-3.60 (m, 1H), 2.22-1.89 (m, 6H), 1.64-1.49 (m, 9H), 1.46-1.11 (m, 16H), 0.98-0.86 (m, 10H), 0.70 (s, 3H).

LCMS Rt=1.268 min in 2.0 min chromatography, 30-90 AB, purity 100%, MS ESI calcd. for $C_{27}H_{42}$ $[M+H-2H_2O]^+$ 367, found 367.

SFC Rt=4.609 min in 10 min chromatography, AD_3_EtOH_DEA_5_40_25ML, 100% de.

Example 84: Synthesis of (3S,5S,8R,9S,10S,13S, 14S,17R)-17-((2S,3R)-4-cyclopentyl-3-hydroxybu-tan-2-yl)-3-ethyl-10,13-dimethylhexadecahydro-1H-cyclopenta[a]phenanthren-3-ol (84)

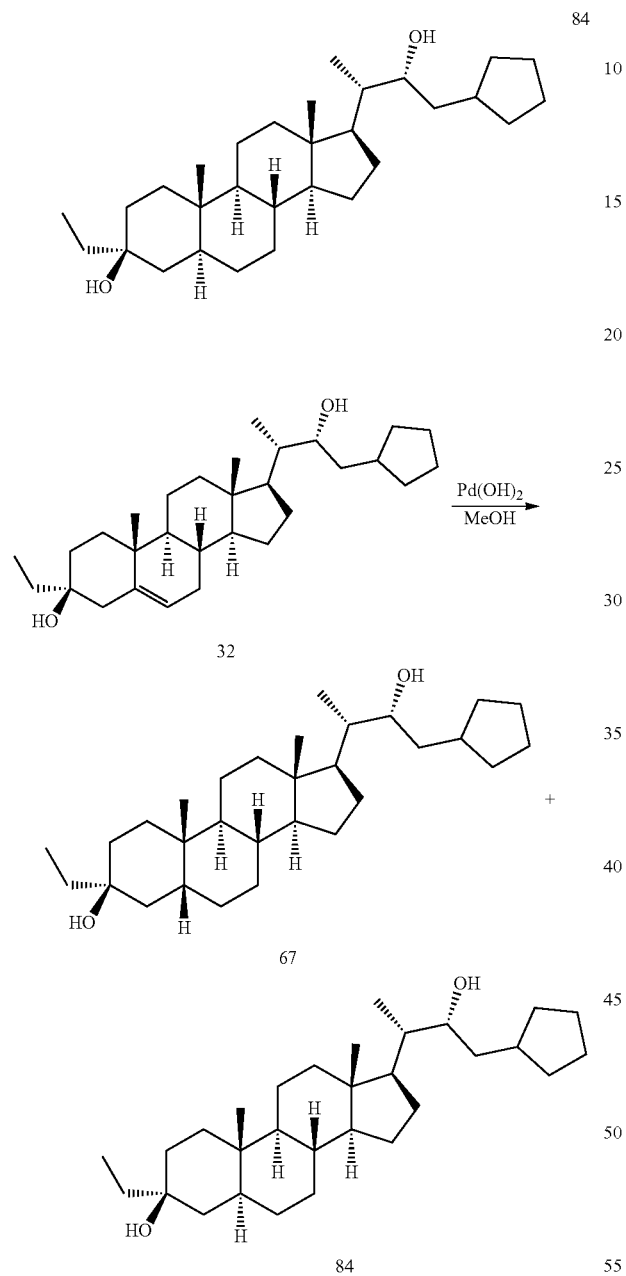

1. Pd(OH)$_2$ (160 mg, dry) was added to a solution of 32 (80 mg, 0.18 mmol) in MeOH (20 mL). The mixture was stirred at 50° C. under H$_2$ (50 Psi) for 48 hrs. The mixture was filtered, concentrated and purified by combi-flash (0~15% of EtOAc in PE) to give 67 (10 mg, 12%) and 84 (30 mg, 37%) as a solid.

84:
$^1$H NMR (400 MHz, CDCl$_3$) δ 3.75-3.66 (m, 1H), 2.00-1.90 (m, 2H), 1.86-1.75 (m, 2H), 1.73-1.55 (m, 11H), 1.53-1.26 (m, 9H), 1.25-1.15 (m, 6H), 1.14-1.03 (m, 5H), 1.02-0.92 (m, 3H), 0.91-0.85 (m, 6H), 0.82 (s, 3H), 0.72-0.58 (m, 4H).

LCMS Rt=1.518 min in 2.0 min chromatography, 30-90AB_E, purity 100%, MS ESI calcd. for C$_{30}$H$_{49}$ [M+H—H$_2$O]$^+$409, found 409.

Example 85: Synthesis of (3S,5S,8R,9S,10S,13S, 14S,17R)-17-((2S,3R)-3-hydroxy-6-methylheptan-2-yl)-10,13-dimethyl-3-(trifluoromethyl)hexadeca-hydro-1H-cyclopenta[a]phenanthren-3-ol (85)

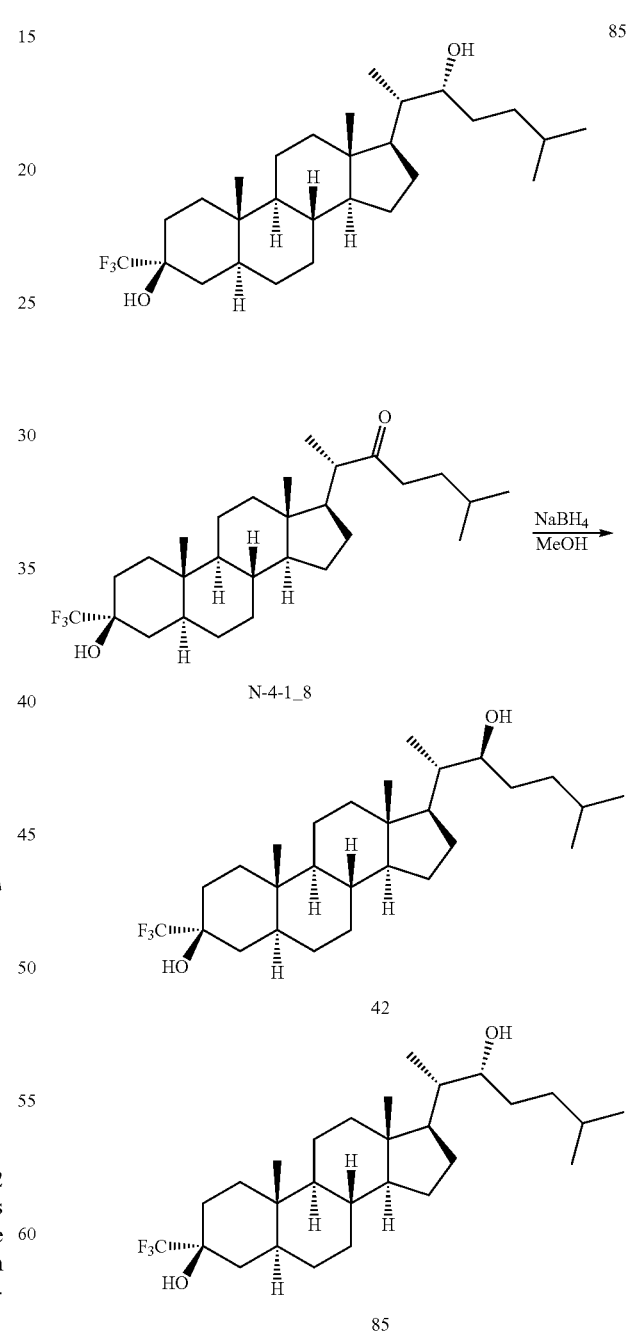

1. NaBH$_4$ (0.96 g, 25.4 mmol) was added in portions to a solution of N-4-1_8 (0.6 g, 1.27 mmol) in THF (10 mL) and MeOH (5 mL) at 15° C. The mixture was stirred at 15° C. for 30 mins. To the mixture was added NH₄Cl (50 mL, 10%). The mixture was extracted with EtOAc (2×50 mL). The combined organic layer was dried over Na₂SO₄, filtered and concentrated under vacuum and purified by flash column (0~15% EtOAc in PE) to give impure 42 and 85. 42 was triturated from MeCN (10 mL) at 15° C. and dried in vacuum to give 42 (153 mg, 25%) as a solid. 85 was purified by flash column (0~15% EtOAc in PE) to provide an oil, which was treated with MeCN (5 mL) and water (5 mL), concentrated in vacuum to give 85 (70 mg, 12%) as a solid.

85:

¹H NMR (400 MHz, CDCl₃) δ 3.66-3.55 (m, 1H), 2.10-1.91 (m, 3H), 1.88-1.78 (m, 1H), 1.72-1.55 (m, 6H), 1.50-1.38 (m, 9H), 1.37-0.95 (m, 10H), 0.94-0.79 (m, 13H), 0.75-0.61 (m, 4H).

LCMS Rt=1.343 min in 2.0 min chromatography, 30-90_AB_E, purity 100%, MS ESI calcd. for C₂₈H₄₆F₃O [M+H—H₂O]⁺ 455, found 455.

HPLC Rt=5.14 min in 10.0 min chromatography, 50-100_AB_E, purity 98.56%.

Example 86: Synthesis of (3S,5S,8R,9S,10S,13S,14S,17R)-3-ethyl-17-((1S,2S)-1-hydroxy-1-(tetrahydro-2H-pyran-4-yl)propan-2-yl)-10,13-dimethyl-hexadecahydro-1H-cyclopenta[a]phenanthren-3-ol (86)

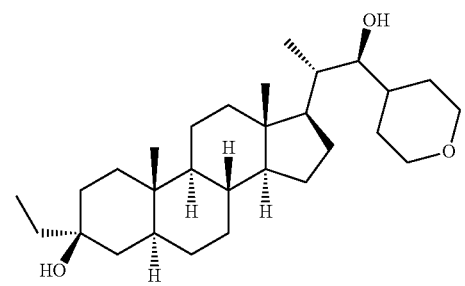

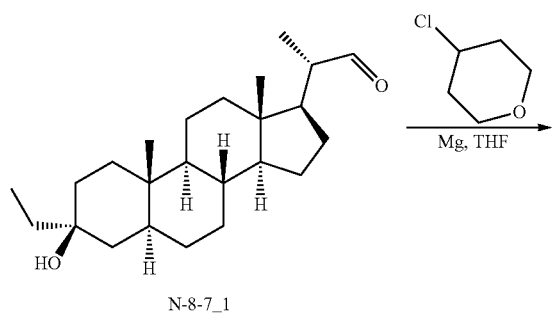

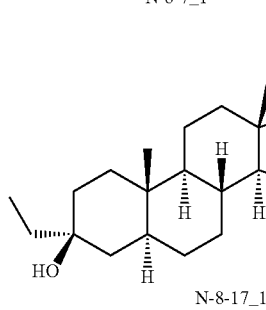

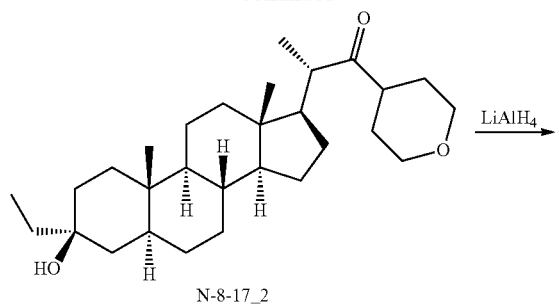

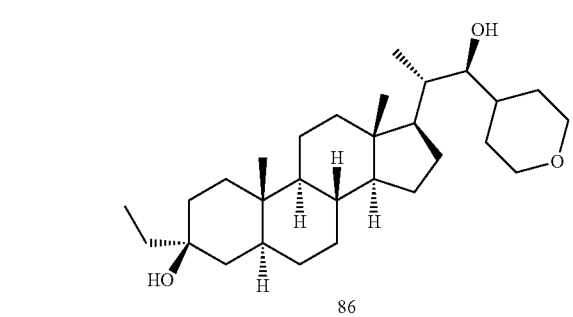

1. A solution of 4-chlorotetrahydro-2H-pyran (1.2 g, 10 mmol) in THF (5 mL) was added dropwise to a mixture of Mg (486 mg, 20 mmol) and I2 (1 mg) at 70° C. The mixture was stirred at 50° C. for 0.5 h, diluted with THF (5 mL) and used directly. To a solution of (tetrahydro-2H-pyran-4-yl) magnesium chloride (4.14 mL, 1 M in THF) was added N-8-7_1 (500 mg, 1.38 mmol) in THF (5 mL) at 0° C. under N₂. Then the mixture was stirred at 15° C. for another 18 hrs. The reaction mixture was quenched with sat. NH₄Cl (5 mL), and the resulting mixture was extracted with EtOAc (2×10 mL). The combined organic layer was washed with brine (5 mL), dried over Na₂SO₄, filtered and concentrated. The residue was purified by flash column (0-15% EtOAc in PE) to give N-8-17_1 (350 mg, 57%) as a solid.

¹H NMR (400 MHz, CDCl₃) δ 4.08-3.91 (m, 2H), 3.43-3.31 (m, 2H), 3.31-3.25 (m, 1H), 1.98-1.91 (m, 2H), 1.91-1.80 (m, 1H), 1.70-1.50 (m, 10H), 1.50-1.41 (m, 2H), 1.41-1.32 (m, 5H), 1.32-1.15 (m, 9H), 1.15-0.92 (m, 6H), 0.92-0.83 (m, 7H), 0.65 (s, 3H).

2. DMP (0.852 g, 2.01 mmol) was added to a solution of N-8-17_1 (300 mg, 0.671 mmol) in DCM (5 mL). After stirring at 15° C. for 10 min, the reaction mixture was quenched with saturated NaHCO₃ (20 mL) until pH of the aqueous layer became about 9. The mixture was filtered. The DCM layer was separated and the aqueous phase was extracted with DCM (2×20 mL). The combined organic phase was washed with saturated Na₂S₂O₃ aqueous (3×20 mL), sat. NaHCO₃ (20 mL), brine (50 mL), dried over Na₂SO₄, filtered, concentrated and purified by combi-flash (0-30% of EtOAc in PE) to give N-8-17_3 (200 mg) as a solid.

¹H NMR (400 MHz, CDCl₃) δ 4.08-3.91 (m, 2H), 3.50-3.31 (m, 2H), 2.73-2.51 (m, 2H), 1.98-1.79 (m, 1H), 1.79-1.42 (m, 16H), 1.42-1.18 (m, 7H), 1.18-0.93 (m, 8H), 0.93-0.79 (m, 6H), 0.68 (s, 4H).

3. LiAlH₄ (50.9 mg, 1.34 mmol) was added to a mixture of N-8-17_3 (200 mg, 0.449 mmol) in THF (5 mL) at 0° C. After stirred at 15° C. for 0.5 h, the reaction mixture was quenched with water (3 mL) and extracted with EtOAc (2×10 mL). The combined organic layer was washed with brine (10 mL), dried over Na₂SO₄, filtered and concentrated. The residue was purified by flash column (0-5% EtOAc in PE) to give 86 (23 mg, 11%) as a solid.

¹H NMR (400 MHz, CDCl₃) δ 4.08-3.91 (m, 2H), 3.41-3.31 (m, 2H), 3.31-3.22 (m, 1H), 2.01-1.79 (m, 3H), 1.70-1.61 (m, 1H), 1.61-1.53 (m, 8H), 1.53-1.51 (m, 1H), 1.51-1.39 (m, 5H), 1.39-1.13 (m, 8H), 1.13-0.92 (m, 5H), 0.92-0.85 (m, 7H), 0.82 (s, 3H), 0.66 (s, 4H).

LCMS Rt=4.832 min in 7 min chromatography, 30-90AB_7MIN_E, purity 100%, MS ESI calcd. for C₂₉H₄₇O [M+H-2H₂O]⁺ 411, found 411.

HPLC Rt=6.338 min in 10 min chromatography, 30-90AB_1.2 mL e. Met, 100% purity.

Example 87: Synthesis of (3S,5R,8R,9S,10S,13S,14S,17R)-17-((2S,3R)-4-(4,4-dimethylcyclohexyl)-3-hydroxybutan-2-yl)-3-ethyl-10,13-dimethylhexadecahydro-1H-cyclopenta[a]phenanthren-3-ol (87)

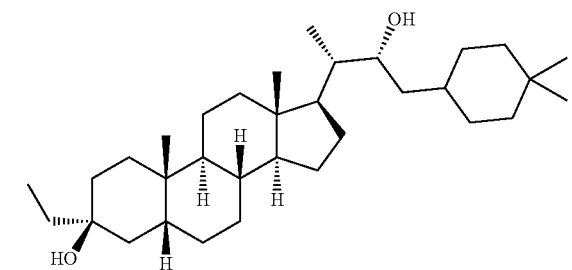

87

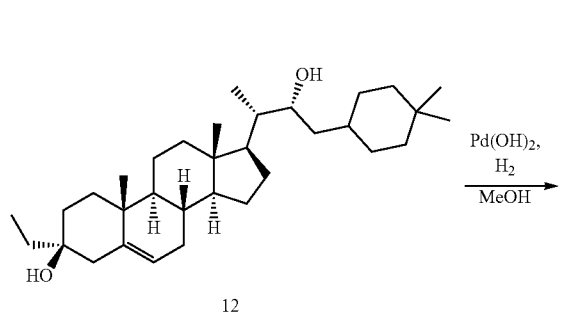

12

Pd(OH)₂, H₂ / MeOH →

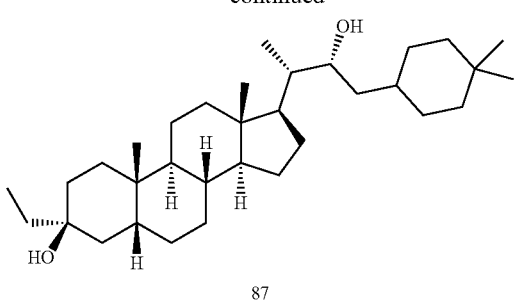

87

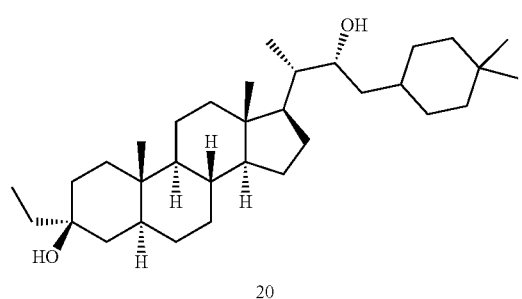

20

1. Pd(OH)₂ (150 mg, dry) was added to a solution of 12 (100 mg, 0.206 mmol) in MeOH (20 mL). The mixture was stirred at 50° C. under H₂ (50 Psi) for 48 hrs. The mixture was filtered, concentrated and purified by combi-flash (0~15% of EtOAc in PE) to give 87 (12 mg, 12%) and 20 (11 mg, 11%) as a solid.

87:

¹H NMR (400 MHz, CDCl₃) δ 3.82-3.75 (m, 1H), 2.00-1.83 (m, 2H), 1.80-1.58 (m, 7H). 1.52-1.42 (m, 4H), 1.40-1.27 (m, 10H), 1.25-1.14 (m, 10H), 1.13-0.98 (m, 6H), 0.96 (s, 3H), 0.94-0.82 (m, 12H), 0.67 (s, 3H).

LCMS Rt=1.734 min in 2.0 min chromatography, 30-90AB_E, purity 100%, MS ESI calcd. for C₃₃H₅₅ [M+H-2H₂O]⁺ 451, found 451.

Example 88: Synthesis of (3S,5S,8R,9R,10S,13S,14S,17R)-17-((2S,3R)-3-hydroxy-6-methylheptan-2-yl)-3,13-dimethylhexadecahydro-1H-cyclopenta[a]phenanthren-3-ol (88)

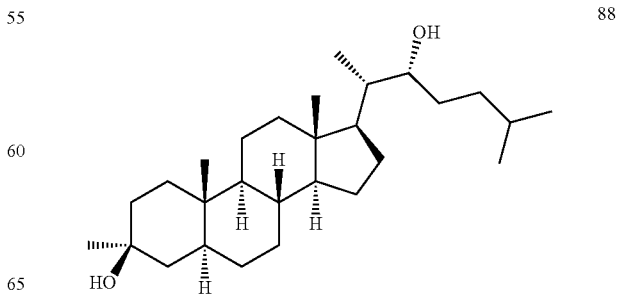

88

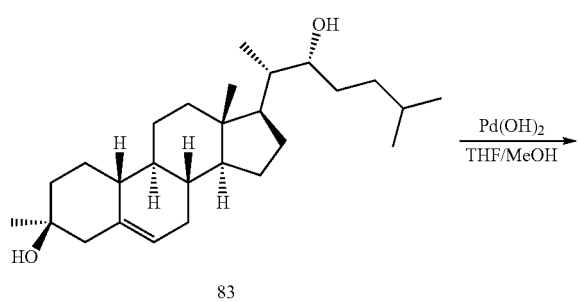

under Ar. The suspension was degassed under vacuum and purged with H₂ three times. The mixture was stirred under H₂ (50 psi) at 50° C. for 12 h to give a black suspension. The reaction mixture was filtered through a pad of Celite and washed with DCM (3 10×50 mL). The filtrate was concentrated under vacuum to provide an oil. The residue was purified by silica gel chromatography (PE/EtOAc=8/1 to 5/1) to afford 88 (18 mg, 12%) as a solid.

$^1$H NMR (400 MHz, CDCl$_3$) δ 3.62-3.59 (m, 1H), 1.97-1.81 (m, 2H), 1.76-1.50 (m, 12H), 1.46-1.28 (m, 5H), 1.24-1.03 (m, 12H), 0.95-0.83 (m, 11H), 0.74-0.57 (m, 5H).

LCMS Rt=1.317 min in 2.0 min chromatography, 30-90 AB, purity 99%, MS ESI calcd. for C$_{27}$H$_4$ [M+H-2H$_2$O]$^+$ 369, found 369.

Example 89: Synthesis of (3S,5S,8R,9S,10S,13S, 14S,17R)-3-ethyl-17-((1S,2S)-1-hydroxy-1-(pyridin-3-yl)propan-2-yl)-10,13-dimethylhexadecahydro-1H-cyclopenta[a]phenanthren-3-ol (89)

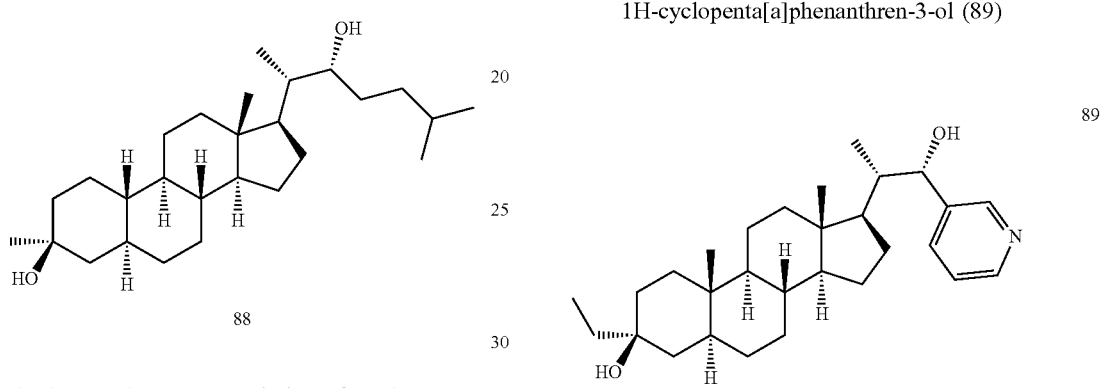

1. Pd(OH)$_2$ (200 mg) was to a solution of 83 (150 mg, 0.372 mmol) in MeOH (3 ml) and THF (3 mL) was added

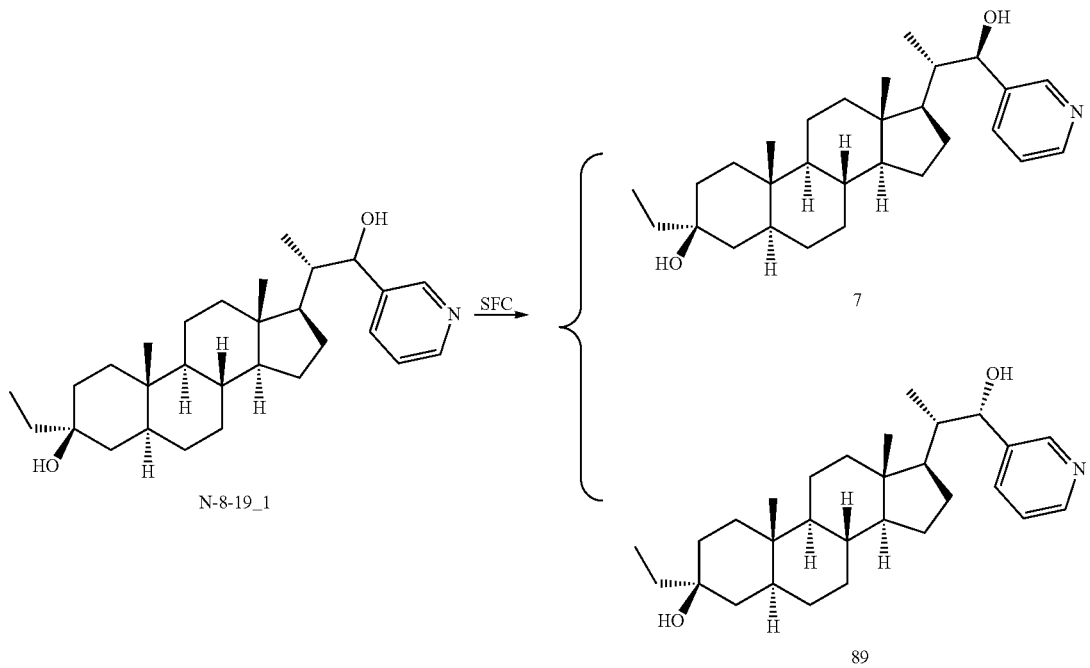

1. N-8-19_1 (3340) (100 mg, 0.227 mmol) was separated by SFC (column: AD (250 mm*30 mm, 5 um), gradient: 50-50% B (A=0.05% $NH_3/H_2O$, B=MeOH), flow rate: 80 mL/min) to give 7 (Peak 1, 57 mg, 57%) and 89 (Peak 2, 8 mg, 8%) as a solid.

SFC Peak 1: Rt=1.798 min and Peak 2 Rt=1.985 min in 3 min chromatography, AD-H_3UM_4_5_40_4ML ("Chiralpak AD-350*4.6 mm I.D., 3 um Mobile phase: A: $CO_2$ B: iso-propanol (0.05% DEA) Gradient: from 5% to 40% of B in 1.4 min and hold 40% for 1.05 min, then 5% of B for 0.35 min Flow rate: 4 mL/min Column temp.: 40° C.").

Example 90: Synthesis of (3S,5S,8R,9S,10S,13S, 14S,17R)-17-((1R,2S)-1-cyclopropyl-1-hydroxypropan-2-yl)-3-ethyl-10,13-dimethylhexadecahydro-1H-cyclopenta[a]phenanthren-3-ol (90)

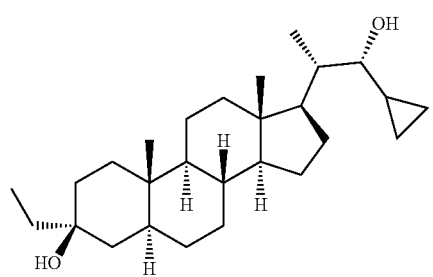

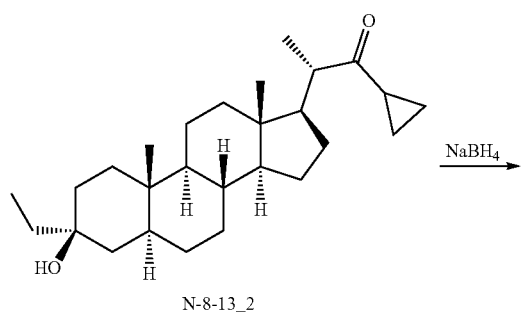

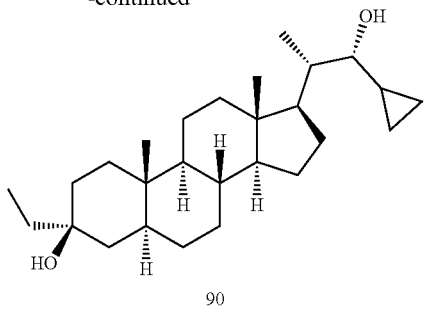

1. $NaBH_4$ (1.18 g, 17.4 mmol) was added five times, every five minutes, to a solution of N-8-13_2 (140 mg, 0.347 mmol) in MeOH (1 mL) and THF (1 mL). The mixture was stirred at 15° C. for 30 minutes. The mixture was quenched with sat.$NH_4Cl$ (50 mL) and extracted with EtOAc (3×20 mL). The combined organic phase was dried over $Na_2SO_4$, filtered, concentrated and purified by combi-flash (25% of EtOAc in PE) to give 10 (26 mg, 19%) as a solid and 90 (12 mg, 9%) as a solid.

90:
$^1$H NMR (400 MHz, $CDCl_3$) δ 3.00-2.80 (m, 1H), 2.01-1.95 (m, 1H), 1.75-1.60 (m, 5H), 1.47-1.18 (m, 13H), 1.15-0.79 (m, 18H), 0.70-0.60 (m, 4H), 0.58-0.50 (m, 1H), 0.48-0.40 (m, 1H), 0.38-0.30 (m, 1H), 0.24-0.16 (m, 1H).

LCMS Rt=3.796 min in 7.0 min chromatography, 30-90AB_7MIN_E, purity 100%, MS ESI calcd. for $C_{27}H_{43}$ $[M+H-2H_2O]^+$ 367, found 367.

HPLC Rt=13.689 min in 30 min chromatography, 70-90AB_1_30MIN·M, purity 98%.

Example 91: Synthesis of (3S,5S,8R,9S,10S,13S, 14S,17R)-17-((2S,3S)-3-hydroxybutan-2-yl)-10,13-dimethyl-3-(trifluoromethyl)hexadecahydro-1H-cyclopenta[a]phenanthren-3-ol (91)

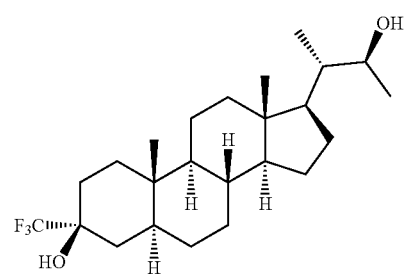

The synthesis of 91 is described in Example 13.

91:
$^1$H NMR (400 MHz, $CDCl_3$) δ 3.98-3.88 (m, 1H), 2.11-2.02 (m, 11H), 2.00 (s, 1H), 1.98-1.88 (m, 2H), 1.85-1.79 (m, 11H), 1.73-1.58 (m, 4H), 1.52-1.20 (m, 11H), 1.19-1.11 (m, 4H), 1.10-1.00 (m, 3H), 0.97-0.89 (m, 4H), 0.85 (s, 3H), 0.75-0.68 (m, 1H), 0.66 (s, 3H).

LCMS Rt=1.155 min in 2.0 min chromatography, 30-90_AB_E, purity 100%, MS ESI calcd. for $C_{24}H_{38}F_3O$ $[M+H—H_2O]^+$ 399, found 399.

HPLC Rt=5.23 min in 10.0 min chromatography, 30-90_AB_E, purity 98.88%, d.e. 100%.

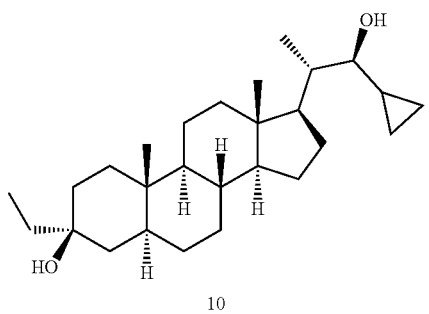

Example 92: Synthesis of (3S,5R,8R,9S,10S,13S, 14S,17R)-17-((2S,3S)-3-hydroxy-6-methylheptan-2-yl)-3,10,13-trimethylhexadecahydro-1H-cyclopenta[a]phenanthren-3-ol (92)

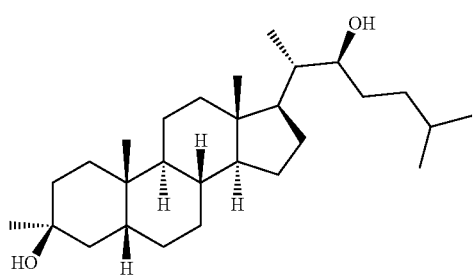

N-4-16_1

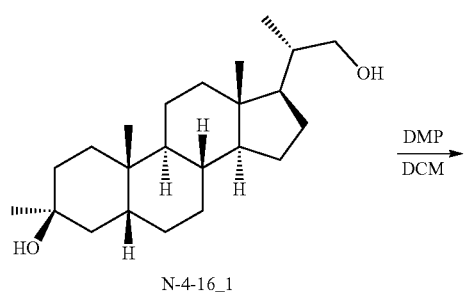

N-4-16_2

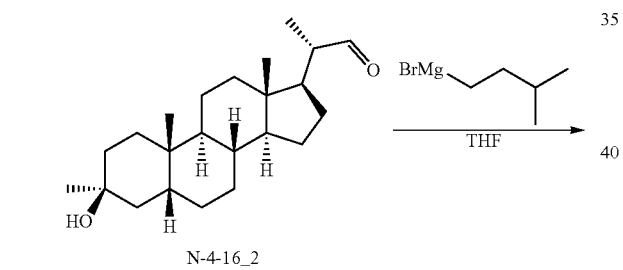

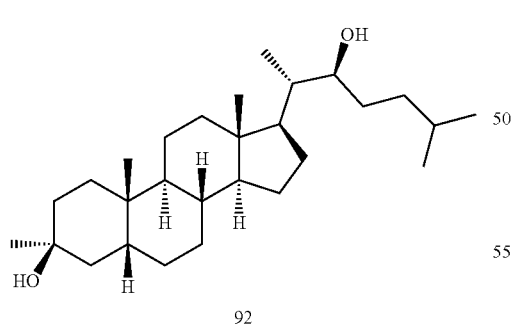

92

1. DMP (2.42 g, 5.72 mmol) was added to a solution of N-4-16_1 (1.00 g, 2.86 mmol) in DCM (20 mL). After that, the reaction was stirred at 15° C. for 10 min. Aqueous saturated NaHCO₃ (20 mL) solution and aqueous saturated Na₂S₂O₃ (20 mL) solution were added to the reaction mixture, then extracted with DCM (2×20 mL). The combined organic layer was washed with aqueous saturated NaHCO₃ (3×60 mL) solution and brine (60 mL), dried over Na₂SO₄, filtered and concentrated under vacuum to give a solid. The residue was purified by silica gel chromatography (PE/EtOAc=0 to 30%) to afford N-4-16_2 (800 mg, 81%) as a solid.

$^1$H NMR (400 MHz, CDCl$_3$) δ 9.58-9.53 (m, 1H), 2.41-2.31 (m, 1H), 1.96-1.81 (m, 4H), 1.89-1.34 (m, 10H), 1.32-1.21 (m, 10H), 1.16-1.09 (m, 5H), 0.97 (s, 3H), 0.89-0.84 (m, 1H), 0.69 (s, 3H).

2. N-4-16_2 (300 mg, 0.86 mmol) in THF (10 mL) was added to a solution of isopentylmagnesium bromide (4.32 mL, 2 M in ether, 8.65 mmol) at 25° C. under N₂. The mixture was stirred at 25° C. for 30 minutes, quenched by saturated NH₄Cl (10 mL) and extracted with ethyl acetate (3×10 mL). The organic layer was washed with brine (20 mL), dried over Na₂SO₄ and filtered, concentrated under vacuum and purified by flash column (0~15% of EtOAc in PE) to give N-4-16 (200 mg, impure) as a solid, which was triturated in MeCN (10 mL) at 25° C. to give 92 (141 mg, 70%) as a solid.

$^1$H NMR (400 MHz, CDCl$_3$) δ 3.67-3.57 (m, 1H), 2.01-1.77 (m, 4H), 1.67-1.57 (m, 4H). 1.55-1.26 (m, 14H), 1.25-1.21 (m, 5H), 1.19-0.99 (m, 7H), 0.96 (s, 3H), 0.93-0.84 (m, 9H), 0.66 (s, 3H).

LCMS Rt=1.367 min in 2 min chromatography, 30-90AB_2MIN_E, purity 100%, MS ESI calcd. for C$_{28}$H$_{47}$ [M+H-2H$_2$O]$^+$383, found 383.

Example 93: Synthesis of (3S,5S,8R,9S,10S,13S, 14S,17R)-3-ethyl-17-((2S,3R)-3-hydroxy-4-phenylbutan-2-yl)-10,13-dimethylhexadecahydro-1H-cyclopenta[a]phenanthren-3-ol (93)

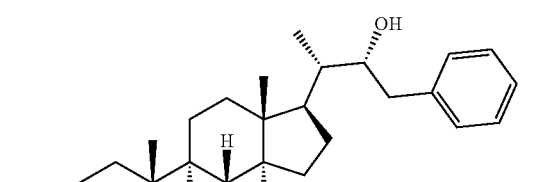

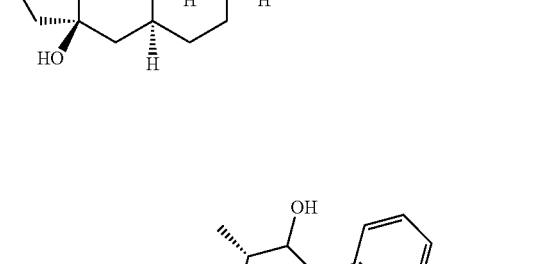

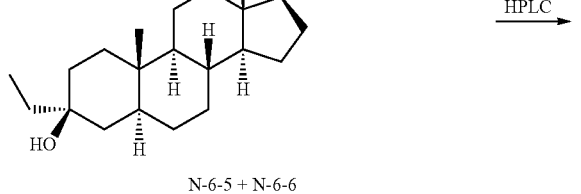

N-6-5 + N-6-6

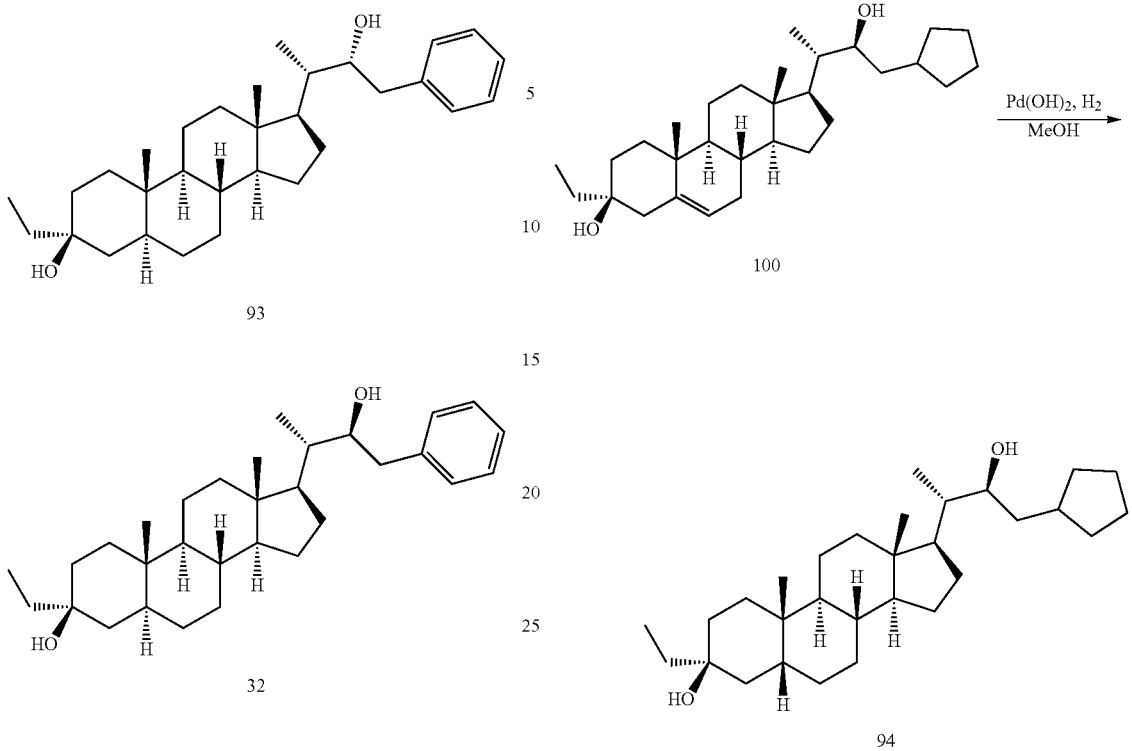

1. A mixture of N-6-5 and N-6-6 (190 mg, 0.420 mmol) was separated by prep. HPLC (Column: YMC-Actus Triart C18 100*30 mm*5 um; condition: water (0.05% HCl)-ACN; Gradient: 90-100% B; Flow rate: 25 mL/min) to give 93 (56 mg, 30%) as a solid and 32 (12 mg, 6%) as a solid.

93:

$^1$H NMR (400 MHz, CDCl$_3$) δ 7.34-7.28 (m, 2H), 7.25-7.18 (m, 3H), 3.95-3.86 (m, 1H), 2.87-2.75 (m, 1H), 2.69-2.58 (m, 1H), 2.01-1.91 (m, 1H), 1.90-1.79 (m, 1H), 1.69-1.58 (m, 4H), 1.55-1.41 (m, 6H), 1.40-1.11 (m, 11H), 1.07-0.95 (m, 6H), 0.91-0.80 (m, 7H), 0.69-0.59 (m, 4H).

LCMS Rt=1.334 min in 2.0 min chromatography, 30-90AB, purity 100%, MS ESI calcd. for C$_{31}$H$_{48}$O$_2$Na [M+Na]$^+$ 475, found 475.

Example 94: Synthesis of (3S,5R,8R,9S,10S,13S,14S,17R)-17-((2S,3S)-4-cyclopentyl-3-hydroxybutan-2-yl)-3-ethyl-10,13-dimethylhexadecahydro-1H-cyclopenta[a]phenanthren-3-ol (94)

1. Pd(OH)$_2$ (300 mg, dry) was added to a solution of 100 (150 mg, 0.338 mmol) in MeOH (20 mL). The mixture was stirred at 50° C. under H$_2$ (50 psi) for 48 hrs. The mixture was filtered, concentrated and purified by combi-flash (0-15% of EtOAc in PE) to give 94 (6 mg, 4%) and 98 (46 mg, 30%) as a solid.

94:

$^1$H NMR (400 MHz, CDCl$_3$) δ 3.78-3.66 (m, 1H), 1.98-1.72 (m, 7H), 1.69-1.59 (m, 4H), 1.48-1.32 (m, 12H), 1.27-1.07 (m, 12H), 1.06-1.00 (m, 3H), 0.97 (s, 3H), 0.94-0.85 (m, 7H), 0.66 (s, 3H).

LCMS Rt=1.639 min in 2.0 min chromatography, 30-90AB_E, purity 98.8%, MS ESI calcd. for C$_{30}$H$_{49}$ [M+H-2H$_2$O]$^+$ 409, found 409.

Example 95: Synthesis of (3S,8S,9S,10R,13S,14S, 17R)-3-(methoxymethyl)-10,13-dimethyl-17-((2S, 3R)-4,4,4-trifluoro-3-hydroxybutan-2-yl)-2,3,4,7,8,9, 10,11,12,13,14,15,16,17-tetradecahydro-1H-cyclopenta[a]phenanthren-3-ol (95)

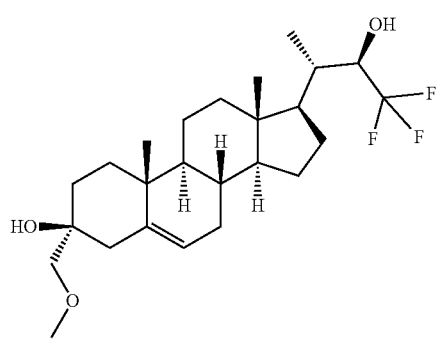

N-004-029A

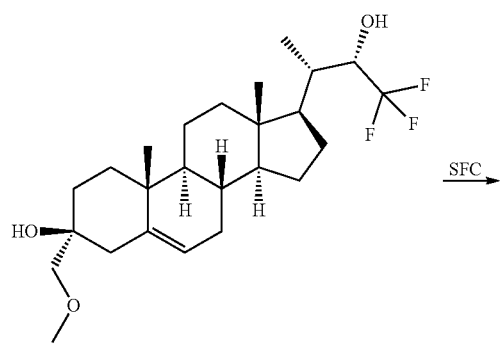

39

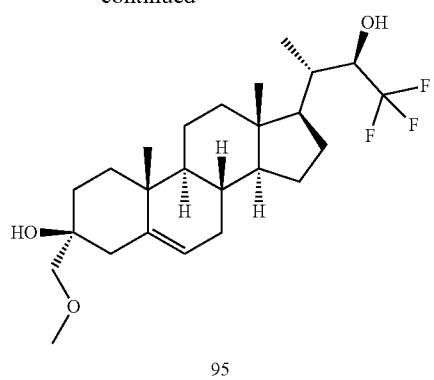

95

1. The N-004-029A (0.45 g, 1.01 mmol) was purified by SFC (Column: AD (250 mm*30 mm, 5 um), Condition: 0.1% NH$_3$H$_2$O ETOH, Begin B: 30%, End B: 30%) to afford 39 (PK1: 120 mg, 26.7%) as a white solid and 95 (PK2: 200 mg, 44.5%) as a white solid.

95:

$^1$H NMR (400 MHz, CDCl$_3$) δ 5.32-5.29 (m, 1H), 4.06-3.99 (m, 1H), 3.37 (s, 3H), 3.30-3.19 (m, 2H), 2.54 (s, 1H), 2.42-2.33 (m, 1H), 2.17-2.07 (m, 1H), 2.20-1.85 (m, 5H), 1.77-1.63 (m, 4H), 1.51-0.83 (m, 17H), 0.73 (s, 3H).

LCMS Rt=1.103 min in 2 min chromatography, 30-90AB_2MIN_E, purity 100%, MS ESI calcd. for C$_{24}$H$_{34}$F$_3$O [M-CH$_5$O$_2$]$^+$ 395, found 395.

Example 96: Synthesis of (3S,5R,8R,9S,10S,13S, 14S,17R)-3-ethyl-17-((2S,3R)-3-hydroxy-6-methyl-heptan-2-yl)-10,13-dimethylhexadecahydro-1H-cyclopenta[a]phenanthren-3-ol (96)

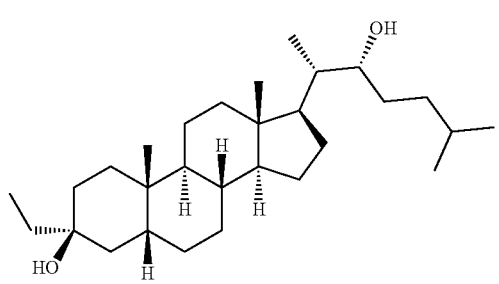

96

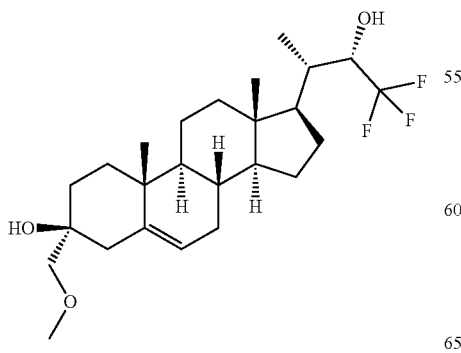

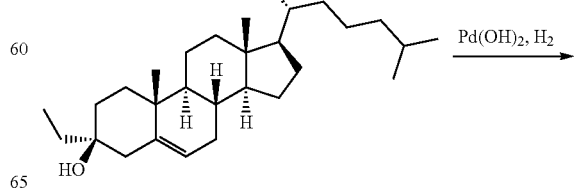

52

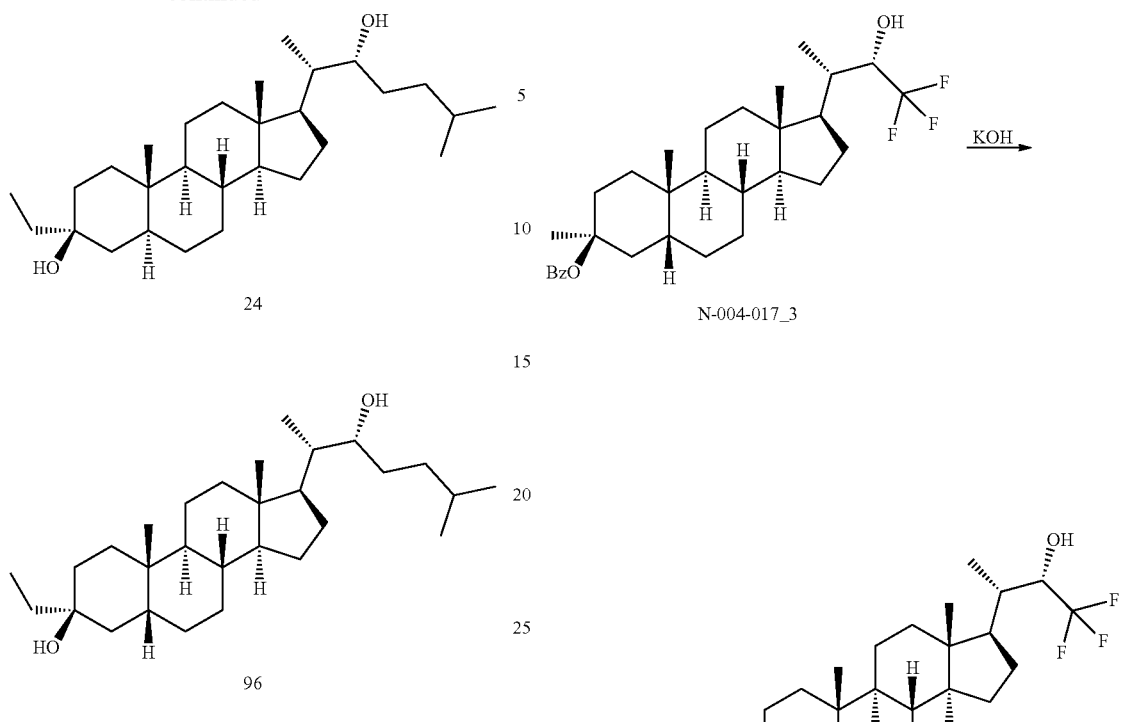

1. Pd(OH)₂ (200 mg) was added to a solution of 52 (50 mg, 0.116 mmol) in MeOH (10 mL). The mixture was stirred at 50° C. under H₂ (50 Psi). The mixture was filtered, concentrated and purified by combi-flash (0-10% of EtOAc in PE) to give 24 (15 mg, 30%) as a solid and 96 (1.2 mg, 3%) as a solid.

96:

$^1$H NMR (400 MHz, CDCl₃) δ 3.67-3.55 (m, 1H), 2.01-1.83 (m, 2H), 1.80-1.62 (m, 4H), 1.61-1.56 (m, 2H), 1.55-1.50 (m, 1H), 1.49-1.31 (m, 10H), 1.30-1.10 (m, 11H), 1.09-1.00 (m, 3H), 0.96 (s, 3H), 0.94-0.86 (m. 12H), 0.67 (s, 3H).

LCMS $t_R$=1.326 min in 2 min chromatography, 30-90AB_ELSD, purity 100.0%, MS ESI calcd. for $C_{29}H_{49}$ [M+H-2H₂O]⁺ 397, found 397.

Example 97: Synthesis of (3S,5R,8R,9S,10S,13S,14S,17R)-3,10,13-trimethyl-17-((2S,3S)-4,4,4-trifluoro-3-hydroxybutan-2-yl)hexadecahydro-1H-cyclopenta[a]phenanthren-3-ol (97)

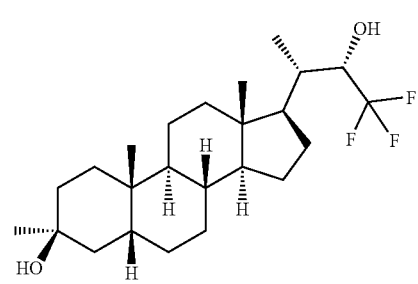

1. To a solution of N-004-017_3 (100 mg, 0.19 mmol) in THF (2 mL) and MeOH (1 mL) and water (1 mL) was added KOH (53.8 mg, 0.96 mmol). The mixture was stirred at 60° C. for 16 hrs. The mixture was poured into water (20 ml) and extracted with EtOAc (2×40 mL). The combined organic layer was washed with brine (30 mL), dried over Na₂SO₄, filtered and concentrated. The residue was purified by flash column (0~15% of EtOAc in PE) to give 97 (80 mg, impure) as a white solid. 97 (80 mg, 0.19 mmol) was purified by flash column (0~10% of EtOAc in PE) to give 97 (60 mg, impure). To a solution of 97 (40 mg, 0.096 mmol) in methanol (3 mL) was added NaBH₄ (10.8 mg, 0.28 mmol) in one portion at 0° C. under N₂. The mixture was stirred at 0° C. for 30 min. The mixture was poured into water (10 mL) and stirred for 20 min. The aqueous phase was extracted with EtOAc (3×10 mL). The combined organic phase was washed with brine (2×20 mL), dried over Na₂SO₄, filtered and concentrated to give a crude product, which was combined with another batch from 20 mg of impure 97, the residue was purified by flash column (0~10% of EtOAc in PE) to give 97 (31 mg, 31%) as a white solid.

$^1$H NMR (400 MHz, CDCl3) δ 4.11-3.96 (m, 1H), 2.18-2.11 (d, $J_{ab}$=6.4 Hz, 1H), 2.02-1.77 (m, 5H), 1.68-1.57 (m, 3H), 1.49-1.24 (m, 11H), 1.23-1.19 (m, 5H), 1.18-1.01 (m, 7H), 0.96 (s, 3H), 0.67 (s, 3H).

LCMS Rt=1.124 min in 2 min chromatography, 30-90AB_2MIN_E.M, purity 100%, MS ESI calcd. for $C_{24}H_{38}F_3O$ [M+H—H₂O]⁺ 399, found 399.

Example 98: Synthesis of (3S,5S,8R,9S,10S,13S, 14S,17R)-17-((2S,3S)-4-cyclopentyl-3-hydroxybutan-2-yl)-3-ethyl-10,13-dimethylhexadecahydro-1H-cyclopenta[a]phenanthren-3-ol (98)

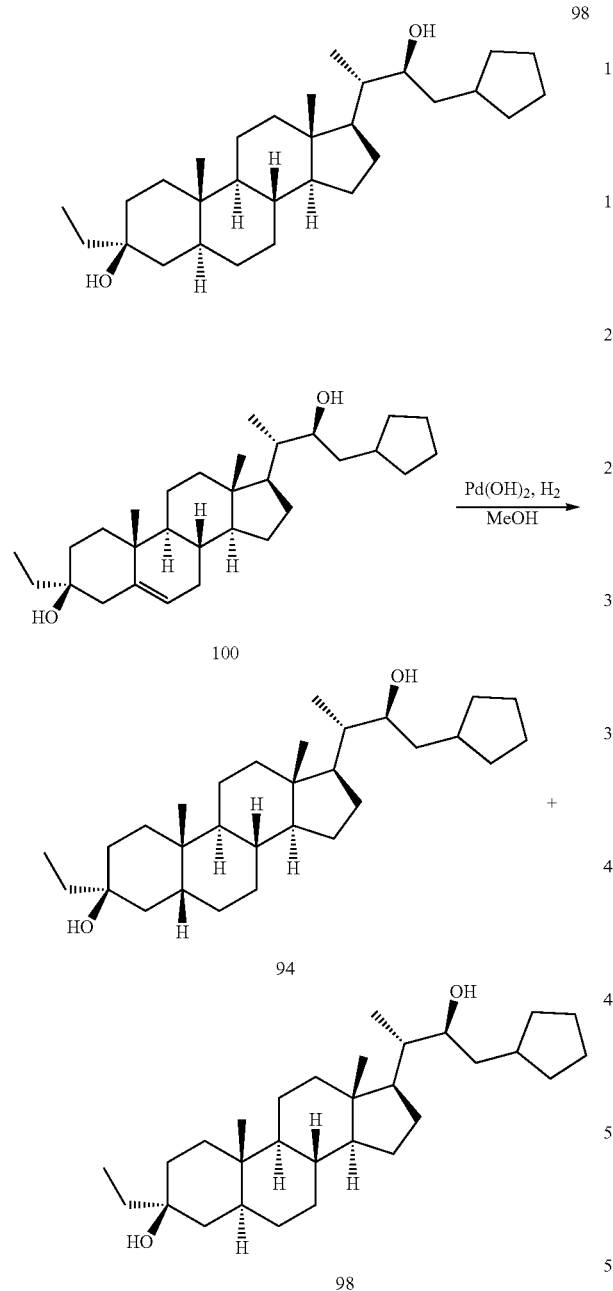

1. Pd(OH)$_2$ (300 mg, dry) was added to a solution of 100 (150 mg, 0.338 mmol) in MeOH (20 mL). The mixture was stirred at 50° C. under H$_2$ (50 psi) for 48 hrs. The mixture was filtered, concentrated and purified by combi-flash (0~15% of EtOAc in PE) to give 94 (6 mg, 4%) and 98 (46 mg, 30%) as a solid.

98:

$^1$H NMR (400 MHz, CDCl$_3$) δ 3.78-3.67 (m, 1H), 1.97-1.74 (m, 6H), 1.68-1.56 (m, 8H), 1.53-1.45 (m, 4H), 1.44-1.31 (m, 10H), 1.28-1.21 (m, 1H), 1.16-0.96 (m, 9H), 0.91-0.85 (m, 6H), 0.82 (s, 3H), 0.69-0.61 (m, 4H).

LCMS Rt=1.582 min in 2.0 min chromatography, 30-90AB_E, purity 100%, MS ESI calcd. for C$_{30}$H$_{49}$ [M+H-2H$_2$O]$^+$409, found 409.

Example 99: Synthesis for (3S,5S,8R,9S,10S,13S, 14S,17R)-17-((2S,3S,E)-3-hydroxy-5-phenylpent-4-en-2-yl)-10,13-dimethyl-3-(trifluoromethyl)hexadecahydro-1H-cyclopenta[a]phenanthren-3-ol (99)

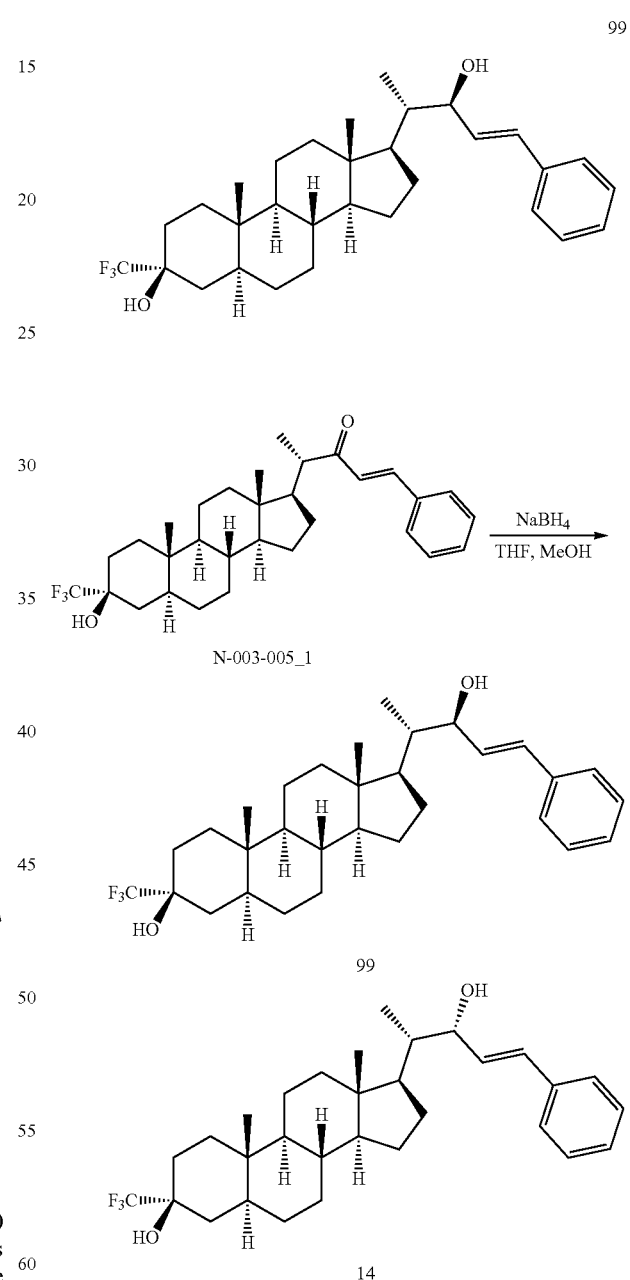

1. NaBH$_4$ (419.0 mmol) was added in portions to a solution of N-003-005_1 (140 mg, 0.278 mmol) in THF (2 mL) and MeOH (1 mL) at 20° C. The mixture was stirred at 20° C. for 10 min. The reaction was quenched with water (20 mL) and NH$_4$Cl (20 mL, sat.). The mixture was extracted with EtOAc (50 mL). The organic layer was concentrated under vacuum and purified by prep-TLC (PE/EtOAc=4/1) to give N-003-005 (50 mg, impure) and 14 (50 mg) both as a solid.

The impure 99 (50 mg) was purified by SFC (Instrument: SFC 1; Column: OD (250 mm*30 mm, 5 um); Condition: 0.1% NH₃H₂O EtOH; Begin B: 40%; End B: 40%; Flow Rate (mL/min): 50; Injections: 60) to provide a solid which was dissolved in MeCN (20 mL) and concentrated in vacuum to give 99 (17 mg) as a solid.

99:

¹H NMR (400 MHz, CDCl₃) δ 7.44-7.36 (m, 2H), 7.36-7.28 (m, 2H), 7.25-7.20 (m, 1H), 6.58 (d, J=16.0 Hz, 1H), 6.24 (dd, J=4.8, 16.0 Hz, 1H), 4.49-4.40 (m, 1H), 2.09-1.91 (m, 4H), 1.86-1.75 (m, 1H), 1.72-1.58 (m, 5H), 1.52-1.04 (m, 14H), 0.94 (d, J=6.4 Hz, 3H), 0.91-0.87 (m, 1H), 0.86 (s, 3H), 0.75-0.70 (m, 1H), 0.69 (s, 3H).

LCMS Rt=1.280 min in 2 min chromatography, 30-90AB_2MIN_E, purity 98.5%, MS ESI calcd. for C₃₁H₄₂F₃O [M+H—H₂O]⁺ 487, found 487.

HPLC Rt=6.29 min in 8 min chromatography, 30-90_AB_1.2 ml, 100% d.e.

Example 100: Synthesis of (3S,8S,9S,10R,13S,14S, 17R)-17-((2S,3S)-4-cyclopentyl-3-hydroxybutan-2-yl)-3-ethyl-10,13-dimethyl-2,3,4,7,8,9,10,11,12,13,14,15,16,17-tetradecahydro-1H-cyclopenta[a]phenanthren-3-ol (100)

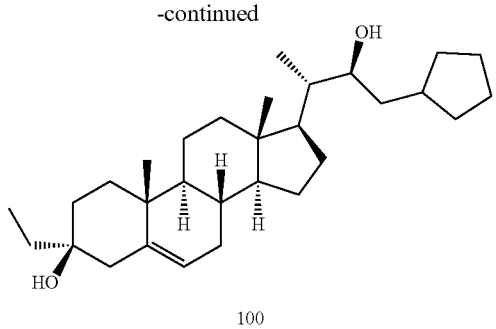

100

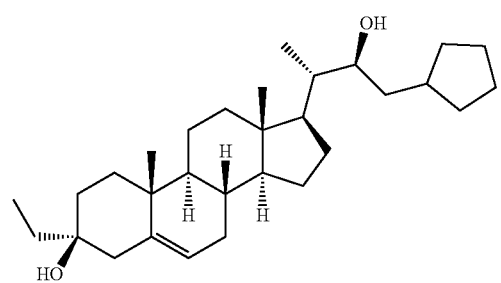

100

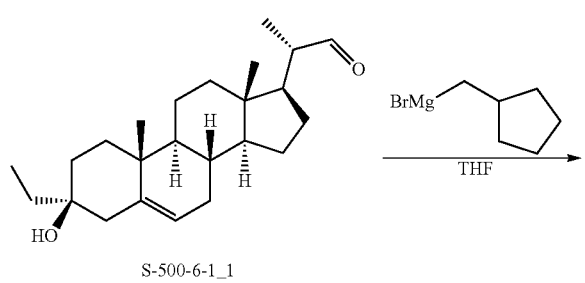

1. A solution of (bromomethyl)cyclopentane (1.8 g, 11.0 mmol) in THF (11 mL) was added dropwise to a suspension of Mg (528 mg, 22.0 mmol) and I₂ (55.8 mg, 0.22 mmol) in THF (3 mL) at 75° C. The mixture was stirred at 75° C. for 1 hr. A mixture of (cyclopentylmethyl)magnesium bromide (11.1 mL, 11.1 mmol, 1M in THF) was slowly added to a solution of 5-500-6-1_1 (800 mg, 2.23 mmol) in THF (30 mL) at 15° C. After addition, the mixture was stirred at 15° C. for 1 hr. The mixture was quenched with sat. NH₄Cl (40 mL) and extracted with EtOAc (3×20 mL). The combined organic phase was washed with brine (2×30 mL), dried over Na₂SO₄, filtered and concentrated and purified by combi-flash (0-15% of EtOAc in PE) to give 100 (350 mg, 35%) as a solid.

¹H NMR (400 MIHL, CDCl₃) δ5.32-5.26 (in, 1H), 3.77-3.69 (m, 1H), 2.41-2.31 (in, 1H), 2.09-1.89 (m, 4H), 1.88-1.69 (m, 4H), 1.68-1.55 (in, 6H), 1.54-1.27 (m, 12H), 1.26-1.15 (in, 2H), 51.14-1.05 (m, 41H), 1.04-0.99 (m, 5H), 0.98-0.88 (in, 4H₁), 0.87-0.81 (m, 3H), 0.69 (s, 3H).

LCMS Rt=5.661 min in 7.0 min chromatography, 30-90AB_E, purity 100%, MS ESI calcd. for C₃₀H₄₇ [M+H-2H₂O]⁺407. found 407.

TABLE 1

Data for Exemplary Compounds.

| Compound | GluN2A PCA EC$_{50}$ (nM) | GluN2A PCA E$_{Max}$ (%) | GluN2B PCA EC$_{50}$ (nM) | GluN2B PCA E$_{Max}$ (%) | GluN2A PCA % potentiation at 1 μM |
|---|---|---|---|---|---|
| 1 | | | | | H |
| 2 | | | | | I |
| 3 | C | D | C | D | |
| 4 | A | D | C | D | I |
| 6 | C | D | C | D | G |
| 7 | | | | | G |
| 8 | C | D | C | D | I |
| 9 | | | | | H |
| 10 | | | | | I |
| 11 | | | | | I |
| 12 | C | D | C | D | G |
| 13 | A | D | A | E | |
| 15 | | | | | H |
| 16 | | | | | H |
| 18 | | | | | G |
| 19 | | | | | H |
| 20 | C | D | C | D | H |
| 21 | | | | | H |
| 22 | | | | | G |
| 23 | C | D | C | E | H |
| 24 | C | D | C | D | |
| 25 | C | D | C | D | |
| 28 | C | D | C | E | |
| 29 | C | D | C | D | |
| 30 | C | E | C | E | |
| 31 | A | E | B | E | |

TABLE 1-continued

Data for Exemplary Compounds.

| Compound | GluN2A PCA EC$_{50}$ (nM) | GluN2A PCA E$_{Max}$ (%) | GluN2B PCA EC$_{50}$ (nM) | GluN2B PCA E$_{Max}$ (%) | GluN2A PCA % potentiation at 1 μM |
|---|---|---|---|---|---|
| 32 | C | D | C | D | G |
| 36 | C | D | C | D | |
| 38 | C | D | C | D | H |
| 39 | | | | | H |
| 40 | C | D | C | E | G |
| 41 | | | | | H |
| 43 | | | | | I |
| 44 | C | D | C | D | |
| 45 | | | | | H |
| 46 | C | D | C | D | H |
| 47 | C | D | C | D | |
| 48 | | | | | H |
| 49 | C | D | C | D | |
| 50 | | | | | H |
| 52 | C | D | C | D | |
| 53 | | | | | H |
| 55 | | | | | H |
| 56 | | | | | I |
| 57 | | | | | I |
| 58 | | | | | H |
| 59 | C | D | C | D | I |
| 62 | | | | | H |
| 64 | | | | | H |
| 65 | | | | | H |
| 67 | C | D | C | D | G |
| 68 | | | | | H |
| 69 | C | D | C | D | G |
| 70 | | | | | H |
| 71 | | | | | H |
| 72 | C | D | C | D | H |
| 73 | | | | | H |
| 74 | | | | | H |
| 75 | C | D | C | D | |
| 77 | C | D | C | D | |
| 79 | C | D | C | D | |
| 80 | | | | | H |
| 81 | | | | | H |
| 82 | C | D | C | D | |
| 83 | | | | | H |
| 84 | C | D | C | D | G |
| 85 | | | | | G |
| 86 | | | | | H |
| 87 | C | D | C | D | G |
| 88 | | | | | H |
| 90 | | | | | G |
| 91 | | | | | H |
| 94 | C | D | C | D | H |
| 95 | | | | | I |
| 96 | B | D | C | D | G |
| 97 | | | | | H |
| 98 | C | D | C | D | H |
| 100 | C | D | C | D | H |

For Table 1, "A" indicates an EC$_{50}$ of 1 to 100 nM, "B" indicates an EC$_{50}$ of greater than 100 nM up to 1 μM, "C" indicates an EC$_{50}$ greater than 1 μM; "D" indicates an E$_{Max}$ of up to 100%, "B" indicates an E$_{max}$ between 100% and 500%, "F" indicates an E$_{max}$ greater than 500%; "G" indicates a % potentiation between and including 10% and −10%, "H" indicates a % potentiation less than −10% and greater than or equal to −40%, and "I" indicates a % potentiation less than −40%.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A pharmaceutical composition comprising a compound of Formula (I-67):

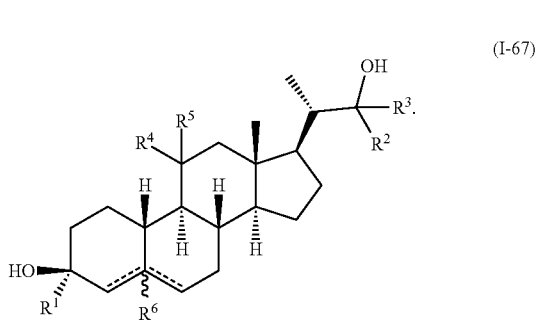
(I-67)

wherein:

$R^1$ is substituted or unsubstituted alkyl;

each of $R^2$ and $R^3$ is independently hydrogen, substituted or unsubstituted alkyl, substituted or unsubstituted carbocyclyl, substituted or unsubstituted heterocyclyl, substituted or unsubstituted aryl, or substituted or unsubstituted heteroaryl, or $R^2$ and $R^3$, together with the carbon atom to which they are attached form a substituted or unsubstituted 3-8 membered ring;

each of $R^4$ and $R^5$ is independently hydrogen, halo, or —$OR^c$, wherein $R^c$ is hydrogen or substituted or unsubstituted $C_1$-$C_6$ alkyl, or $R^4$ and $R^5$, together with the carbon atom to which they are attached form an oxo group;

$R^6$ is absent or hydrogen; and

===== represents a single or double bond, wherein when one of ===== is a double bond, the other ===== is a single bond and $R^6$ is absent; and when both of ===== are single bonds, then $R^6$ is hydrogen; and a pharmaceutically acceptable carrier.

2. The pharmaceutical composition of claim 1, wherein $R^1$ is substituted or unsubstituted $C_1$-$C_6$ alkyl.

3. The pharmaceutical composition of claim 1, wherein $R^1$ is —$CH_3$, —$CF_3$, —$CH_2CH_3$, or —$CH_2OR^A$, wherein $R^A$ is substituted or unsubstituted $C_1$-$C_6$ alkyl.

4. The pharmaceutical composition of claim 1, wherein each of $R^2$ and $R^3$ is independently hydrogen or substituted or unsubstituted alkyl.

5. The pharmaceutical composition of claim 1, wherein each of $R^2$ and $R^3$ is independently hydrogen, —$CF_3$, or —$CH_3$.

6. The pharmaceutical composition of claim 1, wherein $R^4$ and $R^5$, together with the carbon atom to which they are attached form an oxo group.

7. The pharmaceutical composition of claim 1, wherein $R^4$ and $R^5$ are hydrogen.

8. The pharmaceutical composition of claim 1, wherein $R^2$ is substituted or unsubstituted aryl or substituted or unsubstituted heteroaryl and $R^3$ is hydrogen.

9. The pharmaceutical composition of claim 1, wherein $R^2$ is substituted or unsubstituted carbocyclyl or substituted or unsubstituted heterocyclyl and $R^3$ is hydrogen.

10. The pharmaceutical composition of claim 1, wherein the compound of Formula (I-67) is selected from a compound of Formula (I-A67), (I-B67), or (I-C67):

(I-A67)

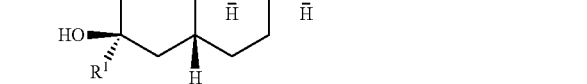
(I-B67)

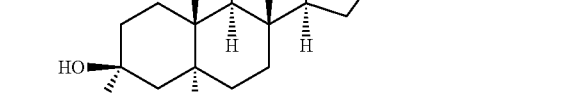
(I-C67)

11. A pharmaceutical composition comprising a pharmaceutically acceptable salt of a compound of Formula (I-67):

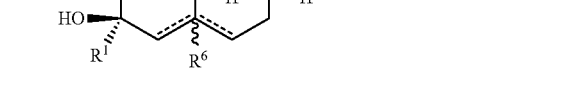
(I-67)

wherein:

$R^1$ is substituted or unsubstituted alkyl;

each of $R^2$ and $R^3$ is independently hydrogen, substituted or unsubstituted alkyl, substituted or unsubstituted carbocyclyl, substituted or unsubstituted heterocyclyl, substituted or unsubstituted aryl, or substituted or unsubstituted heteroaryl, or $R^2$ and $R^3$, together with the carbon atom to which they are attached form a substituted or unsubstituted 3-8 membered ring;

each of $R^4$ and $R^5$ is independently hydrogen, halo, or —$OR^c$, wherein $R^c$ is hydrogen or substituted or unsubstituted $C_1$-$C_6$ alkyl, or $R^4$ and $R^5$, together with the carbon atom to which they are attached form an oxo group;

$R^6$ is absent or hydrogen; and

----- represents a single or double bond, wherein when one of ----- is a double bond, the other ----- is a single bond and $R^6$ is absent; and when both of ----- are single bonds, then $R^6$ is hydrogen; and a pharmaceutically acceptable carrier.

12. The pharmaceutical composition of claim 11, wherein $R^1$ is substituted or unsubstituted $C_1$-$C_6$ alkyl.

13. The pharmaceutical composition of claim 11, wherein $R^1$ is —$CH_3$, —$CF_3$, —$CH_2CH_3$, or —$CH_2OR^A$, wherein $R^A$ is substituted or unsubstituted $C_1$-$C_6$ alkyl.

14. The pharmaceutical composition of claim 11, wherein each of $R^2$ and $R^3$ is independently hydrogen or substituted or unsubstituted alkyl.

15. The pharmaceutical composition of claim 11, wherein each of $R^2$ and $R^3$ is independently hydrogen, —$CF_3$, or —$CH_3$.

16. The pharmaceutical composition of claim 11, wherein $R^4$ and $R^5$, together with the carbon atom to which they are attached form an oxo group.

17. The pharmaceutical composition of claim 11, wherein $R^4$ and $R^5$ are hydrogen.

18. The pharmaceutical composition of claim 11, wherein $R^2$ is substituted or unsubstituted aryl or substituted or unsubstituted heteroaryl and $R^3$ is hydrogen.

19. The pharmaceutical composition of claim 11, wherein $R^2$ is substituted or unsubstituted carbocyclyl or substituted or unsubstituted heterocyclyl and $R^3$ is hydrogen.

20. The pharmaceutical composition of claim 11, wherein the compound of Formula (I-67) is selected from a compound of Formula (I-A67), (I-B67), or (I-C67):

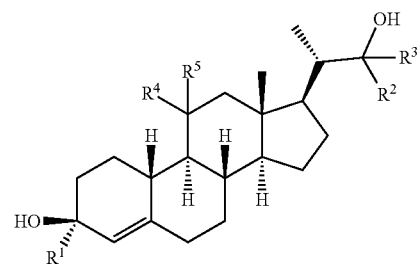
(I-A67)

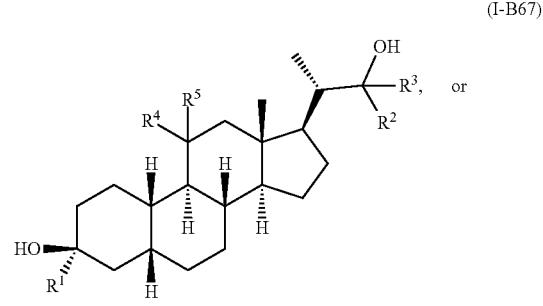
(I-B67)

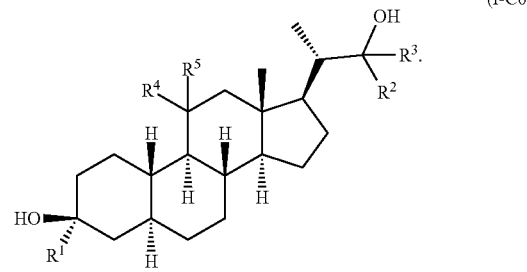
(I-C67)

* * * * *